(12) United States Patent
Gaali et al.

(10) Patent No.: US 9,845,292 B2
(45) Date of Patent: Dec. 19, 2017

(54) SELECTIVE FKBP51 LIGANDS FOR TREATMENT OF PSYCHIATRIC DISORDERS

(71) Applicant: Max-Planck-Gesellschaft zur Förderung der Wissenschaften e.V., Munich (DE)

(72) Inventors: Steffen Gaali, Munich (DE); Felix Hausch, Munich (DE); Alexander Kirschner, Munich (DE); Xixi Feng, Munich (DE); Andreas Bracher, Munich (DE); Gerd Ruehter, Hamburg (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 0 days.

(21) Appl. No.: 15/023,095

(22) PCT Filed: Sep. 15, 2014

(86) PCT No.: PCT/EP2014/002542
§ 371 (c)(1),
(2) Date: Mar. 18, 2016

(87) PCT Pub. No.: WO2015/039758
PCT Pub. Date: Mar. 26, 2015

(65) Prior Publication Data
US 2016/0289184 A1 Oct. 6, 2016

(30) Foreign Application Priority Data

Sep. 19, 2013 (EP) ................................. 13185247
Dec. 10, 2013 (EP) ................................. 13196561
Jan. 16, 2014 (EP) ................................. 14151510

(51) Int. Cl.
| | | |
|---|---|---|
| C07D 211/06 | (2006.01) |
| C07D 295/00 | (2006.01) |
| C07D 207/16 | (2006.01) |
| C07D 401/14 | (2006.01) |
| C07D 401/12 | (2006.01) |
| C07D 405/12 | (2006.01) |
| C07D 279/12 | (2006.01) |
| C07D 211/60 | (2006.01) |
| C07D 211/78 | (2006.01) |
| C12N 9/90 | (2006.01) |
| G06F 19/16 | (2011.01) |

(52) U.S. Cl.
CPC .......... *C07D 207/16* (2013.01); *C07D 211/60* (2013.01); *C07D 211/78* (2013.01); *C07D 279/12* (2013.01); *C07D 401/12* (2013.01); *C07D 401/14* (2013.01); *C07D 405/12* (2013.01); *C12N 9/90* (2013.01); *C12Y 502/01008* (2013.01); *G06F 19/16* (2013.01); *C07B 2200/13* (2013.01)

(58) Field of Classification Search
CPC .............. C07D 211/06; C07D 295/00
USPC ........................................................ 546/184
See application file for complete search history.

(56) References Cited

U.S. PATENT DOCUMENTS

| | | | |
|---|---|---|---|
| 6,133,456 A | * | 10/2000 | Holt ..................... C07D 207/16 540/454 |
| 6,268,384 B1 | | 7/2001 | Novak et al. |
| 6,291,510 B1 | | 9/2001 | Hamilton et al. |
| 2003/0036654 A1 | | 2/2003 | Holt et al. |
| 2011/0229568 A1 | | 9/2011 | Oertel et al. |

FOREIGN PATENT DOCUMENTS

| | | |
|---|---|---|
| EP | 2589383 | 5/2013 |
| WO | WO 2008/055488 | 5/2008 |
| WO | WO 2008/137476 | 11/2008 |

OTHER PUBLICATIONS

Yang et al., Journal of Medicinal Chemistry (2000), 43(6), 1135-1142.*
Blair, et al., "Accelerated neurodegeneration through chaperone-mediated oligomerization of tau". J Clin Invest (2013) 123(10):4158-4169.
Bracher, A.; et al., Structural characterization of the PPIase domain of FKBP51, a cochaperone of human Hsp90. Acta Crystallogr D Biol Crystallogr . (2011) D67:549-559.
Caldwell et al., "Glucocorticoid-regulated genes in eosinophilic esophagitis: A role for FKBP51" J Allerg Clin Immunol (2010) 125:879-888.e8.
Craescu et al., "Three-Dimensional Structure of the Immunophilin-like Domain of FKBP59 in Solution" Biochemistry (1996) 35(34):11045-11052.
Erlejman et al., "Hsp90-binding immunophilins as a potential new platform for drug treatment" Future Med Chem. (2013) 5(5):591-607.

(Continued)

*Primary Examiner* — Niloofar Rahmani
(74) *Attorney, Agent, or Firm* — Knobbe, Martens, Olson & Bear, LLP

(57) ABSTRACT

The present invention relates to compounds of the general formula (I) having a selective FKBP51 ligand scaffold, pharmaceutically acceptable salts of these compounds and pharmaceutical compositions containing at least one of these compounds together with pharmaceutically acceptable carrier, excipient and/or diluents. Said selective FKBP51 ligand compounds can be used for prophylaxis and/or treatment of psychiatric disorders and neurodegenerative diseases, disorders and conditions.

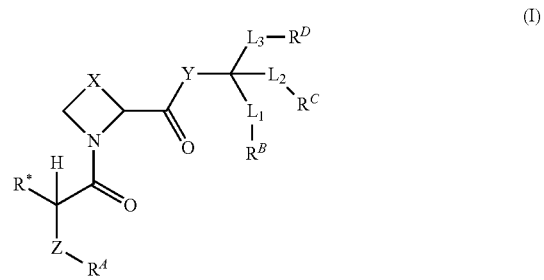

(I)

6 Claims, 32 Drawing Sheets

(56) References Cited

OTHER PUBLICATIONS

Gaali et al., "The Chemical Biology of Immunophilin Ligands," Curr. Med Chem. (2011) 18(35):5355-5379.
Galat et al., "Functional diversity and pharmacological profiles of the FKBPs and their complexes with small natural ligands," Cell. Mol. Life Sci. (2013) 70:3243-3275.
Galigniana et al., "Regulation of the glucocorticoid response to stress-related disorders by the Hsp90-binding immunophilin FKBP51" J. Neurochem. (2012) 122:4-18.
Gopalakrishnan et al, "Evaluation of Synthetic FK506 Analogues as Ligands for the FK506-Binding Proteins 51 and 52,"J. Med. Chem. (2012) 55:4114-4122.
Gopalakrishnan et al, "Exploration of Pipecolate Sulfonamides as Binders of the FK506-Binding Proteins 51 and 52," J. Med. Chem. (2012) 55:4123-4131.
Hou et al., "FKBP5 as a Selection Biomarker for Gemcitabine and Akt Inhibitors in Treatment of Pancreatic Cancer" PLOS One (2012) 7(5):e36252.
Jiang et al., "FK506 Binding Protein Mediates Glioma Cell Growth and Sensitivity to Rapamycin Treatment by Regulating Nf-κB Signaling Pathway" Neoplasia (2013) 10(3):235-243.
Komura et al., "Role for the Nuclear Factor KB Pathway in Transforming Growth Factor —β1 Production in Idiopathic Myelofibrosis: Possible Relationship with FK506 Binding Protein 51 Overexpression" Cancer Res. (2005) 65(8):3281-3289.
Kozany et al., "Fluorescent Probes to Characterise FK506-Binding Proteins," ChemBioChem (2009) 10:1402-1410.
Lepre et al., "Solution structure of FK506 bound to FKBP-12," FEBS Lett (1992) 302(1):89-96.
Li at al., "MicroRNA-100/99a, deregulated in acute lymphoblastic leukaemia, suppress proliferation and promote apoptosis by regulating the FKBP51 and IGF1R/mTOR signalling pathways," Br. J. Cancer (2013) 109:2189-2198.
Romano et al., "FK506 binding protein 51 positively regulates melanoma stemness and metastatic potential," Cell Death Dis. (2013) 4:e578.
Sanchez et al., "Chaperoning steroidal physiology: Lessons from mouse genetic models of Hsp90 and its cochaperones," Biochimica et Biophysica Acta (2012) 1823:722-729.
Schmidt et al., "The Prospect of FKBP51 as a Drug Target," ChemMedChem (2012) 7:1351-1359.
Sich et al., "Solution structure of a neurotrophic ligand bound to FKBP12 and its effects on protein dynamics," Eur. J. Biochem. (2000) 267:5342-5354.
Storer, et al., "FKBP51 and FKBP52 in signaling and disease" Trends Endocrinol Metab (2011) 22(12):481-90.
Tajiri et al., "Association of Eosinophilic Inflammation with FKBP51 Expression in Sputum Cells in Asthma," PLOS One (2013) 8(6):e65284.
Touma et al., "Mice selected for high versus low stress reactivity: A new animal model for affective disorders," Psychoneuroendocrinol. (2008) 33:839-862.
Touma et al., "FK506 Binding Protein 5 Shapes Stress Responsiveness: Modulation of Neuroendocrine Reactivity and Coping Behavior," Biol.Psych. (2011) 70:928-936.
Wang, Z. X., "An exact mathematical expression for describing competitive binding of two different ligands to a protein molecule," FEBS Lett. (1995) 360:111-114.
Wang et al., "Increasing the Efficiency of Ligands for FK506-Binding Protein 51 by Conformational Control ," J Med Chem, (2013) 56:3922-3935.
Warrier, PhD Thesis 2008, University of Toledo, ProQuest LLC, "Role of FKBP51 and FKBP52 in Glucocorticoid Receptor Regulated Metabolism".
International Search Report and Written Opinion dated Dec. 12, 2014 for PCT Application No. PCT/EP2014/002542, filed Sep. 15, 2014.

* cited by examiner

A

B

G)

H)

Hydrophobic core atoms are shown in green (H). Fit inducing atoms are shown in red (I). DH = Donors. A = Acceptors. Hydrophobic interactions are shown in grey. Hydrophilic interactions are shown in dark green.

a) component of crystals

Asymmetric unit      Lattice motif      Unit cell b) unit cell definition

Figure 9

| | ATOM Type | | Resid | | # | X | Y | Z | OCC | B | Mol |
|---|---|---|---|---|---|---|---|---|---|---|---|
| ATOM | 1 | N | GLY | A | 13 | -22.911 | -5.632 | 6.454 | 1.00 | 19.73 | N |
| ATOM | 2 | CA | GLY | A | 13 | -23.116 | -7.001 | 5.874 | 1.00 | 18.60 | C |
| ATOM | 3 | C | GLY | A | 13 | -21.796 | -7.751 | 5.879 | 1.00 | 18.31 | C |
| ATOM | 4 | O | GLY | A | 13 | -20.803 | -7.266 | 6.446 | 1.00 | 18.43 | O |
| ATOM | 5 | N | ALA | A | 14 | -21.784 | -8.926 | 5.254 | 1.00 | 17.11 | N |
| ATOM | 6 | CA | ALA | A | 14 | -20.575 | -9.756 | 5.204 | 1.00 | 16.43 | C |
| ATOM | 7 | CB | ALA | A | 14 | -20.811 | -11.013 | 4.333 | 1.00 | 16.04 | C |
| ATOM | 8 | C | ALA | A | 14 | -19.313 | -8.980 | 4.753 | 1.00 | 15.60 | C |
| ATOM | 9 | O | ALA | A | 14 | -18.276 | -9.067 | 5.430 | 1.00 | 15.76 | O |
| ATOM | 10 | N | PRO | A | 15 | -19.390 | -8.213 | 3.638 | 1.00 | 15.02 | N |
| ATOM | 11 | CA | PRO | A | 15 | -18.163 | -7.500 | 3.213 | 1.00 | 15.39 | C |
| ATOM | 12 | CB | PRO | A | 15 | -18.577 | -6.805 | 1.903 | 1.00 | 15.14 | C |
| ATOM | 13 | CG | PRO | A | 15 | -19.796 | -7.559 | 1.437 | 1.00 | 15.14 | C |
| ATOM | 14 | CD | PRO | A | 15 | -20.506 | -7.952 | 2.707 | 1.00 | 14.93 | C |
| ATOM | 15 | C | PRO | A | 15 | -17.653 | -6.486 | 4.234 | 1.00 | 15.45 | C |
| ATOM | 16 | O | PRO | A | 15 | -16.440 | -6.414 | 4.484 | 1.00 | 15.10 | O |
| ATOM | 17 | N | ALA | A | 16 | -18.558 | -5.712 | 4.835 | 1.00 | 15.25 | N |
| ATOM | 18 | CA | ALA | A | 16 | -18.149 | -4.765 | 5.882 | 1.00 | 15.46 | C |
| ATOM | 19 | CB | ALA | A | 16 | -19.333 | -3.881 | 6.319 | 1.00 | 15.62 | C |
| ATOM | 20 | C | ALA | A | 16 | -17.514 | -5.454 | 7.087 | 1.00 | 15.76 | C |
| ATOM | 21 | O | ALA | A | 16 | -16.559 | -4.931 | 7.681 | 1.00 | 15.12 | O |
| ATOM | 22 | N | THR | A | 17 | -18.014 | -6.643 | 7.433 | 1.00 | 14.45 | N |
| ATOM | 23 | CA | THR | A | 17 | -17.429 | -7.420 | 8.519 | 1.00 | 15.22 | C |
| ATOM | 24 | CB | THR | A | 17 | -18.346 | -8.604 | 8.878 | 1.00 | 15.42 | C |
| ATOM | 25 | OG1 | THR | A | 17 | -19.586 | -8.076 | 9.370 | 1.00 | 19.16 | O |
| ATOM | 26 | CG2 | THR | A | 17 | -17.740 | -9.494 | 9.960 | 1.00 | 15.91 | C |
| ATOM | 27 | C | THR | A | 17 | -16.009 | -7.871 | 8.162 | 1.00 | 13.97 | C |
| ATOM | 28 | O | THR | A | 17 | -15.114 | -7.866 | 9.005 | 1.00 | 13.79 | O |
| ATOM | 29 | N | VAL | A | 18 | -15.785 | -8.233 | 6.903 | 1.00 | 13.61 | N |
| ATOM | 30 | CA | VAL | A | 18 | -14.434 | -8.579 | 6.497 | 1.00 | 13.09 | C |
| ATOM | 31 | CB | VAL | A | 18 | -14.354 | -9.126 | 5.054 | 1.00 | 12.90 | C |
| ATOM | 32 | CG1 | VAL | A | 18 | -12.905 | -9.426 | 4.703 | 1.00 | 11.86 | C |
| ATOM | 33 | CG2 | VAL | A | 18 | -15.168 | -10.386 | 4.957 | 1.00 | 12.22 | C |
| ATOM | 34 | C | VAL | A | 18 | -13.516 | -7.378 | 6.666 | 1.00 | 13.70 | C |
| ATOM | 35 | O | VAL | A | 18 | -12.430 | -7.508 | 7.220 | 1.00 | 13.95 | O |
| ATOM | 36 | N | THR | A | 19 | -13.958 | -6.214 | 6.208 | 1.00 | 14.02 | N |
| ATOM | 37 | CA | THR | A | 19 | -13.177 | -4.971 | 6.396 | 1.00 | 14.82 | C |
| ATOM | 38 | CB | THR | A | 19 | -13.957 | -3.764 | 5.858 | 1.00 | 14.81 | C |
| ATOM | 39 | OG1 | THR | A | 19 | -14.120 | -3.920 | 4.457 | 1.00 | 15.36 | O |
| ATOM | 40 | CG2 | THR | A | 19 | -13.227 | -2.434 | 6.139 | 1.00 | 15.63 | C |
| ATOM | 41 | C | THR | A | 19 | -12.785 | -4.743 | 7.858 | 1.00 | 15.85 | C |
| ATOM | 42 | O | THR | A | 19 | -11.617 | -4.450 | 8.170 | 1.00 | 15.18 | O |
| ATOM | 43 | N | GLU | A | 20 | -13.763 | -4.902 | 8.744 | 1.00 | 16.46 | N |
| ATOM | 44 | CA | GLU | A | 20 | -13.582 | -4.559 | 10.150 | 1.00 | 18.90 | C |
| ATOM | 45 | CB | GLU | A | 20 | -14.925 | -4.365 | 10.850 | 1.00 | 18.73 | C |
| ATOM | 46 | CG | GLU | A | 20 | -15.632 | -3.096 | 10.397 | 1.00 | 23.01 | C |
| ATOM | 47 | CD | GLU | A | 20 | -16.911 | -2.809 | 11.166 | 1.00 | 26.15 | C |
| ATOM | 48 | OE1 | GLU | A | 20 | -16.978 | -3.150 | 12.376 | 1.00 | 29.00 | O |
| ATOM | 49 | OE2 | GLU | A | 20 | -17.846 | -2.232 | 10.549 | 1.00 | 31.17 | O |
| ATOM | 50 | C | GLU | A | 20 | -12.715 | -5.554 | 10.899 | 1.00 | 19.16 | C |
| ATOM | 51 | O | GLU | A | 20 | -11.843 | -5.142 | 11.669 | 1.00 | 19.72 | O |
| ATOM | 52 | N | GLN | A | 21 | -12.933 | -6.845 | 10.629 | 1.00 | 19.01 | N |
| ATOM | 53 | CA | GLN | A | 21 | -12.392 | -7.942 | 11.440 | 1.00 | 19.78 | C |

Figure 9 (cont.)

| | | | | | | | | | | |
|---|---|---|---|---|---|---|---|---|---|---|
| ATOM | 54 | CB | GLN | A | 21 | -13.527 | -8.681 | 12.155 | 1.00 19.45 | C |
| ATOM | 55 | CG | GLN | A | 21 | -14.491 | -7.766 | 12.930 | 1.00 22.82 | C |
| ATOM | 56 | CD | GLN | A | 21 | -15.386 | -8.523 | 13.879 | 1.00 23.52 | C |
| ATOM | 57 | OE1 | GLN | A | 21 | -15.900 | -9.594 | 13.553 | 1.00 29.23 | O |
| ATOM | 58 | NE2 | GLN | A | 21 | -15.579 | -7.969 | 15.075 | 1.00 29.79 | N |
| ATOM | 59 | C | GLN | A | 21 | -11.560 | -8.977 | 10.670 | 1.00 18.23 | C |
| ATOM | 60 | O | GLN | A | 21 | -10.966 | -9.866 | 11.283 | 1.00 18.32 | O |
| ATOM | 61 | N | GLY | A | 22 | -11.535 | -8.876 | 9.340 | 1.00 17.03 | N |
| ATOM | 62 | CA | GLY | A | 22 | -10.794 | -9.833 | 8.506 | 1.00 14.82 | C |
| ATOM | 63 | C | GLY | A | 22 | -9.298 | -9.850 | 8.766 | 1.00 14.31 | C |
| ATOM | 64 | O | GLY | A | 22 | -8.685 | -8.813 | 9.056 | 1.00 13.33 | O |
| ATOM | 65 | N | GLU | A | 23 | -8.716 | -11.039 | 8.662 | 1.00 13.57 | N |
| ATOM | 66 | CA | GLU | A | 23 | -7.276 | -11.238 | 8.755 | 1.00 14.73 | C |
| ATOM | 67 | CB | GLU | A | 23 | -6.991 | -12.720 | 9.052 | 1.00 14.80 | C |
| ATOM | 68 | CG | GLU | A | 23 | -5.504 | -13.035 | 9.220 | 1.00 18.49 | C |
| ATOM | 69 | CD | GLU | A | 23 | -5.201 | -14.528 | 9.396 | 1.00 19.27 | C |
| ATOM | 70 | OE1 | GLU | A | 23 | -6.120 | -15.367 | 9.391 | 1.00 24.89 | O |
| ATOM | 71 | OE2 | GLU | A | 23 | -4.012 | -14.868 | 9.551 | 1.00 26.29 | O |
| ATOM | 72 | C | GLU | A | 23 | -6.583 | -10.836 | 7.442 | 1.00 13.53 | C |
| ATOM | 73 | O | GLU | A | 23 | -7.005 | -11.254 | 6.370 | 1.00 12.11 | O |
| ATOM | 74 | N | ASP | A | 24 | -5.521 | -10.021 | 7.529 | 1.00 12.59 | N |
| ATOM | 75 | CA | ASP | A | 24 | -4.725 | -9.665 | 6.352 | 1.00 11.86 | C |
| ATOM | 76 | CB | ASP | A | 24 | -3.932 | -8.373 | 6.634 | 1.00 12.57 | C |
| ATOM | 77 | CG | ASP | A | 24 | -3.113 | -7.886 | 5.447 | 1.00 13.41 | C |
| ATOM | 78 | OD1 | ASP | A | 24 | -3.024 | -8.579 | 4.403 | 1.00 14.79 | O |
| ATOM | 79 | OD2 | ASP | A | 24 | -2.563 | -6.751 | 5.554 | 1.00 13.74 | O |
| ATOM | 80 | C | ASP | A | 24 | -3.798 | -10.836 | 6.020 | 1.00 12.11 | C |
| ATOM | 81 | O | ASP | A | 24 | -2.869 | -11.137 | 6.771 | 1.00 11.78 | O |
| ATOM | 82 | N | ILE | A | 25 | -4.062 | -11.508 | 4.902 | 1.00 10.96 | N |
| ATOM | 83 | CA | ILE | A | 25 | -3.270 | -12.684 | 4.534 | 1.00 12.33 | C |
| ATOM | 84 | CB | ILE | A | 25 | -4.179 | -13.907 | 4.249 | 1.00 11.60 | C |
| ATOM | 85 | CG1 | ILE | A | 25 | -5.146 | -13.577 | 3.107 | 1.00 13.10 | C |
| ATOM | 86 | CD1 | ILE | A | 25 | -5.970 | -14.795 | 2.608 | 1.00 12.24 | C |
| ATOM | 87 | CG2 | ILE | A | 25 | -4.937 | -14.305 | 5.528 | 1.00 12.59 | C |
| ATOM | 88 | C | ILE | A | 25 | -2.267 | -12.429 | 3.401 | 1.00 12.82 | C |
| ATOM | 89 | O | ILE | A | 25 | -1.683 | -13.378 | 2.841 | 1.00 12.80 | O |
| ATOM | 90 | N | THR | A | 26 | -2.058 | -11.152 | 3.069 | 1.00 13.87 | N |
| ATOM | 91 | CA | THR | A | 26 | -1.015 | -10.754 | 2.117 | 1.00 14.61 | C |
| ATOM | 92 | CB | THR | A | 26 | -1.187 | -9.319 | 1.594 | 1.00 14.25 | C |
| ATOM | 93 | OG1 | THR | A | 26 | -1.050 | -8.399 | 2.678 | 1.00 14.61 | O |
| ATOM | 94 | CG2 | THR | A | 26 | -2.566 | -9.125 | 0.911 | 1.00 13.92 | C |
| ATOM | 95 | C | THR | A | 26 | 0.352 | -10.797 | 2.788 | 1.00 16.25 | C |
| ATOM | 96 | O | THR | A | 26 | 0.479 | -10.546 | 4.002 | 1.00 16.20 | O |
| ATOM | 97 | N | SER | A | 27 | 1.369 | -11.081 | 1.984 | 1.00 17.46 | N |
| ATOM | 98 | CA | SER | A | 27 | 2.753 | -11.063 | 2.455 | 1.00 19.53 | C |
| ATOM | 99 | CB | SER | A | 27 | 3.671 | -11.608 | 1.362 | 1.00 19.15 | C |
| ATOM | 100 | OG | SER | A | 27 | 3.373 | -12.969 | 1.111 | 1.00 25.28 | O |
| ATOM | 101 | C | SER | A | 27 | 3.189 | -9.653 | 2.845 | 1.00 19.75 | C |
| ATOM | 102 | O | SER | A | 27 | 3.898 | -9.450 | 3.839 | 1.00 20.12 | O |
| ATOM | 103 | N | LYS | A | 28 | 2.777 | -8.684 | 2.038 | 1.00 19.81 | N |
| ATOM | 104 | CA | LYS | A | 28 | 3.176 | -7.294 | 2.224 | 1.00 20.73 | C |
| ATOM | 105 | CB | LYS | A | 28 | 2.979 | -6.528 | 0.921 | 1.00 21.10 | C |
| ATOM | 106 | CG | LYS | A | 28 | 4.040 | -6.846 | -0.126 | 1.00 23.68 | C |
| ATOM | 107 | CD | LYS | A | 28 | 3.615 | -6.372 | -1.513 | 1.00 25.98 | C |
| ATOM | 108 | CE | LYS | A | 28 | 4.629 | -6.808 | -2.571 | 1.00 29.63 | C |
| ATOM | 109 | NZ | LYS | A | 28 | 4.457 | -8.231 | -3.019 | 1.00 33.72 | N |

Figure 9 (cont.)

| | | | | | | | | | | |
|---|---|---|---|---|---|---|---|---|---|---|
| ATOM | 110 | C | LYS | A | 28 | 2.436 | -6.606 | 3.368 | 1.00 20.63 | C |
| ATOM | 111 | O | LYS | A | 28 | 2.811 | -5.498 | 3.773 | 1.00 20.75 | O |
| ATOM | 112 | N | LYS | A | 29 | 1.398 | -7.273 | 3.893 | 1.00 19.55 | N |
| ATOM | 113 | CA | LYS | A | 29 | 0.507 | -6.709 | 4.913 | 1.00 19.57 | C |
| ATOM | 114 | CB | LYS | A | 29 | 1.170 | -6.667 | 6.314 | 1.00 20.09 | C |
| ATOM | 115 | CG | LYS | A | 29 | 1.607 | -8.031 | 6.884 | 1.00 19.51 | C |
| ATOM | 116 | CD | LYS | A | 29 | 0.412 | -8.933 | 7.150 | 1.00 21.14 | C |
| ATOM | 117 | CE | LYS | A | 29 | 0.822 | -10.307 | 7.675 | 1.00 23.49 | C |
| ATOM | 118 | NZ | LYS | A | 29 | 0.116 | -11.424 | 6.949 | 1.00 26.27 | N |
| ATOM | 119 | C | LYS | A | 29 | -0.066 | -5.349 | 4.494 | 1.00 19.29 | C |
| ATOM | 120 | O | LYS | A | 29 | -0.015 | -4.376 | 5.271 | 1.00 20.45 | O |
| ATOM | 121 | N | ASP | A | 30 | -0.625 | -5.302 | 3.275 | 1.00 17.91 | N |
| ATOM | 122 | CA | ASP | A | 30 | -1.192 | -4.086 | 2.681 | 1.00 16.78 | C |
| ATOM | 123 | CB | ASP | A | 30 | -0.635 | -3.858 | 1.266 | 1.00 17.45 | C |
| ATOM | 124 | CG | ASP | A | 30 | -0.885 | -5.032 | 0.335 | 1.00 16.86 | C |
| ATOM | 125 | OD1 | ASP | A | 30 | -0.234 | -5.078 | -0.733 | 1.00 17.96 | O |
| ATOM | 126 | OD2 | ASP | A | 30 | -1.720 | -5.909 | 0.668 | 1.00 14.58 | O |
| ATOM | 127 | C | ASP | A | 30 | -2.730 | -4.113 | 2.660 | 1.00 15.96 | C |
| ATOM | 128 | O | ASP | A | 30 | -3.376 | -3.284 | 2.011 | 1.00 16.09 | O |
| ATOM | 129 | N | ARG | A | 31 | -3.284 | -5.099 | 3.369 | 1.00 14.31 | N |
| ATOM | 130 | CA | ARG | A | 31 | -4.715 | -5.345 | 3.492 | 1.00 13.85 | C |
| ATOM | 131 | CB | ARG | A | 31 | -5.391 | -4.225 | 4.307 | 1.00 13.80 | C |
| ATOM | 132 | CG | ARG | A | 31 | -5.003 | -4.253 | 5.798 | 1.00 12.88 | C |
| ATOM | 133 | CD | ARG | A | 31 | -5.582 | -3.047 | 6.561 | 1.00 15.01 | C |
| ATOM | 134 | NE | ARG | A | 31 | -7.017 | -2.943 | 6.356 | 1.00 16.11 | N |
| ATOM | 135 | CZ | ARG | A | 31 | -7.921 | -3.627 | 7.052 | 1.00 14.10 | C |
| ATOM | 136 | NH1 | ARG | A | 31 | -7.545 | -4.476 | 8.001 | 1.00 16.97 | N |
| ATOM | 137 | NH2 | ARG | A | 31 | -9.200 | -3.455 | 6.782 | 1.00 16.27 | N |
| ATOM | 138 | C | ARG | A | 31 | -5.405 | -5.603 | 2.136 | 1.00 12.86 | C |
| ATOM | 139 | O | ARG | A | 31 | -6.630 | -5.463 | 2.015 | 1.00 12.76 | O |
| ATOM | 140 | N | GLY | A | 32 | -4.617 | -6.032 | 1.148 | 1.00 11.67 | N |
| ATOM | 141 | CA | GLY | A | 32 | -5.131 | -6.254 | -0.214 | 1.00 11.15 | C |
| ATOM | 142 | C | GLY | A | 32 | -6.033 | -7.475 | -0.333 | 1.00 10.24 | C |
| ATOM | 143 | O | GLY | A | 32 | -6.854 | -7.577 | -1.252 | 1.00 11.05 | O |
| ATOM | 144 | N | VAL | A | 33 | -5.872 | -8.408 | 0.603 | 1.00 9.60 | N |
| ATOM | 145 | CA | VAL | A | 33 | -6.678 | -9.628 | 0.657 | 1.00 8.72 | C |
| ATOM | 146 | CB | VAL | A | 33 | -5.922 | -10.857 | 0.095 | 1.00 9.32 | C |
| ATOM | 147 | CG1 | VAL | A | 33 | -6.805 | -12.106 | 0.126 | 1.00 8.44 | C |
| ATOM | 148 | CG2 | VAL | A | 33 | -5.414 | -10.602 | -1.321 | 1.00 9.62 | C |
| ATOM | 149 | C | VAL | A | 33 | -6.971 | -9.889 | 2.125 | 1.00 8.90 | C |
| ATOM | 150 | O | VAL | A | 33 | -6.061 | -10.143 | 2.921 | 1.00 8.23 | O |
| ATOM | 151 | N | LEU | A | 34 | -8.251 | -9.836 | 2.468 | 1.00 8.85 | N |
| ATOM | 152 | CA | LEU | A | 34 | -8.690 | -9.956 | 3.849 | 1.00 8.65 | C |
| ATOM | 153 | CB | LEU | A | 34 | -9.438 | -8.680 | 4.271 | 1.00 7.78 | C |
| ATOM | 154 | CG | LEU | A | 34 | -8.658 | -7.359 | 4.246 | 1.00 9.38 | C |
| ATOM | 155 | CD1 | LEU | A | 34 | -9.587 | -6.178 | 4.498 | 1.00 10.37 | C |
| ATOM | 156 | CD2 | LEU | A | 34 | -7.544 | -7.407 | 5.314 | 1.00 11.09 | C |
| ATOM | 157 | C | LEU | A | 34 | -9.616 | -11.155 | 3.970 | 1.00 8.01 | C |
| ATOM | 158 | O | LEU | A | 34 | -10.468 | -11.367 | 3.099 | 1.00 8.23 | O |
| ATOM | 159 | N | LYS | A | 35 | -9.479 | -11.901 | 5.068 | 1.00 8.32 | N |
| ATOM | 160 | CA | LYS | A | 35 | -10.145 | -13.191 | 5.220 | 1.00 9.14 | C |
| ATOM | 161 | CB | LYS | A | 35 | -9.126 | -14.335 | 5.119 | 1.00 8.42 | C |
| ATOM | 162 | CG | LYS | A | 35 | -9.744 | -15.715 | 5.147 | 1.00 10.12 | C |
| ATOM | 163 | CD | LYS | A | 35 | -8.685 | -16.817 | 5.138 | 1.00 9.55 | C |
| ATOM | 164 | CE | LYS | A | 35 | -9.353 | -18.176 | 5.213 | 1.00 8.91 | C |
| ATOM | 165 | NZ | LYS | A | 35 | -8.373 | -19.303 | 5.489 | 1.00 8.05 | N |

Figure 9 (cont.)

| ATOM | 166 | C | LYS | A | 35 | -10.874 | -13.339 | 6.551 | 1.00 | 9.53 | C |
|---|---|---|---|---|---|---|---|---|---|---|---|
| ATOM | 167 | O | LYS | A | 35 | -10.319 | -13.034 | 7.602 | 1.00 | 10.09 | O |
| ATOM | 168 | N | ILE | A | 36 | -12.091 | -13.865 | 6.495 | 1.00 | 9.01 | N |
| ATOM | 169 | CA | ILE | A | 36 | -12.753 | -14.379 | 7.687 | 1.00 | 10.32 | C |
| ATOM | 170 | CB | ILE | A | 36 | -14.030 | -13.568 | 8.063 | 1.00 | 10.26 | C |
| ATOM | 171 | CG1 | ILE | A | 36 | -13.666 | -12.155 | 8.539 | 1.00 | 11.43 | C |
| ATOM | 172 | CD1 | ILE | A | 36 | -14.902 | -11.264 | 8.744 | 1.00 | 12.37 | C |
| ATOM | 173 | CG2 | ILE | A | 36 | -14.800 | -14.290 | 9.178 | 1.00 | 11.48 | C |
| ATOM | 174 | C | ILE | A | 36 | -13.144 | -15.837 | 7.456 | 1.00 | 9.37 | C |
| ATOM | 175 | O | ILE | A | 36 | -13.762 | -16.163 | 6.441 | 1.00 | 8.59 | O |
| ATOM | 176 | N | VAL | A | 37 | -12.778 | -16.729 | 8.380 | 1.00 | 9.41 | N |
| ATOM | 177 | CA | VAL | A | 37 | -13.275 | -18.113 | 8.310 | 1.00 | 8.86 | C |
| ATOM | 178 | CB | VAL | A | 37 | -12.397 | -19.126 | 9.133 | 1.00 | 8.62 | C |
| ATOM | 179 | CG1 | VAL | A | 37 | -13.016 | -20.515 | 9.141 | 1.00 | 10.00 | C |
| ATOM | 180 | CG2 | VAL | A | 37 | -10.984 | -19.152 | 8.555 | 1.00 | 9.35 | C |
| ATOM | 181 | C | VAL | A | 37 | -14.714 | -18.144 | 8.802 | 1.00 | 9.20 | C |
| ATOM | 182 | O | VAL | A | 37 | -15.005 | -17.662 | 9.908 | 1.00 | 9.18 | O |
| ATOM | 183 | N | LYS | A | 38 | -15.596 | -18.688 | 7.966 | 1.00 | 8.57 | N |
| ATOM | 184 | CA | LYS | A | 38 | -17.048 | -18.794 | 8.250 | 1.00 | 10.15 | C |
| ATOM | 185 | CB | LYS | A | 38 | -17.902 | -18.301 | 7.065 | 1.00 | 9.13 | C |
| ATOM | 186 | CG | LYS | A | 38 | -17.735 | -16.812 | 6.670 | 1.00 | 8.99 | C |
| ATOM | 187 | CD | LYS | A | 38 | -17.900 | -15.857 | 7.853 | 1.00 | 8.54 | C |
| ATOM | 188 | CE | LYS | A | 38 | -19.324 | -15.833 | 8.383 | 1.00 | 12.25 | C |
| ATOM | 189 | NZ | LYS | A | 38 | -19.439 | -14.903 | 9.550 | 1.00 | 12.72 | N |
| ATOM | 190 | C | LYS | A | 38 | -17.472 | -20.206 | 8.672 | 1.00 | 11.19 | C |
| ATOM | 191 | O | LYS | A | 38 | -18.486 | -20.379 | 9.389 | 1.00 | 12.27 | O |
| ATOM | 192 | N | ARG | A | 39 | -16.712 | -21.211 | 8.234 | 1.00 | 11.12 | N |
| ATOM | 193 | CA | ARG | A | 39 | -16.914 | -22.594 | 8.639 | 1.00 | 11.42 | C |
| ATOM | 194 | CB | ARG | A | 39 | -17.772 | -23.379 | 7.652 | 1.00 | 11.68 | C |
| ATOM | 195 | CG | ARG | A | 39 | -18.036 | -24.810 | 8.136 | 1.00 | 13.38 | C |
| ATOM | 196 | CD | ARG | A | 39 | -18.931 | -25.557 | 7.209 | 1.00 | 16.40 | C |
| ATOM | 197 | NE | ARG | A | 39 | -20.290 | -25.016 | 7.258 | 1.00 | 18.94 | N |
| ATOM | 198 | CZ | ARG | A | 39 | -21.214 | -25.265 | 6.337 | 1.00 | 19.26 | C |
| ATOM | 199 | NH1 | ARG | A | 39 | -20.915 | -26.027 | 5.290 | 1.00 | 19.47 | N |
| ATOM | 200 | NH2 | ARG | A | 39 | -22.429 | -24.756 | 6.471 | 1.00 | 20.22 | N |
| ATOM | 201 | C | ARG | A | 39 | -15.534 | -23.211 | 8.709 | 1.00 | 11.42 | C |
| ATOM | 202 | O | ARG | A | 39 | -14.779 | -23.187 | 7.743 | 1.00 | 10.08 | O |
| ATOM | 203 | N | VAL | A | 40 | -15.210 | -23.748 | 9.870 | 1.00 | 11.65 | N |
| ATOM | 204 | CA | VAL | A | 40 | -13.935 | -24.435 | 10.075 | 1.00 | 12.21 | C |
| ATOM | 205 | CB | VAL | A | 40 | -13.699 | -24.682 | 11.605 | 1.00 | 12.13 | C |
| ATOM | 206 | CG1 | VAL | A | 40 | -12.554 | -25.641 | 11.829 | 1.00 | 12.54 | C |
| ATOM | 207 | CG2 | VAL | A | 40 | -13.457 | -23.359 | 12.311 | 1.00 | 13.45 | C |
| ATOM | 208 | C | VAL | A | 40 | -13.890 | -25.736 | 9.291 | 1.00 | 12.64 | C |
| ATOM | 209 | O | VAL | A | 40 | -14.850 | -26.514 | 9.282 | 1.00 | 12.82 | O |
| ATOM | 210 | N | GLY | A | 41 | -12.764 | -25.967 | 8.615 | 1.00 | 13.11 | N |
| ATOM | 211 | CA | GLY | A | 41 | -12.600 | -27.138 | 7.782 | 1.00 | 14.31 | C |
| ATOM | 212 | C | GLY | A | 41 | -12.150 | -28.384 | 8.537 | 1.00 | 16.37 | C |
| ATOM | 213 | O | GLY | A | 41 | -12.103 | -28.398 | 9.781 | 1.00 | 16.78 | O |
| ATOM | 214 | N | ASN | A | 42 | -11.826 | -29.410 | 7.760 | 1.00 | 16.66 | N |
| ATOM | 215 | CA | ASN | A | 42 | -11.415 | -30.725 | 8.244 | 1.00 | 18.25 | C |
| ATOM | 216 | CB | ASN | A | 42 | -12.107 | -31.819 | 7.414 | 1.00 | 18.99 | C |
| ATOM | 217 | CG | ASN | A | 42 | -13.613 | -31.717 | 7.457 | 1.00 | 22.34 | C |
| ATOM | 218 | OD1 | ASN | A | 42 | -14.221 | -31.748 | 8.534 | 1.00 | 28.49 | O |
| ATOM | 219 | ND2 | ASN | A | 42 | -14.228 | -31.611 | 6.291 | 1.00 | 24.34 | N |
| ATOM | 220 | C | ASN | A | 42 | -9.926 | -30.935 | 8.114 | 1.00 | 17.99 | C |
| ATOM | 221 | O | ASN | A | 42 | -9.266 | -30.317 | 7.263 | 1.00 | 18.25 | O |

Figure 9 (cont.)

| | | | | | | | | | | |
|---|---|---|---|---|---|---|---|---|---|---|
| ATOM | 222 | N | GLY | A | 43 | -9.395 | -31.845 | 8.930 | 1.00 17.63 | N |
| ATOM | 223 | CA | GLY | A | 43 | -7.997 | -32.257 | 8.789 | 1.00 17.36 | C |
| ATOM | 224 | C | GLY | A | 43 | -7.039 | -31.122 | 9.092 | 1.00 17.81 | C |
| ATOM | 225 | O | GLY | A | 43 | -7.375 | -30.212 | 9.858 | 1.00 18.00 | O |
| ATOM | 226 | N | GLU | A | 44 | -5.848 | -31.176 | 8.495 | 1.00 17.39 | N |
| ATOM | 227 | CA | GLU | A | 44 | -4.821 | -30.184 | 8.759 | 1.00 17.19 | C |
| ATOM | 228 | CB | GLU | A | 44 | -3.596 | -30.801 | 9.450 | 1.00 17.30 | C |
| ATOM | 229 | CG | GLU | A | 44 | -3.837 | -31.288 | 10.854 | 1.00 19.34 | C |
| ATOM | 230 | CD | GLU | A | 44 | -2.604 | -31.920 | 11.487 | 1.00 19.90 | C |
| ATOM | 231 | OE1 | GLU | A | 44 | -1.725 | -32.455 | 10.758 | 1.00 21.23 | O |
| ATOM | 232 | OE2 | GLU | A | 44 | -2.546 | -31.905 | 12.735 | 1.00 23.13 | O |
| ATOM | 233 | C | GLU | A | 44 | -4.331 | -29.509 | 7.493 | 1.00 15.64 | C |
| ATOM | 234 | O | GLU | A | 44 | -3.989 | -28.342 | 7.524 | 1.00 15.28 | O |
| ATOM | 235 | N | GLU | A | 45 | -4.275 | -30.257 | 6.398 | 1.00 14.16 | N |
| ATOM | 236 | CA | GLU | A | 45 | -3.567 | -29.812 | 5.207 | 1.00 13.96 | C |
| ATOM | 237 | CB | GLU | A | 45 | -3.367 | -30.970 | 4.230 | 1.00 15.10 | C |
| ATOM | 238 | CG | GLU | A | 45 | -2.446 | -32.066 | 4.742 | 1.00 17.48 | C |
| ATOM | 239 | CD | GLU | A | 45 | -1.967 | -32.997 | 3.631 | 1.00 21.79 | C |
| ATOM | 240 | OE1 | GLU | A | 45 | -1.441 | -34.085 | 3.957 | 1.00 25.55 | O |
| ATOM | 241 | OE2 | GLU | A | 45 | -2.119 | -32.650 | 2.432 | 1.00 24.46 | O |
| ATOM | 242 | C | GLU | A | 45 | -4.285 | -28.682 | 4.483 | 1.00 13.10 | C |
| ATOM | 243 | O | GLU | A | 45 | -5.497 | -28.615 | 4.508 | 1.00 13.72 | O |
| ATOM | 244 | N | THR | A | 46 | -3.493 | -27.820 | 3.858 | 1.00 11.84 | N |
| ATOM | 245 | CA | THR | A | 46 | -3.956 | -26.776 | 2.923 | 1.00 11.37 | C |
| ATOM | 246 | CB | THR | A | 46 | -3.650 | -25.386 | 3.508 | 1.00 11.60 | C |
| ATOM | 247 | OG1 | THR | A | 46 | -2.240 | -25.246 | 3.700 | 1.00 13.14 | O |
| ATOM | 248 | CG2 | THR | A | 46 | -4.349 | -25.206 | 4.888 | 1.00 11.84 | C |
| ATOM | 249 | C | THR | A | 46 | -3.244 | -27.057 | 1.576 | 1.00 10.76 | C |
| ATOM | 250 | O | THR | A | 46 | -2.218 | -27.724 | 1.570 | 1.00 10.45 | O |
| ATOM | 251 | N | PRO | A | 47 | -3.839 | -26.664 | 0.427 | 1.00 9.83 | N |
| ATOM | 252 | CA | PRO | A | 47 | -3.260 | -27.082 | -0.856 | 1.00 9.89 | C |
| ATOM | 253 | CB | PRO | A | 47 | -4.289 | -26.619 | -1.894 | 1.00 9.61 | C |
| ATOM | 254 | CG | PRO | A | 47 | -5.106 | -25.557 | -1.209 | 1.00 9.45 | C |
| ATOM | 255 | CD | PRO | A | 47 | -5.111 | -25.930 | 0.261 | 1.00 9.22 | C |
| ATOM | 256 | C | PRO | A | 47 | -1.893 | -26.487 | -1.197 | 1.00 9.52 | C |
| ATOM | 257 | O | PRO | A | 47 | -1.568 | -25.369 | -0.776 | 1.00 9.34 | O |
| ATOM | 258 | N | MET | A | 48 | -1.122 | -27.263 | -1.960 | 1.00 9.66 | N |
| ATOM | 259 | CA | MET | A | 48 | 0.188 | -26.853 | -2.449 | 1.00 10.01 | C |
| ATOM | 260 | CB | MET | A | 48 | 1.091 | -28.087 | -2.597 | 1.00 10.68 | C |
| ATOM | 261 | CG | MET | A | 48 | 1.324 | -28.845 | -1.321 | 1.00 12.05 | C |
| ATOM | 262 | SD | MET | A | 48 | 2.231 | -27.861 | -0.103 | 1.00 13.53 | S |
| ATOM | 263 | CE | MET | A | 48 | 2.272 | -29.025 | 1.264 | 1.00 15.06 | C |
| ATOM | 264 | C | MET | A | 48 | 0.073 | -26.189 | -3.813 | 1.00 10.39 | C |
| ATOM | 265 | O | MET | A | 48 | -0.876 | -26.463 | -4.564 | 1.00 10.51 | O |
| ATOM | 266 | N | ILE | A | 49 | 1.054 | -25.347 | -4.146 | 1.00 10.09 | N |
| ATOM | 267 | CA | ILE | A | 49 | 1.135 | -24.759 | -5.475 | 1.00 11.20 | C |
| ATOM | 268 | CB | ILE | A | 49 | 2.415 | -23.906 | -5.687 | 1.00 11.68 | C |
| ATOM | 269 | CG1 | ILE | A | 49 | 2.496 | -22.757 | -4.663 | 1.00 14.83 | C |
| ATOM | 270 | CD1 | ILE | A | 49 | 1.423 | -21.681 | -4.783 | 1.00 20.65 | C |
| ATOM | 271 | CG2 | ILE | A | 49 | 2.509 | -23.414 | -7.149 | 1.00 12.28 | C |
| ATOM | 272 | C | ILE | A | 49 | 1.090 | -25.880 | -6.495 | 1.00 11.42 | C |
| ATOM | 273 | O | ILE | A | 49 | 1.775 | -26.895 | -6.342 | 1.00 9.58 | O |
| ATOM | 274 | N | GLY | A | 50 | 0.262 | -25.696 | -7.520 | 1.00 12.14 | N |
| ATOM | 275 | CA | GLY | A | 50 | 0.058 | -26.739 | -8.519 | 1.00 13.38 | C |
| ATOM | 276 | C | GLY | A | 50 | -1.043 | -27.752 | -8.266 | 1.00 13.71 | C |
| ATOM | 277 | O | GLY | A | 50 | -1.433 | -28.489 | -9.191 | 1.00 14.54 | O |

Figure 9 (cont.)

| | | | | | | | | | | |
|---|---|---|---|---|---|---|---|---|---|---|
| ATOM | 278 | N | ASP | A | 51 | -1.557 | -27.817 | -7.033 | 1.00 12.84 | N |
| ATOM | 279 | CA | ASP | A | 51 | -2.633 | -28.742 | -6.714 | 1.00 12.98 | C |
| ATOM | 280 | CB | ASP | A | 51 | -2.977 | -28.749 | -5.217 | 1.00 11.93 | C |
| ATOM | 281 | CG | ASP | A | 51 | -2.027 | -29.604 | -4.396 | 1.00 14.40 | C |
| ATOM | 282 | OD1 | ASP | A | 51 | -1.146 | -30.273 | -4.987 | 1.00 14.36 | O |
| ATOM | 283 | OD2 | ASP | A | 51 | -2.173 | -29.604 | -3.162 | 1.00 14.03 | O |
| ATOM | 284 | C | ASP | A | 51 | -3.869 | -28.330 | -7.489 | 1.00 13.09 | C |
| ATOM | 285 | O | ASP | A | 51 | -4.096 | -27.133 | -7.678 | 1.00 13.07 | O |
| ATOM | 286 | N | LYS | A | 52 | -4.610 | -29.329 | -7.963 | 1.00 13.40 | N |
| ATOM | 287 | CA | LYS | A | 52 | -5.942 | -29.124 | -8.543 | 1.00 14.18 | C |
| ATOM | 288 | CB | LYS | A | 52 | -6.364 | -30.316 | -9.412 | 1.00 14.53 | C |
| ATOM | 289 | CG | LYS | A | 52 | -7.652 | -30.070 | -10.201 | 1.00 16.88 | C |
| ATOM | 290 | CD | LYS | A | 52 | -7.941 | -31.220 | -11.195 | 1.00 17.62 | C |
| ATOM | 291 | CE | LYS | A | 52 | -9.272 | -31.015 | -11.926 | 1.00 21.19 | C |
| ATOM | 292 | NZ | LYS | A | 52 | -9.673 | -32.157 | -12.777 | 1.00 25.11 | N |
| ATOM | 293 | C | LYS | A | 52 | -6.945 | -28.927 | -7.416 | 1.00 12.65 | C |
| ATOM | 294 | O | LYS | A | 52 | -7.141 | -29.808 | -6.596 | 1.00 13.22 | O |
| ATOM | 295 | N | VAL | A | 53 | -7.582 | -27.763 | -7.375 | 1.00 12.34 | N |
| ATOM | 296 | CA | VAL | A | 53 | -8.514 | -27.449 | -6.284 | 1.00 11.77 | C |
| ATOM | 297 | CB | VAL | A | 53 | -8.112 | -26.127 | -5.535 | 1.00 12.65 | C |
| ATOM | 298 | CG1 | VAL | A | 53 | -6.675 | -26.214 | -4.999 | 1.00 10.88 | C |
| ATOM | 299 | CG2 | VAL | A | 53 | -8.225 | -24.947 | -6.436 | 1.00 13.40 | C |
| ATOM | 300 | C | VAL | A | 53 | -9.951 | -27.384 | -6.812 | 1.00 11.52 | C |
| ATOM | 301 | O | VAL | A | 53 | -10.172 | -26.966 | -7.950 | 1.00 11.12 | O |
| ATOM | 302 | N | TYR | A | 54 | -10.896 | -27.799 | -5.984 | 1.00 11.10 | N |
| ATOM | 303 | CA | TYR | A | 54 | -12.309 | -27.864 | -6.346 | 1.00 12.08 | C |
| ATOM | 304 | CB | TYR | A | 54 | -12.830 | -29.301 | -6.225 | 1.00 13.99 | C |
| ATOM | 305 | CG | TYR | A | 54 | -12.155 | -30.303 | -7.121 | 1.00 16.82 | C |
| ATOM | 306 | CD1 | TYR | A | 54 | -12.799 | -30.789 | -8.265 | 1.00 19.95 | C |
| ATOM | 307 | CE1 | TYR | A | 54 | -12.186 | -31.722 | -9.083 | 1.00 21.32 | C |
| ATOM | 308 | CZ | TYR | A | 54 | -10.915 | -32.177 | -8.763 | 1.00 20.45 | C |
| ATOM | 309 | OH | TYR | A | 54 | -10.295 | -33.105 | -9.568 | 1.00 21.70 | O |
| ATOM | 310 | CE2 | TYR | A | 54 | -10.262 | -31.722 | -7.638 | 1.00 20.15 | C |
| ATOM | 311 | CD2 | TYR | A | 54 | -10.887 | -30.799 | -6.815 | 1.00 18.68 | C |
| ATOM | 312 | C | TYR | A | 54 | -13.076 | -26.988 | -5.372 | 1.00 11.10 | C |
| ATOM | 313 | O | TYR | A | 54 | -13.079 | -27.242 | -4.176 | 1.00 10.43 | O |
| ATOM | 314 | N | VAL | A | 55 | -13.745 | -25.954 | -5.870 | 1.00 10.57 | N |
| ATOM | 315 | CA | VAL | A | 55 | -14.482 | -25.081 | -4.951 | 1.00 9.99 | C |
| ATOM | 316 | CB | VAL | A | 55 | -13.788 | -23.692 | -4.771 | 1.00 9.86 | C |
| ATOM | 317 | CG1 | VAL | A | 55 | -12.338 | -23.874 | -4.288 | 1.00 8.75 | C |
| ATOM | 318 | CG2 | VAL | A | 55 | -13.777 | -22.898 | -6.090 | 1.00 10.67 | C |
| ATOM | 319 | C | VAL | A | 55 | -15.912 | -24.826 | -5.402 | 1.00 10.11 | C |
| ATOM | 320 | O | VAL | A | 55 | -16.222 | -24.943 | -6.574 | 1.00 10.32 | O |
| ATOM | 321 | N | HIS | A | 56 | -16.750 | -24.431 | -4.460 | 1.00 10.63 | N |
| ATOM | 322 | CA | HIS | A | 56 | -17.936 | -23.662 | -4.811 | 1.00 10.90 | C |
| ATOM | 323 | CB | HIS | A | 56 | -19.218 | -24.285 | -4.252 | 1.00 12.26 | C |
| ATOM | 324 | CG | HIS | A | 56 | -19.835 | -25.297 | -5.165 | 1.00 15.20 | C |
| ATOM | 325 | ND1 | HIS | A | 56 | -20.198 | -25.005 | -6.466 | 1.00 20.21 | N |
| ATOM | 326 | CE1 | HIS | A | 56 | -20.712 | -26.084 | -7.027 | 1.00 23.03 | C |
| ATOM | 327 | NE2 | HIS | A | 56 | -20.682 | -27.067 | -6.143 | 1.00 22.57 | N |
| ATOM | 328 | CD2 | HIS | A | 56 | -20.147 | -26.597 | -4.969 | 1.00 19.24 | C |
| ATOM | 329 | C | HIS | A | 56 | -17.722 | -22.243 | -4.290 | 1.00 10.82 | C |
| ATOM | 330 | O | HIS | A | 56 | -17.000 | -22.029 | -3.303 | 1.00 11.02 | O |
| ATOM | 331 | N | TYR | A | 57 | -18.295 | -21.267 | -4.979 | 1.00 9.40 | N |
| ATOM | 332 | CA | TYR | A | 57 | -18.104 | -19.876 | -4.582 | 1.00 8.58 | C |
| ATOM | 333 | CB | TYR | A | 57 | -16.832 | -19.280 | -5.198 | 1.00 8.40 | C |

Figure 9 (cont.)

| | | | | | | | | | | |
|---|---|---|---|---|---|---|---|---|---|---|
| ATOM | 334 | CG | TYR | A | 57 | -16.966 | -18.978 | -6.670 | 1.00 | 8.60 | C |
| ATOM | 335 | CD1 | TYR | A | 57 | -17.396 | -17.720 | -7.109 | 1.00 | 9.64 | C |
| ATOM | 336 | CE1 | TYR | A | 57 | -17.534 | -17.442 | -8.462 | 1.00 | 9.80 | C |
| ATOM | 337 | CZ | TYR | A | 57 | -17.248 | -18.414 | -9.398 | 1.00 | 9.59 | C |
| ATOM | 338 | OH | TYR | A | 57 | -17.398 | -18.103 | -10.742 | 1.00 | 11.47 | O |
| ATOM | 339 | CE2 | TYR | A | 57 | -16.800 | -19.672 | -9.000 | 1.00 | 8.47 | C |
| ATOM | 340 | CD2 | TYR | A | 57 | -16.664 | -19.947 | -7.627 | 1.00 | 6.69 | C |
| ATOM | 341 | C | TYR | A | 57 | -19.290 | -19.024 | -5.001 | 1.00 | 9.32 | C |
| ATOM | 342 | O | TYR | A | 57 | -20.008 | -19.368 | -5.955 | 1.00 | 9.56 | O |
| ATOM | 343 | N | LYS | A | 58 | -19.415 | -17.897 | -4.308 | 1.00 | 9.52 | N |
| ATOM | 344 | CA | LYS | A | 58 | -20.289 | -16.781 | -4.682 | 1.00 | 10.59 | C |
| ATOM | 345 | CB | LYS | A | 58 | -21.415 | -16.622 | -3.665 | 1.00 | 11.00 | C |
| ATOM | 346 | CG | LYS | A | 58 | -22.217 | -17.865 | -3.469 | 1.00 | 13.87 | C |
| ATOM | 347 | CD | LYS | A | 58 | -23.292 | -17.627 | -2.444 | 1.00 | 15.85 | C |
| ATOM | 348 | CE | LYS | A | 58 | -24.162 | -18.855 | -2.264 | 1.00 | 18.50 | C |
| ATOM | 349 | NZ | LYS | A | 58 | -25.439 | -18.366 | -1.626 | 1.00 | 13.58 | N |
| ATOM | 350 | C | LYS | A | 58 | -19.425 | -15.537 | -4.676 | 1.00 | 10.11 | C |
| ATOM | 351 | O | LYS | A | 58 | -18.601 | -15.357 | -3.773 | 1.00 | 10.29 | O |
| ATOM | 352 | N | GLY | A | 59 | -19.567 | -14.694 | -5.690 | 1.00 | 10.13 | N |
| ATOM | 353 | CA | GLY | A | 59 | -18.736 | -13.489 | -5.786 | 1.00 | 10.46 | C |
| ATOM | 354 | C | GLY | A | 59 | -19.577 | -12.289 | -6.190 | 1.00 | 11.38 | C |
| ATOM | 355 | O | GLY | A | 59 | -20.590 | -12.439 | -6.886 | 1.00 | 11.59 | O |
| ATOM | 356 | N | LYS | A | 60 | -19.166 | -11.105 | -5.757 | 1.00 | 11.55 | N |
| ATOM | 357 | CA | LYS | A | 60 | -19.871 | -9.890 | -6.153 | 1.00 | 13.32 | C |
| ATOM | 358 | CB | LYS | A | 60 | -21.099 | -9.658 | -5.273 | 1.00 | 13.40 | C |
| ATOM | 359 | CG | LYS | A | 60 | -20.824 | -9.542 | -3.806 | 1.00 | 13.16 | C |
| ATOM | 360 | CD | LYS | A | 60 | -22.121 | -9.169 | -3.103 | 1.00 | 19.32 | C |
| ATOM | 361 | CE | LYS | A | 60 | -21.960 | -9.167 | -1.621 | 1.00 | 20.68 | C |
| ATOM | 362 | NZ | LYS | A | 60 | -23.314 | -8.931 | -1.006 | 1.00 | 25.83 | N |
| ATOM | 363 | C | LYS | A | 60 | -18.956 | -8.692 | -6.085 | 1.00 | 15.04 | C |
| ATOM | 364 | O | LYS | A | 60 | -17.940 | -8.719 | -5.373 | 1.00 | 14.47 | O |
| ATOM | 365 | N | LEU | A | 61 | -19.308 | -7.639 | -6.822 | 1.00 | 16.95 | N |
| ATOM | 366 | CA | LEU | A | 61 | -18.598 | -6.374 | -6.662 | 1.00 | 19.87 | C |
| ATOM | 367 | CB | LEU | A | 61 | -18.988 | -5.394 | -7.771 | 1.00 | 19.94 | C |
| ATOM | 368 | CG | LEU | A | 61 | -18.821 | -5.885 | -9.209 | 1.00 | 20.61 | C |
| ATOM | 369 | CD1 | LEU | A | 61 | -17.348 | -6.086 | -9.496 | 1.00 | 21.09 | C |
| ATOM | 370 | CD2 | LEU | A | 61 | -19.441 | -4.898 | -10.212 | 1.00 | 20.79 | C |
| ATOM | 371 | C | LEU | A | 61 | -19.022 | -5.816 | -5.314 | 1.00 | 22.25 | C |
| ATOM | 372 | O | LEU | A | 61 | -20.174 | -6.008 | -4.901 | 1.00 | 22.59 | O |
| ATOM | 373 | N | SER | A | 62 | -18.102 | -5.145 | -4.624 | 1.00 | 24.58 | N |
| ATOM | 374 | CA | SER | A | 62 | -18.465 | -4.347 | -3.439 | 1.00 | 27.52 | C |
| ATOM | 375 | CB | SER | A | 62 | -17.215 | -3.775 | -2.767 | 1.00 | 27.13 | C |
| ATOM | 376 | OG | SER | A | 62 | -16.431 | -4.834 | -2.258 | 1.00 | 28.77 | O |
| ATOM | 377 | C | SER | A | 62 | -19.434 | -3.221 | -3.798 | 1.00 | 28.65 | C |
| ATOM | 378 | O | SER | A | 62 | -20.449 | -3.038 | -3.125 | 1.00 | 29.88 | O |
| ATOM | 379 | N | ASN | A | 63 | -19.109 | -2.474 | -4.856 | 1.00 | 30.43 | N |
| ATOM | 380 | CA | ASN | A | 63 | -19.958 | -1.388 | -5.375 | 1.00 | 31.31 | C |
| ATOM | 381 | CB | ASN | A | 63 | -19.106 | -0.203 | -5.849 | 1.00 | 31.70 | C |
| ATOM | 382 | CG | ASN | A | 63 | -18.387 | 0.514 | -4.715 | 1.00 | 32.89 | C |
| ATOM | 383 | OD1 | ASN | A | 63 | -17.274 | 1.030 | -4.899 | 1.00 | 33.96 | O |
| ATOM | 384 | ND2 | ASN | A | 63 | -19.019 | 0.564 | -3.539 | 1.00 | 33.97 | N |
| ATOM | 385 | C | ASN | A | 63 | -20.786 | -1.858 | -6.552 | 1.00 | 31.53 | C |
| ATOM | 386 | O | ASN | A | 63 | -20.321 | -2.671 | -7.360 | 1.00 | 31.96 | O |
| ATOM | 387 | N | GLY | A | 64 | -21.998 | -1.323 | -6.681 | 1.00 | 31.27 | N |
| ATOM | 388 | CA | GLY | A | 64 | -22.860 | -1.671 | -7.815 | 1.00 | 30.52 | C |
| ATOM | 389 | C | GLY | A | 64 | -23.483 | -3.043 | -7.643 | 1.00 | 29.69 | C |

Figure 9 (cont.)

| | | | | | | | | | | |
|---|---|---|---|---|---|---|---|---|---|---|
| ATOM | 390 | O | GLY | A | 64 | -23.451 | -3.613 | -6.542 | 1.00 30.50 | O |
| ATOM | 391 | N | LYS | A | 65 | -24.042 | -3.581 | -8.728 | 1.00 28.66 | N |
| ATOM | 392 | CA | LYS | A | 65 | -24.788 | -4.846 | -8.663 | 1.00 26.71 | C |
| ATOM | 393 | CB | LYS | A | 65 | -26.310 | -4.590 | -8.714 | 1.00 27.86 | C |
| ATOM | 394 | CG | LYS | A | 65 | -26.893 | -3.771 | -7.540 | 1.00 28.19 | C |
| ATOM | 395 | CD | LYS | A | 65 | -26.682 | -4.469 | -6.193 | 1.00 30.49 | C |
| ATOM | 396 | CE | LYS | A | 65 | -27.248 | -3.660 | -5.035 | 1.00 30.89 | C |
| ATOM | 397 | NZ | LYS | A | 65 | -27.073 | -4.391 | -3.743 | 1.00 31.64 | N |
| ATOM | 398 | C | LYS | A | 65 | -24.361 | -5.874 | -9.728 | 1.00 25.18 | C |
| ATOM | 399 | O | LYS | A | 65 | -24.908 | -5.928 | -10.843 | 1.00 24.14 | O |
| ATOM | 400 | N | LYS | A | 66 | -23.370 | -6.689 | -9.376 | 1.00 22.29 | N |
| ATOM | 401 | CA | LYS | A | 66 | -23.015 | -7.843 | -10.194 | 1.00 21.22 | C |
| ATOM | 402 | CB | LYS | A | 66 | -21.894 | -7.537 | -11.192 | 1.00 21.45 | C |
| ATOM | 403 | CG | LYS | A | 66 | -21.733 | -8.616 | -12.272 | 1.00 24.03 | C |
| ATOM | 404 | CD | LYS | A | 66 | -22.682 | -8.386 | -13.466 | 1.00 28.91 | C |
| ATOM | 405 | CE | LYS | A | 66 | -22.889 | -9.663 | -14.283 | 1.00 30.80 | C |
| ATOM | 406 | NZ | LYS | A | 66 | -23.810 | -10.652 | -13.603 | 1.00 31.69 | N |
| ATOM | 407 | C | LYS | A | 66 | -22.615 | -8.993 | -9.299 | 1.00 19.30 | C |
| ATOM | 408 | O | LYS | A | 66 | -21.730 | -8.844 | -8.454 | 1.00 18.38 | O |
| ATOM | 409 | N | PHE | A | 67 | -23.271 | -10.126 | -9.519 | 1.00 17.67 | N |
| ATOM | 410 | CA | PHE | A | 67 | -23.170 | -11.313 | -8.667 | 1.00 16.30 | C |
| ATOM | 411 | CB | PHE | A | 67 | -24.508 | -11.506 | -7.932 | 1.00 16.60 | C |
| ATOM | 412 | CG | PHE | A | 67 | -24.526 | -12.655 | -6.961 | 1.00 15.84 | C |
| ATOM | 413 | CD1 | PHE | A | 67 | -24.099 | -12.483 | -5.645 | 1.00 18.49 | C |
| ATOM | 414 | CE1 | PHE | A | 67 | -24.120 | -13.564 | -4.733 | 1.00 18.43 | C |
| ATOM | 415 | CZ | PHE | A | 67 | -24.599 | -14.798 | -5.146 | 1.00 16.47 | C |
| ATOM | 416 | CE2 | PHE | A | 67 | -25.024 | -14.978 | -6.458 | 1.00 16.61 | C |
| ATOM | 417 | CD2 | PHE | A | 67 | -24.997 | -13.906 | -7.358 | 1.00 16.88 | C |
| ATOM | 418 | C | PHE | A | 67 | -22.852 | -12.514 | -9.547 | 1.00 15.77 | C |
| ATOM | 419 | O | PHE | A | 67 | -23.385 | -12.631 | -10.653 | 1.00 15.73 | O |
| ATOM | 420 | N | ASP | A | 68 | -21.986 | -13.410 | -9.077 | 1.00 14.81 | N |
| ATOM | 421 | CA | ASP | A | 68 | -21.581 | -14.581 | -9.864 | 1.00 15.15 | C |
| ATOM | 422 | CB | ASP | A | 68 | -20.240 | -14.289 | -10.552 | 1.00 15.25 | C |
| ATOM | 423 | CG | ASP | A | 68 | -19.636 | -15.496 | -11.261 | 1.00 16.66 | C |
| ATOM | 424 | OD1 | ASP | A | 68 | -20.299 | -16.100 | -12.141 | 1.00 20.54 | O |
| ATOM | 425 | OD2 | ASP | A | 68 | -18.475 | -15.829 | -10.963 | 1.00 17.01 | O |
| ATOM | 426 | C | ASP | A | 68 | -21.474 | -15.765 | -8.903 | 1.00 15.16 | C |
| ATOM | 427 | O | ASP | A | 68 | -21.093 | -15.604 | -7.749 | 1.00 14.33 | O |
| ATOM | 428 | N | SER | A | 69 | -21.807 | -16.958 | -9.371 | 1.00 15.67 | N |
| ATOM | 429 | CA | SER | A | 69 | -21.776 | -18.110 | -8.485 | 1.00 16.70 | C |
| ATOM | 430 | CB | SER | A | 69 | -23.116 | -18.246 | -7.767 | 1.00 17.39 | C |
| ATOM | 431 | OG | SER | A | 69 | -23.105 | -19.351 | -6.897 | 1.00 20.90 | O |
| ATOM | 432 | C | SER | A | 69 | -21.482 | -19.372 | -9.270 | 1.00 17.24 | C |
| ATOM | 433 | O | SER | A | 69 | -21.864 | -19.490 | -10.425 | 1.00 17.49 | O |
| ATOM | 434 | N | SER | A | 70 | -20.771 | -20.304 | -8.655 | 1.00 17.41 | N |
| ATOM | 435 | CA | SER | A | 70 | -20.601 | -21.623 | -9.265 | 1.00 18.74 | C |
| ATOM | 436 | CB | SER | A | 70 | -19.468 | -22.356 | -8.561 | 1.00 17.89 | C |
| ATOM | 437 | OG | SER | A | 70 | -19.764 | -22.432 | -7.192 | 1.00 13.47 | O |
| ATOM | 438 | C | SER | A | 70 | -21.895 | -22.433 | -9.128 | 1.00 20.71 | C |
| ATOM | 439 | O | SER | A | 70 | -22.098 | -23.434 | -9.803 | 1.00 21.91 | O |
| ATOM | 440 | N | HIS | A | 71 | -22.776 | -22.004 | -8.237 | 1.00 24.06 | N |
| ATOM | 441 | CA | HIS | A | 71 | -23.974 | -22.778 | -7.939 | 1.00 26.66 | C |
| ATOM | 442 | CB | HIS | A | 71 | -24.569 | -22.327 | -6.611 | 1.00 27.81 | C |
| ATOM | 443 | CG | HIS | A | 71 | -23.668 | -22.571 | -5.437 | 1.00 30.53 | C |
| ATOM | 444 | ND1 | HIS | A | 71 | -23.437 | -23.832 | -4.927 | 1.00 33.13 | N |
| ATOM | 445 | CE1 | HIS | A | 71 | -22.629 | -23.741 | -3.884 | 1.00 34.51 | C |

Figure 9 (cont.)

| | | | | | | | | | |
|---|---|---|---|---|---|---|---|---|---|
| ATOM | 446 | NE2 | HIS | A | 71 | -22.317 | -22.469 | -3.709 | 1.00 34.43 | N |
| ATOM | 447 | CD2 | HIS | A | 71 | -22.951 | -21.716 | -4.669 | 1.00 33.11 | C |
| ATOM | 448 | C | HIS | A | 71 | -25.011 | -22.776 | -9.066 | 1.00 28.09 | C |
| ATOM | 449 | O | HIS | A | 71 | -25.860 | -23.678 | -9.133 | 1.00 28.84 | O |
| ATOM | 450 | N | GLU | A | 72 | -24.920 | -21.798 | -9.969 | 1.00 29.10 | N |
| ATOM | 451 | CA | GLU | A | 72 | -25.802 | -21.755 | -11.135 | 1.00 30.50 | C |
| ATOM | 452 | CB | GLU | A | 72 | -25.823 | -20.366 | -11.802 | 1.00 30.94 | C |
| ATOM | 453 | CG | GLU | A | 72 | -24.483 | -19.635 | -11.880 | 1.00 34.37 | C |
| ATOM | 454 | CD | GLU | A | 72 | -24.609 | -18.150 | -11.535 | 1.00 36.58 | C |
| ATOM | 455 | OE1 | GLU | A | 72 | -23.752 | -17.336 | -11.972 | 1.00 36.61 | O |
| ATOM | 456 | OE2 | GLU | A | 72 | -25.565 | -17.803 | -10.810 | 1.00 38.76 | O |
| ATOM | 457 | C | GLU | A | 72 | -25.512 | -22.880 | -12.142 | 1.00 29.99 | C |
| ATOM | 458 | O | GLU | A | 72 | -26.402 | -23.282 | -12.889 | 1.00 30.86 | O |
| ATOM | 459 | N | ARG | A | 73 | -24.284 | -23.393 | -12.143 | 1.00 29.23 | N |
| ATOM | 460 | CA | ARG | A | 73 | -23.956 | -24.605 | -12.899 | 1.00 28.43 | C |
| ATOM | 461 | CB | ARG | A | 73 | -22.563 | -24.521 | -13.537 | 1.00 28.61 | C |
| ATOM | 468 | C | ARG | A | 73 | -24.085 | -25.851 | -12.025 | 1.00 28.23 | C |
| ATOM | 469 | O | ARG | A | 73 | -24.106 | -26.964 | -12.545 | 1.00 28.45 | O |
| ATOM | 470 | N | ASN | A | 74 | -24.191 | -25.651 | -10.706 | 1.00 27.73 | N |
| ATOM | 471 | CA | ASN | A | 74 | -24.305 | -26.734 | -9.714 | 1.00 27.17 | C |
| ATOM | 472 | CB | ASN | A | 74 | -25.720 | -27.329 | -9.744 | 1.00 27.40 | C |
| ATOM | 473 | CG | ASN | A | 74 | -26.022 | -28.249 | -8.546 | 1.00 27.80 | C |
| ATOM | 474 | OD1 | ASN | A | 74 | -25.741 | -27.923 | -7.390 | 1.00 26.72 | O |
| ATOM | 475 | ND2 | ASN | A | 74 | -26.622 | -29.393 | -8.837 | 1.00 27.72 | N |
| ATOM | 476 | C | ASN | A | 74 | -23.218 | -27.810 | -9.880 | 1.00 26.98 | C |
| ATOM | 477 | O | ASN | A | 74 | -23.476 | -29.025 | -9.786 | 1.00 27.10 | O |
| ATOM | 478 | N | GLU | A | 75 | -22.000 | -27.335 | -10.153 | 1.00 25.68 | N |
| ATOM | 479 | CA | GLU | A | 75 | -20.811 | -28.174 | -10.206 | 1.00 24.44 | C |
| ATOM | 480 | CB | GLU | A | 75 | -20.525 | -28.658 | -11.624 | 1.00 24.90 | C |
| ATOM | 481 | CG | GLU | A | 75 | -20.136 | -27.546 | -12.567 | 1.00 27.18 | C |
| ATOM | 482 | CD | GLU | A | 75 | -19.531 | -28.051 | -13.862 | 1.00 32.23 | C |
| ATOM | 483 | OE1 | GLU | A | 75 | -18.738 | -27.300 | -14.470 | 1.00 31.34 | O |
| ATOM | 484 | OE2 | GLU | A | 75 | -19.848 | -29.197 | -14.273 | 1.00 35.54 | O |
| ATOM | 485 | C | GLU | A | 75 | -19.622 | -27.356 | -9.737 | 1.00 22.60 | C |
| ATOM | 486 | O | GLU | A | 75 | -19.601 | -26.135 | -9.914 | 1.00 22.83 | O |
| ATOM | 487 | N | PRO | A | 76 | -18.618 | -28.028 | -9.172 | 1.00 20.62 | N |
| ATOM | 488 | CA | PRO | A | 76 | -17.453 | -27.318 | -8.680 | 1.00 19.04 | C |
| ATOM | 489 | CB | PRO | A | 76 | -16.556 | -28.442 | -8.158 | 1.00 19.05 | C |
| ATOM | 490 | CG | PRO | A | 76 | -17.483 | -29.577 | -7.886 | 1.00 20.48 | C |
| ATOM | 491 | CD | PRO | A | 76 | -18.511 | -29.481 | -8.948 | 1.00 20.49 | C |
| ATOM | 492 | C | PRO | A | 76 | -16.688 | -26.487 | -9.720 | 1.00 16.67 | C |
| ATOM | 493 | O | PRO | A | 76 | -16.609 | -26.826 | -10.915 | 1.00 15.70 | O |
| ATOM | 494 | N | PHE | A | 77 | -16.103 | -25.401 | -9.229 | 1.00 14.50 | N |
| ATOM | 495 | CA | PHE | A | 77 | -15.195 | -24.593 | -10.015 | 1.00 13.21 | C |
| ATOM | 496 | CB | PHE | A | 77 | -15.299 | -23.132 | -9.570 | 1.00 13.18 | C |
| ATOM | 497 | CG | PHE | A | 77 | -14.379 | -22.209 | -10.296 | 1.00 11.69 | C |
| ATOM | 498 | CD1 | PHE | A | 77 | -14.758 | -21.629 | -11.519 | 1.00 14.84 | C |
| ATOM | 499 | CE1 | PHE | A | 77 | -13.885 | -20.763 | -12.196 | 1.00 12.17 | C |
| ATOM | 500 | CZ | PHE | A | 77 | -12.637 | -20.473 | -11.654 | 1.00 14.06 | C |
| ATOM | 501 | CE2 | PHE | A | 77 | -12.257 | -21.051 | -10.429 | 1.00 14.07 | C |
| ATOM | 502 | CD2 | PHE | A | 77 | -13.127 | -21.902 | -9.768 | 1.00 11.82 | C |
| ATOM | 503 | C | PHE | A | 77 | -13.788 | -25.138 | -9.764 | 1.00 13.06 | C |
| ATOM | 504 | O | PHE | A | 77 | -13.381 | -25.296 | -8.610 | 1.00 11.53 | O |
| ATOM | 505 | N | VAL | A | 78 | -13.065 | -25.450 | -10.834 | 1.00 13.00 | N |
| ATOM | 506 | CA | VAL | A | 78 | -11.777 | -26.154 | -10.721 | 1.00 13.68 | C |
| ATOM | 507 | CB | VAL | A | 78 | -11.821 | -27.567 | -11.398 | 1.00 14.48 | C |

Figure 9 (cont.)

| | | | | | | | | | | |
|---|---|---|---|---|---|---|---|---|---|---|
| ATOM | 508 | CG1 | VAL | A | 78 | -10.463 | -28.233 | -11.300 | 1.00 15.86 | C |
| ATOM | 509 | CG2 | VAL | A | 78 | -12.894 | -28.445 | -10.774 | 1.00 14.27 | C |
| ATOM | 510 | C | VAL | A | 78 | -10.645 | -25.336 | -11.322 | 1.00 13.57 | C |
| ATOM | 511 | O | VAL | A | 78 | -10.776 | -24.769 | -12.413 | 1.00 13.88 | O |
| ATOM | 512 | N | PHE | A | 79 | -9.527 | -25.245 | -10.600 | 1.00 12.72 | N |
| ATOM | 513 | CA | PHE | A | 79 | -8.324 | -24.613 | -11.124 | 1.00 12.27 | C |
| ATOM | 514 | CB | PHE | A | 79 | -8.379 | -23.080 | -11.027 | 1.00 12.45 | C |
| ATOM | 515 | CG | PHE | A | 79 | -8.319 | -22.547 | -9.619 | 1.00 12.08 | C |
| ATOM | 516 | CD1 | PHE | A | 79 | -7.135 | -21.979 | -9.131 | 1.00 13.32 | C |
| ATOM | 517 | CE1 | PHE | A | 79 | -7.058 | -21.479 | -7.810 | 1.00 11.69 | C |
| ATOM | 518 | CZ | PHE | A | 79 | -8.188 | -21.565 | -6.990 | 1.00 12.26 | C |
| ATOM | 519 | CE2 | PHE | A | 79 | -9.373 | -22.129 | -7.485 | 1.00 11.66 | C |
| ATOM | 520 | CD2 | PHE | A | 79 | -9.435 | -22.617 | -8.782 | 1.00 11.32 | C |
| ATOM | 521 | C | PHE | A | 79 | -7.083 | -25.194 | -10.427 | 1.00 12.39 | C |
| ATOM | 522 | O | PHE | A | 79 | -7.207 | -25.971 | -9.462 | 1.00 13.01 | O |
| ATOM | 523 | N | SER | A | 80 | -5.922 | -24.854 | -10.968 | 1.00 12.76 | N |
| ATOM | 524 | CA | SER | A | 80 | -4.630 | -25.279 | -10.419 | 1.00 12.92 | C |
| ATOM | 525 | CB | SER | A | 80 | -3.666 | -25.639 | -11.545 | 1.00 14.12 | C |
| ATOM | 526 | OG | SER | A | 80 | -4.179 | -26.769 | -12.229 | 1.00 19.12 | O |
| ATOM | 527 | C | SER | A | 80 | -4.100 | -24.127 | -9.581 | 1.00 11.82 | C |
| ATOM | 528 | O | SER | A | 80 | -3.958 | -22.986 | -10.052 | 1.00 12.95 | O |
| ATOM | 529 | N | LEU | A | 81 | -3.817 | -24.419 | -8.323 | 1.00 11.68 | N |
| ATOM | 530 | CA | LEU | A | 81 | -3.504 | -23.355 | -7.360 | 1.00 11.99 | C |
| ATOM | 531 | CB | LEU | A | 81 | -3.545 | -23.906 | -5.924 | 1.00 10.94 | C |
| ATOM | 532 | CG | LEU | A | 81 | -3.221 | -22.902 | -4.812 | 1.00 11.76 | C |
| ATOM | 533 | CD1 | LEU | A | 81 | -4.366 | -21.867 | -4.656 | 1.00 13.14 | C |
| ATOM | 534 | CD2 | LEU | A | 81 | -2.925 | -23.622 | -3.494 | 1.00 12.08 | C |
| ATOM | 535 | C | LEU | A | 81 | -2.158 | -22.690 | -7.606 | 1.00 11.88 | C |
| ATOM | 536 | O | LEU | A | 81 | -1.162 | -23.372 | -7.836 | 1.00 12.63 | O |
| ATOM | 537 | N | GLY | A | 82 | -2.137 | -21.363 | -7.517 | 1.00 13.12 | N |
| ATOM | 538 | CA | GLY | A | 82 | -0.896 | -20.585 | -7.396 | 1.00 14.98 | C |
| ATOM | 539 | C | GLY | A | 82 | -0.201 | -20.354 | -8.718 | 1.00 16.82 | C |
| ATOM | 540 | O | GLY | A | 82 | 0.941 | -19.850 | -8.742 | 1.00 17.45 | O |
| ATOM | 541 | N | LYS | A | 83 | -0.911 | -20.664 | -9.808 | 1.00 16.82 | N |
| ATOM | 542 | CA | LYS | A | 83 | -0.350 | -20.590 | -11.164 | 1.00 18.04 | C |
| ATOM | 543 | CB | LYS | A | 83 | -0.471 | -21.958 | -11.852 | 1.00 18.38 | C |
| ATOM | 544 | CG | LYS | A | 83 | 0.345 | -23.083 | -11.196 | 1.00 20.21 | C |
| ATOM | 545 | CD | LYS | A | 83 | 1.777 | -22.642 | -10.827 | 1.00 23.72 | C |
| ATOM | 546 | CE | LYS | A | 83 | 2.829 | -23.253 | -11.742 | 1.00 26.64 | C |
| ATOM | 547 | NZ | LYS | A | 83 | 4.220 | -23.105 | -11.165 | 1.00 27.14 | N |
| ATOM | 548 | C | LYS | A | 83 | -0.939 | -19.479 | -12.047 | 1.00 17.81 | C |
| ATOM | 549 | O | LYS | A | 83 | -0.761 | -19.496 | -13.276 | 1.00 18.31 | O |
| ATOM | 550 | N | GLY | A | 84 | -1.622 | -18.517 | -11.426 | 1.00 17.08 | N |
| ATOM | 551 | CA | GLY | A | 84 | -2.221 | -17.406 | -12.160 | 1.00 16.72 | C |
| ATOM | 552 | C | GLY | A | 84 | -3.344 | -17.805 | -13.117 | 1.00 16.24 | C |
| ATOM | 553 | O | GLY | A | 84 | -3.522 | -17.188 | -14.175 | 1.00 18.51 | O |
| ATOM | 554 | N | GLN | A | 85 | -4.119 | -18.811 | -12.752 | 1.00 14.74 | N |
| ATOM | 555 | CA | GLN | A | 85 | -5.300 | -19.183 | -13.541 | 1.00 13.70 | C |
| ATOM | 556 | CB | GLN | A | 85 | -5.584 | -20.664 | -13.407 | 1.00 14.27 | C |
| ATOM | 557 | CG | GLN | A | 85 | -4.502 | -21.505 | -14.066 | 1.00 15.26 | C |
| ATOM | 558 | CD | GLN | A | 85 | -4.776 | -22.984 | -14.033 | 1.00 17.10 | C |
| ATOM | 559 | OE1 | GLN | A | 85 | -5.796 | -23.452 | -13.508 | 1.00 16.74 | O |
| ATOM | 560 | NE2 | GLN | A | 85 | -3.857 | -23.747 | -14.619 | 1.00 19.86 | N |
| ATOM | 561 | C | GLN | A | 85 | -6.498 | -18.371 | -13.091 | 1.00 12.98 | C |
| ATOM | 562 | O | GLN | A | 85 | -7.551 | -18.378 | -13.737 | 1.00 12.62 | O |
| ATOM | 563 | N | VAL | A | 86 | -6.332 | -17.730 | -11.938 | 1.00 12.32 | N |

Figure 9 (cont.)

| | | | | | | | | | | |
|---|---|---|---|---|---|---|---|---|---|---|
| ATOM | 564 | CA | VAL | A | 86 | -7.362 | -16.910 | -11.307 | 1.00 11.14 | C |
| ATOM | 565 | CB | VAL | A | 86 | -8.099 | -17.687 | -10.170 | 1.00 11.56 | C |
| ATOM | 566 | CG1 | VAL | A | 86 | -8.954 | -18.816 | -10.755 | 1.00 9.12 | C |
| ATOM | 567 | CG2 | VAL | A | 86 | -7.099 | -18.247 | -9.144 | 1.00 10.88 | C |
| ATOM | 568 | C | VAL | A | 86 | -6.692 | -15.646 | -10.757 | 1.00 11.51 | C |
| ATOM | 569 | O | VAL | A | 86 | -5.458 | -15.555 | -10.711 | 1.00 11.07 | O |
| ATOM | 570 | N | ILE | A | 87 | -7.491 | -14.666 | -10.347 | 1.00 10.93 | N |
| ATOM | 571 | CA | ILE | A | 87 | -6.929 | -13.428 | -9.779 | 1.00 10.65 | C |
| ATOM | 572 | CB | ILE | A | 87 | -8.025 | -12.396 | -9.410 | 1.00 10.49 | C |
| ATOM | 573 | CG1 | ILE | A | 87 | -9.007 | -12.992 | -8.385 | 1.00 9.55 | C |
| ATOM | 574 | CD1 | ILE | A | 87 | -9.938 | -11.967 | -7.716 | 1.00 11.08 | C |
| ATOM | 575 | CG2 | ILE | A | 87 | -8.734 | -11.881 | -10.695 | 1.00 11.63 | C |
| ATOM | 576 | C | ILE | A | 87 | -6.018 | -13.722 | -8.576 | 1.00 10.12 | C |
| ATOM | 577 | O | ILE | A | 87 | -6.176 | -14.742 | -7.881 | 1.00 8.95 | O |
| ATOM | 578 | N | LYS | A | 88 | -5.041 | -12.844 | -8.351 | 1.00 10.74 | N |
| ATOM | 579 | CA | LYS | A | 88 | -4.052 | -13.072 | -7.290 | 1.00 10.42 | C |
| ATOM | 580 | CB | LYS | A | 88 | -3.085 | -11.883 | -7.191 | 1.00 11.71 | C |
| ATOM | 581 | CG | LYS | A | 88 | -1.903 | -12.132 | -6.255 | 1.00 16.31 | C |
| ATOM | 582 | CD | LYS | A | 88 | -0.736 | -12.840 | -6.960 | 1.00 23.15 | C |
| ATOM | 583 | CE | LYS | A | 88 | 0.131 | -13.620 | -5.978 | 1.00 25.43 | C |
| ATOM | 584 | NZ | LYS | A | 88 | -0.537 | -14.902 | -5.632 | 1.00 26.65 | N |
| ATOM | 585 | C | LYS | A | 88 | -4.685 | -13.345 | -5.926 | 1.00 9.74 | C |
| ATOM | 586 | O | LYS | A | 88 | -4.214 | -14.210 | -5.185 | 1.00 8.94 | O |
| ATOM | 587 | N | ALA | A | 89 | -5.738 | -12.609 | -5.587 | 1.00 9.66 | N |
| ATOM | 588 | CA | ALA | A | 89 | -6.422 | -12.800 | -4.292 | 1.00 8.81 | C |
| ATOM | 589 | CB | ALA | A | 89 | -7.603 | -11.847 | -4.167 | 1.00 9.15 | C |
| ATOM | 590 | C | ALA | A | 89 | -6.876 | -14.241 | -4.065 | 1.00 8.72 | C |
| ATOM | 591 | O | ALA | A | 89 | -6.900 | -14.723 | -2.935 | 1.00 7.96 | O |
| ATOM | 592 | N | TRP | A | 90 | -7.279 | -14.906 | -5.146 | 1.00 7.98 | N |
| ATOM | 593 | CA | TRP | A | 90 | -7.713 | -16.293 | -5.062 | 1.00 7.58 | C |
| ATOM | 594 | CB | TRP | A | 90 | -8.559 | -16.671 | -6.297 | 1.00 7.69 | C |
| ATOM | 595 | CG | TRP | A | 90 | -10.052 | -16.555 | -6.068 | 1.00 7.33 | C |
| ATOM | 596 | CD1 | TRP | A | 90 | -10.757 | -15.445 | -5.626 | 1.00 7.93 | C |
| ATOM | 597 | NE1 | TRP | A | 90 | -12.101 | -15.739 | -5.554 | 1.00 6.25 | N |
| ATOM | 598 | CE2 | TRP | A | 90 | -12.289 | -17.045 | -5.954 | 1.00 8.49 | C |
| ATOM | 599 | CD2 | TRP | A | 90 | -11.016 | -17.584 | -6.279 | 1.00 6.96 | C |
| ATOM | 600 | CE3 | TRP | A | 90 | -10.931 | -18.921 | -6.715 | 1.00 8.39 | C |
| ATOM | 601 | CZ3 | TRP | A | 90 | -12.117 | -19.674 | -6.822 | 1.00 7.70 | C |
| ATOM | 602 | CH2 | TRP | A | 90 | -13.367 | -19.107 | -6.485 | 1.00 8.85 | C |
| ATOM | 603 | CZ2 | TRP | A | 90 | -13.473 | -17.796 | -6.063 | 1.00 9.98 | C |
| ATOM | 604 | C | TRP | A | 90 | -6.560 | -17.256 | -4.858 | 1.00 8.09 | C |
| ATOM | 605 | O | TRP | A | 90 | -6.646 | -18.171 | -4.042 | 1.00 7.45 | O |
| ATOM | 606 | N | ASP | A | 91 | -5.465 | -17.064 | -5.582 | 1.00 8.56 | N |
| ATOM | 607 | CA | ASP | A | 91 | -4.274 | -17.893 | -5.348 | 1.00 9.08 | C |
| ATOM | 608 | CB | ASP | A | 91 | -3.171 | -17.538 | -6.354 | 1.00 8.44 | C |
| ATOM | 609 | CG | ASP | A | 91 | -3.316 | -18.269 | -7.687 | 1.00 9.60 | C |
| ATOM | 610 | OD1 | ASP | A | 91 | -4.034 | -19.285 | -7.756 | 1.00 8.84 | O |
| ATOM | 611 | OD2 | ASP | A | 91 | -2.662 | -17.823 | -8.673 | 1.00 11.17 | O |
| ATOM | 612 | C | ASP | A | 91 | -3.749 | -17.775 | -3.898 | 1.00 8.70 | C |
| ATOM | 613 | O | ASP | A | 91 | -3.348 | -18.772 | -3.272 | 1.00 9.17 | O |
| ATOM | 614 | N | ILE | A | 92 | -3.792 | -16.554 | -3.371 | 1.00 9.33 | N |
| ATOM | 615 | CA | ILE | A | 92 | -3.416 | -16.268 | -1.985 | 1.00 8.40 | C |
| ATOM | 616 | CB | ILE | A | 92 | -3.298 | -14.727 | -1.781 | 1.00 8.64 | C |
| ATOM | 617 | CG1 | ILE | A | 92 | -2.086 | -14.163 | -2.552 | 1.00 7.53 | C |
| ATOM | 618 | CD1 | ILE | A | 92 | -2.043 | -12.601 | -2.515 | 1.00 9.09 | C |
| ATOM | 619 | CG2 | ILE | A | 92 | -3.186 | -14.370 | -0.304 | 1.00 9.13 | C |

Figure 9 (cont.)

| | | | | | | | | | | |
|---|---|---|---|---|---|---|---|---|---|---|
| ATOM | 620 | C   | ILE | A | 92  | -4.425  | -16.869 | -0.994 | 1.00 | 8.42  | C |
| ATOM | 621 | O   | ILE | A | 92  | -4.037  | -17.551 | -0.032 | 1.00 | 8.11  | O |
| ATOM | 622 | N   | GLY | A | 93  | -5.709  | -16.618 | -1.237 | 1.00 | 7.66  | N |
| ATOM | 623 | CA  | GLY | A | 93  | -6.770  | -16.976 | -0.278 | 1.00 | 8.36  | C |
| ATOM | 624 | C   | GLY | A | 93  | -7.021  | -18.465 | -0.214 | 1.00 | 6.96  | C |
| ATOM | 625 | O   | GLY | A | 93  | -7.072  | -19.061 |  0.873 | 1.00 | 7.59  | O |
| ATOM | 626 | N   | VAL | A | 94  | -7.156  | -19.088 | -1.388 | 1.00 | 6.57  | N |
| ATOM | 627 | CA  | VAL | A | 94  | -7.452  | -20.512 | -1.430 | 1.00 | 6.90  | C |
| ATOM | 628 | CB  | VAL | A | 94  | -7.855  | -20.976 | -2.829 | 1.00 | 6.61  | C |
| ATOM | 629 | CG1 | VAL | A | 94  | -8.053  | -22.472 | -2.859 | 1.00 | 8.07  | C |
| ATOM | 630 | CG2 | VAL | A | 94  | -9.124  | -20.264 | -3.264 | 1.00 | 7.75  | C |
| ATOM | 631 | C   | VAL | A | 94  | -6.311  | -21.357 | -0.867 | 1.00 | 7.19  | C |
| ATOM | 632 | O   | VAL | A | 94  | -6.551  | -22.364 | -0.220 | 1.00 | 7.02  | O |
| ATOM | 633 | N   | ALA | A | 95  | -5.074  | -20.895 | -1.051 | 1.00 | 6.78  | N |
| ATOM | 634 | CA  | ALA | A | 95  | -3.911  | -21.561 | -0.457 | 1.00 | 8.30  | C |
| ATOM | 635 | CB  | ALA | A | 95  | -2.630  | -20.807 | -0.905 | 1.00 | 8.13  | C |
| ATOM | 636 | C   | ALA | A | 95  | -3.973  | -21.653 |  1.111 | 1.00 | 8.61  | C |
| ATOM | 637 | O   | ALA | A | 95  | -3.279  | -22.482 |  1.725 | 1.00 | 10.28 | O |
| ATOM | 638 | N   | THR | A | 96  | -4.788  | -20.806 |  1.746 | 1.00 | 7.52  | N |
| ATOM | 639 | CA  | THR | A | 96  | -4.893  | -20.786 |  3.233 | 1.00 | 8.11  | C |
| ATOM | 640 | CB  | THR | A | 96  | -5.107  | -19.347 |  3.828 | 1.00 | 8.05  | C |
| ATOM | 641 | OG1 | THR | A | 96  | -6.412  | -18.860 |  3.479 | 1.00 | 9.72  | O |
| ATOM | 642 | CG2 | THR | A | 96  | -4.037  | -18.358 |  3.352 | 1.00 | 9.01  | C |
| ATOM | 643 | C   | THR | A | 96  | -6.009  | -21.679 |  3.794 | 1.00 | 7.96  | C |
| ATOM | 644 | O   | THR | A | 96  | -6.178  | -21.777 |  5.034 | 1.00 | 7.66  | O |
| ATOM | 645 | N   | MET | A | 97  | -6.782  | -22.306 |  2.900 | 1.00 | 7.24  | N |
| ATOM | 646 | CA  | MET | A | 97  | -7.964  | -23.068 |  3.301 | 1.00 | 8.28  | C |
| ATOM | 647 | CB  | MET | A | 97  | -9.056  | -22.888 |  2.245 | 1.00 | 8.18  | C |
| ATOM | 648 | CG  | MET | A | 97  | -9.493  | -21.452 |  2.114 | 1.00 | 8.12  | C |
| ATOM | 649 | SD  | MET | A | 97  | -10.806 | -21.230 |  0.896 | 1.00 | 7.75  | S |
| ATOM | 650 | CE  | MET | A | 97  | -12.244 | -21.891 |  1.790 | 1.00 | 10.46 | C |
| ATOM | 651 | C   | MET | A | 97  | -7.736  | -24.555 |  3.504 | 1.00 | 9.30  | C |
| ATOM | 652 | O   | MET | A | 97  | -6.941  | -25.162 |  2.792 | 1.00 | 9.03  | O |
| ATOM | 653 | N   | LYS | A | 98  | -8.459  | -25.129 |  4.468 | 1.00 | 9.79  | N |
| ATOM | 654 | CA  | LYS | A | 98  | -8.541  | -26.588 |  4.647 | 1.00 | 11.10 | C |
| ATOM | 655 | CB  | LYS | A | 98  | -8.696  | -26.945 |  6.126 | 1.00 | 11.32 | C |
| ATOM | 656 | CG  | LYS | A | 98  | -7.530  | -26.569 |  7.010 | 1.00 | 15.34 | C |
| ATOM | 657 | CD  | LYS | A | 98  | -7.813  | -27.010 |  8.433 | 1.00 | 22.19 | C |
| ATOM | 658 | CE  | LYS | A | 98  | -6.817  | -26.424 |  9.404 | 1.00 | 25.65 | C |
| ATOM | 659 | NZ  | LYS | A | 98  | -6.748  | -27.304 | 10.612 | 1.00 | 28.62 | N |
| ATOM | 660 | C   | LYS | A | 98  | -9.756  | -27.143 |  3.912 | 1.00 | 11.36 | C |
| ATOM | 661 | O   | LYS | A | 98  | -10.708 | -26.400 |  3.628 | 1.00 | 10.93 | O |
| ATOM | 662 | N   | LYS | A | 99  | -9.737  | -28.449 |  3.633 | 1.00 | 11.51 | N |
| ATOM | 663 | CA  | LYS | A | 99  | -10.853 | -29.130 |  2.989 | 1.00 | 13.72 | C |
| ATOM | 664 | CB  | LYS | A | 99  | -10.559 | -30.636 |  2.774 | 1.00 | 13.89 | C |
| ATOM | 665 | CG  | LYS | A | 99  | -9.417  | -30.952 |  1.783 | 1.00 | 16.30 | C |
| ATOM | 666 | CD  | LYS | A | 99  | -9.430  | -32.422 |  1.323 | 1.00 | 16.91 | C |
| ATOM | 667 | CE  | LYS | A | 99  | -8.157  | -32.768 |  0.517 | 1.00 | 19.90 | C |
| ATOM | 668 | NZ  | LYS | A | 99  | -8.206  | -34.178 |  0.003 | 1.00 | 22.72 | N |
| ATOM | 669 | C   | LYS | A | 99  | -12.121 | -28.928 |  3.830 | 1.00 | 12.57 | C |
| ATOM | 670 | O   | LYS | A | 99  | -12.099 | -29.053 |  5.065 | 1.00 | 13.42 | O |
| ATOM | 671 | N   | GLY | A | 100 | -13.215 | -28.554 |  3.174 | 1.00 | 12.10 | N |
| ATOM | 672 | CA  | GLY | A | 100 | -14.469 | -28.334 |  3.872 | 1.00 | 11.59 | C |
| ATOM | 673 | C   | GLY | A | 100 | -14.648 | -26.948 |  4.468 | 1.00 | 11.29 | C |
| ATOM | 674 | O   | GLY | A | 100 | -15.740 | -26.598 |  4.910 | 1.00 | 12.12 | O |
| ATOM | 675 | N   | GLU | A | 101 | -13.581 | -26.147 |  4.488 | 1.00 | 10.31 | N |

Figure 9 (cont.)

| | | | | | | | | | |
|---|---|---|---|---|---|---|---|---|---|
| ATOM | 676 | CA | GLU A 101 | -13.639 | -24.803 | 5.037 | 1.00 | 9.59 | C |
| ATOM | 677 | CB | GLU A 101 | -12.228 | -24.212 | 5.101 | 1.00 | 9.32 | C |
| ATOM | 678 | CG | GLU A 101 | -12.142 | -22.800 | 5.704 | 1.00 | 8.31 | C |
| ATOM | 679 | CD | GLU A 101 | -10.712 | -22.322 | 5.799 | 1.00 | 11.16 | C |
| ATOM | 680 | OE1 | GLU A 101 | -9.831 | -23.110 | 6.260 | 1.00 | 10.65 | O |
| ATOM | 681 | OE2 | GLU A 101 | -10.484 | -21.163 | 5.424 | 1.00 | 10.49 | O |
| ATOM | 682 | C | GLU A 101 | -14.486 | -23.904 | 4.136 | 1.00 | 9.07 | C |
| ATOM | 683 | O | GLU A 101 | -14.455 | -24.070 | 2.928 | 1.00 | 8.72 | O |
| ATOM | 684 | N | ILE A 102 | -15.194 | -22.936 | 4.730 | 1.00 | 8.33 | N |
| ATOM | 685 | CA | ILE A 102 | -15.783 | -21.823 | 3.963 | 1.00 | 8.22 | C |
| ATOM | 686 | CB | ILE A 102 | -17.341 | -21.753 | 4.087 | 1.00 | 8.55 | C |
| ATOM | 687 | CG1 | ILE A 102 | -17.959 | -23.068 | 3.632 | 1.00 | 9.02 | C |
| ATOM | 688 | CD1 | ILE A 102 | -19.479 | -23.175 | 3.867 | 1.00 | 11.34 | C |
| ATOM | 689 | CG2 | ILE A 102 | -17.910 | -20.578 | 3.249 | 1.00 | 8.08 | C |
| ATOM | 690 | C | ILE A 102 | -15.216 | -20.515 | 4.480 | 1.00 | 7.62 | C |
| ATOM | 691 | O | ILE A 102 | -15.165 | -20.292 | 5.677 | 1.00 | 6.88 | O |
| ATOM | 692 | N | CYS A 103 | -14.818 | -19.630 | 3.573 | 1.00 | 7.10 | N |
| ATOM | 693 | CA | CYS A 103 | -14.352 | -18.346 | 4.011 | 1.00 | 6.82 | C |
| ATOM | 694 | CB | CYS A 103 | -12.817 | -18.256 | 3.943 | 1.00 | 6.99 | C |
| ATOM | 695 | SG | CYS A 103 | -12.092 | -17.926 | 2.309 | 1.00 | 9.23 | S |
| ATOM | 696 | C | CYS A 103 | -15.007 | -17.230 | 3.226 | 1.00 | 6.26 | C |
| ATOM | 697 | O | CYS A 103 | -15.613 | -17.481 | 2.175 | 1.00 | 6.07 | O |
| ATOM | 698 | N | HIS A 104 | -14.917 | -16.023 | 3.791 | 1.00 | 6.38 | N |
| ATOM | 699 | CA | HIS A 104 | -15.230 | -14.765 | 3.112 | 1.00 | 7.21 | C |
| ATOM | 700 | CB | HIS A 104 | -16.147 | -13.894 | 3.962 | 1.00 | 7.55 | C |
| ATOM | 701 | CG | HIS A 104 | -17.553 | -14.408 | 4.028 | 1.00 | 7.27 | C |
| ATOM | 702 | ND1 | HIS A 104 | -18.522 | -13.837 | 4.828 | 1.00 | 7.95 | N |
| ATOM | 703 | CE1 | HIS A 104 | -19.667 | -14.482 | 4.650 | 1.00 | 8.67 | C |
| ATOM | 704 | NE2 | HIS A 104 | -19.462 | -15.473 | 3.793 | 1.00 | 6.24 | N |
| ATOM | 705 | CD2 | HIS A 104 | -18.153 | -15.431 | 3.373 | 1.00 | 6.43 | C |
| ATOM | 706 | C | HIS A 104 | -13.922 | -14.039 | 2.825 | 1.00 | 8.20 | C |
| ATOM | 707 | O | HIS A 104 | -13.026 | -13.976 | 3.685 | 1.00 | 7.98 | O |
| ATOM | 708 | N | LEU A 105 | -13.808 | -13.519 | 1.611 | 1.00 | 8.49 | N |
| ATOM | 709 | CA | LEU A 105 | -12.566 | -12.916 | 1.137 | 1.00 | 9.76 | C |
| ATOM | 710 | CB | LEU A 105 | -11.928 | -13.794 | 0.046 | 1.00 | 10.27 | C |
| ATOM | 711 | CG | LEU A 105 | -10.800 | -14.801 | 0.184 | 1.00 | 13.09 | C |
| ATOM | 712 | CD1 | LEU A 105 | -10.202 | -15.048 | -1.237 | 1.00 | 10.52 | C |
| ATOM | 713 | CD2 | LEU A 105 | -9.689 | -14.374 | 1.155 | 1.00 | 10.60 | C |
| ATOM | 714 | C | LEU A 105 | -12.904 | -11.560 | 0.536 | 1.00 | 10.54 | C |
| ATOM | 715 | O | LEU A 105 | -13.798 | -11.471 | -0.330 | 1.00 | 10.70 | O |
| ATOM | 716 | N | LEU A 106 | -12.221 | -10.513 | 0.991 | 1.00 | 10.60 | N |
| ATOM | 717 | CA | LEU A 106 | -12.323 | -9.205 | 0.362 | 1.00 | 10.90 | C |
| ATOM | 718 | CB | LEU A 106 | -12.608 | -8.137 | 1.405 | 1.00 | 12.23 | C |
| ATOM | 719 | CG | LEU A 106 | -13.274 | -6.845 | 0.981 | 1.00 | 12.55 | C |
| ATOM | 720 | CD1 | LEU A 106 | -13.469 | -5.988 | 2.231 | 1.00 | 14.08 | C |
| ATOM | 721 | CD2 | LEU A 106 | -14.635 | -7.076 | 0.275 | 1.00 | 10.94 | C |
| ATOM | 722 | C | LEU A 106 | -11.023 | -8.914 | -0.390 | 1.00 | 11.16 | C |
| ATOM | 723 | O | LEU A 106 | -9.931 | -9.040 | 0.178 | 1.00 | 10.79 | O |
| ATOM | 724 | N | CYS A 107 | -11.152 | -8.528 | -1.661 | 1.00 | 10.67 | N |
| ATOM | 725 | CA | CYS A 107 | -10.026 | -8.460 | -2.599 | 1.00 | 11.15 | C |
| ATOM | 726 | CB | CYS A 107 | -10.243 | -9.467 | -3.747 | 1.00 | 11.31 | C |
| ATOM | 727 | SG | CYS A 107 | -10.729 | -11.126 | -3.163 | 1.00 | 11.21 | S |
| ATOM | 728 | C | CYS A 107 | -9.903 | -7.042 | -3.169 | 1.00 | 11.54 | C |
| ATOM | 729 | O | CYS A 107 | -10.772 | -6.601 | -3.937 | 1.00 | 11.21 | O |
| ATOM | 730 | N | LYS A 108 | -8.846 | -6.335 | -2.775 | 1.00 | 12.50 | N |
| ATOM | 731 | CA | LYS A 108 | -8.584 | -4.977 | -3.309 | 1.00 | 12.61 | C |

Figure 9 (cont.)

| | | | | | | | | | | |
|---|---|---|---|---|---|---|---|---|---|---|
| ATOM | 732 | CB | LYS | A | 108 | -7.454 | -4.315 | -2.511 | 1.00 13.33 | C |
| ATOM | 733 | CG | LYS | A | 108 | -7.940 | -3.750 | -1.189 | 1.00 16.16 | C |
| ATOM | 734 | CD | LYS | A | 108 | -6.870 | -2.891 | -0.514 | 1.00 23.66 | C |
| ATOM | 735 | CE | LYS | A | 108 | -7.538 | -1.967 | 0.491 | 1.00 26.00 | C |
| ATOM | 736 | NZ | LYS | A | 108 | -6.560 | -1.111 | 1.212 | 1.00 31.42 | N |
| ATOM | 737 | C | LYS | A | 108 | -8.197 | -5.078 | -4.783 | 1.00 12.29 | C |
| ATOM | 738 | O | LYS | A | 108 | -7.703 | -6.114 | -5.200 | 1.00 12.15 | O |
| ATOM | 739 | N | PRO | A | 109 | -8.428 | -4.009 | -5.592 | 1.00 12.57 | N |
| ATOM | 740 | CA | PRO | A | 109 | -8.149 | -4.091 | -7.033 | 1.00 12.80 | C |
| ATOM | 741 | CB | PRO | A | 109 | -8.326 | -2.638 | -7.539 | 1.00 13.01 | C |
| ATOM | 742 | CG | PRO | A | 109 | -8.832 | -1.864 | -6.414 | 1.00 13.51 | C |
| ATOM | 743 | CD | PRO | A | 109 | -9.046 | -2.723 | -5.217 | 1.00 13.38 | C |
| ATOM | 744 | C | PRO | A | 109 | -6.766 | -4.610 | -7.390 | 1.00 12.95 | C |
| ATOM | 745 | O | PRO | A | 109 | -6.621 | -5.318 | -8.403 | 1.00 13.39 | O |
| ATOM | 746 | N | GLU | A | 110 | -5.772 | -4.281 | -6.562 | 1.00 13.30 | N |
| ATOM | 747 | CA | GLU | A | 110 | -4.376 | -4.638 | -6.810 | 1.00 13.71 | C |
| ATOM | 748 | CB | GLU | A | 110 | -3.436 | -4.009 | -5.772 | 1.00 14.31 | C |
| ATOM | 749 | CG | GLU | A | 110 | -3.336 | -2.472 | -5.856 | 1.00 17.63 | C |
| ATOM | 750 | CD | GLU | A | 110 | -4.565 | -1.754 | -5.307 | 1.00 21.46 | C |
| ATOM | 751 | OE1 | GLU | A | 110 | -5.314 | -2.360 | -4.508 | 1.00 17.19 | O |
| ATOM | 752 | OE2 | GLU | A | 110 | -4.775 | -0.571 | -5.685 | 1.00 23.42 | O |
| ATOM | 753 | C | GLU | A | 110 | -4.183 | -6.147 | -6.838 | 1.00 13.37 | C |
| ATOM | 754 | O | GLU | A | 110 | -3.239 | -6.646 | -7.456 | 1.00 13.48 | O |
| ATOM | 755 | N | TYR | A | 111 | -5.101 | -6.858 | -6.183 | 1.00 12.26 | N |
| ATOM | 756 | CA | TYR | A | 111 | -5.086 | -8.315 | -6.156 | 1.00 12.34 | C |
| ATOM | 757 | CB | TYR | A | 111 | -5.125 | -8.807 | -4.710 | 1.00 12.12 | C |
| ATOM | 758 | CG | TYR | A | 111 | -3.874 | -8.449 | -3.955 | 1.00 12.96 | C |
| ATOM | 759 | CD1 | TYR | A | 111 | -2.786 | -9.325 | -3.908 | 1.00 13.60 | C |
| ATOM | 760 | CE1 | TYR | A | 111 | -1.611 | -8.984 | -3.200 | 1.00 14.97 | C |
| ATOM | 761 | CZ | TYR | A | 111 | -1.540 | -7.759 | -2.566 | 1.00 14.69 | C |
| ATOM | 762 | OH | TYR | A | 111 | -0.400 | -7.408 | -1.892 | 1.00 16.24 | O |
| ATOM | 763 | CE2 | TYR | A | 111 | -2.598 | -6.874 | -2.612 | 1.00 14.45 | C |
| ATOM | 764 | CD2 | TYR | A | 111 | -3.759 | -7.223 | -3.308 | 1.00 13.65 | C |
| ATOM | 765 | C | TYR | A | 111 | -6.238 | -8.894 | -6.980 | 1.00 12.29 | C |
| ATOM | 766 | O | TYR | A | 111 | -6.562 | -10.077 | -6.869 | 1.00 13.01 | O |
| ATOM | 767 | N | ALA | A | 112 | -6.836 | -8.058 | -7.822 | 1.00 12.16 | N |
| ATOM | 768 | CA | ALA | A | 112 | -7.939 | -8.487 | -8.673 | 1.00 12.37 | C |
| ATOM | 769 | CB | ALA | A | 112 | -9.282 | -8.052 | -8.103 | 1.00 12.01 | C |
| ATOM | 770 | C | ALA | A | 112 | -7.724 | -7.983 | -10.106 | 1.00 12.34 | C |
| ATOM | 771 | O | ALA | A | 112 | -6.810 | -8.475 | -10.792 | 1.00 12.88 | O |
| ATOM | 772 | N | TYR | A | 113 | -8.537 | -7.023 | -10.554 | 1.00 12.59 | N |
| ATOM | 773 | CA | TYR | A | 113 | -8.498 | -6.548 | -11.955 | 1.00 12.77 | C |
| ATOM | 774 | CB | TYR | A | 113 | -9.876 | -6.657 | -12.605 | 1.00 12.62 | C |
| ATOM | 775 | CG | TYR | A | 113 | -10.405 | -8.076 | -12.613 | 1.00 12.21 | C |
| ATOM | 776 | CD1 | TYR | A | 113 | -10.114 | -8.948 | -13.662 | 1.00 15.68 | C |
| ATOM | 777 | CE1 | TYR | A | 113 | -10.594 | -10.266 | -13.670 | 1.00 13.52 | C |
| ATOM | 778 | CZ | TYR | A | 113 | -11.354 | -10.731 | -12.606 | 1.00 12.08 | C |
| ATOM | 779 | OH | TYR | A | 113 | -11.822 | -12.041 | -12.595 | 1.00 13.05 | O |
| ATOM | 780 | CE2 | TYR | A | 113 | -11.637 | -9.899 | -11.543 | 1.00 9.77 | C |
| ATOM | 781 | CD2 | TYR | A | 113 | -11.166 | -8.560 | -11.547 | 1.00 10.61 | C |
| ATOM | 782 | C | TYR | A | 113 | -7.912 | -5.144 | -12.145 | 1.00 14.06 | C |
| ATOM | 783 | O | TYR | A | 113 | -7.882 | -4.611 | -13.268 | 1.00 13.60 | O |
| ATOM | 784 | N | GLY | A | 114 | -7.443 | -4.560 | -11.052 | 1.00 14.43 | N |
| ATOM | 785 | CA | GLY | A | 114 | -6.695 | -3.297 | -11.116 | 1.00 15.94 | C |
| ATOM | 786 | C | GLY | A | 114 | -7.467 | -2.125 | -11.691 | 1.00 15.75 | C |
| ATOM | 787 | O | GLY | A | 114 | -8.696 | -2.084 | -11.645 | 1.00 15.49 | O |

Figure 9 (cont.)

| ATOM | 788 | N   | SER | A | 115 | -6.722  | -1.163  | -12.237 | 1.00 | 16.71 | N |
|------|-----|-----|-----|---|-----|---------|---------|---------|------|-------|---|
| ATOM | 789 | CA  | SER | A | 115 | -7.322  | 0.033   | -12.823 | 1.00 | 17.73 | C |
| ATOM | 790 | CB  | SER | A | 115 | -6.249  | 1.098   | -13.071 | 1.00 | 18.10 | C |
| ATOM | 791 | OG  | SER | A | 115 | -5.258  | 0.618   | -13.968 | 1.00 | 19.93 | O |
| ATOM | 792 | C   | SER | A | 115 | -8.031  | -0.295  | -14.128 | 1.00 | 18.37 | C |
| ATOM | 793 | O   | SER | A | 115 | -9.009  | 0.349   | -14.481 | 1.00 | 19.13 | O |
| ATOM | 794 | N   | ALA | A | 116 | -7.531  | -1.307  | -14.831 | 1.00 | 18.54 | N |
| ATOM | 795 | CA  | ALA | A | 116 | -8.105  | -1.735  | -16.109 | 1.00 | 18.87 | C |
| ATOM | 796 | CB  | ALA | A | 116 | -7.208  | -2.779  | -16.762 | 1.00 | 18.98 | C |
| ATOM | 797 | C   | ALA | A | 116 | -9.516  | -2.280  | -15.953 | 1.00 | 18.62 | C |
| ATOM | 798 | O   | ALA | A | 116 | -10.381 | -2.029  | -16.793 | 1.00 | 18.65 | O |
| ATOM | 799 | N   | GLY | A | 117 | -9.751  | -3.025  | -14.874 | 1.00 | 17.96 | N |
| ATOM | 800 | CA  | GLY | A | 117 | -11.009 | -3.752  | -14.723 | 1.00 | 18.16 | C |
| ATOM | 801 | C   | GLY | A | 117 | -11.139 | -4.809  | -15.811 | 1.00 | 18.08 | C |
| ATOM | 802 | O   | GLY | A | 117 | -10.140 | -5.247  | -16.385 | 1.00 | 17.19 | O |
| ATOM | 803 | N   | SER | A | 118 | -12.373 | -5.222  | -16.083 | 1.00 | 18.61 | N |
| ATOM | 804 | CA  | SER | A | 118 | -12.643 | -6.245  | -17.099 | 1.00 | 20.07 | C |
| ATOM | 805 | CB  | SER | A | 118 | -12.295 | -7.636  | -16.569 | 1.00 | 19.60 | C |
| ATOM | 806 | OG  | SER | A | 118 | -12.461 | -8.608  | -17.590 | 1.00 | 21.35 | O |
| ATOM | 807 | C   | SER | A | 118 | -14.111 | -6.173  | -17.481 | 1.00 | 20.25 | C |
| ATOM | 808 | O   | SER | A | 118 | -14.957 | -6.789  | -16.838 | 1.00 | 21.43 | O |
| ATOM | 809 | N   | LEU | A | 119 | -14.415 | -5.393  | -18.516 | 1.00 | 21.67 | N |
| ATOM | 810 | CA  | LEU | A | 119 | -15.803 | -5.144  | -18.908 | 1.00 | 21.97 | C |
| ATOM | 811 | CB  | LEU | A | 119 | -15.890 | -3.888  | -19.765 | 1.00 | 22.67 | C |
| ATOM | 812 | CG  | LEU | A | 119 | -15.430 | -2.589  | -19.108 | 1.00 | 23.25 | C |
| ATOM | 813 | CD1 | LEU | A | 119 | -16.374 | -2.195  | -17.981 | 1.00 | 24.69 | C |
| ATOM | 814 | CD2 | LEU | A | 119 | -15.368 | -1.508  | -20.183 | 1.00 | 25.80 | C |
| ATOM | 815 | C   | LEU | A | 119 | -16.412 | -6.317  | -19.671 | 1.00 | 22.00 | C |
| ATOM | 816 | O   | LEU | A | 119 | -15.703 | -7.009  | -20.396 | 1.00 | 22.39 | O |
| ATOM | 817 | N   | PRO | A | 120 | -17.744 | -6.503  | -19.555 | 1.00 | 22.48 | N |
| ATOM | 818 | CA  | PRO | A | 120 | -18.658 | -5.620  | -18.818 | 1.00 | 22.09 | C |
| ATOM | 819 | CB  | PRO | A | 120 | -20.011 | -5.911  | -19.476 | 1.00 | 22.26 | C |
| ATOM | 820 | CG  | PRO | A | 120 | -19.915 | -7.370  | -19.882 | 1.00 | 22.59 | C |
| ATOM | 821 | CD  | PRO | A | 120 | -18.464 | -7.606  | -20.234 | 1.00 | 22.10 | C |
| ATOM | 822 | C   | PRO | A | 120 | -18.765 | -5.863  | -17.313 | 1.00 | 21.94 | C |
| ATOM | 823 | O   | PRO | A | 120 | -19.288 | -5.002  | -16.596 | 1.00 | 22.18 | O |
| ATOM | 824 | N   | LYS | A | 121 | -18.289 | -7.015  | -16.842 | 1.00 | 21.06 | N |
| ATOM | 825 | CA  | LYS | A | 121 | -18.532 | -7.439  | -15.465 | 1.00 | 21.10 | C |
| ATOM | 826 | CB  | LYS | A | 121 | -18.099 | -8.893  | -15.259 | 1.00 | 20.92 | C |
| ATOM | 827 | CG  | LYS | A | 121 | -18.995 | -9.901  | -15.954 | 1.00 | 22.66 | C |
| ATOM | 828 | CD  | LYS | A | 121 | -18.627 | -11.339 | -15.584 | 1.00 | 22.71 | C |
| ATOM | 829 | CE  | LYS | A | 121 | -19.482 | -12.305 | -16.392 | 1.00 | 25.71 | C |
| ATOM | 830 | NZ  | LYS | A | 121 | -19.069 | -13.714 | -16.212 | 1.00 | 30.15 | N |
| ATOM | 831 | C   | LYS | A | 121 | -17.852 | -6.552  | -14.418 | 1.00 | 19.76 | C |
| ATOM | 832 | O   | LYS | A | 121 | -18.483 | -6.197  | -13.416 | 1.00 | 20.32 | O |
| ATOM | 833 | N   | ILE | A | 122 | -16.590 | -6.203  | -14.665 | 1.00 | 18.80 | N |
| ATOM | 834 | CA  | ILE | A | 122 | -15.720 | -5.597  | -13.640 | 1.00 | 18.01 | C |
| ATOM | 835 | CB  | ILE | A | 122 | -14.422 | -6.440  | -13.350 | 1.00 | 17.67 | C |
| ATOM | 836 | CG1 | ILE | A | 122 | -14.694 | -7.968  | -13.288 | 1.00 | 17.53 | C |
| ATOM | 837 | CD1 | ILE | A | 122 | -15.618 | -8.456  | -12.157 | 1.00 | 16.02 | C |
| ATOM | 838 | CG2 | ILE | A | 122 | -13.718 | -5.899  | -12.088 | 1.00 | 17.29 | C |
| ATOM | 839 | C   | ILE | A | 122 | -15.293 | -4.172  | -14.008 | 1.00 | 17.74 | C |
| ATOM | 840 | O   | ILE | A | 122 | -14.514 | -3.979  | -14.942 | 1.00 | 16.87 | O |
| ATOM | 841 | N   | PRO | A | 123 | -15.791 | -3.175  | -13.259 | 1.00 | 17.74 | N |
| ATOM | 842 | CA  | PRO | A | 123 | -15.390 | -1.785  | -13.484 | 1.00 | 17.67 | C |
| ATOM | 843 | CB  | PRO | A | 123 | -16.376 | -0.981  | -12.617 | 1.00 | 17.67 | C |

Figure 9 (cont.)

| | | | | | | | | | | |
|---|---|---|---|---|---|---|---|---|---|---|
| ATOM | 844 | CG | PRO | A | 123 | -17.422 | -1.968 | -12.173 | 1.00 | 18.98 | C |
| ATOM | 845 | CD | PRO | A | 123 | -16.757 | -3.291 | -12.158 | 1.00 | 17.66 | C |
| ATOM | 846 | C | PRO | A | 123 | -13.964 | -1.515 | -13.035 | 1.00 | 17.03 | C |
| ATOM | 847 | O | PRO | A | 123 | -13.315 | -2.377 | -12.415 | 1.00 | 16.10 | O |
| ATOM | 848 | N | SER | A | 124 | -13.478 | -0.316 | -13.342 | 1.00 | 16.78 | N |
| ATOM | 849 | CA | SER | A | 124 | -12.147 | 0.087 | -12.920 | 1.00 | 16.22 | C |
| ATOM | 850 | CB | SER | A | 124 | -11.812 | 1.446 | -13.548 | 1.00 | 16.71 | C |
| ATOM | 851 | OG | SER | A | 124 | -10.521 | 1.839 | -13.167 | 1.00 | 19.54 | O |
| ATOM | 852 | C | SER | A | 124 | -12.046 | 0.141 | -11.387 | 1.00 | 15.54 | C |
| ATOM | 853 | O | SER | A | 124 | -13.000 | 0.544 | -10.710 | 1.00 | 15.95 | O |
| ATOM | 854 | N | ASN | A | 125 | -10.915 | -0.323 | -10.853 | 1.00 | 14.61 | N |
| ATOM | 855 | CA | ASN | A | 125 | -10.585 | -0.215 | -9.410 | 1.00 | 14.48 | C |
| ATOM | 856 | CB | ASN | A | 125 | -10.364 | 1.247 | -9.013 | 1.00 | 14.31 | C |
| ATOM | 857 | CG | ASN | A | 125 | -9.201 | 1.860 | -9.727 | 1.00 | 16.29 | C |
| ATOM | 858 | OD1 | ASN | A | 125 | -8.114 | 1.285 | -9.758 | 1.00 | 16.76 | O |
| ATOM | 859 | ND2 | ASN | A | 125 | -9.415 | 3.049 | -10.309 | 1.00 | 16.82 | N |
| ATOM | 860 | C | ASN | A | 125 | -11.577 | -0.875 | -8.463 | 1.00 | 13.63 | C |
| ATOM | 861 | O | ASN | A | 125 | -11.829 | -0.386 | -7.350 | 1.00 | 13.56 | O |
| ATOM | 862 | N | ALA | A | 126 | -12.117 | -2.008 | -8.906 | 1.00 | 13.26 | N |
| ATOM | 863 | CA | ALA | A | 126 | -13.162 | -2.712 | -8.171 | 1.00 | 12.21 | C |
| ATOM | 864 | CB | ALA | A | 126 | -13.983 | -3.607 | -9.121 | 1.00 | 12.90 | C |
| ATOM | 865 | C | ALA | A | 126 | -12.583 | -3.553 | -7.029 | 1.00 | 12.45 | C |
| ATOM | 866 | O | ALA | A | 126 | -11.575 | -4.269 | -7.185 | 1.00 | 11.74 | O |
| ATOM | 867 | N | THR | A | 127 | -13.218 | -3.429 | -5.871 | 1.00 | 11.19 | N |
| ATOM | 868 | CA | THR | A | 127 | -12.992 | -4.362 | -4.772 | 1.00 | 11.60 | C |
| ATOM | 869 | CB | THR | A | 127 | -13.112 | -3.650 | -3.406 | 1.00 | 12.62 | C |
| ATOM | 870 | OG1 | THR | A | 127 | -12.038 | -2.707 | -3.293 | 1.00 | 12.84 | O |
| ATOM | 871 | CG2 | THR | A | 127 | -13.048 | -4.653 | -2.229 | 1.00 | 12.03 | C |
| ATOM | 872 | C | THR | A | 127 | -14.031 | -5.474 | -4.923 | 1.00 | 11.67 | C |
| ATOM | 873 | O | THR | A | 127 | -15.228 | -5.193 | -5.150 | 1.00 | 11.57 | O |
| ATOM | 874 | N | LEU | A | 128 | -13.575 | -6.723 | -4.786 | 1.00 | 10.89 | N |
| ATOM | 875 | CA | LEU | A | 128 | -14.451 | -7.893 | -4.898 | 1.00 | 9.72 | C |
| ATOM | 876 | CB | LEU | A | 128 | -13.947 | -8.860 | -5.985 | 1.00 | 9.78 | C |
| ATOM | 877 | CG | LEU | A | 128 | -13.539 | -8.284 | -7.344 | 1.00 | 13.40 | C |
| ATOM | 878 | CD1 | LEU | A | 128 | -13.056 | -9.422 | -8.260 | 1.00 | 12.32 | C |
| ATOM | 879 | CD2 | LEU | A | 128 | -14.671 | -7.547 | -7.945 | 1.00 | 13.47 | C |
| ATOM | 880 | C | LEU | A | 128 | -14.592 | -8.652 | -3.585 | 1.00 | 9.03 | C |
| ATOM | 881 | O | LEU | A | 128 | -13.635 | -8.749 | -2.789 | 1.00 | 8.19 | O |
| ATOM | 882 | N | PHE | A | 129 | -15.779 | -9.223 | -3.405 | 1.00 | 7.78 | N |
| ATOM | 883 | CA | PHE | A | 129 | -16.090 | -10.034 | -2.250 | 1.00 | 8.79 | C |
| ATOM | 884 | CB | PHE | A | 129 | -17.293 | -9.450 | -1.489 | 1.00 | 8.84 | C |
| ATOM | 885 | CG | PHE | A | 129 | -17.725 | -10.306 | -0.340 | 1.00 | 9.43 | C |
| ATOM | 886 | CD1 | PHE | A | 129 | -17.088 | -10.184 | 0.902 | 1.00 | 11.11 | C |
| ATOM | 887 | CE1 | PHE | A | 129 | -17.457 | -11.001 | 1.987 | 1.00 | 10.97 | C |
| ATOM | 888 | CZ | PHE | A | 129 | -18.446 | -11.958 | 1.832 | 1.00 | 9.79 | C |
| ATOM | 889 | CE2 | PHE | A | 129 | -19.094 | -12.101 | 0.587 | 1.00 | 12.40 | C |
| ATOM | 890 | CD2 | PHE | A | 129 | -18.720 | -11.282 | -0.497 | 1.00 | 11.47 | C |
| ATOM | 891 | C | PHE | A | 129 | -16.440 | -11.442 | -2.723 | 1.00 | 8.66 | C |
| ATOM | 892 | O | PHE | A | 129 | -17.250 | -11.599 | -3.649 | 1.00 | 9.22 | O |
| ATOM | 893 | N | PHE | A | 130 | -15.862 | -12.454 | -2.082 | 1.00 | 7.68 | N |
| ATOM | 894 | CA | PHE | A | 130 | -16.230 | -13.835 | -2.356 | 1.00 | 7.68 | C |
| ATOM | 895 | CB | PHE | A | 130 | -15.071 | -14.586 | -3.057 | 1.00 | 7.25 | C |
| ATOM | 896 | CG | PHE | A | 130 | -14.715 | -14.043 | -4.401 | 1.00 | 7.62 | C |
| ATOM | 897 | CD1 | PHE | A | 130 | -15.330 | -14.555 | -5.551 | 1.00 | 7.57 | C |
| ATOM | 898 | CE1 | PHE | A | 130 | -15.015 | -14.048 | -6.814 | 1.00 | 7.66 | C |
| ATOM | 899 | CZ | PHE | A | 130 | -14.033 | -13.070 | -6.945 | 1.00 | 6.29 | C |

Figure 9 (cont.)

| | | | | | | | | | | |
|---|---|---|---|---|---|---|---|---|---|---|
| ATOM | 900 | CE2 | PHE | A | 130 | -13.392 | -12.550 | -5.806 | 1.00 | 7.51 | C |
| ATOM | 901 | CD2 | PHE | A | 130 | -13.742 | -13.035 | -4.532 | 1.00 | 8.45 | C |
| ATOM | 902 | C | PHE | A | 130 | -16.540 | -14.605 | -1.084 | 1.00 | 7.37 | C |
| ATOM | 903 | O | PHE | A | 130 | -15.912 | -14.373 | -0.026 | 1.00 | 8.10 | O |
| ATOM | 904 | N | GLU | A | 131 | -17.473 | -15.544 | -1.220 | 1.00 | 7.11 | N |
| ATOM | 905 | CA | GLU | A | 131 | -17.638 | -16.621 | -0.281 | 1.00 | 7.41 | C |
| ATOM | 906 | CB | GLU | A | 131 | -19.107 | -16.776 | 0.085 | 1.00 | 7.57 | C |
| ATOM | 907 | CG | GLU | A | 131 | -19.359 | -17.895 | 1.040 | 1.00 | 8.55 | C |
| ATOM | 908 | CD | GLU | A | 131 | -20.805 | -17.963 | 1.437 | 1.00 | 10.50 | C |
| ATOM | 909 | OE1 | GLU | A | 131 | -21.154 | -17.268 | 2.411 | 1.00 | 8.85 | O |
| ATOM | 910 | OE2 | GLU | A | 131 | -21.574 | -18.704 | 0.775 | 1.00 | 11.65 | O |
| ATOM | 911 | C | GLU | A | 131 | -17.129 | -17.873 | -1.004 | 1.00 | 7.77 | C |
| ATOM | 912 | O | GLU | A | 131 | -17.605 | -18.197 | -2.100 | 1.00 | 7.98 | O |
| ATOM | 913 | N | ILE | A | 132 | -16.133 | -18.526 | -0.419 | 1.00 | 7.20 | N |
| ATOM | 914 | CA | ILE | A | 132 | -15.500 | -19.674 | -1.077 | 1.00 | 7.17 | C |
| ATOM | 915 | CB | ILE | A | 132 | -14.009 | -19.392 | -1.466 | 1.00 | 6.52 | C |
| ATOM | 916 | CG1 | ILE | A | 132 | -13.887 | -18.148 | -2.348 | 1.00 | 7.30 | C |
| ATOM | 917 | CD1 | ILE | A | 132 | -12.424 | -17.713 | -2.579 | 1.00 | 7.27 | C |
| ATOM | 918 | CG2 | ILE | A | 132 | -13.356 | -20.637 | -2.144 | 1.00 | 7.76 | C |
| ATOM | 919 | C | ILE | A | 132 | -15.567 | -20.869 | -0.148 | 1.00 | 8.73 | C |
| ATOM | 920 | O | ILE | A | 132 | -15.291 | -20.750 | 1.059 | 1.00 | 5.79 | O |
| ATOM | 921 | N | GLU | A | 133 | -15.977 | -22.010 | -0.710 | 1.00 | 7.58 | N |
| ATOM | 922 | CA | GLU | A | 133 | -15.964 | -23.294 | -0.002 | 1.00 | 9.95 | C |
| ATOM | 923 | CB | GLU | A | 133 | -17.352 | -23.951 | -0.029 | 1.00 | 9.87 | C |
| ATOM | 924 | CG | GLU | A | 133 | -17.335 | -25.343 | 0.604 | 1.00 | 11.24 | C |
| ATOM | 925 | CD | GLU | A | 133 | -18.701 | -26.051 | 0.633 | 1.00 | 14.98 | C |
| ATOM | 926 | OE1 | GLU | A | 133 | -19.674 | -25.547 | 0.047 | 1.00 | 20.00 | O |
| ATOM | 927 | OE2 | GLU | A | 133 | -18.758 | -27.155 | 1.218 | 1.00 | 19.01 | O |
| ATOM | 928 | C | GLU | A | 133 | -14.959 | -24.219 | -0.690 | 1.00 | 8.74 | C |
| ATOM | 929 | O | GLU | A | 133 | -15.107 | -24.514 | -1.869 | 1.00 | 8.65 | O |
| ATOM | 930 | N | LEU | A | 134 | -13.945 | -24.680 | 0.032 | 1.00 | 8.90 | N |
| ATOM | 931 | CA | LEU | A | 134 | -12.980 | -25.606 | -0.558 | 1.00 | 9.74 | C |
| ATOM | 932 | CB | LEU | A | 134 | -11.599 | -25.443 | 0.097 | 1.00 | 9.38 | C |
| ATOM | 933 | CG | LEU | A | 134 | -10.481 | -26.349 | -0.425 | 1.00 | 9.36 | C |
| ATOM | 934 | CD1 | LEU | A | 134 | -10.305 | -26.176 | -1.925 | 1.00 | 9.88 | C |
| ATOM | 935 | CD2 | LEU | A | 134 | -9.167 | -26.061 | 0.295 | 1.00 | 9.53 | C |
| ATOM | 936 | C | LEU | A | 134 | -13.513 | -27.026 | -0.371 | 1.00 | 9.97 | C |
| ATOM | 937 | O | LEU | A | 134 | -13.639 | -27.515 | 0.762 | 1.00 | 11.00 | O |
| ATOM | 938 | N | LEU | A | 135 | -13.872 | -27.653 | -1.482 | 1.00 | 10.80 | N |
| ATOM | 939 | CA | LEU | A | 135 | -14.492 | -28.984 | -1.454 | 1.00 | 10.69 | C |
| ATOM | 940 | CB | LEU | A | 135 | -15.328 | -29.197 | -2.710 | 1.00 | 11.18 | C |
| ATOM | 941 | CG | LEU | A | 135 | -16.414 | -28.138 | -2.925 | 1.00 | 11.25 | C |
| ATOM | 942 | CD1 | LEU | A | 135 | -16.997 | -28.272 | -4.312 | 1.00 | 15.71 | C |
| ATOM | 943 | CD2 | LEU | A | 135 | -17.482 | -28.197 | -1.858 | 1.00 | 12.21 | C |
| ATOM | 944 | C | LEU | A | 135 | -13.433 | -30.069 | -1.363 | 1.00 | 11.03 | C |
| ATOM | 945 | O | LEU | A | 135 | 13.590 | -31.030 | -0.593 | 1.00 | 11.80 | O |
| ATOM | 946 | N | ASP | A | 136 | -12.359 | -29.901 | -2.131 | 1.00 | 11.46 | N |
| ATOM | 947 | CA | ASP | A | 136 | -11.299 | -30.911 | -2.235 | 1.00 | 12.39 | C |
| ATOM | 948 | CB | ASP | A | 136 | -11.836 | -32.091 | -3.058 | 1.00 | 12.31 | C |
| ATOM | 949 | CG | ASP | A | 136 | -11.113 | -33.403 | -2.780 | 1.00 | 16.23 | C |
| ATOM | 950 | OD1 | ASP | A | 136 | -10.210 | -33.456 | -1.921 | 1.00 | 16.86 | O |
| ATOM | 951 | OD2 | ASP | A | 136 | -11.476 | -34.390 | -3.451 | 1.00 | 19.43 | O |
| ATOM | 952 | C | ASP | A | 136 | -10.071 | -30.343 | -2.939 | 1.00 | 11.93 | C |
| ATOM | 953 | O | ASP | A | 136 | -10.146 | -29.309 | -3.612 | 1.00 | 11.01 | O |
| ATOM | 954 | N | PHE | A | 137 | -8.932 | -31.027 | -2.811 | 1.00 | 11.86 | N |
| ATOM | 955 | CA | PHE | A | 137 | -7.773 | -30.723 | -3.646 | 1.00 | 13.14 | C |

Figure 9 (cont.)

| | | | | | | | | | |
|---|---|---|---|---|---|---|---|---|---|
| ATOM | 956 | CB | PHE | A | 137 | -6.976 | -29.527 | -3.099 | 1.00 12.93 | C |
| ATOM | 957 | CG | PHE | A | 137 | -6.482 | -29.709 | -1.699 | 1.00 11.71 | C |
| ATOM | 958 | CD1 | PHE | A | 137 | -5.243 | -30.316 | -1.461 | 1.00 13.72 | C |
| ATOM | 959 | CE1 | PHE | A | 137 | -4.769 | -30.498 | -0.163 | 1.00 14.00 | C |
| ATOM | 960 | CZ | PHE | A | 137 | -5.514 | -30.062 | 0.912 | 1.00 14.42 | C |
| ATOM | 961 | CE2 | PHE | A | 137 | -6.758 | -29.436 | 0.700 | 1.00 14.84 | C |
| ATOM | 962 | CD2 | PHE | A | 137 | -7.239 | -29.273 | -0.615 | 1.00 13.65 | C |
| ATOM | 963 | C | PHE | A | 137 | -6.887 | -31.954 | -3.808 | 1.00 14.81 | C |
| ATOM | 964 | O | PHE | A | 137 | -6.863 | -32.797 | -2.913 | 1.00 15.23 | O |
| ATOM | 965 | N | LYS | A | 138 | -6.207 | -32.043 | -4.949 | 1.00 16.68 | N |
| ATOM | 966 | CA | LYS | A | 138 | -5.309 | -33.165 | -5.288 | 1.00 19.55 | C |
| ATOM | 967 | CB | LYS | A | 138 | -6.045 | -34.221 | -6.147 | 1.00 20.48 | C |
| ATOM | 968 | CG | LYS | A | 138 | -7.478 | -34.590 | -5.744 | 1.00 22.92 | C |
| ATOM | 969 | CD | LYS | A | 138 | -7.537 | -35.465 | -4.478 | 1.00 26.38 | C |
| ATOM | 970 | CE | LYS | A | 138 | -8.950 | -36.028 | -4.272 | 1.00 27.05 | C |
| ATOM | 971 | NZ | LYS | A | 138 | -9.099 | -36.741 | -2.976 | 1.00 30.32 | N |
| ATOM | 972 | C | LYS | A | 138 | -4.086 | -32.696 | -6.063 | 1.00 20.35 | C |
| ATOM | 973 | O | LYS | A | 138 | -4.167 | -31.775 | -6.870 | 1.00 20.71 | O |
| ATOM | 974 | N | GLY | A | 139 | -2.937 | -33.346 | -5.850 | 1.00 21.86 | N |
| ATOM | 975 | CA | GLY | A | 139 | -1.745 | -33.024 | -6.640 | 1.00 22.56 | C |
| ATOM | 976 | C | GLY | A | 139 | -1.853 | -33.541 | -8.062 | 1.00 23.93 | C |
| ATOM | 977 | O | GLY | A | 139 | -2.657 | -34.443 | -8.329 | 1.00 24.54 | O |
| ATOM | 978 | CBE | DRG | B | 1 | -9.624 | -22.542 | -17.640 | 1.00 20.14 | C |
| ATOM | 979 | CAW | DRG | B | 1 | -8.442 | -22.328 | -18.598 | 1.00 18.93 | C |
| ATOM | 980 | OBM | DRG | B | 1 | -7.392 | -23.274 | -18.265 | 1.00 18.84 | O |
| ATOM | 981 | CAX | DRG | B | 1 | -6.887 | -22.975 | -16.939 | 1.00 19.26 | C |
| ATOM | 982 | CBF | DRG | B | 1 | -8.032 | -23.233 | -15.954 | 1.00 18.99 | C |
| ATOM | 983 | NCE | DRG | B | 1 | -9.174 | -22.338 | -16.239 | 1.00 18.49 | N |
| ATOM | 984 | CBG | DRG | B | 1 | -10.222 | -22.683 | -15.242 | 1.00 19.16 | C |
| ATOM | 985 | CAY | DRG | B | 1 | -11.337 | -21.601 | -15.120 | 1.00 17.25 | C |
| ATOM | 986 | OBN | DRG | B | 1 | -10.749 | -20.317 | -14.954 | 1.00 14.22 | O |
| ATOM | 987 | CBS | DRG | B | 1 | -11.548 | -19.217 | -14.850 | 1.00 13.44 | C |
| ATOM | 988 | CAO | DRG | B | 1 | -10.973 | -18.09 | -14.400 | 1.00 12.72 | C |
| ATOM | 989 | CAK | DRG | B | 1 | -12.904 | -19.256 | -15.188 | 1.00 12.47 | C |
| ATOM | 990 | CAJ | DRG | B | 1 | -13.685 | -18.112 | -152.077 | 1.00 13.74 | C |
| ATOM | 991 | CAL | DRG | B | 1 | -13.104 | -16.931 | -14.617 | 1.00 13.04 | C |
| ATOM | 992 | CBT | DRG | B | 1 | -11.748 | -16.882 | -14.285 | 1.00 11.96 | C |
| ATOM | 993 | CCB | DRG | B | 1 | -11.128 | -15.562 | -13.779 | 1.00 12.97 | C |
| ATOM | 994 | CBC | DRG | B | 1 | -11.200 | -14.451 | -14.844 | 1.00 17.52 | C |
| ATOM | 995 | CAZ | DRG | B | 1 | -10.079 | -14.618 | -15.896 | 1.00 21.08 | C |
| ATOM | 996 | CBR | DRG | B | 1 | -8.687 | -14.328 | -15.306 | 1.00 23.31 | C |
| ATOM | 997 | CAP | DRG | B | 1 | -8.301 | -13.016 | -15.043 | 1.00 24.71 | C |
| ATOM | 998 | CAM | DRG | B | 1 | -7.787 | -15.367 | -15.048 | 1.00 23.64 | C |
| ATOM | 999 | CAN | DRG | B | 1 | -6.518 | -15.106 | -14.518 | 1.00 24.68 | C |
| ATOM | 1000 | CBV | DRG | B | 1 | -6.145 | -13.783 | -14.240 | 1.00 24.19 | C |
| ATOM | 1001 | OBH | DRG | B | 1 | -4.931 | -13.418 | -13.742 | 1.00 24.60 | O |
| ATOM | 1002 | CAA | DRG | B | 1 | -4.063 | -14.438 | -13.288 | 1.00 22.96 | C |
| ATOM | 1003 | CBW | DRG | B | 1 | -7.032 | -12.747 | -14.507 | 1.00 25.83 | C |
| ATOM | 1004 | OBI | DRG | B | 1 | -6.641 | -11.466 | -14.235 | 1.00 25.97 | O |
| ATOM | 1005 | CAB | DRG | B | 1 | -6.498 | -10.741 | -15.475 | 1.00 28.37 | C |
| ATOM | 1006 | OBO | DRG | B | 1 | -11.989 | -15.195 | -12.649 | 1.00 11.66 | O |
| ATOM | 1007 | C | DRG | B | 1 | -11.386 | -15.040 | -11.440 | 1.00 11.47 | C |
| ATOM | 1008 | O | DRG | B | 1 | -10.163 | -15.125 | -11.331 | 1.00 11.93 | O |
| ATOM | 1009 | CA | DRG | B | 1 | -12.279 | -14.765 | -10.225 | 1.00 10.49 | C |
| ATOM | 1010 | CB | DRG | B | 1 | -12.006 | -15.857 | -9.182 | 1.00 10.37 | C |
| ATOM | 1011 | CAU | DRG | B | 1 | -12.554 | -17.211 | -9.695 | 1.00 8.55 | C |

Figure 9 (cont.)

| | | | | | | | | | | |
|---|---|---|---|---|---|---|---|---|---|---|
| ATOM | 1012 | CAV | DRG | B | 1 | -14.070 | -17.112 | -9.865 | 1.00 | 9.52 | C |
| ATOM | 1013 | CBD | DRG | B | 1 | -14.485 | -16.006 | -10.866 | 1.00 | 9.57 | C |
| ATOM | 1014 | N | DRG | B | 1 | -13.709 | -14.741 | -10.657 | 1.00 | 10.07 | N |
| ATOM | 1015 | CBQ | DRG | B | 1 | -14.284 | -13.545 | -10.894 | 1.00 | 10.47 | C |
| ATOM | 1016 | OAG | DRG | B | 1 | -13.614 | -12.530 | -10.738 | 1.00 | 10.70 | O |
| ATOM | 1017 | CCD | DRG | B | 1 | -15.738 | -13.459 | -11.373 | 1.00 | 11.06 | C |
| ATOM | 1018 | CCA | DRG | B | 1 | -16.385 | -12.063 | -11.087 | 1.00 | 12.49 | C |
| ATOM | 1019 | CBA | DRG | B | 1 | -17.742 | -11.907 | -11.797 | 1.00 | 12.79 | C |
| ATOM | 1020 | CAT | DRG | B | 1 | -18.554 | -10.734 | -11.278 | 1.00 | 14.38 | C |
| ATOM | 1021 | CAS | DRG | B | 1 | -18.758 | -10.764 | -9.764 | 1.00 | 13.14 | C |
| ATOM | 1022 | CAH | DRG | B | 1 | -17.624 | -11.138 | -9.034 | 1.00 | 12.57 | C |
| ATOM | 1023 | CAI | DRG | B | 1 | -16.507 | -11.773 | -9.572 | 1.00 | 12.86 | C |
| ATOM | 1024 | CBU | DRG | B | 1 | -15.709 | -13.694 | -12.896 | 1.00 | 11.47 | C |
| ATOM | 1025 | CAR | DRG | B | 1 | -16.404 | -14.772 | -13.462 | 1.00 | 11.82 | C |
| ATOM | 1026 | CAQ | DRG | B | 1 | -14.992 | -12.806 | -13.709 | 1.00 | 11.36 | C |
| ATOM | 1027 | CBX | DRG | B | 1 | -14.964 | -12.997 | -15.107 | 1.00 | 13.43 | C |
| ATOM | 1028 | OBJ | DRG | B | 1 | -14.275 | -12.162 | -15.949 | 1.00 | 14.13 | O |
| ATOM | 1029 | CAC | DRG | B | 1 | -13.605 | -11.032 | -15.356 | 1.00 | 14.61 | C |
| ATOM | 1030 | CBZ | DRG | B | 1 | -15.652 | -14.078 | -15.667 | 1.00 | 12.30 | C |
| ATOM | 1031 | OBL | DRG | B | 1 | -15.637 | -14.244 | -17.026 | 1.00 | 13.63 | O |
| ATOM | 1032 | CAE | DRG | B | 1 | -14.548 | -15.006 | -17.551 | 1.00 | 13.39 | C |
| ATOM | 1033 | CBY | DRG | B | 1 | -16.364 | -14.965 | -14.865 | 1.00 | 13.52 | C |
| ATOM | 1034 | OBK | DRG | B | 1 | -17.028 | -15.998 | -15.486 | 1.00 | 14.34 | O |
| ATOM | 1035 | CAD | DRG | B | 1 | -17.682 | -16.912 | -14.571 | 1.00 | 17.29 | C |

SELECTIVE FKBP51 LIGANDS FOR TREATMENT OF PSYCHIATRIC DISORDERS

The present invention relates to selective FKBP51 ligand derivatives and stereoisomeric forms, prodrugs, solvates, hydrates and/or pharmaceutically acceptable salts of these compounds as well as pharmaceutical compositions containing at least one of these selective FKBP51 ligand derivatives together with pharmaceutically acceptable carrier, excipient and/or diluents. Said selective FKBP51 ligand derivatives have been identified to specifically inhibit the FKBP51 compared to FKBP52, and are useful for the treatment of psychiatric disorders and neurodegenerative diseases, metabolic disorders and obesity, or for treating prostate cancer or malignant melanoma. The present invention also relates to methods to identify, optimize or design selective FKBP51 ligand derivatives.

BACKGROUND OF THE INVENTION

The FK506-binding protein (FKBP) family of immunophilins consists of proteins with a variety of protein-protein interaction domains and versatile cellular functions. This highly conserved protein family binds with immunosuppressive drugs, such as FK506 and rapamycin. This protein family displays peptidyl propyl isomerase (PPIase) activity as seen with cyclophilins and parvulins. FKBP12, a 12 kD protein is the most widely studied member of this family.

The immunosuppressant drugs FK506, rapamycin, and cyclosporin are well known as potent T-cell specific immunosuppressants, and are effective against autoimmunity, transplant or graft rejection, inflammation, allergic responses, other autoimmune or immune-mediated diseases, and infectious diseases.

FK506 and rapamycin apart from binding to FKBP12 also interact and inhibit calcineurin (CaN) and mTOR respectively thereby mediating their immunosuppressive action.

The high molecular weight multidomain homologs of FKBP12, FKBP51 and FKBP 52, act as cochaperones for the heat shock protein 90 (Hsp90) and modulate the signal transduction of the glucocorticoid receptor by participating in the Heat shock protein 90 (Hsp90)-steroid receptor complex.

In this complex, FKBP51 and FKBP52 modulate the binding competence and signalling of steroid hormone receptors and thereby regulate the cellular responsiveness to circulating hormone levels. This is supported by a natural animal model (squirrel monkey) and by knockout mice, where the crucial role of FKBP51 and FKBP52 on the Glucocorticoid Receptor (GR) Progesterone Receptor (PR) or Androgen Receptor (AR) activity have been clearly demonstrated. Moreover, polymorphisms in the FKBP51-encoding gene of psychiatric patients have been associated with numerous stress-related psychiatric disorders (Schmidt et al., ChemMedChem 2012, 7, 1351-1359).

The immunosuppressive compounds disclosed in the prior art suppress the immune system, by definition, and also exhibit other toxic side effects. Accordingly, there is a need for non-immunosuppressant, small molecule compounds, and compositions and methods for use of such compounds, that are useful in treating psychiatric disorders and neurodegenerative diseases, disorders and conditions.

FKBP51 and FKBP52 have repeatedly been shown to regulate biological processes in opposite directions. Most importantly, FKBP51 and FKBP52 antagonize each other in the regulation of the glucocorticoid receptor and other steroid hormone receptors (Storer, C. L.; Dickey, C. A.; Galigniana, M. D.; Rein, T.; Cox, M. B., FKBP51 and FKBP52 in signaling and disease. *Trends Endocrinol Metab* 2011, 22, (12), 481-90). Therefore, there is a strong need for selective inhibitors that can discriminate between FKBP51 and FKBP52 (Schmidt et al ChemMedChem 2012, 7, 1351-1359). There is also a strong need for drugs to treat neuronal atrophy or degeneration or to enhance neurogenesis in diseases like depression, physical nerve injury and Alzheimer's, Huntington's, Parkinson's disease, ischemia or traumatic brain injury.

Selective inhibition of FKBP51 versus FKBP52 by small molecule inhibitors is very important to obtain more beneficial effects in these disorders. Selectivity between FKBP51 and FKBP52 represents a huge and unsolved hurdle, since the residues within the active site are completely conserved both on the sequence and the structural level (Bracher, A.; Kozany, C.; Thost, A. K.; Hausch, F., Structural characterization of the PPIase domain of FKBP51, a cochaperone of human Hsp90. *Acta Crystallogr D Biol Crystallogr* 2011, 67, (Pt 6), 549-59). Indeed, all known ligands for FKBP51 or FKBP52 show only negligible selectivity between these two FKBP homologs. The present invention describes the first ligands that are selective for FKBP51 compared to FKBP52. This selectivity for FKBP51 translates into an improved stimulation of neuritogenesis. The selectivity for FKBP51 is achieved by a conformational change in FKBP51 that is induced by the described FKBP51-selective ligands, which are much less favourable for FKBP52. This induced fit is the basis for rational design and synthesis of selective FKBP51 inhibitors.

It is the object of the present invention to provide compounds and/or pharmaceutically acceptable salts thereof which selectively inhibit FKBP51 but which show no immunosuppressive activity and improved stimulation of neuritogenesis.

A further aspect of the invention is to provide compounds and/or pharmaceutically acceptable salts thereof which can be used as pharmaceutically active agents, especially for the treatment of psychiatric disorders and neurodegenerative diseases, cancers like prostate cancer, acute lymphoblastic leukaemia or malignant melanoma, obesity, metabolic syndrome, diabetes, asthma, sleeping disorders, vision disorders and/or improving vision, for treating memory impairment and/or enhancing memory performance and for treating alopecia, as well as compositions comprising at least one of those compounds and/or pharmaceutically acceptable salts thereof as pharmaceutically active ingredients.

Furthermore, it is the object of the present invention to provide methods for identifying, optimizing and designing compounds as selective inhibitors of FKBP51 based on the structural information specific for the induced fit conformation, which is the underlying basis for the FKBP51-selectivity.

The object of the present invention is solved by the teaching of the independent claims. Further advantageous features, aspects and details of the invention are evident from the dependent claims, the description, and the examples of the present application.

DESCRIPTION OF THE INVENTION

The novel selective FKBP51 ligand derivatives according to the present invention are represented by the following general formula (I):

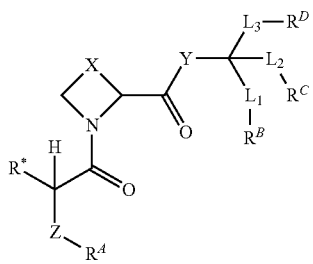
(I)

wherein

X represents —CH$_2$—, —CH$_2$CH$_2$—, —CH$_2$CH$_2$CH$_2$—, —CH=CH—, —CH=CHCH$_2$—, —CH$_2$SCH$_2$—, —CH$_2$OCH$_2$—, —SCH$_2$—, —SCH$_2$CH$_2$—, —CHFCH$_2$—, —CH(CH$_3$)CH$_2$—, —CH(CH$_3$)CH$_2$CH$_2$—, —CH$_2$CH(CH$_3$)—, —C(CH$_3$)$_2$—CH$_2$—,

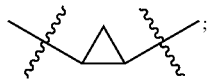

Y represents —NH—, —O—;

Z represents a covalent bond, —NHCO—, —CHR$^{39}$—NHCO—, —CH(NHCOR$^{39}$)—;

R* represents —R$^{18}$, —CH$_2$—R$^{18}$, —R, —CH$_2$—R, —CH(OR')R", —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —CH$_2$-cyclo-C$_3$H$_5$, —CH$_2$-cyclo-C$_6$H$_{11}$, —CH$_2$—CH=CH$_2$, —CH$_2$-cyclo-C$_6$H$_9$, -Ph, —CH$_2$-Ph, -cyclo-C$_6$H$_{11}$, -cyclo-C$_5$H$_9$, —CH$_2$—C(CH$_3$)=CH$_2$, —CH(CH$_3$)-cyclo-C$_3$H$_5$, —CH(CH$_3$)—CH=CH$_2$;

R** represents

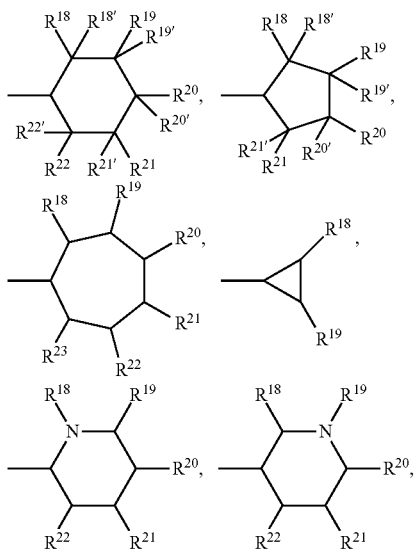

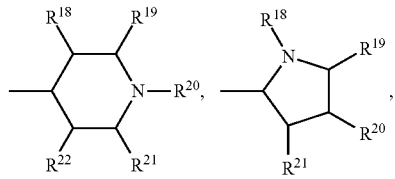

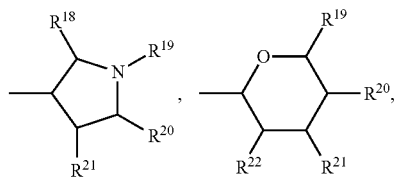

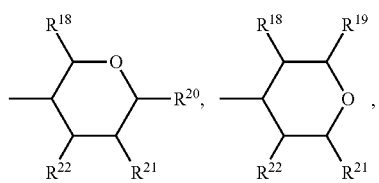

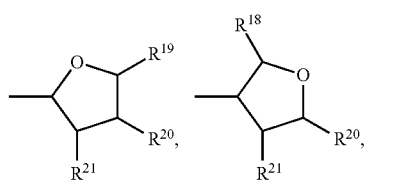

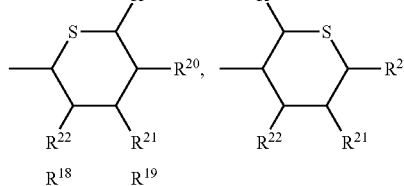

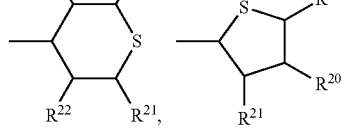

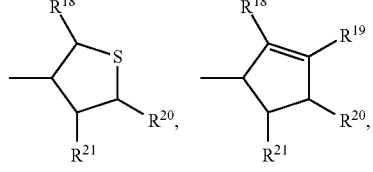

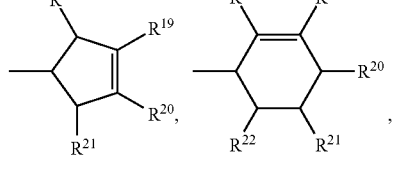

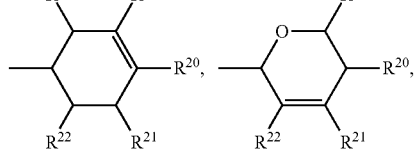

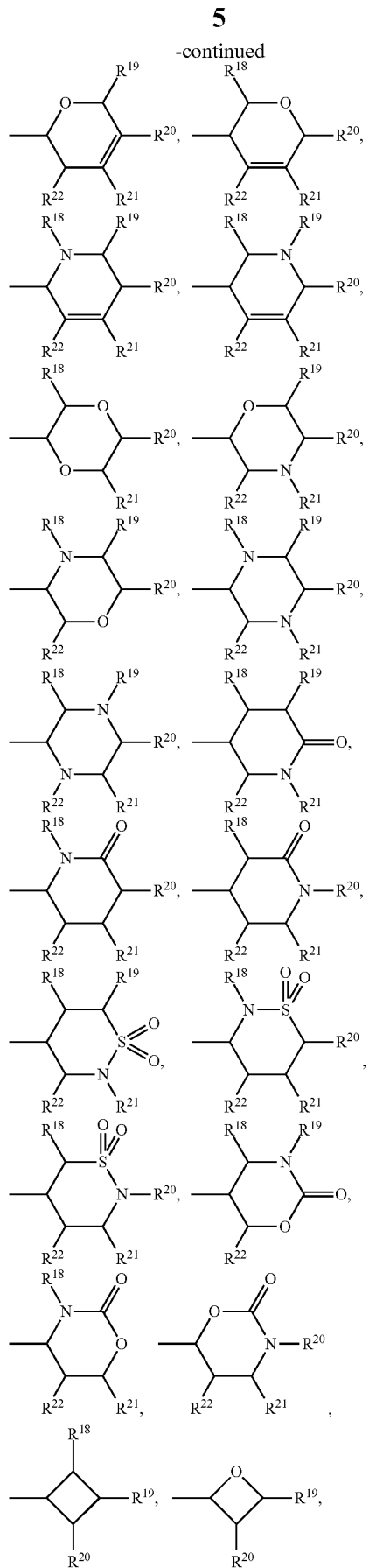
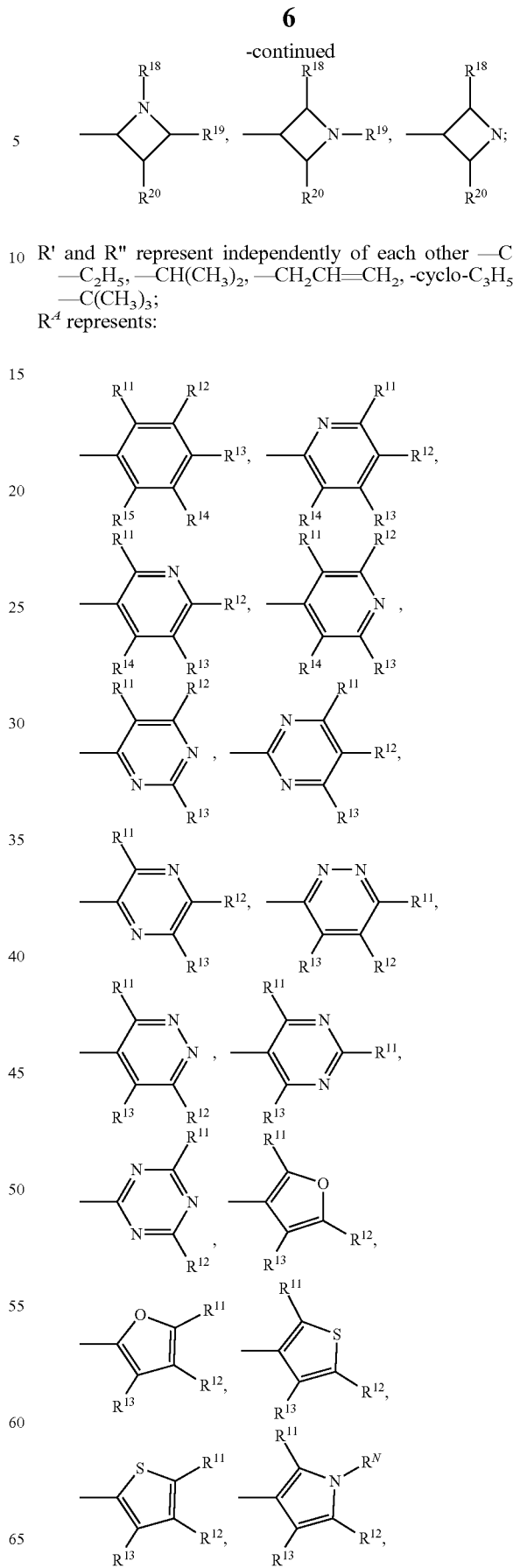
R' and R" represent independently of each other —CH$_3$, —C$_2$H$_5$, —CH(CH$_3$)$_2$, —CH$_2$CH=CH$_2$, -cyclo-C$_3$H$_5$, or —C(CH$_3$)$_3$;
R$^A$ represents:

-continued
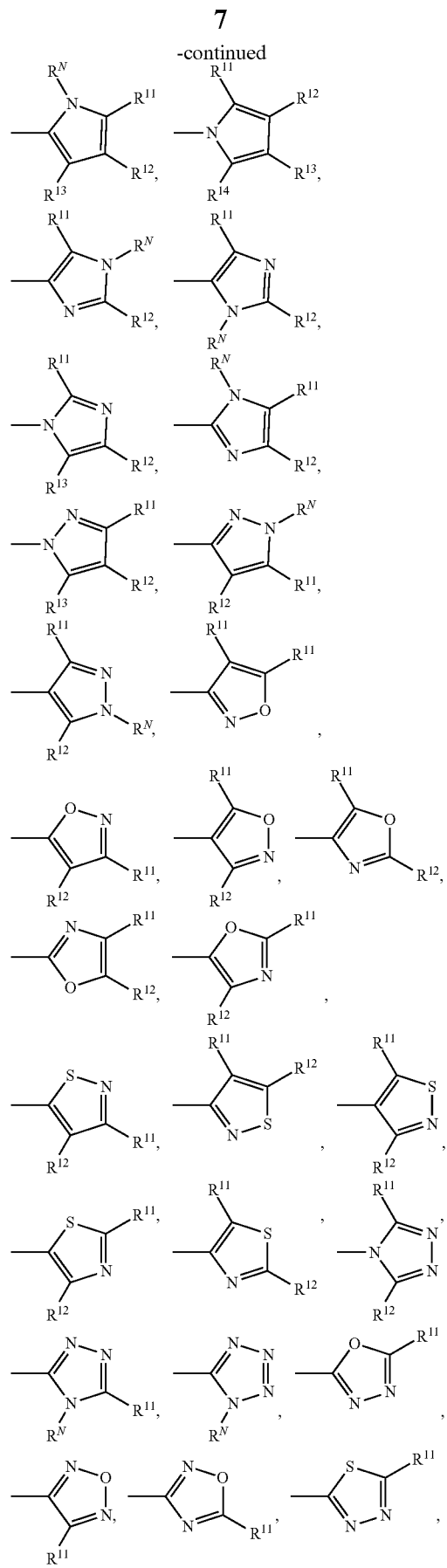
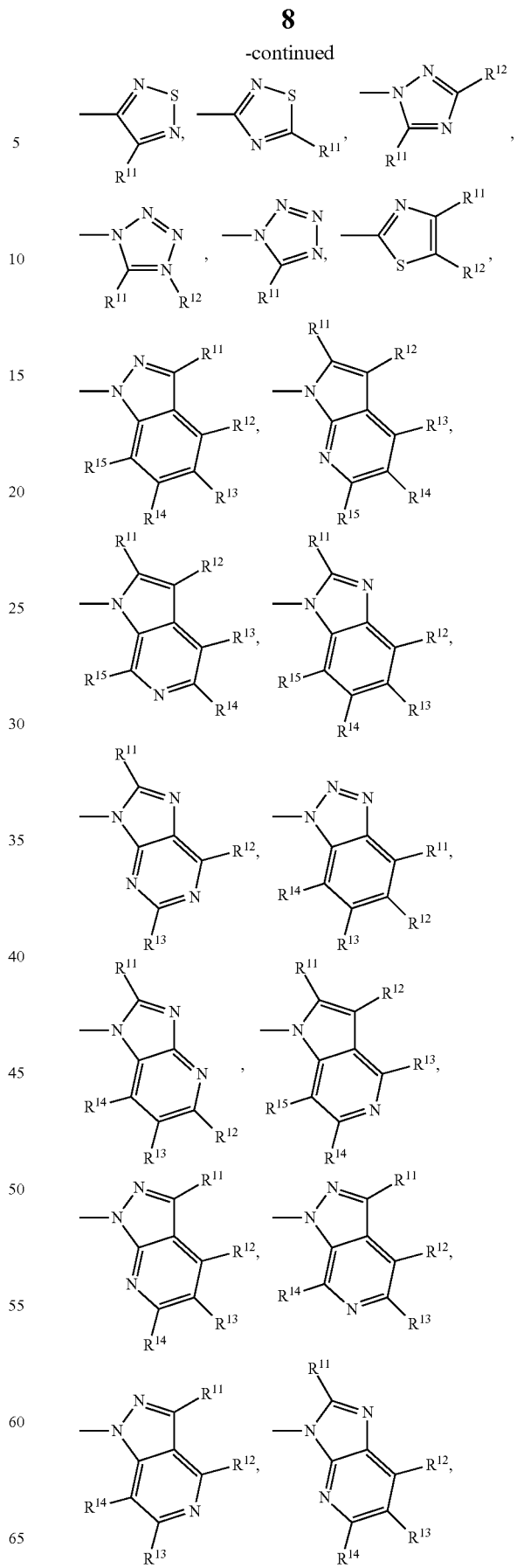

-continued
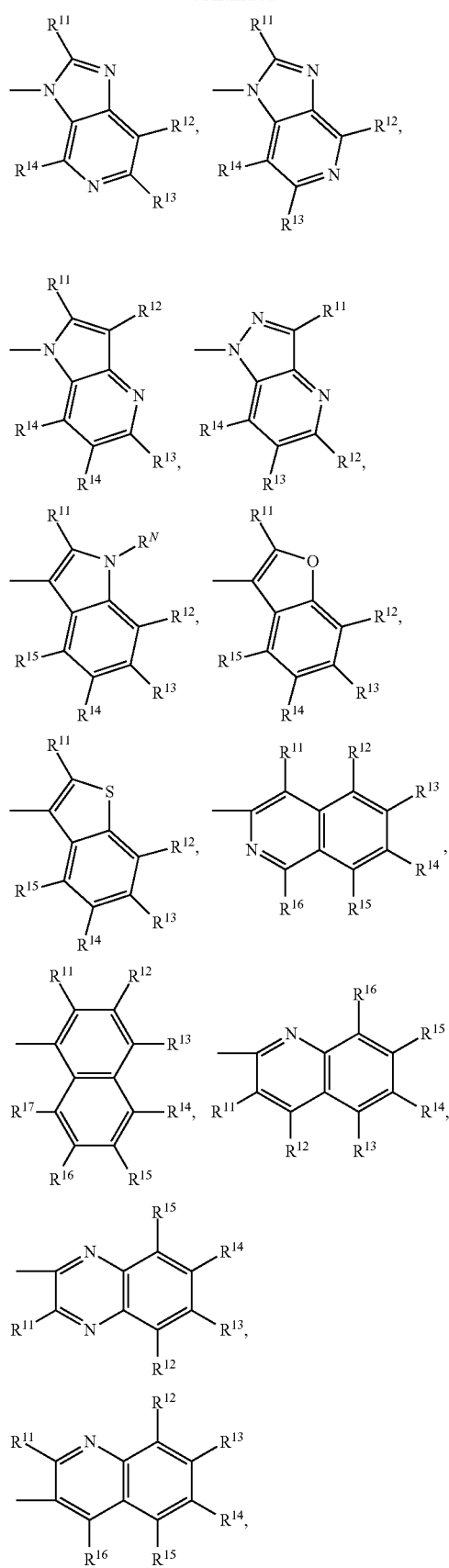
-continued
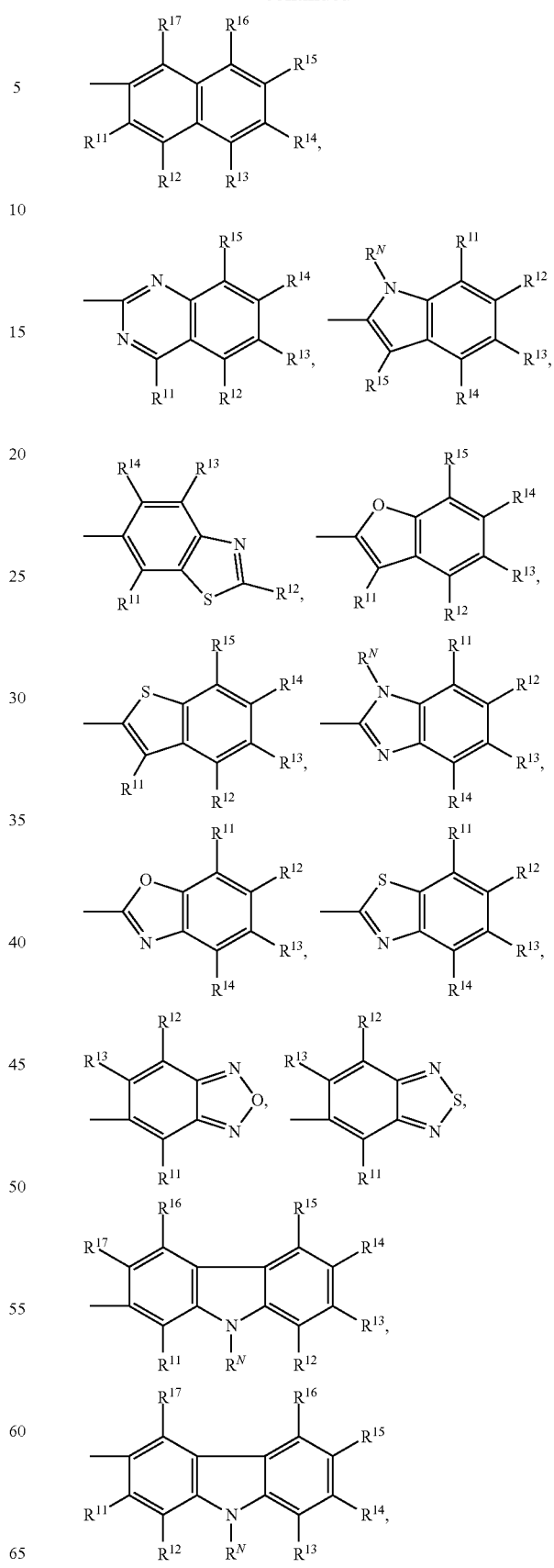

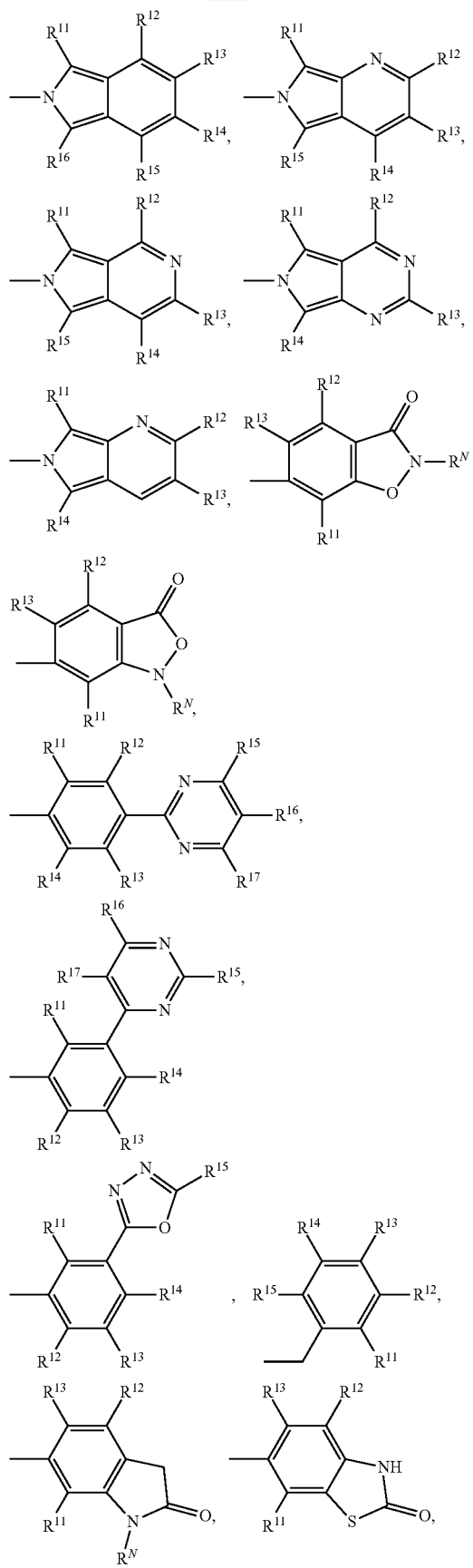
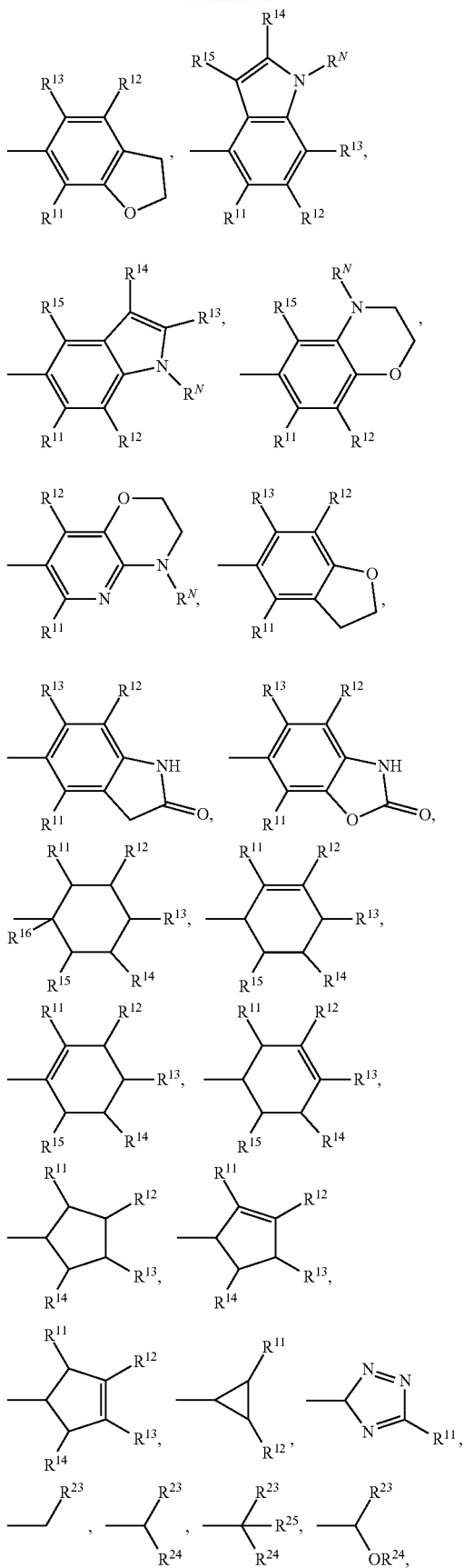

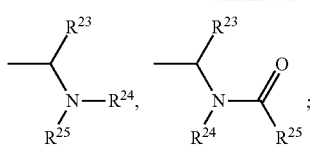
$R^B$ represents: $R^{26}$ or
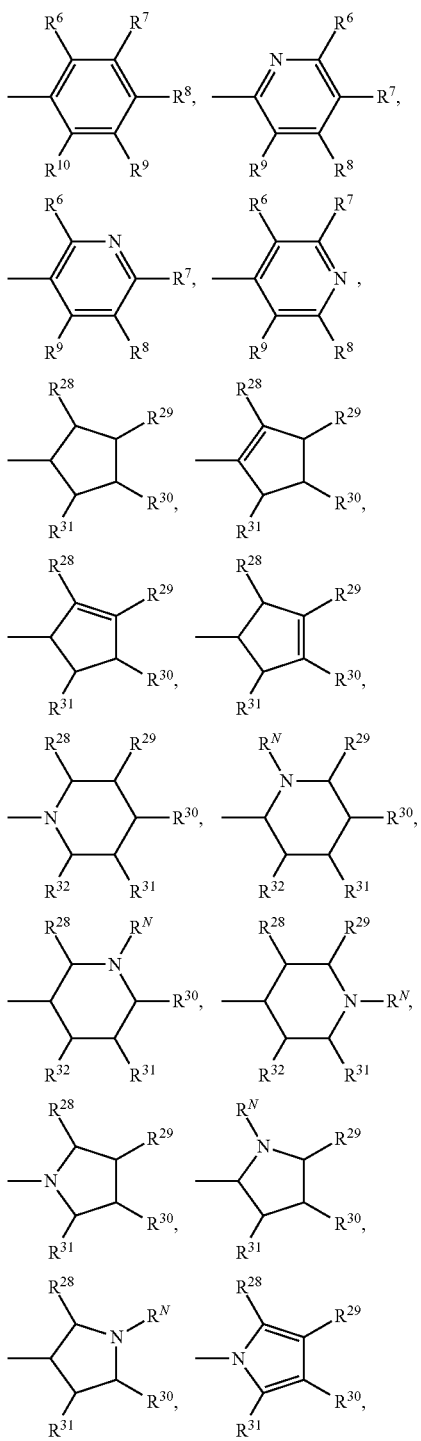
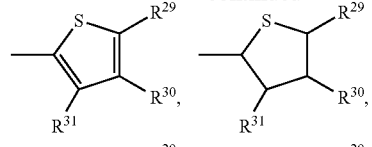
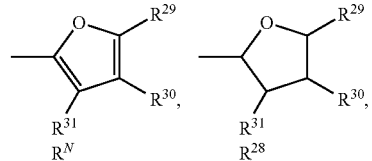
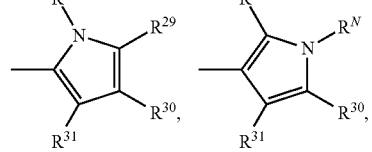
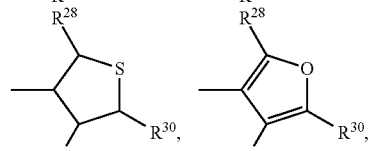
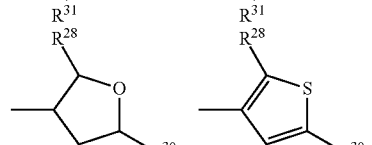
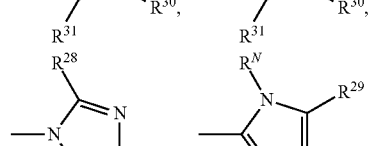
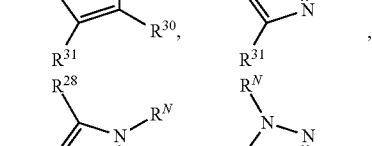
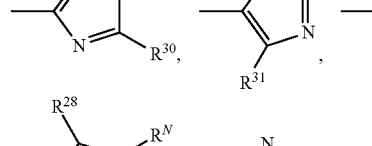
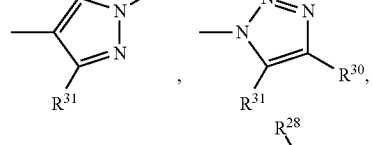
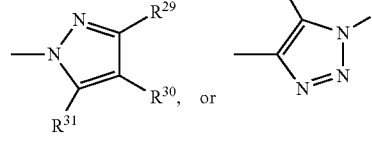
$R^C$ represents: $R^{27}$ or
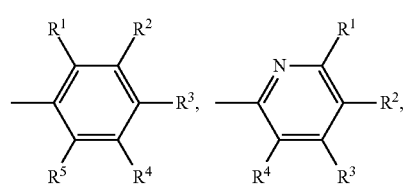

-continued
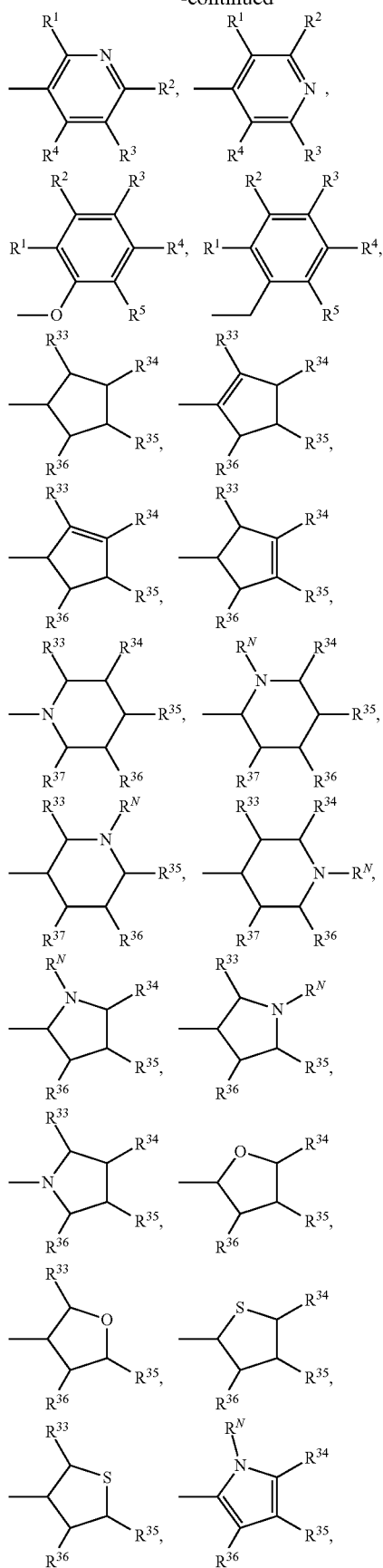
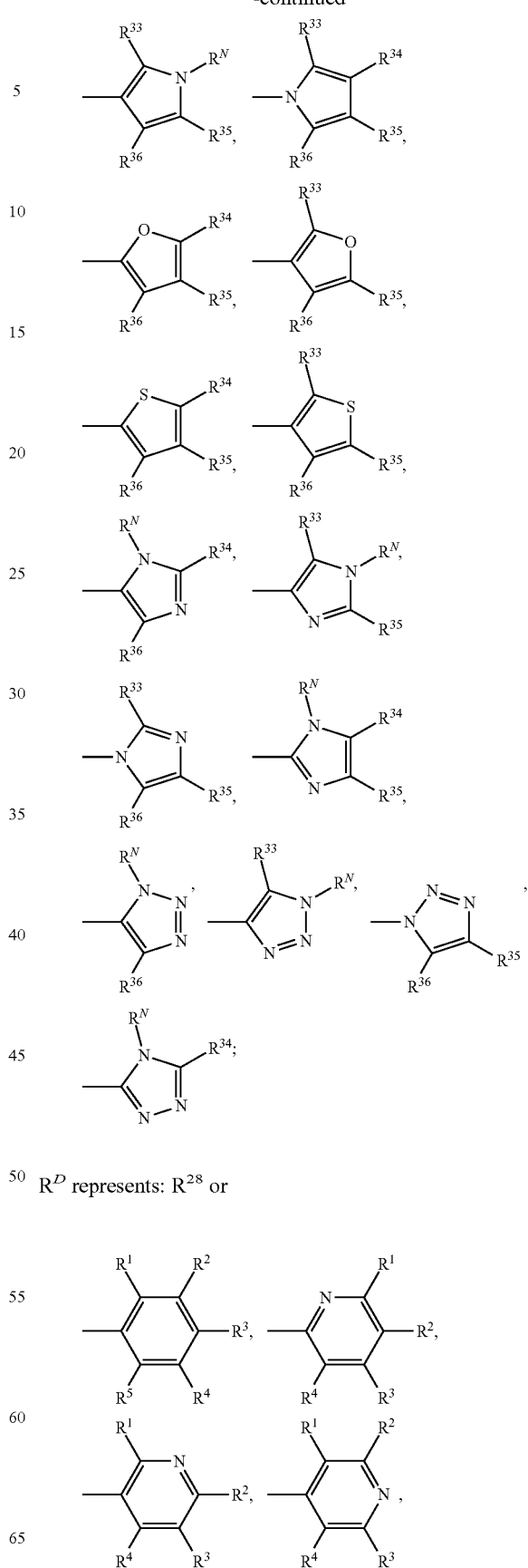
$R^D$ represents: $R^{28}$ or

-continued

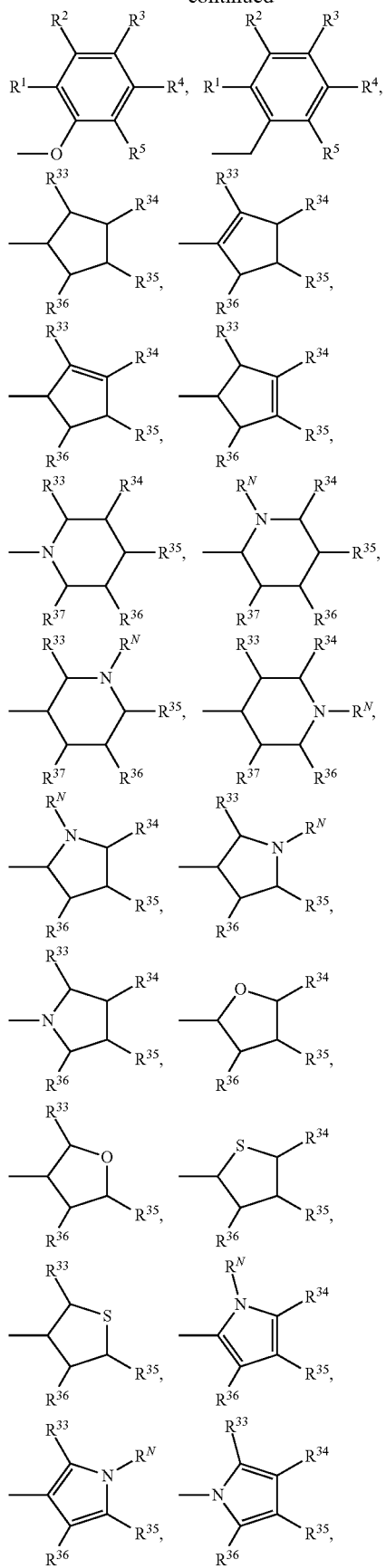
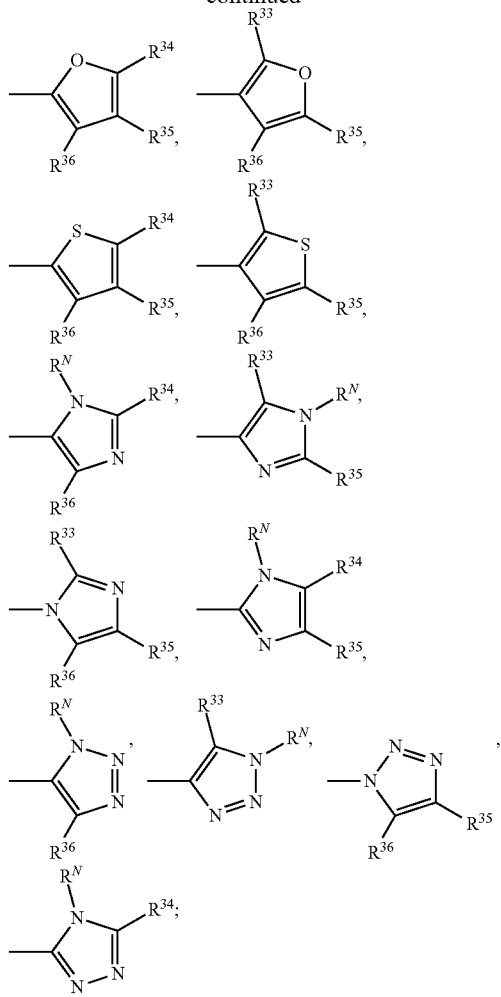

$R^1$-$R^{22}$, $R^{18'}$-$R^{22'}$, $R^{26}$-$R^{39}$ represent independently of each other —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OCH$_2$—COOH, —OPh, —OCH$_2$-Ph, —OCPh$_3$, —CH$_2$—OH, —C$_2$H$_4$—OH, —C$_3$H$_6$—OH, —CH(OH)—CH$_2$—OH, —CH$_2$—OCH$_3$, —C$_2$H$_4$—OCH$_3$, —C$_3$H$_6$—OCH$_3$, —C$_4$H$_8$—OCH$_3$, —CH$_2$—OC$_2$H$_5$, —C$_2$H$_4$—OC$_2$H$_5$, —C$_3$H$_6$—OC$_2$H$_5$, —C$_4$H$_8$—OC$_2$H$_5$, —CH$_2$—OC$_3$H$_7$, —C$_2$H$_4$—OC$_3$H$_7$, —C$_3$H$_6$—OC$_3$H$_7$, —C$_4$H$_8$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —C$_4$H$_8$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —C$_4$H$_8$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —C$_4$H$_8$—OC(CH$_3$)$_3$, —CH$_2$—OC$_4$H$_9$, —C$_2$H$_4$—OC$_4$H$_9$, —C$_3$H$_6$—OC$_4$H$_9$, —C$_4$H$_8$—OC$_4$H$_9$, —CH$_2$—OPh, —C$_2$H$_4$—OPh, —C$_3$H$_6$—OPh, —C$_4$H$_8$—OPh, —CH$_2$—OCH$_2$-Ph, —C$_2$H$_4$—OCH$_2$-Ph, —C$_3$H$_6$—OCH$_2$-Ph, —C$_4$H$_8$—OCH$_2$-Ph, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —P(O)(OH)$_2$, —P(O)(OCH$_3$)$_2$, —P(O)(OC$_2$H$_5$)$_2$, —P(O)(OCH(CH$_3$)$_2$)$_2$, —C(OH)[P(O)(OH)$_2$]$_2$, —Si(CH$_3$)$_2$(C(CH$_3$)$_3$), —Si(C$_2$H$_5$)$_3$, —Si(CH$_3$)$_3$, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CH₂—CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCOCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —SO₂NHCH₃, —SO₂NHC₂H₅, —SO₂NHC₃H₇, —SO₂NH-cyclo-C₃H₅, —SO₂NHCH(CH₃)₂, —SO₂NHC(CH₃)₃, —SO₂N(CH₃)₂, —SO₂N(C₂H₅)₂, —SO₂N(C₃H₇)₂, —SO₂N(cyclo-C₃H₅)₂, —SO₂N[CH(CH₃)₂]₂, —SO₂N[C(CH₃)₃]₂, —O—S(=O)CH₃, —O—S(=O)C₂H₅, —O—S(=O)C₃H₇, —O—S(=O)-cyclo-C₃H₅, —O—S(=O)CH(CH₃)₂, —O—S(=O)C(CH₃)₃, —S(=O)(=NH)CH₃, —S(=O)(=NH)C₂H₅, —S(=O)(=NH)C₃H₇, —S(=O)(=NH)-cyclo-C₃H₅, —S(=O)(=NH)CH(CH₃)₂, —S(=O)(=NH)C(CH₃)₃, —NH—SO₂—CH₃, —NH—SO₂—C₂H₅, —NH—SO₂—C₃H₇, —NH—SO₂-cyclo-C₃H₅, —NH—SO₂—CH(CH₃)₂, —NH—SO₂—C(CH₃)₃, —O—SO₂—CH₃, —O—SO₂—C₂H₅, —O—SO₂—C₃H₇, —O—SO₂-cyclo-C₃H₅, —O—SO₂—CH(CH₃)₂, —O—SO₂—jC(CH₃)₃, —OCF₃, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CS—N(C₃H₇)₂, —NH—CO—NHC₃H₇, —NH—CO—N(C₃H₇)₂, —NH—CO—NH[CH(CH₃)₂], —NH—CO—NH[C(CH₃)₃], —NH—CO—N(CH₃)₂, —NH—CO—N(C₂H₅)₂, —NH—CO—NH-cyclo-C₃H₅, —NH—CO—N(cyclo-C₃H₅)₂, —NH—CO—N[CH(CH₃)₂]₂, —NH—CS—N(C₂H₅)₂, —NH—CO—N[C(CH₃)₃]₂, —NH—CS—NH₂, —NH—CS—NHCH₃, —NH—CS—N(CH₃)₂, —NH—CS—NHC₂H₅, —NH—CS—NHC₃H₇, —NH—CS—NH-cyclo-C₃H₅, —NH—CS—NH[CH(CH₃)₂], —NH—CS—NH[C(CH₃)₃], —NH—CS—N(cyclo-C₃H₅)₂, —NH—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—C(=NH)—NHC₃H₇, —O—CO—NH-cyclo-C₃H₅, —NH—C(=NH)—NH-cyclo-C₃H₅, —NH—C(=NH)—NH[CH(CH₃)₂], —O—CO—NH[CH(CH₃)₂], —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —O—CO—NHC₃H₇, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃H₅, —O—CO—OCH(CH₃)₂, —O—CO—OC(CH₃)₃, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₅H₉, -cyclo-C₆H₁₁, —CH₂-cyclo-C₆H₁₁, —CH₂—CH₂-cyclo-C₆H₁₁, -cyclo-C₇H₁₃, -cyclo-C₈H₁₅, -Ph, —CH₂-Ph, —CH₂—CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)—, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH=CH₂, —CH=C(CH₃)—CH=CH₂, —CH=CH—C(CH₃)=CH₂, —CH=CH—CH=CH—CH₃, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH —$CH_3$)—$C(C_2H_5)$=$CH_2$, —$CH_2$—$C(C_3H_7)$=$CH_2$, —$CH_2$—$C(C_2H_5)$=$CH$—$CH_3$, —$CH(C_2H_5)$—$CH$=$CH$—$CH_3$, —$C(C_4H_9)$=$CH_2$, —$C(C_3H_7)$=$CH$—$CH_3$, —$C(C_2H_5)$=$CH$—$C_2H_5$, —$C(C_2H_5)$=$C(CH_3)_2$, —$C[CH(CH_3)(C_2H_5)]$=$CH_2$, —$C[CH_2$—$CH(CH_3)_2]$=$CH_2$, —$C_2H_4$—$CH$=$CH$—$CH$=$CH_2$, —$CH_2$—$CH$=$CH$—$CH_2$—$CH$=$CH_2$, —$C_3H_6$—$C$≡$C$—$CH_3$, —$CH_2$—$CH$=$CH$—$CH$=$CH$—$CH_3$, —$CH$=$CH$—$CH$=$CH$—$C_2H_5$, —$CH_2$—$CH$=$CH$—$C(CH_3)$=$CH_2$, —$CH_2$—$CH$=$C(CH_3)$—$CH$=$CH_2$, —$CH_2$—$C(CH_3)$=$CH$—$CH$=$CH_2$, —$CH(CH_3)$—$CH_2$—$C$≡$CH$, —$CH(CH_3)$—$CH$=$CH$—$CH$=$CH_2$, —$CH$=$CH$—$CH_2$—$C(CH_3)$=$CH_2$, —$CH(CH_3)$—$C$≡$C$—$CH_3$, —$CH$=$CH$—$CH(CH_3)$—$CH$=$CH_2$, —$CH$=$C(CH_3)$—$CH_2$—$CH$=$CH_2$, —$C_2H_4$—$CH(CH_3)$—$C$≡$CH$, —$C(CH_3)$=$CH$—$CH_2$—$CH$=$CH_2$, —$CH$=$CH$—$CH$=$C(CH_3)_2$, —$CH_2$—$CH(CH_3)$—$CH_2$—$C$≡$CH$, —$CH$=$CH$—$C(CH_3)$=$CH$—$CH_3$, —$CH$=$C(CH_3)$—$CH$=$CH$—$CH_3$, —$CH_2$—$CH(CH_3)$—$C$≡$CH$, —$C(CH_3)$=$CH$—$CH$=$CH$—$CH_3$, —$CH$=$C(CH_3)$—$C(CH_3)$=$CH_2$, —$C(CH_3)$=$CH$—$C(CH_3)$=$CH_2$, —$C(CH_3)$=$C(CH_3)$—$CH$=$CH_2$, —$CH$=$CH$—$CH$=$CH$—$CH$=$CH_2$, —$C$≡$CH$, —$C$≡$C$—$CH_3$, —$CH_2$—$C$≡$CH$, —$C_2H_4$—$C$≡$CH$, —$CH_2$—$C$≡$C$—$CH_3$, —$C$≡$C$—$C_2H_5$, —$C_3H_6$—$C$≡$CH$, —$C_2H_4$—$C$≡$C$—$CH_3$, —$CH_2$—$C$≡$C$—$C_2H_5$, —$C$≡$C$—$C_3H_7$, —$CH(CH_3)$—$C$≡$CH$, —$C_4H_8$—$C$≡$CH$, —$C_2H_4$—$C$≡$C$—$C_2H_5$, —$CH_2$—$C$≡$C$—$C_3H_7$, —$C$≡$C$—$C_4H_9$, —$C$≡$C$—$C(CH_3)_3$, —$CH(CH_3)$—$C_2H_4$—$C$≡$CH$, —$CH_2$—$CH(CH_3)$—$C$≡$C$—$CH_3$, —$CH(CH_3)$—$CH_2$—$C$≡$C$—$CH_3$, —$CH(CH_3)$—$C$≡$C$—$C_2H_5$, —$CH_2$—$C$≡$C$—$CH(CH_3)_2$, —$C$≡$C$—$CH(CH_3)$—$C_2H_5$, —$C(CH_3)_2$—$C$≡$C$—$CH_3$, —$CH(C_2H_5)$—$C$≡$C$—$CH_3$, —$C(CH_3)_2$—$C$≡$C$—$CH_3$, —$CH(C_2H_5)$—$CH_2$—$C$≡$CH$, —$CH_2$—$CH(C_2H_5)$—$C$≡$CH$, —$C(CH_3)_2$—$CH_2$—$C$≡$CH$, —$CH_2$—$C(CH_3)_2$—$C$≡$CH$, —$CH(CH_3)$—$CH(CH_3)$—$C$≡$CH$, —$CH(C_3H_7)$—$C$≡$CH$, —$C(CH_3)(C_2H_5)$—$C$≡$CH$, —$CH_2$—$CH(C$≡$CH)_2$, —$C$≡$C$—$C$≡$CH$, —$CH_2$—$C$≡$C$—$C$≡$CH$, —$C$≡$C$—$C$≡$C$—$CH_3$, —$CH(C$≡$CH)_2$, —$C_2H_4$—$C$≡$C$—$C$≡$CH$, —$CH_2$—$C$≡$C$—$CH_2$—$C$≡$CH$, —$C$≡$C$—$C_2H_4$—$C$≡$CH$, —$CH_2$—$C$≡$C$—$C$≡$C$—$CH_3$, —$C$≡$C$—$CH_2$—$C$≡$C$—$CH_3$, —$C$≡$C$—$C$≡$C$—$C_2H_5$, —$C(C$≡$CH)_2$—$CH_3$, —$C$≡$C$—$CH(CH_3)$—$C$≡$CH$, —$CH(CH_3)$—$C$≡$C$—$C$≡$CH$, —$CH(C$≡$CH)$—$CH_2$—$C$≡$CH$, —$CH(C$≡$CH)$—$C$≡$C$—$CH_3$,

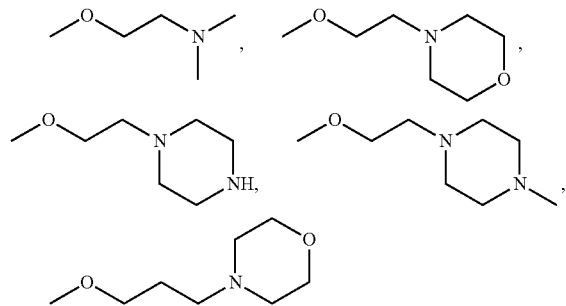

or
$R^{18}$ and $R^{18'}$ or $R^{19}$ and $R^{19'}$ or $R^{20}$ and $R^{20'}$ or $R^{21}$ and $R^{21'}$ or $R^{22}$ and $R^{22'}$ can form together =O,

or =$CR^{23'}R^{24'}$, wherein $R^{23'}$ and $R^{24'}$ represent of each other —H, —$CH_3$, —$C_2H_5$, —$CF_3$, —$CH_2CF_3$, —$C_2F_5$;
$R^{23}$-$R^{25}$ represent independently of each other —H, —$CH_2$—$OCH_3$, —$C_2H_4$—$OCH_3$, —$C_3H_6$—$OCH_3$, —$CH_2$—$OC_2H_5$, —$C_2H_4$—$OC_2H_5$, —$C_3H_6$—$OC_2H_5$, —$CH_2$—$OC_3H_7$, —$C_2H_4$—$OC_3H_7$, —$C_3H_6$—$OC_3H_7$, —$CH_2$—$O$-cyclo-$C_3H_5$, —$C_2H_4$—$O$-cyclo-$C_3H_5$, —$C_3H_6$—$O$-cyclo-$C_3H_5$, —$CH_2$—$OCH(CH_3)_2$, —$C_2H_4$—$OCH(CH_3)_2$, —$C_3H_6$—$OCH(CH_3)_2$, —$CH_2$—$OC(CH_3)_3$, —$C_2H_4$—$OC(CH_3)_3$, —$C_3H_6$—$OC(CH_3)_3$, —$CH_2$—$OC_4H_9$, —$C_2H_4$—$OC_4H_9$, —$C_3H_6$—$OC_4H_9$, —$CH_2$—$OPh$, —$C_2H_4$—$OPh$, —$C_3H_6$—$OPh$, —$CH_2$—$OCH_2$-$Ph$, —$C_2H_4$—$OCH_2$-$Ph$, —$C_3H_6$—$OCH_2$-$Ph$, —$CH_2F$, —$CHF_2$, —$CF_3$, —$CH_2Cl$, —$CH_2Br$, —$CH_2I$, —$CH_2$—$CH_2F$, —$CH_2$—$CHF_2$, —$CH_2$—$CF_3$, —$CH_2$—$CH_2Cl$, —$CH_2$—$CH_2Br$, —$CH_2$—$CH_2I$, -cyclo-$C_8H_{15}$, -Ph, —$CH_2$-Ph, —$CH_2$—$CH_2$-Ph, —$CH$=$CH$-Ph, —$CPh_3$, —$CH_3$, —$C_2H_5$, —$C_3H_7$, —$CH(CH_3)_2$, —$C_4H_9$, —$CH_2$—$CH(CH_3)_2$, —$CH(CH_3)$—$C_2H_5$, —$C(CH_3)_3$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$CH(C_2H_5)_2$, —$C_2H_4$—$CH(CH_3)_2$, —$C_6H_{13}$, —$C_7H_{15}$, —$C_8H_{17}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$CH$=$CH_2$, —$CH_2$—$CH$=$CH_2$, —$C(CH_3)$=$CH_2$, —$CH$=$CH$—$CH_3$, —$C_2H_4$—$CH$=$CH_2$, —$CH_2$—$CH$=$CH$—$CH_3$, —$CH$=$CH$—$C_2H_5$, —$CH_2$—$C(CH_3)$=$CH_2$, —$CH(CH_3)$—$CH$=$CH$, —$CH$=$C(CH_3)_2$, —$C(CH_3)$=$CH$—$CH_3$, —$CH$=$CH$—$CH$=$CH_2$, —$C_3H_6$—$CH$=$CH_2$, —$C_2H_4$—$CH$=$CH$—$CH_3$, —$CH_2$—$CH$=$CH$—$C_2H_5$, —$CH$=$CH$—$C_3H_7$, —$CH_2$—$CH$=$CH$—$CH_2$, —$CH$=$CH$—$CH$=$CH$—$CH_3$, —$CH$=$CH$—$CH_2$—$CH$=$CH_2$, —$C(CH_3)$=$CH$—$CH$=$CH_2$, —$CH$=$C(CH_3)$—$CH$=$CH_2$, —$C_2H_4$—$C(CH_3)$=$CH_2$, —$CH_2$—$CH(CH_3)$—$CH$=$CH_2$, —$CH(CH_3)$—$CH_2$—$CH$=$CH_2$, —$CH_2$—$CH$=$C(CH_3)_2$, —$CH_2$—$C(CH_3)$=$CH$—$CH_3$, —$CH(CH_3)$—$CH$=$CH$—$CH_3$, —$CH$=$CH$—$CH(CH_3)_2$, —$CH$=$C(CH_3)$—$C_2H_5$, —$C(CH_3)$=$CH$—$C_2H_5$, —$C(CH_3)$=$C(CH_3)_2$, —$C(CH_3)_2$—$CH$=$CH_2$, —$CH(CH_3)$—$C(CH_3)$=$CH_2$, —$C(CH_3)$=$CH$—$CH$=$CH_2$, —$CH$=$C(CH_3)$—$CH$=$CH_2$, —$CH$=$CH$—$C(CH_3)$=$CH_2$, —$C_4H_8$—$CH$=$CH_2$, —$C_3H_6$—$CH$=$CH$—$CH_3$, —$C_2H_4$—$CH$=$CH$—$C_2H_5$, —$CH_2$—$CH$=$CH$—$C_3H_7$, —$CH$=$CH$—$C_4H_9$, —$C_3H_6$—$C(CH_3)$=$CH_2$, —$C_2H_4$—$CH(CH_3)$—$CH$=$CH_2$, —$CH_2$—$CH(CH_3)$—$CH_2$—$CH$=$CH_2$, —$C_2H_4$—$CH$=$C(CH_3)_2$, —$CH(CH_3)$—$C_2H_4$—$CH$=$CH_2$, —$C_2H_4$—$C(CH_3)$=$CH$—$CH_3$, —$CH_2$—$CH(CH_3)$—$CH$=$CH$—$CH_3$, —$CH(CH_3)$—$CH_2$—$CH$=$CH$—$CH_3$, —$CH_2$—$CH$=$CH$—$CH(CH_3)_2$, —$CH_2$—$CH$=$C(CH_3)$—$C_2H_5$, —$CH_2$—$C(CH_3)$=$CH$—$C_2H_5$, —$CH(CH_3)$—$CH$=$CH$—$C_2H_5$, —$CH$=$CH$—$CH_2$—$CH(CH_3)_2$, —$CH$=$CH$—$CH(CH_3)$—$C_2H_5$, —$CH$=$C(CH_3)$—$C_3H_7$, —$C(CH_3)$=$CH$—$C_3H_7$, —$CH_2$—$CH(CH_3)$—$C(CH_3)$=$CH_2$, —$C[C(CH_3)_3]$=$CH_2$, —$CH(CH_3)$—$CH_2$—$C(CH_3)$ =CH₂, —CH(CH₃)—CH(CH₃)—CH=CH₂, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH₂—C≡CH, —CH(CH₃)—CH=CH—CH=CH₂, —CH=CH—CH₂—C(CH₃)=CH₂, —CH(CH₃)—C≡C—CH₃, —CH=CH—CH₂—CH(CH₃)—CH=CH₂, —CH=C(CH₃)—CH=CH₂, —C₂H₄—CH(CH₃)—C≡CH, —C(CH₃)=CH—CH₂—CH=CH₂, —CH=CH—C(CH₃)=CH(CH₃)₂, —CH₂—CH(CH₃)—CH₂—C≡CH, —CH=CH—CH(CH₃)=CH—CH₃, —CH=C(CH₃)—CH=CH—CH₃, —CH₂—CH(CH₃)—C≡CH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃;

R^N represents —H, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —CHO, —COCH₃, —COC₂H₅, —COC₃H₇, —CO-cyclo-C₃H₅, —COCH(CH₃)₂, —COC(CH₃)₃, —COCN, —COOCH₃, —COOC₂H₅, —COOC₃H₇, —COO-cyclo-C₃H₅, —COOCH(CH₃)₂, —COOC(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —SO₂CH₃, —SO₂C₂H₅, —SO₂C₃H₇, —SO₂-cyclo-C₃H₅, —SO₂CH(CH₃)₂, —SO₂C(CH₃)₃, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₈H₁₅, -Ph, —CH₂-Ph, —CH₂—CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅—C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)₂—CH=CH₂, —C(CH₃)=CH—CH=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH₂, —CH=CH—C₂H₄—CH=CH₂, —CH₂—C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH (CH₃)₂, —C(CH₃)═C(CH₃)—C₂H₅, —CH═CH—C(CH₃)₃, —C(CH₃)₂—C(CH₃)═CH₂, —CH(C₂H₅)—C(CH₃)═CH₂, —C(CH₃)(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₉)═CH₂, —C(C₃H₇)═CH—CH₃, —C(C₂H₅)═CH—C₂H₅, —C(C₂H₅)═C(CH₃)₂, —C[CH(CH₃)(C₂H₅)]═CH₂, —C[CH₂—CH(CH₃)₂]═CH₂, —C₂H₄—CH═CH—CH═CH₂, —CH₂—CH═CH—CH₂—CH═CH₂, —C₃H₆—C≡C—CH₃, —CH₂—CH═CH—CH═CH—CH₃, —CH═CH—CH═CH—C₂H₅, —CH₂—CH═CH—C(CH₃)═CH₂, —CH₂—CH═C(CH₃)—CH═CH₂, —CH₂—C(CH₃)═CH—CH═CH₂, —CH(CH₃)—CH₂—C≡CH, —CH(CH₃)—CH═CH—CH═CH₂, —CH═CH—CH₂—C(CH₃)═CH₂, —CH(CH₃)—C≡C—CH₃, —CH═CH—CH(CH₃)—CH═CH₂, —CH═C(CH₃)—CH₂—CH═CH₂, —C₂H₄—CH(CH₃)—C≡CH, —C(CH₃)═CH—CH₂—CH═CH₂, —CH═CH—CH═C(CH₃)₂, —CH₂—CH(CH₃)—CH₂—C≡CH, —CH═CH—C(CH₃)═CH—CH₃, —CH═C(CH₃)—CH═CH—CH₃, —CH₂—CH(CH₃)—C≡CH, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH═CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃;

L₁, L₂ and L₃ represent independently of each other:
a bond, —CH₂—, —C₂H₄—, —C₃H₆—, —C₄H₈—, —C₅H₁₀—, —C₆H₁₂—, —C₇H₁₄—, —C₈H₁₆—, —C₉H₁₈—, —C₁₀H₂₀—, —CH(CH₃)—, —C[(CH₃)₂]—, —CH₂—CH(CH₃)—, —CH(CH₃)—CH₂—, —CH(CH₃)—C₂H₄—, —CH₂—CH(CH₃)—CH₂—, —C₂H₄—CH(CH₃)—, —CH₂—C[(CH₃)₂]—, —C[(CH₃)₂]—CH₂—, —CH(CH₃)—CH(CH₃)—, —C[(C₂H₅)(CH₃)]—, —CH(C₃H₇)—, —CH₂CH₂O—, —(CH₂—CH₂—O)ₙ—CH₂—CH₂—, —C(CH₃)═CH—C(CH₃)═CH—, —C₂H₄—CH═CH—CH═CH—, —CH₂—CH═CH—CH₂—CH═CH—, —C₃H₆—C≡C—CH₂—, —CH₂—CH═CH—CH═CH—CH₂—, —CH═CH—CH═CH—C₂H₄—, —CH₂—CH═CH—C(CH₃)═CH—, —CH₂—CH═C(CH₃)—CH═CH—, —CH₂—C(CH₃)═CH—CH═CH—, —CH═CH—, —CH(CH₃)—CH═CH—CH═CH—, —CH═CH—CH₂—C(CH₃)═CH—, —CH(CH₃)— C≡C—CH₂—, —CONH—, —NHCO—, —CH₂—CONH—, —CONH—CH₂—, —NHCO—CH₂—, —CH₂—NHCO—;

wherein n is an integer from 1 to 10; or

L₁-R$^B$ and L₂-R$^C$ or L₁-R$^B$ and L₃-R$^D$ or L₂-R$^C$ and L₃-R$^D$ can form together a cyclic ring selected from the group consisting of:

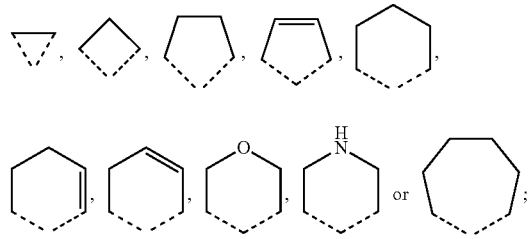

and enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof, with the proviso that said compound is not selected from the group consisting of:

the compounds having X═—CH₂CH₂CH₂—, Y═—O—, Z=a bond, R*═—CH₃, —CH₂CH₃, —CH(CH₃)₂, —CH(CH₃)CH₂CH₃, -cyclo-C₅H₉, -cyclo-C₆H₁₁, -Ph, or —CH₂Ph, R$^A$=-Ph, L₁-R$^B$═—H,

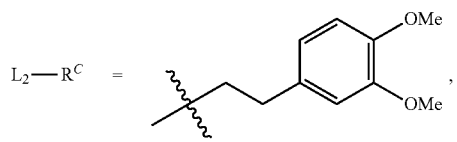

L₃-R$^D$═—CH₃, or

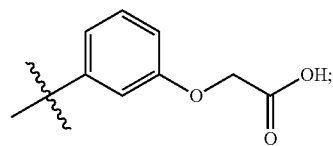 [SMILES: *c1cccc(OCC(=O)O)c1]

the compounds having X═—CH₂CH₂CH₂—, Y═—O—, Z=a bond, R*═—CH₂CH₃,

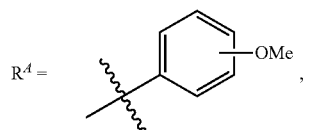

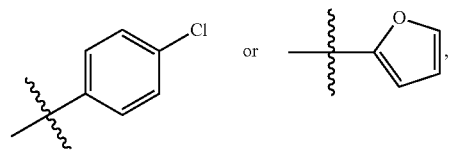

$L_1$-$R^B$=—H,

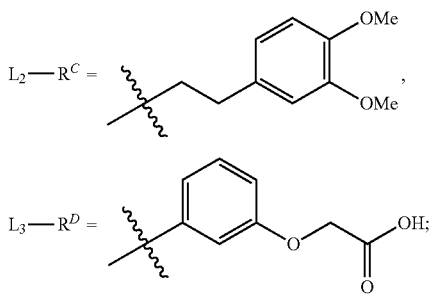

the compounds having X=—CH$_2$CH$_2$CH$_2$—, Y=—O—, Z=a bond, R*=—CH$_2$CH$_3$, —CH$_2$CH$_2$CH$_3$, —CH$_2$CH=CH$_2$, —CH(CH$_3$)$_2$, or -cyclo-C$_3$H$_5$,

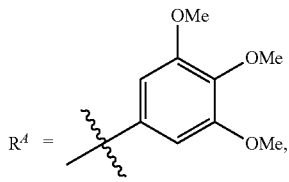

$L_1$-$R^B$=—H,

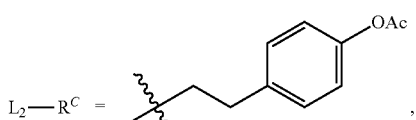

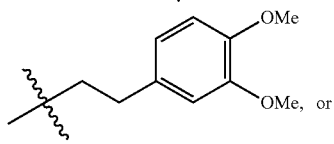

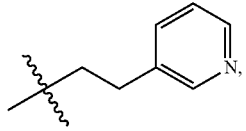

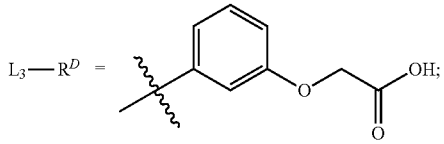

the compounds having X=—CH$_2$CH$_2$—, Y=—O—, Z=a bond, R*=—CH$_2$CH$_3$,

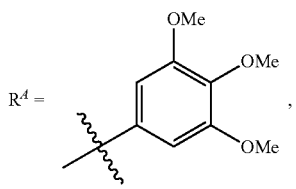 [SMILES: *c1cc(OC)c(OC)c(OC)c1]

$L_1$-$R^B$=—H,

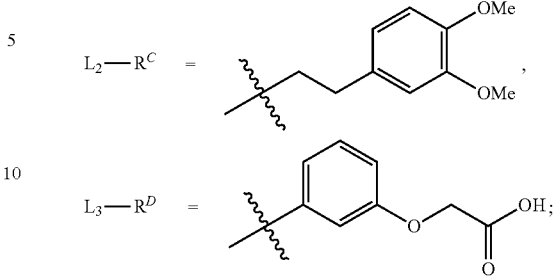

the compounds having X=—CH$_2$CH$_2$CH$_2$—, Y=—O—, Z=a bond, R*=—CH$_3$, —CH$_2$CH$_3$, or —CH$_2$CH$_2$CH$_3$, $R^A$=—CH$_3$, —CH$_2$CH$_3$, or —CH$_2$CH$_2$CH$_3$, $L_1$-$R^B$=—H,

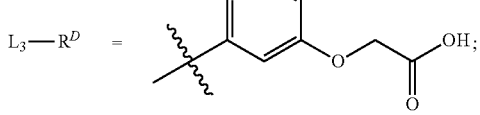

or
the compound having X=—CH$_2$CH$_2$CH$_2$—, Y=—O—, Z=a bond, R*=—OPh, $R^A$=-cyclo-C$_5$H$_9$, $L_1$-$R^B$=—H, $L_2$-$R^C$=—CH$_2$CH$_2$Ph,

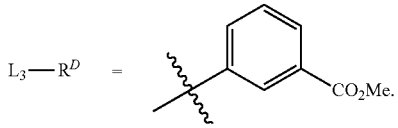

The above disclaimer excludes the compounds of US 2003 0036654 A1.

FKBP inhibitors or FKBP ligands as used herein are defined as compounds that (i) inhibit the peptidyl-prolyl isomerase activity of FKBPs (PPIase inhibitors, also referred to as rotamase inhibitors) or (ii) displace FK506 or FK506 analogs from the PPIase active site of FKBPs or (iii) bind to the FK506-binding domain of FKBPs as determined by isothermal calorimetry, surface plasmon resonance, tryptophan quenching, NMR or x-ray crystallography.

Selective FKBP51 inhibitors or FKBP ligands as used herein are defined as compounds that
(i) inhibit the PPIase activity of FKBP51, (ii) displace FK506 or FK506 analogs from the PPIase active site of FKBP51 or (iii) bind to the FK506-binding domain of FKBP51, each preferably over FKBP52 with a selectivity factor of >5, preferably >50, more preferably >500 and most preferably >5000.

An INDUCED-FIT FKBP51 INHIBITOR (iFit ligand) is defined by its ability to induce a conformational change which leads to an extended binding pocket in FKBP51 and resulting in a preference for FKBP51 over FKBP52. Specifically, when co-crystallized with FKBP51 or fragments thereof, an INDUCED-FIT FKBP51 INHIBITOR will yield an INDUCED-FIT FKBP51 STRUCTURE, an INDUCED-FIT FKBP51 BINDING SITE or an INDUCED-FIT FKBP51 BINDING SURFACE as defined herein.

The expression prodrug is defined as a pharmacological substance, a drug, which is administered in an inactive or significantly less active form. Once administered, the prodrug is metabolized in the body in vivo into the active compound.

The expression tautomer is defined as an organic compound that is interconvertible by a chemical reaction called tautomerization. Tautomerization can be catalyzed preferably by bases or acids or other suitable compounds.

The compounds according to the following subformula (Ia) of formula (I) are preferred:

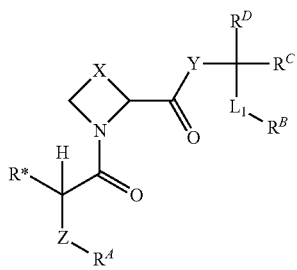

(Ia)

wherein

X represents —CH$_2$—, —CH$_2$CH$_2$—, —CH$_2$CH$_2$CH$_2$, —CH=CH—, —CH=CHCH$_2$—, —CH$_2$SCH$_2$—, —CH$_2$OCH$_2$—, —SCH$_2$—, —SCH$_2$CH$_2$—, —CHFCH$_2$—, —CH(CH$_3$)CH$_2$—, —CH(CH$_3$)CH$_2$CH$_2$—, —CH$_2$CH(CH$_3$)—, —C(CH$_3$)$_2$—CH$_2$—, or

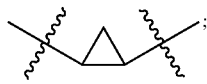 [SMILES: *C1CC1*]

;

Y represents —NH—, or —O—;
Z represents a covalent bond, —NHCO—, —CHR$^{39}$—NHCO—, or —CH(NHCOR$^{39}$)—;
R*, R$^A$, R$^B$ are defined as for the general formula (I), or preferably have the other definitions as disclosed herein;
R$^C$ represents —R$^{38}$;
R$^D$ represents —H, —CH$_3$, —CH$_2$F, —CHF$_2$, —CF$_3$, —C$_2$H$_5$, —CH$_2$OH, —CH$_2$OMe, —CH$_2$NH$_2$, —CH$_2$NHCH$_3$, —CH$_2$N(CH$_3$)$_2$, —CH$_2$NHCOH, —CH$_2$NHCOCH$_3$; or
R$^C$ and R$^D$ can form together a carbocyclic ring selected from the group consisting of:

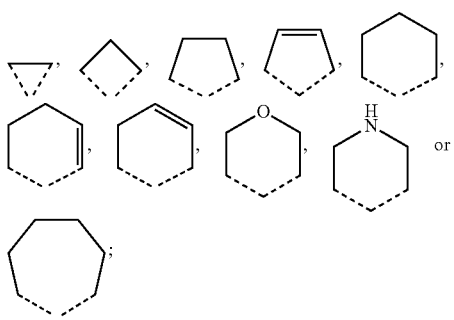

;

R$^{38}$ and R$^{39}$ are defined as for the general formula (I);
L$_1$ represents a bond, —CH$_2$—, —C$_2$H$_4$—, —C$_3$H$_6$—, —C$_4$H$_8$—, —C$_5$H$_{10}$—, —C$_6$H$_{12}$—, —C$_7$H$_{14}$—, —C$_8$H$_{16}$—, —C$_9$H$_{18}$—, —C$_{10}$H$_{20}$—, —CH(CH$_3$)—, —C[(CH$_3$)$_2$]—, —CH$_2$—CH(CH$_3$)—, —CH(CH$_3$)—CH$_2$—, —CH(CH$_3$)—C$_2$H$_4$—, —CH$_2$—CH(CH$_3$)—CH$_2$—, —C$_2$H$_4$—CH(CH$_3$)—, —CH$_2$—C[(CH$_3$)$_2$]—, —C[(CH$_3$)$_2$]—CH$_2$—, —CH(CH$_3$)—CH(CH$_3$)—, —C[(C$_2$H$_5$)(CH$_3$)]—, —CH(C$_3$H$_7$)—, —CH$_2$CH$_2$O—, —(CH$_2$—CH$_2$—O)$_n$—CH$_2$—CH$_2$—, —C(CH$_3$)=CH—C(CH$_3$)=CH—, —C$_2$H$_4$—CH=CH—CH=CH—, —CH$_2$—CH=CH—CH$_2$—CH=CH—, —C$_3$H$_6$—C≡C—CH$_2$—, —CH$_2$—CH=CH—CH=CH—CH$_2$—, CH=CH—CH=CH—C$_2$H$_4$—, —CH$_2$—CH=CH—C(CH$_3$)=CH—, —CH$_2$—CH=C(CH$_3$)—CH=CH—, —CH$_2$—C(CH$_3$)=CH—CH=CH—, —CH(CH$_3$)—CH=CH—CH=CH—, —CH=CH—CH$_2$—C(CH$_3$)=CH—, —CH(CH$_3$)—C≡C—CH$_2$—, —(C=O)NH—, —NH(C=O)—, —CH$_2$(C=O)NH—, —(C=O)NHCH$_2$—, —NH(C=O)CH$_2$—, or —CH$_2$NH(C=O)—,
wherein n is an integer from 1 to 10.

Further the compounds according to the following formula (Ib) are preferred:

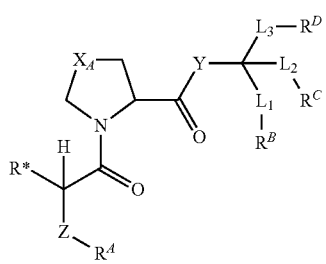

(Ib)

wherein

X$_A$ represents —CH$_2$—, —CH$_2$CH$_2$—, or —CH=CH—;
Y represents —NH—, or —O—;
Z represents a covalent bond, or —NHCO—;
R* represents —R$^{38}$, —CH$_2$—R$^{38}$, —R**, —CH(OR')R'', —CH(CH$_3$)$_2$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —CH$_2$-cyclo-C$_6$H$_9$, -cyclo-C$_6$H$_{11}$, -cyclo-C$_5$H$_9$, —CH$_2$—C(CH$_3$)=CH$_2$, —CH(CH$_3$)-cyclo-C$_3$H$_5$, —CH(CH$_3$)—CH=CH$_2$;
R** represents

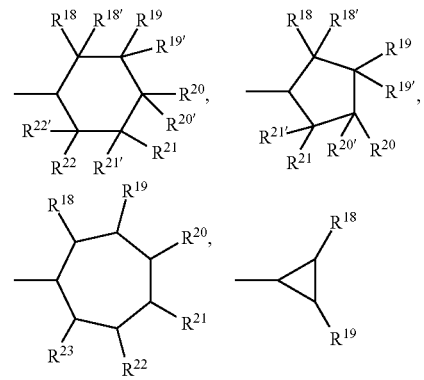

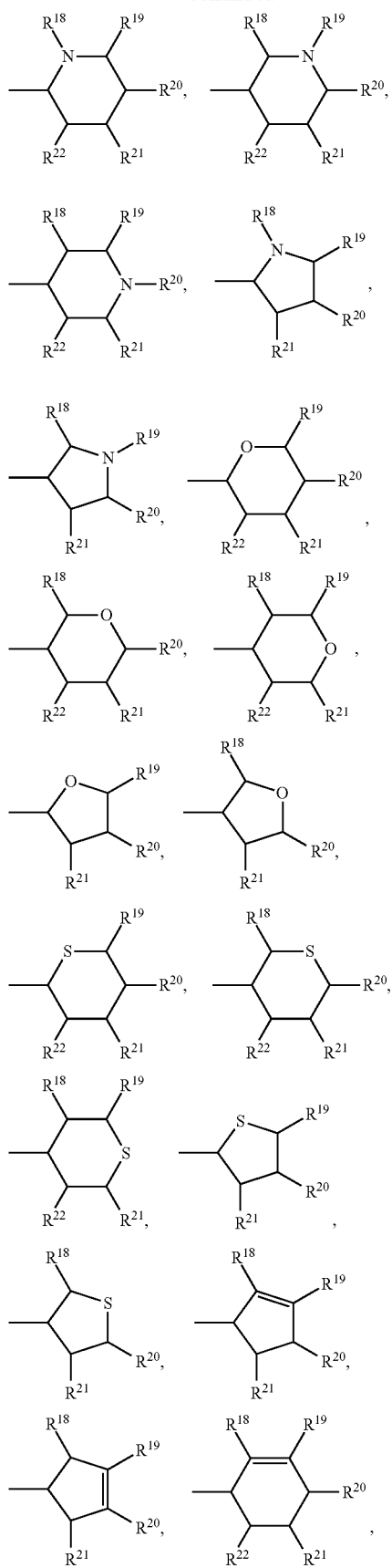
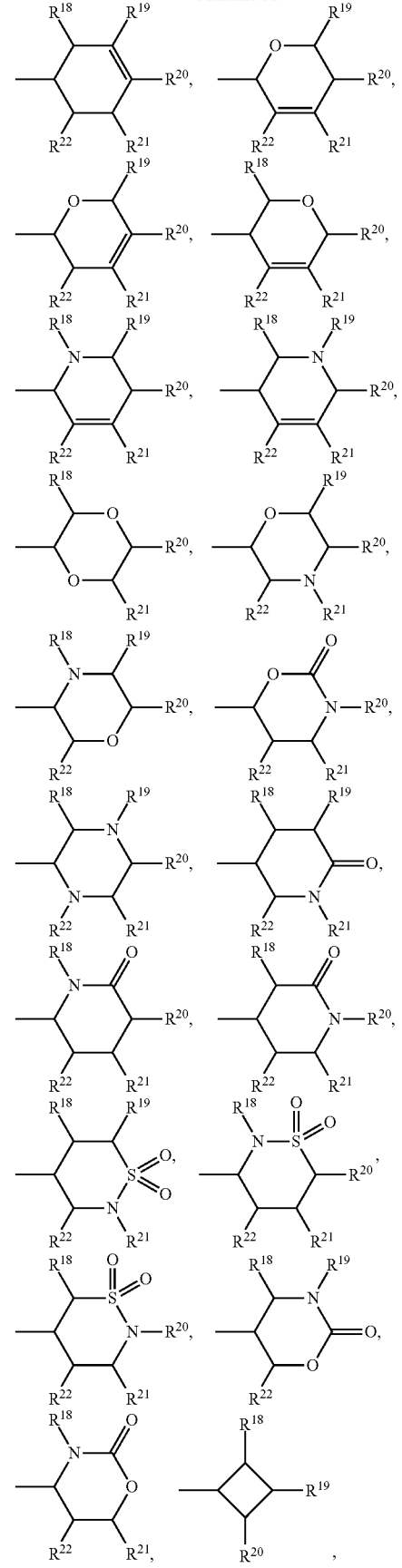

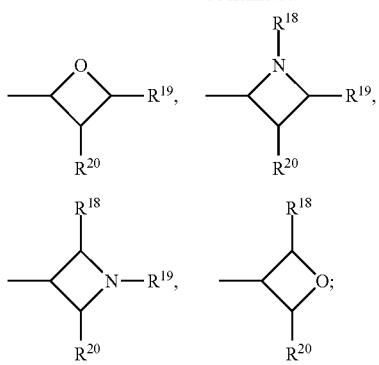
R' and R" represent independently of each other —CH$_3$, —C$_2$H$_5$, —CH(CH$_3$)$_2$, —CH$_2$CH=CH$_2$, -cyclo-C$_3$H$_5$, or —C(CH$_3$)$_3$;
R$^{38}$ represents R$^{18}$, but not —CH$_2$—CH=CH$_2$ or —CH$_2$-cyclo-C$_3$H$_5$;
R$^A$ represents:
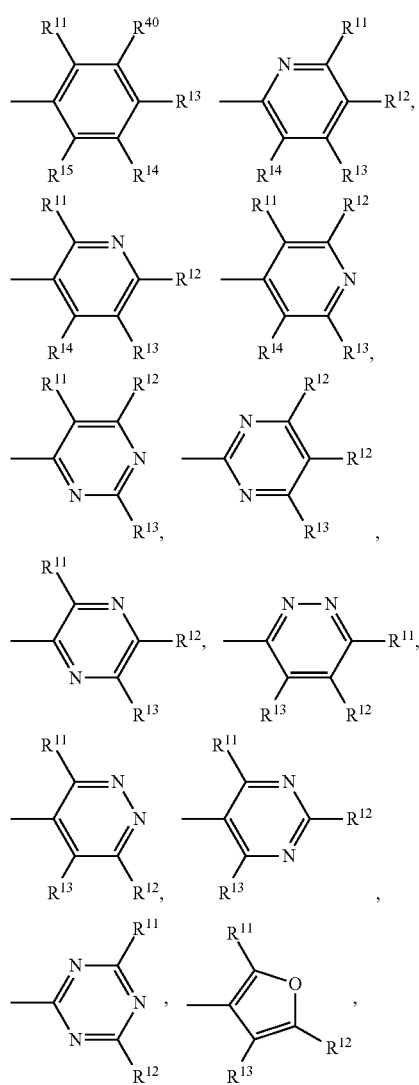
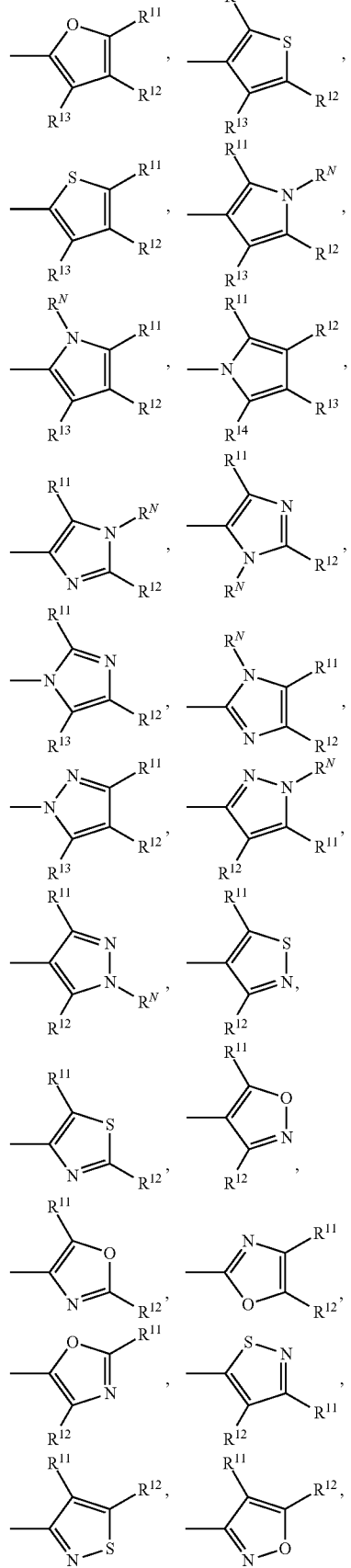

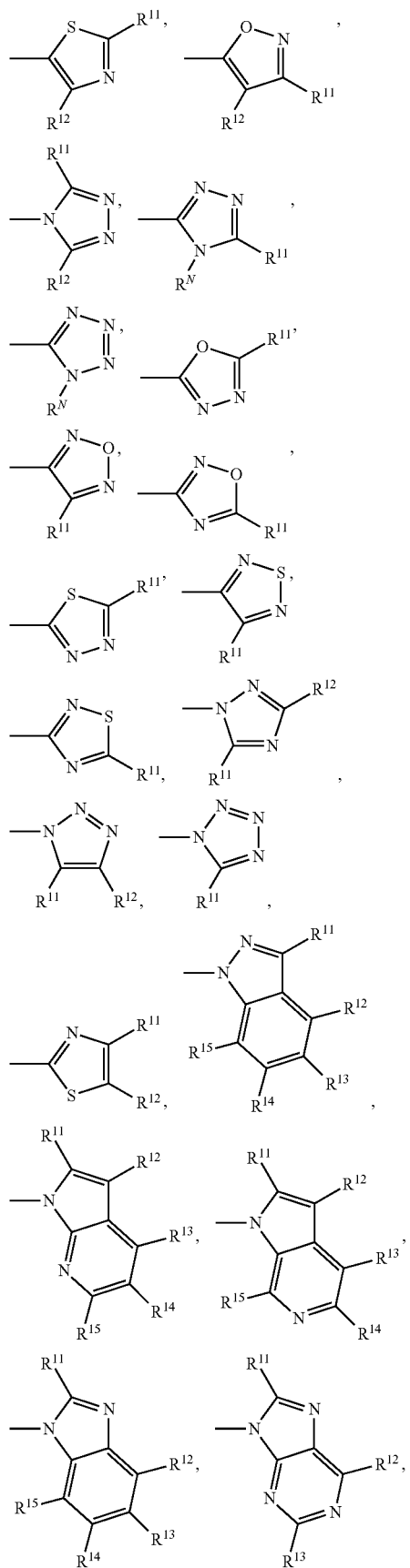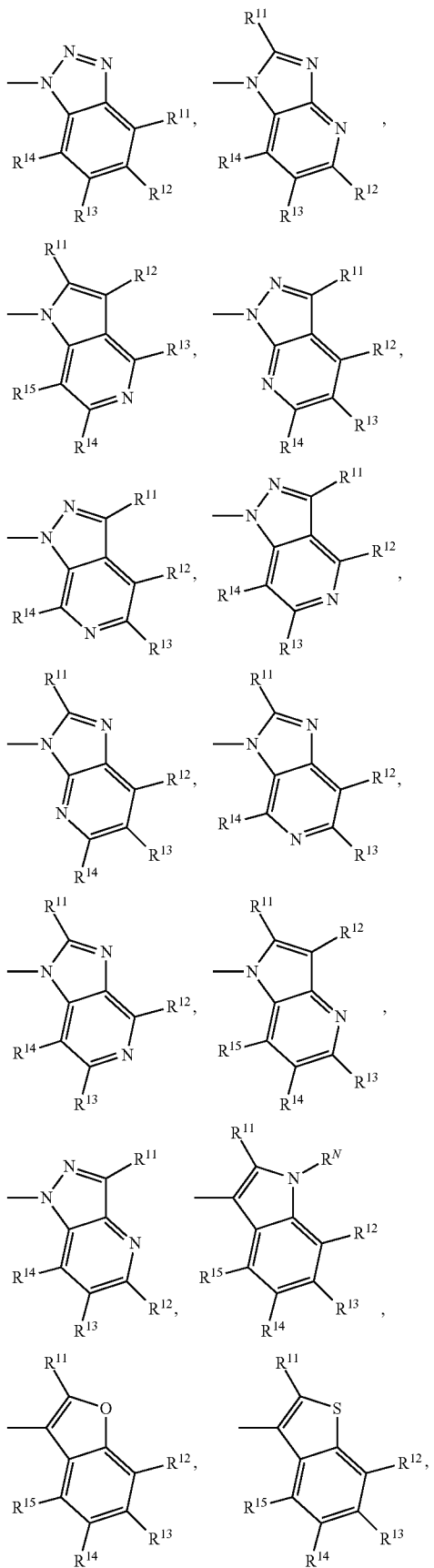

-continued
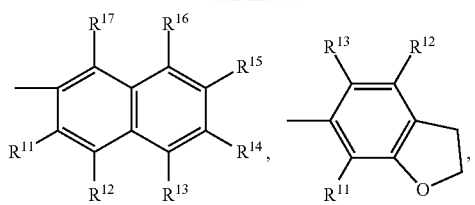
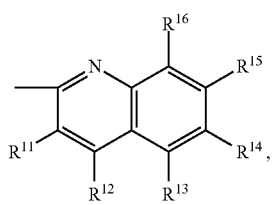
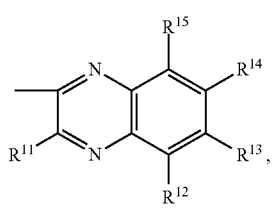
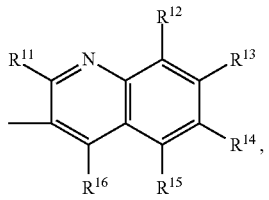
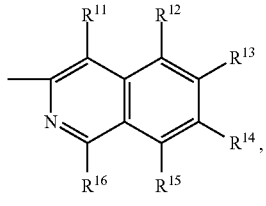
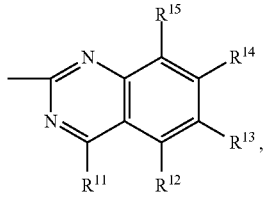
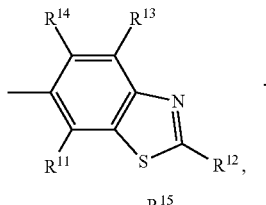
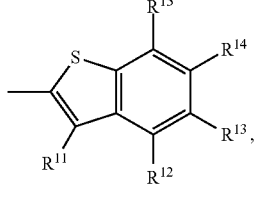
-continued
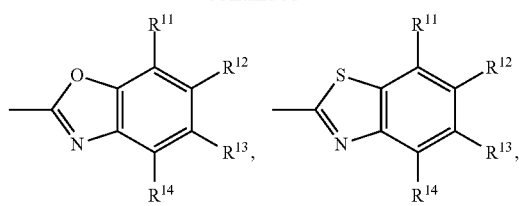
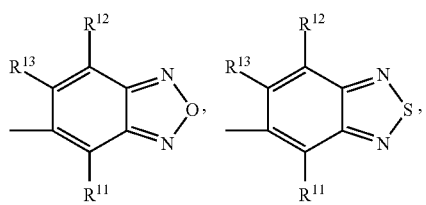
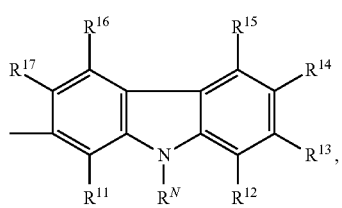
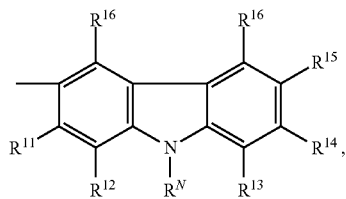
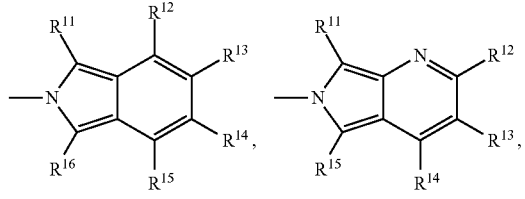
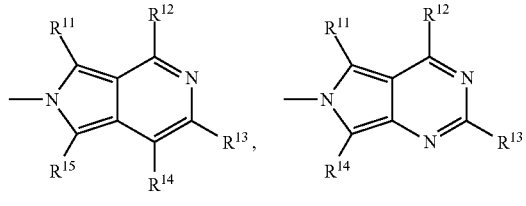
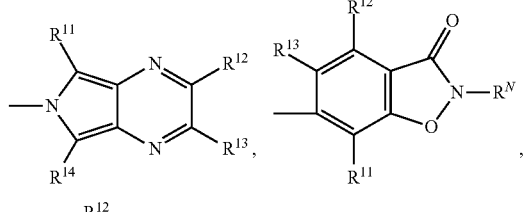
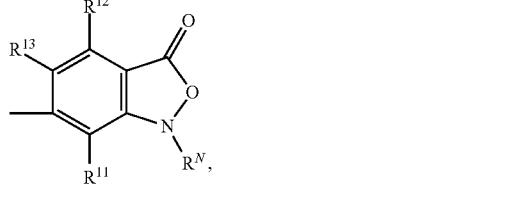

-continued

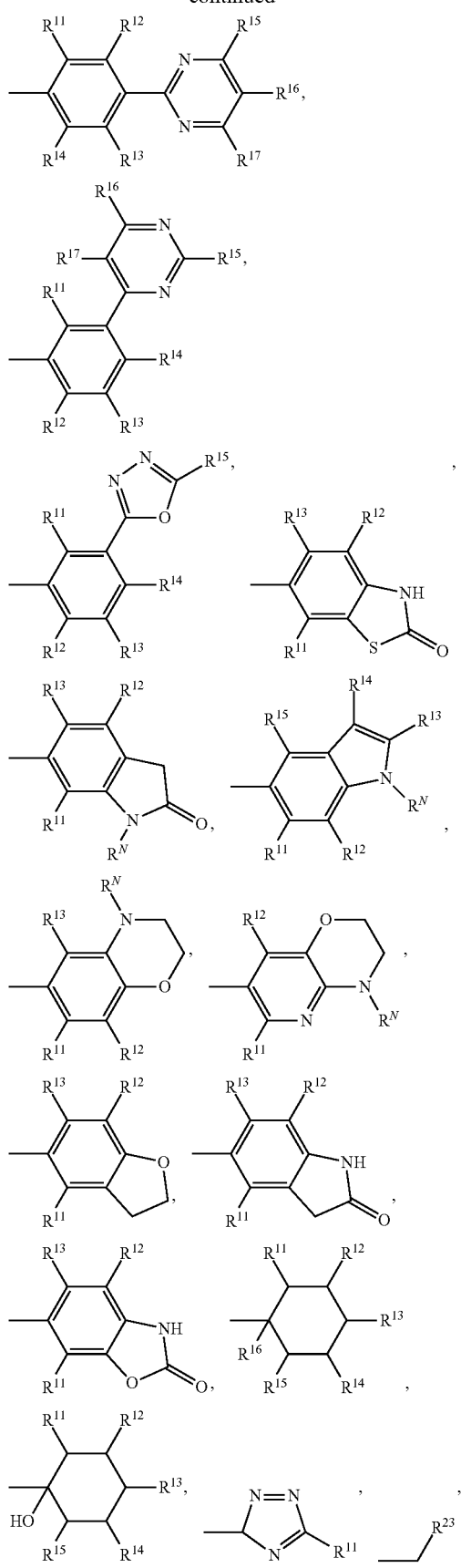

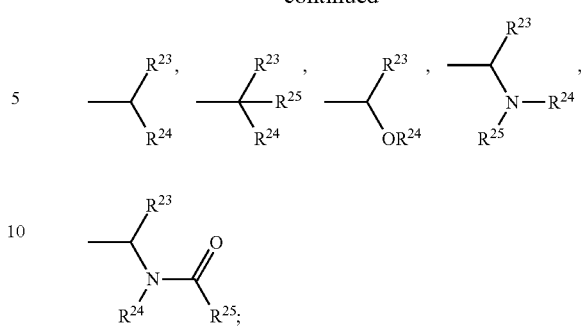

$R^B$, $R^C$ and $R^D$ are defined as for the general formula (I);

$R^1$-$R^{37}$, $R^{18'}$-$R^{22'}$ and $R^N$ are defined as for the general formula (I);

$R^{40}$ represents $R^{12}$, but not —H;

$L_1$, $L_2$ and $L_3$ represent independently of each other:

a bond, —CH$_2$—, —C$_2$H$_4$—, —C$_3$H$_6$—, —C$_4$H$_8$—, —C$_5$H$_{10}$—, —C$_6$H$_{12}$—, —C$_7$H$_{14}$—, —C$_8$H$_{16}$—, —C$_9$H$_{18}$—, —C$_{10}$H$_{20}$—, —CH(CH$_3$)—, —C[(CH$_3$)$_2$]—, —CH$_2$—CH(CH$_3$)—, —CH(CH$_3$)—CH$_2$—, —CH(CH$_3$)—C$_2$H$_4$—, —CH$_2$—CH(CH$_3$)—CH$_2$—, —C$_2$H$_4$—CH(CH$_3$)—, —CH$_2$—C[(CH$_3$)$_2$]—, —C[(CH$_3$)$_2$]—CH$_2$—, —CH(CH$_3$)—CH(CH$_3$)—, —C[(C$_2$H$_5$)(CH$_3$)]—, —CH(C$_3$H$_7$)—, —CH$_2$CH$_2$O—, —(CH$_2$—CH$_2$—O)$_n$—CH$_2$—CH$_2$—, —C(CH$_3$)=CH—C(CH$_3$)=CH—, —C$_2$H$_4$—CH=CH—CH=CH—, —CH$_2$—CH=CH—CH$_2$—CH=CH—, —C$_3$H$_6$—C≡C—CH$_2$—, —CH$_2$—CH=CH—CH=CH—CH$_2$—, —CH=CH—CH=CH—C$_2$H$_4$—, —CH$_2$—CH=CH—C(CH$_3$)=CH—, —CH$_2$—CH=C(CH$_3$)—CH=CH—, —CH$_2$—C(CH$_3$)=CH—CH=CH—, —CH(CH$_3$)—CH=CH—CH=CH—, —CH=CH—CH$_2$—C(CH$_3$)=CH—, —CH(CH$_3$)—C≡C—CH$_2$—, —CONH—, —NHCO—, —CH$_2$—CONH—, —CONH—CH$_2$—, —NHCO—CH$_2$—, —CH$_2$—NHCO—;

wherein n is an integer from 1 to 10; or $L_1$-$R^B$ and $L_2$-$R^C$ or $L_1$-$R^B$ and $L_3$-$R^D$ or $L_2$-$R^C$ and $L_3$-$R^D$ can form together a cyclic ring selected from the group consisting of:

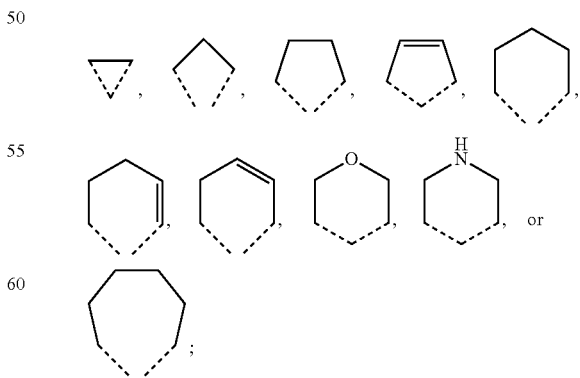

More preferred are the compounds according to the following formula (Ic):

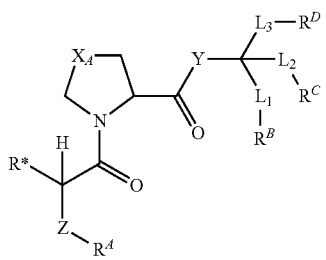
wherein
$X_A$ represents —CH$_2$—, or —CH$_2$CH$_2$—;
Y represents —NH—, or —O—;
Z represents a covalent bond, or —NHCO—;
R* represents
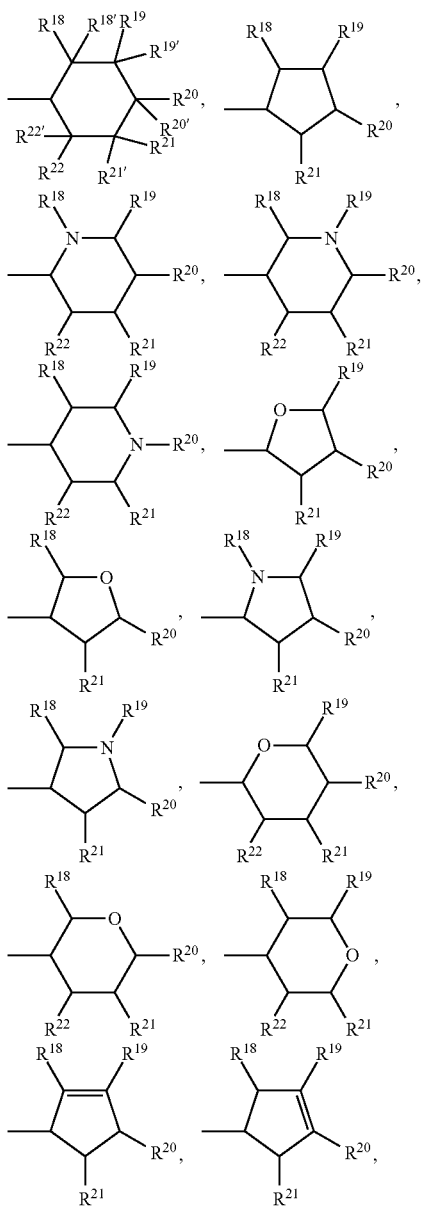
(Ic)
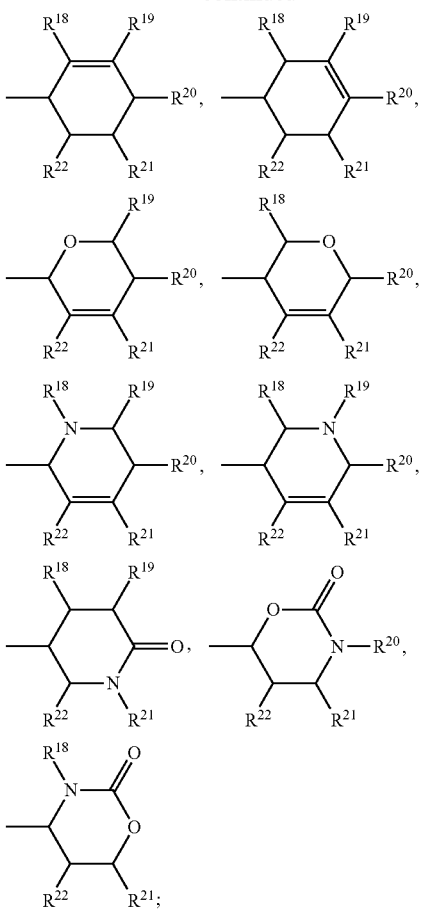
$R^A$ represents
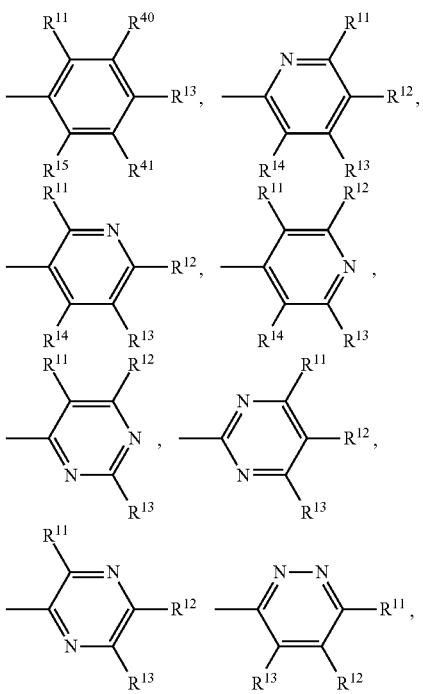

-continued
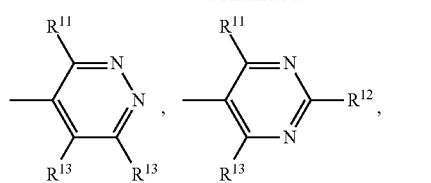
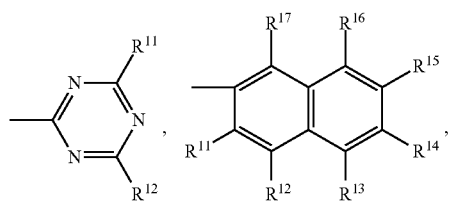
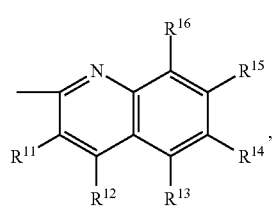
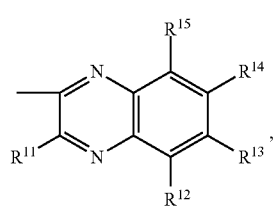
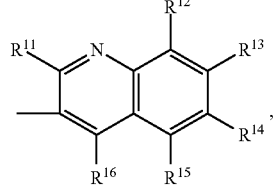
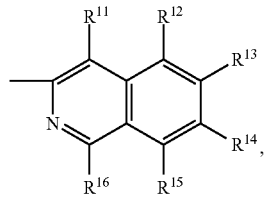
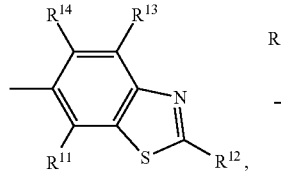
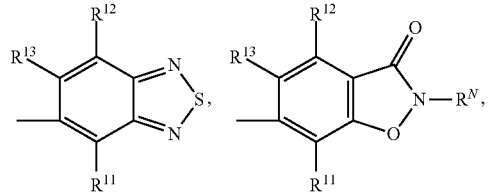
-continued
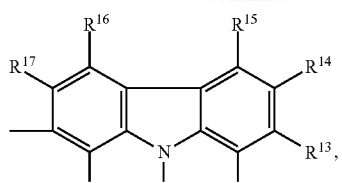
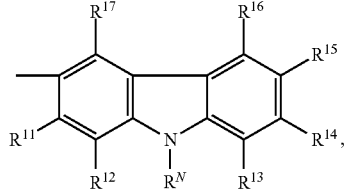
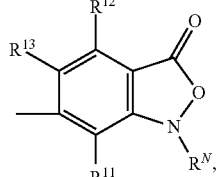
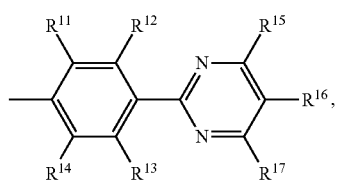
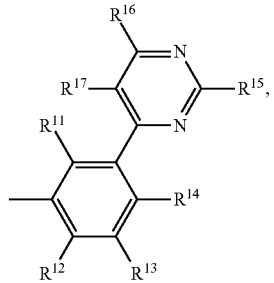
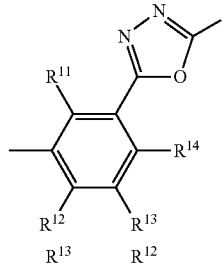
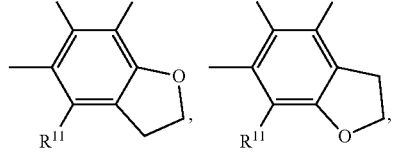
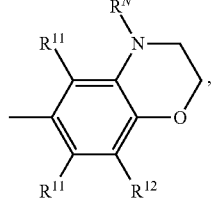

-continued

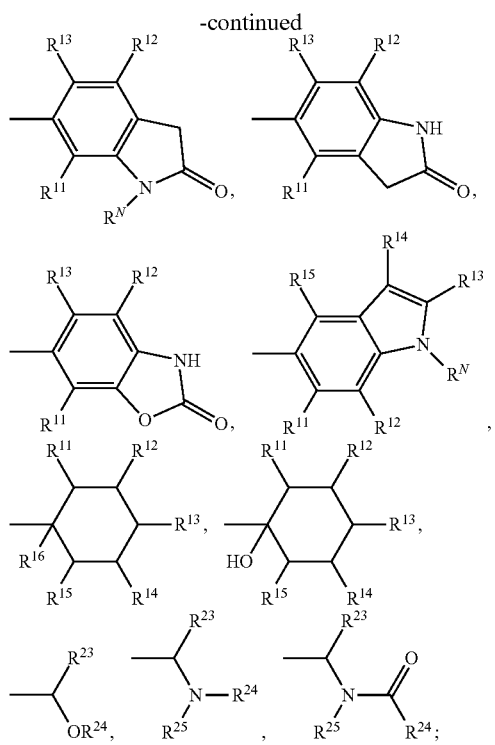

$R^B$, $R^C$ and $R^D$ are defined as for the general formula (I);
$R^1$-$R^{37}$, $R^{18'}$-$R^{22'}$ and $R^N$ are defined as for the general formula (I); or
$R^{40}$ represents $R^{12}$, but not —H;
$R^{41}$ represents $R^{14}$, but not —H;
$L_1$, $L_2$ and $L_3$ represent independently of each other:
a bond, —CH$_2$—, —C$_2$H$_4$—, —C$_3$H$_6$—, —C$_4$H$_8$—, —C$_5$H$_{10}$—, —C$_6$H$_{12}$—, —C$_7$H$_{14}$—, —C$_8$H$_{16}$—, —C$_9$H$_{18}$—, —C$_{10}$H$_{20}$—, —CH(CH$_3$)—, —C[(CH$_3$)$_2$]—, —CH$_2$—CH(CH$_3$)—, —CH(CH$_3$)—CH$_2$—, —CH(CH$_3$)—C$_2$H$_4$—, —CH$_2$—CH(CH$_3$)—CH$_2$—, —C$_2$H$_4$—CH(CH$_3$)—, —CH$_2$—C[(CH$_3$)$_2$]—, —C[(CH$_3$)$_2$]—CH$_2$, —CH(CH$_3$)—CH(CH$_3$)—, —C[(C$_2$H$_5$)(CH$_3$)]—, —CH(C$_3$H$_7$)—, —CH$_2$CH$_2$O—, —(CH$_2$—CH$_2$—O)$_n$—CH$_2$—CH$_2$—, —C(CH$_3$)=CH—C(CH$_3$)=CH—, —C$_2$H$_4$—CH=CH—CH=CH—, —CH$_2$—CH=CH—CH$_2$—CH=CH—, —C$_3$H$_6$—C≡C—CH$_2$—, —CH$_2$—CH=CH—CH=CH—CH$_2$—, —CH=CH—CH=CH—C$_2$H$_4$—, —CH$_2$—CH=CH—C(CH$_3$)=CH—, —CH$_2$—CH=C(CH$_3$)—CH=CH—, —CH$_2$—C(CH$_3$)=CH—CH=CH—, —CH(CH$_3$)—CH=CH—CH=CH—, —CH=CH—CH$_2$—C(CH$_3$)=CH—, —CH(CH$_3$)—C≡C—CH$_2$—, —CONH—, —NHCO—, —CH$_2$—CONH—, —CONH—CH$_2$—, —NHCO—CH$_2$—, —CH$_2$—NHCO—;
wherein n is an integer from 1 to 10; or
$L_1$-$R^B$ and $L_2$-$R^C$ or $L_1$-$R^B$ and $L_3$-$R^D$ or $L_2$-$R^C$ and $L_3$-$R^D$ can form together a cyclic ring selected from the group consisting of:

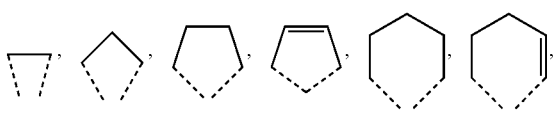

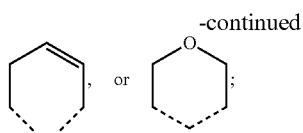

Even more preferred are the compounds according to the following formula (Id):

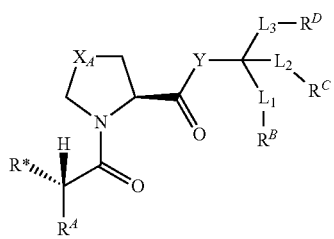

wherein
$X_A$ represents —CH$_2$—, or —CH$_2$CH$_2$—;
Y represents —NH—, or —O—;
R* represents

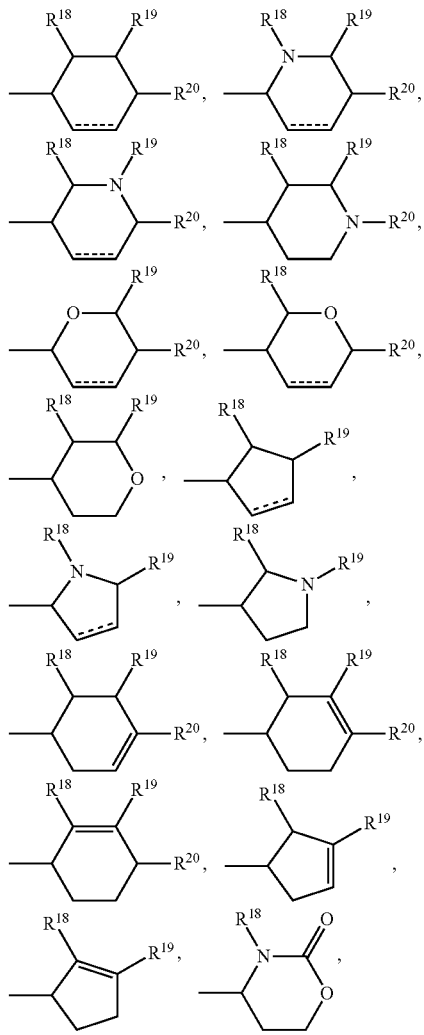

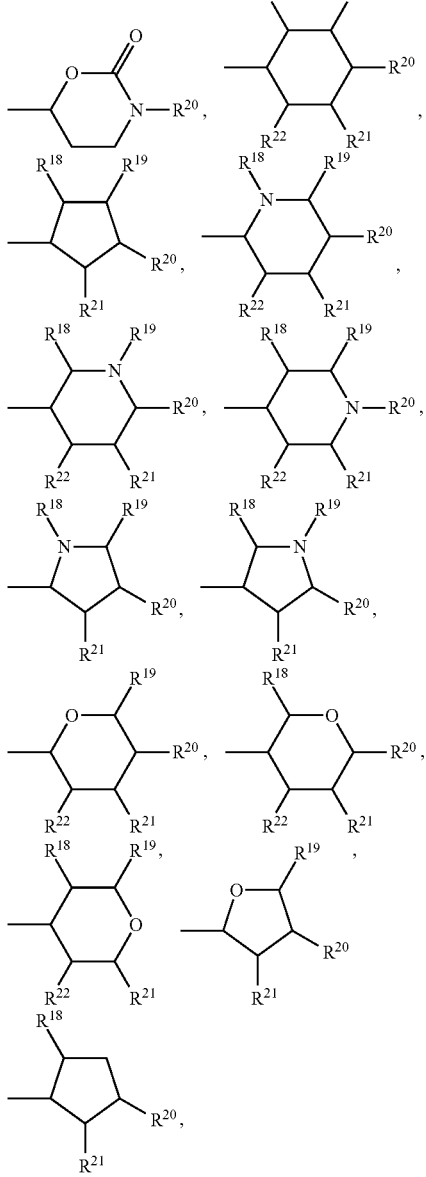
and
"·····" represents a single or double bond;
$R^A$ represents:
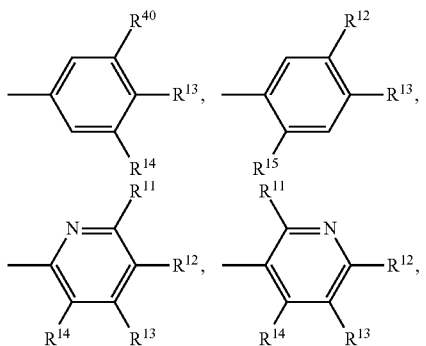
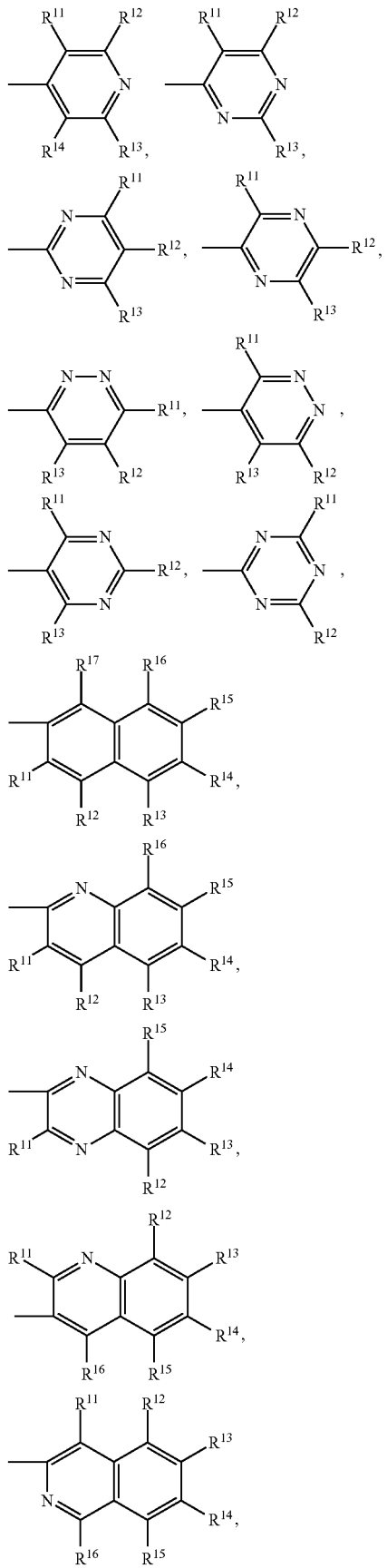

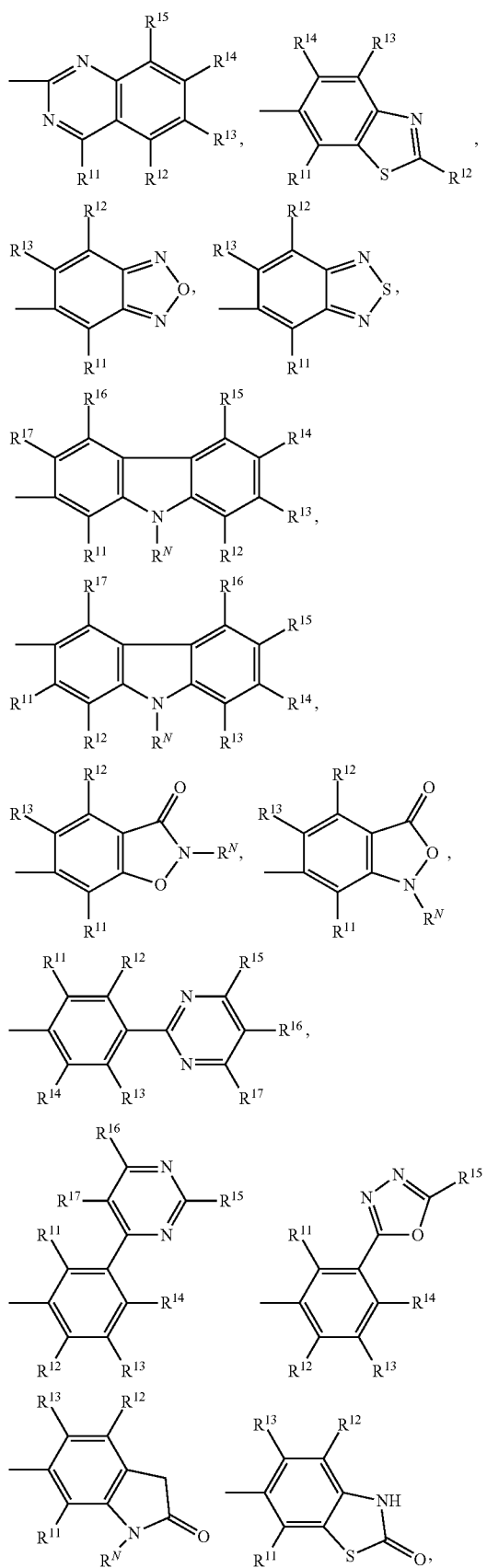
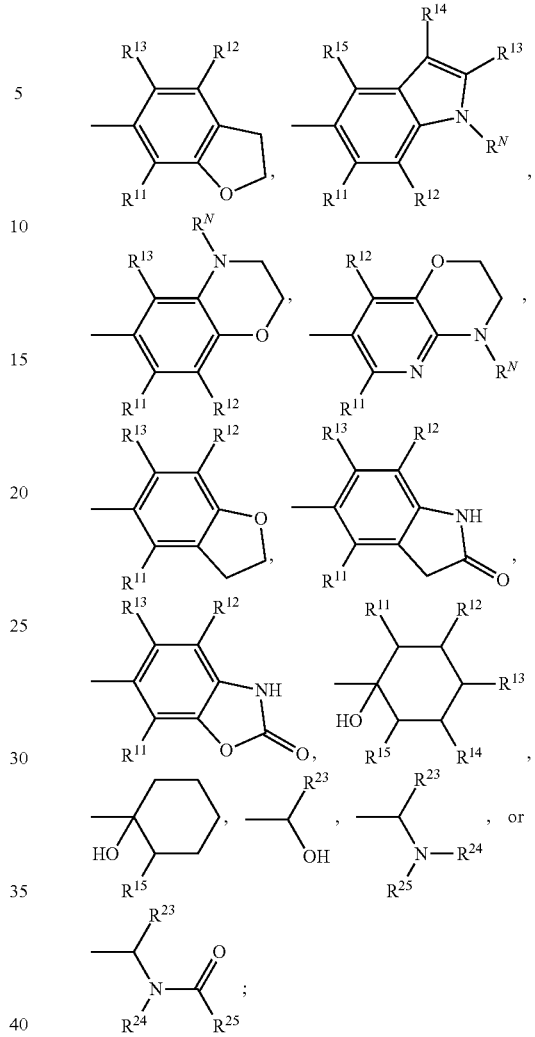

$R^B$, $R^C$ and $R^D$ are defined as for the general formula (I);
$R^1$-$R^{22}$, $R^{26}$-$R^{39}$ and $R^N$ are defined as for the general formula (I);
$R^{40}$ represents $R^{12}$, but not —H;
$L_1$, $L_2$ and $L_3$ represent independently of each other:
a bond, —CH$_2$—, —C$_2$H$_4$—, —C$_3$H$_6$—, —C$_4$H$_8$—, —C$_5$H$_{10}$—, —C$_6$H$_{12}$—, —C$_7$H$_{14}$—, —C$_8$H$_{16}$—, —C$_9$H$_{18}$—, —C$_{10}$H$_{20}$—, —CH(CH$_3$)—, —C[(CH$_3$)$_2$]—, —CH$_2$—CH(CH$_3$)—, —CH(CH$_3$)—CH$_2$—, —CH(CH$_3$)—C$_2$H$_4$—, —CH$_2$—CH(CH$_3$)—CH$_2$—, —C$_2$H$_4$—CH(CH$_3$)—, —CH$_2$—C[(CH$_3$)$_2$]—, —C[(CH$_3$)$_2$]—CH$_2$—, —CH(CH$_3$)—CH(CH$_3$)—, —C[(C$_2$H$_5$)(CH$_3$)]—, —CH(C$_3$H$_7$)—, —CH$_2$CH$_2$O—, —(CH$_2$—CH$_2$—O)$_n$—CH$_2$—CH$_2$—, —C(CH$_3$)=CH—C(CH$_3$)=CH—, —C$_2$H$_4$—CH=CH—CH=CH—, —CH$_2$—CH=CH—CH$_2$—CH=CH—, —C$_3$H$_6$—C≡C—CH$_2$—, —CH$_2$—CH=CH—CH=CH—CH$_2$, —CH=CH—CH=CH—C$_2$H$_4$—, —CH$_2$—CH=CH—C(CH$_3$)=CH—, —CH$_2$—CH=C(CH$_3$)—CH=CH—, —CH$_2$—C(CH$_3$)=CH—CH=CH—, —CH(CH$_3$)—CH=CH—CH=CH—, —CH=CH—CH$_2$—C(CH$_3$)=CH—, —CH(CH$_3$)—C≡C—CH$_2$—, —CONH—, —NHCO—, —CH$_2$—CONH—, —CONH—CH$_2$—, —NHCO—CH$_2$—, —CH$_2$—NHCO—;
wherein n is an integer from 1 to 10; or $L_1\text{-}R^B$ and $L_2\text{-}R^C$ or $L_1\text{-}R^B$ and $L_3\text{-}R^D$ or $L_2\text{-}R^C$ and $L_3\text{-}R^D$ can form together a cyclic ring selected from the group consisting of:

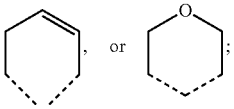

Even more preferred are the compounds according to the following formula (Ie):

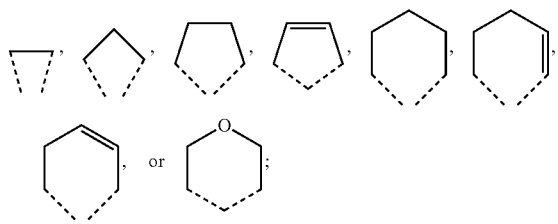

wherein
$X_A$ represents —CH$_2$—, or —CH$_2$CH$_2$—;
Y represents —NH—, or —O—;
R* represents

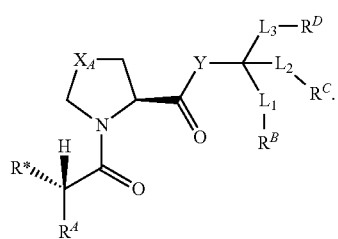

and
" ----- " represents a single or double bond;
$R^A$ represents:

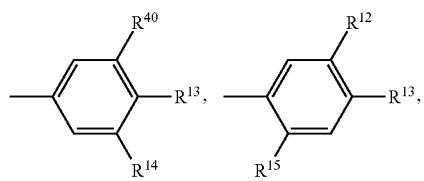

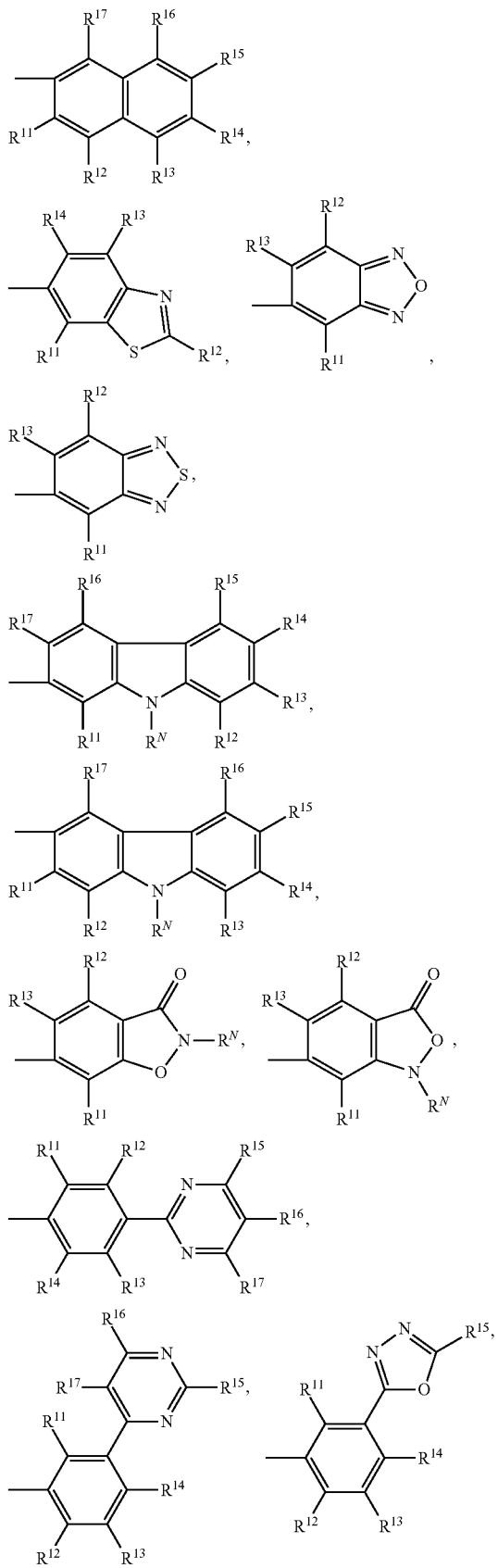

-continued

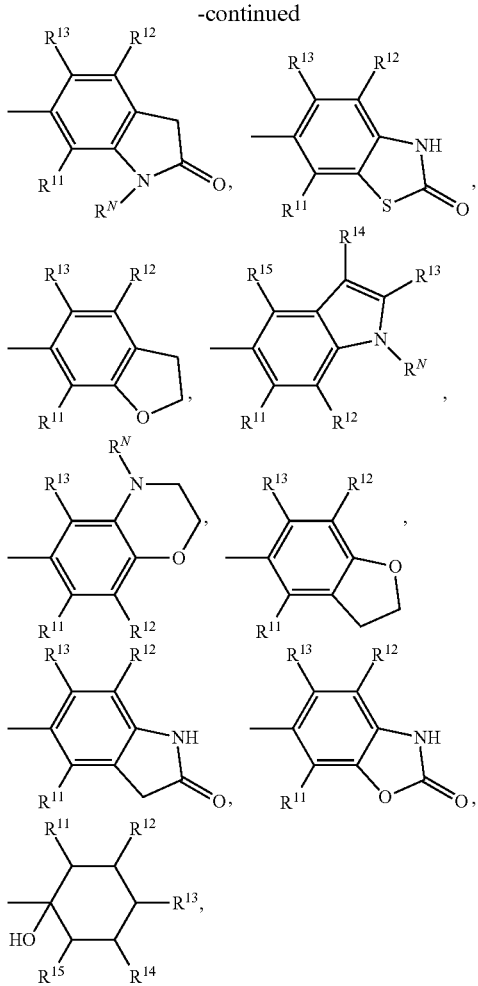

or more conservative

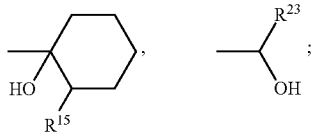

$R^B$, $R^C$ and $R^D$ are defined as for the general formula (I);
$R^1$-$R^{22}$, $R^{26}$-$R^{39}$ and $R^N$ are defined as for the general formula (I);
$R^{40}$ represents $R^{12}$, but not —H;
$L_1$, $L_2$ and $L_3$ represent independently of each other:
a bond, —CH$_2$—, —C$_2$H$_4$—, —C$_3$H$_6$—, —C$_4$H$_8$—, —C$_5$H$_{10}$—, —C$_6$H$_{12}$—, —C$_7$H$_{14}$—, —C$_8$H$_{16}$—, —C$_9$H$_{18}$—, —C$_{10}$H$_{20}$—, —CH(CH$_3$)—, —C[(CH$_3$)$_2$]—, —CH$_2$—CH(CH$_3$)—, —CH(CH$_3$)—CH$_2$—, —CH(CH$_3$)—C$_2$H$_4$—, —CH$_2$—CH(CH$_3$)—CH$_2$—, —C$_2$H$_4$—CH(CH$_3$)—, —CH$_2$—C[(CH$_3$)$_2$]—, —C[(CH$_3$)$_2$]—CH$_2$—, —CH(CH$_3$)—CH(CH$_3$)—, —C[(C$_2$H$_5$)(CH$_3$)]—, —CH(C$_3$H$_7$)—, —CH$_2$CH$_2$O—, —(CH$_2$—CH$_2$—O)$_n$—CH$_2$CH$_2$—, —C(CH$_3$)═CH—C(CH$_3$)═CH—, —C$_2$H$_4$—CH═CH—CH═CH—, —CH$_2$—CH═CH—CH$_2$—, —C$_3$H$_6$—C≡C—CH$_2$—, —CH$_2$—CH═CH—CH═CH—CH$_2$—, —CH═CH—CH═CH—C$_2$H$_4$—, —CH$_2$—CH═CH—C(CH$_3$)═CH—, —CH$_2$—CH═C(CH$_3$)—CH═CH—, —CH$_2$—C(CH$_3$)═CH—CH═CH—, —CH(CH$_3$)—CH═CH—CH═CH—, —CH═CH—CH$_2$—C(CH$_3$)═CH—, —CH(CH$_3$)—C≡C—CH$_2$—, —CONH—, —NHCO—, —CH$_2$CONH—, —CONH—CH$_2$—, —NHCO—CH$_2$—, —CH$_2$—NHCO—;
wherein n is an integer from 1 to 10; or
$L_1$-$R^B$ and $L_2$-$R^C$ or $L_1$-$R^B$ and $L_3$-$R^D$ or $L_2$-$R^C$ and $L_3$-$R^D$ can form together a cyclic ring selected from the group consisting of:

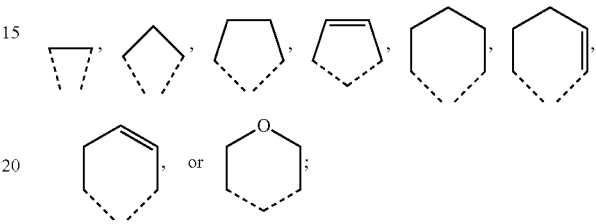

Even more preferred are the compounds according to the following formula (If):

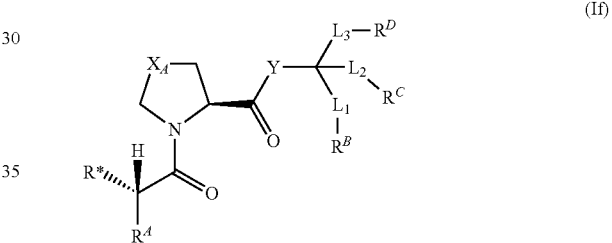

wherein
$X_A$ represents —CH$_2$—, or —CH$_2$CH$_2$—;
Y represents —NH—, or —O—;
R* represents

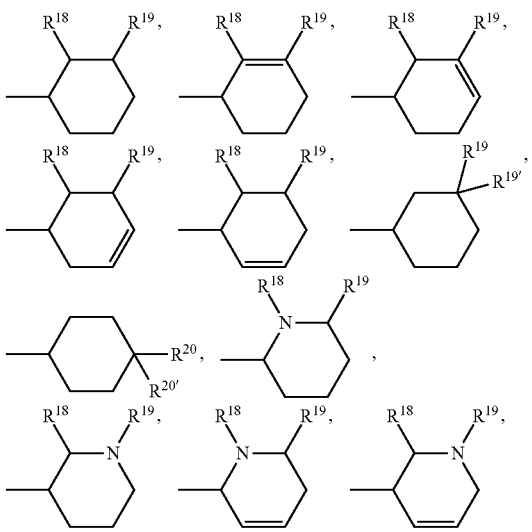

-continued
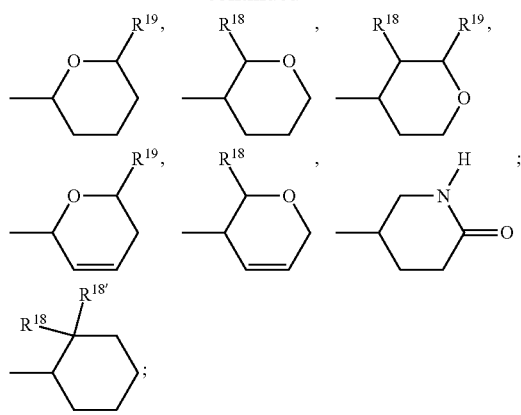
R$^A$ represents:
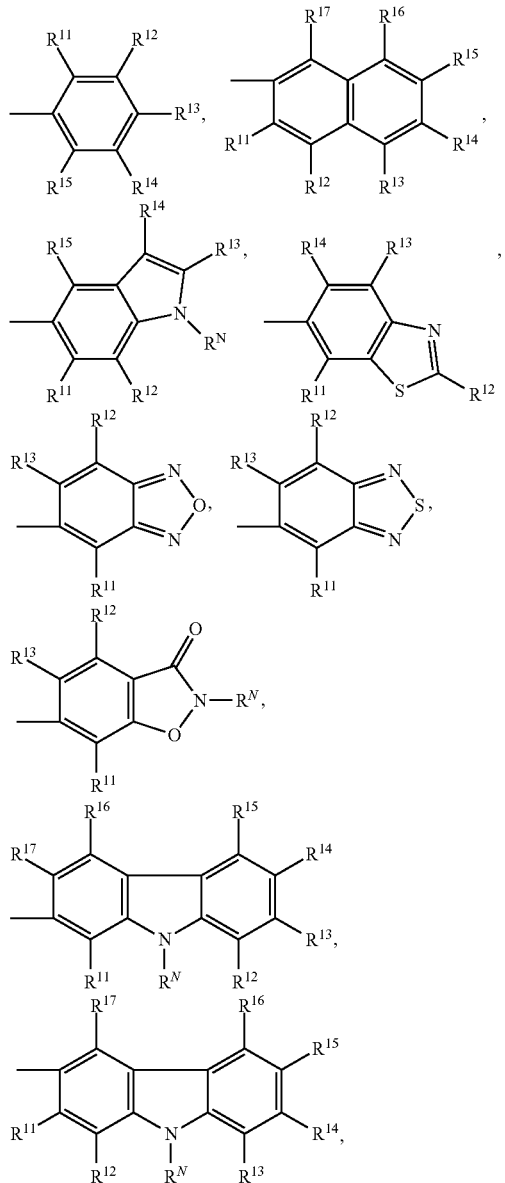
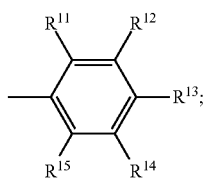
wherein at least one of R$^{11}$-R$^{15}$ is not —H, if R$^A$ is
R$^B$, R$^C$ and R$^D$ are defined as for the general formula (I); R$^1$-R$^{20}$, R$^{18'}$-R$^{19'}$, R$^{28}$-R$^{37}$ and R$^N$ are defined as for the general formula (I) or $R^{18}$ and $R^{18'}$ or $R^{19}$ and $R^{19'}$ can form together

$=CH_2$, or $=C(CH_3)_2$;

$L_1$, $L_2$ and $L_3$ represent independently of each other:
a bond, —$CH_2$—, —$C_2H_4$—, —$C_3H_6$—, —$C_4H_8$—, —$C_5H_{10}$—, —$C_6H_{12}$—, —$C_7H_{14}$—, —$C_8H_{16}$—, —$C_9H_{18}$—, —$C_{10}H_{20}$—, —$CH(CH_3)$—, —$C[(CH_3)_2]$—, —$CH_2$—$CH(CH_3)$—, —$CH(CH_3)$—$CH_2$—, —$CH(CH_3)$—$C_2H_4$—, —$CH_2$—$CH(CH_3)$—$CH_2$—, —$C_2H_4$—$CH(CH_3)$—, —$CH_2$—$C[(CH_3)_2]$—, —$C[(CH_3)_2]$—$CH_2$—, —$CH(CH_3)$—$CH(CH_3)$—, —$C[(C_2H_5)(CH_3)]$—, —$CH(C_3H_7)$—, —$CH_2CH_2O$—, —$(CH_2$—$CH_2$—$O)_n$—$CH_2$—$CH_2$—, —$C(CH_3)$=$CH$—$C(CH_3)$=$CH$—, —$C_2H_4$—$CH$=$CH$—$CH$=$CH$—, —$CH_2$—$CH$=$CH$—$CH_2$—$CH$=$CH$—, —$C_3H_6$—$C$≡$C$—$CH_2$—, —$CH_2$—$CH$=$CH$—$CH$=$CH$—$CH_2$—, —$CH$=$CH$—$CH$=$CH$—$C_2H_4$—, —$CH_2$—$CH$=$CH$—$C(CH_3)$=$CH$—, —$CH_2$—$CH$=$C(CH_3)$—$CH$=$CH$—, —$CH_2$—$C(CH_3)$=$CH$—$CH$=$CH$—, —$CH(CH_3)$—$CH$=$CH$—$CH$=$CH$—, —$CH$=$CH$—$CH_2$—$C(CH_3)$=$CH$—, —$CH(CH_3)$—$C$≡$C$—$CH_2$—, —$CONH$—, —$NHCO$—, —$CH_2$—$CONH$—, —$CONH$—$CH_2$—, —$NHCO$—$CH_2$—, —$CH_2$—$NHCO$—;

wherein n is an integer from 1 to 10; or $L_1$-$R^B$ and $L_2$-$R^C$ or $L_1$-$R^B$ and $L_3$-$R^D$ or $L_2$-$R^C$ and $L_3$-$R^D$ form together a cyclic ring selected from the group consisting of:

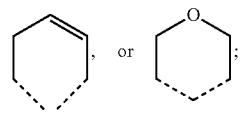

Further, the following formulas (II)-(V) of formula (I) are more preferred:

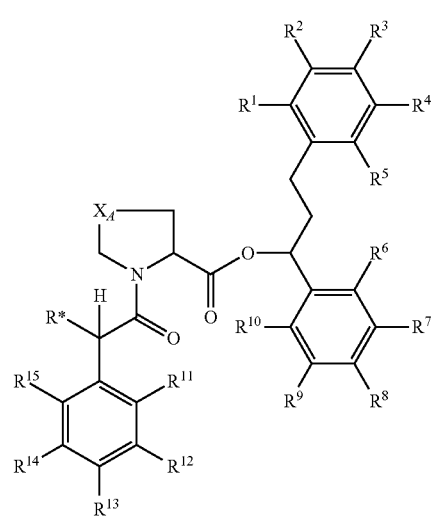
(II)

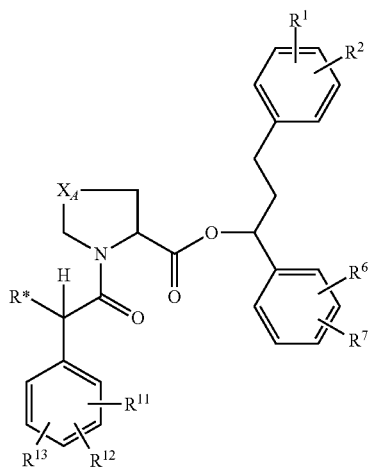
(III)

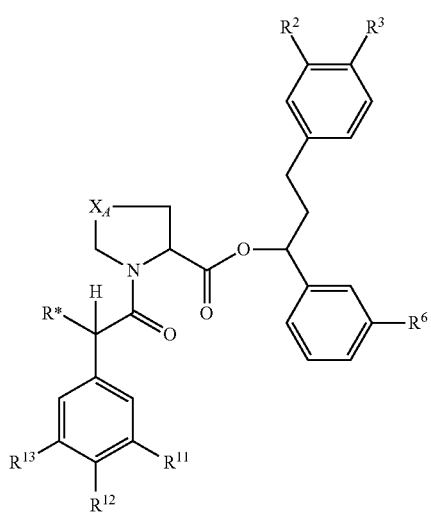
(IV)

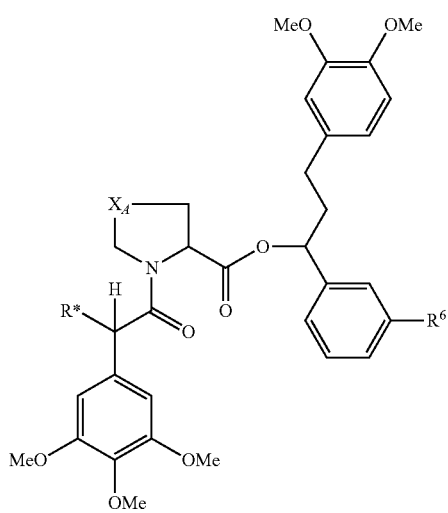
(V)

wherein $X_A$ represents —$CH_2$—, —$CH_2CH_2$—, —$CH$=$CH$—, —$CH_2$—$S$—, or —$S$—$CH_2$—; and preferably —$CH_2$—, —$CH_2CH_2$—, or —$CH$=$CH$—, and more preferably —$CH_2$— or —$CH_2CH_2$—, and most preferably —$CH_2CH_2$—.

R* represents —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —CH₂-cyclo-C₃H₅, —CH₂-cyclo-C₆H₁₁, —CH₂—CH=CH₂, —CH₂-cyclo-C₆H₉, R¹-R¹⁵ represent independently of each other —H, —OH, —OCH₃, —OC₂H₅, —OC₃H₇, —O-cyclo-C₃H₅, —OCH(CH₃)₂, —OC(CH₃)₃, —OC₄H₉, —OCH₂—COOH, —OPh, —OCH₂-Ph, —OCPh₃, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —SH, —SCH₃, —SC₂H₅, —SC₃H₇, —S-cyclo-C₃H₅, —SCH(CH₃)₂, —SC(CH₃)₃, —NO₂, —F, —Cl, —Br, —I, —P(O)(OH)₂, —P(O)(OCH₃)₂, —P(O)(OC₂H₅)₂, —P(O)(OC(CH₃)₃)₂, —C(OH)[P(O)(OH)₂]₂, —Si(CH₃)₂(C(CH₃)₃), —Si(C₂H₅)₃, —Si(CH₃)₃, —N₃, —CN, —OCN, —NCO, —SCN, —NCS, —CHO, —COCH₃, —COC₂H₅, —COC₃H₇, —CO-cyclo-C₃H₅, —COCH(CH₃)₂, —COC(CH₃)₃, —COOH, —COCN, —COOCH₃, —COOC₂H₅, —COOC₃H₇, —COO-cyclo-C₃H₅, —COOCH(CH₃)₂, —COOC(CH₃)₃, —OOC—CH₃, —OOC—C₂H₅, —OOC—C₃H₇, —OOC-cyclo-C₃H₅, —OOC—CH(CH₃)₂, —OOC—C(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —NHCOCH₃, —NHCOC₂H₅, —NHCOC₃H₇, —NHCO-cyclo-C₃H₅, —NHCO—CH(CH₃)₂, —NHCO—C(CH₃)₃, —NHCO—OCH₃, —NHCO—OC₂H₅, —NHCO—OC₃H₇, —NHCO—O-cyclo-C₃H₅, —NHCO—OCH(CH₃)₂, —NHCO—OC(CH₃)₃, —NH₂, —NHCH₃, —NHC₂H₅, —NHC₃H₇, —NH-cyclo-C₃H₅, —NHCH(CH₃)₂, —NHC(CH₃)₃, —N(CH₃)₂, —N(C₂H₅)₂, —N(C₃H₇)₂, —N(cyclo-C₃H₅)₂, —N[CH(CH₃)₂]₂, —N[C(CH₃)₃]₂, —SOCH₃, —SOC₂H₅, —SOC₃H₇, —SO-cyclo-C₃H₅, —SOCH(CH₃)₂, —SOC(CH₃)₃, —SO₂CH₃, —SO₂C₂H₅, —SO₂C₃H₇, —SO₂-cyclo-C₃H₅, —SO₂CH(CH₃)₂, —SO₂C(CH₃)₃, —SO₃H, —SO₃CH₃, —SO₃C₂H₅, —SO₃C₃H₇, —SO₃-cyclo-C₃H₅, —SO₃CH(CH₃)₂, —SO₃C(CH₃)₃, —SO₂NH₂, —SO₂NHCH₃, —SO₂NHC₂H₅, —SO₂NHC₃H₇, —SO₂NH-cyclo-C₃H₅, —SO₂NHCH(CH₃)₂, —SO₂NHC(CH₃)₃, —SO₂N(CH₃)₂, —SO₂N(C₂H₅)₂, —SO₂N(C₃H₇)₂, —SO₂N(cyclo-C₃H₅)₂, —SO₂N[CH(CH₃)₂]₂, —SO₂N[C(CH₃)₃]₂, —O—S(=O)CH₃, —O—S(=O)C₂H₅, —O—S(=O)C₃H₇, —O—S(=O)-cyclo-C₃H₅, —O—S(=O)CH(CH₃)₂, —O—S(=O)C(CH₃)₃, —S(=O)(=NH)CH₃, —S(=O)(=NH)C₂H₅, —S(=O)(=NH)C₃H₇, —S(=O)(=NH)-cyclo-C₃H₅, —S(=O)(=NH)CH(CH₃)₂, —S(=O)(=NH)C(CH₃)₃, —NH—SO₂—CH₃, —NH—SO₂—C₂H₅, —NH—SO₂—C₃H₇, —NH—SO₂-cyclo-C₃H₅, —NH—SO₂—CH(CH₃)₂, —NH—SO₂—C(CH₃)₃, —O—SO₂—CH₃, —O—SO₂—C₂H₅, —O—SO₂—C₃H₇, —O—SO₂-cyclo-C₃H₅, —O—SO₂—CH(CH₃)₂, —O—SO₂—C(CH₃)₃, —OCF₃, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —O—COOCH₃, —O—COOC₂H₅, —O—COOC₃H₇, —O—COO-cyclo-C₃H₅, —O—COOCH(CH₃)₂, —O—COOC(CH₃)₃, —NH—CO—NH₂, —NH—CO—NHCH₃, —NH—CO—NHC₂H₅, —NH—CS—N(C₃H₇)₂, —NH—CO—NHC₃H₇, —NH—CO—N(C₃H₇)₂, —NH—CO—NH[CH(CH₃)₂], —NH—CO—NH[C(CH₃)₃], —NH—CO—N(CH₃)₂, —NH—CO—N(C₂H₅)₂, —NH—CO—NH-cyclo-C₃H₅, —NH—CO—N(cyclo-C₃H₅)₂, —NH—CO—N[CH(CH₃)₂]₂, —NH—CS—N(C₂H₅)₂, —NH—CO—N[C(CH₃)₃]₂, —NH—CS—NH₂, —NH—CS—NHCH₃, —NH—CS—N(CH₃)₂, —NH—CS—NHC₂H₅, —NH—CS—NHC₃H₇, —NH—CS—NH-cyclo-C₃H₅, —NH—CS—NH[CH(CH₃)₂], —NH—CS—NH[C(CH₃)₃], —NH—CS—N(cyclo-C₃H₅)₂, —NH—CS—N[CH(CH₃)₂]₂, —NH—CS—N[C(CH₃)₃]₂, —NH—C(=NH)—NH₂, —NH—C(=NH)—NHCH₃, —NH—C(=NH)—NHC₂H₅, —NH—C(=NH)—NHC₃H₇, —O—CO—NH-cyclo-C₃H₅, —NH—C(=NH)—NH-cyclo-C₃H₅, —NH—C(=NH)—NH[CH(CH₃)₂], —O—CO—NH[CH(CH₃)₂], —NH—C(=NH)—NH[C(CH₃)₃], —NH—C(=NH)—N(CH₃)₂, —NH—C(=NH)—N(C₂H₅)₂, —NH—C(=NH)—N(C₃H₇)₂, —NH—C(=NH)—N(cyclo-C₃H₅)₂, —O—CO—NHC₃H₇, —NH—C(=NH)—N[CH(CH₃)₂]₂, —NH—C(=NH)—N[C(CH₃)₃]₂, —O—CO—NH₂, —O—CO—NHCH₃, —O—CO—NHC₂H₅, —O—CO—NH[C(CH₃)₃], —O—CO—N(CH₃)₂, —O—CO—N(C₂H₅)₂, —O—CO—N(C₃H₇)₂, —O—CO—N(cyclo-C₃H₅)₂, —O—CO—N[CH(CH₃)₂]₂, —O—CO—N[C(CH₃)₃]₂, —O—CO—OCH₃, —O—CO—OC₂H₅, —O—CO—OC₃H₇, —O—CO—O-cyclo-C₃H₅, —O—CO—OCH(CH₃)₂, —O—CO—OC(CH₃)₃, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₈H₁₅, -Ph, —CH₂-Ph, —CH₂CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH=CH₂, —CH₂—CH=CH₂, —C(CH₃)=CH₂, —CH=CH—CH₃, —C₂H₄—CH=CH₂, —CH₂—CH=CH—CH₃, —CH=CH—C₂H₅, —CH₂—C(CH₃)=CH₂, —CH(CH₃)—CH=CH, —CH=C(CH₃)₂, —C(CH₃)=CH—CH₃, —CH=CH—CH=CH₂, —C₃H₆—CH=CH₂, —C₂H₄—CH=CH—CH₃, —CH₂—CH=CH—C₂H₅, —CH=CH—C₃H₇, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —C₂H₄—C(CH₃)=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH=CH—CH(CH₃)₂, —CH=CH—CH=CH(CH₃)₂, —CH=C(CH₃)—C₂H₅, —C(CH₃)=CH—C₂H₅, —C(CH₃)=C —(CH₃)₂, —C(CH₃)₂—CH═CH₂, —CH(CH₃)—C(CH₃)═CH₂, —C(CH₃)═CH—CH═CH₂, —CH═C(CH₃)—CH═CH₂, —CH═CH—C(CH₃)═CH₂, —C₄H₈—CH═CH₂, —C₃H₆—CH═CH—CH₃, —C₂H₄—CH═CH—C₂H₅, —CH₂—CH═CH—C₃H₇, —CH═CH—C₄H₉, —C₃H₆—C(CH₃)═CH₂, —C₂H₄—CH(CH₃)—CH═CH₂, —CH₂—CH(CH₃)—CH₂—CH═CH₂, —C₂H₄—CH═C(CH₃)₂, —CH(CH₃)—C₂H₄—CH═CH₂, —C₂H₄—C(CH₃)═CH—CH₃, —CH₂—CH(CH₃)—CH═CH—CH₃, —CH(CH₃)—CH₂—CH═CH—CH₃, —CH₂—CH═CH—CH(CH₃)₂, —CH₂—CH═C(CH₃)—C₂H₅, —CH₂—C(CH₃)═CH—C₂H₅, —CH(CH₃)—CH═CH—C₂H₅, —CH═CH—CH₂—CH(CH₃)₂, —CH═CH—CH(CH₃)—C₂H₅, —CH═C(CH₃)—C₃H₇, —C(CH₃)═CH—C₃H₇, —CH₂—CH(CH₃)—C(CH₃)═CH₂, —C[C(CH₃)₃]═CH₂, —CH(CH₃)—CH₂—C(CH₃)═CH₂, —CH(CH₃)—CH(CH₃)—CH═CH₂, —CH═CH—C₂H₄—CH═CH₂, —CH₂—C(CH₃)₂—CH═CH₂, —C(CH₃)₂—CH₂—CH═CH₂, —CH₂—C(CH₃)═C(CH₃)₂, —CH(CH₃)—CH═C(CH₃)₂, —C(CH₃)₂—CH═CH—CH₃, —CH═CH—CH₂—CH═CH—CH₃, —CH(CH₃)—C(CH₃)═CH—CH₃, —CH═C(CH₃)—CH(CH₃)₂, —C(CH₃)═CH—CH(CH₃)₂, —CH(CH₃)₂, —C(CH₃)═C(CH₃)—C₂H₅, —CH═CH—C(CH₃)₃, —C(CH₃)₂—C(CH₃)═CH₂, —CH(C₂H₅)—C(CH₃)═CH₂, —C(CH₃)(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₉)═CH₂, —C(C₃H₇)═CH—CH₃, —C(C₂H₅)═CH—C₂H₅, —C(C₂H₅)═C(CH₃)₂, —C[CH(CH₃)(C₂H₅)]═CH₂, —C[CH₂—CH(CH₃)₂]═CH₂, —C₂H₄—CH═CH—CH₂, —CH₂—CH═CH—CH₂—CH═CH₂, —C₃H₆—C≡C—CH₃, —CH₂—CH═CH—CH═CH—CH₃, —CH═CH—CH═CH—C₂H₅, —CH₂—CH═CH—C(CH₃)═CH₂, —CH₂—CH═C(CH₃)—CH═CH₂, —CH₂—C(CH₃)═CH—CH═CH₂, —CH(CH₃)—CH₂—C≡CH, —CH(CH₃)—CH═CH—CH═CH₂, —CH═CH—CH₂—C(CH₃)═CH₂, —CH(CH₃)—C≡C—CH₃, —CH═CH—CH(CH₃)—CH═CH₂, —CH═C(CH₃)—CH₂—CH═CH₂, —C₂H₄—CH(CH₃)—C≡CH, —C(CH₃)═CH—CH₂—CH═CH₂, —CH═CH—CH═C(CH₃)₂, —CH₂—CH(CH₃)—CH₂—C≡CH, —CH═CH—C(CH₃)═CH—CH₃, —CH₂—CH(CH₃)—C≡CH, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH═CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —C≡CH, —CH₂—CH(C≡CH)₂, —C≡C—C≡CH, —CH₂—C≡C—C≡CH, —C≡C—C≡C—CH₃, —CH(C≡CH)—C₂H₄—C≡CH, —CH₂—C≡C—

—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃,

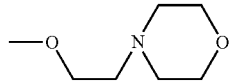

and wherein at least one of R¹¹-R¹⁵ is not —H;
More preferred are the compounds of the following formula (VI) and (VIa):

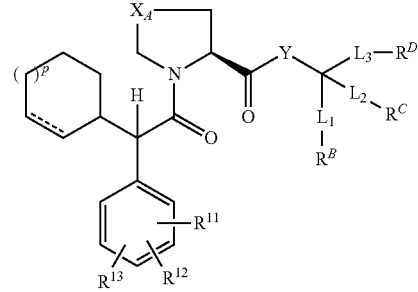
(VI)

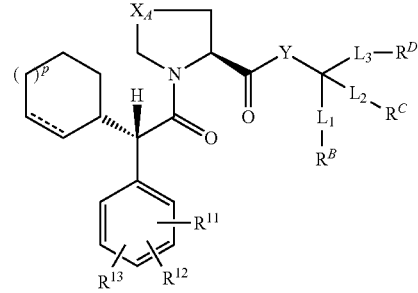
(VIa)

wherein
$X_A$ represents —CH₂—, —CH₂CH₂—, —CH═CH—, —CH₂—S—, or —S—CH₂—;
Y represents —NH—, or —O—;
p is an integer of 0 or 1;
"⸺" represents a C═C bond or a C—C bond;
$R^{11}$-$R^{13}$ represent independently of each other —H, —OH, —OCH₃, —OC₂H₅, —OC₃H₇, —O-cyclo-C₃H₅, —OCH(CH₃)₂, —OC(CH₃)₃, —OC₄H₉, —OCH₂—COOH, —OPh, —OCH₂-Ph, —OCPh₃, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —SH, —SCH₃, —SC₂H₅, —SC₃H₇, —S-cyclo-C₃H₅, —SCH(CH₃)₂, —SC(CH₃)₃, —NO₂, —F, —Cl, —Br, —I, —P(O)(OH)₂, —P(O)(OCH₃)₂, —P(O)(OC₂H₅)₂, —P(O)(OCH(CH₃)₂)₂, —C(OH)[P(O)(OH)₂]₂, —Si —(CH$_3$)$_2$C(C(CH$_3$)$_3$), —Si(C$_2$H$_5$)$_3$, —Si(CH$_3$)$_3$, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(OH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$—Cyclo-O$_3$H$_5$, —SO$_3$CH(CH$_3$)$_2$, —SO$_3$C(CH$_3$)$_3$, —SO$_2$NH$_2$, —SO$_2$NHCH$_3$, —SO$_2$NHC$_2$H$_5$, —SO$_2$NHC$_3$H$_7$, —SO$_2$NH-cyclo-C$_3$H$_5$, —SO$_2$NHCH(CH$_3$)$_2$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N(cyclo-C$_3$H$_5$)$_2$, —SO$_2$N[CH(CH$_3$)$_2$]$_2$, —SO$_2$N[C(CH$_3$)$_3$]$_2$, —O—S(=O)CH$_3$, —O—S(=O)C$_2$H$_5$, —O—S(=O)C$_3$H$_7$, —O—S(=O)-cyclo-C$_3$H$_5$, —O—S(=O)CH(CH$_3$)$_2$, —O—S(=O)C(CH$_3$)$_3$, —S(=O)(=NH)CH$_3$, —S(=O)(=NH)C$_2$H$_5$, —S(=O)(=NH)C$_3$H$_7$, —S(=O)(=NH)-cyclo-C$_3$H$_5$, —S(=O)(=NH)CH(CH$_3$)$_2$, —S(=O)(=NH)C(CH$_3$)$_3$, —NH—SO$_2$—CH$_3$, —NH—SO$_2$—C$_2$H$_5$, —NH—SO$_2$—C$_3$H$_7$, —NH—SO$_2$-cyclo-C$_3$H$_5$, —NH—SO$_2$—CH(CH$_3$)$_2$, —NH—SO$_2$—C(CH$_3$)$_3$, —O—SO$_2$—CH$_3$, —O—SO$_2$—C$_2$H$_5$, —O—SO$_2$—C$_3$H$_7$, —O—SO$_2$-cyclo-C$_3$H$_5$, —O—SO$_2$—CH(CH$_3$)$_2$, —O—SO$_2$—C(CH$_3$)$_3$, —OCF$_3$, —CH$_2$—OCF$_3$, —C$_2$H$_4$—OCF$_3$, —C$_3$H$_6$—OCF$_3$, —OC$_2$F$_5$, —CH$_2$—OC$_2$F$_5$, —C$_2$H$_4$—OC$_2$F$_5$, —C$_3$H$_6$—OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CS—N(C$_3$H$_7$)$_2$, —NH—CO—NHC$_3$H$_7$, —NH—CO—N(C$_3$H$_7$)$_2$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—NH-cyclo-C$_3$H$_5$, —NH—CO—N(cyclo-C$_3$H$_5$)$_2$, —NH—CO—N[CH(CH$_3$)$_2$]$_2$, —NH—CS—N(C$_2$H$_5$)$_2$, —NH—CO—N[C(CH$_3$)$_3$]$_2$, —NH—CS—NH$_2$, —NH—CS—NHCH$_3$, —NH—CS—N(CH$_3$)$_2$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —O—CO—NH-cyclo-C$_3$H$_5$, —NH—C(=NH)—NH-cyclo-C$_3$H$_5$, —NH—C(=NH)—NH[CH(CH$_3$)$_2$] —O—CO—NH[CH(CH$_3$)$_2$], —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —O—CO—NHC$_3$H$_7$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_8$H$_{15}$, -Ph, —CH$_2$-Ph, —CH$_2$CH$_2$-Ph, —CH=CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)=C(CH$_3$)$_2$, —C(CH$_3$)$_2$—CH=CH$_2$, —CH(CH$_3$)—C(CH$_3$)=CH$_2$, —C(CH$_3$)$_2$—CH=CH—CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —C$_2$H$_4$—CH=C(CH$_3$)$_2$, —CH(CH$_3$)—C$_2$H$_4$—CH=CH$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —C[C(CH$_3$)$_3$]=CH$_2$, —CH(CH$_3$)—CH$_2$—C(CH$_3$)=CH$_2$, —CH(CH$_3$)—CH(CH$_3$)—CH=CH$_2$, —CH=CH—C$_2$H$_4$—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH=CH—CH$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C —(CH₃)₃, —C(CH₃)₂—C(CH₃)═CH₂, —CH(C₂H₅)—C(CH₃)═CH₂, —C(CH₃)(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₉)═CH₂, —C(C₃H₇)═CH—CH₃, —C(C₂H₅)═CH—C₂H₅, —C(C₂H₅)═C(CH₃)₂, —C[CH(CH₃)(C₂H₅)]═CH₂, —C[CH₂—CH(CH₃)₂]═CH₂, —C₂H₄—CH═CH—CH═CH₂, —CH₂—CH═CH—CH₂—CH═CH₂, —C₃H₆—C≡C—CH₃, —CH₂—CH═CH—CH═CH—CH₃, —CH═CH—CH═CH—C₂H₅, —CH₂—CH═CH—C(CH₃)═CH₂, —CH₂—CH═C(CH₃)—CH═CH₂, —CH₂—C(CH₃)═CH—CH═CH₂, —CH(CH₃)—CH₂—C≡CH, —CH(CH₃)—CH═CH—CH═CH₂, —CH═CH—CH₂—C(CH₃)═CH₂, —CH(CH₃)—C≡C—CH₃, —CH═CH—CH(CH₃)—CH═CH₂, —CH═C(CH₃)—CH₂—CH═CH₂, —C₂H₄—CH(CH₃)—C≡CH, —C(CH₃)═CH—CH₂—CH═CH₂, —CH═CH—CH═C(CH₃)₂, —CH═C(CH₃)—CH═CH—CH₃, —CH₂—CH(CH₃)—CH₂—C≡CH, —CH═CH—C(CH₃)═CH—CH₃, —CH═C(CH₃)—CH═CH—CH₃, —CH₂—CH(CH₃)—C≡CH, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH₂, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₆)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃, wherein at least one of $R^{11}$-$R^{13}$ is not —H, and $R^B$, $R^C$, $R^D$, $L_1$, $L_2$, and $L_3$ have the meanings and preferred meanings as disclosed herein or as defined in general formula (I).

$X_A$ represents preferably —CH₂—, —CH₂CH₂—, or —CH═CH—, more preferably —CH₂— or —CH₂CH₂—, and most preferably —CH₂CH₂—.

p represents preferably 1.

Preferably $R^{11}$-$R^{13}$ represent independently of each other —H, —OH, —OCH₃, —OC₂H₅, —OC₃H₇, —O-cyclo-C₃H₅, —OCH(CH₃)₂, —OC(CH₃)₃, —OC₄H₉, —OCH₂—COOH, —OPh, —OCH₂-Ph, —OCPh₃, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —F, —Cl, —Br, or —I.

More preferred are the compounds of the following formula (VIb) and (VIc):

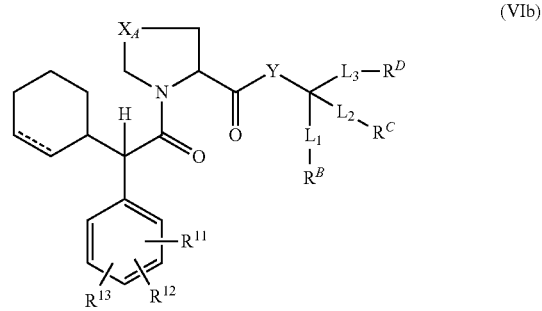

(VIb)

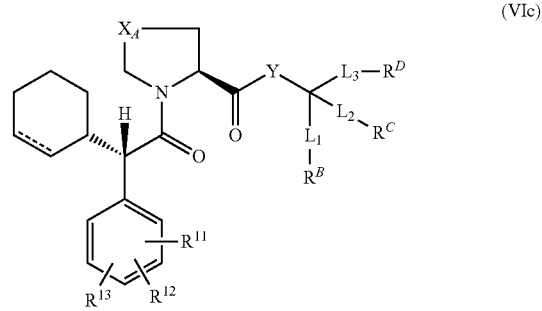

(VIc)

wherein
the residues $X_A$, $R^{11}$-$R^{13}$, Y, $R^B$, $R^C$, $R^D$, $L_1$, $L_2$, and $L_3$ have the meanings as defined above for the general formula (VI) and also the preferred meanings for $X_A$ and $R^{11}$-$R^{13}$ as defined above for the general formula (VI).

More preferred are the compounds of the following formula (VId) and (VIe):

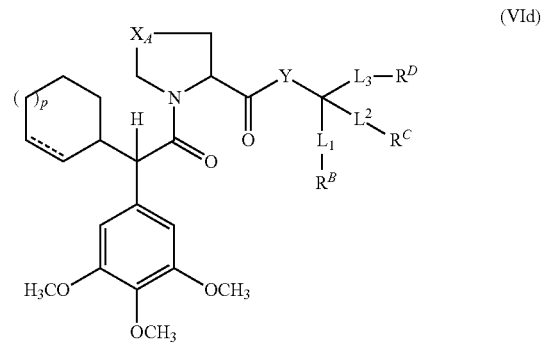

(VId)

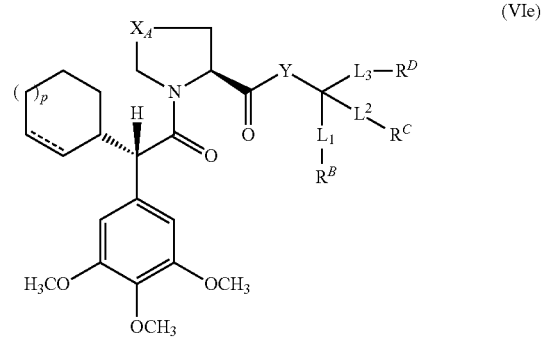

(VIe)

wherein the residues $X_A$, Y, p, $R^B$, $R^C$, $R^D$, $L_1$, $L_2$, and $L_3$ have the meanings as defined above for the general formula (VI) and also the preferred meanings for $X_A$ and p as defined above for the general formula (VI).

More preferred are the compounds of the following formula (VIf) and (VIg):

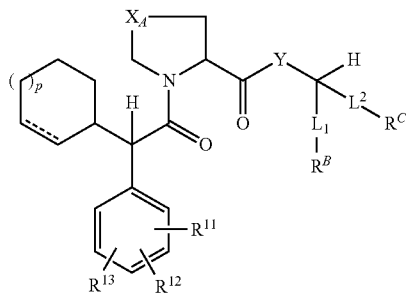

(VIf)

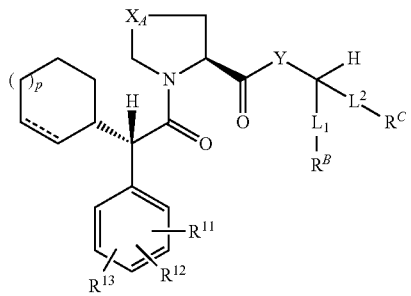

(VIg)

wherein the residues $X_A$, $R^{11}$-$R^{13}$, Y, p, $R^B$, $R^C$, $L_1$, and $L_2$ have the meanings as defined above for the general formula (VI) and also the preferred meanings for $X_A$, p and $R^{11}$-$R^{13}$ as defined above for the general formula (VI).

Preferably in the general formula (VI) to (VIg) two of the substituents $R^{11}$-$R^{13}$ are different from hydrogen and still more preferably all three substituents $R^{11}$-$R^{13}$ are different from hydrogen. Moreover in all general formula (VI) to (VIg) it is preferred if one of the substituents $R^{11}$-$R^{13}$ is in meta or para position, more preferably two of the substituents $R^{11}$-$R^{13}$ are in meta position or one substituent is in meta and the other one is in para position. Most preferably, two substituents of $R^{11}$-$R^{13}$ are in meta and the third substituent is in para position.

More preferred are the compounds of the following formula (VIh) and (VIj):

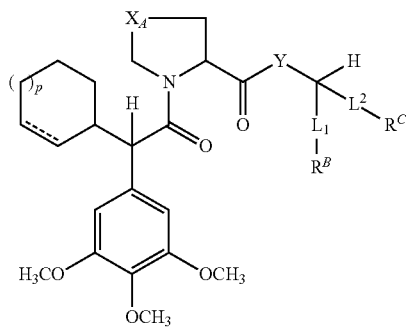

(VIh)

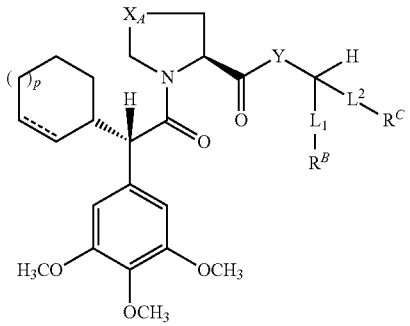

(VIj)

wherein the residues $X_A$, Y, p, $R^B$, $R^C$, $L_1$, and $L_2$ have the meanings as defined above for the general formula (VI) and also the preferred meanings for $X_A$ and p as defined above for the general formula (VI).

Even more preferred are the compounds of the following formula (VII):

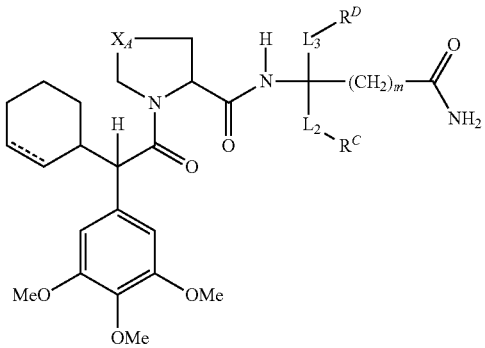

(VII)

wherein $X_A$ represents —$CH_2$—, —$CH_2CH_2$—, —CH=CH—, —$CH_2$—S—, —S—$CH_2$—;

m is an integer from 1 to 5;

"⇌" represents a C=C bond or a C—C bond;

$L_2$ and $L_3$ represent independently of each other: a bond, —$CH_2$—, —$C_2H_4$—, —$C_3H_6$—, —$C_4H_8$—, —$C_5H_{10}$—, —$C_6H_{12}$—, —$C_7H_{14}$—, —$C_8H_{16}$—, —$C_9H_{18}$—, —$C_{10}H_{20}$—, —CH($CH_3$)—, —C[($CH_3)_2$]—, —$CH_2$—CH($CH_3$)—, —CH($CH_3$)—$CH_2$—, —CH($CH_3$)—$C_2H_4$—, —$CH_2$—CH($CH_3$)—$CH_2$—, —$C_2H_4$—CH($CH_3$)—, —$CH_2$—C[($CH_3)_2$]—, —C[($CH_3)_2$]—$CH_2$—, —CH($CH_3$)—CH($CH_3$)—, —C[($C_2H_5$)($CH_3$)]—, —CH($C_3H_7$)—, —($CH_2$—$CH_2$—O)$_n$—$CH_2$—$CH_2$—, —C($CH_3$)=CH—C($CH_3$)=CH—, —$C_2H_4$—CH=CH—CH=CH—, —$CH_2$—CH=CH—$CH_2$—CH=CH—, —$C_3H_6$—C≡C—$CH_2$—, —$CH_2$—CH=CH—CH=CH—$CH_2$—, —CH=CH—CH=CH—$C_2H_4$—, —$CH_2$—CH=CH—C($CH_3$)=CH—, —$CH_2$—CH=C($CH_3$)—CH=CH—, —$CH_2$—C($CH_3$)=CH—CH=CH—, —CH($CH_3$)—CH=CH—CH=CH—, —CH=CH—CH($CH_3$)—CH=CH—, —CH($CH_3$)—C≡C—$CH_2$—;

wherein n is an integer from 1 to 10; and $R^C$, $R^D$, $L_2$, and $L_3$ have the meanings and preferred meanings as disclosed herein.

Most preferred are the compounds of the formula (VIII):

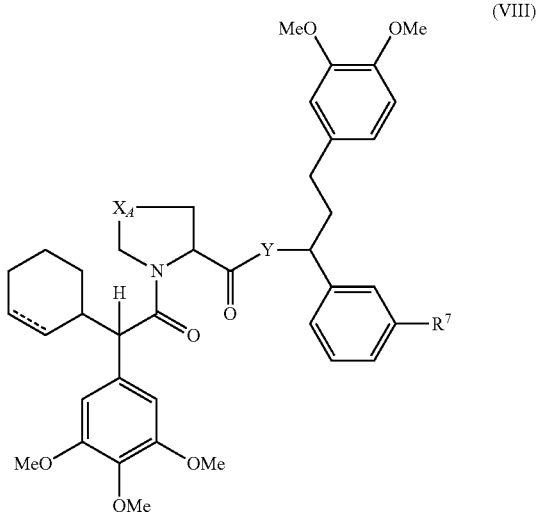

(VIII)

wherein
$X_A$ represents —$CH_2$—, —$CH_2CH_2$—, —CH=CH—, —$CH_2$—S—, or —S—$CH_2$—;
Y represents —NH—, or —O—;
"⤳" represents a C=C bond or a C—C bond;
$R^7$ has the meanings and the preferred meanings as disclosed herein.

In all general formula (I)-(VIII) disclosed herein the following substituent is preferred as residue $R^A$

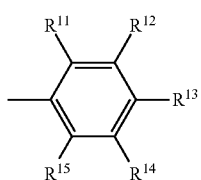

wherein
at least three of the substituents $R^{11}$-$R^{15}$ represent independently of each other a $C_1$-$C_4$-alkoxy group, hydroxy group, $C_1$-$C_3$-hydroxyalkyl group or $C_2$-$C_7$-alkoxyalkyl group and more preferably at least three of the substituents $R^{11}$-$R^{15}$ represent independently of each other —OH, —$OCH_3$, —$OC_2H_5$, —$OC_3H_7$, —O-cyclo-$C_3H_5$, —$OCH(CH_3)_2$, —$OC(CH_3)_3$, —$OC_4H_9$, —$OCH_2$—COOH, —$CH_2$—OH, —$C_2H_4$—OH, —$C_3H_6$—OH, —CH(OH)—$CH_2$—OH, —$CH_2$—$OCH_3$, —$C_2H_4$—$OCH_3$, —$C_3H_6$—$OCH_3$, —$CH_2$—$OC_2H_5$, —$C_2H_4$—$OC_2H_5$, —$C_3H_6$—$OC_2H_5$, —$CH_2$—$OC_3H_7$, —$C_2H_4$—$OC_3H_7$, —$C_3H_6$—$OC_3H_7$, —$CH_2$—O-cyclo-$C_3H_5$, —$C_2H_4$—O-cyclo-$C_3H_5$, —$C_3H_6$—O-cyclo-$C_3H_5$, —$CH_2$—$OCH(CH_3)_2$, —$C_2H_4$—$OCH(CH_3)_2$, —$C_3H_6$—$OCH(CH_3)_2$, —$CH_2$—$OC(CH_3)_3$, —$C_2H_4$—$OC(CH_3)_3$, —$C_3H_6$—$OC(CH_3)_3$, —$CH_2$—$OC_4H_9$, —$C_2H_4$—$OC_4H_9$, or —$C_3H_6$—$OC_4H_9$. Still more preferred are —$OCH_3$, —$OC_2H_5$, —$OC_3H_7$, —O-cyclo-$C_3H_5$, —$OCH(CH_3)_2$, —$OC_4H_9$, —$OCH_2$—COOH, —$CH_2$—OH, —$C_2H_4$—OH, —$C_3H_6$—OH, —$CH_2$—$OCH_3$, —$C_2H_4$—$OCH_3$, —$CH_2$—$OC_2H_5$, —$CH_2$—O-cyclo-$C_3H_5$, —$CH_2$—$OCH(CH_3)_2$, and even more preferred are —$OCH_3$, —$OC_2H_5$, —$OC_3H_7$, —O-cyclo-$C_3H_5$, —$CH_2$—OH, —$C_2H_4$—OH, —$C_3H_6$—OH, —$CH_2$—$OCH_3$, —$C_2H_4$—$OCH_3$, —$CH_2$—$OC_2H_5$, and even more preferred are —$OCH_3$, —$OC_2H_5$, —$OC_3H_7$, —O-cyclo-$C_3H_5$, —$CH_2$—$OCH_3$, —$C_2H_4$—$OCH_3$, —$CH_2$—$OC_2H_5$, and most preferred are —$OCH_3$, —$OC_2H_5$, —$CH_2$—$OCH_3$.

Still more preferably $R^{11}$ and $R^{15}$ are hydrogen and $R^{12}$-$R^{14}$ represent independently of each other a $C_1$-$C_4$-alkoxy group, hydroxy group, $C_1$-$C_3$-hydroxyalkyl group or $C_2$-$C_7$-alkoxyalkyl group and more preferably at least three of the substituents $R^{12}$-$R^{14}$ represent independently of each other —OH, —$OCH_3$, —$OC_2H_5$, —$OC_3H_7$, —O-cyclo-$C_3H_5$, —$OCH(CH_3)_2$, —$OC(CH_3)_3$, —$OC_4H_9$, —$OCH_2$—COOH, —$CH_2$—OH, —$C_2H_4$—OH, —$C_3H_6$—OH, —CH(OH)—$CH_2$—OH, —$CH_2$—$OCH_3$, —$C_2H_4$—$OCH_3$, —$C_3H_6$—$OCH_3$, —$CH_2$—$OC_2H_5$, —$C_2H_4$—$OC_2H_5$, —$C_3H_6$—$OC_2H_5$, —$CH_2$—$OC_3H_7$, —$C_2H_4$—$OC_3H_7$, —$C_3H_6$—$OC_3H_7$, —$CH_2$—O-cyclo-$C_3H_5$, —$C_2H_4$—O-cyclo-$C_3H_5$, —$C_3H_6$—O-cyclo-$C_3H_5$, —$CH_2$—$OCH(CH_3)_2$, —$C_2H_4$—$OCH(CH_3)_2$, —$C_3H_6$—$OCH(CH_3)_2$, —$CH_2$—$OC(CH_3)_3$, —$C_2H_4$—$OC(CH_3)_3$, —$C_3H_6$—$OC(CH_3)_3$, —$CH_2$—$OC_4H_9$, —$C_2H_4$—$OC_4H_9$, or —$C_3H_6$—$OC_4H_9$. Still more preferred are —$OCH_3$, —$OC_2H_5$, —$OC_3H_7$, —O-cyclo-$C_3H_5$, —$OCH(CH_3)_2$, —$OC_4H_9$, —$OCH_2$—COOH, —$CH_2$—OH, —$C_2H_4$—OH, —$C_3H_6$—OH, —$CH_2$—$OCH_3$, —$C_2H_4$—$OCH_3$, —$CH_2$—$OC_2H_5$, —$CH_2$—O-cyclo-$C_3H_5$, —$CH_2$—$OCH(CH_3)_2$, and even more preferred are —$OCH_3$, —$OC_2H_5$, —$OC_3H_7$, —O-cyclo-$C_3H_5$, —$CH_2$—OH, —$C_2H_4$—OH, —$C_3H_6$—OH, —$CH_2$—$OCH_3$, —$C_2H_4$—$OCH_3$, —$CH_2$—$OC_2H_5$, and even more preferred are —$OCH_3$, —$OC_2H_5$, —$OC_3H_7$, —O-cyclo-$C_3H_5$, —$CH_2$—$OCH_3$, —$C_2H_4$—$OCH_3$, —$CH_2$—$OC_2H_5$, and most preferred are —$OCH_3$, —$OC_2H_5$, —$CH_2$—$OCH_3$.

Moreover in all general formula (I)-(VIII) disclosed herein R* represents preferably:
—R, —$CH_2$—R, —$CH(CH_3)_2$, —$C_4H_9$, —$CH_2$—CH($CH_3)_2$, —$CH(CH_3)$—$C_2H_5$, —$C_5H_{11}$, —$CH(CH_3)$—$C_3H_7$, —$CH_2$—$CH(CH_3)$—$C_2H_5$, —$CH(CH_3)$—$CH(CH_3)_2$, —$CH(C_2H_5)_2$, —$C_2H_4$—$CH(CH_3)_2$, —$C_6H_{13}$, —$CH_2$-cyclo-$C_3H_5$, —$CH_2$-cyclo-$C_6H_{11}$, —$CH_2$—CH=$CH_2$, —$CH_2$-cyclo-$C_6H_9$, -Ph, —$CH_2$-Ph; and
R** represents

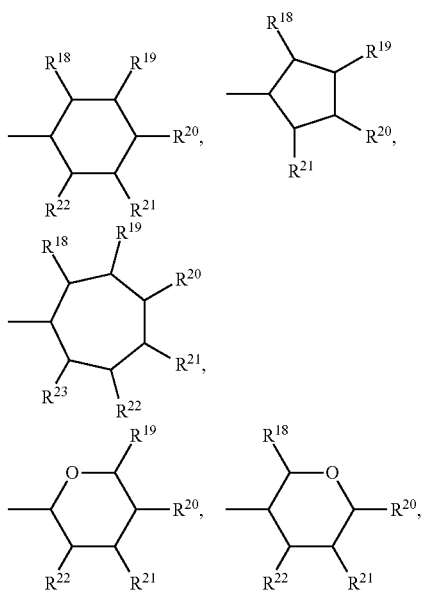

-continued

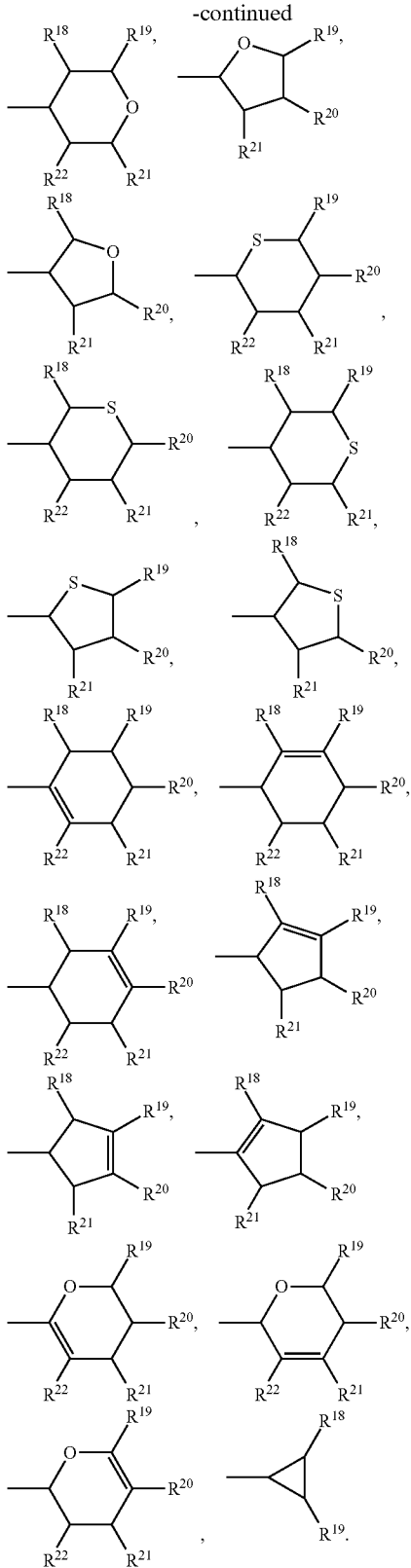

In all general formula (I)-(VIII) disclosed herein R* represents more preferably:

—R, —CH$_2$—R, —CH(CH$_3$)—C$_3$H$_7$, —CH$_2$—CH(CH$_3$)—C$_2$H$_5$, —CH(CH$_3$)—CH(CH$_3$)$_2$, —CH(C$_2$H$_5$)$_2$, —C$_2$H$_4$—CH(CH$_3$)$_2$, —CH$_2$-cyclo-C$_3$H$_5$, —CH$_2$-cyclo-C$_6$H$_{11}$, —CH$_2$—CH═CH$_2$, —CH$_2$-cyclo-C$_6$H$_9$, -Ph, —CH$_2$-Ph; and R** represents

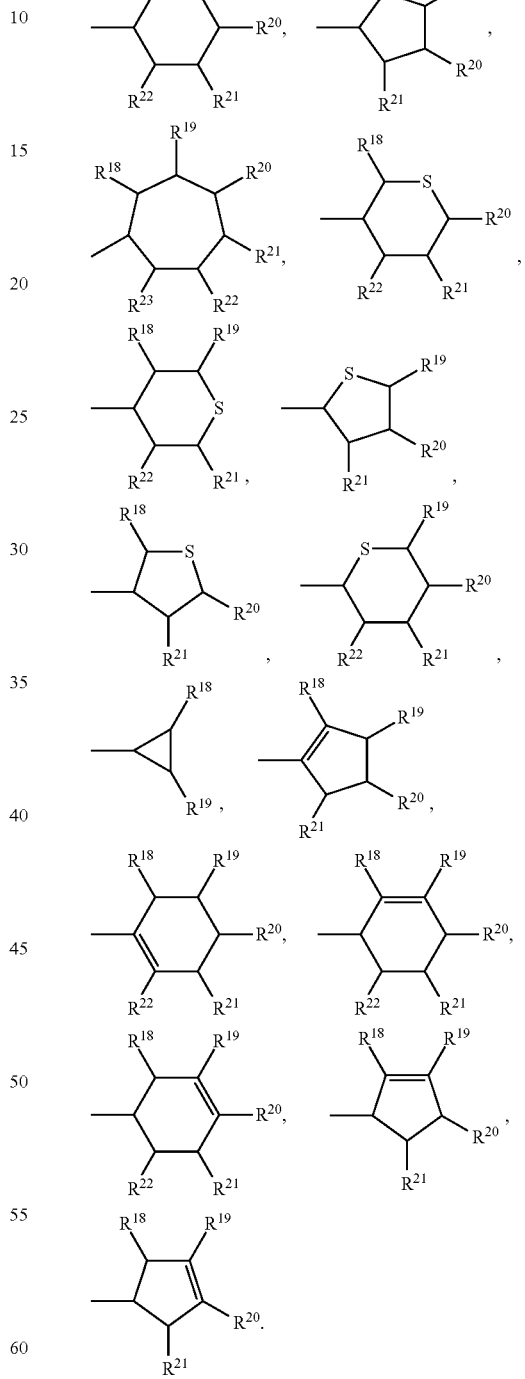

In all general formula (I)-(VIII) disclosed herein R* represents still more preferably:

—R, —CH$_2$—R, —CH$_2$-cyclo-C$_6$H$_{11}$, —CH$_2$—CH═CH$_2$, —CH$_2$-cyclo-C$_6$H$_9$, -Ph, —CH$_2$-Ph; and R** represents

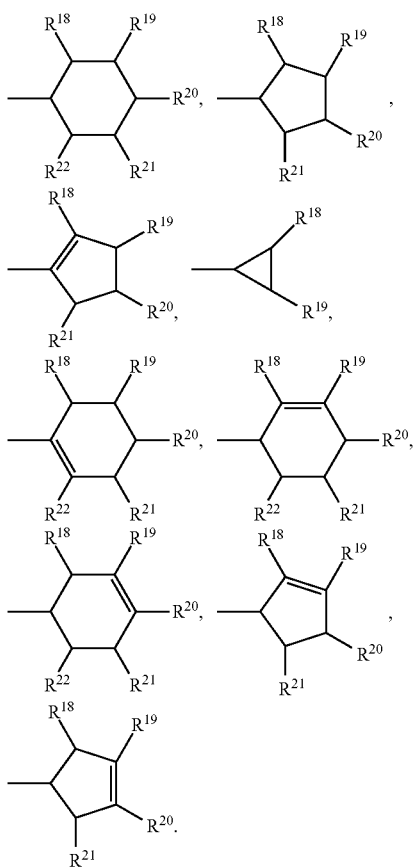

In all general formula (I)-(VIII) disclosed herein R* represents even more preferably:

-cyclo-$C_5H_9$, —$CH_2$-cyclo-$C_5H_9$, -cyclo-$C_6H_{11}$, —$CH_2$-cyclo-$C_6H_{11}$, -Ph, —$CH_2$-Ph,

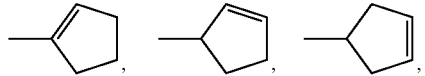

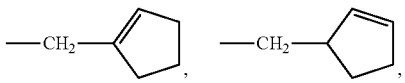

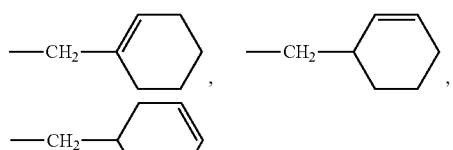

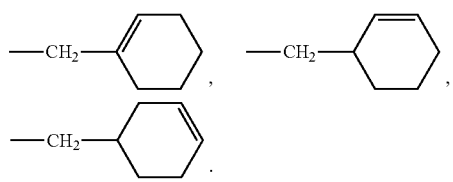

More preferred are compound selected from the group consisting of:

| A02 | 2-(3-((R)-3-(3,4-Dimethoxyphenyl)-1-(((S)-1-((S)-2-(3,4,5-trimethoxyphenyl) pent-4-enoyl)piperidine-2-carbonyl)oxy)propyl) phenoxy)acetic acid, |
|---|---|
| A03 | 2-(3-((R)-3-(3,4-dimethoxyphenyl)-1-(((S)-1-((S)-2-(3,4,5-trimethoxyphenyl)pent-4-enoyl)pyrrolidine-2-carbonyl)oxy)propyl)phenoxy)acetic acid, |
| A04 | (S)-1,7-di(pyridin-3-yl)heptan-4-yl 1-((S)-2-(3,4,5-trimethoxyphenyl)pent-4-enoyl)piperidine-2-carboxylate, |
| A05 | (S)-N-((R)-3-(3,4-dimethoxyphenyl)-1-(3-(2-morpholinoethoxy)phenyl)propyl)-1-((S)-2-(3,4,5-trimethoxyphenyl)pent-4-enoyl)piperidine-2-carboxamide, |
| A06 | 2-(3-((R)-3-(3,4-Dimethoxyphenyl)-1-(((S)-1-((S)-2-(3,4,5-trimethoxyphenyl)pent-4-enoyl)-1,2,3,6-tetrahydropyridine-2-carbonyl)oxy)propyl)phenoxy) acetic acid, |
| A08 | (S)-(R)-3-(3,4-dimethoxyphenyl)-1-(3-(2-morpholinoethoxy)phenyl)propyl-1-((S)-3-cyclopropyl-2-(3,4,5-trimethoxyphenyl)propanoyl)piperidine-2-carboxylate, |
| A09 | (S)-(R)-3-(3,4-dimethoxyphenyl)-1-(3-(2-morpholinoethoxy)phenyl)propyl-1-((S)-3-cyclopropyl-2-(3,4,5-trimethoxyphenyl)propanoyl)pyrrolidine-2-carboxylate, |
| A10 | 2-(3-((R)-3-(3,4-dimethoxyphenyl)-1-(((S)-1-((S)-3-phenyl-2-(3,4,5-trimethoxyphenyl)propanoyl)piperidine-2-carbonyl)oxy)propyl) phenoxy)acetic acid, |
| A11 | 2-(3-((R)-1-(((S)-1-((S)-2-((S)-Cyclohex-2-en-1-yl)-2-(3,4,5-trimethoxyphenyl)acetyl)piperidine-2-carbonyl)oxy)-3-(3,4-dimethoxyphenyl)propyl)phenoxy) acetic acid, |
| A12 | (S)-(R)-3-(3,4-Dimethoxyphenyl)-1-(3-(2-morpholinoethoxy)phenyl)propyl-1-((S)-2-((S)-cyclohex-2-en-1-yl)-2-(3,4,5-trimethoxyphenyl)acetyl)piperidine-2-carboxylate, |
| A13 | (S)-1,7-Di(pyridin-3-yl)heptan-4-yl-1-((S)-2-((S)-cyclohex-2-en-1-yl)-2-(3,4,5-trimethoxy phenyl) acetyl)piperidine-2-carboxylate, |
| A14 | (S)-2-(3,4-Dimethoxyphenoxy)ethyl-1-((S)-2-((R)-cyclohex-2-en-1-yl)-2-(3,4,5-trimethoxy phenyl)acetyl)piperidine-2-carboxylate, |

| | |
|---|---|
| A15 | (S)-(R)-3-(3,4-dimethoxyphenyl)-1-(3-(2-morpholinoethoxy)phenyl)propyl-1-((S)-2-((R)-cyclohex-2-en-1-yl)-2-(3,4,5-trimethoxyphenyl)acetyl)pyrrolidine-2-carboxylate, |
| A16 | 2-(3-((R)-1-((S)-1-((S)-2-((R)-Cyclohex-2-en-1-yl)-2-(3,4,5-trimethoxyphenyl)acetyl)piper-idine-2-carboxamido)-3-(3,4-dimethoxyphenyl)propyl)phenoxy) acetic acid, |
| A17 | 2-(3-((R)-1-(((S)-1-((S)-2-Cyclohexyl-2-(3,4,5-trimethoxyphenyl)acetyl)piperidine-2-carbonyl)oxy)-3-(3,4-dimethoxyphenyl)propyl)phenoxy)acetic acid, |
| A18 | (S)-(R)-3-(3,4-dimethoxyphenyl)-1-(3-(2-morpholinoethoxy)phenyl)propyl-1-((S)-2-cyclohexyl-2-(3,4,5-trimethoxyphenyl)acetyl)piperidine-2-carboxylate, |
| A19 | (2S)-1,7-di(pyridin-3-yl)heptan-4-yl 1-(2-cyclohexyl-2-(3,4,5-trimethoxy phenyl)acetyl)piperidine-2-carboxylate, |
| A20 | (S)-2-(3,4-dimethoxyphenoxy)ethyl-1-((S)-2-cyclohexyl-2-(3,4,5-trimethoxy phenyl)acetyl)piperidine-2-carboxylate, |
| A21 | (S)-(R)-3-(3,4-dimethoxyphenyl)-1-(3-(2-morpholinoethoxy)phenyl)propyl-1-((S)-2-cyclohexyl-2-(3,4,5-trimethoxyphenyl) acetyl)pyrrol-idine-2-carboxylate, |
| A22 | 2-(3-((R)-1-((S)-1-((S)-2-cyclohexyl-2-(3,4,5-trimethoxyphenyl)acetyl)piperidine-2-carboxamido)-3-(3,4-dimethoxyphenyl)propyl)phenoxy)acetic acid, |
| A23 | 2-(3-(1-(((2S)-1-(2-benzamido-2-cyclohexylacetyl) piperidine-2-carbonyl)oxy)-3-(3,4-dimethoxyphenyl)propyl)phenoxy) acetic acid, |
| A24 | 2-(3-(1-(((2S)-1-(2-cyclohexyl-2-(2-hydroxy benzamido)acetyl)piperidine-2-carbonyl)oxy)-3-(3,4-dimethoxyphenyl) propyl)phenoxy)acetic acid, |
| A25 | 2-(3-(1-(((2S)-1-(2-cyclohexyl-2-(picolinamido) acetyl)piperidine-2-carbonyl)oxy)-3-(3,4-dimethoxyphenyl)propyl)phenoxy) acetic acid, |
| A26 | 2-(3-(1-(((2S)-1-(2-(cyclohexanecarboxamido)-2-cyclohexylacetyl)piperidine-2-carbonyl)oxy)-3-(3,4-dimethoxyphenyl)propyl)phenoxy)acetic acid, |
| A27 | 2-(3-(1-(((2S)-1-(2-cyclohexyl-2-(3H-1,2,4-triazole-3-carboxamido)acetyl)piperidine-2-carbonyl)oxy)-3-(3,4-dimethoxyphenyl) propyl)phenoxy)acetic acid, |
| A28 | 2-(3-(1-(((2S)-1-(2-cyclohexyl-2-(3,5-dichloro benzamido)acetyl)piperidine-2-carbonyl)oxy)-3-(3,4-dimethoxyphenyl) propyl)phenoxy)acetic acid, |
| A29 | (S)-(R)-3-(3,4-dimethoxyphenyl)-1-(3-(2-morpholinoethoxy)phenyl)propyl 1-((2S,3R)-2-cyclohexyl-3-hydroxybutanoyl)piperidine-2-carboxylate, |
| A30 | (S)-(R)-3-(3,4-dimethoxyphenyl)-1-(3-(2-morpholinoethoxy)phenyl)propyl 1-((2S,3R,E)-2-cyclohexyl-3-hydroxyhex-4-enoyl)piperidine-2-carboxylate, |
| A31 | (S)-(R)-3-(3,4-dimethoxyphenyl)-1-(3-(2-morpholinoethoxy)phenyl)propyl 1-((2S,3R)-2-cyclohexyl-3-(methoxymethoxy)-5-methylhexanoyl)piperidine-2-carboxylate, |
| A32 | (S)-(R)-3-(3,4-dimethoxyphenyl)-1-(3-(2-morpholinoethoxy)phenyl)propyl 1-((2S,3R)-2-cyclohexyl-3-hydroxy-5-methylhexanoyl)piperidine-2-carboxylate, |
| A36 | 2-(3-((R)-1-(((S)-1-((S)-2-cyclohexyl-2-(3-fluorophenyl)acetyl)piperidine-2-carbonyl)oxy)-3-(3,4-dimethoxyphenyl)propyl) phenoxy)acetic acid |
| A37 | 2-(3-((R)-1-(((S)-1-((R)-2-cyclohexylpropanoyl)piperidine-2-carbonyl)oxy)-3-(3,4-dimethoxyphenyl)propyl)phenoxy)acetic acid |
| A38 | 2-(3-((R)-1-(((S)-1-((R)-2-cyclohexylpent-4-enoyl)piperidine-2-carbonyl)oxy)-3-(3,4-dimethoxyphenyl)propyl)phenoxy) acetic acid |
| B01 | (S)-N-((S)-1-amino-1-oxopropan-2-yl)-1-((S)-2-cyclohexyl-2-(3,4,5-trimethoxyphenyl)acetyl)piperidine-2-carboxamide, |
| B02 | (S)-N-((R)-1-amino-1-oxopropan-2-yl)-1-((S)-2-cyclohexyl-2-(3,4,5-trimethoxyphenyl)acetyl)piperidine-2-carboxamide, |
| B03 | (S)-N-((S)-1-amino-3-methyl-1-oxobutan-2-yl)-1-((S)-2-cyclohexyl-2-(3,4,5-trimethoxyphenyl)acetyl)piperidine-2-carboxamide, |
| B04 | (S)-N-((R)-1-amino-3-methyl-1-oxobutan-2-yl)-1-((S)-2-cyclohexyl-2-(3,4,5-trimethoxyphenyl)acetyl)piperidine-2-carboxamide, |
| B05 | (S)-N-((S)-1-amino-1-oxo-3-phenylpropan-2-yl)-1-((S)-2-cyclohexyl-2-(3,4,5-trimethoxyphenyl)acetyl)piperidine-2-carboxamide, |
| B06 | (S)-N-((R)-1-amino-1-oxo-3-phenylpropan-2-yl)-1-((S)-2-cyclohexyl-2-(3,4,5-trimethoxyphenyl)acetyl)piperidine-2-carboxamide, |
| B07 | (S)-N-((S)-1-amino-3-cyclohexyl-1-oxopropan-2-yl)-1-((S)-2-cyclohexyl-2-(3,4,5-trimethoxyphenyl)acetyl)piperidine-2-carboxamide, |
| B08 | (S)-N-((S)-1-amino-1-oxo-4-phenylbutan-2-yl)-1-((S)-2-cyclohexyl-2-(3,4,5-trimethoxyphenyl)acetyl)piperidine-2-carboxamide, |
| B09 | (S)-N-((S)-1-amino-4-cyclohexyl-1-oxobutan-2-yl)-1-((S)-2-cyclohexyl-2-(3,4,5-trimethoxyphenyl)acetyl)piperidine-2-carboxamide, |
| B10 | (S)-N-(2-amino-2-oxoethyl)-1-((S)-2-cyclohexyl-2-(3,4,5-trimethoxyphenyl)acetyl)piperidine-2-carboxamide, |
| B11 | (S)-N-(1-amino-2-methyl-1-oxopropan-2-yl)-1-((S)-2-cyclohexyl-2-(3,4,5-trimethoxyphenyl)acetyl)piperidine-2-carboxamide, |
| B12 | (S)-N-((S)-1-amino-1-oxobutan-2-yl)-1-((S)-2-cyclohexyl-2-(3,4,5-trimethoxyphenyl)acetyl)piperidine-2-carboxamide, |
| B13 | (S)-N-((R)-1-amino-1-oxobutan-2-yl)-1-((S)-2-cyclohexyl-2-(3,4,5-trimethoxyphenyl)acetyl)piperidine-2-carboxamide, |

| | |
|---|---|
| B14 | (S)-N-((2S,3S)-1-amino-3-methyl-1-oxopentan-2-yl)-1-((S)-2-cyclohexyl-2-(3,4,5-trimethoxyphenyl)acetyl)piperidine-2-carboxamide, |
| B15 | (S)-N-((2R,3R)-1-amino-3-methyl-1-oxopentan-2-yl)-1-((S)-2-cyclohexyl-2-(3,4,5-trimethoxyphenyl)acetyl)piperidine-2-carboxamide, |
| B16 | (S)-N-((S)-2-amino-2-oxo-1-phenylethyl)-1-((S)-2-cyclohexyl-2-(3,4,5-trimethoxyphenyl)acetyl)piperidine-2-carboxamide, |
| B17 | (S)-N-((R)-2-amino-2-oxo-1-phenylethyl)-1-((S)-2-cyclohexyl-2-(3,4,5-trimethoxyphenyl)acetyl)piperidine-2-carboxamide, |
| B18 | (S)-N-((S)-2-amino-1-cyclohexyl-2-oxoethyl)-1-((S)-2-cyclohexyl-2-(3,4,5-trimethoxyphenyl)acetyl)piperidine-2-carboxamide, |
| B19 | (S)-N-((S)-1-amino-4-hydroxy-1-oxobutan-2-yl)-1-((S)-2-cyclohexyl-2-(3,4,5-trimethoxyphenyl)acetyl)piperidine-2-carboxamide, |
| B20 | (S)-N-((R)-1-amino-4-hydroxy-1-oxobutan-2-yl)-1-((S)-2-cyclohexyl-2-(3,4,5-trimethoxyphenyl)acetyl)piperidine-2-carboxamide, |
| B21 | (S)-N-((R)-1-amino-3-hydroxy-1-oxopropan-2-yl)-1-((S)-2-cyclohexyl-2-(3,4,5-trimethoxyphenyl)acetyl)piperidine-2-carboxamide, |
| B22 | (S)-N-((S)-1-amino-3-hydroxy-1-oxopropan-2-yl)-1-((S)-2-cyclohexyl-2-(3,4,5-trimethoxyphenyl)acetyl)piperidine-2-carboxamide, |
| B23 | (S)-2-((S)-1-((S)-2-cyclohexyl-2-(3,4,5-trimethoxyphenyl)acetyl)piperidine-2-carboxamido)pentanediamide, |
| B24 | (R)-2-((S)-1-((S)-2-cyclohexyl-2-(3,4,5-trimethoxyphenyl)acetyl)piperidine-2-carboxamido)pentanediamide, |
| B25 | (S)-N-(4-amino-2-methyl-4-oxobutan-2-yl)-1-((S)-2-cyclohexyl-2-(3,4,5-trimethoxyphenyl)acetyl)piperidine-2-carboxamide, |
| B26 | (S)-N-(1-carbamoylcyclopropyl)-1-((S)-2-cyclohexyl-2-(3,4,5-trimethoxyphenyl)acetyl)piperidine-2-carboxamide, |
| B27 | (S)-N-(1-carbamoylcyclobutyl)-1-((S)-2-cyclohexyl-2-(3,4,5-trimethoxyphenyl)acetyl)piperidine-2-carboxamide, |
| B28 | (S)-N-(1-carbamoylcyclopentyl)-1-((S)-2-cyclohexyl-2-(3,4,5-trimethoxyphenyl)acetyl)piperidine-2-carboxamide, |
| B29 | (S)-N-(3-amino-3-oxopropyl)-1-((S)-2-cyclohexyl-2-(3,4,5-trimethoxyphenyl)acetyl)piperidine-2-carboxamide, |
| B30 | (S)-N-((S)-1-amino-4-methyl-1-oxopentan-2-yl)-1-((S)-2-cyclohexyl-2-(3,4,5-trimethoxyphenyl)acetyl)piperidine-2-carboxamide, |
| B31 | (S)-N-(1-carbamoylcyclohexyl)-1-((S)-2-cyclohexyl-2-(3,4,5-trimethoxyphenyl) acetyl)piperidine-2-carboxamide |
| B32 | (S)-N-(1-carbamoylcyclohexyl)-1-((S)-2-cyclohexyl-2-(3,4,5-trimethoxyphenyl) acetyl)piperidine-2-carboxamide |
| B33 | (S)-N-(1-((2-amino-2-oxoethyl)carbamoyl)cyclopentyl)-1-((S)-2-cyclohexyl-2-(3,4,5-trimethoxyphenyl)acetyl)piperidine-2-carboxamide |
| B34 | (S)-N-((R)-1-amino-3-(1H-imidazol-4-yl)-1-oxopropan-2-yl)-1-((S)-2-cyclohexyl-2-(3,4,5-trimethoxyphenyl)acetyl)piperidine-2-carboxamide |
| B35 | (S)-N-((S)-1-amino-3-(1H-imidazol-4-yl)-1-oxopropan-2-yl)-1-((S)-2-cyclohexyl-2-(3,4,5-trimethoxyphenyl)acetyl)piperidine-2-carboxamide |
| C01 | (S)-methyl 1-((S)-2-cyclohexyl-2-(3,4,5-trimethoxyphenyl)acetyl)piperidine-2-carboxylate, |
| C02 | (S)-ethyl 1-((S)-2-cyclohexyl-2-(3,4,5-trimethoxyphenyl)acetyl)piperidine-2-carboxylate, |
| C03 | (S)-propyl 1-((S)-2-cyclohexyl-2-(3,4,5-trimethoxyphenyl)acetyl)piperidine-2-carboxylate, |
| C04 | (S)-isopropyl 1-((S)-2-cyclohexyl-2-(3,4,5-trimethoxyphenyl)acetyl)piperidine-2-carboxylate, |
| C05 | (S)-1-((S)-2-cyclohexyl-2-(3,4,5-trimethoxyphenyl)acetyl)-N-ethylpiperidine-2-carboxamide, |
| C07 | (S)-(S)-sec-butyl-1-((S)-2-cyclohexyl-2-(3,4,5-trimethoxyphenyl)acetyl) piperidine-2-carboxylate |
| C08 | (S)-(R)-sec-butyl-1-((S)-2-cyclohexyl-2-(3,4,5-trimethoxyphenyl)acetyl) piperidine-2-carboxylate |
| C09 | (S)-pentan-3-yl-1-((S)-2-cyclohexyl-2-(3,4,5-trimethoxyphenyl)acetyl) piperidine-2-carboxylate |
| C10 | (S)-tert-butyl-1-((S)-2-cyclohexyl-2-(3,4,5-trimethoxyphenyl)acetyl) piperidine-2-carboxylate |
| C11 | (S)-1-methylcyclopentyl-1-((S)-2-cyclohexyl-2-(3,4,5-trimethoxyphenyl) acetyl)piperidine-2-carboxylate |
| C12 | (S)-tetrahydro-2H-pyran-4-yl-1-((S)-2-cyclohexyl-2-(3,4,5-trimethoxyphenyl)acetyl)piperidine-2-carboxylate |
| C13 | (S)-cyclopentyl-1-((S)-2-cyclohexyl-2-(3,4,5-trimethoxyphenyl)acetyl) piperidine-2-carboxylate |
| C14 | (S)-cyclopent-3-en-1-yl-1-((S)-2-cyclohexyl-2-(3,4,5-trimethoxyphenyl) acetyl)piperidine-2-carboxylate |
| C15 | (2S)-cyclohex-2-en-1-yl-1-((S)-2-cyclohexyl-2-(3,4,5-trimethoxyphenyl) acetyl)piperidine-2-carboxylate |
| C16 | (S)-cycloheptyl-1-((S)-2-cyclohexyl-2-(3,4,5-trimethoxyphenyl)acetyl) piperidine-2-carboxylate |
| C17 | (S)-allyl-1-((S)-2-cyclohexyl-2-(3,4,5-trimethoxyphenyl)acetyl)piperidine-2-carboxylate |
| C18 | (S)-2-methoxyethyl-1-((S)-2-cyclohexyl-2-(3,4,5-trimethoxyphenyl)acetyl) piperidine-2-carboxylate |

| | |
|---|---|
| C19 | (S)-2-(benzyloxy)ethyl-1-((S)-2-cyclohexyl-2-(3,4,5-trimethoxyphenyl)acetyl)piperidine-2-carboxylate |
| C20 | (S)-2-hydroxyethyl-1-((S)-2-cyclohexyl-2-(3,4,5-trimethoxyphenyl)acetyl)piperidine-2-carboxylate |
| C21 | (S)-3-(benzyloxy)propyl-1-((S)-2-cyclohexyl-2-(3,4,5-trimethoxyphenyl)acetyl)piperidine-2-carboxylate |
| C22 | (S)-2-hydroxyethyl-1-((S)-2-cyclohexyl-2-(3,4,5-trimethoxyphenyl)acetyl)piperidine-2-carboxylate |
| C23 | (S)-4-methoxybutyl-1-((S)-2-cyclohexyl-2-(3,4,5-trimethoxyphenyl)acetyl)piperidine-2-carboxylate |
| C24 | (S)-(R)-1-(benzyloxy)propan-2-yl-1-((S)-2-cyclohexyl-2-(3,4,5-trimethoxyphenyl)acetyl)piperidine-2-carboxylate |
| C25 | (R)-(R)-1-(benzyloxy)propan-2-yl-1-((S)-2-cyclohexyl-2-(3,4,5-trimethoxyphenyl)acetyl)piperidine-2-carboxylate |

Synthetic Methods

In scheme 1 the general synthetic approach for the compound of the general formula (I) is depicted. A synthetic building block A can be easily obtained by alkylation at Cα-position of carboxyl amide coupled with a chiral auxiliary such as oxazolidone (a) or pseudoephedrine (a) (step i)). A synthetic building block B can be available by coupling reaction of an N-protected proline derivative C1 with a suitable alcohol or amine D (step ii)). Said alcohol or amine is commercially available or can be obtained synthetically. Alternatively, a synthetic building block E can be obtained by coupling reaction of the synthetic building block A and a protected ester C2 (step iii)). The compounds of the general formula (I) are prepared by the further coupling reaction of the synthetic building blocks A and B or D and E under well-known coupling reaction condition of carboxylic acid and amine group (step iv)).

In scheme 2 it is shown that the compounds of the general formula (VII) can be prepared conveniently by solid phase synthesis. Various Fmoc-protected amino acids are firstly coupled with the Sieber-amide resin. After deprotection of Fmoc group from the amino acid bound to the resin, a Fmoc-protected proline derivative is coupled . . . . After deprotection of Fmoc group from the proline derivative bound to the resin, the free amine group of the resulting proline derivative is coupled with the synthetic building block A. The inventive compounds are obtained by the acidic cleavage from the resin.

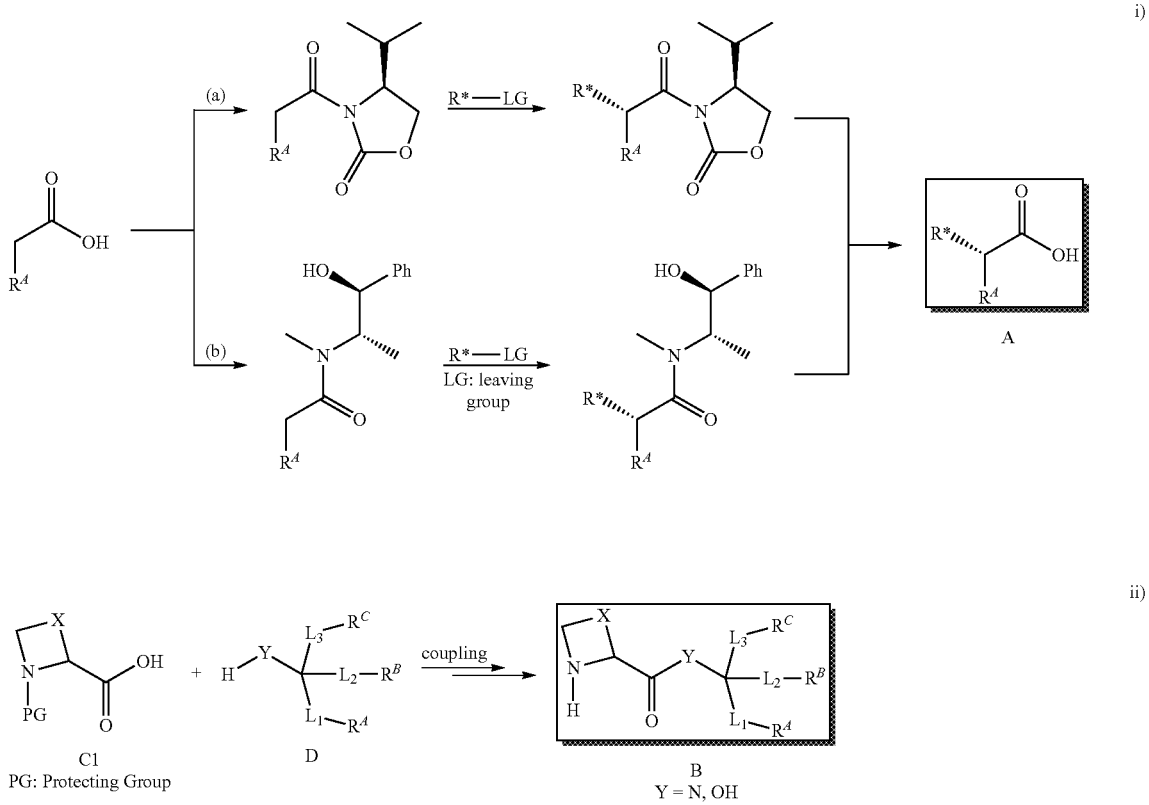

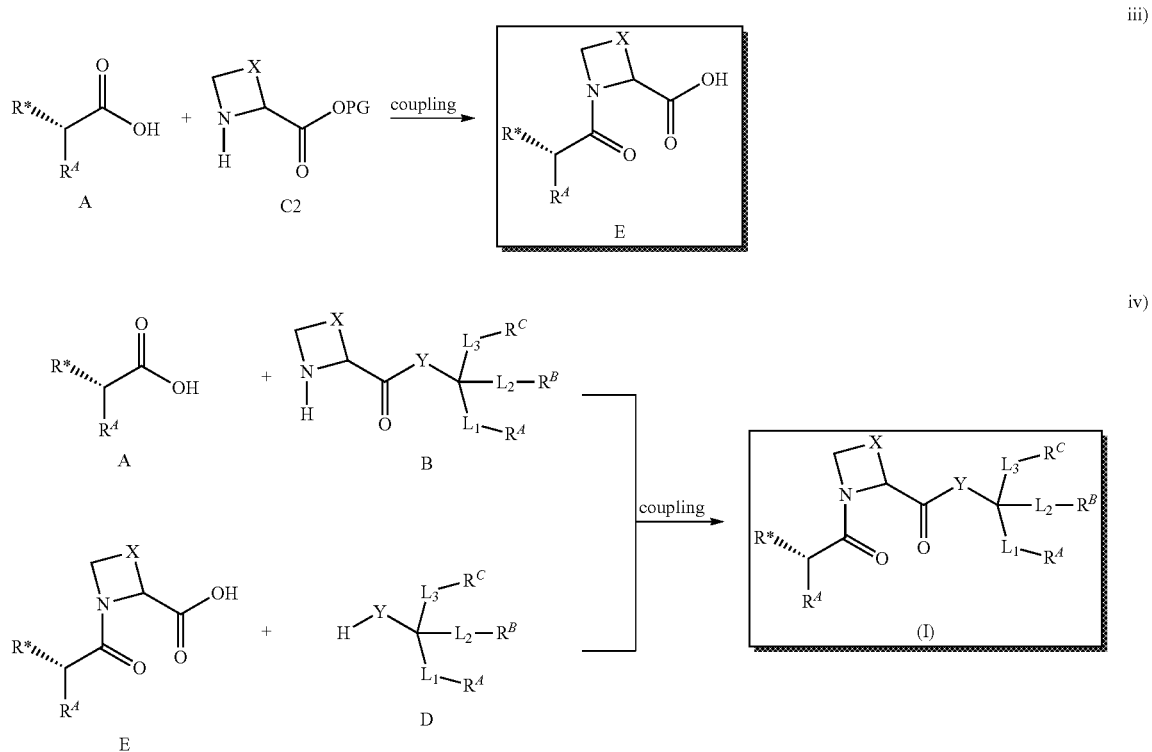
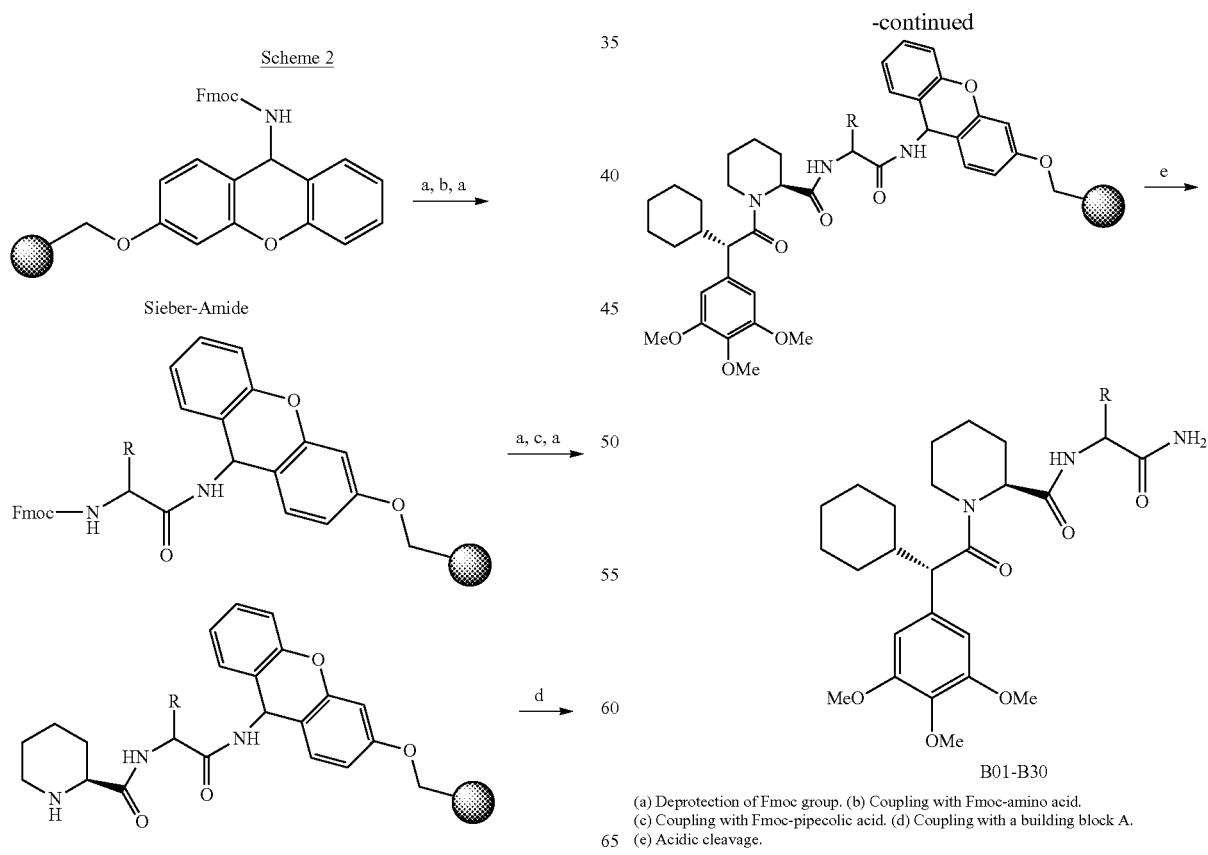
(a) Deprotection of Fmoc group. (b) Coupling with Fmoc-amino acid.
(c) Coupling with Fmoc-pipecolic acid. (d) Coupling with a building block A.
(e) Acidic cleavage.

Selective Inhibition of the Compounds of the General Formula (I) Against FKBP51

In the present invention, in vitro fluorescence polarization assays with the compounds of the general formula (I) were performed to determine the binding affinities for FKBP51 and FKBP52 or for the isolated FK506-binding domains of FKBP51 and FKBP52 (Example 6A and 6B). Binding to the isolated FK506-binding domains is reliably indicative of binding to the full length proteins. The affinities for the isolated FK506-binding domains and for full-length FKBP51 or FKBP52 are the same for all compounds tested so far (Kozany et al, ChemBioChem 2009, 10, 1402-1410).

Surprisingly, it was found by these assays that Ca-substitutents (R*) consistently induce a selectivity for FKBP51 vs. FKBP52. Furthermore, it was also proved that R*-substituents of the compounds of the general formula (I) substantially increase the affinity for FKBP51 compared to all known non-immunosupressive FKBP51 ligands so far. In Tables 4 and 5 the binding and selectivity data of exemplary compounds of the general formula (I) are summarized.

Thus, an embodiment of the present invention refers to compounds of the general formula (I), the subformulas (Ia-f, II-VIII) for use as selective FKBP51 inhibitor.

Furthermore, it was found that compounds of the general formula (I), the subformulas (Ia-f, II-VIII) can also inhibit FKBP51 homologs, or other FKBP mutants with mutation corresponding to Lys58, Lys60 and Phe129 of FKBP51 or to FKBP homologs or mutants where the residue corresponding to Phe67 of FBKP51 had been mutated to smaller amino acids, e.g, like in $FKBP^{Phe67Val}$.

Therefore, another embodiment of the present invention is directed to compounds of the general formula (I), the subformulas (Ia-f, II-VIII) for use as inhibitor of FKBP51 homologs, or other FKBP mutants with mutation corresponding to Lys58, Lys60, Phe67 and Phe129 of FKBP51.

N2a Cellular Assay

FK506 analogs have repeatedly been described as neuroprotective and neuroregenerative agents in the prior arts, but the relevant targets have never been identified. In the present invention, it is proved that inhibition of FKBP51, which has emerged as a promising target for psychiatric disorders, accounts for the neuritotrophic effect of FKBP ligands.

Using a neurite outgrowth assay with N2a neuroblastoma cells, which are a recognized model for neuronal differentiation, we surprisingly found that selective inhibition of FKBP51 over FKBP52 is important for a robust stimulation of neurite outgrowth. The selective FKBP51 inhibitors A17 and A18 both led to a stronger enhancement of neurite outgrowth compared to the prototypical, unselective FKBP ligand FK506 (FIG. 1). Moreover, this stimulation by selective FKBP51 inhibitors was largely sustained over a broad concentration range (1-1000 nM, FIGS. 1A and 1D), whereas the neurite outgrowth stimulating effect of FK506 was lost at higher concentrations (300-1000 nM, FIG. 1B). This is due to the concomitant inhibition of FKBP52 by the unselective FK506, since higher concentrations of FK506 also blocked the stimulating effect evoked by selective FKBP51 inhibition (achieved by treatment with 100 nM of compound A17, FIG. 1C).

Selective FKBP51 ligands such as A17 were also able to protect the neutrite outgrowth of N2a from the suppressing effect of high steroid concentrations (e.g., 1 µM of the MR agonist aldosterone or 1 µM of the GR agonist RU26988, FIGS. 2A and 2C). This protective effect was not observed by the unselective FKBP ligand FK506 (FIG. 2B).

Forced Swim Test

To demonstrate the usefulness of selective FKBP51 inhibitors we tested compound A18 in the Forced Swim Test, the classical test for antidepressant activity. In this animal model, A18 elicited a more active stress-coping behavior (FIG. 2D), thus providing the first proof of concept for FKBP51 inhibitors as a novel pharmacological treatment of stress-related disorders.

Pharmaceutical Composition

The present invention also comprises pharmaceutically acceptable salts of the compounds according to the general formula (I) and the subformulas (Ia-f, II-VIII), all stereoisomeric forms of the compounds according to the general formula (I) and the subformulas (Ia-f, II-VIII) as well as solvates, especially hydrates or prodrugs thereof.

In case, the inventive compounds bear basic and/or acidic substituents, they may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples for suitable inorganic or organic bases are, for example, NaOH, KOH, $NH_4OH$, tetraalkylammonium hydroxide, lysine or arginine and the like. Salts may be prepared in a conventional manner using methods well known in the art, for example by treatment of a solution of the compound of the general formula (I) and the subformulas (Ia-f, II-VIII) with a solution of an acid, selected out of the group mentioned above.

Some of the compounds of the present invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain compounds of the general formula (I) and the subformulas (Ia-f, II-VIII) may exist in the form of optical isomers if substituents with at least one asymmetric center are present, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses. Where a compound according to the general formula (I) contains an alkene moiety, the alkene can be presented as a cis or trans isomer or a mixture thereof. When an isomeric form of a compound of the invention is provided substantially free of other isomers, it will preferably contain less than 5% w/w, more preferably less than 2% w/w and especially less than 1% w/w of the other isomers.

Another aspect of the present invention relates to the use of the inventive selective FKBP51 ligand derivatives as drugs, i.e. as pharmaceutically active agents applicable in medicine.

Surprisingly it was found that the above-mentioned selective FKBP51 ligand derivatives as well as the pharmaceutical compositions comprising said selective FKBP51 ligand derivatives are useful for the selective inhibition of FKBP51.

Therefore one aspect of the present invention is that the compounds according to the general formula (I) and the subformulas (Ia-f, II-VIII) are suitable for use as inhibitor of FK506-binding proteins (FKBP). It is preferred if said compound is suitable for use as selective inhibitor of the FK506-binding protein 51 (FKBP51).

FKBP51 has been implicated in numerous in human diseases (Schmidt et al., ChemMedChem 2012, 7, 1351-1359; Gaali et al, Curr Med Chem 2011, 18, 5355-5379; Galigniana et al, J. Neurochem 2012, 122, 4-18; Erlejman et al, Futue Med Chem 2013, 5, 591-607; Sanchez, biochim Biophys Acta Mol Cell Res 2012r, 1823, 722-729).

Thus, the selective FKBP51 ligand compounds of the present invention can be used for treatment, or for the preparation of a pharmaceutical formulation for prophylaxis and treatment of these FKBP51-associated diseases. These include psychiatric and neurodegenerative diseases, disorders and conditions, for metabolic diseases such as localized adiposity or obesity, for sleep disorders, neuroprotection or neuroregeneration, for the treatment of neurological disorders, for the treatment of diseases relating to neurodegeneration, for the treatment of cancers such as malignant melanoma or acute lymphoblastic leukemia and especially steroid-hormone dependent cancers such as prostate cancer, for the treatment of glucocorticoid hyposensitivity syndromes and for peripheral glucocorticoid resistance, for asthma, especially steroid-resistant asthma, and for the treatment of infectious diseases, for the treatment of alopecia and promoting hair growth, for the treatment or prevention of multi-drug resistance, for stimulating neurite growth or neuroregeneration, for neuroprotection, for the use as wound healing agents for treating wounds resulting from injury or surgery; for the use in antiglaucomatous medications for treating abnormally elevated intraocular pressure; for the use in limiting or preventing hemorrhage or neovascularization for treating macular degeneration, and for treating oxidative damage to eye tissues, for treating a vision disorder, for improving vision, for treating memory impairment or enhancing memory performance.

The selective FKBP51 ligand compounds of the present invention are preferably suitable for treatment, or for the preparation of a pharmaceutical formulation for prophylaxis and treatment of psychiatric diseases. It is especially preferred if this psychiatric diseases is an affective disorder (ICD-10 classification: F30-F39) or an anxiety disorder.

Affective disorder is a mental disorder characterized by dramatic changes or extremes of mood. The affective disorder according to the invention is selected from the group comprising or consisting of depression, bipolar disorder, mania, substance induced mood disorder and seasonal affective disorder (SAD). Among the psychiatric diseases and disorders, the most preferred is depression, the most commonly diagnosed psychiatric disorder.

The anxiety disorder according to the invention is selected from the group comprising or consisting of generalized anxiety disorder, panic disorder, panic disorder with agoraphobia, phobias, obsessive-compulsive disorder, post-traumatic stress disorder, separation anxiety and childhood anxiety disorders.

Among the hundreds of different neurodegenerative disorders, the attention has been given only to a handful, including Alzheimer's Disease (Blair et al, J Clin Invest 2013, DOI: 10.1172/JCI69003), Parkinson's Disease, and amyotrophic lateral sclerosis.

Among the glucocorticoid hyposensitivity syndromes, the attention has been given to the group of related diseases enclosing resistant asthma (Tajiri et al, PLOS One 2013, 8, e65284), eosinophilic esophagitis (Caldwell et al, J Allerg Clin Immunol 2010, 125, 879-888), AIDS, rheumatoid arthritis, hypertension and diabetes, metabolic syndrome or obesity (Warrier, PhD Thesis 2008, University of Toledo, ProQuest LLC, "Role of FKBP51 and FKBP52 in Glucocorticoid Receptor Regulated Metabolism").

Among the cancers, the attention has been given to malignant melanoma (Romano et al, Cell Death Dis 2013, 4, e578), acute lymphoblastic leukemia (Li at al, Br J Cancer, 2013, DOI: 10.1038/bjc.2013.562), gliomas (Jiang et al, Neoplasia 2013, 10, 235-243), idiopathic myelofibrosis (Komura et al, Cancer Res 2005, 65, 3281-3289), pancreatic and breast cancers (Hou & Wang, PLOS One 2012, 7, e36252), steroid-hormone dependent cancers or prostate cancer.

Among the hundreds of infectious diseases, the attention has been given to malaria and the Legionnaires' disease (Gaali et al, Curr Med Chem 2011, 18, 5355-5379).

Among the vision disorders, the attention has been given to visual impairments; orbital disorders; disorders of the lacrimal apparatus; disorders of the eyelids; disorders of the conjunctiva; disorders of the Cornea; cataract; disorders of the uveal tract; disorders of the retina; disorders of the optic nerve or visual pathways; free radical induced eye disorders and diseases; immunologically-mediated eye disorders and diseases; eye injuries; and symptoms and complications of eye disease, eye disorder, or eye injury.

Therefore, another aspect of the present invention is directed to pharmaceutical compositions comprising at least one compound of the present invention as active ingredient, together with at least one pharmaceutically acceptable carrier, excipient and/or diluents. The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one compound according to the present invention and/or a pharmaceutical acceptable salt thereof as active ingredient.

The pharmaceutical compositions according to the present invention containing at least one compound according to the present invention, and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and coloring agents may also be incorporated into the tablet or capsule. Powders and tablets may contain about 5 to about 95 weight % of the benzothiophene-1,1-dioxide derived compound and/or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavoring agents as well as preservatives may also be included, where appropriate. The disintegrants, diluents, lubricants, binders etc. are discussed in more detail below.

Moreover, the pharmaceutical compositions of the present invention may comprise an additional pharmaceutically active compound or drug. The pharmaceutically active compound or drug may belong to the group of glucocorticoids. Thus an embodiment of the current invention comprises the administration of a compound of the current invention in addition to a co-administration of glucocorticoids.

Moreover, the pharmaceutical compositions of the present invention may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient (s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix. Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscarmellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5 weight % of the composition, preferably from about 0.1 to about 1 weight %.

Said pharmaceutical compositions may further comprise at least one active selective FKBP51 ligand of the general formulas (I) and subformulas (Ia-f, II-VIII).

The pharmaceutical compositions may further comprise at least one further active agent. It is preferred if this active agent is selected from the group consisting of antidepressant and other psychotropic drugs. It is further preferred if the antidepressant is selected from amitriptyline, amioxide clomipramine, doxepine, duloxetine, imipramine trimipramine, mirtazapine, reboxetine, citaloprame, fluoxetine, moclobemide and sertraline.

Method for Crystallizing FKBP51

The protein-ligand complex was prepared by mixing a solution of a construct of FKBP51 comprising residues 16-140 and carrying mutation A19T in an appropriate buffer with ligand dissolved in DMSO (Bracher et al., Acta Cryst D, 2011, D67, 549-559). For crystallization by the hanging-drop isothermal vapor diffusion method, 1 µl of the protein-ligand complex solution was mixed with 1 µl of a precipitant solution containing 25-35% PEG-3350, 0.2 M ammonium acetate and 0.1 M HEPES-NaOH pH 7.5, and equilibrated at 20° C. against 500 µl of the precipitant solution. Crystal formation took several days to weeks.

Single crystals were harvested and cryo-mounted for X-ray diffraction data collection at synchrotron light sources at 100 K. The oscillation data images were integrated and processed using the programs XDS, Pointless, Scala and Truncate. The structures were solved by molecular replacement using the program Molrep and the apo structure as a search template. The programs Coot and Refmac were used for model building and refinement.

TABLE 1

Pairwise RMSD deviation for crystal structures of FKBP51 apo structures (3O5P[1], 3O5Q[1]), FKBP51 complexes with unselective ligands (3O5R[1], 4DRK[2], 4DRO[2], 4DRQ[4], 4JFK[3]), and FKBP51 complexes with FKBP51-selective induced-fit ligands (A09, A12, A22, A01). Structures were superpositioned pair wise as described below.

|  | 3O5P | 3O5Q | 3O5R | 4DRK | 4DRO | 4DRQ | 4JFK | A09 | A12 (Form I) | A12 (Form II) | A22 | A01 |
|---|---|---|---|---|---|---|---|---|---|---|---|---|
| 3O5P | 0 | 0.347 | 0.706 | 0.987 | 0.417 | 0.376 | 0.617 | 1.124 | 1.384 | 1.381 | 1.355 | 2.16 |
| 3O5Q | 0.347 | 0 | 0.449 | 0.893 | 0.536 | 0.33 | 0.222 | 1.181 | 1.442 | 1.38 | 1.223 | 1.713 |
| 3O5R | 0.706 | 0.449 | 0 | 0.92 | 0.499 | 0.341 | 0.491 | 1.144 | 1.41 | 1.419 | 1.356 | 2.11 |
| 4DRK | 0.987 | 0.893 | 0.92 | 0 | 0.898 | 0.901 | 0.84 | 1.092 | 1.306 | 1.333 | 1.177 | 1.992 |
| 4DRO | 0.417 | 0.536 | 0.499 | 0.898 | 0 | 0.369 | 0.455 | 1.153 | 1.389 | 1.411 | 1.194 | 2.056 |
| 4DRQ | 0.321 | 0.33 | 0.341 | 0.864 | 0.369 | 0 | 0.207 | 1.437 | 1.441 | 1.306 | 1.255 | 1.884 |
| 4JFK | 0.617 | 0.222 | 0.491 | 0.84 | 0.455 | 0.207 | 0 | 1.436 | 1.528 | 1.37 | 1.411 | 2.121 |
| A09 | 1.124 | 1.181 | 1.144 | 1.092 | 1.153 | 1.437 | 1.436 | 0 | 0.941 | 0.897 | 0.997 | 1.4 |
| A12 (Form I) | 1.384 | 1.442 | 1.41 | 1.306 | 1.389 | 1.441 | 1.528 | 0.941 | 0 | 0.498 | 0.877 | 1.485 |
| A12 (Form II) | 1.381 | 1.38 | 1.419 | 1.333 | 1.411 | 1.306 | 1.37 | 0.897 | 0.498 | 0 | 0.857 | 1.541 |
| A22 | 1.355 | 1.223 | 1.356 | 1.177 | 1.194 | 1.255 | 1.411 | 0.997 | 0.877 | 0.857 | 0 | 1.899 |
| A01 | 2.16 | 1.713 | 2.11 | 1.992 | 2.056 | 1.884 | 2.121 | 1.4 | 1.485 | 1.541 | 1.899 | 0 |

[1]Bracher et al., Acta Crystallogr D, 2011, 549-559.
[2]Gopalakrishnan et al, J Med Chem, 2012, 55, 4114-4122.
[3]Wang et al, J Med Chem, 2013, 56, 3922-3935
[4]Gopalakrishnan et al, J Med Chem, 2012, 55, 4123-4131

Induced Fit Structure of FKBP51

The present invention is also directed to structures of FKBP51 that are indicative of FKBP51-selective ligands, preferably structures of FKBP51 in complex with an inventive compound according to the general formula (I), preferred the subformulas (Ia-f, II-VIII), and more preferred subformula (VIII).

Thus the present invention also relates to the crystal form of FKBP51 and a compound or inhibitor as defined in claim 1.

In an embodiment of the present invention, the crystal form of FKBP51 and an inhibitor is characterized as having a space group of $P2_12_12$ and having unit cell dimension of $a_1=48\pm3$ Å, $b_1=60\pm3$ Å, $c_1=38\pm3$ Å, $\alpha_1=90\pm3°$, $\beta_1=90\pm3°$ and $\gamma_1=90\pm3°$ or having a space group of $P2_12_12$ and having unit cell dimension of $a_2=45\pm3$ Å, $b_1=48\pm3$ Å, $c_2=57\pm3$ Å, $\alpha_2=90\pm3°$, $\beta_2=90\pm3°$ and $\gamma_2=90\pm3°$ or, having a space group of $C222_1$ and having unit cell dimension of $a_3=49\pm3$ Å, $b_1=85\pm3$ Å, $c_1=61\pm3$ Å, $\alpha_1=90\pm3°$, $\beta_1=90\pm3°$ and $\gamma_1=90\pm3°$. Preferred, said crystal form of FKBP51 is characterized by the atomic structure coordinates of FIG. 9.

In the present invention, the crystal structures of the compounds of the general formula (I), preferred subformulas (Ia-f, II-VIII), and more preferred subformula (VIII)

were solved to understand the structural basis of the selectivity (A09, A12, A22, see Table 1). The coordinates of a representative structure (of A12 crystal form I) are provided in FIG. 9. The three major interactions of the ligand with the protein are the two hydrogen bonds to Ile87 and Tyr113, contacts with Tyr57 and Asp68, and the hydrophobic interaction with amino acids Val86, Ile87 and Trp90 at the bottom of the binding pocket (FIG. 5a).

Bellow is important sequence (SEQ ID NO: 1) of Human FKBP51(13-139)$^{419T}$ and Residues of the FKBP51 BINDING SITE are highlighted in bold.

GLY ALA PRO ALA THR VAL THR GLU$^{20}$ GLN GLY GLU ASP

ILE THR SER LYS LYS ASP$^{30}$ ARG GLY VAL LEU LYS ILE

VAL LYS ARG VAL$^{40}$ GLY ASN GLY GLU GLU THR PRO MET

ILE GLY$^{50}$ ASP LYS VAL TYR VAL HIS TYR LYS GLY LYS$^{60}$

LEU SER ASN GLY LYS LYS PHE ASP SER SER$^{70}$ HIS ASP

ARG ASN GLU PRO PHE VAL PHE SER$^{80}$ LEU GLY LYS GLY

GLN VAL ILE LYS ALA TRP$^{90}$ ASP ILE GLY VAL ALA THR

MET LYS LYS GLY$^{100}$ GLU ILE CYS HIS LEU LEU CYS LYS

PRO GLU$^{110}$ TYR ALA TYR GLY SER ALA GLY SER LEU

PRO$^{120}$ LYS ILE PRO SER ASN ALA THR LEU PHE PHE$^{130}$

GLU ILE GLU LEU LEU ASP PHE LYS GLY.

For identification, design or optimization purposes related to FKBP51-selective inhibitors the FKBP51 BINDING SITE contains amino acids corresponding to Tyr57, Lys58, Gly59, Lys60, Lys66, Phe67, Asp68, Phe77, Gly84, Gln85, Val86, Ile87, Trp90, Tyr113, Ser118, Lys121, Ile122, Phe129, and Phe130. Preferred residues are Tyr57, Phe67, Asp68, Phe77, Gln85, Val86, Ile87, Trp90, Tyr113, Ile122, and Phe130 (FKBP51 numbering). More preferred residues are Tyr57, Phe67, Asp68, Val86, Ile87, Trp90, and Tyr113. These residues are highly conserved within the FKBP family. Other FKBP homologs can be used as a framework (e.g., FKBP12, FKBP12.6 or FKBP52) and equivalent positions in other FKBPs can be easily identified by sequence or structural alignments known in the art or as described (Galat, Cell Mol Life Sci 2013, 70, 3243-3275).

The FKBP51 BINDING SITE is defined as the part of FKBP51 containing the amino acids Tyr57, Lys58, Gly59, Lys60, Lys66, Phe67, Asp68, Phe77, Gly84, Gln85, Val86, Ile87, Trp90, Tyr113, Ser118, Lys121, Ile122, Phe129, and Phe130 or preferable the amino acid residues Tyr57, Phe67, Asp68, Phe77, Gln85, Val86, Ile87, Trp90, Tyr113, Ile122, and Phe130 (FKBP51 numbering) or at least the amino acid residues Y57, F67, D68, V86, I87, W90, and Y113.

Examples for a FKBP51 BINDING SITE are provided by the structure in FIG. 9 or by the FKBP51 structures published in Bracher et al., Acta Crystallogr D, 2011, 549-559, Gopalakrishnan et al, J Med Chem, 2012, 55, 4114-4122, Wang et al, J Med Chem, 2013, 56, 3922-3935, or Gopalakrishnan et al, J Med Chem, 2012, 55, 4123-4131.

For the purpose of identifying, designing or optimizing FKBP51-selective inhibitors a FKBP51-LIKE BINDING SITE will contain >50%, preferred >60%, more preferred >70%, most preferred >90% of amino acids corresponding to the above mentioned residues. Alternatively, a FKBP51-LIKE BINDING SITE may contain sequence derivations retaining up to >50% sequence identity, preferred >60% sequence identity, more preferred >70% sequence identity, most preferred >90% sequence identity with the residues of the FKBP51 BINDING SITE.

A FKBP51-LIKE BINDING SITE can be easily superpositioned or structurally aligned with the residues of the FKBP51 BINDING SITE or with the backbone atoms of the FKBP51 BINDING SITE residues (e.g., using programs like Coot, LSQKAP, CCP4 6.1 or Pymol). For the purpose of identifying, designing or optimizing FKBP51-selective inhibitors a FKBP51-LIKE BINDING SITE will contain residues at the position of >50%, preferred >60%, more preferred >70%, most preferred >90% of the residues of the FKBP51 BINDING SITE. Alternatively or in addition, the residues of a FKBP51-LIKE BINDING SITE can be superpositioned with the FKBP51 BINDING SITE included in FIG. 9 in a way, that an RMSD of <3 Å, preferred <2 Å, more preferred <1.5 Å, more further preferred <1.3 Å, more further preferred <1 Å, and most preferred <0.8 Å can be obtained.

For identification, design or optimization purposes for FKBP51-selective inhibitors according to this invention the FKBP51 BINDING SURFACE is defined as the amino acid atoms Y57CE1, Y57CE2, Y57CZ, Y57OH, D68CB, D68CG, D68OD2, F77CE2, F77CZ, V86CA, V86C, V86CB, V86CG1, I87N, I87CA, I87CB, I87CG1, I87CG2, W90CG, W90CD1, W90CD2, W90CE2, W90CE3, W90NE1, W90CZ2, W90CZ3, W90CH2, Y113CE2, Y113CZ, Y113OH, I122CD1, F130CE1, F130CZ (FIG. 9, tables 6-10). Preferred atoms are Y57CE1, Y57CE2, Y57CZ, Y57OH, D68CB, D68OD2, V86CA, V86C, V86CB, V86CG1, I87N, I87CG2, W90CG, W90CD2, W90CE2, W90CE3, W90NE1, W90CZ2, W90CZ3, W90CH2, Y113CE2, Y113CZ, Y113OH, F130CE1, F130CZ. Most preferred atoms are Y57CE1, Y57OH, D68OD2, V86CA, V86C, V86CB, I87N, I87CG2, W90CD2, W90CE2, W90CE3, W90NE1, W90CZ2, W90CZ3, W90CH2, Y113CE2, Y113CZ, Y113OH.

The atom as described above is defined as follows: alphabetical abbreviation of an amino acid+sequence number of said amino acid+atom type (relative atom identifier). For example, the atom Y57OH means an oxygen atom (OH is atom type or relative atom identifier) of a tyrosine (Y, TYR) having sequence number 57 and thus it is the ATOM 338 as defined in FIG. 9.

Therefore, the above-defined FKBP51 BINDING SURFACE can be defined identically as the amino acid atoms ATOM 336, ATOM 339, ATOM 337, ATOM 338, ATOM 422, ATOM 423, ATOM 425, ATOM 501, ATOM 500, ATOM 564, ATOM 561, ATOM 565, ATOM 566, ATOM 570, ATOM 571, ATOM 572, ATOM 573, ATOM 575, ATOM 595, ATOM 596, ATOM 599, ATOM 598, ATOM 600, ATOM 597, ATOM 603, ATOM 601, ATOM 602, ATOM 780, ATOM 778, ATOM 779, ATOM 837, ATOM 898, ATOM 899.

A FKBP51-LIKE BINDING SURFACE can be superpositioned with the atoms of the FKBP51 BINDING SURFACE e.g., using programs like Coot, LSQKAP, CCP4 6.1 or Pymol). For the purpose of identifying, designing or optimizing FKBP51-selective inhibitors a FKBP51-LIKE BINDING SURFACE will contain atoms at the position of >50%, preferred >60%, more preferred >70%, most preferred >90% of the atoms of the FKBP51 BINDING SURFACE. Alternatively or in addition, the atoms of a FKBP51-LIKE BINDING SURFACE can be superpositioned with a FKBP51 BINDING SURFACE provided in FIG. 9 or in tables 6-10 in a way, that an RMSD of <3 Å, preferred <2

Å, more preferred <1.5 Å, more further preferred <1.3 Å, more further preferred <1 Å, and most preferred <0.8 Å can be obtained.

The induced-fit structures that will accommodate FKBP51-selective ligands can be defined by a characteristic conformational change of phenylalanine 67 (Phe67), which is flipped out of the binding pocket in contrast to the crystal structure of unselective ligands like FK506 or the FK506 analog IF63 (FIG. 4A and FIG. 5C). This conformational change opens a new hole or pocket to accommodate the $C_\alpha$ substituent (FIGS. 5A and 5B). The conformational change can be specified by the distances between F67 and I87, between F67 and W90 and/or between F67 and F130 (FIG. 6), or by the dihedral angle that defines the orientation of the phenyl ring of F67 (FIG. 4, Table 2). Specifically, compounds of the general formula I or subformulas (Ia-f, II-VIII) will increase the F67CZ-I87CD1 distance from around 7 Å to >8 Å, preferably >10 Å, or more preferably >12 Å. Likewise the distance of F67CZ-W90CE2 will be increased from about 7 Å to >8 Å, preferentially >10 Å, or more preferentially >12 Å. The distance of F67CZ-F130CZ will be increased from about 4 Å to >5 Å, preferably >8 Å, or more preferably >10 Å. The distance of F67CZ-Y113-OH will be increased from about 7 Å to >8 Å, preferably >10 Å, or more preferably >13 Å. The distance of F67CZ-G59CA will be increased from about 4 Å to >4.5 Å, preferably >5 Å, or more preferably >5.5 Å. The distance of F67CA-I87N will be increased from about 15 Å to >15.5 Å, preferably >16 Å. The distance of F67CA-Y113OH will be increased from about 10.5 Å to >11 Å, preferably >11.5 Å, or more preferably ≥12 Å.

In an alternative definition, compounds of the general formula I or subformulas (Ia-f, II-VIII) will flip F67CZ of the induced-fit structures compared to F67CZ of the overlaid apo structure by greater than 4 Å, preferentially >6 Å and more preferentially >8 Å. Alternatively, compounds of the general formula I or subformulas (Ia-f, II-VIII) will rotate F67 defined by the dihedral angle F67 N-$C_\alpha$-$C_\beta$-$C_\gamma$ from >55° as observed in apo structures or cocrystal structures with unselective ligands to <-100°, preferably <-120° or more preferably <-140° (FIG. 4 and Table 2). These parameters can be obtained by structural analysis like x-ray cocrystallography or NMR and specifically for the fk1 domain of FKBP51 by the protocol described in the prior art (by Bracher et al, Acta Cryst, 2011, D67, 549-559).

The induced-fit structures that will accommodate FKBP51-selective ligands can also be defined by a characteristic hole or pocket that is caused by conformational change of phenylalanine 67 and which is not present in FKBP51 structures in the absence of FKBP51-selective ligands such as those ligands of the general formula (I), preferred the subformulas (Ia-f, II-VIII), and more preferred subformula (VIII). This hole or pocket is normally occupied by atoms F67CD1 and F67CE1 of residue F67 of FKBP51. In induced-fit structures of FKBP51 this hole or pocket is occupied by atoms that are characteristic for FKBP51-selective ligands such as those of the general formula (I), preferred the subformulas (Ia-f, II-VIII), and more preferred subformula (VIII), e.g. CAH, CAI, CAS or CAT of A12, CAU, CAZ or CAS of A22, CAY, CBX or CAX of A09, CAA or CAK of A01 (Table 6-10). When superimposed with any of the FKBP51 BINGING SURFACES shown in Table 6-10, the CENTER OF A HOLE of a FKBP51 BINGING SURFACE or a FKBP51-LIKE BINGING SURFACE will have the coordinates from x=-18.800 to -18.100, y=-11.400 to -10.600, z=-10.100 to -9.400 or x=-17.650 to -16.950, y=-11.800 to -11.000, z=-9.500 to -8.700, preferably x=-18.700 to -18.200, y=-11.300 to -10.700, z=-10.000 to -9.500 or x=-17.550 to -17.050, y=-11.700 to -11.100, z=-9.400 to -8.800, more preferably x=-18.600 to -18.300, y=-11.200 to -10.800, z=-9.900 to -9.600 or x=-17.450 to -17.150, y=-11.600 to -11.200, z=-9.300 to -8.900, most preferably x=-18.500 to -18.400, y=-11.100 to -10.900, z=-9.800 to -9.700 or x=-17.350 to -17.250, y=-11.500 to -11.300, z=-9.200 to -9.000.

Alternatively, the INDUCED-FIT FKBP51 BINDING SURFACE or the INDUCED-FIT FKBP51-LIKE BINDING SURFACE can be defined as a FKBP51 BINDING SURFACE or a FKBP51-LIKE BINDING SURFACE that does not contain atoms, preferentially not contain protein atoms, between any of the following pairs of atoms (or equivalent atoms), preferentially between at least three of the following pairs of atoms, more preferentially between at least six of the following pairs of atoms, most preferentially between all of the following pairs of atoms: W90CG-Y113 OH or W90CG-V86CA or W90CG-I87N or W90CG-F77CZ or W90CG-Y57OH or F130CZ-Y113OH or F130CZ-I87N or F130CZ-V86CA or F130CZ-F77CZ or F77CZ-Y57OH or F130CZ-I122CD1 or F77CZ-Y113OH or F77CZ-I122CD1 or F77CZ-Y57OH or F77CZ-

TABLE 2

Specification of the induced conformational change. Distance of F67 CZ to G59CA, I87N, I87CD1, W90CE2, Y113OH, F130CZ, and F67CZ apo in Å. Distance of F67CA to I87NH and Y113OH. Distance of F67CZ of co-crystal structures to F67CZ of the apo structure without ligand in Å. Dihedral angle of F67 N—$C_\alpha$—$C_\beta$—$C_\gamma$.

|  | Name | F67 CZ to I87 CD | F67 CA to I87 NH | F67 CZ to W90 CD | F67 CZ to F130 CZ | F67 CZ to Y113 OH | F67 CA to Y113 OH | F67 CZ to G59 CA | F67 CZ to F67 CZ apo (3O5Q) | F67 N-CA-CB-CG |
|---|---|---|---|---|---|---|---|---|---|---|
| selective | 51FK1/A01 | 15.2 | 16.4 | 12.8 | 10.9 | 15.2 | 12.1 | 5.5 | 9.0 | -152.2° |
|  | 51FK1/A09 | 15.0 | 16.0 | 12.8 | 10.8 | 15.0 | 12.0 | 6.0 | 9.2 | -165.3° |
|  | 51FK1/A12 | 15.2 | 16.1 | 12.5 | 10.9 | 15.0 | 12.0 | 6.0 | 9.2 | -177.0° |
| un-selective | 51FK1/FK506[1] (3O5R) | 7.3 | 15.2 | 7.3 | 3.8 | 6.9 | 10.4 | 3.6 | 0.3 | 63.8° |
|  | 51FK1/2a[2] (4DRK) | 7.1 | 14.9 | 7.3 | 3.7 | 6.6 | 10.0 | 3.6 | 0.2 | 58.9° |
|  | 51FK1/5a[3] (4JFI) | 7.1 | 14.8 | 7.2 | 3.7 | 6.4 | 10.1 | 3.8 | <0.1 | 65.3° |
|  | 51FK1/20[4] (4DRQ) | 7.2 | 14.9 | 7.4 | 3.9 | 7.1 | 10.8 | 4.0 | <0.1 | 69.0° |
| apo | 51FK1 Apo (3O5Q) | 7.0 | 14.4 | 7.0 | 3.7 | 6.6 | 9.8 | 3.7 | — | 63.5° |

[1]Bracher et al., Acta Crystallogr D, 2011, 549-559.
[2]Gopalakrishnan et al, J Med Chem, 2012, 55, 4114-4122.
[3]Wang et al, J Med Chem, 2013, 56, 3922-3935
[4]Gopalakrishnan et al, J Med Chem, 2012, 55, 4123-4131

I122CGD1 or Y57OH-Y113OH or Y57OH-V86N or Y57OH-I122CD1 or Y113OH-V86CA or Y113OH-I122CD1.

The "apo" or "apo structure" is crystal structure of a protein or an enzyme without an inhibitor or a ligand.

The term "pocket" refers to a region of protein or enzyme structure that as a result of its shape and charge, favourably associates with a ligand or an inhibitor. The term "pocket" includes, but is not limited to, cleft, channel or site.

Hydrophobic interaction(s): hydrophobic interaction is defined as the interactions between the nonpolar molecules. In the present application, hydrophobic interactions mean preferred interactions between hydrophobic amino acid residues of FKBP 51 and FKBP 51 ligand or inhibitor.

The term FKBP51 STRUCTURE refers to a set of coordinates for FKBP51 amino acid residues, preferentially for amino acid residue 13-139. An FKBP51-LIKE STRUCTURE contains coordinates corresponding to >20% of FKBP51(13-139) amino acid residues, preferentially >40% of FKBP51(13-139) amino acid residues, more preferentially >60% of FKBP51(13-139) amino acid residues, even more preferentially >80% of FKBP51(13-139) amino acid residues, and most preferentially >90% of FKBP51(13-139) amino acid residues. When superimposed with the coordinates shown in FIG. 9, a FKBP51 STRUCTURE or a FKBP51-LIKE STRUCTURE will have an RMSD of <3 Å, preferentially <2 Å, more preferentially <1 Å, and most preferentially <0.5 Å.

An INDUCED-FIT FKBP51 STRUCTURE can be defined as containing an INDUCED-FIT FKBP51-BINDING SITE or an INDUCED-FIT FKBP51-BINDING SURFACE. An example of an INDUCED-FIT FKBP51 STRUCTURE is shown in FIG. 9.

An INDUCED-FIT FKBP51-LIKE STRUCTURE can be defined as containing an INDUCED-FIT FKBP51-LIKE BINDING SITE or an INDUCED-FIT FKBP51-LIKE BINDING SURFACE.

An INDUCED-FIT FKBP51 STRUCTURE or an INDUCED-FIT FKBP51-LIKE STRUCTURE can be further defined as having an RMSD (root mean square deviation), after overlay or superposition (as in Table 1) with the coordinates of the structure of FKBP51 shown in FIG. 9) of <2 Å, preferred <1.5 Å, more preferred <1.3 Å, most preferred <1 Å.

AN INDUCED-FIT FKBP51 BINDING SITE or an INDUCED-FIT FKBP51-LIKE BINDING SITE can be defined as a FKBP51 BINDING SITE or a FKBP51-LIKE BINDING SITE and additionally 1) having a distance between $C_\zeta$ of F67 and $C_\delta$ of I87 of >8 Å, preferably >10 Å, or more preferably >12 Å; or
2) having a distance between $C_\alpha$ of F67 (F67CA) and the backbone nitrogen of I87 (I87N) of >15.5 Å, preferably >15.7 Å, or more preferably >15.9 Å; or
3) having a distance between $C_\zeta$ of F67 (F67CZ) and $C_\theta$ of W90 (W90 (CE2) of >8 Å, preferentially >10 Å, or more preferentially >12 Å; or
4) having a distance between $C_\zeta$ of F67 (F67CZ) and $C_\zeta$ of F130 (F130CZ) of >5 Å, preferably >8 Å, or more preferably >10 Å; or
5) having a distance between $C_\zeta$ of F67 (F67CZ) and the ε-oxygen of Y113 (Y113OH) of >8 Å, preferably >10 Å, or more preferably >13 Å; or 6) having a distance between $C^\alpha$ of F67 (F67CA) and the ε-oxygen of Y113 (Y113OH) of >11 Å, preferably >11.5 Å, or more preferably ≥12 Å; or
7) having a dihedral angle F67 N-$C_\alpha$-$C_\beta$-$C_\gamma$ of <−100°, preferably <−120° or more preferably <−140°; or
8) not containing atoms, preferentially not proteins atoms, between G59N-I122CA or between G59CA-I122CD.

An INDUCED-FIT FKBP51 BINDING SURFACE or an INDUCED-FIT FKBP51-LIKE BINDING SURFACE can be defined as a FKBP51 BINDING SURFACE or a FKBP51-LIKE BINDING SURFACE that
1) when superimposed with any of the FKBP51-BINDING SURFACES of Table 6-10 does not have atoms, preferably not protein atoms, of which the center is within a radius of <1.5 Å, preferred <1 Å, more preferred <0.5 Å, even more preferred <0.3 Å, and most preferred <0.1 Å of the CENTER OF A HOLE (as defined above) or
2) when superimposed with any of the INDUCED-FIT FKBP51-BINDING SURFACES of Table 6-10 has an RMSD of <0.57 Å, preferred <0.485 Å, more preferred <0.4 Å, more further preferred <0.315 Å, and most preferred <0.23 Å.

Such an INDUCED-FIT FKBP51 STRUCTURE, INDUCED-FIT FKBP51-LIKE STRUCTURE, INDUCED-FIT FKBP51 BINDING SITE, INDUCED-FIT FKBP51-LIKE BINDING SITE, INDUCED-FIT FKBP51 BINDING SURFACE or a INDUCED-FIT FKBP51-LIKE BINDING SURFACE is a preferred subject matter of the present invention.

The structural coordinates of a FKBP51 STRUCTURE, a FKBP51 BINDING SITE, a FKBP51 BINDING SURFACE or FKBP51-LIKE or INDUCED-FIT FKBP51 STRUCTURE, a INDUCED-FIT FKBP51 BINDING SITE, or a INDUCED-FIT FKBP51 BINDING SURFACE therefore can be determined experimentally using X-ray cocrystallography (Bracher et al, Acta Cryst 2011, D67, 549-559) or by NMR as described for FKBP12 (Lepre et al, FEBS Lett 1992, 302, 89-96; Sich et al, Eur J Biochem 2000, 267, 5342-5355) or FKBP52 (Craescu et al. Biochemistry 1996, 35, 11045-11052), ideally in complex with a compound of the general formula I or subformulas (Ia-f, II-VIII) or any other selective inhibitors like these identified by the screening method disclosed herein. Alternatively, structural coordinates of the FKBP51 STRUCTURE, a FKBP51 BINDING SITE, a FKBP51 BINDING SURFACE or FKBP51-LIKE or INDUCED-FIT FKBP51 STRUCTURE, a INDUCED-FIT FKBP51 BINDING SITE, or a INDUCED-FIT FKBP51 BINDING SURFACE can be obtained through modelling techniques well known in the art.

The embodiment of the present invention is a crystal form of FKBP51 characterized by the atomic structure coordinates of FIG. 9.

In an embodiment of the present invention is preferred crystal form of FKBP51 containing a FKBP51 BINDING SITE and/or a FKBP51 BINDING SURFACE, wherein the FKBP51 BINDING SITE contains the amino acids Tyr57, Lys58, Gly59, Lys60, Lys66, Phe67, Asp68, Phe77, Gly84, Gln85, Val86, Ile87, Trp90, Tyr113, Ser118, Lys121, Ile122, Phe129, and Phe130; and the FKBP51 BINDING SURFACE contains the amino acid atoms Y57CE1, Y57CE2, Y57CZ, Y57OH, D68CB, D68CG, D68OD2, F77CZ, V86CA, V86C, V86CB, V86CG1, I87N, I87CA, I87CB, I87CG1, I87CG2, W90CG, W90CD1, W90CD2, W90CE2, W90CE3, W90NE1, W90CZ2, W90CZ3, W90CH2, Y13CE2, Y113CZ, Y113OH, I122CD1, F130CD1, F130CZ.

In another embodiment of the present invention, the crystal form of FKBP51 contains preferably further an INDUCED-FIT FKBP51 BINDING SITE and an INDUCED-FIT FKBP51-LIKE BINDING SURFACE.

For identification, design or optimization purposes for FKBP51-selective inhibitors, another embodiment of the present invention is directed to a FKBP51 STRUCTURE, a FKBP51 BINDING SITE, a FKBP51 BINDING SURFACE or FKBP51-LIKE BINDING SITE or FKBP51-LIKE BINDING SURFACE or INDUCED-FIT variants therefore, where F67 has been mutated to or replaced by a smaller residue (e.g. Val, Ala, Gly) or where atoms corresponding to F67CD1 and F67CE1 of F67 are missing.

Rational Drug Design of Selective FKBP51 Inhibitors

The generation of strong, robust and predictable selectivity for FKBP51 vs FKBP52 was highly unanticipated. Unexpectedly, the reason for the selectivity for FKBP51 displayed by compounds of the general formula I or subformulas (Ia-f, II-VIII) was found to be a conformational change that is induced in the structure of FKBP51 by these compounds but not any other (unselective) FKBP ligand investigated so far. The hole or pocket formed by the conformational change in FKBP51 accommodates the R* group of the general formula I or subformulas (Ia-f, II-VIII), which is the distinguishing feature of the selective FKBP51 inhibitors of this invention compared to all other FKBP51 ligands tested so far.

An important aspect of the invention is the use of the INDUCED-FIT FKBP51 STRUCTURE, the INDUCED-FIT FKBP51 BINDING SITE or the INDUCED_FIT BINDING SURFACE or FKBP51-LIKE variants thereof disclosed herein, describing the induced-fit binding mode, for the identification, optimization and/or design of inhibitors selective for FKBP51.

Further important aspects of the invention are related to the use of the crystal forms of FKBP51 for the determination of the three-dimensional structure of FKBP51 and for the identification, optimization and/or design of selective inhibitors of FKBP51. The term "use of the crystal form of FKBP51" especially refers to the use of the structure and structure coordinates of the crystals of FKBP51 with an inhibitor and preferably with a compound of any one of general formula (I)-(VIII) as inhibitor in order to identify selective inhibitors of FKBP51 in, for instance, a compound library, to optimize known inhibitors of FKBP51, especially in regard to selectivity or to design novel selective inhibitors of FKBP51.

Knowing the exact positions of the atoms of the amino acids in the active sites of FKBP51 in the discovered induced-fit conformation provides the possibility to design FKBP51-selective inhibitors, identify FKBP51-selective inhibitors e.g. from a compound library or optimize a known inhibitor by increasing the affinity for FKBP51, the selectivity for FKBP51 or other parameters that have to be compatible with binding to FKBP51. Design, identification and optimization of suitable inhibitors can be performed with standard computer based methods and software programs well known in the art.

A variety of commercially available software programs are available for conducting the analysis and comparison of data in the computer-based system. One skilled in the art will readily recognize which of the available algorithms or implementing software packages for conducting computer analyses can be utilized or adapted for use in the computer-based system. A target structural motif or target motif refers to any rationally selected sequence or combination of sequences in which the sequence(s) are chosen based on a three-dimensional configuration or electron density map which is formed upon the folding of the target motif. There are a variety of target motifs known in the art. Protein target motifs include, but are not limited to, enzymatic active sites, structural subdomains, epitopes, functional domains and signal sequences. A variety of structural formats for the input and output means can be used to input and output the information in the computer-based systems of the present invention.

A variety of comparing means can be used to compare a target sequence or target motif with the data storage means to identify structural motifs or interpret electron density maps derived in part from the atomic coordinate/x-ray diffraction data. One skilled in the art can readily recognize any one of the publicly available computer modeling programs that can be used.

Suitable software that can be used to view, analyze, design, and/or model a protein comprise MOLOC (Roche, 1985), FRED, MAIN, FlexX, Gold, XtalView, Alchemy™, LabVision™, Sybyl™, Molcadd™, Leapfrog™, Matchmaker™, Genefold™ and Sitel™ (available from Tripos Inc., St. Louis, Mo.); Quanta™, Cerius2™, X-Plor™, CNS™, Catalyst™, Modeller™, ChemX™, Ludi™, Insight™, Discover™, Cameleon™ and Iditis™ (available from Accelrys Inc., Princeton N.J.); Rasmol™ (available from Glaxo Research and Development, Greenford, Middlesex, U.K.); MOE™ (available from Chemical Computing Group, Montreal, Quebec, Canada); Maestro™ (available from Shrödinger Inc.); COOT/CCP4; Midas/MidasPlus™ (available from UCSF, San Francisco, Calif.); JyMol, Pymol (Schrödinger LLC); Jmol (freeware on the internet); VRML, (webviewer—freeware on the internet); Chime (MDL—freeware on the internet); AutoDock (available from The Scripps Research Institute); MOIL (available from University of Illinois, Urbana-Champaign, Ill.); MacroModel™ and GRASP™ (available from Columbia University, New York, N.Y.); Ribbon™ (available from University of Alabama, Tuscaloosa, Ala.); NAOMI™ (available from Oxford University, Oxford, UK); Explorer Eyechem™ (available from Silicon Graphics Inc., Mountain View, Calif.); Univision™ (available from Cray Research Inc., Seattle Wash.); Molscript™ and O (available from Uppsala University, Uppsala, Sweden); Chem 3D™ and Protein Expert™ (available from Cambridge Scientific); and upgraded versions thereof.

Thus in a further aspect the present invention is related to methods for designing, identifying and optimizing inhibitors of FKBP51 by applying the crystal form and the related structure coordinates of the crystal form or at least of one of the active sites in order to identify, design or optimize inhibitors by means of computer based methods or software programs.

In the present invention, further FKBP51-selective ligands can be identified using a pharmacophore reflecting the features that will induce the above described conformational change and will lead to FKBP51 selectivity. This pharmacophore can be used for computer-assisted in silico searches, screenings, modeling, or guiding the selection or virtual evaluation of potential FKBP51 ligands.

The major interactions of unselective FKBP ligands with FKBP51 are two hydrogen bonds accepted from I87 and Y113 and the hydrophobic interactions with F77, V86, I87, and W90 at the bottom of the binding pocket. Additional interactions are (aromatic) hydrogen bonds to D68 and Y113 and Van-der-Waals or dipolar contacts with D68, S118, or K121. These interactions are also observed to a substantial extent in most cocrystal structures of FKBP51-selective ligands. The corresponding two hydrogen acceptors A1 and A2 and hydrophobic moieties H1, H2 or H3 can be used to define a general FKBP-binding pharmacophore, defined for example by the distances between these moieties, which are reasonably conserved between most FKBP ligands when bound to FKBPs (FIG. 7 A-H and Table 3).

Additional constraints could be the hydrogen donors D (FIG. 7 A-D) and the groups R1 and R2 (FIGS. 7 A-F and H). Compounds that fulfill these constraints have a high likelihood of having binding affinity to FKBPs in general. The FKBP51-selective pharmacophore is characterized by an additional substituent I1 and I2 (FIGS. 7B and 7C) or I1, I2 and I3 (FIGS. 7A and 7D) (e.g., additional hydrophobic moiety), which can be defined by the spatial orientation relative to the above mentioned interaction points A1, H1, H2 or H3 (Table 3). Compounds that can fulfill these pharmacophore constraints ideally in an energetically favorable conformation have a strong likelihood of having selectivity for FKBP51 over FKBP52. Specifically, compounds within the scope of this invention can adopt a conformation with a moiety I with distances of I-A1>7 Å, preferably >8 Å, or more preferably >9 Å; and/or of I-A2>3.5 Å, preferably >4 Å, or more preferably >5 Å; of I-H>5.5 Å, preferably >6.5 Å, or more preferably >7.5 Å.

Thus, an object of the present invention is related to a SELECTIVE FKBP51 INHIBITOR-LIKE PHARMACOPHORE MODEL that features a hydrophobic group I with distances of I-A1>7 Å, preferably >8 Å, or more preferably >9 Å; of I-A2>3.5 Å, preferably >4 Å, or more preferably >5 Å; and of I-H>5.5 Å, preferably >6.5 Å, or more preferably >7.5 Å.

TABLE 3

Distance constraints for a pharmacophore model of INDUCED-FIT FKBP51 INHIBITORS or FKBP51-selective inhibitors. Core atoms A1, A2, H1-H3, and D) are defined for each compound in FIG. 7. DH or D = Hydrogen bond donors. A (A1-A3) = Hydrogen bond acceptors. H (H1-H3) = Atoms involved in hydrophobic interactions with FKBP51. I (I1-I3) = Atoms of FKBP51-selecitve ligands or of INDUCED-FIT FKBP51 INHIBITORS that induce the conformational change of Phe67 or that are located in the CENTER OF A HOLE. O = Oxygen of the C9-carbonyl of known unselective FKBP ligands.
Quantification of the Pharmacophore (Length in Å), derived from the cocrystal structures

|  | A12 FIG. 9 | A01 Tab 10 | A09 Tab 9 | A02 | Range | PDB: | FK506[1] 3O5R | IF63[2] 4DRK | 3[2] 4DRN | 20[3] 4DRQ | Range |
|---|---|---|---|---|---|---|---|---|---|---|---|
| A1-A2 | 4.4 | 4.5 | 3.8 | 4.0 | 3.8-4.5 | A1-A2 | 4.7 | 4.6 | 4.6 | 4.7 | 4.6-4.7 |
| A1-H1 | 2.9 | 2.8 | 3.2 | 3.1 | 2.9-3.2 | A1-H1 | 2.9 | 2.9 | 2.8 | 2.9 | 2.8-2.9 |
| A1-H2 | 3.6 | 3.4 | 4.6 | 4.0 | 3.4-4.6 | A1-H2 | 3.8 | 3.5 | 3.5 | 4.6 | 3.5-4.6 |
| A1-H3 | 4.6 | 4.4 | — | — | 4.4-4.6 | A1-H3 | 4.8 | 4.5 | 4.5 | 3.5 | 3.5-4.8 |
| A2-H1 | 4.0 | 4.0 | 4.3 | 4.1 | 4.0-4.3 | A2-H1 | 3.9 | 3.9 | 4.0 | 3.8 | 3.8-4.0 |
| A2-H2 | 4.9 | 4.9 | 4.7 | 4.6 | 4.6-4.9 | A2-H2 | 4.6 | 4.6 | 4.6 | 4.7 | 4.6-4.7 |
| A2-H3 | 4.7 | 4.7 | — | — | 4.7 | A2-H3 | 4.9 | 4.9 | 4.9 | 4.9 | 4.9 |
| A1-I1 | 6.8 | 7.6 | 7.6 | 7.0 | 6.8-7.6 | A1-O | 6.9 | 6.7 | 6.7 | 6.0 | 6.0-6.9 |
| A1-I2 | 7.4 | 7.8 | 8.5 | 8.3 | 7.4-8.5 |  |  |  |  |  |  |
| A1-I3 | 9.8 | — | 7.6 | — | 7.6-9.8 |  |  |  |  |  |  |
| A2-I1 | 3.2 | 3.4 | 4.1 | 3.1 | 3.1-4.1 | A2-O | 3.0 | 3.1 | 3.1 | 2.5 | 2.5-3.1 |
| A2-I2 | 4.6 | 3.5 | 5.0 | 4.5 | 3.5-5.0 |  |  |  |  |  |  |
| A2-I3 | 5.5 | — | 4.4 | — | 4.4-5.5 |  |  |  |  |  |  |
| H1-I1 | 6.1 | 6.2 | 6.9 | 6.0 | 6.1-6.9 | H1-O | 5.2 | 5.2 | 5.0 | 4.2 | 4.2-5.2 |
| H1-I2 | 7.3 | 6.3 | 8.1 | 7.1 | 6.3-8.1 |  |  |  |  |  |  |
| H1-I3 | 8.5 | — | 7.0 | — | 7.0-8.5 |  |  |  |  |  |  |
| H2-I1 | 6.7 | 6.7 | 6.3 | 6.0 | 6.0-6.7 | H2-O | 4.3 | 4.3 | 4.1 | 3.7 | 3.7-4.3 |
| H2-I2 | 7.9 | 7.1 | 7.6 | 7.0 | 7.0-7.9 |  |  |  |  |  |  |
| H2-I3 | 8.9 | — | 6.5 | — | 6.5-8.9 |  |  |  |  |  |  |
| H3-I1 | 5.0 | 5.8 | — | — | 5.0-5.8 | H3-O | 5.4 | 5.4 | 5.3 | 4.6 | 4.6-5.4 |
| H3-I2 | 7.0 | 6.3 | — | — | 6.3-7.0 |  |  |  |  |  |  |
| H3-I3 | 7.9 | — | — | — | 7.9 |  |  |  |  |  |  |
| D-I1 | 4.9 | 4.5 | 4.4 | 4.8 | 4.4-4.9 | D-O | 4.3 | — | 4.5 | 2.8 | 2.8-4.3 |
| D-I2 | 5.9 | 5.7 | 5.4 | 5.7 | 5.4-5.9 |  |  |  |  |  |  |
| D-I3 | 5.9 | — | 5.9 | — | 5.9 |  |  |  |  |  |  |
| D-Asp | 3.4 | 3.2 | 3.2 | 3.4 | 3.2-3.4 | D-Asp | 2.7 | — | 2.8 | 3.0 | 2.7-3.0 |

[1]Bracher et al., Acta Crystallogr D, 2011, 549-559.
[2]Gopalakrishnan et al, J Med Chem, 2012, 55, 4114-4122.
[3]Gopalakrishnan et al, J Med Chem, 2012, 55, 4123-4131

A further aspect of the present invention is directed to the use of general formula I or subformulas (Ia-f, II-VIII) for the generation of an INDUCED-FIT FKBP51 STRUCTURE, an INDUCED-FIT FKBP51 BINDING SITE or an INDUCED-FIT FKBP51 BINDING SURFACE or FKBP51-LIKE variants thereof.

The atomic coordinate/x-ray diffraction data may be used to create a physical model which can be used to design molecular models of compounds that should have the ability or property to inhibit and/or interact with the determined active sites or other structural or functional domains or subdomains of the FKBP51 such as an INDUCED-FIT FKBP51-LIKE BINDING SITE or an INDUCED-FIT FKBP51-LIKE BINDING SURFACE. Alternatively, the atomic coordinate/x-ray diffraction data of the complex may be represented as atomic model output data on computer readable media which can be used in a computer modeling system to calculate different molecules expected to inhibit and/or interact with the determined active sites, or other structural or functional domains or subdomains of the FKBP51. For example, computer analysis of the data allows one to calculate the three-dimensional interaction of the FKBP51 and the compound to confirm that the compound binds to, or changes the conformation of, particular the FK506 domain(s) or subdomain(s) of FKBP51. Compounds identified from the analysis of the physical or computer model can then be synthesized and tested for biological activity with an appropriate assay.

Another aspect of the present invention relates to the use of said crystal form of FKBP51 for the determination of the three-dimensional structure of FKBP51 and for the identification and/or design of selective inhibitors of FKBP51.

Thus the present invention is also directed to a method for designing a compound that selectively interacts with or inhibits FKBP51, comprising the steps of
(a) generating a three-dimensional model of FKBP51 using the structure coordinates as listed in FIG. 9; and
(b) employing said three-dimensional model to design or to identify or to optimize a compound that should have the ability to selectively interact with or inhibit FKBP51.

The term "using the structure coordinates as listed in FIG. 9" means that at least some of the structure coordinates and preferably the structure coordinates of the INDUCED-FIT FKBP51-LIKE BINDING SITE and/or the INDUCED-FIT FKBP51-LIKE BINDING SURFACE are used.

Preferred is the following method comprising the steps of:
(a) generating a three-dimensional model of a FKBP51 STRUCTURE or FKBP51-LIKE STRUCTURE containing or comprising an INDUCED-FIT FKBP51 BINDING SITE or an INDUCED-FIT FKBP51-BINDING SURFACE or FKBP51-LIKE variants thereof; and
(b) employing said three-dimensional model to design a compound that should have the ability to interact with or inhibit FKBP51, preferably to interact with or inhibit FKBP51 selectively.

The generation of a three-dimensional model of FKBP51 in accordance with step (a) of said method could also involve the application of a root mean square deviation so that a preferred method comprises the following steps:
(a) generating a three-dimensional model of FKBP51 using the structure coordinates as listed in FIG. 9 and a root mean square deviation from the backbone atoms or from the alpha carbon backbone atoms of said amino acids of not more than 3.0 Å; and
(b) employing said three-dimensional model to design a compound that should have the ability to interact with or inhibit FKBP51.

In another embodiment of the present invention, in said method the three-dimensional model of an INDUCED-FIT FKBP51 STRUCTURE, an INDUCED-FIT FKBP51 BINDING SITE and/or of an INDUCED-FIT FKBP51 BINDING SURFACE and/or FKBP51-LIKE variants thereof is generated by using the structure coordinates as listed in FIG. 9 and/or in Tab. 6-10 and said three-dimensional model is employed to design, identify or optimize a compound that should have the ability to interact with or bind to, preferentially selectively bind to, FBKP51.

The term "root mean square deviation or RMSD" means the square root of the arithmetic mean of the squares of the deviations from the mean. It is a way to express the deviation or variation from a trend or object. For purposes of this invention, the "root mean square deviation" defines the variation in the backbone of a protein from the backbone of FKBP51, an active site, a binding pocket, or a portion thereof, as defined by the structure coordinates of FKBP51 described herein. It would be apparent to the skilled person that calculation of root mean square deviation involves a standard error.

A preferred embodiment of the present invention refers to the methods disclosed herein, wherein the root mean square deviation from the backbone atoms of said amino acids of not more than 2.0 Å and more preferably not more than 1.0 Å. The interaction of the selected compound with the FKBP51 leads most preferably to inhibition.

The term "compound" as used herein preferably refers to a small chemical molecule. The above method refers to the design of a compound on the basis of the crystal structure coordinates of a crystal form of FKBP51 which should have the ability to interact with or preferably inhibit FKBP51. Such a designed compound could be a completely novel compound, thus not existing before or could be a derivative of a known compound, for instance, derived by scaffold hopping. In order to verify the inhibitory activity of the compound, actual synthesis of the compound is desired with subsequent testing of the compound in a suitable assay in order to determine the inhibitory activity of FKBP51. Examples 6-B provides a suitable assay for testing the inhibitory effect of potential inhibitors of FKBP51.

Thus the above method preferably further comprises the step of
(c) obtaining the designed compound; and
(d) contacting the obtained designed compound with FKBP51 in order to determine the inhibitory effect on FKBP51.

For screening purposes of a compound library in order to identify an inhibitor of FKBP51 or for optimization of a known inhibitor of FKBP51 in order to increase the inhibitory potential of this known inhibitor, the following method for identifying and/or optimizing a compound that selectively inhibits or should selectively inhibit FKBP51 is provided, comprising the steps of
(a) generating a three-dimensional model of FKBP51 containing or comprising an INDUCED-FIT FKBP51 STRUCTURE, an INDUCED-FIT FKBP51 BINDING SITE or an INDUCED-FIT FKBP51 BINDING SURFACE or INDUCED-FIT FKBP51-LIKE STRUCTURE, an INDUCED-FIT FKBP51-LIKE BINDING SITE or an INDUCED-FIT FKBP51-LIKE BINDING SURFACE variants thereof; and
(b) employing said three-dimensional model to identify or optimize a compound that should have the ability to selectively inhibit FKBP51.

Moreover the present invention is also directed to a method for designing a compound that selectively interacts with or inhibits FKBP51, comprising the steps of
(a) generating a three-dimensional model of an INDUCED-FIT FKBP51-LIKE BINDING SITE or an INDUCED-FIT FKBP51-LIKE BINDING SURFACE
(b) employing said three-dimensional model to identify or select from an ensemble of compounds or from a chemical library a compound or a subset of compounds that should have the ability to interact with or inhibit FKBP51 better or more selectively than other ensemble or library members Also in this method, step (a) could involve the root mean square deviation and thus read as follows:
(a) generating a three-dimensional model of FKBP51 using the structure coordinates as listed in FIG. 9, wherein the root mean square deviation of the backbone atoms of the FKBP51 amino acid residues is not more than 3 Å.

In case an inhibitor is identified from a compound library or in case a known inhibitor is optimized by theoretical chemical modifications, testing of the actual compound is desired in order to verify the inhibitory effect and to continue the optimization process. Thus preferably the above method for identifying and/or optimizing a compound further comprising the steps of (c) obtaining the identified or optimized compound; and
(d) contacting the identified or optimized compound with FKBP51 in order to determine the inhibitory effect on FKBP51.

It is not necessary to use all the structure coordinates as listed in FIG. 9, it might also be sufficient to use a selected set of structure coordinates as presented in FIG. 9. Thus only the structure coordinates of the FKBP51 BINDING SITE, the FKBP51 BINDING SURFACE, the INDUCED-FIT FKBP51-LIKE BINDING SITE or the INDUCED-FIT FKBP51-LIKE BINDING SURFACE could be used. Moreover it might also not to be necessary to generate a three-dimensional model of the complete FKBP51. It could also be sufficient to generate a model of one, two, three or all four active sites of FKBP51 and more preferably to generate a model of the FK506-binding domain of FKBP51.

Thus another aspect of the present invention is directed to a method for designing, identifying or optimizing a compound which should have the ability to inhibit FKBP51, wherein the three-dimensional model of the FKBP51 BINDING SITE, the FKBP51 BINDING SURFACE, and/or the INDUCED-FIT FKBP51-LIKE BINDING SITE or the INDUCED-FIT FKBP51-LIKE BINDING SURFACE. Such a compound is identified or optimized by using the structure coordinates as listed in FIG. 9 and wherein said three-dimensional model is employed to design, identify or optimize a compound that should have the ability to interact with or bind to the FKBP51 BINDING SITE, the FKBP51 BINDING SURFACE and/or the INDUCED-FIT FKBP51-LIKE BINDING SITE and/or the INDUCED-FIT FKBP51-LIKE BINDING SURFACE. Such a compound should have the ability to inhibit FKBP51 and preferably inhibit FKBP51 selectively, i.e. without inhibiting FKBP52.

In some instances it may be particularly advantageous to delete and/or exchange and/or add amino acids or even complete domains to the native FKBP51. This may be particularly interesting with regard to at least one of the FKBP51 BINDING SITE, the FKBP51 BINDING SURFACE, the INDUCED-FIT FKBP51-LIKE BINDING SITE and the INDUCED-FIT FKBP51-LIKE BINDING SURFACE. However, since the INDUCED-FIT FKBP51 BINDING SITE is the central element of the present invention the structure of the active site and its INDUCED-FIT FKBP51 BINDING SURFACE is the major claim and the prerequisite of the structure based drug design. Basically, we also claim shorter variants of FKBP51 comprising the amino acids necessary to form at least the active site.

Consequently, the present invention is also directed to FKBP51 selective inhibitors which are designed or identified by one of the methods disclosed herein.

Such FKBP51 selective inhibitors induced the fit as described herein involving the flipping of the F67 amino acid in FKBP51.

Such FKBP51 selective inhibitors form a hydrogen bond through a heteroatom A1 (preferably N or O) to the backbone amide group of I87 (i.e. with the hydrogen of the amino group of I87) and another hydrogen bond through a heteroatom A2 (preferably N or O) to the hydroxy group of Y113 (i.e. to the hydrogen of the hydroxy group of Y113) and a third hydrogen bond to the oxygen of the carboxy group of D68 through a hydrogen atom which is attached to a donor D and has hydrophobic interactions with F77, V86, I87, and W90 and comprises a saturated, partly unsaturated or fully unsaturated carbocycle or heterocycle for an hydrophobic interaction with Trp90 and an alkyl, alkenyl, alkynyl, cycloalkyl, cycloalkenyl, or cycloalkdienyl residue comprising the terminal or ring carbon atoms I1 and I2 which have hydrophobic interactions with F67, K121 and F130 of FKBP51, wherein the distance I1-A1 is >7 Å, the distance I2-A1 is >7 Å, the distance I1-A2 is >3 Å, and the distance I2-A2 is >4 Å, and said FKBP51 selective inhibitor comprises at least two cyclic moieties, has preferably a bicyclic structure, contains between 30 and 80 carbon atoms and 1, 2, 3, 4 or 5 nitrogen atoms and between 5 and 15 oxygen atoms, while preferably S, P, I, Br, Cl, B, Si are not contained in the FKBP51 selective inhibitor.

Compounds that induced the above describe conformational change in FKBP51 will be selective for FKBP51 and therefore better suited for the treatment of FKBP51-associated disorder such as psychiatric disorders and neurodegenerative diseases, disorders and conditions.

Consequently, the present invention is also directed to the medical use of substances that induce the conformational change disclosed in the invention. Specifically, we claim the medical use of an INDUCED-FIT FKBP51 INHIBITOR or pharmaceutically acceptable salts thereof for treating depression, physical nerve injury, Alzheimer's, Huntington's, Parkinson's disease, ischemia, traumatic brain injury, prostate cancer, acute lymphoblastic leukaemia, malignant melanoma, obesity, metabolic syndrome, diabetes, asthma, sleeping disorders, vision disorders, memory impairment, alopecia.

The following abbreviations are used for the common and modified amino acids referred to herein.

| Abbreviation | Amino acid |
| --- | --- |
| Ala (A) | Alanine |
| Arg (R) | Arginine |
| Asn (N) | Asparagine |
| Asp (D) | Aspartic acid (Aspartate) |
| Cys (C) | Cysteine |
| Gln (Q) | Glutamine |
| Glu (E) | Glutamic acid (Glutamate) |
| Gly (G) | Glycine |
| His (H) | Histidine |
| Ile (I) | Isoleucine |
| Leu (L) | Leucine |
| Lys (K) | Lysine |
| Met (M) | Methionine |
| Nle (N) | Norleucine |
| Phe (F) | Phenylalanine |
| Pro (P) | Proline |
| Ser (S) | Serine |
| Thr (T) | Threonine |
| Trp (W) | Tryptophan |
| Tyr (Y) | Tyrosine |
| Val (V) | Valine |

(B) FK506 does not rescue reduced neurite length triggered by 1 µM Ru26988 in N2a-cells. Aldosterone enhances neurite outgrowth of N2a-cells until an optimal concentration of 100 nM. Higher concentrations lead to a reduction of neurite outgrowth (U-shaped dose-dependency). Reduction of neuronal differentiation cannot be blocked by addition of the unselective ligand FK506 (in contrast to selective FKBP51 ligands).

(C) A17 rescues Ru26988 effect. A17 dose-dependently rescues the reduction of total neurite length triggered by high aldosterone concentrations. A17 reverts the reduction of neurite outgrowth triggered by aldosterone (1 µM) in a dose-dependent manner.

(D) The analog A18 enhanced struggling time and reduced floating time in a forced swim test.

(E) The selective FKBP51 inhibitor A18 enhances the regulation of stress hormone secretion in test.

Figure 3:
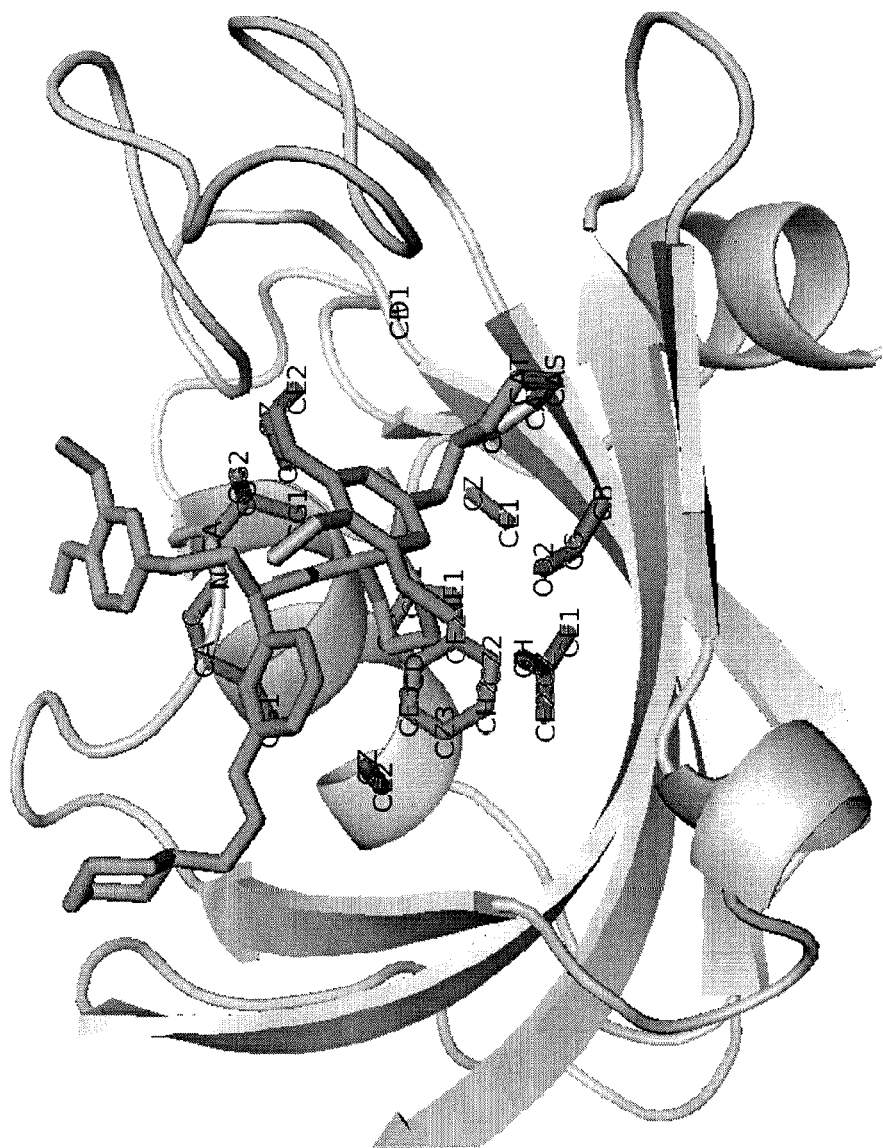

FIG. 3: The backbone of FKBP51 is shown as green cartoon. A12 is shown in orange sticks, the atoms of the FKBP51-BINDING SITE are shown as gray sticks, with the atom names shown in black.

Figure 4:
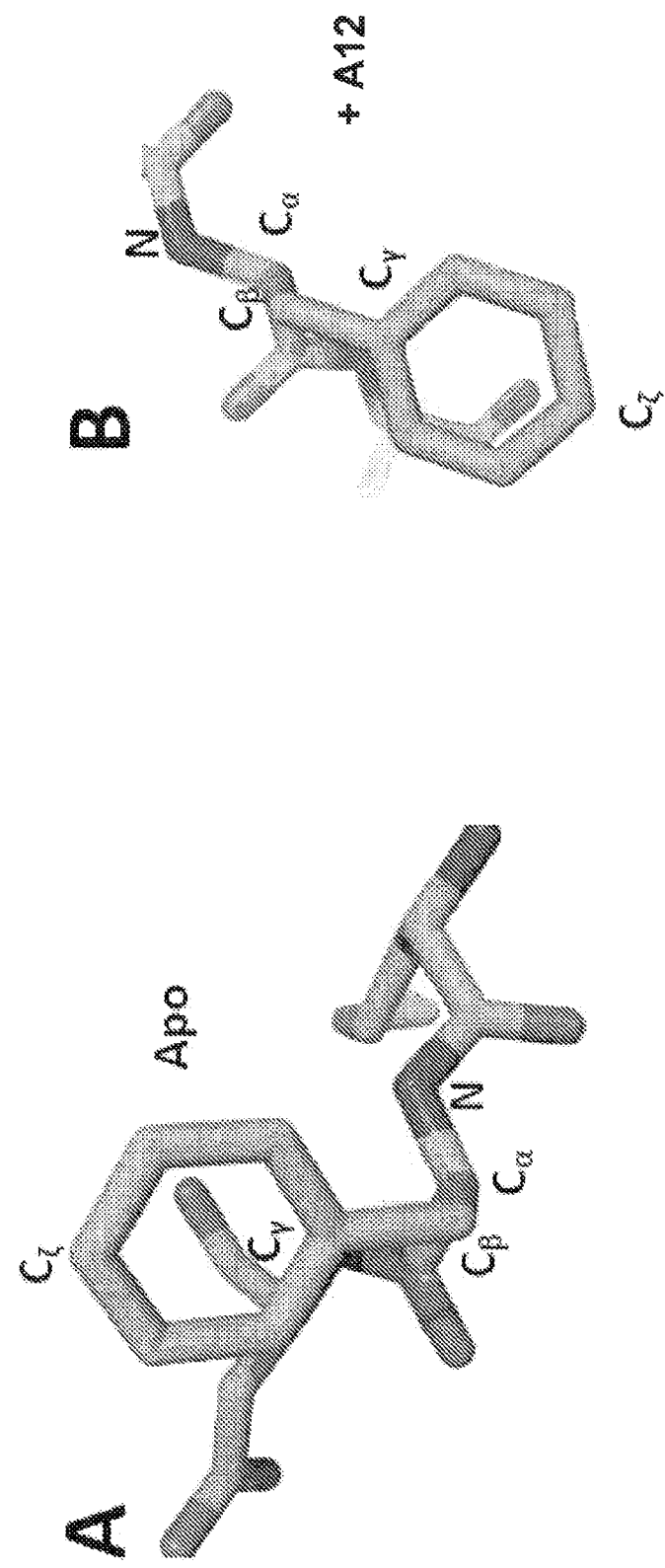

FIG. 4: Conformational reorganization of F67: (A) apo crystal structure of FKBP51FK1; (B) crystal structure FKBP51FK1 and A12. The dihedral angle N-Cα-Cβ-Cγ defining the conformational flip is indicated.

Figure 5:
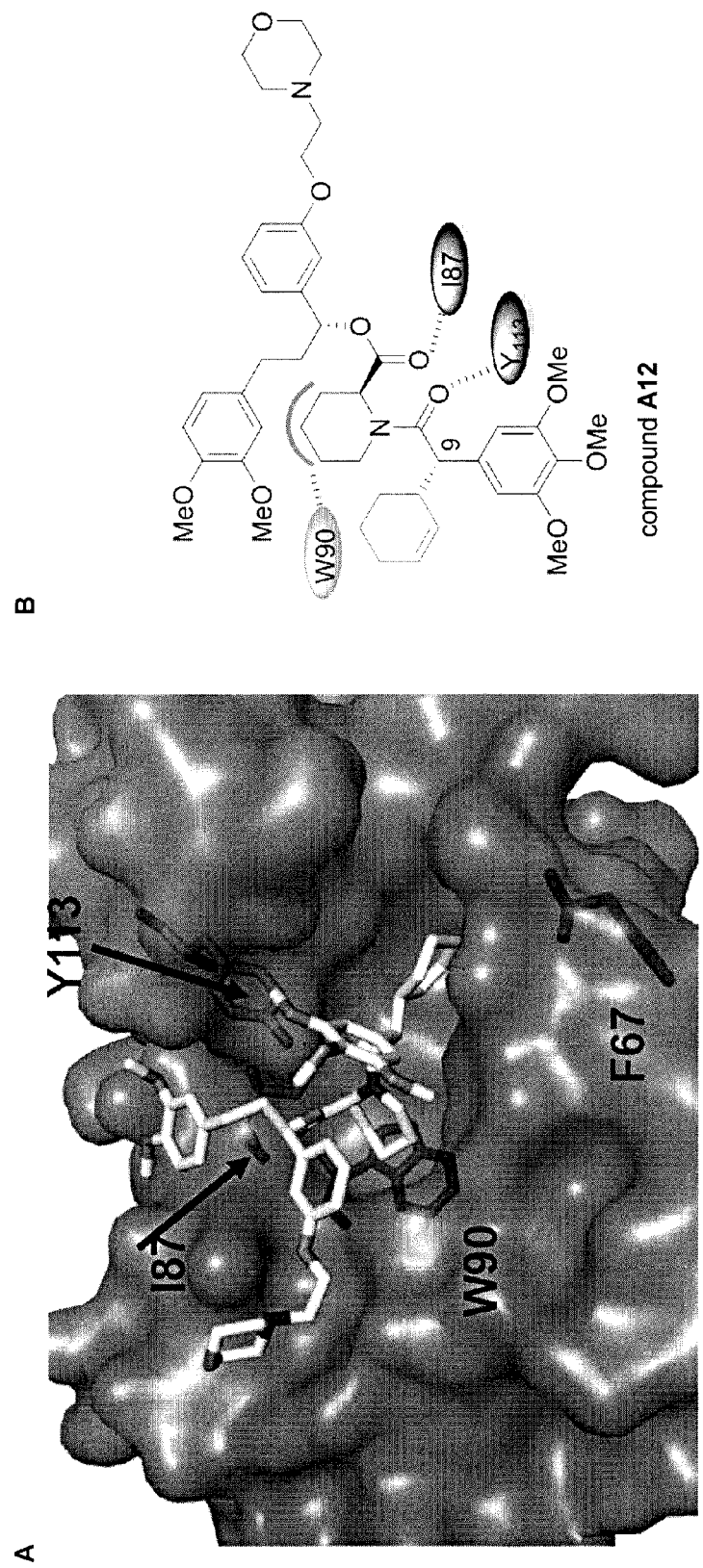
Figure 5:
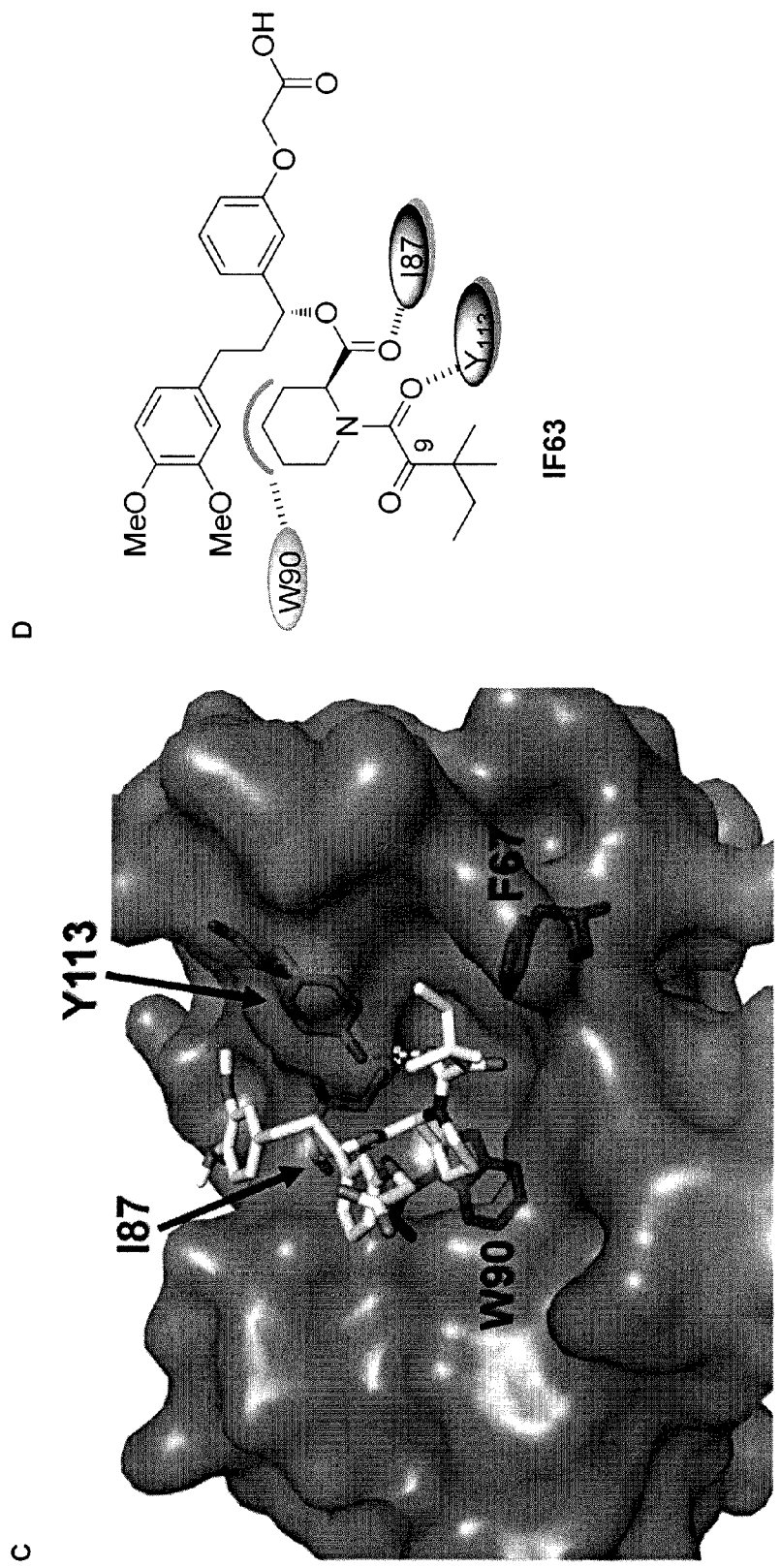

FIG. 5: (A) Crystal structure of FKBP51 and inhibitor A12. (B) Chemical structure of the FKBP51-selective inhibitor A12. Conserved hydrogen bonds with I87 and Y113 are shown as dotted lines, hydrophobic interaction with W90 are indicated in grey. (C) FKBP51-unselective ligand IF63 is not able to induce the induced-fit structure which is characterized by the conformational change of phenylalanine 67 (Phe67), which flips out of the binding pocket as demonstrated by the FKBP51-unselective ligand as shown in FIG. 5a. (D) The three major interactions of the FKBP51-unselective ligand IF63 with the protein which are the two hydrogen bonds to Ile87 and Tyr113 through Tyr57 and Asp68 and the hydrophobic interaction with the amino acids Val86, Ile87 and Trp90 at the bottom of the binding pocket.

Figure 6:
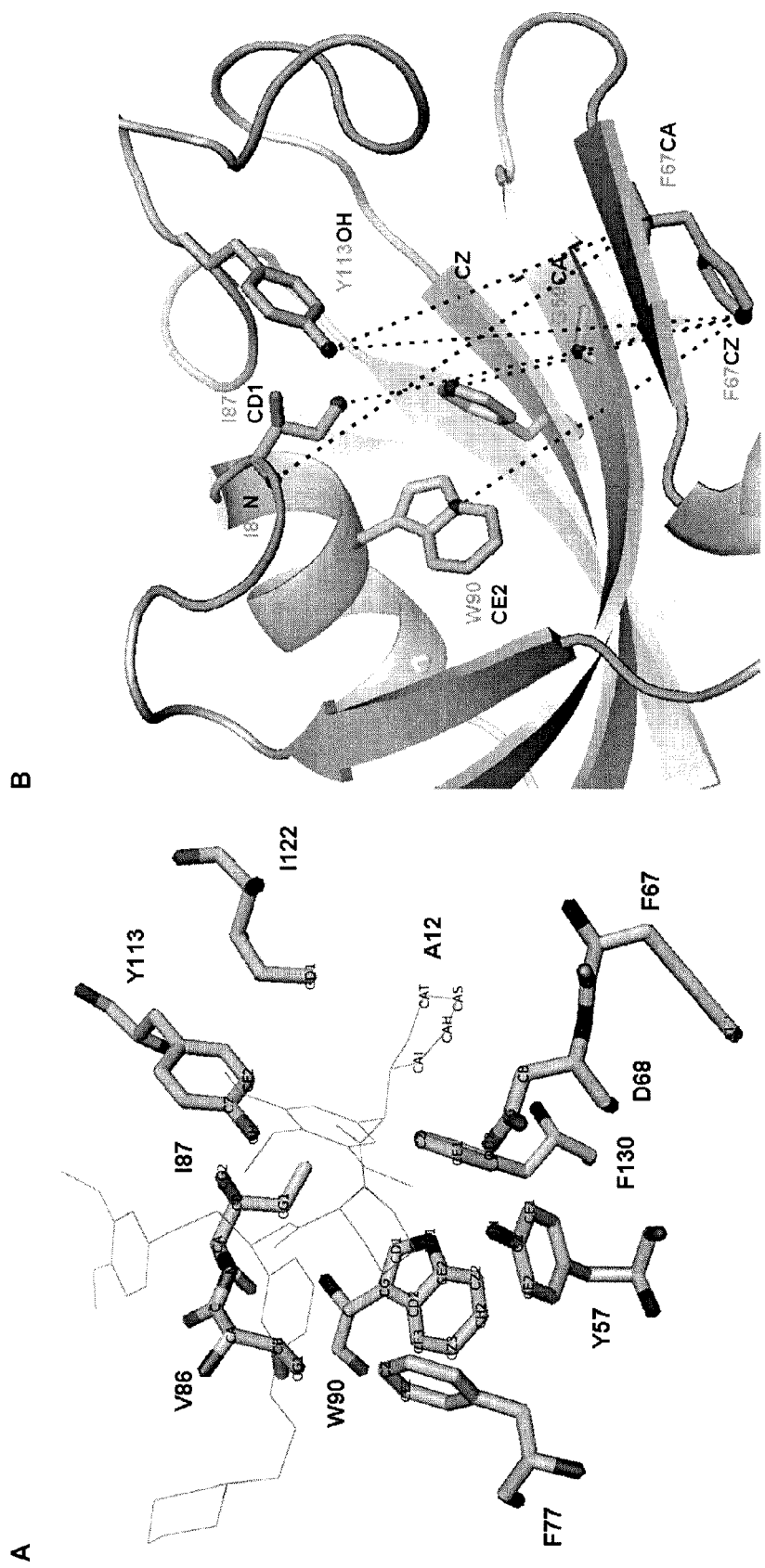

FIG. 6:
(A) Cocrystal Structure of A12 in complex with FKBP51 (Form I). Preferred residues of the INDUCED-FIT FKBP51 BINDING SITE are shown in green sticks and labelled in bold. Atoms constituting the INDUCED-FIT FKBP51 BINDING SURFACE are labelled with their atoms numbers. The INDUCED-FIT FKBP51 INHIBITOR A12 is shown in pink lines, atoms of A12 that induce the fit and occupy the CENTER OF A HOLE are labelled (CAI-CAT).
(B) Crystal structure of FKBP51 a in complex with inhibitor A12 (not shown) showing the key residues G59, F67, I87, W90, Y113 and F130 and the distances that can be used to quantify the conformational change of F67.

Figure 7:
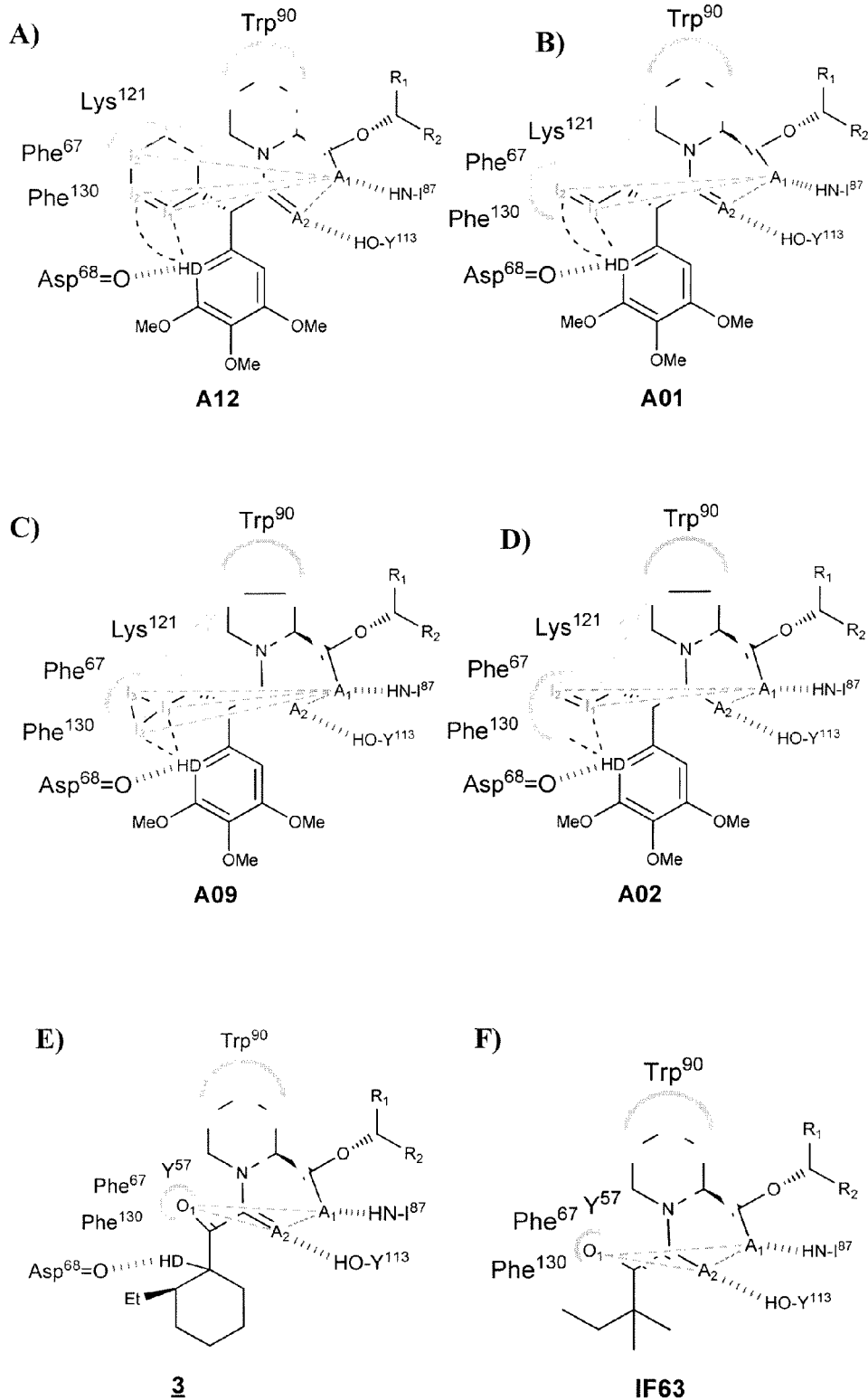
Figure 7:
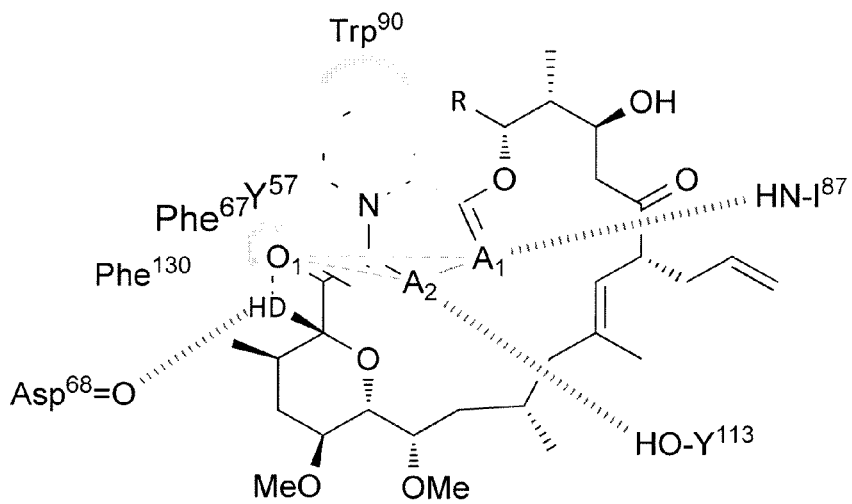
Figure 7:
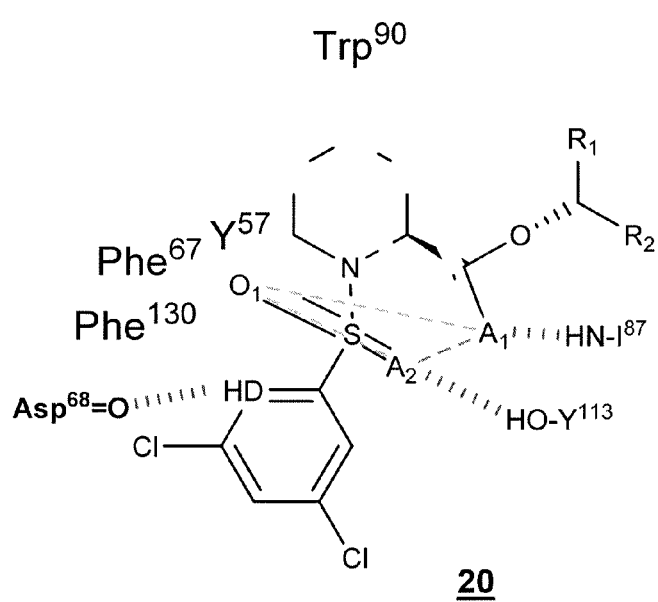

FIG. 7: Pharmacophore model for selective FKBP51 ligands (A) A12, (B) A01, (C) A09, (D) A02, and for non-selective ligands (E) from 4DRN[2], (F) from 4DRK[2], (G) 3O5R[1], (H) 4DRQ[3].

[1]Bracher et al., Acta Crystallogr D, 2011, 549-559.
[2]Gopalakrishnan et al, J Med Chem, 2012, 55, 4114-4122.
[3]Gopalakrishnan et al, J Med Chem, 2012, 55, 4123-4131

Figure 8:
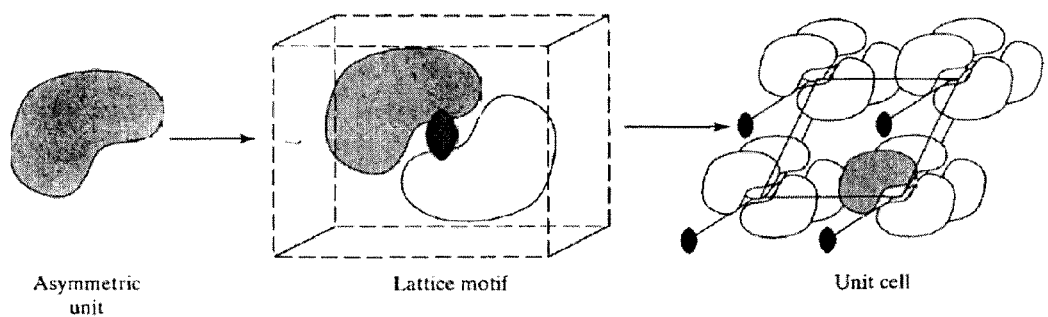
Figure 8:
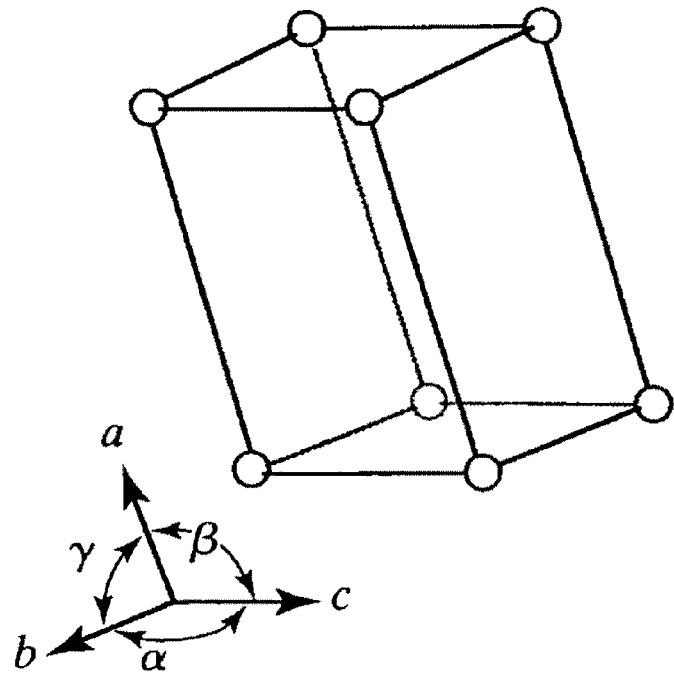

FIG. 8: (a) Component of a crystal. The asymmetric unit is that part of the crystal that shows no symmetry. A symmetry operator (for example, a C2 axis) generates the lattice motif. Repeating this motif by translation generates the corner of the unit cell, which is the basic repeating unit of the crystal lattice; (b) unit cell definition.

FIG. 9: Coordinates for the complex of FKBP51$^{A19T}$ with A12 (Form I). Coordinates of the Ligand A12 are in bold.

EXAMPLES

Abbreviations

DCM dichloromethane
DIPEA N,N-Diisopropylethylamine
DMF Dimethylformamide
DMSO Dimethyl sulfoxide
EtOAc Ethylacetate
Fmoc Fluorenylmethyloxycarbonyl
HATU 2-(7-Aza-1H-benzotriazole-1-yl)-1,1,3,3-tetramethyluronium hexafluorophosphate
HOBt Hydroxybenzotriazole
tBu tert-butyl
TEA triethylamine
TFA trifluoroacetic acid
THF Tetrahydrofuran
TMSCl trimethylsilyl chloride General Information Solvents were purchased from Roth or Sigma Aldrich with qualities, ROTOSOLV, ROTIPURAN; ROTIDRY or HPLC quality with ≥99% purity. Anhydrous solvents were used from Sigma Aldrich with sure seals. All reactions were carried out with magnetic stirring and, when air or moisture sensitive, in flame-dried glassware under argon (Westfalen, 99.999 Vol % Klasse 5.0). Syringes were used to transfer reagents. Reagents used in very moisture-sensitive reactions were dried overnight under high vacuum ($<1\times10^{-2}$ mbar). 1D $^{1}$H, $^{13}$C-NMR and 2D HSQC, HMBC and COSY were recorded at the department of chemistry and pharmacy of the LMU on a Bruker AC 300, a Bruker XL 400, or a Bruker AMX 600 at room temperature. Chemical shifts for $^{1}$H or $^{13}$C are given in ppm (δ) relative to tetramethylsilane (TMS) as internal standard. CDCl$_3$ and d6-DMSO were used as solvents. $^{1}$H and $^{13}$C spectra were calibrated on the specific solvent. The coupling constants (J) are given in Hertz (Hz). The multiplicities are abbreviated as singlet (s), doublet (d), triplet (t), quartet (q) and multiplet (m). Mass spectra (m/z) were recorded on a Thermo Finnigan LCQ DECA XP Plus mass spectrometer at the Max Planck Institute of Psychiatry, while the high resolution mass spectrometry was carried out at MPI for Biochemistry (Microchemistry Core facility) on Varian Mat711 mass spectrometer. The purity of the compounds was verified by reversed phase HPLC. All gradients were started after 1 min of equilibration with starting percentage of solvent mixture. For manual column chromatography, Silicagel 60 (Roth) with a particle size of 0.04-0.063 mm was used. Automated flash chromatography was performed, using an Interchim Puriflash 430 with an UV detector at 254 nm. Preparative thin layer chromatography (TLC) was performed on glass plates coated with 2 mm SiO$_2$ (Merck SIL-G-200, F-254). For TLC aluminum plates coated with SiO$_2$ (Merck 60, F-254) were used. The spots were visualized by UV light and/or by staining of the TLC plate with one of the solutions below followed, if necessary, by heating with a heat gun.

HPLC

The purity of the compounds was verified by reversed phase HPLC. All gradients were started after 1 min of equilibration with starting percentage of solvent mixture.

Analytical:
Pump: Beckman System Gold 125S Solvent Module
Detector: Beckman System Gold Diode Array Detector Module 168
Column: Phenomenex Jupiter 4μ Proteo 90 Å, 250×4.6 mm 4 micron
Solvent A: 95% $H_2O$
  5% $CH_3CN$
  0.1% TFA
Solvent B: 95% $CH_3CN$
  5% $H_2O$
  0.1% TFA
Standard Gradient: 0-100% B in 20 min, 1 ml/min
Detection wavelength: 220 nm/280 nm Chiral:
Pump: Waters 515 HPLC Pump
Detector: LDC Analytical Spectromonitor 5000 Photodiode Array Detector
Column: DAICEL Chemical Industries LTD. Chiralcel OD-H
Solvent A: Hexane
Solvent B: i-propanol
Standard Gradient: 1:1 60 min, 0.5 ml/min
Detection wavelength: 220 nm Preparative:
Pump: Beckman System Gold Programmable Solvent Module 126 NMP
Detector: Beckman Programmable Detector Module 166
Column: Phenomenex Jupiter 10μ Proteo 90 Å, 250×21.2 mm 10 micron
Methods: Described at the specific compound Semi-Preparative:
Pump: Beckman System Gold 125S Solvent Module
Detector: Beckman System Gold Diode Array Detector Module 168
Column: Phenomenex Jupiter 10μ Proteo 90 Å, 250×10 mm 10 micron
Methods: Described at the specific compound LC-MS:
Pump: Beckman System Gold 125S Solvent Module
Detector: System Gold Diode Array Detector Module 168
Column: YMC Pack Pro C8, 100×4.6 mm, 3 μm
Solvent A: 95% $H_2O$
  5% $CH_3CN$
  0.1% Formic acid
Solvent B: 95% $CH_3CN$
  5% $H_2O$
  0.1% Formic acid
Standard Gradient: 0-100% B in 11 min, 1 ml/min
Detection wavelength: 220 nm, 280 nm General Coupling Reaction Procedures All reactions were carried out with magnetic stirring and, when air or moisture sensitive, in flame-dried glassware under argon (Westfalen, 99.999 Vol % Klasse 5.0). Syringes were used to transfer reagents. Reagents used in very moisture-sensitive reactions were dried overnight under high vacuum (<1×10$^{-2}$ mbar).

Synthetic Procedures of Synthetic Building Blocks A

Example 1-1

Preparation of (E)-3-(3,4-Dimethoxyphenyl)-1-(3-hydroxyphenyl) prop-2-en-1-one (2)

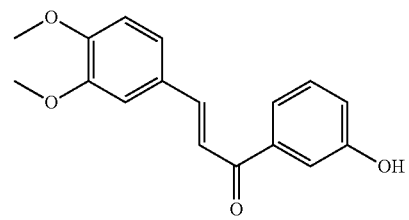

2 was synthesized according to Gopalakrishnan et al, Evaluation of Synthetic FK506 Analogs as Ligands for the FK506-Binding Proteins 51 and 52, JMC, 2012, 55, 4114-4122.

Example 1-2

Preparation of 3-(3,4-Dimethoxyphenyl)-1-(3-hydroxyphenyl) propan-1-one (3)

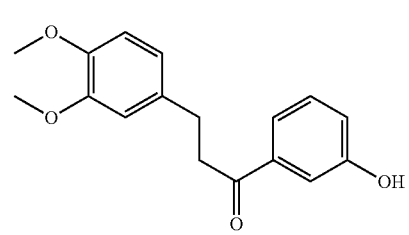

3 was synthesized according to Gopalakrishnan et al, Evaluation of Synthetic FK506 Analogs as Ligands for the FK506-Binding Proteins 51 and 52, JMC, 2012, 55, 4114-4122.

Example 1-3

Preparation of tert-Butyl-2-[3-{3-(3,4-dimethoxyphenyl) propanoyl}phenoxy] acetate (4a)

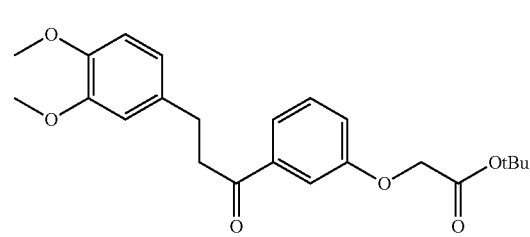

4a was synthesized according to Gopalakrishnan et al, Evaluation of Synthetic FK506 Analogs as Ligands for the FK506-Binding Proteins 51 and 52, JMC, 2012, 55, 4114-4122.

Example 1-4

Preparation of (R)-tert-Butyl-2-[3-{3-(3,4-dimethoxyphenyl)-1-hydroxypropyl}phenoxy] acetate (5a)

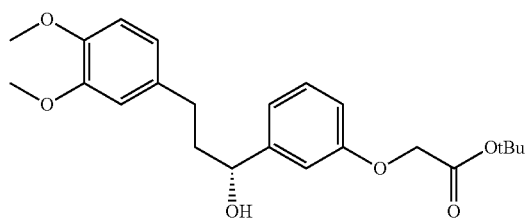

5a was synthesized according to Gopalakrishnan et al, Evaluation of Synthetic FK506 Analogs as Ligands for the FK506-Binding Proteins 51 and 52, JMC, 2012, 55, 4114-4122.

Example 1-5

Preparation of (S)-1-(((9H-Fluoren-9-yl)methoxy)carbonyl)piperidine-2-carboxylic acid (6a)

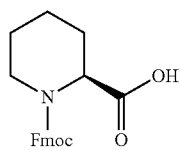

6a was synthesized according to Gopalakrishnan et al, Evaluation of Synthetic FK506 Analogs as Ligands for the FK506-Binding Proteins 51 and 52, JMC, 2012, 55, 4114-4122.

Example 1-6

Preparation of (S)-1-[9H-Fluoren-9-yl]methyl-ester-2-[(R)-1-{3-(2-tert-butoxy-2-oxo-ethoxy)phenyl}-3-(3,4-dimethoxyphenyl)propyl]piperidin-2-carboxylate (7a)

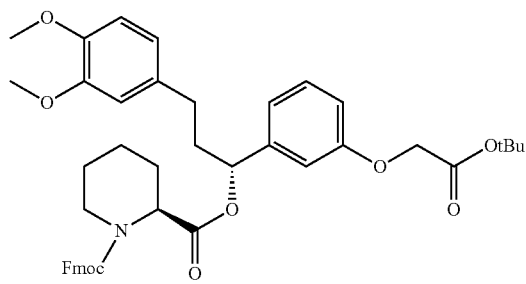

7a was synthesized according to Gopalakrishnan et al, Evaluation of Synthetic FK506 Analogs as Ligands for the FK506-Binding Proteins 51 and 52, JMC, 2012, 55, 4114-4122.

Example 1-7

Preparation of (S)-[(R)-1-{3-(2-tert-Butoxy-2-oxoethoxy)phenyl}-3-(3,4-dimethoxyphenyl) propyl] piperidin-2-carboxylate (8a)

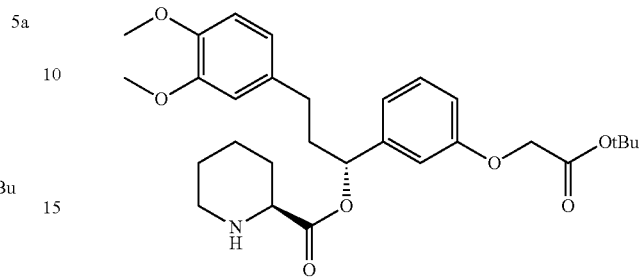

8a was synthesized according to Gopalakrishnan et al, Evaluation of Synthetic FK506 Analogs as Ligands for the FK506-Binding Proteins 51 and 52, JMC, 2012, 55, 4114-4122.

Example 1-8

Preparation of Oxycarbonyl-2-((R)-3-(3,4-dimethoxyphenyl)-1-(3-(2-morpholinoethoxy) phenyl) propyl) (S)-1-(9H-Fluoren-9-yl)methylpiperidine-2-carboxylate (9a)

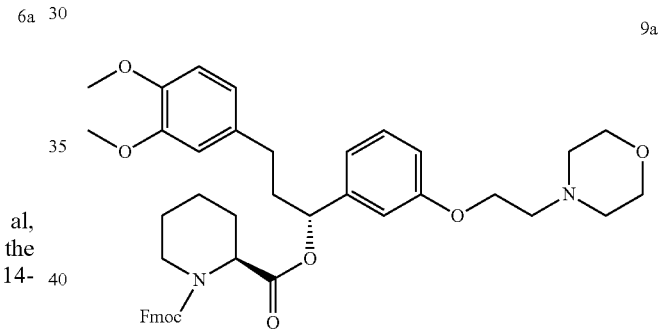

9a was synthesized according to Gopalakrishnan et al, Evaluation of Synthetic FK506 Analogs as Ligands for the FK506-Binding Proteins 51 and 52, JMC, 2012, 55, 4114-4122.

Example 1-9

Preparation of (S)-((R)-3-(3,4-Dimethoxyphenyl)-1-(3-(2-morpholinoethoxy)phenyl)propyl) piperidine-2-carboxylate (10a)

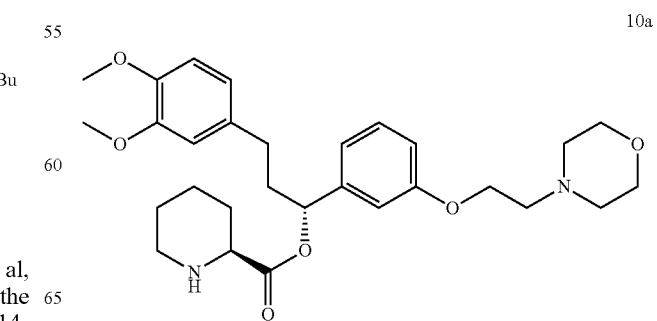

10a was synthesized oil according to Gopalakrishnan et al, Evaluation of Synthetic FK506 Analogs as Ligands for the FK506-Binding Proteins 51 and 52, JMC, 2012, 55, 4114-4122.

Example 1-10

Preparation of (R)-(R)-3-(3,4-Dimethoxyphenyl)-1-(3-(2-morpholinoethoxy)phenyl)propyl-thiomorpholine-3-carboxylate (10b)

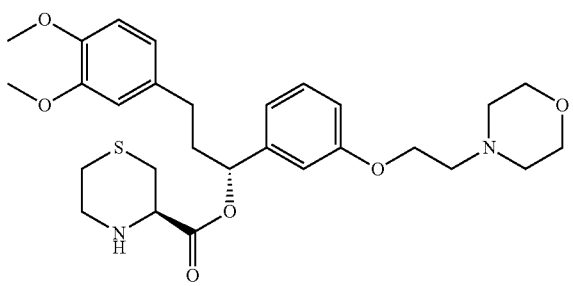

10b

A solution of alcohol 5b (0.10 g, 0.25 mmol), Fmoc-thiopipecolate 6b (92 mg, 0.37 mmol), and catalytic amount of DMAP (3 mg, 25 μmol) in 10 mL DCM was treated with EDC (53 mg, 0.28 mmol). The mixture was stirred for 14 h at RT. The crude product was concentrated, flash chromatographed (DCM/MeOH 97:3) and consequently dissolved in 1.8 mL DCM. Then 0.2 mL 4-methylpiperidine was added and the mixture was stirred for 14 h at RT. 4-Methylpiperidine and DCM were evaporated under reduced pressure. The raw product was purified by flash chromatography (DCM/MeOH 92:8). 10b was obtained as a slight yellow oil (32 mg, 0.13 mmol, 48%).

TLC [MeOH/DCM 8:92]: $R_f$=0.18.

HPLC [0-100% Solvent B, 20 min]: $R_t$=11.7 min, purity (220 nm)=92%

$^1$H NMR (300 MHz, d6-DMSO) δ 7.24-7.16 (m, 1H), 6.91-6.73 (m, 5H), 6.66 (td, J=8.2, 7.8, 2.0 Hz, 1H), 5.63 (dd, J=8.4, 4.7 Hz, 1H), 4.09-4.00 (m, 2H), 3.97 (t, J=3.6 Hz, 1H), 3.72-3.67 (m, 6H), 3.58-3.51 (m, 4H), 3.06-2.85 (m, 3H), 2.69-2.60 (m, 2H), 2.60-2.50 (m, 2H), 2.47-2.39 (m, 5H), 2.17-2.04 (m, 2H), 1.98 (d, J=14.7 Hz, 2H).

$^{13}$C NMR (75 MHz, d6-DMSO) δ 170.62, 158.91, 148.86, 147.47, 142.32, 133.89, 129.68, 120.20, 118.75, 114.35, 112.88, 111.96, 74.91, 66.47, 65.39, 59.53, 57.34, 55.87, 54.09, 46.21, 38.16, 31.03, 28.82, 27.36.

Mass: (ESI$^+$), calculated 531.25 [$C_{28}H_{38}N_2O_6S$+H]$^+$, found 531.21 [M+H]$^+$.

Example 1-11

Preparation of (S)-1-((9H-Fluoren-9-yl)methyl)ester-2-((R)-3-(3,4-dimethoxyphenyl)-1-(3-(2-morpholinoethoxy) phenyl)propyl) pyrrolidine-2-carboxylate (9c)

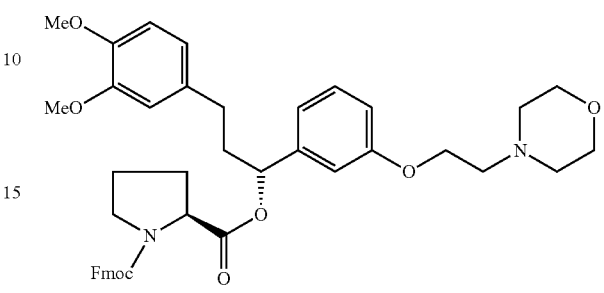

9c 5b (200 mg, 0.50 mmol), Fmoc-proline 6c (185 mg, 0.55 mmol) and DMAP (12 mg, 0.10 mmol) were dissolved in DCM at 0° C. then EDC (143 mg, 0.75 mmol) was added and the reaction was allowed to warm to RT, followed by stirring for 14 hours. The raw product was subjected to column chromatography (gradient 0%-5% MeOH in DCM). 9c (276 mg, 0.383 mmol, 77%) was obtained as a slight yellow oil.

TLC [MeOH/DCM 5:95]: $R_f$=0.2.

HPLC [0-100% Solvent B, 20 min]: $R_t$=16.7 min, purity (220 nm)=98%

$^1$H NMR (400 MHz, CDCl$_3$): δ 7.78-7.67 (m, 2H), 7.65-7.53 (m, 1H), 7.53-7.45 (m, 1H), 7.42-7.26 (m, 3H), 7.25-7.18 (m, 1H), 6.94-6.53 (m, 7H), 5.73 (dt, J=8.0, 5.8 Hz, 1H), 4.49 (dt, J=8.9, 3.7 Hz, 1H), 4.41 (dd, J=10.1, 6.8 Hz, 2H), 4.34-4.13 (m, 1H), 4.14-4.07 (m, 2H), 3.85-3.82 (m, 6H), 3.77-3.66 (m, 4H), 3.31 (td, J=9.1, 3.2 Hz, 1H), 3.26-3.14 (m, 1H), 3.07 (dt, J=10.4, 6.8 Hz, 1H), 2.80 (dt, J=6.9, 5.7 Hz, 4H), 2.64-2.52 (m, 4H), 2.35-2.18 (m, 1H), 2.15-1.96 (m, 2H), 1.95-1.76 (m, 2H).

$^{13}$C NMR (125 MHz, CDCl$_3$) δ 171.90, 159.63, 157.44, 150.39, 148.33, 144.14, 143.58, 139.48, 135.20, 129.28, 127.63, 126.29, 125.14, 121.85, 120.96, 119.20, 115.53, 114.12, 113.68, 113.06, 77.03, 67.50, 67.38, 66.80, 63.34, 56.83, 54.73, 52.94, 48.12, 47.31, 36.38, 34.08, 28.00, 24.98.

Mass (ESI$^+$): calculated [$C_{43}H_{48}N_2O_8$+H]$^+$ 721.35, found 721.25 [M+H]$^+$.

Example 1-12

Preparation of (S)-(R)-3-(3,4-Dimethoxyphenyl)-1-(3-(2-morpholinoethoxy)phenyl)propyl-pyrrolidine-2-carboxylate (10c)

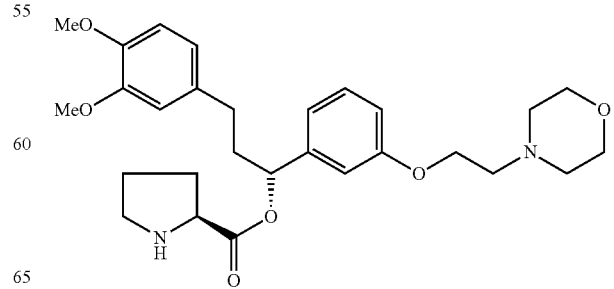

10c 9c (234 mg, 0.32 mmol) was dissolved in 1.8 mL dry DCM, then 200 µL 4-methylpiperidine was added and stirred for 14 h. The product was purified using flash chromatography (gradient 0%-10% MeOH in DCM) to obtain 10c (140 mg, 0.28 mmol, 86%) as a yellow oil.

TLC [MeOH/DCM 6:94]: $R_f$=0.10.

HPLC [0-100% Solvent B, 20 min]: $R_t$=11.6 min, purity (220 nm)=92%.

$^1$H NMR (300 MHz, CDCl$_3$) δ 7.25-7.18 (m, 1H), 6.94-6.83 (m, 2H), 6.83-6.72 (m, 2H), 6.70-6.61 (m, 2H), 5.72 (dd, J=7.9, 5.9 Hz, 1H), 4.64 (dd, J=7.8, 5.3 Hz, 1H), 4.14-4.07 (m, 2H), 3.85-3.82 (m, 6H), 3.77-3.66 (m, 4H), 3.31 (td, J=9.1, 3.2 Hz, 1H), 3.26-3.14 (m, 1H), 3.07 (dt, J=10.4, 6.8 Hz, 1H), 2.80 (dt, J=6.9, 5.7 Hz, 4H), 2.64-2.52 (m, 4H), 2.35-2.18 (m, 1H), 2.15-1.96 (m, 2H), 1.95-1.76 (m, 2H).

$^{13}$C NMR (75 MHz, CDCl$_3$) δ 172.34, 158.73, 148.77, 147.17, 146.44, 141.28, 134.43, 133.35, 129.43, 119.09, 118.46, 113.45, 113.13, 111.75, 111.19, 73.61, 66.82, 65.70, 59.64, 57.63, 55.92, 54.05, 40.65, 31.64, 29.89, 24.75.

Mass (ESI$^+$): calculated [C$_{28}$H$_{38}$N$_2$O$_6$+H]$^+$ 499.28, found 499.22 [M+H]$^+$.

Example 1-13

Preparation of (S)-1-((9H-Fluoren-9-yl)methyl)ester-2-(1,7-di(pyridin-3-yl)heptan-4-yl) piperidine-2-dicar-boxylate (9d)

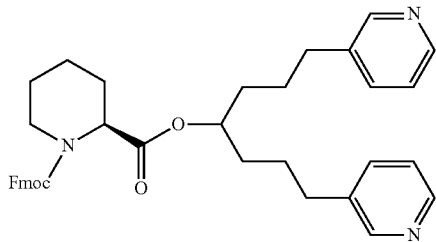

A solution of alcohol 5c (0.30 g, 1.1 mmol) and carboxylic acid 6a (0.39 g, 1.1 mmol) in 10 mL DCM was treated with EDC (0.23 g, 1.2 mmol). The reaction mixture was stirred for 14 h at RT. The solvent was removed in vacuo and the crude mixture was purified by flash chromatography (gradient 0%-100% EtOAc in cyclohexane) to afford 9d as a yellow oil (0.49 g, 0.8 mmol, 73%).

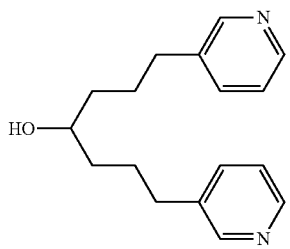

TLC [EtOAc 99%+1% TEA]: $R_f$=0.2.

LCMS: [0-100% Solvent B, 10 min]: $R_t$=7.1 min, purity (220 nm)=96%.

$^1$H NMR (300 MHz, CDCl$_3$) δ 8.47-8.34 (m, 4H), 7.77 (d, J=7.1 Hz, 2H), 7.63-7.56 (m, 2H), 7.53-7.45 (m, 2H), 7.45-7.27 (m, 4H), 7.24-7.06 (m, 2H), 4.93 (dd, J=29.0, 23.9 Hz, 2H), 4.50-4.23 (m, 3H), 4.23-4.01 (m, 1H), 2.67-2.47 (m, 4H), 2.23 (d, J=13.3 Hz, 1H), 1.82-1.38 (m, 10H), 1.35-1.16 (m, 4H).

$^{13}$C NMR (75 MHz, CDCl$_3$) δ 171.54, 156.48, 149.32, 147.14, 143.57, 141.28, 137.13, 135.83, 127.71, 127.04, 125.09, 123.28, 120.07, 74.16, 67.71, 60.38, 54.22, 47.09, 41.86, 33.45, 32.37, 29.69, 26.28, 24.46, 21.27, 20.55, 14.25.

Mass: (ESI$^+$), calculated 604.32 [C$_{38}$H$_{41}$N$_3$O$_4$+H]$^+$, found 604.30 [M+H]$^+$.

Example 1-14

Preparation of (S)-1,7-Di(pyridin-3-yl)heptan-4-yl piperidine-2-carboxylate (10d)

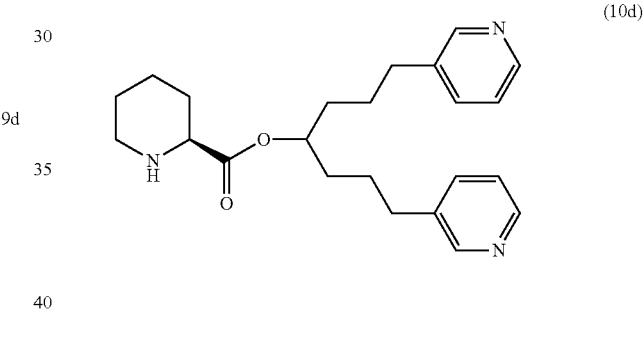

9d (0.44 g, 0.73 mmol) was dissolved in 1.8 mL dry DCM, then 0.2 mL 4-Methylpiperidin was added and stirred for 14 h at RT. The crude mixture was concentrated and purified by flash chromatography (gradient 0%-15% MeOH in DCM). 10d (0.22 g, 0.58 mmol, 80%) was obtained as a slight yellow oil.

TLC [MeOH/DCM 10:90]: $R_f$=0.42.

HPLC [0-50% Solvent B, 20 min]: Rt=9.0 min, purity (220 nm)=90%.

$^1$H NMR (300 MHz, CDCl$_3$) δ 8.46-8.38 (m, 4H), 7.42-7.38 (m, 2H), 7.18-7.14 (m, J=7.5 Hz, 2H), 4.83 (tt, J=6.3, 4.9 Hz, 1H), 3.16-3.03 (m, 2H), 2.73 (dt, J=12.2, 5.2 Hz, 1H), 2.62-2.56 (m, 4H), 2.12 (ddt, J=12.0, 7.5, 5.9 Hz, 1H), 2.00 (s, 1H), 1.78-1.69 (m, 1H), 1.69-1.63 (m, 4H), 1.62-1.56 (m, 3H), 1.55-1.51 (m, 1H), 1.51-1.46 (m, 4H).

$^{13}$C NMR (75 MHz, CDCl$_3$) δ 169.23, 149.61, 147.27, 137.42, 137.13, 136.99, 136.08, 135.90, 123.48, 75.55, 56.98, 45.31, 43.48, 36.56, 32.26, 27.26, 26.20, 22.20.

Mass: (ESI$^+$), calculated 382.25 [C$_{23}$H$_{31}$N$_3$O$_2$+H]$^+$, found 382.20 [M+H]$^+$.

Example 1-15

Preparation of (S)-1-((9H-Fluoren-9-yl)methyl)ester-2-((R)-1-(3-(2-(tert-butoxy)-2-oxoethoxy)phenyl)-3-(3,4-dimethoxyphenyl)propyl) piperidine-2-carboxylate (7b)

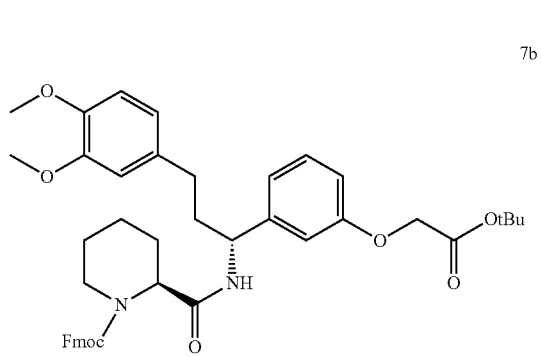

6a (0.25 g, 0.71 mmol), DIPEA (0.37 g, 2.85 mmol) and HATU (410 mg, 1.07 mmol) were dissolved in 1.5 mL DMF and stirred for 30 min. Then (R)-tert-butyl-2-(3-(1-amino-3-(3,4-dimethoxyphenyl)propyl)phenoxy)acetate 5e (0.29 g, 0.71 mmol) dissolved in 2 mL DCM was added to the reaction mixture and stirred at RT for 14 h. The solvent was removed in vacuo and the crude product was purified by flash chromatography (EtOAc/cyclohexane 3:7) to afford 7b (0.48 g, 0.65 mmol, 92%) as a slightly yellow solid.

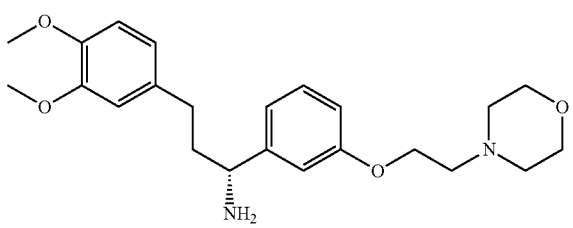

TLC [EtOAc/cyclohexane 3:7]: $R_f$=0.25.

HPLC [0-100% Solvent B, 20 min]: $R_t$=20.5 min, purity (220 nm)=98%

$^1$H NMR (400 MHz, DMSO) δ 7.83-7.80 (m, 2H), 7.63-7.58 (m, 2H), 7.46-7.39 (m, 4H), 7.32-7.20 (m, 2H), 7.04-7.02 (m, 2H), 6.88-6.84 (m, 3H), 6.80-6.74 (m, 2H), 5.20-5.17 (m, 1H), 5.00-4.93 (m, 4H), 4.83 (t, J=6.2 Hz, 1H), 4.17-4.11 (m, 1H), 3.83 (s, 3H), 3.75 (s, 3H), 3.53-3.47 (m, 1H), 2.82 (t, J=4.3 Hz, 1H), 2.69 (t, J=7.9 Hz, 2H), 2.34-2.20 (m, 2H), 2.08-1.91 (m, 2H), 1.79-1.66 (m, 3H), 1.34 (s, 9H).

$^{13}$C NMR (101 MHz, DMSO) δ 170.45, 168.32, 162.49, 158.23, 155.70, 148.71, 147.54, 145.61, 144.45, 141.16, 134.01, 129.35, 128.18, 127.22, 125.45, 120.40, 119.48, 113.43, 112.65, 112.08, 81.47, 64.94, 59.93, 55.91, 54.51, 51.97, 46.97, 41.90, 38.41, 36.27, 32.22, 31.25, 28.31, 26.80, 24.78, 21.20.

Mass: (ESI$^+$), calculated 531.25 [$C_{44}H_{50}N_2O_8$+H]$^+$, found 531.21 [M+H]$^+$.

Example 1-16

Preparation of tert-Butyl-2-(3-((R)-3-(3,4-dimethoxyphenyl)-1-((S)-piperidine-2-carboxamido)propyl)phenoxy) acetate (8b)

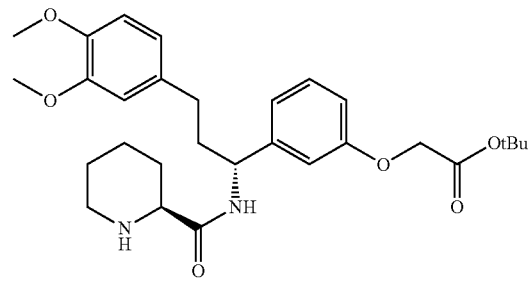

7b (0.43 mg, 0.59 mmol) was dissolved in 4.5 mL dry DCM, then was added 0.5 mL 4-methylpiperidine and stirred for 14 h. The raw product was concentrated and subjected to flash chromatography (gradient 0-100% EtOAc in cyclohexane, then EtOAc/MeOH 99:1, 1% TEA). 8b (160 mg, 0.312, 53%) was obtained as a white solid.

TLC [EtOAc/MeOH 99:1, 1% TEA]: $R_f$=0.20.

HPLC [0-100% Solvent B, 20 min]: $R_t$=14.8 min, purity (220 nm)=95%

$^1$H NMR (300 MHz, CDCl$_3$) δ 7.26-7.20 (m, 1H), 7.18 (d, J=9.4 Hz, 1H), 6.94-6.88 (m, 1H), 6.86 (dd, J=2.6, 1.5 Hz, 1H), 6.78-6.72 (m, 2H), 6.69-6.64 (m, 2H), 4.96 (q, J=7.7 Hz, 1H), 4.49 (s, 2H), 3.85 (s, 3H), 3.83 (s, 3H), 3.23-3.15 (m, 1H), 3.02-2.91 (m, 1H), 2.68-2.58 (m, 1H), 2.59-2.50 (m, 2H), 2.21-2.00 (m, 4H), 1.98-1.87 (m, 1H), 1.80-1.70 (m, 1H), 1.59-1.49 (m, 1H), 1.47 (s, 9H).

$^{13}$C NMR (75 MHz, CDCl$_3$) δ 172.71, 167.65, 158.24, 148.73, 146.82, 144.02, 133.90, 129.60, 120.08, 119.82, 113.37, 112.87, 111.74, 111.20, 82.20, 65.69, 60.12, 55.90, 52.51, 45.68, 37.93, 32.24, 29.75, 28.02, 25.69, 23.88.

Mass: (ESI+), calculated 530.30 [$C_{29}H_{40}N_2O_6$+H]$^+$, found 530.28 [M+H]$^+$.

Synthetic Procedures of Synthetic Building Blocks B

Example 2-1

Preparation of Pentafluorophenyl 2-(3,4,5-trimethoxyphenyl) acetate (12)

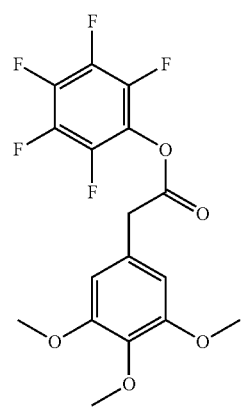

2-(3,4,5-Trimethoxyphenyl)acetic acid 11 (8.2 g, 36.2 mmol) was dissolved in 140 ml dry DCM (then EDC (10.4 g 54.3 mmol) was added and stirred for 15 min at RT 2,3,4,5,6-pentafluorophenol (10.0 g, 54.3 mmol) was dissolved in 60 ml dry DCM and added to the solution. The mixture was stirred for 6 h at RT and then concentrated and subjected to flash chromatography (EtOAc/cyclohexane, 2:8). 12 (13.4 g, 34.1 mmol, 94%) was obtained as a white solid.

TLC [EtOAc/cyclohexane, 2:8]: $R_f$=0.31.

HPLC [0-100% Solvent B, 30 min]: $R_t$=25.8 min, purity (220 nm)=95%.

$^1$H-NMR (300 MHz, CDCl3): δ=6.56 (s, 2H), 3.90 (s, 2H), 3.87 (s, 6H), 3.85 (s, 3H).

$^{13}$C-NMR (150 MHz, CDCl3): δ=167.39, 153.48, 137.59, 127.47, 106.19, 60.855, 56.12, 40.37.

HRMS (ESI$^+$): calculated [$C_{17}H_{13}F_5O_5$+H$^+$] 393.0756, found 393.0711 [M]+H$^+$.

Example 2-2

Preparation of (S)-4-isopropyl-3-[2-(3,4,5-trimethoxyphenyl)acetyl]oxazolidin-2-one (13)

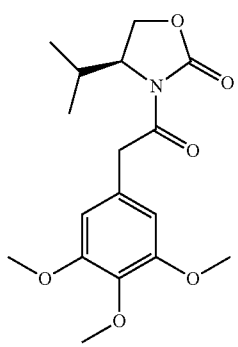

13 n-Butyllithium (2.5 M in Cyclohexane, 1.4 mL, 3.6 mmol) was added to (S)-4-Isopropyl-oxazolidin-2-one (0.46 g, 3.6 mmol) dissolved in 17 mL dry THF at −78° C., then was stirred for 1 h −78° C. After that 12 (1.4 g, 3.6 mmol) dissolved in 17 mL dry THF was added to the above solution and stirred for 2 h at −78° C. and 14 h at 0° C. The reaction mixture was quenched by adding sat. NH$_4$Cl solution. The aqueous solution was extracted with DCM. The org. phases were dried over MgSO$_4$. The crude product was concentrated and purified by column chromatography (EtOAc/cyclohexane, 1:2). 13 was afforded as a yellow oil (0.67 mg, 1.98 mmol, 53%).

TLC [EtOAc/cyclohexane, 2:8]: $R_f$=0.31.

HPLC [0-100% Solvent B, 30 min]: Rt=22.4 min, purity (220 nm)=98%.

$^1$H-NMR (300 MHz, CDCl$_3$): δ=6.56 (s, 2H), 4.43-4.41 (m, 2H), 4.38-4.17 (m, 3H), 3.85 (d, 9H), 2.38-2.27 (m, 1H), 0.96 (d, J=6 Hz, 3H), 0.85 (d, J=6 Hz, 3H).

$^{13}$C-NMR (150 MHz, CDCl$_3$): δ=167.39, 153.48, 137.59, 127.47, 106.19, 60.855, 56.12, 40.37.

Mass (ESI$^+$): calculated [$C_{17}H_{23}NO_6$+H$^+$] 338.16, found 338.20 [M]+H$^+$.

Example 2-3

Preparation of (S)-4-Isopropyl-3-((S)-2-(3,4,5-trimethoxyphenyl)pent-4-enoyl)oxazolidin-2-one (14)

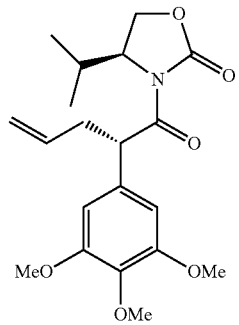

14

13 (2.0 g, 5.9 mmol) was dissolved in 5 mL anhydrous THF, cooled to −78° C. and then NaHMDS (7.1 mL, 7.1 mmol, 1M in THF) was added to the solution. After stirring for 30 min at −78° C., the reaction was stirred for another 30 min at 0° C., then allylbromide (0.63 mL, 7.1 mmol) was added and stirred for 2 h at −78° C., and another 10 h at 0° C. The reaction was quenched by the addition of saturated NH$_4$Cl solution. The biphasic aqueous solution was extracted with DCM. The organic phases were combined and dried over MgSO$_4$. The crude mixture was concentrated and purified by column chromatography (EtOAc/cyclohexane, 2:8). 14 was obtained as yellow oil (1.0 g, 2.7 mmol, 45%, d.r. >95:5).

TLC [EtOAc/cyclohexane 2:8]: $R_f$=0.31.

HPLC [0-100% Solvent B, 30 min]: $R_t$=25.0 min, purity (220 nm)=98%.

$^1$H NMR (600 MHz, CDCl$_3$) δ 6.60 (s, 2H), 5.80-5.70 (m, 1H), 5.20-5.15 (dd, J=9.5, 5.8 Hz, 1H), 5.14-5.07 (dq, J=17.1, 1.6 Hz, 1H), 5.04-4.98 (dq, J=10.2, 1.1 Hz, 1H), 4.40-4.34 (m, 1H), 4.18-4.13 (m, 2H), 3.85-3.82 (s, 6H), 3.83-3.79 (s, 3H), 2.93-2.84 (m, 1H), 2.52-2.44 (m, 1H), 2.43-2.35 (m, 1H), 0.92-0.84 (m, 6H).

$^{13}$C NMR (150 MHz, CDCl$_3$) δ 173.36, 153.67, 153.04, 137.10, 135.07, 133.80, 117.14, 105.43, 62.99, 60.82, 58.93, 56.12, 47.79, 38.67, 28.37, 17.88, 14.58.

HRMS (EI$^+$): calculated [$C_{20}H_{27}NO_6$+H]$^+$ 378.19, found 378.13 [M+H]$^+$.

Example 2-4

Preparation of (S)-2-(3,4,5-Trimethoxyphenyl)pent-4-enoic acid (15)

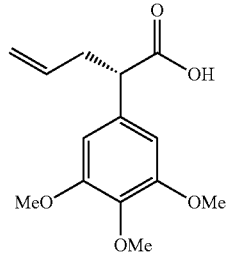

15

14 (0.70 g, 1.86 mmol) was dissolved in 10 mL THF/H$_2$O (1:1) and cooled to 0° C. for 5 min. Then LiOH (89 mg, 3.71 mmol) was added followed by addition of H$_2$O$_2$ (0.60 mL, 7.42 mmol). The reaction mixture was stirred at 0° C. for 4 h. The reaction was quenched by the addition of 1.5 M Na$_2$SO$_3$. The aqueous solution was diluted with brine and extracted with DCM. Then, the aqueous phase was acidified to pH<2 and further extracted with DCM. The organic layers were combined and dried over MgSO$_4$. The raw product was concentrated and purified using flash chromatography (gradient 0%-30% EtOAc in n-hexane, 0.1% AcOH). 15 (324 mg, 1.22 mmol, 66%) was obtained as a yellow oil.

TLC [EtOAc/n-hexane 1:2]: R$_f$=0.22.

HPLC [0-100% Solvent B, 30 min]: R$_t$=17.9 min, purity (220 nm)=98%.

$^1$H NMR (300 MHz, CDCl$_3$) δ 6.56 (d, J=1.1 Hz, 2H), 5.84-5.67 (m, 1H), 5.19-5.00 (m, 2H), 3.87-3.84 (m, J=0.7 Hz, 9H), 3.58 (dd, J=8.6, 6.9 Hz, 1H), 2.88-2.75 (m, 1H), 2.53 (dtt, J=14.5, 6.8, 1.4 Hz, 1H).

$^{13}$C NMR (75 MHz, CDCl$_3$) δ 178.95, 153.31, 137.47, 134.79, 133.38, 117.31, 105.08, 60.81, 56.14, 51.50, 37.18, 20.72.

Mass: (ESI+), calculated 287.12 [C$_{14}$H$_{18}$O$_5$+H]$^+$, found 287.13 [M+H]$^+$.

Example 2-5

Preparation of (S)-3-((S)-2-((S)-cyclohex-2-en-1-yl)-2-(3,4,5-trimethoxyphenyl)acetyl)-4-isopropyl-oxazolidin-2-one (16a)

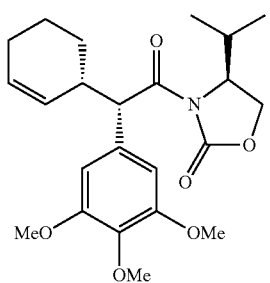

16a

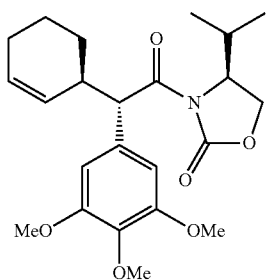

16b dr=85:15

13 (3.0 g, 8.89 mmol) was dissolved in 1 mL anhydrous THF and cooled to −78° C. Then NaHMDS (14.23 mL, 14.23 mmol, 1 M in THF) was added dropwise and stirred for 1 h. The reaction mixture was briefly warmed to 0° C. and cooled again to −78° C. cyclohexene bromide (1.0 mL, 8.9 mmol) was added dropwise and stirred for 1 h at −78° C. finally it was slowly warmed to 0° C. and stirred for another 14 h. The reaction mixture was quenched with sat. NH$_4$Cl solution and extracted with DCM. The organic phase was dried over MgSO$_4$ and the solvent was removed in vacuo. The raw product was purified using column chromatography (EtOAc/cyclohexane 1:3) to obtain a mixture of 16a/b (2.03 g, 4.9 mmol, 55%) as yellow orange solid. A dr at C$_β$ of 85:15 was determined via $^{13}$C NMR. The distribution shown above is based on the co-crystal structure with A12.

TLC [EtOAc/n-hexane 1:2]: R$_f$=0.5.

HPLC 16a/b [55-65% Solvent B, 20 min]: Rt=20.3 min, purity (220 nm)≥99%.

HPLC 16a/b [55-65% Solvent B, 20 min]: Rt=16.6 min, purity (220 nm)≥99%.

$^1$H NMR (300 MHz, d6-DMSO) major diastereomer δ 6.54-6.53 (s, 2H), 5.74-5.66 (m, 1H), 5.61-5.54 (dd, J=10.3, 2.3 Hz, 1H), 4.73-4.67 (d, J=11.2 Hz, 1H), 4.49-4.42 (m, 1H), 4.34-4.27 (m, 1H), 4.20-4.15 (dd, J=9.0, 3.1 Hz, 1H), 3.70-3.69 (s, 6H), 3.62-3.60 (s, J=1.9 Hz, 3H), 1.68-1.55 (m, 3H), 1.47-1.35 (m, 2H), 1.34-1.20 (dd, J=14.4, 7.5 Hz, 2H), 1.11-0.98 (m, 1H), 0.73-0.69 (d, J=7.0 Hz, 3H), 0.35-0.32 (d, J=6.8, 3H).

$^{13}$C NMR (75 MHz, d6-DMSO) major diastereomer δ 172.85, 172.83, 153.81, 153.09, 137.22, 133.09, 129.97, 128.88, 106.30, 63.53, 60.45, 57.97, 56.30, 54.06, 37.30, 28.12, 26.52, 25.25, 20.99, 17.56, 14.44.

Mass: (ESI$^+$), calculated 418.22 [C$_{23}$H$_{31}$NO$_6$+H]$^+$, found 418.25 [M+H]$^+$.

Example 2-6

Preparation of (S)-2-((R)-Cyclohex-2-en-1-yl)-2-(3,4,5-trimethoxyphenyl)acetic acid (17)

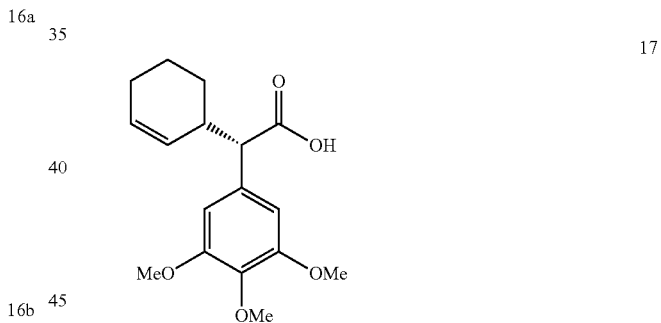

17

16 (0.65 mg, 1.56 mmol) was dissolved in 13 mL THF/H$_2$O 8:5 at RT. Then lithium hydroxide (75 mg, 3.12 mmol) and hydrogen peroxide (0.68 mL, 28.1 mmol) were added and stirred until complete dissolved. The reaction mixture was cooled to 0° C. and stirred for 4 h and another 2 h at RT. Finally the reaction was quenched with 5 mL 1.5 M Na$_2$SO$_3$ solution and was subsequently diluted with brine and extracted with DCM. The aqueous phase was acidified to pH<2 and extracted again with DCM. All organic phases were checked with TLC and LCMS, product containing phases were combined, dried over MgSO$_4$ and concentrated. 17 (470 mg, 1.53 mmol, 96%) was obtained without further purification as a yellow oil with a dr 85:15 (determined via $^{13}$C NMR).

TLC [EtOAc/n-hexane 1:1.5, 1% AcOH]: R$_f$=0.40.

HPLC [55-65% Solvent B, 20 min]: Rt=19.0 min, purity (220 nm)=98%.

$^1$H NMR (300 MHz, d6-DMSO) major diastereomer δ 6.61 (s, 2H), 5.72 (dd, J=10.0, 2.3 Hz, 1H), 5.61 (d, J=10.3 Hz, 1H), 3.72 (s, 6H), 3.62 (s, 3H), 3.50 (dtd, J=8.6, 6.1, 1.1

Hz, 1H), 3.13 (dd, J=11.1, 4.6 Hz, 1H), 1.91 (s, 2H), 1.41-1.20 (m, 3H), 1.10-0.91 (m, 1H).

$^{13}$C NMR (75 MHz, d6-DMSO) major diastereomer δ 174.80, 159.27, 153.00, 136.89, 134.47, 129.95, 128.78, 105.95, 60.30, 57.67, 56.28, 38.26, 26.37, 25.16, 20.75, Mass: (ESI$^+$), calculated 307.15 [C$_{17}$H$_{22}$O$_5$+H]$^+$, found 307.18 [M+H]$^+$.

Example 2-7

Preparation of (S)-3-((S)-2-Cyclohexyl-2-(3,4,5-trimethoxyphenyl)acetyl)-4-isopropyl oxazolidin-2-one (18)

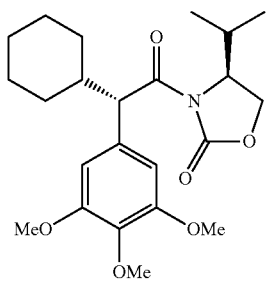

18

16 (0.20 mg, 0.48 mmol) was dissolved in 10 mL of MeOH and placed in an autoclave (Roth, Lab autoclave model II). Palladium on activated charcoal (10% Pd basis, 20 mg, 18.8 µmol) was added and the autoclave was flushed with argon and hydrogen gas. Finally it was filled with 30 bar hydrogen gas and the reaction mixture stirred for 2 d. The reaction progress was monitored by LCMS. If educt was still present another amount of Palladium on activated charcoal (10% Pd basis, 10 mg, 9.40 µmol) was added and above described procedure repeated. The palladium containing crude product was filtered through celite and concentrated. 18 (188 mg, 0.45 mmol, 94%, dr 99:1) was obtained as slight yellow oil and used without further purification. No residual 16 could be observed in the NMR spectra. The diastereomeric rate was determined by HPLC.

TLC [EtOAc/n-hexane 1:2]: R$_f$=0.5.

HPLC [60-70% Solvent B, 20 min]: R$_t$=17.9 min, purity (220 nm)=98%, dr ≥99:1.

$^1$H NMR (300 MHz, d6-DMSO) δ 6.56 (s, 2H), 4.79 (d, J=10.6 Hz, 1H), 4.38 (dt, J=7.3, 3.5 Hz, 1H), 4.27-4.21 (m, 2H), 3.71 (s, 6H), 3.61 (s, 3H), 2.25 (td, J=7.0, 3.4 Hz, 1H), 2.04 (d, J=10.9 Hz, 1H), 1.65 (d, J=11.0 Hz, 2H), 1.56 (d, J=8.0 Hz, 2H), 1.25-0.99 (m, 6H), 0.84 (d, J=1.6 Hz, 3H), 0.80 (d, J=6.9 Hz, 3H).

$^{13}$C NMR (75 MHz, d6-DMSO) δ 173.58, 154.13, 153.06, 137.13, 133.36, 108.74, 106.47, 63.15, 60.37, 58.76, 56.19, 53.74, 31.49, 30.26, 28.33, 26.28, 25.80, 25.66, 17.88, 14.63.

Mass: (ESI$^+$), calculated 420.24 [C$_{23}$H$_{33}$NO$_6$+H]$^+$, found 420.25 [M+H]$^+$.

Example 2-8

Preparation of (S)-2-Cyclohexyl-2-(3,4,5-trimethoxyphenyl)acetic acid (19)

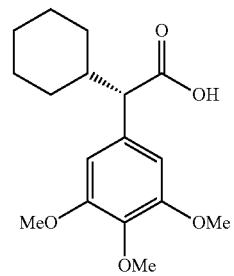

19

18 (0.50 g, 1.19 mmol) was dissolved in 6 mL THF/H$_2$O 8:5 and cooled to 0° C., then lithium hydroxide (57.1 mg, 2.38 mmol) and hydrogen peroxide (0.52 mL, 21.45 mmol) were added and stirred for 24 h. Subsequently the reaction mixture was quenched by adding 5 mL of a 1.5 M Na$_2$SO$_3$ solution. Finally the reaction was quenched with 5 mL 1.5 M Na$_2$SO$_3$ solution and was subsequently diluted with brine and extracted with DCM. The aqueous phase was acidified to pH<2 and extracted again with DCM. All organic phases were checked with TLC and LCMS, product containing phases were combined, dried over MgSO$_4$ and concentrated. 19 (220 mg, 0.71 mmol, 60%) was obtained as a pale yellow oil without further purification.

TLC [EtOAc/n-hexane 1:1.5, 1% AcOH]: R$_f$=0.33.

HPLC [60-70% Solvent B, 20 min]: R$_t$=14.4 min, purity (220 nm)=95%

$^1$H NMR (300 MHz, CDCl$_3$) δ 6.54 (s, 2H), 3.84 (s, 6H), 3.82 (s, 3H), 3.12 (d, J=10.7 Hz, 1H), 2.01-1.83 (m, 3H), 1.81-1.59 (m, 3H), 1.42-1.21 (m, 2H), 1.20-0.99 (m, 3H).

$^{13}$C NMR (75 MHz, CDCl$_3$) δ 179.31, 153.13, 137.33, 132.79, 105.60, 60.80, 58.89, 56.12, 40.86, 31.91, 30.25, 26.23, 25.91.

Example 2-9

Preparation of N-((1S,2S)-1-Hydroxy-1-phenylpropan-2-yl)-N-methyl-2-(3,4,5-trimethoxy phenyl)acetamide (20)

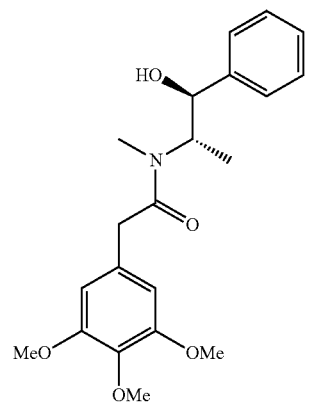

20

Trimethoxyphenyl acetic acid 11 (5.0 g, 22.1 mmol), triethylamine (3.5 mL, 46.0 mmol), EDC-HCl (3.9 g, 20.26 mmol) and HOAt (2.76 g, 20.26 mmol) were dissolved in DCM at 0° C. Then (S,S)-pseudoephedrine (3.0 g, 18.4 mmol) was added and the reaction was stirred at RT for 14 h. The crude product was concentrated and purified using flash chromatography (gradient 0%-100% EtOAc in cyclohexane). 20 (6.37 g, 17.06 mmol, 92%) was obtained as a white solid.

TLC [EtOAc, 1% TEA]: R*f*=0.33.

HPLC [0-100% Solvent B, 20 min]: R*t*=14.4 min, purity (220 nm)≥99%.

¹H NMR (300 MHz, CDCl₃) δ 7.38-7.20 (m, 5H), 6.47 (s, 2H), 4.66-4.40 (m, 1H), 4.25-3.94 (m, 1H), 3.84 (s, 6H), 3.82 (s, 3H), 3.65 (s, 2H), 2.85 (s, 3H), 1.11-1.02 (m, 3H).

¹³C NMR (75 MHz, CDCl₃) δ 173.11, 153.10, 142.00, 136.81, 130.26, 128.65, 128.40, 127.78, 126.77, 126.49, 105.74, 75.43, 60.81, 58.73, 56.13, 42.02, 32.76, 14.40.

Mass: (ESI⁺), calculated 374.20 [C₂₁H₂₇NO₅+H]⁺, found 374.20 [M+H]⁺.

Example 2-10

Preparation of (S)-3-Cyclopropyl-N-((1S,2S)-1-hydroxy-1-phenylpropan-2-yl)-N-methyl-2-(3,4,5-trimethoxyphenyl)propanamide (21)

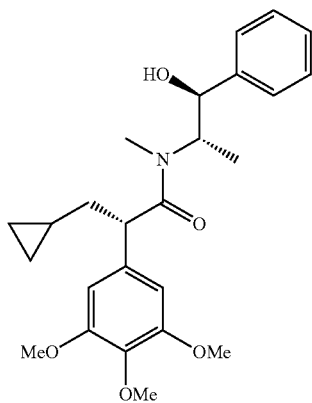

21

20 (1.0 g, 2.7 mmol) and lithium chloride (0.68 mg, 16.07 mmol) were put each into a Schlenck flask and kept under high vacuum for 14 h. Additionally LiCl was heated to 150° C. using an oil bath. Then 20 was dissolved in 18 mL anhydrous THF and added to the dry LiCl. The mixture was cooled to −78° C. LDA (2.95 mL, 5.89 mmol, 2.0 M in THF/heptane/ethylbenzene) was added dropwise and then stirred for 1 h. The reaction mixture was warmed to 0° C., and stirred for 15 min, finally warmed briefly to RT, then cooled again to 0° C. and treated with cyclopropylmethylbromide (1.3 mL, 13.4 mmol). The reaction mixture was stirred for 2 h at 0° C. then slowly warmed to RT and stirred for another 14 h. The raw product was diluted with brine, acidified with 1 M HCl to pH~2 and extracted with DCM. The organic phases were combined and dried over MgSO₄. The crude product was concentrated and purified by flash chromatography (gradient 0%-50% EtOAc in cyclohexane). 21 (0.65 g, 1.51 mmol, 56%) was obtained as yellow crystals.

TLC [MeOH/DCM, 5:95]: R*f*=0.40.

HPLC [0-100% Solvent B, 20 min]: R*t*=14.4 min, purity (220 nm)=98%, dr 95:5.

¹H NMR (300 MHz, CDCl₃) δ 7.41 (s, 1H), 7.38-7.31 (m, 2H), 7.28 (d, J=1.0 Hz, 2H), 6.52 (s, 2H), 4.58 (d, J=6.3 Hz, 1H), 4.14 (d, J=7.1 Hz, 1H), 3.87-3.80 (m, 9H), 3.65 (t, J=7.2 Hz, 1H), 2.79 (s, 3H), 2.12-1.93 (m, 1H), 1.58-1.46 (m, 1H), 1.14 (d, J=6.8 Hz, 3H), 0.67 (s, 1H), 0.43 (dd, J=8.5, 4.6 Hz, 2H), 0.23-0.00 (m, 2H).

¹³C NMR (75 MHz, CDCl₃) δ 175.54, 153.41, 142.33, 136.85, 135.47, 128.31, 127.60, 126.37, 104.71, 75.45, 60.83, 56.18, 50.68, 40.34, 27.33, 14.17, 9.42, 4.66, 4.63.

Mass: (ESI⁺), calculated 428.24 [C₂₅H₃₃NO₅+H]⁺, found 428.52 [M+H]⁺.

Example 2-11

Preparation of (S)-3-cyclopropyl-2-(3,4,5-trimethoxyphenyl)propanoic acid (22)

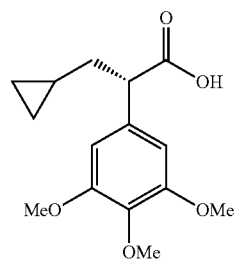

22

21 (0.28 mg, 0.66 mmol) was dissolved in 4 mL dioxane at RT. 4 mL of a 4 M solution of H₂SO₄ in water were added dropwise. The mixture was refluxed for 4 h (150° C.). The reaction was quenched by addition of 50% (w/v) NaOH followed by extraction with DCM. The aqueous phase was acidified with 1 M HCl to pH<2 and extracted again. The organic layers of the acidic extraction were combined and dried over MgSO₄. The raw product was concentrated and purified using preparative TLC (MeOH/DCM, 9:91, 1% AcOH). 22 (68 mg, 0.24 mmol, 37%) was obtained as a yellow oil.

TLC [EtOAc/cyclohexane, 1:1, 1% AcOH]: R*f*=0.35.

HPLC [0-100% Solvent B, 20 min]: R*t*=15.1 min, purity (220 nm)=95%.

¹H NMR (300 MHz, CDCl₃) δ 6.57 (s, 2H), 3.87 (s, 6H), 3.84 (s, 3H), 3.62 (dd, J=8.2, 7.0 Hz, 1H), 1.91 (dt, J=13.9, 7.8 Hz, 1H), 1.75 (dt, J=13.7, 6.8 Hz, 1H), 0.75-0.61 (m, 1H), 0.49-0.41 (m, 2H), 0.16-0.04 (m, 2H).

¹³C NMR (75 MHz, CDCl₃) δ 179.79, 153.24, 137.35, 134.17, 105.09, 60.44, 56.14, 52.16, 38.39, 9.20, 4.46.

Mass: (ESI⁺), calculated 281.14 [C₁₅H₂₀O₅+H]⁺, found 281.37 [M+H]⁺.

Example 2-12

Preparation of (S)-3-phenyl-2-(3,4,5-trimethoxyphenyl)propanoic acid (24)

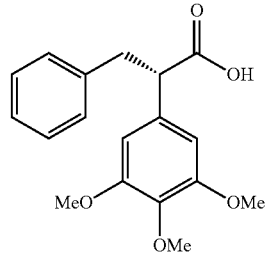

24

20 (0.5 g, 1.34 mmol) and dry lithium chloride (0.34 g, 8.03 mmol, dried as described for 21) were dissolved in 5 mL anhydrous THF and cooled to −78° C. LDA (1.4 mL, 2.95 mmol) was added and stirred for 1 h. The reaction mixture was warmed to 0° C., and stirred for 15 min, finally warmed briefly to RT, then cooled again to 0° C. and treated with benzyl bromide (0.8 mL, 6.69 mmol). The reaction mixture was stirred at 0° C. for 14 h. The crude product was concentrated and purified by flash chromatography (gradient, 0%-40% EtOAc in cyclohexane). 23 (0.33 mg, 0.77 mmol, 58%) was obtained as a yellow oil which was directly further reacted.

23

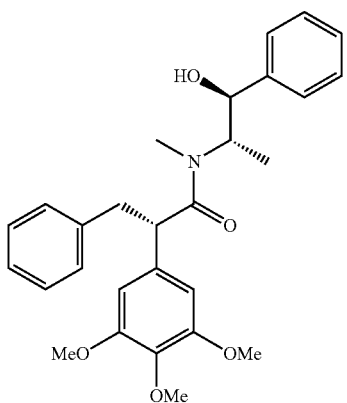

TLC [EtOAc/cyclohexane, 2:1]: $R_f$=0.33.

HPLC [0-100% Solvent B, 20 min]: $R_t$=23.5 min, purity (220 nm)=95%, dr=95:5.

Mass (ESI$^+$), calculated 464.24 $[C_{28}H_{33}NO_5+H]^+$, found 464.27 $[M+H]^+$.

23 (0.28 mg, 0.60 mmol) was dissolved in 4 mL dioxane and then 3.5 mL of a 4 M aq solution of $H_2SO_4$ was added. The mixture was refluxed for 4 h. (150° C.). The reaction was quenched by addition of 50% (w/v) NaOH then was extracted with DCM. Now was acidified with 1 M HCl to pH<2 and again extracted. These organic layers were combined and dried over MgSO$_4$. The raw product was purified using preparative TLC (EtOAc/cyclohexane, 3:7, 4% AcOH). 24 (113 mg, 0.36 mmol, 60%) was obtained as a yellow oil.

TLC [EtOAc/cyclohexane, 3:7, 4% AcOH]: $R_f$=0.42.

HPLC [0-100% Solvent B, 20 min]: $R_t$=19.9 min, purity (220 nm)≥99%.

$^1$H NMR (300 MHz, CDCl$_3$) δ 7.29-7.20 (m, 3H), 7.14 (dd, J=7.9, 1.7 Hz, 2H), 6.53 (s, 2H), 3.85 (s, 6H), 3.84 (s, 3H), 3.40 (dd, J=13.8, 8.5 Hz, 2H), 3.04 (dd, J=13.7, 6.8 Hz, 1H).

$^{13}$C NMR (75 MHz, cdcl$_3$) δ 178.92, 153.27, 138.58, 137.50, 133.49, 130.37, 128.90, 128.41, 126.54, 105.19, 60.84, 56.16, 53.59, 39.38, 20.76, 1.03.

Mass: (ESI$^+$), calculated 317.14 $[C_{18}H_{20}O_5+H]^+$, found 317.13 $[M+H]^+$.

Synthetic Procedures of Synthetic Building Blocks E

Example 2-13

Preparation of (S)-Methyl 2-(2-nitrophenylsulfonamido)pent-4-enoate (25)

25

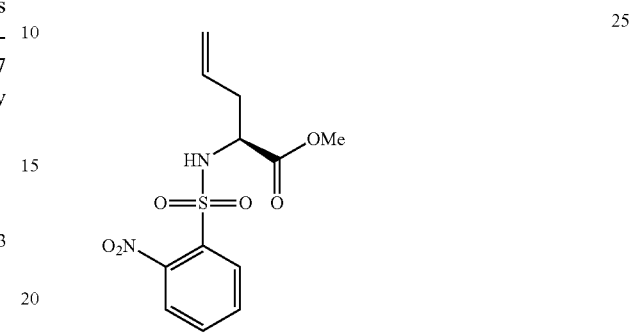

25 was synthesized according to Varray et al ( ). L-allyl-glycine (1.0 g, 8.69 mmol) was dissolved in 10 mL MeOH, cooled to 0° C., and then 3 mL TMS-Cl was added. The mixture was allowed to warm to RT and stirred for 24 h. The solvent was removed in vacuo and the resulting white oil was dissolved in hot EtOAc and precipitated with hexane. L-allyl-glycine methylester (1.1 g, 8.51 mmol, 98%) was obtained as white crystals without further purification and reacted with o-nitrobenzenesulfonyl chloride (2.08 g, 9.37 mmol). For this it was dissolved in 15 mL anhydrous DCM, then TEA (1.40 mL, 17.03 mmol) was added and stirred for 5 h. The reaction mixture was diluted with DCM and washed with brine. The aqueous phases were reextracted with DCM. The organic phases were combined, dried over MgSO$_4$, and the solvent was removed in vacuo. The product was purified using flash chromatography (gradient 0%-30% EtOAc in cyclo-hexene). 25 (1.22 g, 3.88 mmol, 46%) was obtained as a slightly yellow solid.

TLC [EtOAc/cyclohexane, 1:1.5]: $R_f$=0.40.

HPLC [0-100% Solvent B, 20 min]: $R_t$=17.3 min, purity (220 nm)=98%.

HRMS (EI$^+$): calculated $[C_{12}H_{14}N_2O_6S+H]^+$ 315.0651, found 315.0637 $[M+H]^+$.

Example 2-14

Preparation of (S)-Methyl 2-(N-allyl-2-nitrophenylsulfonamido) pent-4-enoate (26)

26

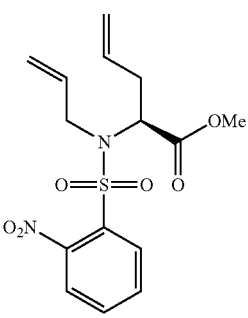

26 was synthesized according to Varray et al. 25 (1.0 g, 3.18 mmol) was dissolved in 25 mL DMF. Then allylbromide (0.44 mL, 5.10 mmol) and potassium carbonate (2.40 g, 17.18 mmol) were added and stirred at RT for 10 h. The raw product mixture was diluted with H$_2$O and then extracted with DCM. The organic solvent was removed in vacuo and the organic phase was dried over MgSO$_4$. 26 (0.94 g, 2.64 mmol, 83%) was obtained without further purification as an orange oil.

TLC [EtOAc/cyclohexane, 3:7]: R$_f$=0.24.

HPLC [0-100% Solvent B, 20 min]: R$_t$=19.1 min, purity (220 nm)=95%.

HRMS (EI$^+$): calculated [C$_{15}$H$_{18}$N$_2$O$_6$S+H]$^+$ 355.0963, found 355.0936 [M+H]$^+$.

Example 2-15

Preparation of (S)-Methyl 1,2,3,6-tetrahydropyridine-2-carboxylate (27)

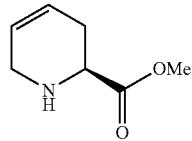

27

27 was synthesized according to Varray et al. 26 (0.90 g, 2.54 mmol) was dissolved in 200 mL dry DCM, then Grubbs II catalyst (0.22 g, 0.25 mmol) was added. The reaction was stirred for 2.5 h, then 50 mL 15% H$_2$O$_2$ was added and stirred for 15 min. The aqueous phase was extracted with DCM and the organic phases were combined and dried over MgSO$_4$. The raw product was subjected to flash chromatography (gradient 0%-40% EtOAc in cyclohexane) to give 26a (0.74 g, 2.27 mmol, 89%) as a dark brown oil.

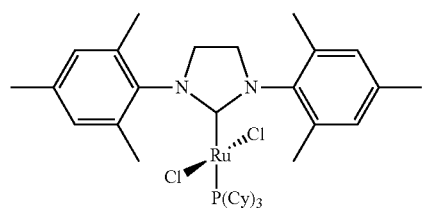

Grubbs Cat. II. generation

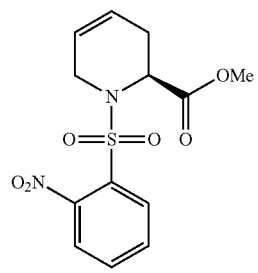

26a 26a (0.64 g, 1.96 mmol) was dissolved in 1 mL dry CH$_3$CN, then Cs$_2$CO$_3$ (1.0 g, 3.10 mmol) and Thiophenol (0.23 mL, 2.25 mmol) was added and stirred for 1.5 h. The suspension turned from light yellow into a strong yellow slurry. The reaction mixture was subsequently diluted with DCM and extracted with H$_2$O. The aqueous Phase was reextracted with DCM. The organic phases were combined and dried over MgSO$_4$. The crude product was concentrated and purified using flash chromatography (gradient 0%-10% MeOH in DCM) to give 27 (0.22 g, 1.59 mmol, 81%) as a dark brown oil.

TLC [MeOH/DCM, 5:95]: R$_f$=0.25, stained with KMnO$_4$ stain

HPLC: not UV active.

HRMS (EI$^+$): calculated [C$_7$H$_{11}$NO$_2$+H]$^+$ 142.0868, found 142.0864 [M+H]$^+$.

Example 2-16

Preparation of (S)-Methyl-1-((S)-2-(3,4,5-trimethoxyphenyl)pent-4-enoyl)-1,2,3,6-tetrahydro-pyridine-2-carboxylate (28)

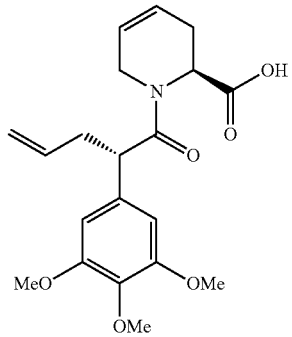

28

15 (0.14 g, 0.53 mmol), HATU (0.22 g, 0.58 mmol) and DIPEA (0.36 mL, 2.13 mmol) were dissolved in 2 mL dry DCM and stirred for 15 min. Then 27 (75 mg, 0.53 mmol) in 1 mL dry DCM was added and stirred for 14 h at RT. The crude product was diluted with DCM and washed with brine. The organic layer was dried over MgSO$_4$, concentrated and the methyl ester was cleaved by dissolving in 1 mL 1:1 THF/H$_2$O and addition of LiOH (10 mg, 0.42 mmol). The mixture was stirred for 14 h then was diluted with brine and extracted with DCM. The aqueous layer was acidified to pH=2 and again extracted with DCM. The organic phases were combined and dried over MgSO$_4$. 28 (84 mg, 0.22 mmol, 79%) was obtained without further purification as a pale yellow oil. The diastereomeric rate was determined by HPLC.

TLC [EtOAc/cyclohexane, 2:1]: R$_f$=0.60.

HPLC [0-100% Solvent B, 20 min]: R$_t$=15.6 min, purity (220 nm)=95%, dr 95:5.

$^1$H NMR (300 MHz, CDCl$_3$) δ 6.45 (s, 2H), 5.81 (ddd, J=13.8, 6.9, 3.9 Hz, 1H), 5.76-5.66 (m, 1H), 5.62 (dd, J=6.7, 1.6 Hz, 1H), 5.56 (dd, J=10.2, 2.9 Hz, 1H), 5.09-4.97 (m, 2H), 4.12-4.03 (m, 1H), 3.83 (s, 6H), 3.81 (s, 3H), 3.79-3.72 (m, 2H), 3.63-3.51 (m, 1H), 2.85 (d, J=6.4 Hz, 1H), 2.70 (dd, J=17.4, 5.9 Hz, 1H), 2.43 (m, 2H).

$^{13}$C NMR (75 MHz, CDCl$_3$) δ 176.22, 172.77, 153.28, 136.85, 136.32, 133.90, 123.33, 122.98, 116.51, 105.05, 60.86, 56.11, 50.17, 49.37, 43.19, 39.33, 26.36.

Mass: (ESI$^+$), calculated 376.18 [C$_{20}$H$_{25}$NO$_6$+H]$^+$, found 376.28 [M+H]$^+$.

Coupling Reaction of Synthetic Building Blocks A and B or D and E

Example 3-A

General Synthesis Procedure A for (the Coupling of Morpholine Containing Top-Groups (Block B))

The alkylated acid (20 mg, 75 μmol) was dissolved in 300 μL DCM or DMF, then DIPEA (41 μL, 0.24 mmol) and HATU (46 mg, 0.12 mmol) were added and stirred for 15 min. Subsequently, the different top groups (block B) with a free secondary amine (32 mg, 60 μmol) in 300 μL DCM were added and stirred for 14 h. The reaction mixture was concentrated and flash chromatographed or purified by preparative HPLC.

Example 3-B

General Synthesis Procedure B for the Coupling of Free Acid Top-Groups (Block B)

The alkylated acid (57 mg, 0.21 mmol) and DIPEA (0.13 mL, 0.78 mmol) were dissolved in dry DCM (2 mL) at RT and stirred for 15 min. Then, HATU (110 mg, 0.29 mmol) was added and stirred for another 15 min. Subsequently, the different top groups (block B) with a free secondary amine (32 mg, 0.06 mmol) in 300 μL DCM was added and stirred for 14 h. The raw product was purified with flash chromatography and then the acid was liberated using 10% TFA in DCM at RT for 5 h. The reaction mixture was concentrated and flash chromatographed or purified by preparative HPLC.

Reference Example 3-1

Preparation of 2-(3-((R)-3-(3,4-Dimethoxyphenyl)-1-(((S)-1-((S)-2-(3,4,5-trimethoxyphenyl) pent-4-enoyl)piperidine-2-carbonyl)oxy)propyl) phenoxy) acetic acid (A01)

General synthesis procedure B for free acid ligands with 8a (0.10 g, 0.20 mmol) and 15 (57 mg, 0.21 mmol) was used. The crude product was purified using flash chromatography (gradient 0%-10% MeOH in DCM) to obtain A01 (38 mg, 54 μmol, 55%) as a colorless oil. The diastereomeric rate was determined by HPLC.

TLC [EtOAc/cyclohexane, 1:1, 1% AcOH]: $R_f$=0.28.

HPLC [60-80% Solvent B, 20 min]: $R_t$=8.1 min, purity (220 nm)=95%, dr 95:5.

$^1$H NMR (599 MHz, d6-DMSO) δ 7.20 (dd, J=7.8, 0.8 Hz, 1H), 6.85-6.71 (m, 4H), 6.67 (d, J=2.0 Hz, 1H), 6.59 (s, 2H), 6.56 (dd, J=8.2, 2.0 Hz, 1H), 5.76-5.64 (m, 1H), 5.48 (dd, J=8.7, 4.6 Hz, 1H), 5.22 (dd, J=5.9, 2.5 Hz, 1H), 5.03-4.92 (m, 2H), 4.65 (s, 2H), 3.71 (t, J=2.3 Hz, 3H), 3.69 (s, 3H), 3.68 (s, 4H), 3.64 (s, 3H), 3.61 (s, 1H), 3.51 (s, 3H), 2.75-2.64 (m, 2H), 2.44-2.37 (m, 2H), 2.34-2.25 (m, 2H), 2.15-2.06 (m, 2H), 1.84 (ddd, J=34.5, 8.0, 5.4 Hz, 2H), 1.63-1.52 (m, 2H), 1.05-0.95 (m, 2H).

$^{13}$C NMR (151 MHz, CDCl3) δ 176.94, 175.44, 175.30, 162.96, 157.84, 153.83, 152.17, 147.35, 141.80, 141.17, 140.09, 138.19, 134.63, 125.13, 123.41, 121.43, 117.28, 110.32, 80.06, 69.53, 64.83, 61.09, 60.78, 60.65, 60.51, 56.95, 52.14, 42.66, 35.80, 31.40, 29.98, 25.70.

Mass: (ESI$^+$), calculated 728.30 $[C_{39}H_{47}NO_{11}+Na]^+$, found 728.40 $[M+H]^+$.

Example 3-2

Preparation of 2-(3-((R)-3-(3,4-dimethoxyphenyl)-1-(((S)-1-((S)-2-(3,4,5-trimethoxyphenyl)pent-4-enoyl)pyrrolidine-2-carbonyloxy)propyl)phenoxy) acetic acid A02

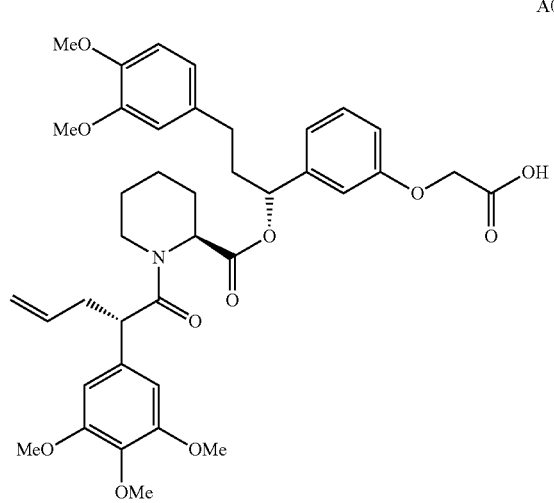

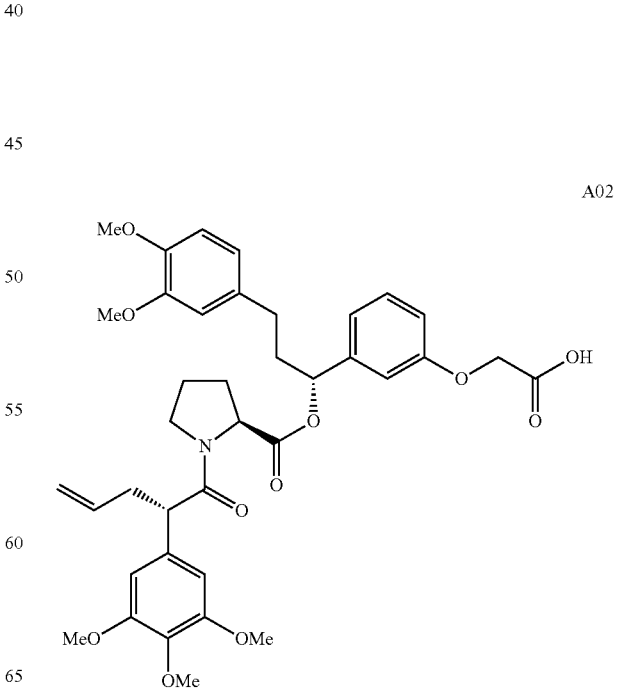

Example 3-3

Preparation of (S)-(R)-3-(3,4-dimethoxyphenyl)-1-(3-(2-morpholinoethoxy)phenyl)propyl1-((S)-2-(3,4,5-trimethoxyphenyl) pent-4-enoyl)piperidine-2-carboxylate A03

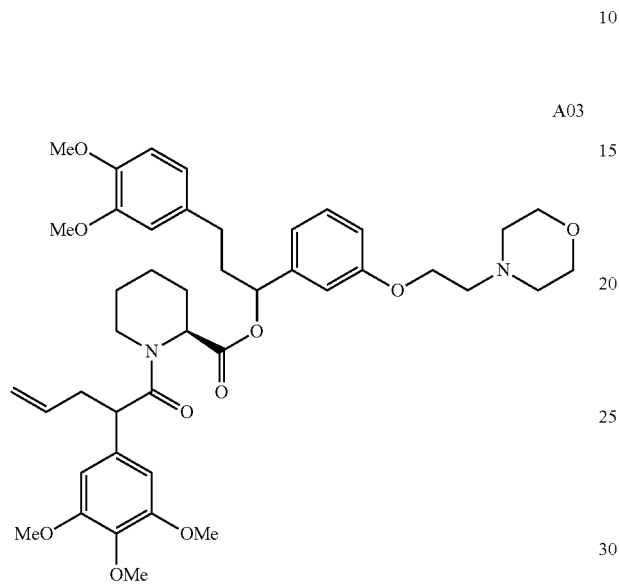

General synthesis procedure A for morpholine ligands with 8a (190 mg, 371 µmol) and 15 (99 mg, 371 µmol) was used. The crude product was purified using flash chromatography (gradient 0%-80% EtOAc in cylcohexane) to obtain A03 (163 mg, 4 µmol, 58%) as a white foam. The diastereomeric rate was determined by HPLC.

TLC [98:1:1 EtOAc/MeOH/TEA]: $R_f$=0.25.

HPLC [0-100% Solvent B, 20 min]: $R_t$=15.9 min, purity (220 nm)=99%, dr ≥99:1.

$^1$H NMR (600 MHz, CDCl$_3$) δ 7.17-7.13 (t, J=7.6, 1.0 Hz, 1H), 6.88-6.84 (m, 1H), 6.80-6.75 (m, 3H), 6.66-6.62 (m, 2H), 6.40-6.39 (s, 2H), 5.82-5.73 (m, 2H), 5.62-5.58 (dd, J=8.1, 5.5 Hz, 1H), 5.46-5.43 (m, 1H), 5.08-5.02 (dd, J=17.2, 1.7 Hz, 1H), 5.01-4.97 (m, 1H), 4.16-4.09 (s, 2H), 3.85-3.84 (d, J=1.4 Hz, 6H), 3.83-3.83 (s, 2H), 3.79-3.78 (s, 3H), 3.77-3.72 (m, 5H), 3.69-3.68 (s, 6H), 2.85-2.79 (m, 3H), 2.63-2.58 (m, 4H), 2.56-2.51 (m, 1H), 2.49-2.43 (m, 1H), 2.42-2.36 (m, 1H), 2.33-2.27 (d, J=13.3 Hz, 1H), 2.14-2.06 (m, 1H), 1.98-1.90 (m, 1H), 1.74-1.66 (m, 2H), 1.62-1.57 (d, J=12.7 Hz, 2H).

$^{13}$C NMR (150 MHz, CDCl$_3$) δ 172.11, 170.67, 158.76, 153.37, 148.96, 147.47, 141.98, 136.86, 136.79, 134.78, 120.30, 118.71, 116.34, 114.30, 114.00, 111.85, 111.39, 105.08, 77.16, 76.09, 66.97, 65.76, 60.86, 57.78, 56.44, 56.12, 56.06, 55.97, 54.22, 52.21, 49.35, 43.54, 39.61, 38.36, 31.44.

Mass: (ESI$^+$), calculated 761.40 [C$_{42}$H$_{54}$N$_2$O$_{10}$S+H]$^+$, found 761.44 [M+H]$^+$.

Example 3-4

Preparation of (S)-1,7-di(pyridin-3-yl)heptan-4-yl 1-((S)-2-(3,4,5-trimethoxyphenyl)pent-4-enoyl)piperidine-2-carboxylate (A04)

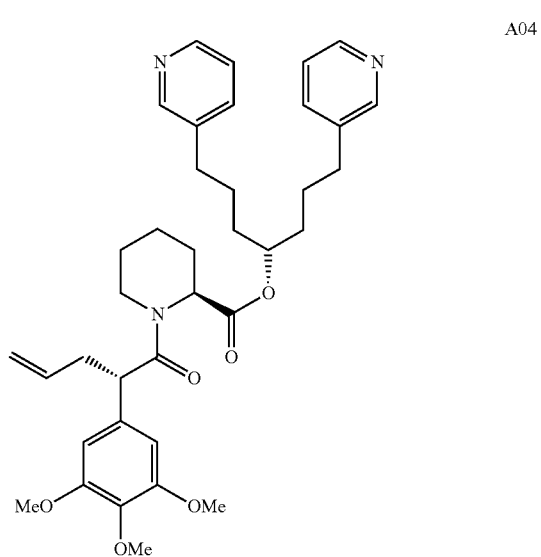

Example 3-5

Preparation of (S)-N-((R)-3-(3,4-dimethoxyphenyl)-1-(3-(2-morpholinoethoxy)phenyl)propyl)-1-((S)-2-(3,4,5-trimethoxyphenyl)pent-4-enoyl)piperidine-2-carboxamide (A05)

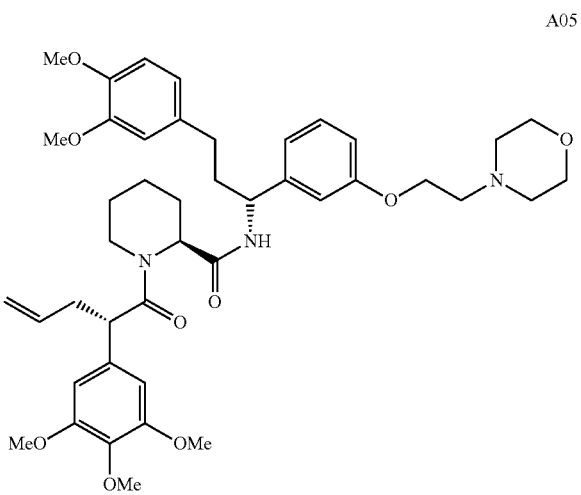

Example 3-6

Preparation of 2-(3-((R)-3-(3,4-Dimethoxyphenyl)-1-(((S)-1-((S)-2-(3,4,5-trimethoxyphenyl) pent-4-enoyl)-1,2,3,6-tetrahydropyridine-2-carbonyl)oxy)propyl)phenoxy) acetic acid (A06)

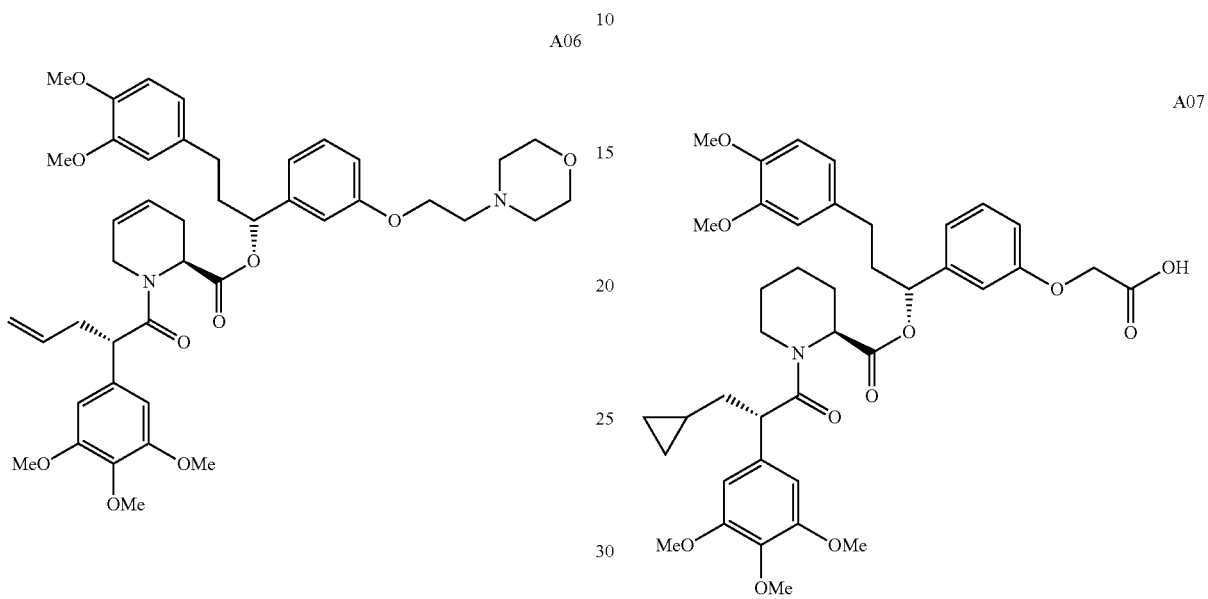

28 (20 mg, 53 µmol), DMAP (1.0 mg, 5.3 µmol) and DCC (7.0 mg, 59 µmol) were dissolved in 1 mL DCM at 0° C. and stirred for 15 min. Then 10a (23 mg, 59 µmol) in 500 µL DCM was added, and the mixture was allowed to warm to RT and stirred for 14 h. The crude product was concentrated and purified using flash chromatography (gradient 0%-8% MeOH in DCM). A06 (17 mg, 22.4 µmol, 42%) was obtained as a colorless oil. The diastereomeric rate was determined by HPLC.

TLC [MeOH/DCM, 6:94]: $R_f$=0.42.

HPLC [0-100% Solvent B, 20 min]: $R_t$=16.6 min, purity (220 nm)=98%, dr 95:5.

$^1$H NMR (400 MHz, d6-DMSO) δ 7.23 (ddd, J=10.0, 7.7, 3.1 Hz, 1H), 7.14-7.08 (m, 1H), 6.88-6.77 (m, 2H), 6.72-6.56 (m, 3H), 6.55 (s, 1H), 6.44 (d, J=7.7 Hz, 1H), 5.71-5.63 (m, 1H), 5.57 (d, J=2.8 Hz, 1H), 5.49-5.45 (m, 1H), 5.38 (dd, J=8.5, 5.1 Hz, 1H), 5.29 (dt, J=5.7, 2.6 Hz, 1H), 4.98 (dd, J=17.2, 2.1 Hz, 1H), 4.91 (dd, J=10.2, 2.2 Hz, 1H), 4.08-4.03 (m, 3H), 3.72-3.69 (m, 3H), 3.67-3.63 (m, 6H), 3.60 (s, 3H), 3.57 (s, 3H), 3.55 (s, 2H), 3.54 (s, 2H), 3.50-3.47 (m, 2H), 2.69 (dd, J=12.8, 6.1 Hz, 2H), 2.67-2.61 (m, 3H), 2.43 (t, J=5.0 Hz, 3H), 2.30 (dd, J=8.8, 7.0 Hz, 2H), 2.24 (t, J=7.4 Hz, 2H), 1.95 (d, J=6.5 Hz, 2H).

$^{13}$C NMR (101 MHz, d6-DMSO) δ 173.73, 172.42, 158.74, 153.18, 149.05, 147.40, 142.24, 136.62, 134.74, 133.73, 133.41, 130.14, 124.03, 122.95, 120.36, 118.25, 116.77, 114.02, 112.69, 112.22, 105.67, 75.54, 66.62, 65.79, 60.30, 57.54, 56.39, 56.30, 56.02, 55.92, 55.75, 54.07, 51.56, 49.97, 49.38, 48.03, 42.98, 33.65, 31.71, 27.03, 26.55, 24.84.

Mass: (ESI$^+$), calculated 759.39 [C$_{43}$H$_{54}$N$_2$O$_{10}$+H]$^+$, found 759.42 [M+H]$^+$.

Reference Example 3-7

Preparation of 2-(3-((R)-1-(((S)-1-((S)-3-cyclopropyl-2-(3,4,5-trimethoxyphenyl)propanoyl)piperidine-2-carbonyl)oxy)-3-(3,4-dimethoxyphenyl)propyl)phenoxy)acetic acid (A07)

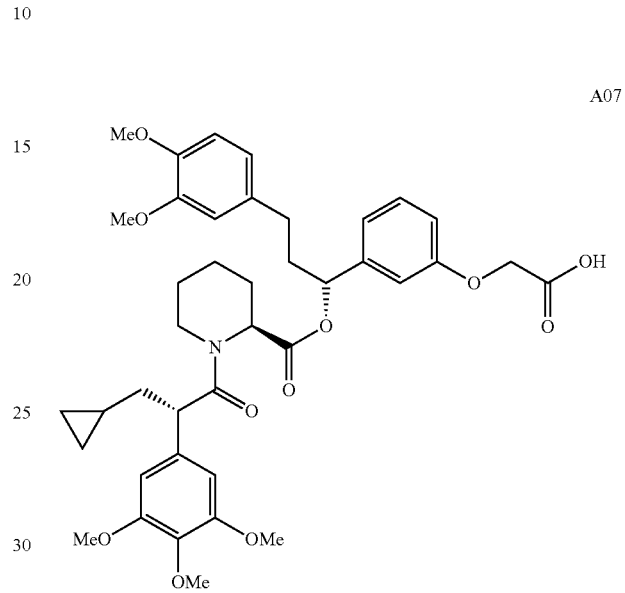

General synthesis procedure B for free acid ligands with 8a (100 mg, 0.20 mmol) and 22 (55 mg, 0.20 mmol) 57.0 mg, 0.21 mmol) was used. The crude product was concentrated and purified using flash chromatography (gradient 0%-10% MeOH in DCM) to obtain A07 (38 mg, 54 µmol, 55%) as a colorless oil. The diastereomeric rate was determined by HPLC.

TLC [MeOH/DCM, 6:94]: $R_f$=0.27.

HPLC [0-100% Solvent B, 20 min]: $R_t$=19.3 min, purity (220 nm)=95%, dr=95:5.

$^1$H NMR (400 MHz, d6-DMSO) δ 7.22 (s, 1H), 7.12 (dd, J=15.6, 7.9 Hz, 1H), 6.85-6.69 (m, 3H), 6.63-6.55 (m, 2H), 6.51 (s, 1H), 5.50 (dd, J=8.2, 5.2 Hz, 1H), 5.25 (s, 1H), 4.64 (s, 2H), 3.71 (d, J=2.0 Hz, 2H), 3.68 (s, 3H), 3.67 (s, 3H), 3.60 (d, J=2.5 Hz, 1H), 3.56 (s, 6H), 3.53 (s, 3H), 2.68-2.60 (m, 1H), 2.52 (t, J=5.3 Hz, 2H), 2.45-2.40 (s, 2H), 2.38-2.33 (m, 2H), 2.14 (d, J=12.0 Hz, 1H), 1.94-1.84 (m, 2H), 1.64-1.57 (m, 4H), 0.63-0.56 (m, 1H), 0.36-0.28 (m, 2H), 0.07--0.03 (m, 2H).

$^{13}$C NMR (101 MHz, d6-DMSO) δ 172.66, 170.73, 170.52, 158.01, 153.09, 149.14, 147.59, 142.39, 136.43, 135.93, 133.44, 129.79, 120.34, 113.88, 112.82, 112.64, 112.34, 109.94, 105.52, 75.34, 64.87, 60.20, 57.45, 56.30, 55.95, 55.88, 52.05, 47.92, 43.37, 30.92, 26.67, 21.10, 14.38, 9.71, 4.73.

Mass: (ESI$^+$), calculated 720.34 [C$_{40}$H$_{49}$NO$_{11}$+H]$^+$, found 720.32 [M+H]$^+$.

Example 3-8

Preparation of (S)-(R)-3-(3,4-dimethoxyphenyl)-1-(3-(2-morpholinoethoxy)phenyl)propyl-1-((S)-3-cyclopropyl-2-(3,4,5-trimethoxyphenyl)propanoyl)piperidine-2-carboxylate (A08)

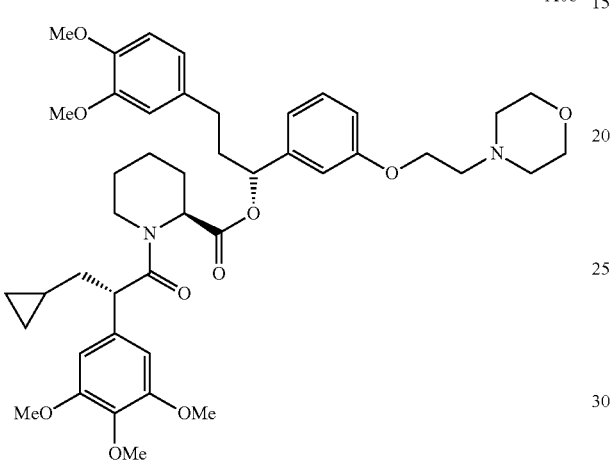

General synthesis procedure A for morpholine ligands with 22 (8 mg, 29 μmol) and 10a (14 mg, 27 μmol) was used. Then was purified using flash chromatography (gradient 0%-10% MeOH in DCM) to obtain A08 (6 mg, 7.74 μmol, 29%) as a colorless oil. The diastereomeric rate was determined by HPLC.

TLC [MeOH/DCM, 8:92]: $R_f$=0.52.

HPLC [0-100% Solvent B, 20 min]: $R_t$=15.1 min, purity (220 nm)=95%, dr 95:5

$^1$H NMR (600 MHz, CDCl$_3$) δ 7.26-7.24 (m, 1H), 7.02-6.97 (m, 1H), 6.90-6.71 (m, 5H), 6.60 (s, 2H), 5.45-5.43 (m, 1H), 4.88-4.86 (m, 1H), 4.08-4.05 (m, 2H), 3.84-3.74 (m, 6H), 3.72-3.70 (m, 8H), 3.70-3.59 (m, 2H), 3.55-3.53 (m, J=4.7 Hz, 4H), 3.49-3.45 (m, 1H), 2.76-2.64 (m, 4H), 2.53-2.41 (m, 5H), 2.16-2.06 (m, 3H), 1.99-1.97 (m, J=7.2 Hz, 1H), 1.92-1.82 (m, 3H), 1.74-1.60 (m, 3H), 0.88-0.75 (m, 1H), 0.31-0.20 (m, 2H), 0.05--0.06 (m, 2H).

$^{13}$C NMR (125 MHz, CDCl$_3$) δ 175.62, 170.15, 159.63, 156.01, 150.39, 148.33, 143.58, 137.88, 135.20, 132.08, 129.28, 121.85, 119.20, 115.53, 114.12, 113.68, 113.06, 107.04, 77.03, 67.38, 66.80, 60.70, 58.74, 56.83, 54.73, 52.94, 48.18, 43.29, 36.38, 34.08, 33.96, 25.91, 25.47, 22.24, 9.61, 7.11.

Mass: (ESI$^+$), calculated 775.42 [C$_{44}$H$_{58}$N$_2$O$_{10}$+H]$^+$, found 775.48 [M+H]$^+$.

Example 3-9

Preparation of (S)-(R)-3-(3,4-dimethoxyphenyl)-1-(3-(2-morpholinoethoxy)phenyl)propyl-1-((S)-3-cyclopropyl-2-(3,4,5-trimethoxyphenyl)propanoyl)pyrrolidine-2-carboxylate (A09)

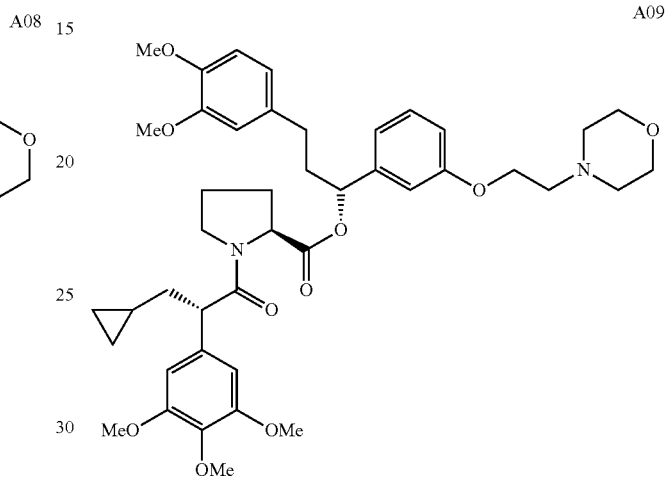

General synthesis procedure A for morpholine ligands with 10c (40 mg, 80 μmol) and 22 (22 mg, 80 μmol) was used. Then was purified using preparative HPLC (gradient 55%-70% Solvent B in Solvent A, 20 min) to obtain A09 (17 mg, 7.7 μmol, 28%) as a colorless oil. The diastereomeric rate was determined by HPLC.

TLC [MeOH/DCM, 8:92]: $R_f$=0.44.

HPLC [0-100% Solvent B, 20 min]: $R_t$=16.3 min, purity (220 nm)=95%, dr 95:5

$^1$H NMR (400 MHz, d6-DMSO) δ 7.52 (d, J=7.7 Hz, 1H), 7.33-7.20 (m, 1H), 6.97-6.85 (m, 2H), 6.84-6.78 (m, 2H), 6.64-6.56 (m, 2H), 6.50 (s, 1H), 5.54 (ddd, J=37.2, 8.3, 4.8 Hz, 2H), 4.46 (dd, J=8.6, 3.4 Hz, 1H), 4.41-4.29 (m, 3H), 3.84-3.74 (m, 3H), 3.73-3.69 (m, 5H), 3.69-3.67 (m, 5H), 3.61-3.58 (m, 3H), 3.56-3.49 (m, 6H), 2.59 (s, 4H), 2.47 (p, J=1.8 Hz, 1H), 2.38-2.28 (m, 1H), 2.23-2.05 (m, 2H), 1.93-1.76 (m, 2H), 1.75-1.65 (m, 1H), 1.37-1.26 (m, 1H), 1.22 (dt, J=12.1, 6.8 Hz, 2H), 0.60 (s, 1H), 0.36-0.22 (m, 2H), 0.02 (qd, J=10.2, 4.6 Hz, 2H).

$^{13}$C NMR (101 MHz, d6-DMSO) δ 171.83, 171.50, 158.19, 153.15, 152.99, 149.04, 147.39, 142.69, 136.39, 135.86, 133.76, 133.68, 123.98, 120.49, 114.37, 112.75, 112.42, 105.67, 75.17, 63.75, 62.51, 60.23, 56.30, 55.99, 55.78, 52.16, 49.87, 46.13, 30.78, 29.12, 24.88, 21.14, 14.40, 9.61, 8.81, 4.85.

Mass: (ESI$^+$), calculated 761.40 [C$_{43}$H$_{56}$N$_2$O$_{10}$+H]$^+$, found 761.41 [M+H]$^+$.

Example 3-10

Preparation of 2-(3-((R)-3-(3,4-dimethoxyphenyl)-1-(((S)-1-((S)-3-phenyl-2-(3,4,5-trimethoxyphenyl)propanoyl)piperidine-2-carbonyl)oxy)propyl) phenoxy)acetic acid (A10)

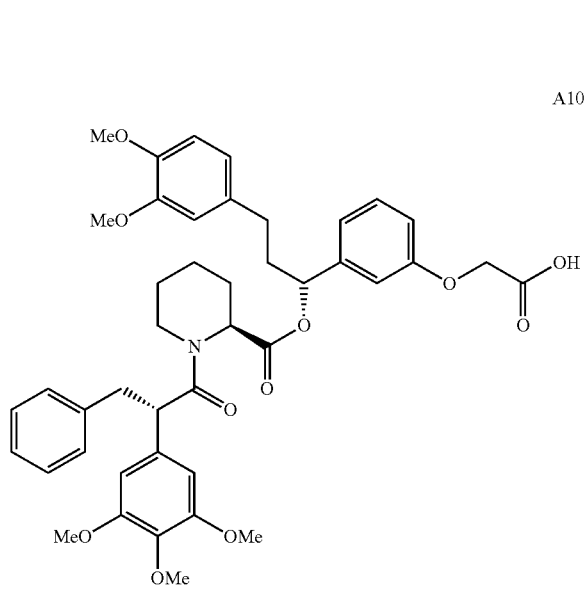

General synthesis procedure B for free acid ligands with 24 (68 mg, 0.21 mmol) and 8a (100 mg, 0.20 mmol) was used. Then was purified using reversed phase flash (Gradient 40%-70% MeOH in H$_2$O+1% AcOH) to obtain A10 (49 mg, 0.13 mmol, 49%) as a slight yellow oil. The diastereomeric rate was determined by HPLC.

TLC [MeOH/DCM, 8:92]: R$_f$=0.20.

HPLC [isochratic 60% B, 20 min]: R$_t$=10.4 min, purity (220 nm)=98%, dr 95:5.

$^1$H NMR (599 MHz, d6-DMSO) δ 7.27-7.03 (m, 6H), 6.86-6.65 (m, 5H), 6.59 (s, 2H), 5.50 (dd, J=8.2, 5.1 Hz, 1H), 5.19 (dd, J=6.0, 2.5 Hz, 1H), 4.61 (s, 2H), 4.35 (dd, J=8.9, 6.0 Hz, 1H), 3.99 (d, J=13.2 Hz, 1H), 3.70 (s, 3H), 3.69 (s, 3H), 3.66 (s, 1H), 3.62 (s, 6H), 3.53 (d, J=0.7 Hz, 3H), 3.31-3.26 (m, 2H), 2.85 (dd, J=13.5, 5.9 Hz, 1H), 2.70 (td, J=13.4, 2.9 Hz, 1H), 2.43 (ddd, J=14.0, 9.0, 5.7 Hz, 1H), 2.33 (dt, J=14.0, 8.1 Hz, 1H), 2.08 (d, J=13.4 Hz, 1H), 1.88 (qd, J=8.5, 8.0, 5.4 Hz, 2H), 1.54-1.44 (m, 2H), 1.44-1.35 (m, 1H), 1.12-1.03 (m, 1H), 1.01-0.93 (m, 1H).

$^{13}$C NMR (151 MHz, d6-DMSO) δ 172.30, 170.60, 158.34, 153.05, 149.12, 147.61, 142.67, 140.25, 136.47, 135.16, 133.44, 130.00, 129.79, 129.59, 129.38, 129.37, 128.49, 128.26, 126.26, 120.50, 118.49, 113.89, 112.61, 112.53, 112.42, 105.76, 75.42, 65.12, 60.25, 56.09, 55.98, 55.86, 55.72, 52.13, 49.02, 43.34, 41.21, 38.10, 31.04, 26.52, 20.78.

Mass: (ESI$^-$), calculated 756.34 [C$_{43}$H$_{49}$NO$_{11}$+H]$^-$, found 756.33 [M+H]$^+$.

Example 3-11

Preparation of 2-(3-((R)-1-(((S)-1-((S)-2-((S)-Cyclohex-2-en-1-yl)-2-(3,4,5-trimethoxyphenyl)acetyl)piperidine-2-carbonyl)oxy)-3-(3,4-dimethoxyphenyl)propyl)phenoxy) acetic acid (A11)

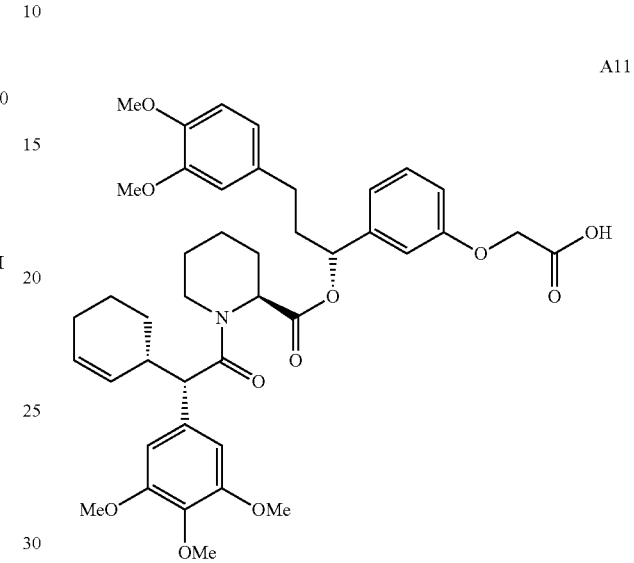

General synthesis procedure B for free acid ligands with 8a (50 mg, 0.20 mmol) and 17 (29.8 mg, 0.20 mmol) was used. Then was purified using flash chromatography (gradient 0%-4% MeOH in DCM) to obtain A11 (25 mg, 33.5 μmol, 67%, dr 85:15) as a slight yellow oil. The dr was determined by NMR.

TLC [MeOH/DCM, 6:94]: R$_f$=0.12.

HPLC [0-100% Solvent B, 20 min]: R$_t$=20.0 min, purity (220 nm)=98%.

$^1$H NMR (600 MHz, d6-DMSO) major diastereomer δ 7.08 (td, J=8.1, 1.7 Hz, 1H), 6.80 (dd, J=8.3, 1.1 Hz, 1H), 6.75 (ddd, J=8.3, 2.6, 0.9 Hz, 1H), 6.69-6.66 (m, 2H), 6.64 (d, J=11.4 Hz, 2H), 6.60-6.58 (m, 1H), 6.38-6.34 (m, 1H), 5.69-5.65 (m, 1H), 5.59 (dq, J=9.8, 3.6 Hz, 1H), 5.52 (dd, J=10.0, 2.4 Hz, 1H), 5.47-5.40 (m, 1H), 5.30-5.25 (m, 1H), 4.62 (d, J=1.3 Hz, 1H), 4.13 (d, J=13.4 Hz, 1H), 3.71 (d, J=0.8 Hz, 1H), 3.69 (s, 3H), 3.68 (s, 3H), 3.62-3.61 (m, 3H), 3.59 (s, 3H), 3.57 (s, 3H), 3.53 (d, J=0.7 Hz, 3H), 2.82-2.71 (m, 2H), 2.67-2.53 (m, 1H), 2.42-2.32 (m, 1H), 2.25 (ddt, J=24.0, 13.8, 8.2 Hz, 2H), 2.11 (d, J=12.9 Hz, 1H), 1.90 (s, 2H), 1.84-1.73 (m, 2H), 1.62-1.51 (m, 2H), 1.24-1.12 (m, 1H), 1.06 (dtd, J=22.1, 12.1, 3.1 Hz, 1H)

$^{13}$C NMR (151 MHz, d6-DMSO) major diastereomer δ 171.70, 170.42, 158.01, 152.87, 149.01, 147.50, 142.19, 136.44, 133.42, 129.78, 128.05, 120.17, 118.44, 113.74, 112.91, 112.46, 112.01, 106.25, 105.80, 75.23, 64.94, 60.03, 56.06, 56.05, 55.92, 55.76, 52.41, 51.92, 43.29, 38.91, 38.02, 30.80, 26.69, 25.42, 21.21.

Mass: (ESI$^+$), calculated 746.35 [C$_{42}$H$_{51}$NO$_{11}$+H]$^+$, found 746.38 [M+H]$^+$.

Example 3-12

Preparation of (S)-(R)-3-(3,4-Dimethoxyphenyl)-1-(3-(2-morpholinoethoxy)phenyl)propyl-1-((S)-2-((S)-cyclohex-2-en-1-yl)-2-(3,4,5-trimethoxyphenyl)acetyl)piperidine-2-carboxylate (A12)

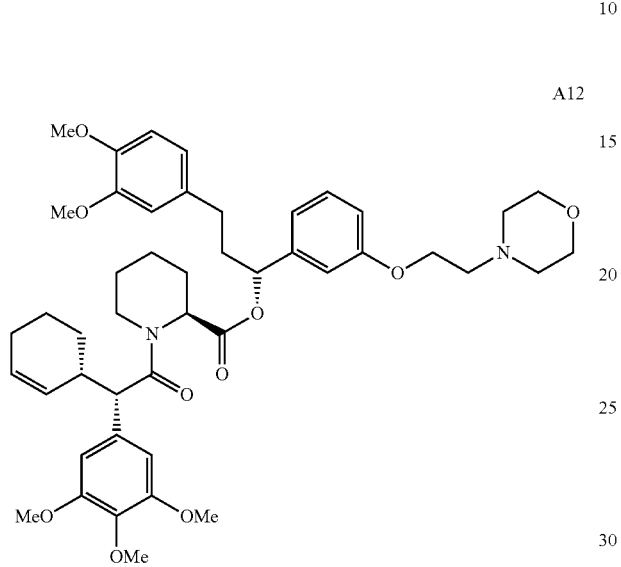

A12

General synthesis procedure A for morpholine ligands with 17 (10 mg, 33 μmol) and 10a (17 mg, 33 μmol) was used. The product was purified using flash chromatography (gradient 0%-6% MeOH in DCM). A12 (16 mg, 20 μmol, 75%, dr 85:15) was obtained as a colorless oil. The dr was determined by NMR.

TLC [MeOH/DCM, 6:94]: $R_f$=0.22.

HPLC [50-60% Solvent B, 20 min]: $R_t$=10.5 min, purity (220 nm)=98%.

$^1$H NMR (400 MHz, d6-DMSO) major diastereomer δ 7.08 (t, J=7.9 Hz, 1H), 6.93-6.87 (m, 1H), 6.83-6.76 (m, 2H), 6.72 (q, J=2.5, 2.0 Hz, 1H), 6.68 (d, J=2.0 Hz, 1H), 6.62 (d, J=11.1 Hz, 2H), 6.36 (t, J=7.1 Hz, 1H), 5.69-5.63 (m, 1H), 5.55-5.49 (m, 1H), 5.47-5.38 (m, 1H), 5.26 (s, 1H), 4.06 (dd, J=14.6, 6.1 Hz, 2H), 3.72-3.70 (m, 2H), 3.69 (s, 3H), 3.67 (s, 3H), 3.61 (t, J=1.5 Hz, 1H), 3.58 (s, 1H), 3.55 (s, 2H), 3.53 (s, 2H), 3.29-3.27 (m, 10H), 2.82-2.70 (m, 2H), 2.65-2.56 (m, 1H), 2.32-2.22 (m, 2H), 2.11 (d, J=13.2 Hz, 2H), 1.90 (s, 2H), 1.80 (dt, J=14.9, 6.8 Hz, 3H), 1.59 (d, J=13.8 Hz, 3H), 1.49-1.36 (m, 1H), 1.21 (d, J=3.6 Hz, 3H), 0.88-0.77 (m, 2H).

$^{13}$C NMR (101 MHz, d6-DMSO) major diastereomer δ 172.07, 170.39, 158.51, 153.10, 148.83, 147.53, 142.35, 136.56, 133.51, 130.70, 129.85, 128.16, 120.38, 118.26, 114.15, 112.85, 112.65, 112.33, 106.17, 75.31, 66.60, 65.63, 60.20, 60.11, 57.40, 56.45, 56.04, 55.93, 55.77, 54.00, 52.60, 52.01, 51.96, 43.13, 37.92, 30.92, 28.64, 28.01, 26.71, 25.32, 22.42, 21.21, 20.82.

Mass: (ESI$^+$), calculated 801.43 [C$_{46}$H$_{60}$N$_2$O$_{10}$+H]$^+$, found 801.42 [M+H]$^+$.

Example 3-13

Preparation of (S)-1,7-Di(pyridin-3-yl)heptan-4-yl-1-((S)-2-((S)-cyclohex-2-en-1-yl)-2-(3,4,5-trimethoxy phenyl) acetyl)piperidine-2-carboxylate (A13)

A13

17 (42 mg, 0.14 mmol) was dissolved in 500 μL DMF, then HATU (91 mg, 0.25 mmol) and DIPEA (86 μL, 0.50 mmol) were added and stirred for 30 min. Then 10d (48 mg, 0.14 mmol) in 500 μL DMF was added and stirred for 14 h. Subsequently, 3 mL H$_2$O/MeOH 1:1 with 0.1% TFA was added and subjected to reversed phase flash chromatography (gradient 0%-45% MeOH in H$_2$O+0.1% TFA). A13 (53 mg, 79 μmol, 63%, 85:15) was obtained as a yellow oil. The dr was determined by NMR.

TLC [MeOH/DCM, 15:85]: $R_f$=0.25.

HPLC [0-100% Solvent B, 20 min]: $R_t$=13.2 min, purity (220 nm)=95%.

$^1$H NMR (300 MHz, CDCl$_3$) major diastereomer δ 8.69 (d, J=15.8 Hz, 4H), 8.23 (dd, J=24.2, 7.7 Hz, 2H), 7.81 (s, 2H), 6.51 (d, J=12.9 Hz, 2H), 5.83-5.68 (m, 1H), 5.65-5.48 (m, 1H), 5.30 (s, 1H), 4.84 (s, 1H), 3.85-3.82 (m, 1H), 3.81 (s, 3H), 3.78 (s, 6H), 3.63-3.43 (m, 1H), 2.95-2.84 (m, 2H), 2.80-2.67 (m, 4H), 2.21 (d, J=12.9 Hz, 2H), 1.99 (s, 3H), 1.76-1.34 (m, 14H), 1.12 (d, J=11.3 Hz, 1H).

$^{13}$C NMR (75 MHz, CDCl$_3$) major diastereomer δ 172.71, 172.51, 171.03, 170.84, 152.77, 145.17, 144.97, 141.86, 141.49, 139.45, 136.89, 133.18, 130.02, 128.94, 126.52, 105.84, 72.97, 60.90, 56.13, 53.91, 52.42.

Mass: (ESI$^+$), calculated 670.39 [C$_{40}$H$_{51}$N$_3$O$_6$+H]$^+$, found 670.39 [M+H]$^+$.

Example 3-14

Preparation of (S)-2-(3,4-Dimethoxyphenoxy)ethyl-1-((S)-2-((R)-cyclohex-2-en-1-yl)-2-(3,4,5-trimethoxyphenyl)acetyl)piperidine-2-carboxylate (A14)

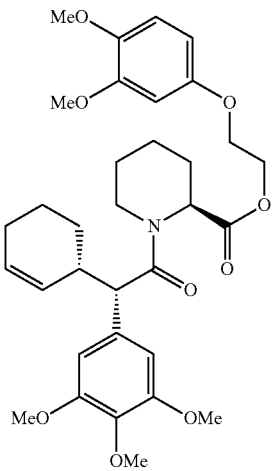

17 (45 mg, 0.15 mmol) was dissolved in 700 μL dry DMF then N-ethyl-N-isopropylpropan-2-amine (102 μL, 0.60 mmol) and HATU (83 mg, 0.22 mmol) was added and stirred for 15 min. Then 10e (45 mg, 0.15 mmol) was dissolved in 600 μL DCM/DMF 1:1 and added to the reaction mixture. Then was stirred for 14 h at RT. The product was purified using flash chromatography (Gradient 0%-50% EtOAc in cyclohexane). A14 (12 mg, 20 μmol, 13%, dr 85:15) was obtained as a slight yellow oil. The dr was determined by NMR.

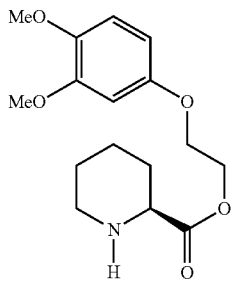

TLC [EtOAc/cyclohexane, 1:1]: $R_f$=0.29.

HPLC [60-80% Solvent B, 20 min]: $R_t$=12.0 min, purity (220 nm)=95%.

$^1$H NMR (400 MHz, d6-DMSO) major diastereomer δ 6.81-6.77 (m, 1H), 6.67 (d, J=6.9 Hz, 1H), 6.59 (s, 2H), 6.46 (d, J=2.7 Hz, 1H), 5.68-5.63 (m, 1H), 5.55-5.52 (m, 1H), 5.15-5.12 (m, 1H), 4.44-4.39 (m, 1H), 4.16-4.10 (m, 2H), 4.02-3.95 (m, 2H), 3.82-3.76 (m, 1H), 3.69 (s, 3H), 3.67 (s, 6H), 3.66 (s, 3H), 3.62-3.60 (m, 3H), 3.59-3.52 (m, 1H), 2.73-2.66 (m, 2H), 2.09-2.01 (m, 1H), 1.98-1.86 (m, 3H), 1.84-1.73 (m, 2H), 1.70-1.52 (m, 3H), 1.32 (d, J=7.5 Hz, 2H).

$^{13}$C NMR (101 MHz, d6-DMSO) major diastereomer δ 172.25, 171.15, 153.21, 152.92, 150.00, 143.62, 136.44, 134.87, 133.53, 131.40, 128.24, 113.13, 106.42, 104.61, 101.36, 66.53, 63.39, 60.70, 56.48, 56.37, 56.19, 55.83, 52.76, 52.36, 43.22, 38.91, 26.91, 26.74, 26.58, 25.39, 21.13, 20.93.

Mass: (ESI+), calculated 598.30 [$C_{33}H_{43}NO_9$+H]$^+$, found 598.28 [M+H]$^+$.

Example 3-15

Preparation of (S)-(R)-3-(3,4-dimethoxyphenyl)-1-(3-(2-morpholinoethoxy)phenyl)propyl-1-((S)-2-((R)-cyclohex-2-en-1-yl)-2-(3,4,5-trimethoxyphenyl)acetyl)pyrrolidine-2-carboxylate (A15)

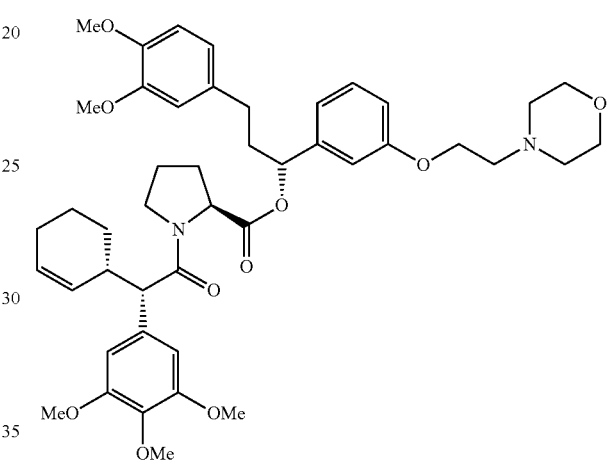

General synthesis procedure A for morpholine ligands with 17 (30 mg, 98 μmol) and 10c (40 mg, 80 μmol). The product was purified using flash chromatography. A15 (44 mg, 20 μmol, 70%, dr 85:15) was obtained as colorless oil. The dr was determined by NMR.

TLC [MeOH/DCM, 8:92]: $R_f$=0.29.

HPLC [0-100% Solvent B, 20 min]: $R_t$=16.6 min, purity (220 nm)=98%.

$^1$H NMR (400 MHz, d6-DMSO) major diastereomer δ 7.24-7.14 (m, 1H), 6.94 (d, J=29.5 Hz, 1H), 6.88-6.78 (m, 2H), 6.70 (dd, J=6.1, 2.0 Hz, 1H), 6.68-6.63 (m, 1H), 6.63-6.59 (m, 1H), 6.57 (d, J=5.9 Hz, 2H), 5.72-5.64 (m, 1H), 5.58 (ddd, J=14.8, 10.1, 2.2 Hz, 1H), 5.41 (ddd, J=12.6, 8.2, 5.0 Hz, 1H), 5.09 (dd, J=10.2, 2.5 Hz, 1H), 4.47 (ddd, J=14.3, 8.6, 3.1 Hz, 1H), 4.22-4.13 (m, 1H), 3.73-3.71 (m, 1H), 3.70 (s, 2H), 3.68 (s, 3H), 3.64-3.61 (m, 3H), 3.55 (s, 3H), 3.54 (d, J=1.5 Hz, 4H), 3.32 (s, 9H), 3.23-3.19 (m, 1H), 2.89-2.74 (m, 2H), 2.75-2.61 (m, 2H), 2.46-2.24 (m, 2H), 2.25-2.13 (m, 2H), 1.97-1.86 (m, 2H), 1.80-1.67 (m, 3H), 1.67-1.54 (m, 1H), 1.53-1.29 (m, 3H), 1.27-1.14 (m, 1H).

$^{13}$C NMR (101 MHz, d6-DMSO) major diastereomer δ 171.90, 171.05, 159.55, 153.08, 149.26, 147.35, 142.64, 136.73, 133.54, 130.79, 129.87, 129.38, 128.68, 120.50, 114.23, 112.82, 112.32, 106.54, 106.04, 75.16, 67.84, 66.99, 60.86, 59.81, 58.96, 57.75, 56.19, 54.80, 53.88, 47.26, 32.66, 30.54, 29.34, 28.63, 25.48, 24.79, 21.81, 21.31.

Mass: (ESI-), calculated 787.42 [$C_{45}H_{58}N_2O_{10}$+H]$^-$, found 787.35 [M+H]$^+$.

Example 3-16

Preparation of 2-(3-((R)-1-((S)-1-((S)-2-((R)-Cyclohex-2-en-1-yl)-2-(3,4,5-trimethoxyphenyl)acetyl)piper-idine-2-carboxamido)-3-(3,4-dimethoxyphenyl)propyl)phenoxy) acetic acid (A16)

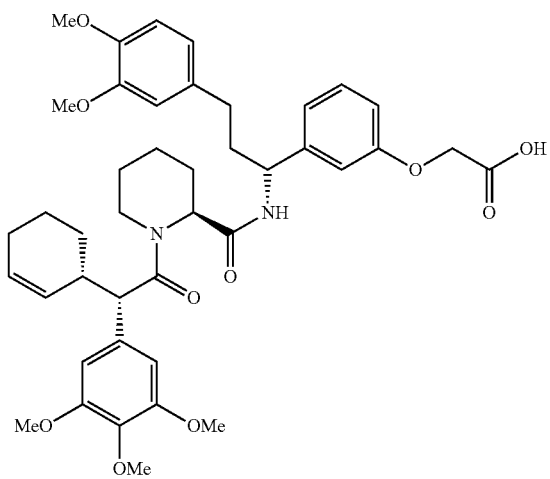

A16

General synthesis procedure B for free acid ligands with 8b (50 mg, 0.20 mmol) and 17 (30 mg, 0.20 mmol) was used. The product was purified using preparative TLC (MeOH/DCM 8:92) to obtain A16 (25 mg, 33.5 μmol, 67%, dr 85:15) as a slight yellow oil. The diastereomeric rate was determined by NMR.

TLC [MeOH/DCM, 8:92]: $R_f$=0.29.

HPLC [0-100% Solvent B, 20 min]: $R_t$=11.7 min, purity (220 nm)=98%.

$^1$H NMR (400 MHz, dmso) major diastereomer δ 7.10-7.05 (m, 1H), 6.92-6.86 (m, 1H), 6.81 (t, J=8.4 Hz, 1H), 6.72 (dq, J=11.8, 2.0 Hz, 2H), 6.69-6.64 (m, 1H), 6.63-6.57 (m, 1H), 6.56-6.51 (m, 2H), 5.70-5.61 (m, 1H), 5.53 (d, J=10.2 Hz, 1H), 5.12-5.04 (m, 1H), 4.79-4.66 (m, 2H), 4.66-4.53 (m, 3H), 3.73-3.69 (m, 2H), 3.69-3.66 (m, 6H), 3.62-3.60 (m, 1H), 3.55-3.51 (m, 9H), 2.93-2.81 (m, 2H), 2.79-2.67 (m, 2H), 2.40-2.27 (m, 2H), 2.16-2.02 (m, 2H), 1.96-1.84 (m, 2H), 1.84-1.73 (m, 3H), 1.56 (d, J=8.2 Hz, 2H), 1.31 (d, J=9.6 Hz, 1H).

$^{13}$C NMR (101 MHz, dmso) δ 172.44, 170.72, 170.56, 158.10, 152.97, 149.05, 147.45, 145.74, 136.42, 134.04, 133.70, 131.15, 129.51, 128.15, 120.46, 113.07, 112.76, 112.70, 112.19, 106.01, 64.77, 63.52, 60.15, 56.41, 55.97, 55.92, 55.78, 52.86, 52.23, 51.90, 43.24, 38.97, 38.62, 32.03, 27.78, 27.48, 26.54, 25.31, 21.12, 20.41.

Mass: (ESI$^-$), calculated 745.37 [C$_{42}$H$_{52}$N$_2$O$_{10}$+H]$^+$, found 745.40 [M−H]$^+$.

Example 3-17

Preparation of 2-(3-((R)-1-(((S)-1-((S)-2-Cyclohexyl-2-(3,4,5-trimethoxyphenyl)acetyl)piperidine-2-carbonyl)oxy)-3-(3,4-dimethoxyphenyl)propyl)phenoxy)acetic acid (A17)

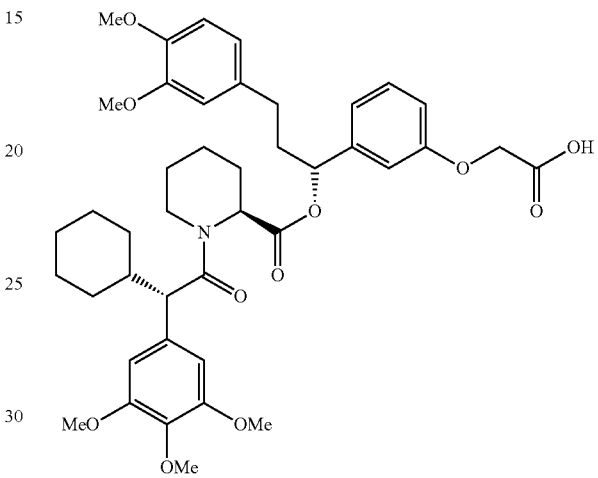

A17

General synthesis procedure B for free acid ligands with 8a (96 mg, 0.20 mmol) and 19 (58 mg, 0.20 mmol) was used. The crude product was purified using preparative TLC (EtOAc/cyclohexane 1:1.5+1% AcOH) to obtain 56 (17 mg, 33.5 μmol, 23%) as a colorless oil.

TLC [EtOAc/cyclohexane 1:1]: $R_f$=0.20.

HPLC [0-100% Solvent B, 20 min]: $R_t$=20.6 min, purity (220 nm)≥99%.

$^1$H NMR (599 MHz, d6-DMSO) δ 7.03 (t, J=7.9 Hz, 1H), 6.90-6.84 (m, 1H), 6.83-6.73 (m, 2H), 6.70-6.65 (m, 2H), 6.62 (s, 1H), 6.57 (dd, J=8.1, 2.0 Hz, 1H), 6.28 (d, J=7.6 Hz, 1H), 5.40 (dd, J=7.6, 6.0 Hz, 1H), 5.27 (dd, J=5.8, 2.4 Hz, 1H), 4.36 (s, 2H), 4.19 (d, J=13.4 Hz, 1H), 3.69 (s, 3H), 3.67 (s, 3H), 3.60 (s, 1H), 3.58 (s, 6H), 3.51 (s, 3H), 3.48-3.43 (m, 1H), 2.67-2.60 (m, 1H), 2.37-2.29 (m, 2H), 2.22 (dt, J=13.9, 8.1 Hz, 1H), 2.14-2.06 (m, 2H), 1.99-1.91 (m, 2H), 1.78-1.69 (m, 2H), 1.63 (d, J=12.4 Hz, 1H), 1.54-1.41 (m, 2H), 1.35-1.28 (m, 1H), 1.19 (d, J=17.2 Hz, 2H), 1.15-1.02 (m, 2H), 0.96-0.85 (m, 2H), 0.80 (ddt, J=20.6, 12.1, 7.3 Hz, 2H).

$^{13}$C NMR (151 MHz, d6-DMSO) δ 172.48, 172.08, 170.61, 158.61, 152.66, 149.15, 147.47, 142.13, 136.20, 134.32, 133.43, 120.48, 118.07, 113.80, 113.07, 112.53, 112.13, 106.25, 75.16, 66.46, 60.33, 56.62, 55.90, 55.74, 53.12, 52.03, 43.53, 41.10, 37.94, 32.41, 31.32, 30.58, 29.98, 26.87, 26.32, 25.93, 25.38, 20.93.

Mass: (ESI$^-$), calculated 748.37 [C$_{42}$H$_{53}$NO$_{11}$+H]$^+$, found 768.41[M+H]$^+$.

Example 3-18

Preparation of (S)-(R)-3-(3,4-dimethoxyphenyl)-1-(3-(2-morpholinoethoxy)phenyl)propyl-1-((S)-2-cyclohexyl-2-(3,4,5-trimethoxyphenyl)acetyl)piperidine-2-carboxylate (A18)

Example 3-19

Preparation of (2S)-1,7-di(pyridin-3-yl)heptan-4-yl 1-(2-cyclohexyl-2-(3,4,5-trimethoxy phenyl)acetyl) piperidine-2-carboxylate A19

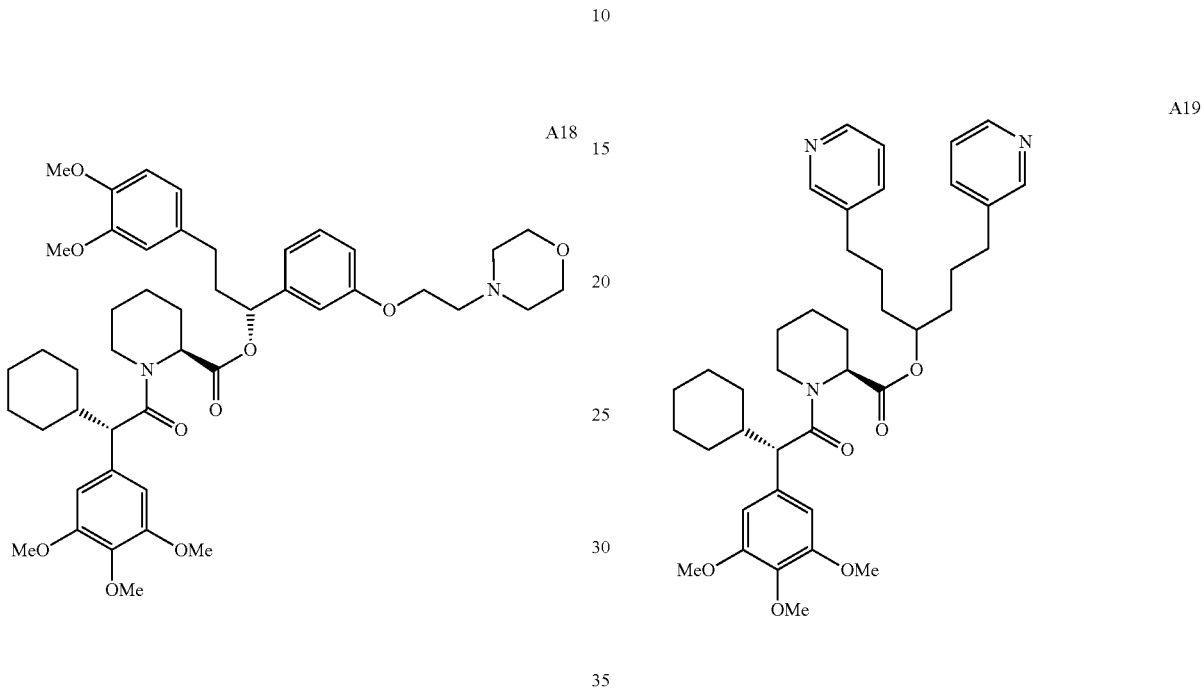

General synthesis procedure A for morpholine ligands with 19 (30 mg, 97 μmol) and 10a (50 mg, 97 μmol). The product was purified using flash chromatography (gradient 0%-15% MeOH in DCM). A18 (11 mg, 13.6 μmol, 14%) was obtained as a colorless oil.

TLC [MeOH/DCM 6:94]: $R_f$=0.44.

HPLC [0-100% Solvent B, 20 min]: $R_t$=17.7 min, purity (220 nm)=98%.

¹H NMR (400 MHz, d6-DMSO) δ 7.08 (t, J=7.9 Hz, 1H), 6.93-6.87 (m, 1H), 6.83-6.76 (m. 2H). 6.72 (a. J=2.5. 2.0 Hz. 1H). 6.68 (d. J=2.0 Hz. 1H). 6.62 (d. J=11.1 Hz, 2H), 6.36 (t, J=7.1 Hz, 1H), 5.47-5.38 (m, 1H), 5.26 (s, 1H), 4.06 (dd, J=14.6, 6.1 Hz, 2H), 3.72-3.70 (m, 2H), 3.69 (s, 3H), 3.67 (s, 3H), 3.61 (t, J=1.5 Hz, 1H), 3.58 (s, 1H), 3.55 (s, 3H), 3.53 (s, 3H), 3.29-3.27 (m, 10H), 2.82-2.70 (m, 2H), 2.65-2.56 (m, 1H), 2.32-2.22 (m, 2H), 2.11 (d, J=13.2 Hz, 2H), 1.90 (s, 2H), 1.80 (dt, J=14.9, 6.8 Hz, 4H), 1.59 (d, J=13.8 Hz, 4H), 1.49-1.36 (m, 1H), 1.21 (d, J=3.6 Hz, 3H), 0.88-0.77 (m, 2H).

¹³C NMR (151 MHz, d6-DMSO) δ 172.55, 170.94, 162.94, 153.03, 149.33, 147.72, 137.03, 133.56, 129.26, 120.19, 112.20, 75.37, 60.37, 56.68, 55.84, 55.30, 53.99, 51.62, 46.53, 43.54, 36.39, 32.08, 30.77, 27.00, 25.93, 25.39, 21.16, 17.17, 9.63.

Mass: (ESI⁻), calculated 803.34 [$C_{46}H_{62}N_2O_{10}$+H]⁺, found 803.38[M+H]⁺.

19 (39 mg, 0.13 mmol) was dissolved in 500 μL DMF, then HATU (48 mg, 0.13 mmol) and DIPEA (86 μL, 0.50 mmol) were added and stirred for 30 min. Then 10d (48 mg, 0.125 mmol) in 500 μL DMF was added and stirred for 16 h. The raw product was purified by flash chromatography MeOH/EE 1:9. A19 (62 mg, 92 μmol, 73%, 85:15) was obtained as a white solid.

TLC [MeOH/EE, 10:90+0.1% TEA]: $R_f$=0.45.

LCMS [0-100% Solvent B, 20 min]: $R_t$=13.2 min, purity (220 nm)=95%.

¹H NMR (400 MHz, DMSO) δ 8.40-8.34 (m, 4H), 7.58-7.52 (m, 2H), 7.32-7.25 (m, 2H), 6.61-6.57 (s, 2H), 5.18-5.12 (d, J=5.3 Hz, 1H), 4.81-4.73 (m, 1H), 4.25-4.15 (d, J=14.1 Hz, 1H), 3.73-3.70 (s, 2H), 3.66-3.63 (s, 6H), 3.63-3.62 (s, 1H), 3.62-3.60 (s, 3H), 2.73-2.64 (m, 2H), 2.64-2.53 (m, 3H), 2.48-2.41 (m, 4H), 2.09-2.02 (m, 2H), 1.77-1.66 (m, 2H), 1.68-1.46 (m, 6H), 1.42-1.27 (m, 5H), 1.25-1.05 (m, 4H).

¹³C NMR (100 MHz, DMSO) δ 172.06, 170.67, 152.47, 149.48, 147.13, 137.18, 135.64, 133.82, 123.40, 105.78, 73.21, 59.85, 55.63, 52.78, 51.64, 43.04, 40.70, 39.52, 32.81, 31.62, 31.51, 29.81, 26.34, 26.16, 25.62, 25.09, 20.61.

Mass: (ESI⁺), calculated 672.40 [$C_{40}H_{53}N_3O_6$+H]⁺, found 672.44 [M+H]⁺.

147

Example 3-20

Preparation of (S)-2-(3,4-dimethoxyphenoxy)ethyl-1-((S)-2-cyclohexyl-2-(3,4,5-trimethoxy phenyl) acetyl)piperidine-2-carboxylate A20

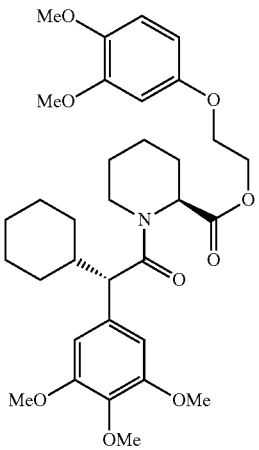

A20

19 (37 mg, 0.12 mmol) was dissolved in 500 μL dry DMF then N-ethyl-N-isopropylpropan-2-amine (82 μL, 0.48 mmol) and HATU (46 mg, 0.12 mmol) was added and stirred for 15 min. Then 10e (37 mg, 0.12 mmol) was dissolved in 500 μL DCM/DMF 1:1 and added to the reaction mixture. Then was stirred for 14 h at RT. The product was purified using flash chromatography (Gradient 0%-50% EtOAc in cyclohexane). A20 (9 mg, 15 μmol, 17%) was obtained as a slight yellow oil.

TLC [EtOAc/cyclohexane, 1:1.5]: $R_f$=0.26.

HPLC [0-100% Solvent B, 20 min]: $R_t$=21.0 min, purity (220 nm)=95%.

$^1$H NMR (400 MHz, d6-DMSO) δ 6.83-6.79 (d, J=8.8 Hz, 1H), 6.59-6.57 (s, 2H), 6.50-6.48 (d, J=2.8 Hz, 1H), 6.34-6.30 (dd, J=8.7, 2.8 Hz, 1H), 5.17-5.14 (m, 1H), 4.19-4.12 (m, 2H), 4.04-3.96 (m, 2H), 3.87-3.79 (m, 1H), 3.71-3.71 (s, 3H), 3.69-3.69 (s, 6H), 3.68-3.68 (s, 3H), 3.63-3.63 (s, 3H), 3.55-3.47 (m, 1H), 2.85-2.76 (m, 2H), 2.09-1.99 (m, 2H), 1.98-1.87 (q, J=10.9 Hz, 2H), 1.77-1.69 (d, J=10.2 Hz, 1H), 1.64-1.53 (m, 4H), 1.25-1.04 (m, 5H), 0.97-0.86 (m, 1H), 0.84-0.74 (m, 1H).

$^{13}$C NMR (101 MHz, d6-DMSO) δ 172.17, 170.74, 152.55, 152.42, 149.66, 143.35, 136.02, 133.60, 112.72, 105.88, 104.33, 100.94, 65.96, 62.75, 59.89, 56.07, 55.73, 55.40, 53.04, 51.84, 39.52, 31.89, 29.81, 26.54, 26.34, 26.12, 25.65, 25.04, 24.21, 20.53.

Mass: (ESI+), calculated 600.32 $[C_{33}H_{46}NO_9+H]^+$, found 600.25 $[M+H]^+$.

148

Example 3-21

Preparation of (S)-(R)-3-(3,4-dimethoxyphenyl)-1-(3-(2-morpholinoethoxy)phenyl)propyl-1-((S)-2-cyclohexyl-2-(3,4,5-trimethoxyphenyl) acetyl)pyrrol-idine-2-carboxylate A21

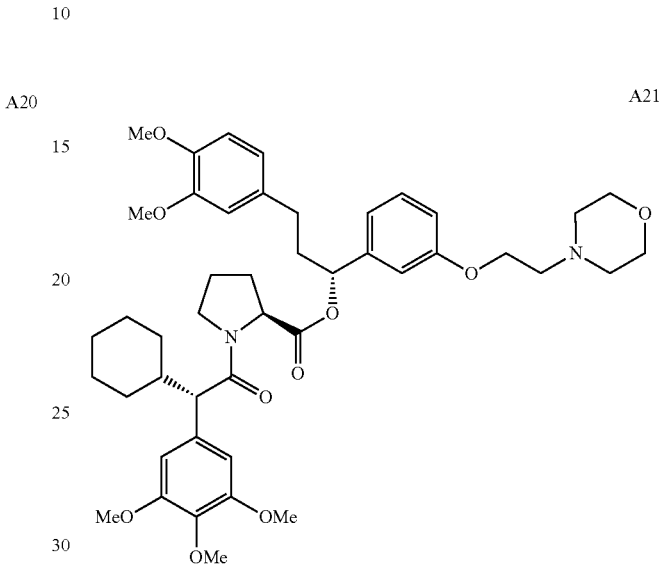

A21

General synthesis procedure A was used with 19 (100 mg, 100 μmol) and 10c (50 mg, 100 μmol). The crude product was purified using flash chromatography. A21 (50 mg, 20 μmol, 63%) was obtained as colorless oil.

TLC [MeOH/DCM, 8:92]: $R_f$=0.35.

HPLC [0-100% Solvent B, 20 min]: $R_t$=17.0 min, purity (220 nm)=97%.

$^1$H NMR (600 MHz, CDCl$_3$) Rotamers are present. Major rotamer: δ 7.17-7.13 (m, 1H), 7.04 (dd, J=7.7, 0.9 Hz, 0H), 7.00 (t, J=2.0 Hz, 1H), 6.87 (dd, J=8.4, 2.6 Hz, 0H), 6.79 (d, J=8.3 Hz, 0H), 6.77 (s, 1H), 6.70-6.67 (m, 0H), 6.47 (s, 1H), 5.52 (dd, J=7.8, 5.6 Hz, 1H), 4.63 (dd, J=8.6, 2.6 Hz, 1H), 4.19-4.05 (m, 3H), 3.86 (s, 3H), 3.84 (s, 3H), 3.82 (d, J=0.9 Hz, 1H), 3.77 (s, 3H), 3.76-3.74 (m, 2H), 3.72-3.69 (m, 2H), 3.66 (s, 6H), 3.63-3.58 (m, 1H), 3.56-3.52 (m, 1H), 2.89 (bs, 1H), 2.67 (bs, 2H), 2.57 (bs, 2H), 2.48-2.29 (m, 3H), 2.19-2.10 (m, 2H), 2.09-1.97 (m, 2H), 1.96-1.86 (m, 2H), 1.74-1.60 (m, 2H), 1.53-1.48 (m, 1H), 1.46-1.41 (m, 1H), 1.40-1.36 (m, 3H), 1.33-1.28 (m, 3H), 1.16-1.10 (m, 2H), 0.95-0.86 (m, 2H), 0.80-0.72 (m, 1H).

$^{13}$C NMR (151 MHz, CDCl$_3$) Rotamers are present. Major rotamer: δ 171.74, 171.59, 159.16, 153.09, 148.94, 147.36, 141.74, 136.98, 133.73, 133.43, 129.55, 120.47, 119.51, 114.14, 113.81, 112.07, 111.83, 111.50, 111.40, 106.09, 77.16, 75.88, 66.92, 65.74, 60.98, 59.12, 57.84, 57.42, 56.34, 56.14, 56.10, 56.06, 56.02, 54.20, 47.68, 47.01, 41.37, 38.76, 38.23, 37.53, 32.83, 32.39, 31.68, 31.62, 31.08, 30.77, 29.97, 29.32, 26.67, 26.34, 24.81, 22.59, 21.19.

Mass: (ESI$^-$), calculated 789.43 $[C_{45}H_{58}N_2O_{10}+H]^-$, found 789.40 $[M+H]^+$.

149

Example 3-22

Preparation of 2-(3-((R)-1-((S)-1-((S)-2-cyclohexyl-2-(3,4,5-trimethoxyphenyl)acetyl)piperidine-2-carboxamido)-3-(3,4-dimethoxyphenyl)propyl)phenoxy)acetic acid A22

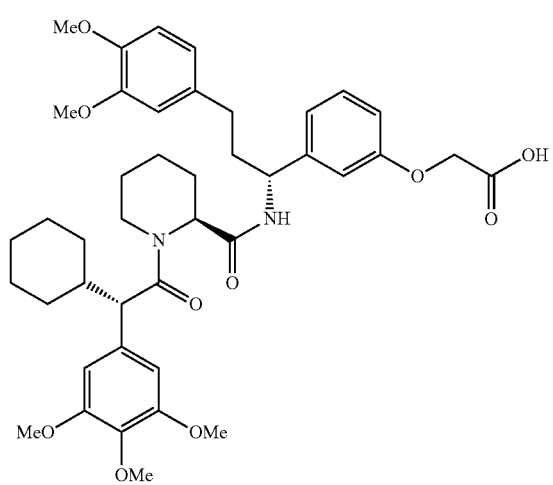

A22

General synthesis procedure B for free acid ligands with 8b (50 mg, 0.20 mmol) and 19 (30 mg, 0.20 mmol) was used. The product was purified using preparative HPLC (Gradient: 65-75% B in 20 min) to obtain A22 (15 mg, 20 µmol, 24%) as an colourless oil.

TLC [MeOH/DCM, 8:92]: $R_f$=0.29.

HPLC [0-100% Solvent B, 20 min]: $R_t$=11.7 min, purity (220 nm)=99%.

$^1$H NMR (400 MHz, dmso, major rotamer) δ 7.13-7.08 (m, 1H), 6.95-6.90 (m, 1H), 6.84 (t, J=8.4 Hz, 1H), 6.75 (dq, J=11.8, 2.0 Hz, 2H), 6.72-6.67 (m, 1H), 6.66-6.60 (m, 1H), 6.59-6.54 (m, 2H), 5.15-5.07 (m, 1H), 4.82-4.69 (m, 1H), 4.69-4.56 (m, 3H), 3.76-3.72 (m, 1H), 3.72-3.69 (m, 6H), 3.65-3.64 (m, 1H), 3.58-3.54 (m, 9H), 2.96-2.84 (m, 2H), 2.82-2.70 (m, 2H), 2.43-2.30 (m, 2H), 2.19-2.05 (m, 2H), 1.99-1.87 (m, 2H), 1.88-1.76 (m, 3H), 1.59 (d, J=8.2 Hz, 2H), 1.34 (d, J=9.6 Hz, 1H), 1.16-1.10 (m, 2H), 0.95-0.86 (m, 2H).

$^{13}$C NMR (101 MHz, dmso) δ 171.99, 170.28, 170.12, 157.65, 152.52, 148.61, 147.00, 145.30, 135.97, 133.59, 130.71, 127.70, 120.01, 112.62, 112.31, 112.26, 111.74, 105.56, 64.33, 63.08, 59.70, 55.96, 55.52, 55.48, 55.34, 52.42, 51.79, 51.45, 42.79, 39.52, 38.52, 38.17, 31.59, 27.34, 27.03, 26.09, 24.87, 20.68, 19.97.

Mass: (ESI$^-$), calculated 745.37 [C$_{42}$H$_{52}$N$_2$O$_{10}$+H]$^+$, found 745.40 [M–H]$^+$.

150

Ligand Synthesis by Solid Phase Coupling Reaction

Example 3-C

General Synthetic Procedure C for Solid Phase Coupling Reaction

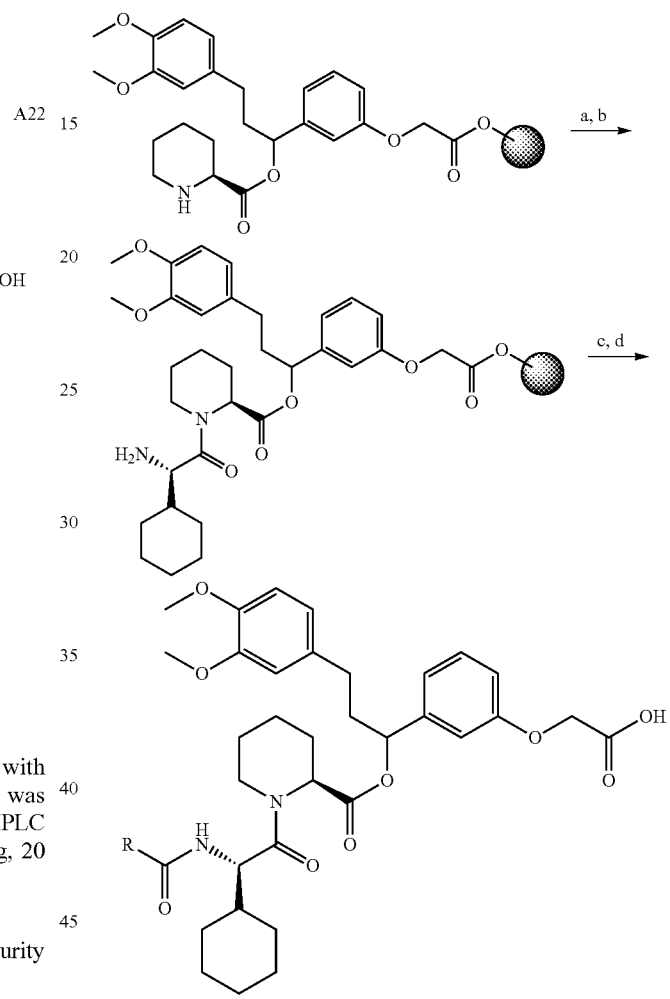

A23-28

Reagents and conditions: (a) 3eq Fmoc-D-Chg, 3eq HATU, 3eq HOAt, 6eq DIEA, DMF/NMP. (b) 5% 4-Methylpiperidin/DMF (c) 3eq benzoic acid derivatives, 3eq HATU, 3eq HOAt, 6eq DIEA, DMF/NMP. (d) 1% TFA/99%/DCM.

The resin was prepared according to Gopalakrishnan et al, (Exploration of Pipecolate Sulfonamides as Binders of the FK506-Binding Proteins 51 and 52, 2012, 55, 4123-4131). To the resin was added a solution of Fmoc-Chg-OH (760 µmol, 3 eq.), HATU (290 mg, 760 µmol, 3 eq.), HOAt (104 mg, 760 µmol, 4.8 eq.) and DIEA (260 µL, 1.5 mmol, 6 eq.) in 1 mL DMF/NMP. The reaction mixture was stirred for 3 h. The resin was washed with DMF (3×7 mL), THF (3×7 mL), DCM (3×7 mL), Et$_2$O (3×7 mL). A solution of benzoic acid derivative (760 µmol, 3 eq.), HATU (290 mg, 760 µmol, 3 eq.), HOAt (104 mg, 760 µmol, 4.8 eq.) and DIEA (260 µL, 1.5 mmol, 6 eq.) in 1 mL DMF/NMP was added to the resin. The reaction mixture was stirred for 2 h followed by washing with NMP, DMF, THF, DCM and Et$_2$O each 3×1 mL. The resin was dried overnight in vacuo. The final compounds were cleaved from the resin using 1.5 mL TFA/DCM 1:99. Purification was performed by preparative HPLC.

Example 3-23

Preparation of 2-(3-(1-(((2S)-1-(2-benzamido-2-cyclohexylacetyl) piperidine-2-carbonyl)oxy)-3-(3,4-dimethoxyphenyl)propyl)phenoxy)acetic acid A23

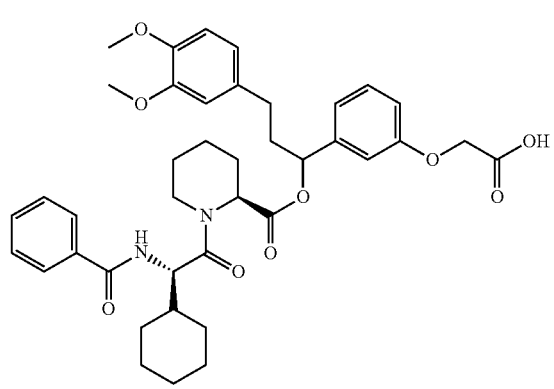

A23

General procedure C for solid phase organic synthesis was used. A23 (2.9 mg, 4.2 μmol).
HPLC [0-100% Solvent B, 20 min]: $R_t$=19.7 min.
Mass: (ESI$^-$), calculated 701.34 [C40H48N2O9+H]$^-$, found 701.38 [M+H]$^+$.

Example 3-24

Preparation of 2-(3-(1-(((2S)-1-(2-cyclohexyl-2-(2-hydroxy benzamido)acetyl)piperidine-2-carbonyl)oxy)-3-(3,4-dimethoxyphenyl) propyl)phenoxy)acetic acid A24

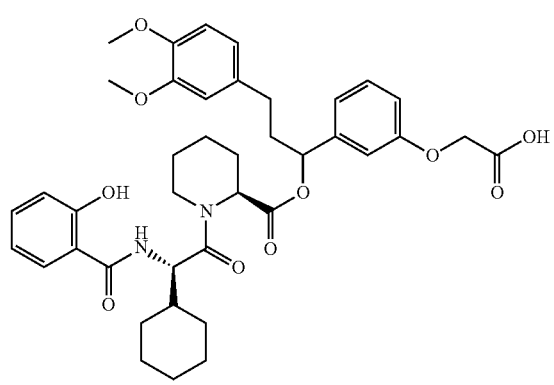

A24

General procedure C for solid phase organic synthesis was used. A24 (1.7 mg, 2.3 μmol).
HPLC [0-100% Solvent B, 20 min]: $R_t$=20.6 min.
Mass: (ESI$^-$), calculated 717.34 [C40H48N2O10+H]$^-$, found 717.50 [M+H]$^+$.

Example 3-25

Preparation of 2-(3-(1-(((2S)-1-(2-cyclohexyl-2-(picolinamido) acetyl)piperidine-2-carbonyl)oxy)-3-(3,4-dimethoxyphenyl)propyl)phenoxy) acetic acid A25

A25

General procedure C for solid phase organic synthesis was used. A25 (3.2 mg, 4.6 μmol).
HPLC [0-100% Solvent B, 20 min]: $R_t$=19.7 min.
Mass: (ESI$^-$), calculated 702.34 [C39H47N3O9+H]$^-$, found 702.50 [M+H]$^+$.

Example 3-26

Preparation of 2-(3-(1-(((2S)-1-(2-(cyclohexanecarboxamido)-2-cyclohexylacetyl)piperidine-2-carbonyl)oxy)-3-(3,4-dimethoxyphenyl)propyl)phenoxy) acetic acid A26

A26

General procedure C for solid phase organic synthesis was used. A26 (2.8 mg, 3.9 μmol).
HPLC [0-100% Solvent B, 20 min]: $R_t$=20.6 min.
Mass: (ESI$^-$), calculated 707.39 [C40H54N2O9+H]$^-$, found 707.46 [M+H]$^+$.

Example 3-27

Preparation of 2-(3-(1-(((2S)-1-(2-cyclohexyl-2-(3H-1,2,4-triazole-3-carboxamido)acetyl)piperidine-2-carbonyl)oxy)-3-(3,4-dimethoxyphenyl) propyl) phenoxy)acetic acid A27

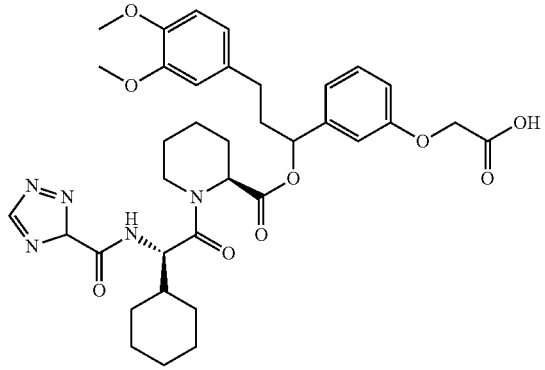
A27

General procedure C for solid phase organic synthesis was used. A27 (2.7 mg, 3.8 µmol).

HPLC [0-100% Solvent B, 20 min]: $R_f$=17.2 min.

Mass: (ESI⁻), calculated 692.33 [C40H54N2O9+H]⁻, found 692.35 [M+H]⁺.

Example 3-28

Preparation of 2-(3-(1-(((2S)-1-(2-cyclohexyl-2-(3,5-dichloro benzamido)acetyl)piperidine-2-carbonyl)oxy)-3-(3,4-dimethoxyphenyl) propyl)phenoxy)acetic acid A28

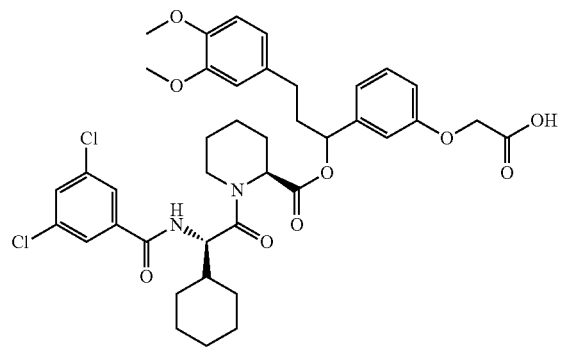
A28

General procedure C for solid phase organic synthesis was used. A28 (0.6 mg, 0.7 µmol).

HPLC [0-100% Solvent B, 20 min]: $R_f$=21.5 min.

Mass: (ESI⁻), calculated 769.26 [C40H54N2O9+H]⁻, found 769.21 [M+H]⁺.

Example 3-D

General Synthetic Procedure for Aldol Products

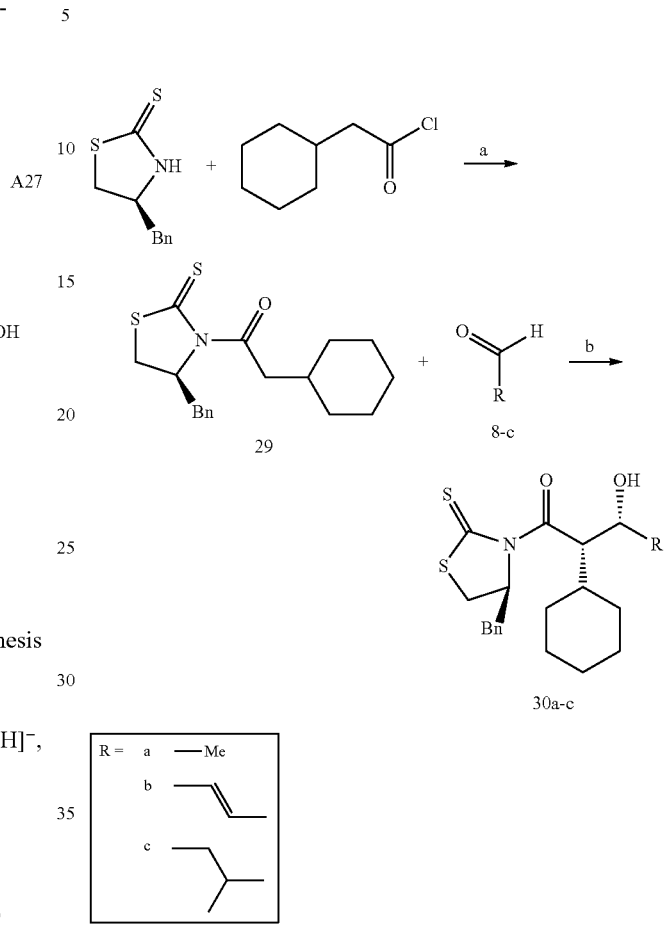

(a) n-BuLi, THF, -78° C.-RT, 21 h, 93% (b) TiCl4, TMEDA, DCM, 0° C., 5 h, 28-71%

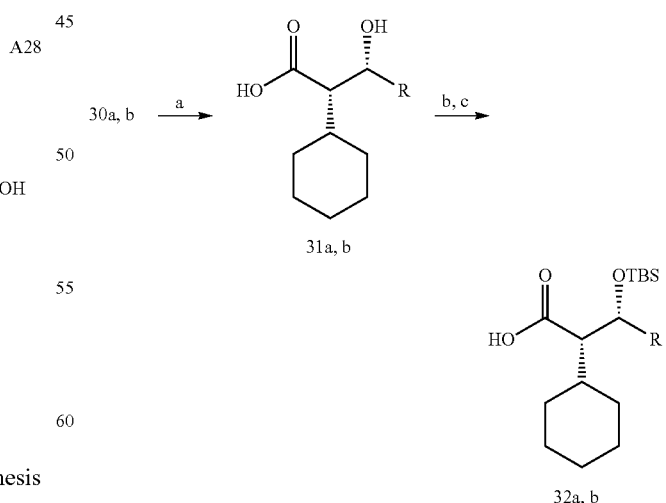

(a) LiOH, H2O2, THF/H2O, RT, 2 h, 79-100% (b)TBSOTf, 2, 6-Lutidine, DCM, -78 C. 2 h (c) K2CO3, MeOH/H2O/THF, RT, 1 h, 29-41% (2 steps)

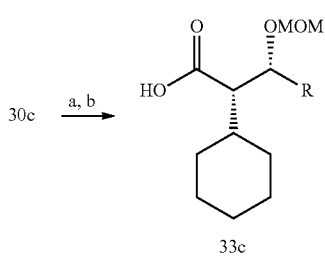

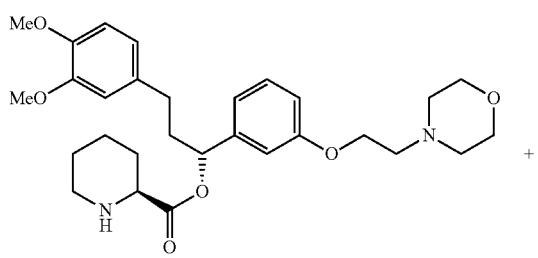

(a) MOMCl, DIPEA, DCM, 0° C., 2.5 h (b) LiOH, H₂O₂, THF/H₂O, RT, 2 h, 40-41% (2 steps)

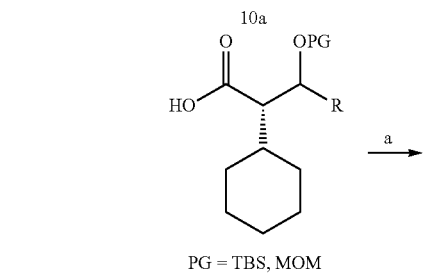

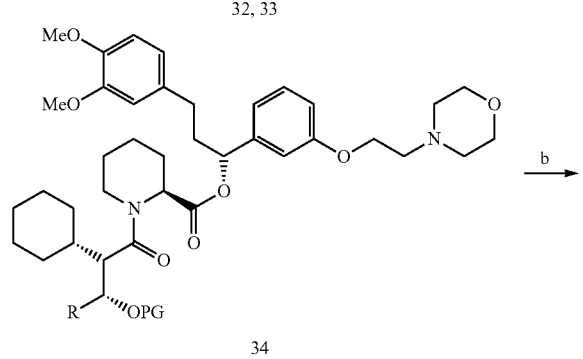

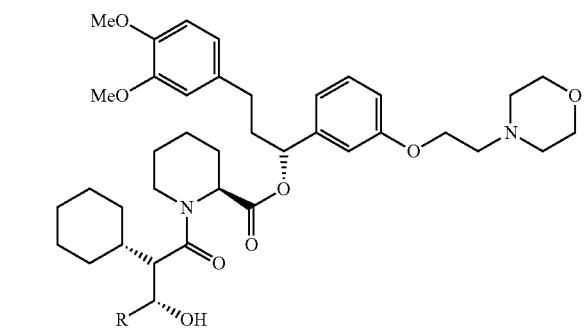

(a) PyBroP, DIPEA, DCM, RT, 16 h, 21-82% (b) HCl, EtOH, RT, 20 h, 13-90%

Example 3-29

Preparation of (S)-1-(4-benzyl-2-thioxothiazolidin-3-yl)-2-cyclohexylethanone 29

To a solution of (S)-4-benzylthiazolidine-2-thione (1 g, 4.78 mmol) in THF (dry, 50 mL) was added n-BuLi (2.87 mL, 7.17 mmol, 2.5 M) at −78° C. The resulting mixture was stirred at that temperature for 1.5 h, then 2-cyclohexylacetyl chloride (1.10 ml, 7.17 mmol) was added. The temperature was maintained at −78° C. for 2.5 h. Then the reaction mixture was allowed to warm to RT and stirred for 16 h. After an aqueous work up with saturated NH4Cl solution the crude product was purified by flash chromatography (cyclohexane) to afford 29 as a yellow crystalline solid (1.48 g, 4.45 mmol, 93%).

TLC [cyclohexane/EE, 8:2]: Rf=0.6

Mass (ESI+), calculated 333.12 [C18H23NOS2+H]⁺, found=334.04 [M+H]⁺.

Example 3-30

Preparation of (2S,3R)-1-((S)-4-benzyl-2-thioxothiazolidin-3-yl)-2-cyclohexyl-3-hydroxybutan-1-one 30a 29 (200 mg, 0,600 mmol) in DCM (dry, 2 mL) was cooled to 0° C. Then TiCl4 (660 µl, 0.660 mmol, 1 M) was added drop wise. After 5 min TMEDA (226 µl, 1.50 mmol) was added and the resulting dark red enolate was stirred for 20 min at 0° C. the. Acetaldehyde (0.10 mL, 1.80 mmol) was then added drop wise and it was stirred for 4 h at 0° C.

After an aqueous work up with half-saturated NH4Cl solution the crude product was purified by flash chromatography (0-100% DCM in cyclohexane) to afford 30a as yellow oil (116.6 mg, 0.31 mmol, 52%).

TLC [DCM]: Rf=0.19

Mass (ESI+), calculated 378.57 [C20H27NO2S2+H]⁺, found=377.88 [M+H]⁺.

Example 3-31

Preparation of (2S,3R,E)-1-((S)-4-benzyl-2-thioxothiazolidin-3-yl)-2-cyclohexyl-3-hydroxyhex-4-en-1-one 30b 30b was synthesized according to 30a with (E)-but-2-enal (0.15 mL, 1.80 mmol) to afford 30b as yellow solid (171.3 mg, 0.43 mmol, 71%).

TLC [DCM]: Rf=0.39

Mass (ESI+), calculated 404.17 [C22H29NO2S2+H]⁺, found=404.01 [M+H]⁺.

Example 3-32

Preparation of (2S,3R)-1-((S)-4-benzyl-2-thioxothiazolidin-3-yl)-2-cyclohexyl-3-hydroxy-5-methylhexan-1-one 30c 30c was synthesized according to 30a with 3-methylbutanal (0.19 mL, 1.80 mmol) to afford 30c as yellow solid (172 mg, 0.41 mmol, 68.3%).

TLC [DCM]: Rf=0.52

Mass (ESI+), calculated 420.20 [C23H33NO2S2+H]⁺, found=420.04 [M+H]⁺.

Example 3-33

Preparation of
(2S,3R)-2-cyclohexyl-3-hydroxybutanoic acid 31a 30a (115 mg, 0.305 mmol) was dissolved in THF/H2O (8:5, 6.5 mL). Then LiOH (32.8 mg, 1.37 mmol) and H2O2 (0.15 mL, 1.47 mmol, 30% Wt) were added and it was stirred at RT for 2 h. The reaction mixture was quenched with NaaSO3 solution (1.5 M) and it was extracted with DCM, whereby the organic layer was discarded. The aqueous layer was acidified and the product was extracted several times with DCM. The combined organics were dried over anhydrous MgSO4 filtrated and concentrated to afford 31a (23.5 mg, 0.15 mmol. 50%) as colourless oil.

Example 3-34

Preparation of
(2S,3R,E)-2-cyclohexyl-3-hydroxyhex-4-enoic acid 31b 31b was synthesized according to 31a with 30b (120 mg, 0.297 mmol), LiOH (32.0 mg, 1.34 mmol) and H2O2 (76 µL, 0.74 mmol, 30% Wt) to afford 31b as colourless oil (50 mg, 0.23 mmol, 79%).

TLC [cyclohexane/EE, 1:1]: Rf=0.26

Example 3-35

Preparation of (2S,3R)-3-((tert-butyldimethylsilyl)oxy)-2-cyclohexylbutanoic acid 32a 31a (23 mg, 0.123 mmol) was dissolved in DCM (dry, 1 mL) and 2,6-Lutidine (71.9 µl, 0.617 mmol) was added. It was cooled to −78° C. and TBSOTf (85 µl, 0.370 mmol) was added dropwise. The reaction mixture was stirred for 2 h and then quenched with sat. NaHCO3 solution. The layers were separated and it was extracted with Et2O. The solvent was removed, after drying over MgSO4 and filtration. Then the residue was dissolved in MeOH/THF (1 mL, 1:1). A solution of K2CO3 (37.5 mg, 0.272 mmol) in H2O (0.5 mL) was added and it was stirred at RT for 1 h.

The organic layer was evaporated and the aqueous layer, when pH >7, was extracted with DCM, whereby the organic layer was discarded. Then the aqueous layer was acidified and the product was extracted several times with DCM. The combined organics were dried over anhydrous MgSO4 filtrated and concentrated to afford 32a (14 mg, 0.05 mmol, 38%) as colourless oil.

TLC [cyclohexane/EE, 4:6]: Rf=0.20

Example 3-36

Preparation of (2S,3R,E)-3-((tert-butyldimethylsilyl)oxy)-2-cyclohexylhex-4-enoic acid 32b 32b was synthesized according to 32a with 31b (50 mg, 0.236 mmol), TBSOTf (162 µl, 0.707 mmol) and 2,6-Lutidine (137 µl, 1.178 mmol) in DCM (dry, 2 mL) and K2CO3 (71.6 mg, 0.518 mmol) in H2O (0.4 mL) to afford 32b as colourless oil (22 mg, 0.068 mmol, 29%).

TLC [cyclohexane/EE, 1:1]: Rf=0.65

Example 3-37

Preparation of (2S,3R)-2-cyclohexyl-3-(methoxymethoxy)-5-methylhexanoic acid 33c 30b (170 mg, 0.407 mmol) and DIPEA (213 µl, 1.221 mmol) were dissolved in DCM (dry, 0.5 mL) and cooled to 0° C. Then MOM-Cl (155 µl, 2.035 mmol) was added and it was stirred at RT for 2.5 h. The reaction mixture was diluted with DCM and washed with half-saturated NH4Cl solution and half-saturated NaHCO3 solution I. The organic layer was dried over MgSO4, filtrated and the solvent was removed under vacuum. Then the residue was dissolved in THF/H2O (8:5, 1.3 mL) followed by the addition of LiOH (43.9 mg, 1.832 mmol) and H2O2 (104 µl, 1.018 mmol, 30% Wt). The reaction mixture was stirred at RT for 2 h and then quenched with Na2SO3 solution (1.5 M) and it was extracted with DCM, whereby the organic layer was discarded. The aqueous layer was acidified and the product was extracted several times with DCM. The combined organics were dried over anhydrous MgSO4 filtrated and concentrated to afford 33c (46 mg, 0.167 mmol. 41%) as colourless oil.

TLC [cyclohexane/EE, 1:1]: Rf=0.45

Example 3-38

Preparation of (S)-(R)-3-(3,4-dimethoxyphenyl)-1-(3-(2-morpholinoethoxy)phenyl)propyl 1-((2S,3R)-3-((tert-butyldimethylsilyl)oxy)-2-cyclohexylbutanoyl)piperidine-2-carboxylate 34a 10a (39.2 mg, 0.077 mmol), 32a (23 mg, 0.077 mmol), PyBrop (53.5 mg, 0.115 mmol) and DIPEA (40.1 µl, 0.23 mmol) were stirred in DCM (dry, 1 mL) at RT for 16 h. The crude product was directly loaded on silica and purified by flash chromatography (0-100% EE+2% MeOH+0.1% TEA in cyclohexane) to afford 34a as a light yellow oil (28.9 mg, 0.037 mmol, 47.5%).

TLC [EE+2% MeOH+1% TEA]: Rf=0.42

Mass (ESI+), calculated 795.50 [C45H70N2O8Si+H]+, found 795.68=[M+H]+.

Example 3-39

Preparation of (S)-(R)-3-(3,4-dimethoxyphenyl)-1-(3-(2-morpholinoethoxy)phenyl)propyl 1-((2S,3R,E)-3-((tert-butyldimethylsilyl)oxy)-2-cyclohexylhex-4-enoyl)piperidine-2-carboxylate 34b 34b was synthesized according to 34a with 32b (20 mg, 0.061 mmol), 10a (34.5 mg, 0.067 mmol), PyBrop (42.8 mg, 0.092 mmol) and DIPEA (32.1 µl, 0.184 mmol) in DCM (dry, 1 mL) to afford 34b as colourless oil (33.6 mg, 0.041 mmol, 66.8%).

TLC [EE+2% MeOH+1% TEA]: Rf=0.59

Mass: (ESI+), calculated 821.51 [C47H72N2O8Si+H]+, found 821.59=[M+H]+.

Example 3-40

Preparation of (S)-(R)-3-(3,4-dimethoxyphenyl)-1-(3-(2-morpholinoethoxy)phenyl)propyl 1-((2S,3R)-2-cyclohexyl-3-hydroxybutanoyl)piperidine-2-carboxylate A29

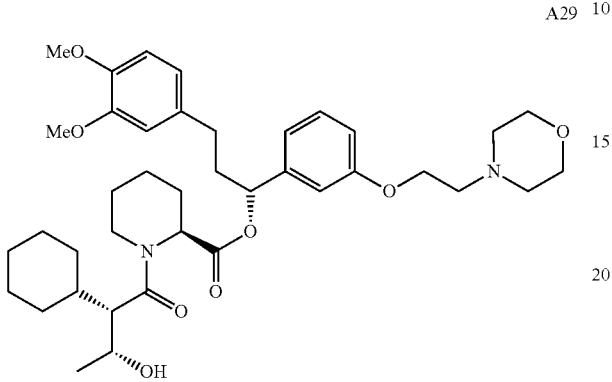

34a (28 mg, 0.035 mmol) was stirred in EtOH (0.94 mL) and concentrated HCl (60 µL) at RT for 20 h. The crude product was directly loaded on silica and purified by flash chromatography (EE+2% MeOH+0.1% TEA) to afford A29 as a colourless oil (28.9 mg, 0.037 mmol, 47.5%).

TLC [EE+5% MeOH+1% TEA]: Rf=0.27
Mass: (ESI+), calculated 681.41 [C39H56N2O8+H]+, found=681.87 [M+H]+.

Example 3-41

Preparation of (S)-(R)-3-(3,4-dimethoxyphenyl)-1-(3-(2-morpholinoethoxy)phenyl)propyl 1-((2S,3R,E)-2-cyclohexyl-3-hydroxyhex-4-enoyl)piperidine-2-carboxylate A30

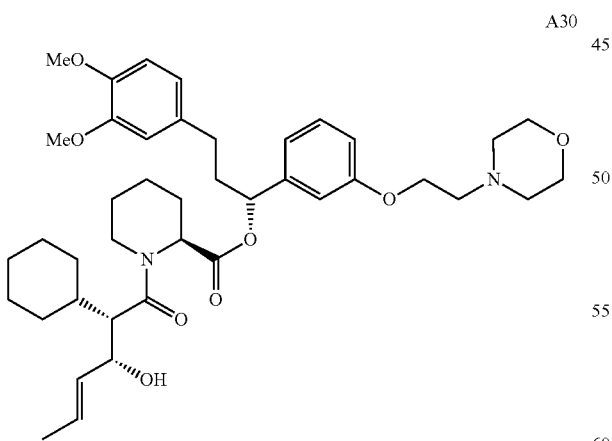

A30 was synthesized according to A29 with 34b (33 mg, 0.040 mmol) to afford A30 as colourless oil (3.88 mg, 5.36 µmol, 13.4%).

LCMS (0-100% Solvent B, 20 min): Rt=9.5 min
Mass: (ESI+), calculated 723.46 [C41H58N2O8+H]+, found=707.42 [M+H]+.

Example 3-42

Preparation of (S)-(R)-3-(3,4-dimethoxyphenyl)-1-(3-(2-morpholinoethoxy)phenyl)propyl 1-((2S,3R)-2-cyclohexyl-3-(methoxymethoxy)-5-methylhexanoyl)piperidine-2-carboxylate A31

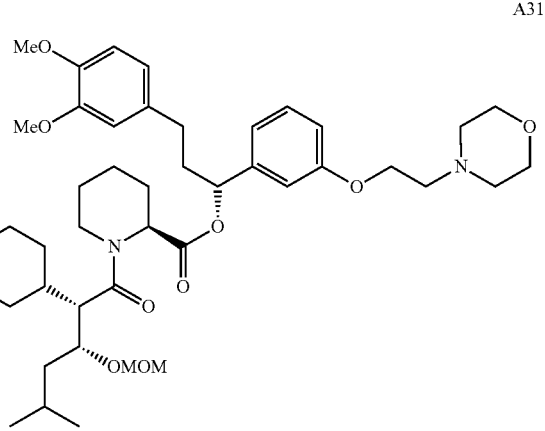

A31 was synthesized according to 34a with 33c (30 mg, 0.110 mmol), 10a (62.1 mg, 0.121 mmol), PyBrop (77 mg, 0.165 mmol) and DIPEA (57.7 µl, 0.330 mmol) in DCM (dry, 3 mL) to afford A31 as colourless oil (19 mg, 0.025 mmol, 22.6%).

TLC [EE+2% MeOH+1% TEA]: Rf=0.37
Mass: (ESI+), calculated 767.48 [C44H66N2O9+H]+, found 767.58=[M+H]+.

Example 3-43

Preparation of (S)-(R)-3-(3,4-dimethoxyphenyl)-1-(3-(2-morpholinoethoxy)phenyl)propyl 1-((2S,3R)-2-cyclohexyl-3-hydroxy-5-methylhexanoyl)piperidine-2-carboxylate A32

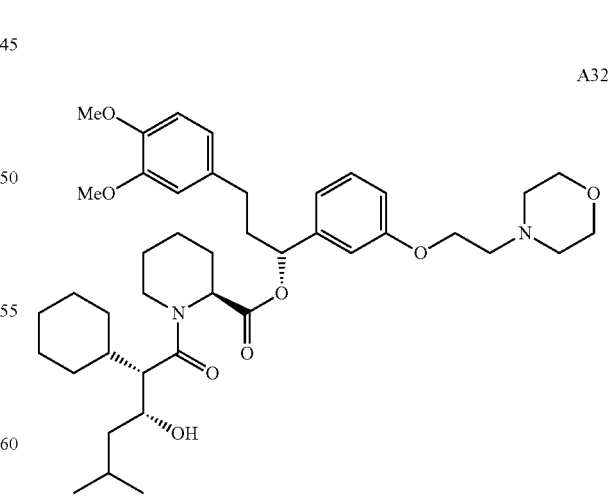

A32 was synthesized according to A29 with A31 (19 mg, 0.025 mmol) in 44 h to afford A32 as light yellow oil (11.2 mg, 0.016 mmol, 62.6%).

TLC [EE+5% MeOH+1% TEA]: Rf=0.59

Mass: (ESI+), calculated 707.43 [C42H62N2O8+H]*, found=723.50 [M+H]+.

Reference Example 3-44

Preparation of (S)-(R)-3-(3,4-Dimethoxyphenyl)-1-(3-(2-morpholinoethoxy)phenyl)propyl-1-((S)-2-(3,4,5-trimethoxyphenyl)pent-4-enoyl)pyrrolidine-2-carboxylate (A33)

Reference Example 3-45

Preparation of (R)-(R)-3-(3,4-Dimethoxyphenyl)-1-(3-(2-morpholinoethoxy)phenyl)propyl-4-((S)-2-(3,4,5-trimethoxyphenyl)pent-4-enoyl)thiomorpholine-3-carboxylate (A34)

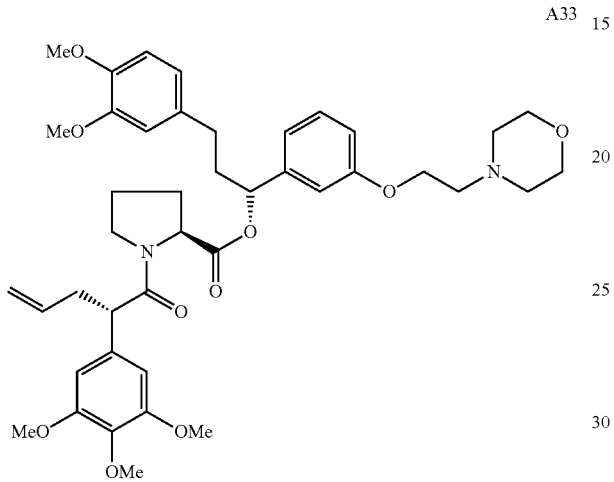

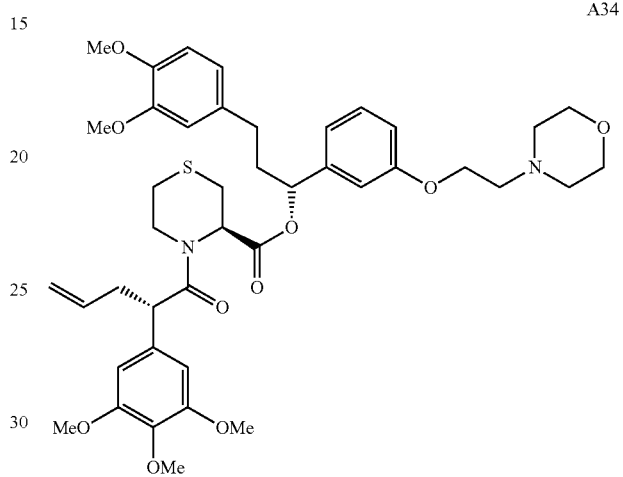

General synthesis procedure A for morpholine ligands with 10c (31 mg, 62 µmol) and 15 (17 mg, 62 µmol) was used. Then the crude product was purified using flash chromatography (gradient 0%-10% MeOH in DCM) to obtain A33 (31 mg, 44 µmol, 67%) as a light yellow oil. The diastereomeric rate was determined by HPLC.

TLC [MeOH/DCM, 3:97, 1% TEA]: $R_f$=0.24.

HPLC [0-100% Solvent B, 20 min]: $R_t$=15.8 min, purity (220 nm)=95%, dr 95:5.

$^1$H NMR (400 MHz, d6-DMSO) δ 7.17 (t, J=7.9 Hz, 1H), 6.86 (t, J=1.9 Hz, 1H), 6.82-6.77 (m, 2H), 6.73-6.68 (m, 2H), 6.64-6.57 (m, 1H), 6.49 (s, 2H), 5.77-5.62 (m, 1H), 5.48 (dd, J=8.3, 5.0 Hz, 1H), 5.05-4.87 (m, 3H), 4.45 (dd, J=8.7, 3.4 Hz, 1H), 4.17-4.02 (m, 3H), 3.77 (dd, J=8.5, 6.0 Hz, 1H), 3.74-3.62 (m, 6H), 3.59-3.46 (m, 9H), 3.28-3.18 (m, 4H), 2.68-2.57 (m, 4H), 2.52-2.37 (m, 5H), 2.31-2.11 (m, 5H), 1.83-1.73 (m, 2H).

$^{13}$C NMR (100 MHz, d6-DMSO) δ 171.88, 170.71, 158.80, 153.15, 149.10, 147.33, 142.50, 137.04, 136.45, 135.00, 133.82, 129.55, 120.44, 118.37, 116.77, 114.28, 112.73, 112.34, 112.06, 105.68, 75.33, 66.60, 65.65, 60.08, 59.00, 57.39, 55.95, 54.07, 49.32, 46.83, 38.96, 38.10, 30.91, 29.17, 24.83.

Mass: (ESI+), calculated 747.39 [C42H54N2O10+H]+, found 747.51 [M+H]+.

General synthesis procedure A for morpholine ligands with 10b (32 mg, 60 µmol) and 15 (20 mg, 75 µmol) was used. The crude product was purified using flash chromatography (gradient 0%-80% EtOAc in cylcohexane) to obtain A34 (31 mg, 4 µmol, 67%) as a light yellow oil. The diastereomeric rate was determined by HPLC.

TLC [EtOAc/cyclohexane, 3:7, 4% AcOH]: $R_f$=0.42.

HPLC [0-100% Solvent B, 20 min]: $R_t$=15.88 min, purity (220 nm)=92%, dr ≥99:1.

$^1$H NMR (400 MHz, d6-DMSO) δ 7.29-7.23 (m, 1H), 7.16 (t, J=7.8 Hz, 1H), 6.95-6.57 (m, 5H), 6.52 (s, 2H), 5.71-5.65 (m, 1H), 5.62-5.54 (m, 1H), 5.03-4.87 (m, 2H), 4.10-4.04 (m, 3H), 3.73 (d, J=2.2 Hz, 3H), 3.69 (s, 3H), 3.69-3.67 (m, 6H), 3.62 (d, J=2.3 Hz, 3H), 3.60 (s, 3H), 3.57 (s, 2H), 3.55 (s, 2H), 3.48 (d, J=1.9 Hz, 1H), 3.32 (s, 1H), 3.14-3.08 (m, 1H), 2.91 (dd, J=13.9, 4.0 Hz, 1H), 2.75-2.62 (m, 5H), 2.53-2.44 (m, 6H), 2.38-2.29 (m, 1H).

$^{13}$C NMR (101 MHz, d6-DMSO) δ 172.40, 168.83, 158.77, 153.39, 153.14, 149.03, 149.01, 147.44, 142.29, 142.22, 136.93, 136.73, 135.78, 135.03, 133.78, 129.93, 120.46, 116.81, 114.19, 112.68, 112.28, 105.51, 75.80, 66.52, 65.46, 60.19, 56.36, 56.00, 55.90, 55.79, 55.75, 55.35, 54.01, 52.52, 52.20, 51.58, 47.42, 44.49, 33.69, 31.73, 31.00, 26.99, 24.85, 22.54.

Mass: (ESI+), calculated 779.36 [C42H54N2O10S+H]+, found 779.37 [M+H]+.

163
Reference Example 3-46

Preparation of 2-(3-((1R)-1-(((2S)-1-(2-cyclohexyl-2-phenylacetyl)piperidine-2-carbonyl)oxy)-3-(3,4 dimethoxyphenyl)propyl)phenoxy)acetic acid

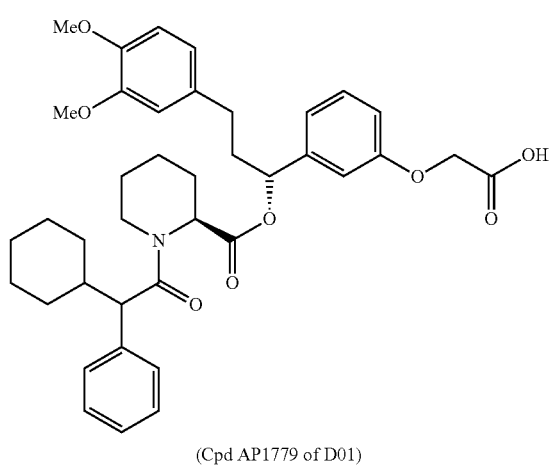

(Cpd AP1779 of D01)

2-cyclohexyl-2-phenylacetic acid (87.8 mg, 0.4 mmol), 8a (50 mg, 0.1 mmol), COMU (94.6 mg, 0.22 mmol) and 2,2,6,6-tetramethylpiperidine (67.8 µL, 0.40 mmol) were stirred in DMF (1.5 mL) for 25 h at RT. The reaction mixture was directly loaded on silica and purified by flash chromatography (gradient 0-10% EtOAc in cyclohexane). The tert-butyl ester was stirred in DCM/TFA (2 mL, 1:1) for 6 h at RT and then poured into saturated NaHCO$_3$. The free carboxylic acid was extracted with DCM. The combined organic layers were dried over MgSO$_4$, filtered and purified by preparative chromatography (gradient 0-30% EtOAc+1% HCOOH in cyclohexane) to obtain A35 (58.4 mg, 88.8 µmol, 88.3%) as a colourless oil.

TLC [EtOAc/cyclohexane, 1:1+1% HCOOH]: R$_f$=0.33

$^1$H NMR (599 MHz, CDCl$_3$) major diastereomer δ 7.28-7.25 (m, 2H), 7.23-7.17 (m, 2H), 7.17-7.12 (m, 1H), 7.11-7.06 (m, 1H), 6.93-6.81 (m, 2H), 6.81-6.72 (m, 2H), 6.69-6.61 (m, 2H), 5.56 (dd, J=8.6, 5.3 Hz, 1H), 5.52-5.45 (m, 1H), 4.66-4.53 (m, 2H), 4.02-3.92 (m, 1H), 3.84 (s, 3H), 3.83 (s, 3H), 3.46 (d, J=9.9 Hz, 1H), 3.24-3.15 (m, 1H), 2.74 (td, J=13.6, 3.0 Hz, 1H), 2.62-2.46 (m, 2H), 2.42-2.36 (m, 1H), 2.18-2.09 (m, 1H), 1.95-1.82 (m, 2H), 1.82-1.75 (m, 1H), 1.64-1.51 (m, 4H), 1.50-1.39 (m, 2H), 1.34-1.22 (m, 3H), 1.15-1.06 (m, 2H), 0.93-0.84 (m, 1H), 0.74-0.66 (m, 1H).

$^{13}$C NMR major diastereomer δ 172.64, 171.25, 170.32, 157.64, 148.77, 147.22, 141.97, 138.50, 137.70, 133.58, 129.57, 128.75, 128.46, 128.19, 126.89, 120.20, 119.75, 114.52, 111.99, 111.77, 111.66, 111.27, 111.13, 75.77, 65.16, 55.90, 55.83, 54.94, 52.18, 43.73, 41.11, 37.81, 36.76, 32.72, 31.68, 31.12, 30.61, 29.67, 26.78, 26.50, 26.11, 25.46, 24.86, 20.96.

HPLC [70-80% Solvent B, 20 min]: Rt=13.4 min, purity (220 nm)=100%.

Mass: (ESI$^+$), calculated 658.34 [C$_{39}$H$_{47}$NO$_8$+H]$^+$, found 658.17 [M+H]$^+$.

164
Example 3-47

Preparation of 2-(3-((R)-1-(((S)-1-((S)-2-cyclohexyl-2-(3-fluorophenyl)acetyl)piperidine-2-carbonyl)oxy)-3-(3,4-dimethoxyphenyl)propyl) phenoxy) acetic acid

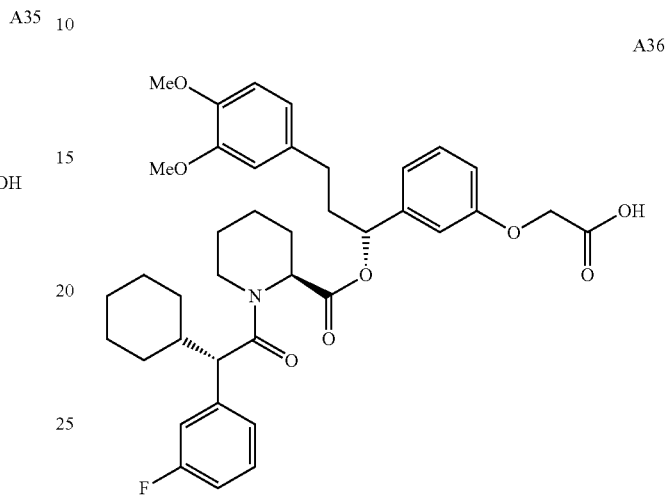

(S)-2-cyclohexyl-2-(3-fluorophenyl)acetic acid (13 mg, 0.06 mmol), 8a (28 mg, 0.06 mmol), COMU (25.9 mg, 0.06 mmol) and 2,2,6,6-tetramethylpiperidine (18.6 µL, 0.11 mmol) were stirred in DMF (1.0 mL) for 1 h at RT. The resulting orange reaction mixture was directly loaded on silica and purified by flash chromatography (gradient 0-10% EtOAc in cyclohexane).

The tert-butyl ester was stirred in DCM/TFA (2.0 mL, 1:1) for 1 h at RT and then poured into sat. NaHCO$_3$. The free carboxylic acid was extracted with DCM. The combined organic layers were dried over MgSO$_4$, filtered and purified by preparative chromatography (gradient 0-30% EtOAc+1% HCOOH in hexane) to obtain A36 (18.2 mg, 26.9 µmol, 47.8%) as a colourless oil.

TLC [EtOAc/cyclohexane, 1:1+1% HCOOH]: R$_f$=0.26.

HPLC [50-100% Solvent B, 20 min]: Rt=17.2 min, purity (220 nm)=99%.

$^1$H NMR (599 MHz, CDCl$_3$) δ 7.22-7.10 (m, 2H), 7.04-6.98 (m, 2H), 6.93-6.83 (m, 2H), 6.82-6.74 (m, 2H), 6.66-6.63 (m, 2H), 6.57 (d, J=7.6 Hz, 1H), 5.57 (dd, J=8.6, 5.3 Hz, 1H), 5.47-5.43 (m, 1H), 4.65-4.50 (m, 3H), 3.97-3.90 (m, 1H), 3.85-3.82 (m, 6H), 3.50-3.43 (m, 1H), 2.89-2.80 (m, 1H), 2.60-2.50 (m, 2H), 2.47-2.39 (m, 1H), 2.34-2.21 (m, 2H), 2.14-2.07 (m, 1H), 2.03-1.98 (m, 1H), 1.94-1.81 (m, 2H), 1.72-1.65 (m, 2H), 1.63-1.58 (m, 2H), 1.50-1.43 (m, 1H), 1.29-1.22 (m, 3H), 1.11 (qd, J=9.3, 2.8 Hz, 2H), 0.92-0.86 (m, 1H), 0.72 (qd, J=12.0. 4.2 Hz. 1H).

$^{13}$C NMR (151 MHz, CDCl$_3$) δ 172.34, 171.52, 170.09, 157.63, 148.80, 147.28, 142.02, 133.43, 129.86, 129.80, 129.61, 124.48, 120.20, 119.65, 115.65, 115.51, 114.85, 113.98, 113.84, 111.74, 111.43, 111.33, 111.28, 77.20, 76.98, 76.77, 75.86, 65.25, 55.90, 55.83, 54.60, 52.36, 43.71, 41.22, 37.78, 32.59, 31.17, 30.55, 26.91, 26.41, 26.04, 25.44, 20.95.

Mass: (ESI$^+$), calculated 676.33 [C$_{39}$H$_{46}$FNO$_8$+H]$^+$, found 676.26 [M+H]$^+$.

Example 3-48

Preparation of (R)-4-benzyl-3-(2-cyclohexylacetyl)oxazolidin-2-one

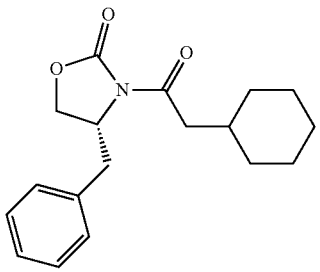 [SMILES: O=C(CC1CCCCC1)N1C(=O)OC[C@H]1Cc1ccccc1]

To a solution of (R)-4-benzyloxazolidin-2-one (500 mg, 2.82 mmol) in THF (25.0 mL) was added BuLi (1.7 mL, 4.23 mmol) at −78° C. and the resulting mixture was stirred at that temperature for 1.5 h, whereby it turned into a orange solution. To the resulting mixture was added 2-cyclohexylacetyl chloride (0.65 mL, 4.23 mmol) at −78° C. The reaction was stirred at that temperature for 2.5 h and was then slowly warmed to RT.

After stirring at 16 h the colourless reaction mixture was quenched with saturated NH₄Cl solution. The aqueous layer was extracted with Et₂O. The combined organic layers were washed with brine, dried over MgSO4, filtrated, and concentrated under reduced pressure. The crude product was purified by flash chromatography (gradient 0-10% EtOAc in cyclohexane) to yield (R)-4-benzyl-3-(2-cyclohexylacetyl)oxazolidin-2-one (850 mg, 2.82 mmol, quant.) as a colourless solid.

TLC [EtOAc/cyclohexane, 2:8]: $R_f$=0.3.

$^1$H NMR (599 MHz, CDCl$_3$) δ 7.35-7.31 (m, 2H), 7.29-7.26 (m, 1H), 7.23-7.20 (m, 2H), 4.70-4.65 (m, 1H), 4.21-4.14 (m, 2H), 3.31 (dd, J=13.4, 3.4 Hz, 1H), 2.90-2.86 (m, 1H), 2.81-2.73 (m, 2H), 1.94-1.87 (m, 1H), 1.81-1.64 (m, 5H), 1.35-1.24 (m, 2H), 1.17 (qt, J=12.7, 3.5 Hz, 1H), 1.09-0.99 (m, 2H).

$^{13}$C NMR (151 MHz, CDCl$_3$) δ 172.59, 153.40, 135.33, 129.39, 128.92, 128.90, 127.30, 66.05, 55.19, 42.65, 37.99, 34.29, 33.11, 33.06, 26.19, 26.12, 26.10.

Mass: (ESI$^+$), calculated 302.18 [C$_{18}$H$_{23}$NO$_3$+H]$^+$, found 302.14 [M+H]$^+$.

Example 3-49

Preparation of (R)-4-benzyl-3-((R)-2-cyclohexylpent-4-enoyl)oxazolidin-2-one

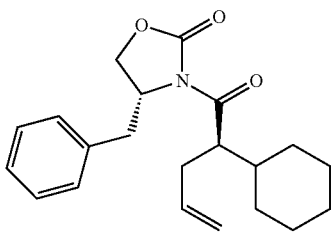 [SMILES: C=CC[C@@H](C(=O)N1C(=O)OC[C@H]1Cc1ccccc1)C1CCCCC1]

NaHMDS (1.5 mL, 1.5 mmol, 1.0 M in THF) was added to a solution of (R)-4-benzyl-3-(2-cyclohexylacetyl)oxazolidin-2-one (300 mg, 1.0 mmol) in THF (2.0 mL) at −78° C. and stirred for 1 h, whereby it turned into a light yellow solution. Allyl bromide (129 μL, 1.5 mmol) was then added dropwise. The reaction was stirred for 1 h at −78° C. and then for 16 h at 4° C.

The reaction mixture was quenched with saturated NH₄Cl solution and the aqueous layer was extracted with Et₂O. The combined organic layers were washed with brine, dried over MgSO4, filtrated, and concentrated under reduced pressure. The crude product was purified by flash chromatography (gradient 0-5% EtOAc in cyclohexane) to yield the title compound (249 mg, 0.72 mmol, 73.2%) as a colourless solid.

TLC [EtOAc/cyclohexane, 2:8]: $R_f$=0.43.

$^1$H NMR (599 MHz, CDCl$_3$) δ 7.47-6.99 (m, 5H), 5.90-5.71 (m, 1H), 5.07 (dq, J=17.0, 1.5 Hz, 1H), 5.02-4.98 (m, 1H), 4.67 (ddt, J=10.3, 6.7, 3.2 Hz, 1H), 4.17-4.05 (m, 2H), 3.90 (ddd, J=9.6, 7.6, 4.4 Hz, 1H), 3.30 (dd, J=13.4, 3.3 Hz, 1H), 2.62 (dd, J=13.4, 10.1 Hz, 1H), 2.51-2.32 (m, 2H), 1.87-1.79 (m, 1H), 1.77-1.58 (m, 4H), 1.30-1.15 (m, 3H), 1.17-1.04 (m, 2H), 1.00 (qd, J=12.4, 3.6 Hz, 1H).

$^{13}$C NMR (151 MHz, CDCl$_3$) δ 175.83, 153.22, 135.64, 135.55, 129.38, 128.88, 127.22, 116.88, 65.69, 55.64, 47.40, 40.05, 38.06, 33.78, 31.17, 29.66, 26.28.

Mass: (ESI$^+$), calculated 342.21 [C$_{21}$H$_{27}$NO$_3$+H]$^+$, found 342.27 [M+H]$^+$.

Example 3-50

Preparation of (R)-4-benzyl-3-((R)-2-cyclohexylpropanoyl) oxazolidin-2-one

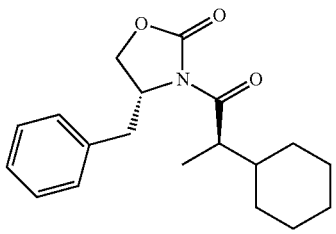 [SMILES: C[C@@H](C(=O)N1C(=O)OC[C@H]1Cc1ccccc1)C1CCCCC1]

NaHMDS (1.0 mL, 1.0 mmol, 1.0 M in THF) was added to a solution of (R)-4-benzyl-3-(2-cyclohexylacetyl)oxazolidin-2-one (200 mg, 0.66 mmol) in THF (2.0 mL) at −78° C. and stirred for 1 h, whereby it turned into a light yellow solution. Iodomethane (415 μL, 6.64 mmol) was then added dropwise. The reaction was stirred for 2.5 h at −78° C. and then for 16 h at 4° C.

The reaction mixture was quenched with saturated NH₄Cl solution and the aqueous layer was extracted with Et₂O. The combined organic layers were washed with brine, dried over MgSO4, filtrated, and concentrated under reduced pressure. The crude product was purified by flash chromatography (gradient 0-5% EtOAc in cyclohexane) to yield the title compound (163 mg, 0.52 mmol, 78.0%) as a colourless solid.

TLC [EtOAc/cyclohexane, 2:8]: $R_f$=0.43.

$^1$H NMR (300 MHz, CDCl$_3$) δ 7.48-7.10 (m, 5H), 4.66 (ddt, J=10.0, 6.6, 3.3 Hz, 1H), 4.22-4.11 (m, 2H), 3.64 (p, J=7.0 Hz, 1H), 3.28 (dd, J=13.2, 3.2 Hz, 1H), 2.75 (dd, J=13.3, 9.6 Hz, 1H), 1.79-1.53 (m, 6H), 1.29-0.89 (m, 8H).

$^{13}$C NMR (75 MHz, CDCl$_3$) δ 177.16, 153.12, 135.38, 129.40, 128.89, 127.27, 65.88, 55.44, 42.62, 40.47, 37.89, 31.47, 29.03, 26.30, 26.25, 14.16.

Mass: (ESI$^+$), calculated 316.19 [C$_{19}$H$_{25}$NO$_3$+H]$^+$, found 316.03 [M+H]$^+$.

Example 3-51

Preparation of (R)-2-cyclohexylpropanoic acid

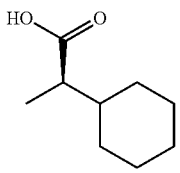

LiOH (51.3 mg, 2.14 mmol) and H$_2$O$_2$ (243 μl, 2.38 mmol) were added to a solution of (R)-4-benzyl-3-((R)-2-cyclohexylpropanoyl)oxazolidin-2-one (150 mg, 0.48 mmol) in THF/H$_2$O (6.5 mL, 8:5) at 0° C. The resulting turbid solution was stirred at that temperature for 1.5 h and at RT for 1.5 h.

Then reaction mixture was quenched with saturated Na$_2$SO$_3$ solution at 0° C. and it was extracted with DCM. Then the aqueous layer was acidified with concentrated HCl to pH=1 and extracted with DCM. These layers were combined, dried over MgSO$_4$ and the solvent was removed. The title compound (74.3 mg, 0.48 mmol, quant.) was obtained without further purification as a colourless oil.

TLC [EtOAc/cyclohexane, 4:6]: R$_f$=0.44.

$^1$H NMR (300 MHz, CDCl$_3$) δ 2.27 (p, J=7.1 Hz, 1H), 1.84-1.42 (m, 6H), 1.38-0.76 (m, 8H).

$^{13}$C NMR (75 MHz, CDCl$_3$) δ 182.63, 45.25, 40.44, 31.12, 29.37, 26.26, 26.25, 26.21, 13.64.

Mass: (ESI$^+$), calculated 157.12 [C$_9$H$_{16}$O$_2$+H]$^+$, found 157.08 [M+H]$^+$.

Example 3-52

Preparation of 2-(3-((R)-1-(((S)-1-((R)-2-cyclohexylpropanoyl) piperidine-2-carbonyl)oxy)-3-(3,4-dimethoxyphenyl)propyl)phenoxy)acetic acid

A37

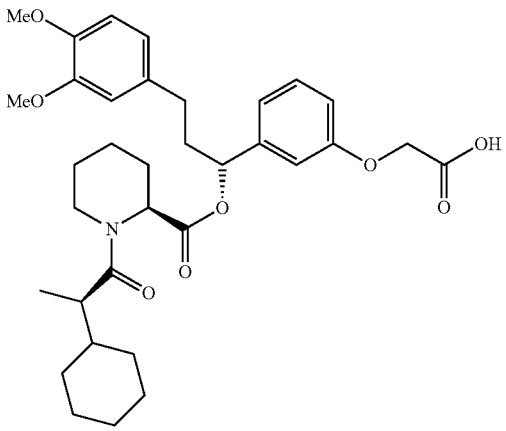

8a (49.3 mg, 0.10 mmol), (R)-2-cyclohexylpropanoic acid (15 mg, 0.10 mmol), COMU (61.7 mg, 0.14 mmol) and DIPEA (33.5 μL, 0.19 mmol) were stirred in DMF (1.0 mL) for 20 h at RT. The orange reaction mixture was diluted with Et$_2$O and washed with brine. The combined organic layers were dried over MgSO$_4$, filtrated and the solvent was removed under reduced pressure.

The crude tert-butyl ester was stirred in DCM/TFA (2.0 mL, 1:1) for 1 h at RT and then poured into saturated NaHCO$_3$. The free carboxylic acid was extracted with DCM. The combined organic layers were dried over MgSO$_4$, filtered and purified by flash chromatography (gradient 0-40% EtOAc+0.5% HCOOH in cyclohexane) to obtain A37 (44.6 mg, 74.9 μmol, 78.0%) as a light yellow oil.

TLC [EtOAc/cyclohexane, 1:1+1% HCOOH]: R$_f$=0.16.

HPLC [50-100% Solvent B, 20 min]: Rt=15.0 min, purity (220 nm)=94%.

$^1$H NMR (300 MHz, CDCl$_3$) δ 7.24-7.18 (m, 1H), 6.89-6.82 (m, 2H), 6.81-6.74 (m, 2H), 6.72-6.61 (m, 2H), 5.66 (dd, J=8.7, 4.9 Hz, 1H), 5.53-5.46 (m, 1H), 4.70-4.56 (m, 2H), 3.93-3.87 (m, 1H), 3.85 (s, 3H), 3.84 (s, 3H), 3.37-3.21 (m, 1H), 2.71-2.47 (m, 3H), 2.42-2.31 (m, 1H), 2.26-2.13 (m, 1H), 2.15-2.04 (m, 1H), 1.89-1.46 (m, 10H), 1.44-1.37 (m, 2H), 1.22-1.10 (m, 2H), 1.02 (d, J=6.8 Hz, 3H), 0.95-0.78 (m, 2H).

$^{13}$C NMR (75 MHz, CDCl$_3$) δ 177.32, 171.32, 170.34, 163.23, 158.01, 148.91, 147.38, 142.08, 133.43, 129.65, 120.18, 119.41, 115.65, 111.71, 111.37, 110.14, 76.35, 65.46, 60.42, 55.91, 55.86, 52.28, 43.51, 41.19, 40.53, 38.03, 31.90, 31.44, 29.51, 27.21, 26.88, 26.38, 26.27, 26.22, 25.50, 21.07, 14.32.

Mass: (ESI$^+$), calculated 596.32 [C$_{34}$H$_{45}$NO$_8$+H]$^+$, found 595.96 [M+H]$^+$.

Example 3-53

Preparation of 2-(3-((R)-1-(((S)-1-((R)-2-cyclohexylpent-4-enoyl)piperidine-2-carbonyl)oxy)-3-(3,4-dimethoxyphenyl)propyl)phenoxy) acetic acid

A38

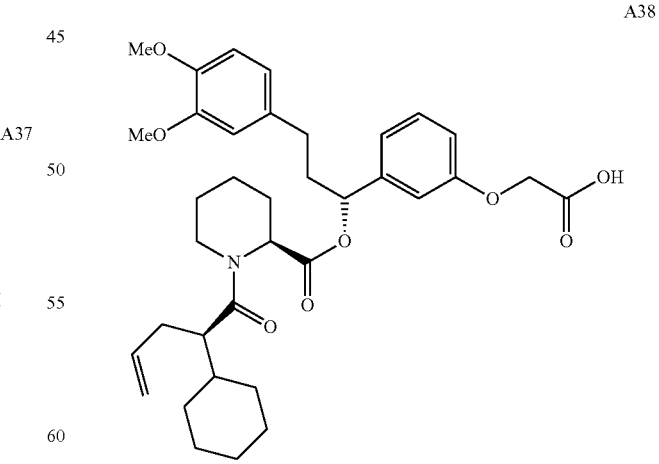

8a (141 mg, 0.27 mmol), (R)-2-cyclohexylpent-4-enoic acid (50 mg, 0.27 mmol), COMU (176 mg, 0.41 mmol) and DIPEA (96 μl, 0.55 mmol) were stirred in DMF (3.0 mL) for 20 h at RT. The resulting dark red reaction mixture was directly loaded on silica and purified by flash chromatography (gradient 0-20% EtOAc in cyclohexane). The tert-butyl ester was stirred in DCM/TFA (2.0 mL, 1:1) for 1 h at RT and then poured into sat. NaHCO$_3$. The free carboxylic acid was extracted with DCM. The combined organic layers were dried over MgSO$_4$, filtered and purified by preparative chromatography (gradient 0-10% EtOAc+1% HCOOH in hexane) to obtain A38 (13.4 mg, 21.6 μmol, 7.8%) as a yellow colourless oil.

TLC [EtOAc/cyclohexane, 1:1+1% HCOOH]: R$_f$=0.19.

HPLC [50-100% Solvent B, 20 min]: Rt=16.0 min, purity (220 nm)=98%.

$^1$H NMR (599 MHz, DMSO-d6) δ 7.31-7.19 (m, 1H), 6.91-6.87 (m, 1H), 6.86-6.77 (m, 3H), 6.75-6.70 (m, 1H), 6.67-6.60 (m, 1H), 5.78-5.68 (m, 1H), 5.67-5.63 (m, 1H), 5.37-5.30 (m, 1H), 5.07-4.90 (m, 2H), 4.85 (d, J=10.2 Hz, 1H), 4.63-4.56 (m, 2H), 4.00 (d, J=13.4 Hz, 1H), 3.69 (s, 3H), 3.68 (s, 3H), 2.95 (t, J=13.1 Hz, 1H), 2.70-2.62 (m, 1H), 2.46-2.38 (m, 1H), 2.27-2.13 (m, 3H), 2.13-1.94 (m, 2H), 1.84-1.73 (m, 1H), 1.68-1.48 (m, 5H), 1.45-1.38 (m, 2H), 1.37-1.24 (m, 2H), 1.20-1.02 (m, 4H), 0.92 (p, J=12.7, 11.1 Hz, 2H).

$^{13}$C NMR (599 MHz, DMSO-d6) δ 174.30, 170.79, 170.58, 158.36, 149.06, 147.47, 142.26, 137.00, 133.67, 129.98, 120.35, 119.12, 116.34, 114.28, 112.73, 112.53, 112.33, 75.77, 66.32, 65.16, 55.92, 55.76, 51.90, 47.41, 45.65, 43.66, 38.15, 34.22, 31.07, 29.91, 27.01, 26.41, 26.35, 25.52, 21.17.

Mass: (ESI$^+$), calculated 622.34 [C$_{36}$H$_{47}$NO$_8$+H]$^+$, found 622.17 [M+H]$^+$.

Example 4-A

General Synthetic Procedure D for Solid Phase Coupling Reaction

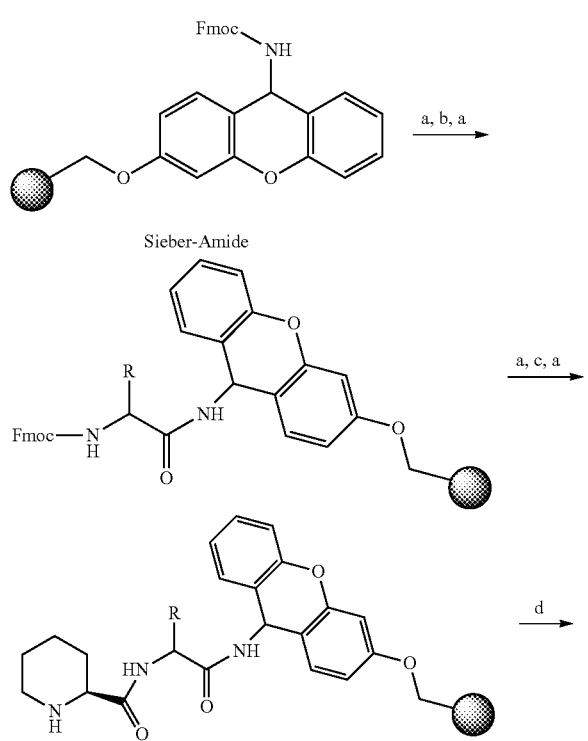

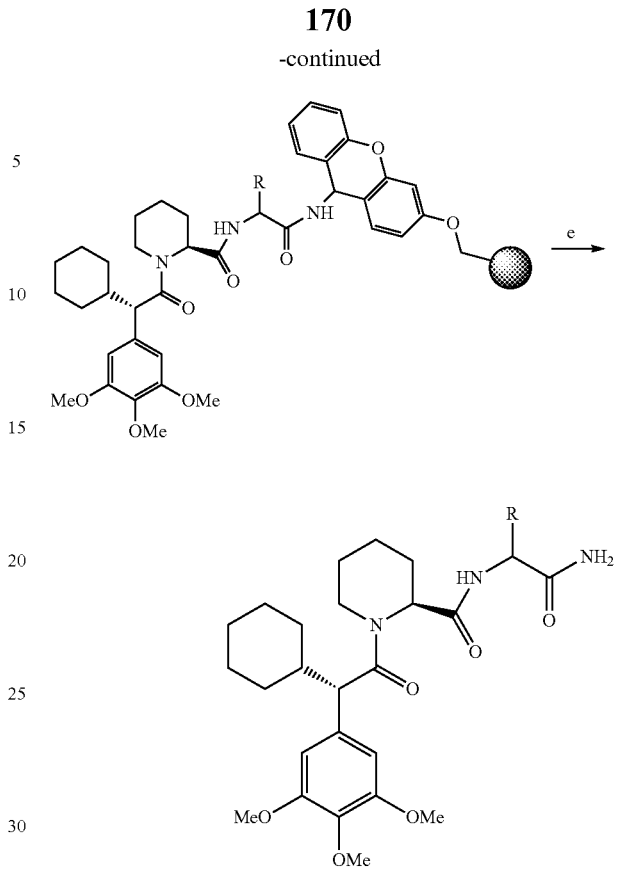

Reagents and conditions: (a) 20% 4-me-piperidine/DCM. (b) 4.8eq HBTU, 4.8eq HOBt, 10eq DIEA, 5eq Fmoc-aminoacid. (c) 3.8eq HBTU, 3.8eq HOBt, 8eq DIEA, Fmoc-Pipercolic acid. (d) 2eq HATU, 4eq DIEA, 2eq A. (e) 1%/TFA/1%TIS/98% DCM. Overall yield 20-70%

All steps were performed at rt. Sieber amide resin (108 mg, 80 μmol) was treated with 20% 4-methylpiperidine in DMF (2 mL) for 20 min. The resin was filtered and washed with DMF (2 mL×4). To the resin was added a solution of the top-group fmoc protected amino acid (400 μmol, 5 eq.), HBTU (145 mg, 386 μmol, 4.8 eq.), HOBt (52 mg, 386 μmol, 4.8 eq.) and DIEA (140 μL, 800 μmol, 10 eq.) in 2 mL DMF. The mixture was mixed on a shaker for 2 hours. The resin was filtered and washed with DMF (2 mL×4). The fmoc deprotection and washing was performed as before. (S)-N-Fmoc-piperidine-2-carboxylic acid (112 mg, 320 μmol, 4 eq.), HBTU (115 mg, 304 μmol, 3.8 eq.), HOBt (41 mg, 304 μmol, 4.8 eq.) and DIEA (120 μL, 640 μmol, 8 eq.) in 2 mL DMF was added to the resin and mixed for 2 hours. Washing and deprotecting as before was repeated followed by the addition of A (48 mg, 160 μmol, 2 eq.), HATU (61 mg, 160 μmol, 2 eq.) and DIEA (60 μl, 320 μmol, 4 eq.). The suspension was mixed for 16 hours. The resin was washed with DMF (2 mL×4), methanol (2 mL×2), dichloromethane (2 mL×4) and ether (2 mL×4) then dried in vacuo. The compounds were cleaved from the resin using 2 mL of 1% TFA/1% TIS/98% DCM for 2 minutes. This was repeated 5 times and after every step was neutralized using 20 ml sat. NaHCO$_3$ solution. The aqueous solution was extracted three times with dichloromethane.

Example 4-1

Preparation of (S)-N-((S)-1-amino-1-oxopropan-2-yl)-1-((S)-2-cyclohexyl-2-(3,4,5-trimethoxyphenyl)acetyl)piperidine-2-carboxamide B01

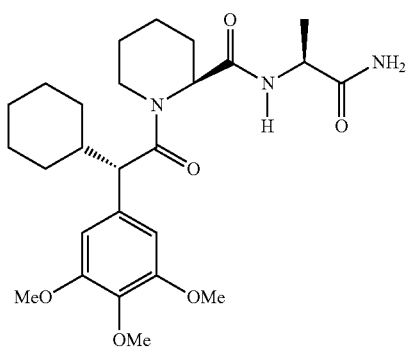

B01

General procedure D was used and B01 was obtained as colourless oil (15 mg, 31 μmol).

HPLC [0-100% Solvent B, 20 min]: $R_t$=16.4 min, purity (220 nm)=96%.

Mass: (ESI$^-$), calculated 490.29 [C26H40N3O6+H]$^-$, found 490.20 [M+H]$^+$.

Example 4-2

Preparation of (S)-N-((R)-1-amino-1-oxopropan-2-yl)-1-((S)-2-cyclohexyl-2-(3,4,5-trimethoxyphenyl)acetyl)piperidine-2-carboxamide B02

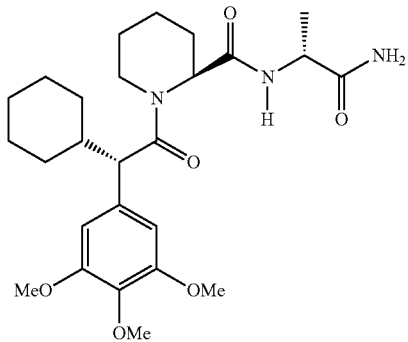

B02

General procedure D was used and B02 was obtained as colourless oil (8 mg, 17 μmol).

HPLC [0-100% Solvent B, 20 min]: $R_t$=17.1 min, purity (220 nm)=96%.

Mass: (ESI$^-$), calculated 490.29 [C26H40N3O6+H]$^-$, found 490.19 [M+H]$^+$.

Example 4-3

Preparation of (S)-N-((S)-1-amino-3-methyl-1-oxobutan-2-yl)-1-((S)-2-cyclohexyl-2-(3,4,5-trimethoxyphenyl)acetyl)piperidine-2-carboxamide B03

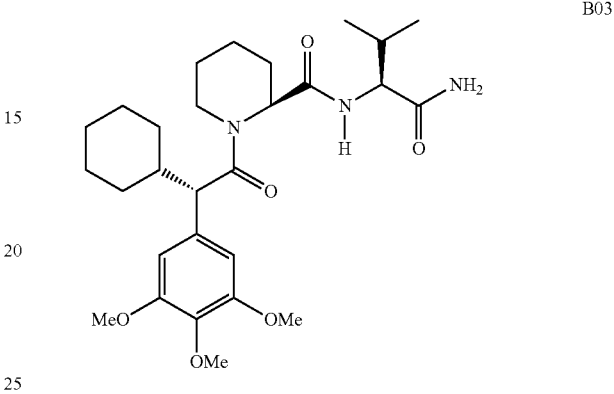

B03

General procedure D was used and B01 was obtained as white crystals (24 mg, 46 μmol).

LCMS [0-100% Solvent B, 20 min]: $R_t$=9.2 min, purity (220 nm)=96%.

Mass: (ESI$^-$), calculated 518.32 [C28H44N3O6+H]$^-$, found 518.20 [M+H]$^+$.

Example 4-4

Preparation of (S)-N-((R)-1-amino-3-methyl-1-oxobutan-2-yl)-1-((S)-2-cyclohexyl-2-(3,4,5-trimethoxyphenyl)acetyl)piperidine-2-carboxamide B04

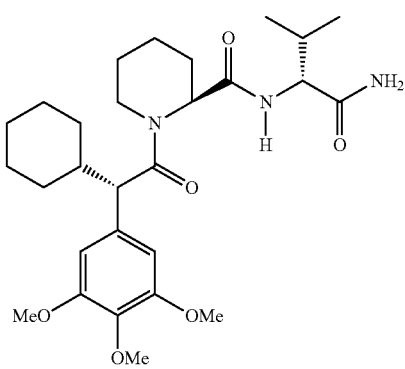

B04

General procedure D was used and B01 was obtained as white solid (31 mg, 63 μmol).

LCMS [0-100% Solvent B, 20 min]: $R_t$=9.1 min, purity (220 nm)=96%.

Mass: (ESI$^-$), calculated 518.32 [C28H44N3O6+H]$^-$, found 518.30 [M+H]$^+$.

Example 4-5

Preparation of (S)-N-((S)-1-amino-1-oxo-3-phenyl-propan-2-yl)-1-((S)-2-cyclohexyl-2-(3,4,5-trimethoxyphenyl)acetyl)piperidine-2-carboxamide B05

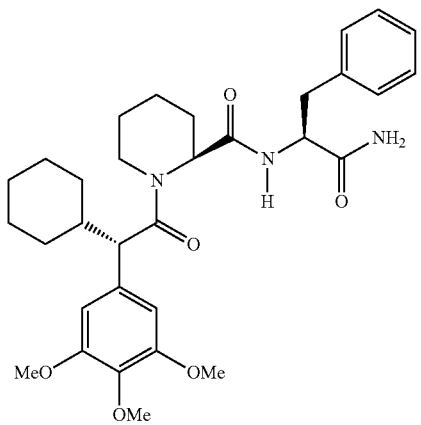

General procedure D was used and B05 was obtained as white solid (15 mg, 23 μmol).

HPLC [0-100% Solvent B, 20 min]: $R_t$=19.1 min, purity (220 nm)=97%.

Mass: (ESI⁻), calculated 566.32 [C32H43N3O6+H]⁻, found 566.25 [M+H]⁺.

Example 4-6

Preparation of (S)-N-((R)-1-amino-1-oxo-3-phenyl-propan-2-yl)-1-((S)-2-cyclohexyl-2-(3,4,5-trimethoxyphenyl)acetyl)piperidine-2-carboxamide B06

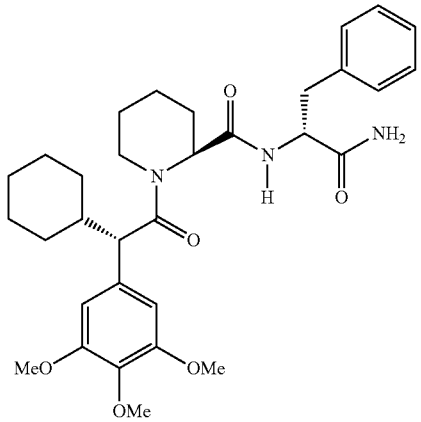

General procedure D was used and B06 was obtained as white solid (19 mg, 34 μmol).

HPLC [0-100% Solvent B, 20 min]: $R_t$=19.4 min, purity (220 nm)=99%.

Mass: (ESI⁻), calculated 566.32 [C32H43N3O6+H]⁻, found 566.10 [M+H]⁺.

Example 4-7

Preparation of (S)-N-((S)-1-amino-3-cyclohexyl-1-oxopropan-2-yl)-1-((S)-2-cyclohexyl-2-(3,4,5-trimethoxyphenyl)acetyl)piperidine-2-carboxamide B07

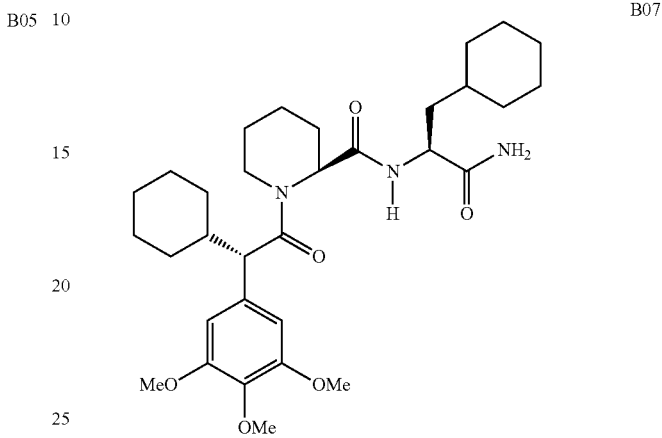

General procedure D was used and B07 was obtained as white solid (19 mg, 34 μmol).

LCMS [30-100% Solvent B, 10 min]: $R_t$=10.8 min, purity (220 nm)=99%.

Mass: (ESI⁻), calculated 572.37 [C32H49N3O6+H]⁻, found 572.27 [M+H]⁺.

Example 4-8

Preparation of (S)-N-((S)-1-amino-1-oxo-4-phenylbutan-2-yl)-1-((S)-2-cyclohexyl-2-(3,4,5-trimethoxyphenyl)acetyl)piperidine-2-carboxamide (S)-N-((S)-1-amino-1-oxo-4-phenylbutan-2-yl)-1-((S)-2-cyclohexyl-2-(3,4,5-trimethoxyphenyl)acetyl)piperidine-2-carboxamide B08

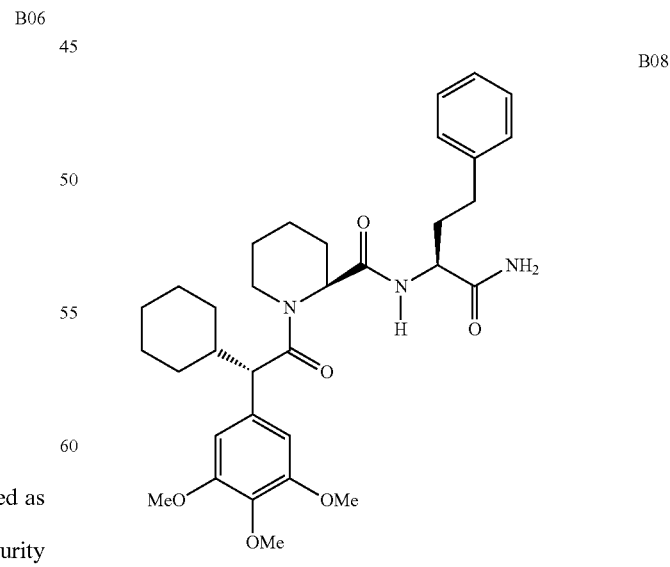

General procedure D was used and B08 was obtained as white solid (34 mg, 58 μmol).

HPLC [0-100% Solvent B, 10 min]: R$_t$=19.2 min, purity (220 nm)=96%.

Mass: (ESI$^-$), calculated 580.34 [C33H45N3O6+H]$^-$, found 580.30 [M+H]$^+$.

Example 4-9

Preparation of (S)-N-((S)-1-amino-4-cyclohexyl-1-oxobutan-2-yl)-1-((S)-2-cyclohexyl-2-(3,4,5-trimethoxyphenyl)acetyl)piperidine-2-carboxamide B09

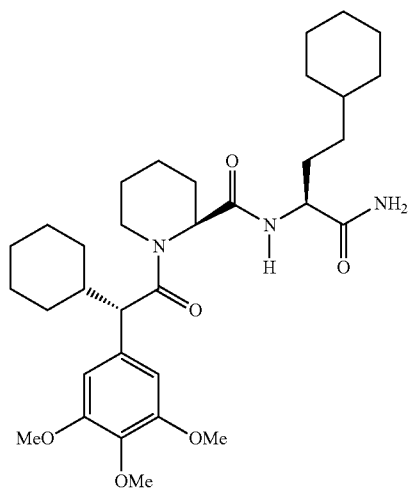

B09

General procedure D was used and B09 was obtained as pale white oil (13 mg, 20 μmol).

HPLC [0-100% Solvent B, 10 min]: R$_t$=19.2 min, purity (220 nm)=96%.

Mass: (ESI$^-$), calculated 586.39 [C33H51N3O6+H]$^-$, found 586.15 [M+H]$^+$.

Example 4-10

Preparation of (S)-N-(2-amino-2-oxoethyl)-1-((S)-2-cyclohexyl-2-(3,4,5-trimethoxyphenyl)acetyl)piperidine-2-carboxamide B10

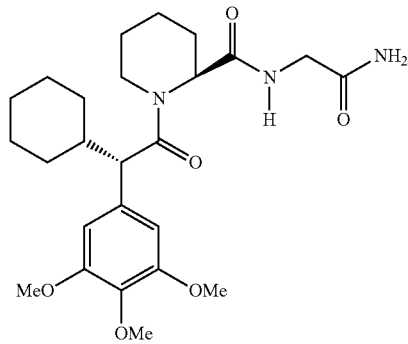

B10

General procedure D was used and B10 was obtained as colourless oil (34 mg, 58 μmol).

HPLC [0-100% Solvent B, 20 min]: R$_t$=19.2 min, purity (220 nm)=96%.

Mass: (ESI$^-$), calculated 580.34 [C25H37N3O6+H]$^-$, found 580.30 [M+H]$^+$.

Example 4-11

(S)-N-(1-amino-2-methyl-1-oxopropan-2-yl)-1-((S)-2-cyclohexyl-2-(3,4,5-trimethoxyphenyl)acetyl)piperidine-2-carboxamide B11

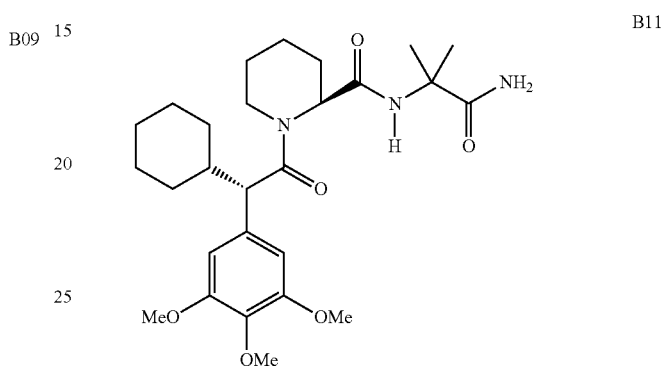

B11

General procedure D was used and B11 was obtained as pale white oil (29 mg, 58 μmol).

HPLC [0-100% Solvent B, 20 min]: R$_t$=17.1 min, purity (220 nm)=96%.

Mass: (ESI$^-$), calculated 504.31 [C27H41N3O6+H]$^-$, found 504.10 [M+H]$^+$.

Example 4-12

Preparation of (S)-N-((S)-1-amino-1-oxobutan-2-yl)-1-((S)-2-cyclohexyl-2-(3,4,5-trimethoxyphenyl)acetyl)piperidine-2-carboxamide B12

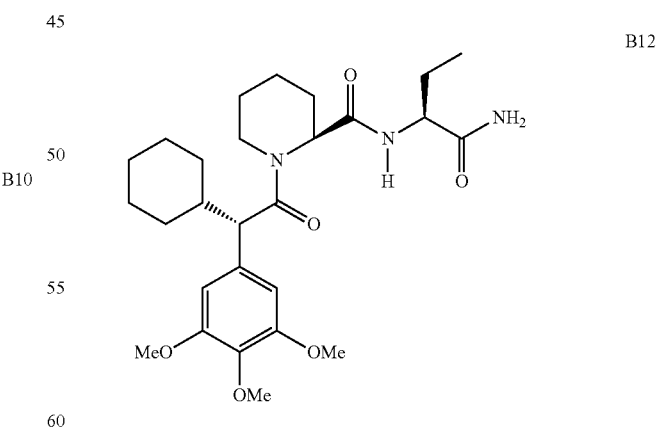

B12

General procedure D was used and B12 was obtained as pale yellow oil (29 mg, 58 μmol).

HPLC [0-100% Solvent B, 20 min]: R$_t$=17.8 min, purity (220 nm)=96%.

Mass: (ESI$^-$), calculated 504.31 [C27H41N3O6+H]$^-$, found 504.13 [M+H]$^+$.

Example 4-13

Preparation of (S)-N-((R)-1-amino-1-oxobutan-2-yl)-1-((S)-2-cyclohexyl-2-(3,4,5-trimethoxyphenyl)acetyl)piperidine-2-carboxamide B13

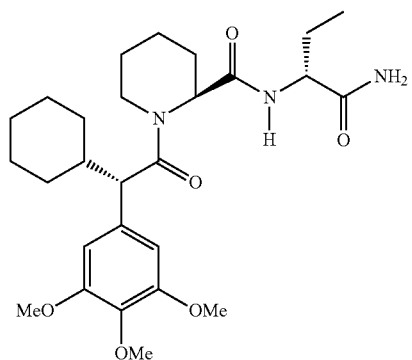

B13

General procedure D was used and B13 was obtained as pale yellow oil (29 mg, 53 μmol).

HPLC [0-100% Solvent B, 20 min]: $R_t$=17.3 min, purity (220 nm)=95%.

Mass: (ESI$^-$), calculated 504.31 [C27H41N3O6+H]$^-$, found 504.17 [M+H]$^+$.

Example 4-14

Preparation of (S)-N-((2S,3S)-1-amino-3-methyl-1-oxopentan-2-yl)-1-((S)-2-cyclohexyl-2-(3,4,5-trimethoxyphenyl)acetyl)piperidine-2-carboxamide B14

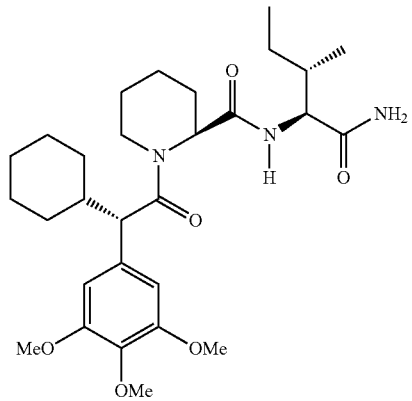

B14

General procedure D was used and B14 was obtained as yellow oil (25 mg, 47 μmol).

HPLC [0-100% Solvent B, 20 min]: $R_t$=18.3 min, purity (220 nm)=97%.

Mass: (ESI$^-$), calculated 532.34 [C29H45N3O6+H]$^-$, found 532.30 [M+H]$^+$.

Example 4-15

Preparation of (S)-N-((2R,3R)-1-amino-3-methyl-1-oxopentan-2-yl)-1-((S)-2-cyclohexyl-2-(3,4,5-trimethoxyphenyl)acetyl)piperidine-2-carboxamide B15

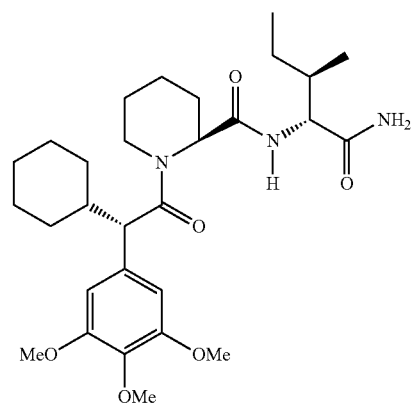

B15

General procedure D was used and B15 was obtained as yellow oil (39 mg, 73 μmol).

HPLC [0-100% Solvent B, 20 min]: $R_t$=18.0 min, purity (220 nm)=95%.

Mass: (ESI$^-$), calculated 532.34 [C29H45N3O6+H]$^-$, found 532.10 [M+H]$^+$.

Example 4-16

Preparation of (S)-N-((S)-2-amino-2-oxo-1-phenylethyl)-1-((S)-2-cyclohexyl-2-(3,4,5-trimethoxyphenyl)acetyl)piperidine-2-carboxamide B16

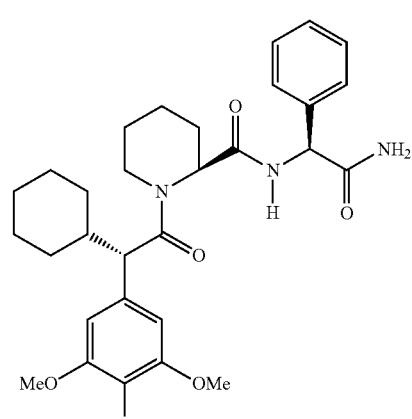

B16

General procedure D was used and B16 was obtained as pale yellow oil (38 mg, 69 μmol).

HPLC [0-100% Solvent B, 20 min]: $R_t$=18.6 min, purity (220 nm)=97%.

Mass: (ESI$^-$), calculated 552.31 [C31H41N3O6+H]$^-$, found 552.30 [M+H]$^+$.

Example 4-17

Preparation of (S)-N-((R)-2-amino-2-oxo-1-phenylethyl)-1-((S)-2-cyclohexyl-2-(3,4,5-trimethoxyphenyl)acetyl)piperidine-2-carboxamide B17

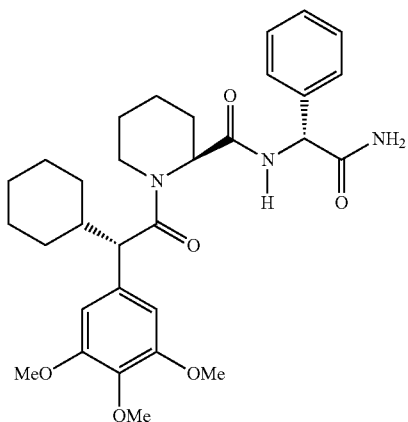

General procedure D was used and B17 was obtained as pale yellow oil (29 mg, 53 μmol).

HPLC [0-100% Solvent B, 20 min]: $R_t$=17.8 min, purity (220 nm)=98%.

Mass: (ESI−), calculated 552.31 [C31H41N3O6+H]−, found 552.10 [M+H]+.

Example 4-18

(S)-N-((S)-2-amino-1-cyclohexyl-2-oxoethyl)-1-((S)-2-cyclohexyl-2-(3,4,5-trimethoxyphenyl)acetyl)piperidine-2-carboxamide B18

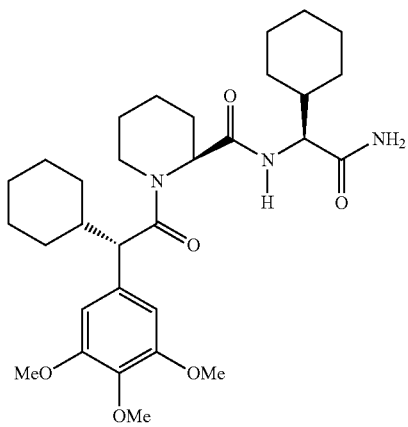

General procedure D was used and B18 was obtained as colourless oil (22 mg, 39 μmol).

HPLC [0-100% Solvent B, 20 min]: $R_t$=18.7 min, purity (220 nm)=98%.

Mass: (ESI−), calculated 558.36 [C31H47N3O6+H]−, found 558.20 [M+H]+.

Example 4-19

Preparation of (S)-N-((S)-1-amino-4-hydroxy-1-oxobutan-2-yl)-1-((S)-2-cyclohexyl-2-(3,4,5-trimethoxyphenyl)acetyl)piperidine-2-carboxamide B19

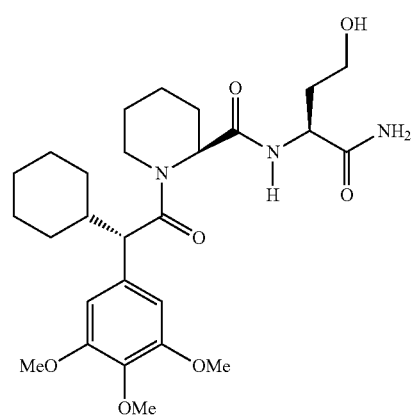

General procedure D was used and B19 was obtained as colourless oil (25 mg, 39 μmol).

LCMS [0-100% Solvent B, 20 min]: $R_t$=9.3 min, purity (220 nm)=97%.

Mass: (ESI−), calculated 520.30 [C27H41N3O7+H]−, found 520.20 [M+H]+.

Example 4-20

Preparation of (S)-N-((R)-1-amino-4-hydroxy-1-oxobutan-2-yl)-1-((S)-2-cyclohexyl-2-(3,4,5-trimethoxyphenyl)acetyl)piperidine-2-carboxamide B20

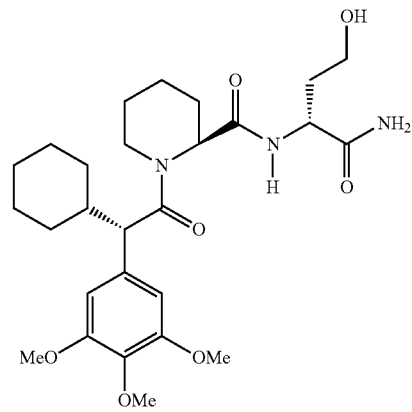

General procedure D was used and B20 was obtained as colourless oil (4 mg, 8 μmol).

LCMS [0-100% Solvent B, 20 min]: $R_t$=9.4 min, purity (220 nm)=93%.

Mass: (ESI⁻), calculated 520.30 [C27H41N3O7+H]⁻, found 520.20 [M+H]⁺.

Example 4-21

Preparation of (S)-N-((R)-1-amino-3-hydroxy-1-oxopropan-2-yl)-1-((S)-2-cyclohexyl-2-(3,4,5-trimethoxyphenyl)acetyl)piperidine-2-carboxamide B21

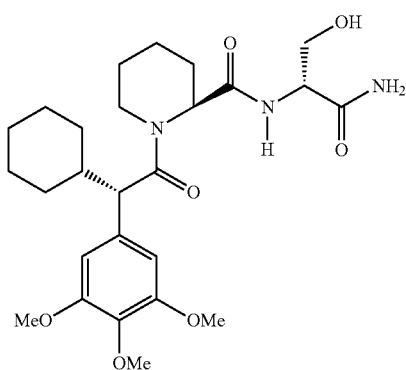

B21

General procedure D was used and B21 was obtained as pale yellow oil (28 mg, 55 μmol).

HPLC [0-100% Solvent B, 20 min]: $R_t$=15.4 min, purity (220 nm)=90%.

Mass: (ESI⁻), calculated 506.29 [C26H39N3O7+H]⁻, found 506.30 [M+H]⁺.

Example 4-22

Preparation of (S)-N-((S)-1-amino-3-hydroxy-1-oxopropan-2-yl)-1-((S)-2-cyclohexyl-2-(3,4,5-trimethoxyphenyl)acetyl)piperidine-2-carboxamide B22

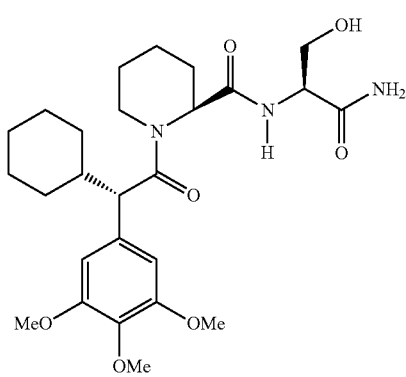

B22

General procedure D was used and B22 was obtained as pale yellow oil (32 mg, 63 μmol).

HPLC [0-100% Solvent B, 20 min]: $R_t$=15.8 min, purity (220 nm)=93%.

Mass: (ESI⁻), calculated 506.29 [C26H39N3O7+H]⁻, found 506.14 [M+H]⁺.

Example 4-23

Preparation of (S)-2-((S)-1-((S)-2-cyclohexyl-2-(3,4,5-trimethoxyphenyl)acetyl)piperidine-2-carboxamido)pentanediamide B23

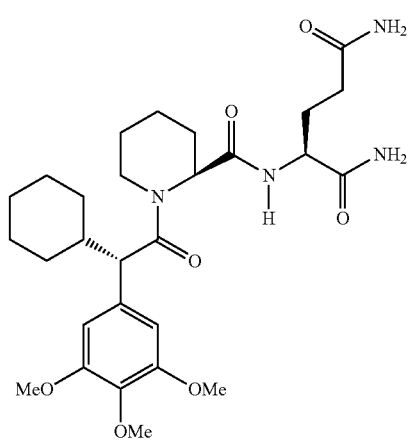

B23

General procedure D was used and B23 was obtained as colorless oil (25 mg, 46 μmol).

HPLC [0-100% Solvent B, 20 min]: $R_t$=15.1 min, purity (220 nm)=97%.

Mass: (ESI⁻), calculated 547.31 [C28H42N4O7+H]⁻, found 547.14 [M+H]⁺.

Example 4-24

Preparation of (R)-2-((S)-1-((S)-2-cyclohexyl-2-(3,4,5-trimethoxyphenyl)acetyl)piperidine-2-carboxamido)pentanediamide B24

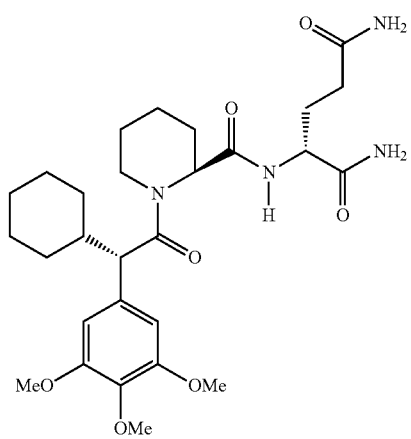

B24

General procedure D was used and B24 was obtained as colorless oil (28 mg, 51 μmol).

HPLC [0-100% Solvent B, 20 min]: $R_t$=14.8 min, purity (220 nm)=97%.

Mass: (ESI⁻), calculated 547.31 [C28H42N4O7+H]⁻, found 547.20 [M+H]⁺.

Example 4-25

Preparation of (S)-N-(4-amino-2-methyl-4-oxobutan-2-yl)-1-((S)-2-cyclohexyl-2-(3,4,5-trimethoxyphenyl)acetyl)piperidine-2-carboxamide B25

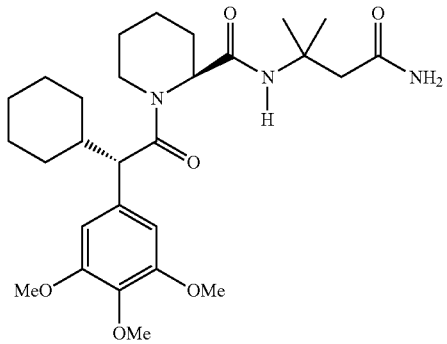

B25

General procedure D was used and B25 was obtained as colorless oil (34 mg, 66 μmol).

HPLC [0-100% Solvent B, 15 min]: $R_t$=14.6 min, purity (220 nm)=98%.

Mass: (ESI⁻), calculated 518.32 [C28H43N3O6+H]⁻, found 518.12 [M+H]⁺.

Example 4-26

Preparation of (S)-N-(1-carbamoylcyclopropyl)-1-((S)-2-cyclohexyl-2-(3,4,5-trimethoxyphenyl)acetyl)piperidine-2-carboxamide B26

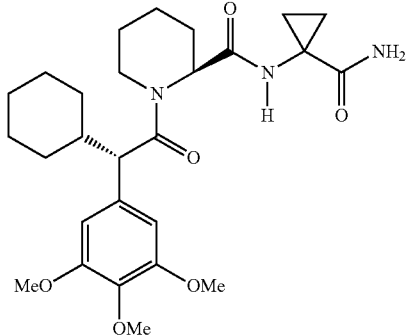

B26

General procedure D was used and B26 was obtained as colorless oil (31 mg, 62 μmol).

HPLC [0-100% Solvent B, 20 min]: $R_t$=16.8 min, purity (220 nm)=98%.

Mass: (ESI⁻), calculated 502.29 [C27H39N3O6+H]—, found 502.27 [M+H]⁺.

Example 4-27

Preparation of (S)-N-(1-carbamoylcyclobutyl)-1-((S)-2-cyclohexyl-2-(3,4,5-trimethoxyphenyl)acetyl)piperidine-2-carboxamide B27

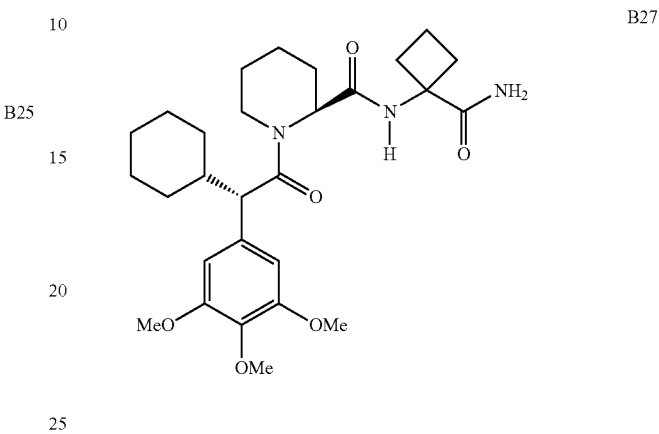

B27

General procedure D was used and B27 was obtained as colourless oil (34 mg, 66 μmol).

LCMS [0-100% Solvent B, 20 min]: $R_t$=8.9 min, purity (220 nm)=98%.

Mass: (ESI⁻), calculated 516.31 [C28H41N3O6+H]⁻, found 516.14 [M+H]⁺.

Example 4-28

Preparation of (S)-N-(1-carbamoylcyclopentyl)-1-((S)-2-cyclohexyl-2-(3,4,5-trimethoxyphenyl)acetyl)piperidine-2-carboxamide B28

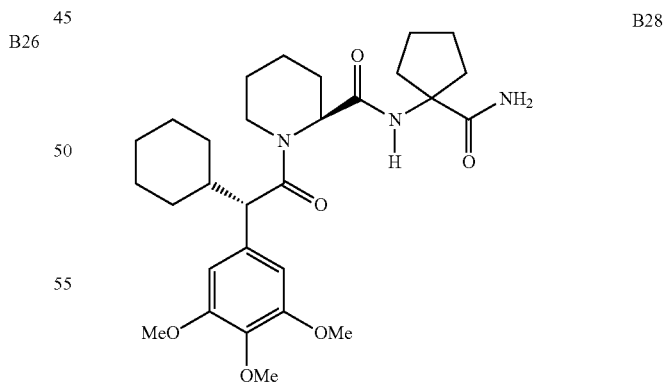

B28

General procedure D was used and B28 was obtained as colourless oil (32 mg, 60 μmol).

HPLC [0-100% Solvent B, 20 min]: $R_t$=18.1 min, purity (220 nm)=99%.

Mass: (ESI⁻), calculated 530.32 [C29H43N3O6+H]⁻, found 530.30 [M+H]⁺.

Example 4-29

Preparation of (S)-N-(3-amino-3-oxopropyl)-1-((S)-2-cyclohexyl-2-(3,4,5-trimethoxyphenyl)acetyl)piperidine-2-carboxamide B29

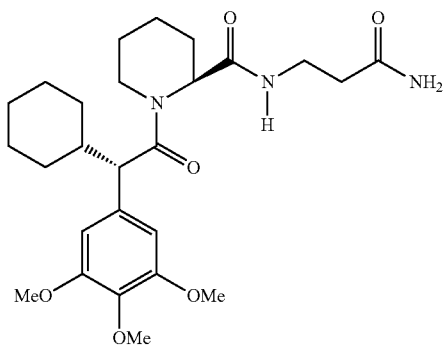

General procedure D was used and B29 was obtained as colourless oil (29 mg, 59 µmol).

HPLC [0-100% Solvent B, 20 min]: R$_t$=15.9 min, purity (220 nm)=98%.

Mass: (ESI⁻), calculated 490.29 [C26H39N3O6+H]⁻, found 490.20 [M+H]⁺.

Example 4-30

Preparation of (S)-N-((S)-1-amino-4-methyl-1-oxopentan-2-yl)-1-((S)-2-cyclohexyl-2-(3,4,5-trimethoxyphenyl)acetyl)piperidine-2-carboxamide B30

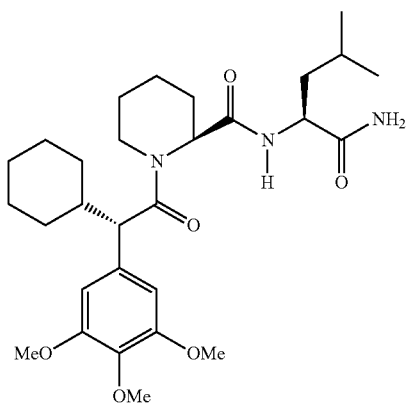

General procedure D was used and B30 was obtained as colourless oil (31 mg, 58 µmol).

HPLC [0-100% Solvent B, 20 min]: R$_t$=18.8 min, purity (220 nm)=97%.

Mass: (ESI⁻), calculated 532.34 [C29H45N3O6+H]⁻, found 532.24 [M+H]⁺.

Example 4-31

(S)-N-(1-carbamoylcyclohexyl)-1-((S)-2-cyclohexyl-2-(3,4,5-trimethoxyphenyl) acetyl)piperidine-2-carboxamide B31

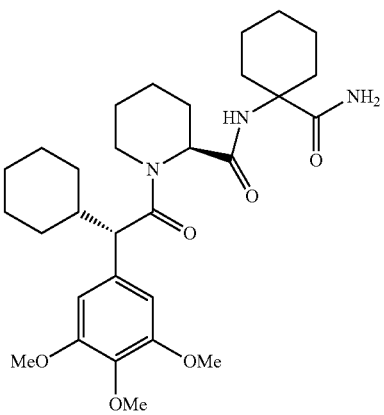

General procedure D was used and B31 was obtained as colourless oil (34 mg, 63 µmol).

HPLC [0-100% Solvent B, 20 min]: R$_t$=18.9 min, purity (220 nm)=98%.

Mass: (ESI⁻), calculated 544.34 [C$_{30}$H$_{45}$N$_3$O$_6$+H]⁺, found 544.17 [M+H]⁺.

Example 4-32

(S)-N-(1-carbamoylcyclohexyl)-1-((S)-2-cyclohexyl-2-(3,4,5-trimethoxyphenyl) acetyl)piperidine-2-carboxamide B32

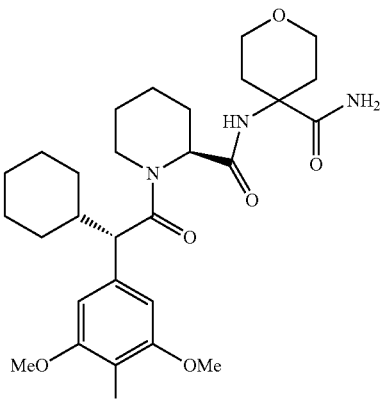

General procedure D was used and B32 was obtained as colourless oil (33 mg, 60 µmol).

HPLC [0-100% Solvent B, 20 min]: R$_t$=18.9 min, purity (220 nm)=98%.

Mass: (ESI⁻), calculated 546.32 [C$_{29}$H$_{44}$N$_3$O$_7$+H]⁺, found 546.03 [M+H]⁺.

Example 4-33

(S)-N-(1-((2-amino-2-oxoethyl)carbamoyl)cyclopentyl)-1-((S)-2-cyclohexyl-2-(3,4,5-trimethoxyphenyl)acetyl)piperidine-2-carboxamide B33

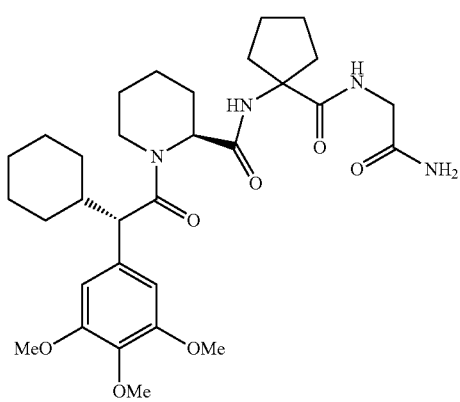

B33

General procedure D was used and B33 was obtained as colourless oil (29 mg, 49 μmol).

HPLC [0-100% Solvent B, 20 min]: $R_t$=19.1 min, purity (220 nm)=91%.

Mass: (ESI⁻), calculated 587.34 $[C_{31}H_{47}N_4O_7+H]^+$, found 587.24 $[M+H]^+$.

Example 4-34

(S)-N-((R)-1-amino-3-(1H-imidazol-4-yl)-1-oxopropan-2-yl)-1-((S)-2-cyclohexyl-2-(3,4,5-trimethoxyphenyl)acetyl)piperidine-2-carboxamide B34

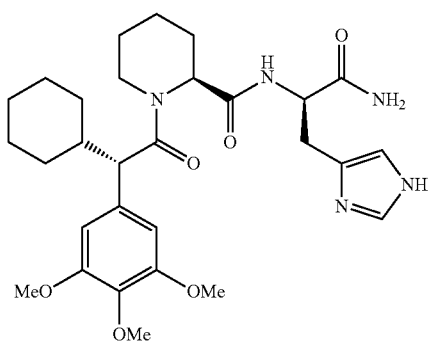

B34

HPLC [0-100% Solvent B, 20 min]: $R_t$=13.2 min, purity (220 nm)=99%.

Mass: (ESI⁻), calculated 556.31 $[C_{29}H_{42}N_5O_6+H]^+$, found 556.30 $[M+H]^+$.

Example 4-35

(S)-N-((S)-1-amino-3-(1H-imidazol-4-yl)-1-oxopropan-2-yl)-1-((S)-2-cyclohexyl-2-(3,4,5-trimethoxyphenyl)acetyl)piperidine-2-carboxamide B35

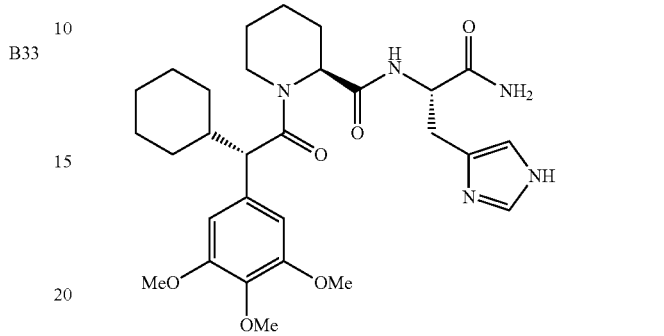

B35

General procedure D was used and B35 was obtained as colourless oil (3 mg, 23 μmol).

HPLC [0-100% Solvent B, 20 min]: $R_t$=13.7 min, purity (220 nm)=99%.

Mass: (ESI⁻), calculated 556.31 $[C_{29}H_{42}N_5O_6+H]^+$, found 556.29 $[M+H]^+$.

Example 5-A

General Synthetic Procedures for Coupling of Synthetic Building Blocks A and B (Coupled with Alcohol and Amine)

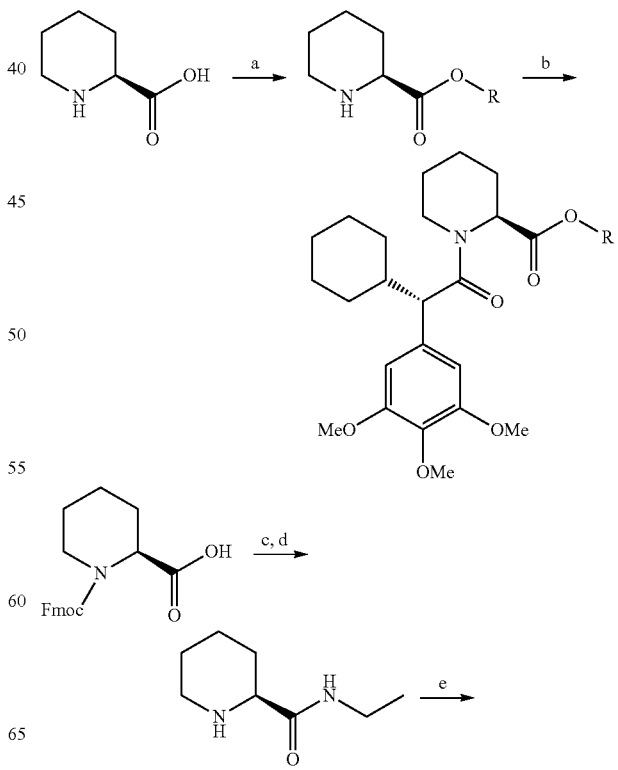

-continued

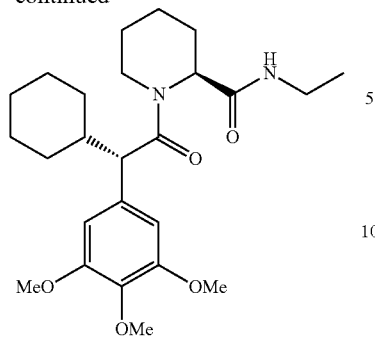

Ligand Synthesis: Reagents and conditions: (a) SOCl₂, R—OH, reflux, 60-80%. (b) HATU, DIEA, DCM/DMF, rt, 60-90%. (c) HATU, DIEA, ethanolamine, rt, 80%. (d) 4-Me-Piperidine, DCM, 80%. (e) HATU, DIEA, DCM/DMF, rt, 70%.

(S)-pipecolinic acid was dissolved in 3 mL of alcohol followed by the addition of 2 eq Thionylchloride at rt. The reaction mixture was refluxed for 5 h and quenched with NaHCO₃. The raw product was extracted, dried over MgSO₄ and used without further purification.

Example 5-1

Preparation of (S)-methyl 1-((S)-2-cyclohexyl-2-(3,4,5-trimethoxyphenyl)acetyl)piperidine-2-carboxylate C01

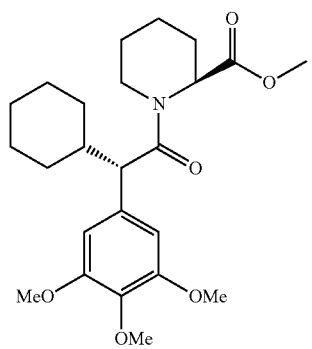

19 (107 mg, 349 µmol), HATU (133 mg, 349 µmol) and DIEA (238 µL, 1.4 mmol) were dissolved in 2 mL DCM and stirred for 15 min at rt followed by the addition of (S)-methyl piperidine-2-carboxylate (50 mg, 349 µmol). The crude product was purified using flash chromatography (EtOAc/Hexane 2:1). C01 (76 mg, 175 µmol, 50%) was obtained as colorless oil.

TLC [EtOAc/Cyclohexane, 1:2]: $R_f$=0.42.

HPLC [0-100% Solvent B, 20 min]: $R_t$=20.4 min, purity (220 nm)=99%.

Mass: (ESI⁻), calculated 434.25 $[C_{42}H_{52}N_2O_{10}+H]^+$, found 434.17 $[M-H]^+$.

Example 5-2

Preparation of (S)-ethyl 1-((S)-2-cyclohexyl-2-(3,4,5-trimethoxyphenyl)acetyl)piperidine-2-carboxylate C02

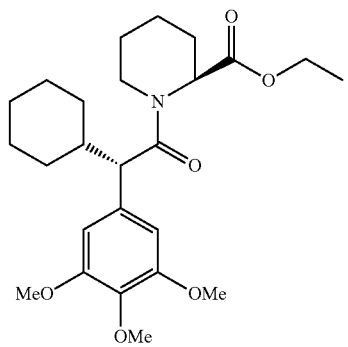

19 (107 mg, 349 µmol), HATU (30 mg, 97 µmol) and DIEA (66 µL, 389 µmol) were dissolved in 500 µL DCM and stirred for 15 min at rt followed by the addition of (S)-ethyl piperidine-2-carboxylate (15 mg, 97 µmol). The reaction mixture was stirred for 16 h The crude product was purified using flash chromatography (EtOAc/Hexane 1:2). C02 (11 mg, 24 µmol, 25%) was obtained as colorless oil.

TLC [EtOAc/Cyclohexane, 1:2]: $R_f$=0.34.

HPLC [0-100% Solvent B, 20 min]: $R_t$=21.2 min, purity (220 nm)=99%.

Mass: (ESI⁻), calculated 448.27 $[C_{42}H_{52}N_2O_{10}+H]^+$, found 448.20 $[M-H]^+$.

Example 5-3

Preparation of (S)-propyl 1-((S)-2-cyclohexyl-2-(3,4,5-trimethoxyphenyl)acetyl)piperidine-2-carboxylate C03

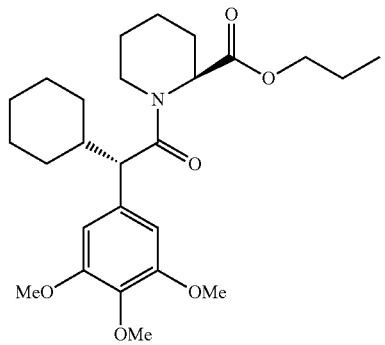

19 (138 mg, 449 µmol), HATU (171 mg, 449 µmol) and DIEA (305 µL, 1.8 mmol) were dissolved in 2 mL DMF and stirred for 15 min at it followed by the addition of (S)-ethyl piperidine-2-carboxylate (15 mg, 97 µmol). The crude product was purified using flash chromatography (EtOAc/Hexane 1:2). C03 (127 mg, 275 µmol, 61%) was obtained as colorless oil.

TLC [EtOAc/Cyclohexane, 1:2]: $R_f$=0.39.

HPLC [0-100% Solvent B, 20 min]: R$_t$=22.0 min, purity (220 nm)=96%.

Mass: (ESI$^-$), calculated 462.29 [C$_{42}$H$_{52}$N$_2$O$_{10}$+H]$^+$, found 462.23 [M−H]$^+$.

Example 5-4

Preparation of (S)-isopropyl 1-((S)-2-cyclohexyl-2-(3,4,5-trimethoxyphenyl)acetyl)piperidine-2-carboxylate C04

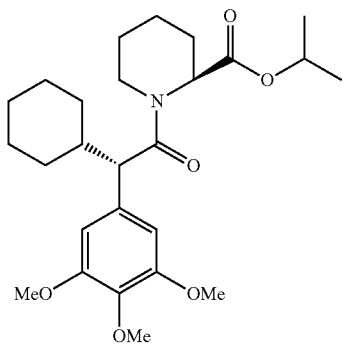

C04

19 (63 mg, 204 μmol), HATU (78 mg, 204 μmol) and DIEA (139 μL, 816 μmol) were dissolved in 2 mL DCM and stirred for 15 min at rt followed by the addition of (S)-ethyl piperidine-2-carboxylate (15 mg, 97 μmol). The crude product was purified using flash chromatography (EtOAc/Hexane 1:2). C04 (37 mg, 80 μmol, 40%) was obtained as colorless oil.

TLC [EtOAc/Cyclohexane, 1:2]: R$_f$=0.43.

HPLC [0-100% Solvent B, 20 min]: R$_t$=21.9 min, purity (220 nm)=96%.

Mass: (ESI$^-$), calculated 462.29 [C$_{42}$H$_{52}$N$_2$O$_{10}$+H]$^+$, found 462.20 [M−H]$^+$.

Example 5-5

Preparation of (S)-1-((S)-2-cyclohexyl-2-(3,4,5-trimethoxyphenyl)acetyl)-N-ethylpiperidine-2-carboxamide C05

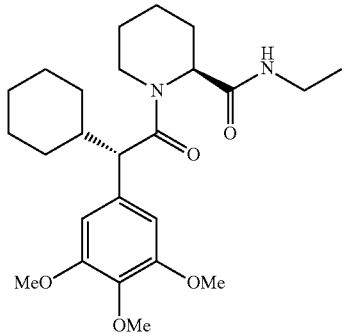

C05

19 (79 mg, 256 μmol), HATU (97 mg, 256 μmol) and DIEA (174 μL, 1024 μmol) were dissolved in 2 mL DCM and stirred for 15 min at rt followed by the addition of (S)-ethyl (S)-N-ethylpiperidine-2-carboxamide (40 mg, 97 μmol). The crude product was purified using flash chromatography (EtOAc/Hexane 1:2). C05 (68 mg, 152 μmol, 60%) was obtained as colorless oil.

TLC [EtOAc/Cyclohexane, 1:2]: R$_f$=0.37.

HPLC [0-100% Solvent B, 20 min]: R$_t$=18.8 min, purity (220 nm)=96%.

Mass: (ESI$^-$), calculated 447.28 [C$_{42}$H$_{52}$N$_2$O$_{10}$+H]$^+$, found 447.20 [M−H]$^+$.

Example 5-6

Preparation of (S)-1-((S)-2-cyclohexyl-2-(3,4,5-trimethoxyphenyl)acetyl)piperidine-2-carboxylic acid C06

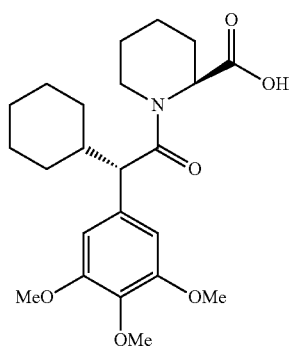

C06

C02 (148 mg, 329 μmol) was dissolved in THF/H$_2$O followed by the addition of 493 μl 1M LiOH (aq). The reaction mixture was stirred at rt for 16 h. Brine was added and the aqueous solution extracted with DCM. The organic phase was discarded and the aqueous phase acidified to pH=2 followed by extraction with DCM. The solution was dried over MgSO4 and the solvent reduced in vacuo. C06 was obtained as a white foam (130 mg, 310 μmol, 94%)

TLC [EtOAc/Cyclohexane, 1:2+0.1% AcOH]: R$_f$=0.15.

HPLC [0-100% Solvent B, 20 min]: R$_t$=13.4 min, purity (220 nm)=95%.

Mass: (ESI$^-$), calculated 419.23 [C$_{42}$H$_{52}$N$_2$O$_{10}$+H]$^+$, found 419.17 [M−H]$^+$.

Example 5-7

(S)-(S)-sec-butyl-1-((S)-2-cyclohexyl-2-(3,4,5-trimethoxyphenyl)acetyl)piperidine-2-carboxylate C07

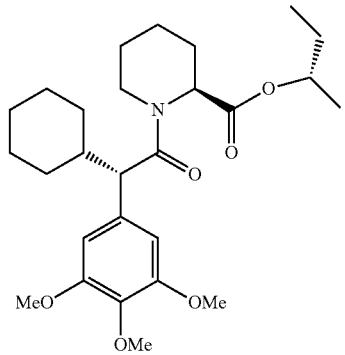

C07

19 (20.81 mg, 0.067 mmol), HATU (25.7 mg, 0.067 mmol) and N-ethyl-N-isopropylpropan-2-amine (45.0 µl, 0.270 mmol) were dissolved in 500 µl DMF and stirred for 1 min. (S)-(S)-sec-butyl piperidine-2-carboxylate (12.5 mg, 0.067 mmol) dissolved in 500 µl DCM was added and stirred for 16 h. The crude product was concentrated and purified using flash chromatography (gradient 0-20% EtOAc in cyclohexane) C07 was obtained as a pale yellow oil (30 mg, 63 µmol, 93%).

TLC [EtOAc/cyclohexane, 4:6]: $R_f$=0.39.

HPLC [0-100% Solvent B, 20 min]: $R_t$=22.9 min, purity (220 nm)=98%.

Mass: (ESI$^-$), calculated 476.30 [$C_{27}H_{42}NO_6$+H]$^+$, found 476.36 [M+H]$^+$.

$^1$H NMR (300 MHz, CDCl$_3$) major rotamer δ 6.49 (s, 2H), 5.33 (d, J=5.4 Hz, 1H), 4.71 (q, J=6.4 Hz, 1H), 3.97 (d, J=13.6 Hz, 1H), 3.83 (s, 9H), 3.36 (d, J=9.8 Hz, 1H), 3.00-2.86 (m, 1H), 2.29-2.20 (m, 1H), 2.18-2.06 (m, 2H), 1.88 (d, J=13.3 Hz, 1H), 1.75-1.51 (m, 6H), 1.37-1.20 (m, 4H), 1.19-1.06 (m, 3H), 1.01 (d, J=6.2 Hz, 3H), 0.89-0.73 (m, 2H), 0.69 (t, J=7.4 Hz, 3H).

$^{13}$C NMR (75 MHz, CDCl$_3$) major rotamer δ 172.50, 171.03, 153.08, 136.93, 133.79, 106.00, 77.16, 73.03, 52.36, 32.91, 30.83, 28.72, 26.74, 26.36, 26.31, 25.78.

Example 5-8

(S)-(R)-sec-butyl-1-((S)-2-cyclohexyl-2-(3,4,5-trimethoxyphenyl)acetyl)piperidine-2-carboxylate C08

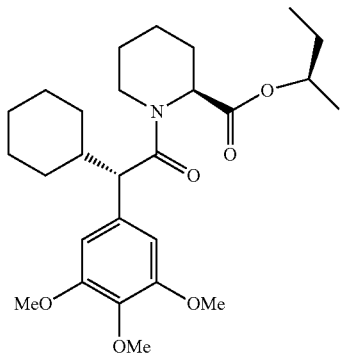

C08

19 (24.97 mg, 0.081 mmol), HATU (30.8 mg, 0.081 mmol) and N-ethyl-N-isopropylpropan-2-amine (54.0 µl, 0.324 mmol) were dissolved in 500 µl DMF and stirred for 1 min. (S)-(R)-sec-butyl piperidine-2-carboxylate (12.5 mg, 0.067 mmol) dissolved in 500 µl DCM was added and stirred for 16 h. The crude product was concentrated and purified using flash chromatography (gradient 0-20% EtOAc in cyclohexane) C08 was obtained as a pale yellow oil (35 mg, 74 µmol, 91%).

TLC [EtOAc/cyclohexane, 2:8]: $R_f$=0.22.

HPLC [0-100% Solvent B, 20 min]: $R_t$=22.9 min, purity (220 nm)=98%.

Mass: (ESI$^-$), calculated 476.30 [$C_{27}H_{42}NO_6$+H]$^+$, found 476.23 [M+H]$^+$.

$^1$H NMR (300 MHz, CDCl$_3$) major rotamer δ 6.49 (s, 2H), 5.33 (d, J=5.4 Hz, 1H), 4.71 (q, J=6.4 Hz, 1H), 3.97 (d, J=13.6 Hz, 1H), 3.83 (s, 9H), 3.36 (d, J=9.8 Hz, 1H), 3.00-2.86 (m, 1H), 2.29-2.20 (m, 1H), 2.18-2.06 (m, 2H), 1.88 (d, J=13.3 Hz, 1H), 1.75-1.51 (m, 6H), 1.37-1.20 (m, 4H), 1.19-1.06 (m, 3H), 1.01 (d, J=6.2 Hz, 3H), 0.89-0.73 (m, 2H), 0.69 (t, J=7.4 Hz, 3H).

$^{13}$C NMR (75 MHz, CDCl$_3$) major rotamer δ 172.50, 171.03, 153.08, 136.93, 133.79, 106.00, 77.16, 73.03, 52.36, 32.91, 30.83, 28.72, 26.74, 26.36, 26.31, 25.78.

Example 5-9

(S)-pentan-3-yl-1-((S)-2-cyclohexyl-2-(3,4,5-trimethoxyphenyl)acetyl)piperidine-2-carboxylate C09

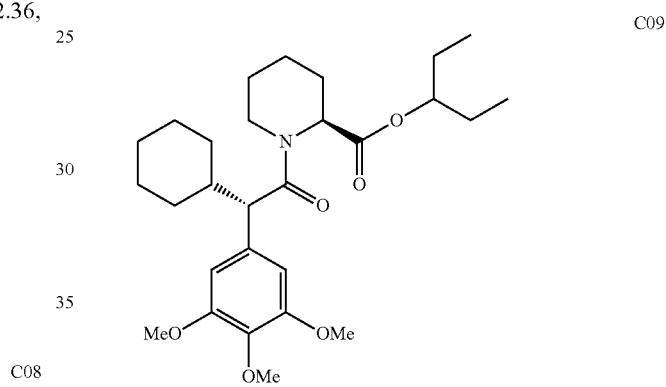

C09

19 (38.7 mg, 0.125 mmol), N-ethyl-N-isopropylpropan-2-amine (16.21 mg, 0.125 mmol) and HATU (47.7 mg, 0.125 mmol) were dissolved in 600 µL DMF followed by the addition of (S)-pentan-3-yl piperidine-2-carboxylate (25.0 mg, 0.125 mmol) dissolved in 600 µL DCM. The reaction mixture was stirred at rt for 16 h. The crude product was concentrated and purified using flash chromatography (gradient 0-20% EtOAc in cyclohexane). C09 was obtained as a colorless oil (48 mg, 98 µmol, 78%).

TLC [EtOAc/cyclohexane, 3:7]: $R_f$=0.47.

HPLC [0-100% Solvent B, 20 min]: $R_t$=23.5 min, purity (220 nm)=90%.

Mass: (ESI$^-$), calculated 490.32 [$C_{28}H_{44}NO_6$+H]$^+$, found 490.19 [M+H]$^+$.

$^1$H NMR (300 MHz, CDCl$_3$) major rotamer δ 6.49 (s, 2H), 5.36 (d, J=5.3 Hz, 1H), 4.85 (q, J=6.0 Hz, 1H), 3.99 (d, J=13.8 Hz, 1H), 3.84-3.80 (m, 9H), 3.37 (d, J=9.9 Hz, 1H), 2.94 (td, J=13.0, 2.8 Hz, 1H), 2.27 (d, J=14.1 Hz, 1H), 2.09 (dt, J=17.1, 9.4 Hz, 2H), 1.88 (d, J=13.2 Hz, 1H), 1.73-1.53 (m, 6H), 1.39-1.21 (m, 4H), 1.20-1.05 (m, 2H), 0.98-0.86 (m, 3H), 0.72 (dt, J=9.2, 7.4 Hz, 8H).

$^{13}$C NMR (75 MHz, CDCl$_3$) major rotamer δ 172.51, 171.22, 153.07, 136.93, 133.79, 105.99, 78.45, 77.16, 60.89, 56.45, 56.27, 55.11, 52.28, 43.77, 41.40, 32.87, 30.83, 27.05, 26.90, 26.75, 26.55, 26.47, 26.37, 26.30, 21.18, 9.72, 9.60.

Example 5-10

(S)-tert-butyl-1-((S)-2-cyclohexyl-2-(3,4,5-trimethoxyphenyl)acetyl)piperidine-2-carboxylate C10

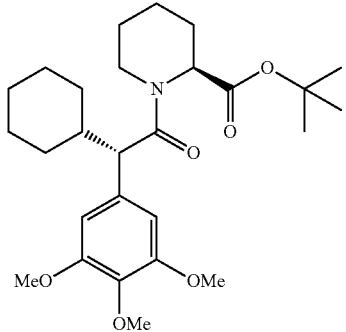

C10

19 (33.3 mg, 0.108 mmol), DIEA (0.074 ml, 0.432 mmol) and HATU (41.0 mg, 0.108 mmol) were dissolved in 500 μL DMF and stirred for 5 min at RT. (S)-tert-butyl piperidine-2-carboxylate (20 mg, 0.108 mmol) dissolved in 500 μL DCM was added and stirred for 16 h at rt. The crude product was concentrated and purified using flash chromatography (gradient 0-20% EtOAc in cyclohexane) C10 was obtained as a colorless oil (15 mg, 32 μmol, 30%).

HPLC [0-100% Solvent B, 20 min]: $R_t$=22.8 min, purity (220 nm)=91%.

Mass: (ESI$^-$), calculated 476.30 [$C_{27}H_{42}NO_6$+H]$^+$, found 476.02 [M+H]$^+$.

$^1$H NMR (400 MHz, d6-DMSO) major rotamer δ 6.17 (s, 2H), 4.54-4.49 (m, 1H), 3.69 (d, J=13.5 Hz, 1H), 2.86 (s, 9H), 2.42-2.32 (m, 1H), 1.64-1.40 (m, 2H), 1.34-1.09 (m, 6H), 1.07-0.87 (m, 5H), 0.83-0.58 (m, 12H), 0.55-0.24 (m, 2H).

$^{13}$C NMR (101 MHz, d6-DMSO) major rotamer δ 171.99, 170.13, 152.44, 136.04, 133.78, 105.82, 80.37, 59.80, 55.73, 52.84, 52.19, 42.73, 40.80, 39.52, 31.73, 29.72, 27.65, 27.34, 27.11, 26.60, 26.11, 25.58, 25.10, 20.47.

Example 5-11

(S)-1-methylcyclopentyl-1-((S)-2-cyclohexyl-2-(3,4,5-trimethoxyphenyl)acetyl) piperidine-2-carboxylate C11

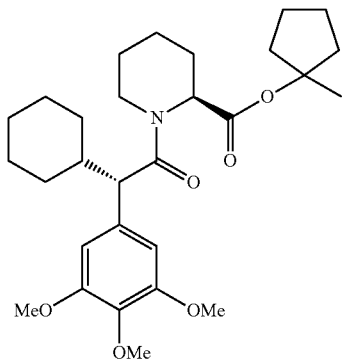

C11

19 (46.7 mg, 0.151 mmol), HATU (57.6 mg, 0.151 mmol) and DIEA (60 μl, 0.344 mmol) were dissolved in 500 μL DMF and stirred for 1 min at rt. (S)-1-methylcyclopentyl piperidine-2-carboxylate (32 mg, 0.151 mmol) dissolved in 500 μL DCM was added and stirred at rt for 3 h. The crude product was concentrated and purified using flash chromatography (gradient 0-20% EtOAc in cyclohexane) C11 was obtained as a colorless oil (56 mg, 112 μmol, 74%).

TLC [EtOAc/cyclohexane, 3:7]: $R_f$=0.49.

HPLC [0-100% Solvent B, 20 min]: $R_t$=23.7 min, purity (220 nm)=98%.

Mass: (ESI$^-$), calculated 502.32 [$C_{29}H_{44}NO_6$+H]$^+$, found 502.12 [M+H]$^+$.

$^1$H NMR (400 MHz, dmso) δ 6.63 (s, 2H), 5.04-4.98 (m, 1H), 4.18 (d, J=13.2 Hz, 1H), 3.72 (s, 6H), 3.61 (s, 3H), 3.17 (d, J=5.2 Hz, 1H), 2.78 (t, J=12.4 Hz, 1H), 2.01 (dd, J=22.6, 10.2 Hz, 3H), 1.85-1.53 (m, 9H), 1.55-1.28 (m, 6H), 1.29-1.02 (m, 8H), 0.85 (dq, J=41.6, 13.6, 12.4 Hz, 2H).

$^{13}$C NMR (100 MHz, dmso) δ 172.02, 170.11, 152.59, 136.38, 133.82, 105.83, 89.93, 59.97, 55.57, 52.08, 42.84, 40.85, 39.52, 38.30, 37.92, 31.74, 29.77, 26.53, 26.11, 25.56, 25.16, 23.76, 23.38, 23.06, 22.94, 20.60.

Example 5-12

(S)-tetrahydro-2H-pyran-4-yl-1-((S)-2-cyclohexyl-2-(3,4,5-trimethoxyphenyl) acetyl)piperidine-2-carboxylate C12

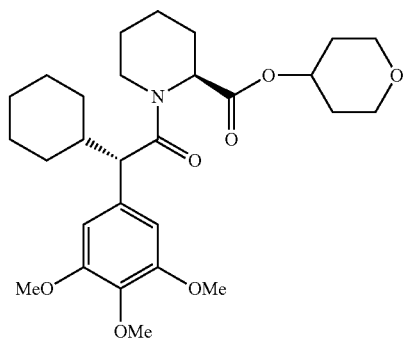

C12

C06 (20 mg, 0.048 mmol), tetrahydro-2H-pyran-4-ol (9.74 mg, 0.095 mmol) and N,N-dimethylpyridin-4-amine (1.747 mg, 0.014 mmol) were dissolved in dry DCM and cooled to 0° C. EDC (18.28 mg, 0.095 mmol) was added and the reaction was allowed to warm to it over night. The crude product was concentrated and purified using flash chromatography (gradient 0-30% EtOAc in cyclohexane) C12 was obtained as a colorless oil (14 mg, 28 μmol, 58%).

TLC [EtOAc/cyclohexane, 3:7]: $R_f$=0.19.

HPLC [0-100% Solvent B, 20 min]: $R_t$=21.0 min, purity (220 nm)=90%.

Mass: (ESI$^-$), calculated 504.30 [$C_{28}H_{42}NO_7$+H]$^+$, found 504.20 [M+H]$^+$.

Example 5-13

(S)-cyclopentyl-1-((S)-2-cyclohexyl-2-(3,4,5-trimethoxyphenyl)acetyl)piperidine-2-carboxylate
C13

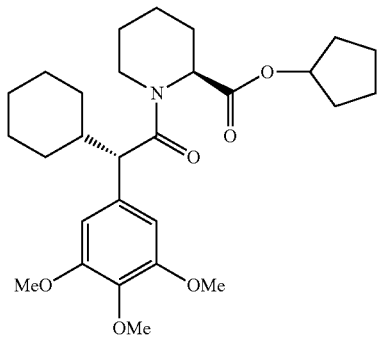

C06 (20 mg, 0.048 mmol) and DBU (8.5 µL, 0.057) were dissolved in 1 mL MeCN followed by the addition of bromo-cyclopentane (7.8 mg, 0.052 mmol). The reaction was stirred at it for 16 h. The crude product was concentrated and purified using flash chromatography (EtOAc/cyclohexane, 1:2). C13 was obtained as a pale yellow oil (10 mg, 20.5 µmol, 44%).

TLC [EtOAc/cyclohexane, 1:2]: $R_f$=0.58.

HPLC [0-100% Solvent B, 20 min]: $R_t$=23.0 min, purity (220 nm)=98%.

Mass: (ESI$^-$), calculated 488.30 $[C_{28}H_{42}NO_6+H]^+$, found 488.30 $[M+H]^+$.

Example 5-14

(S)-cyclopent-3-en-1-yl-1-((S)-2-cyclohexyl-2-(3,4,5-trimethoxyphenyl)acetyl) piperidine-2-carboxylate
C14

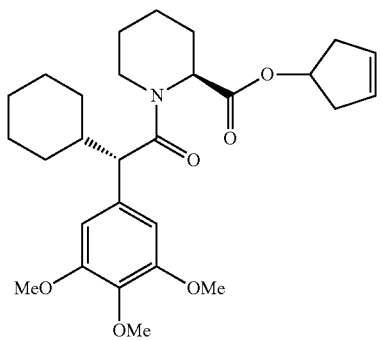

C06 (110 mg, 0.36 mmol), HATU (130 mg, 0.36 mmol) and DIEA (243 µl, 0.36 mmol) were dissolved in 500 µL DMF and stirred for 1 min at rt. (S)-cyclopent-3-en-1-yl piperidine-2-carboxylate (70 mg, 0.36 mmol) dissolved in 500 µL DCM was added and stirred at rt for 3 h. The crude product was concentrated and purified using flash chromatography (EtOAc/cyclohexane, 1:2). C14 was obtained as a white solid (120 mg, 112 µmol, 69%).

TLC [EtOAc/cyclohexane, 1:2]: $R_f$=0.52.

HPLC [0-100% Solvent B, 20 min]: $R_t$=22.6 min, purity (220 nm)=98%.

Mass: (ESI$^-$), calculated 426.29 $[C_{28}H_{39}NO_6+H]^+$, found 486.16 $[M+H]^+$.

$^1$H NMR (400 MHz, CDCl$_3$) major rotamer δ 6.46 (s, 1H), 5.59-5.53 (m, 2H), 5.27 (d, J=5.5 Hz, 1H), 5.25-5.20 (m, 1H), 3.94 (d, J=13.7 Hz, 1H), 3.85-3.78 (m, 9H), 3.35 (d, J=9.8 Hz, 1H), 2.92 (td, J=13.2, 2.9 Hz, 2H), 2.85-2.75 (m, 3H), 2.65-2.53 (m, 3H), 2.45-2.36 (m, 1H), 2.22 (d, J=13.5 Hz, 1H), 2.17-1.98 (m, 2H), 1.92-1.82 (m, 1H), 1.71-1.54 (m, 3H), 1.35-1.23 (m, 2H), 1.19-1.05 (m, 1H), 0.94-0.82 (m, 2H), 0.79-0.66 (m, 2H).

$^{13}$C NMR (101 MHz, CDCl$_3$) major rotamer δ 172.50, 171.16, 152.89, 136.67, 133.58, 128.00, 127.89, 105.68, 74.73, 60.76, 56.09, 54.97, 52.19, 43.60, 41.19, 39.55, 39.40, 32.71, 30.67, 26.89, 26.56, 26.19, 26.15, 25.51, 20.99.

Example 5-15

(2S)-cyclohex-2-en-1-yl-1-((S)-2-cyclohexyl-2-(3,4,5-trimethoxyphenyl)acetyl) piperidine-2-carboxylate
C15

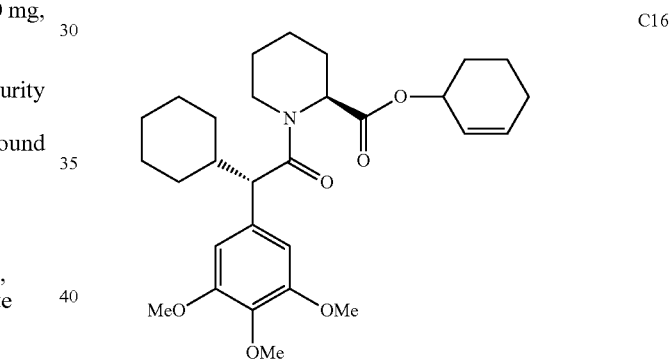

C06 (20 mg, 0.048 mmol) and DBU (8.5 µL, 0.057) were dissolved in 1.0 mL MeCN followed by the addition of bromo-cyclohexane (6.0 µL, 0.052 mmol). The reaction was stirred at it for 16 h. The crude product was concentrated and purified using flash chromatography (EtOAc/cyclohexane, 1:2) C15 was obtained as a yellow oil (6 mg, diastereomeric mixture, 13 µmol, 30%).

TLC [EtOAc/cyclohexane, 1:2]: $R_f$=0.60.

HPLC [0-100% Solvent B, 20 min]: $R_t$=23.2 min, purity (220 nm)=90%.

Mass: (ESI$^-$), calculated 500.30 $[C_{29}H_{42}NO_6+H]^+$, found 500.17 $[M+H]^+$.

$^1$H NMR (300 MHz, CDCl$_3$) mixture of diastereomers δ 6.49 (s, 2H), 5.88-5.81 (m, 1H), 5.61-5.47 (m, 1H), 5.35-5.31 (m, 1H), 5.21-5.10 (m, 1H), 4.01-3.91 (m, 2H), 3.83 (s, 6H), 3.82 (s, 3H), 3.14 (d, J=9.5 Hz, 1H), 2.14-2.01 (m, 5H), 1.97-1.82 (m, 3H), 1.66 (t, J=13.6 Hz, 7H), 1.50-1.01 (m, 6H), 0.84 (ddd, J=38.8, 22.8, 10.6 Hz, 2H).

$^{13}$C NMR (75 MHz, CDCl$_3$) mixture of diastereomers δ 172.42, 170.59, 152.87, 133.90, 133.28, 132.67, 125.08, 105.50, 68.49, 60.51, 56.28, 52.27, 43.39, 41.00, 32.70, 29.66, 27.81, 27.20, 26.28, 25.05, 20.82, 18.37.

Example 5-16

(S)-cycloheptyl-1-((S)-2-cyclohexyl-2-(3,4,5-trimethoxyphenyl)acetyl)piperidine-2-carboxylate C16

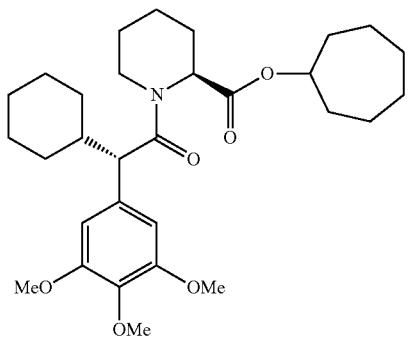

C06 (10 mg, 0.024 mmol) and DBU (5.0 µL, 0.029) were dissolved in 1.0 mL MeCN followed by the addition of bromo-cycloheptane (8.0 µL, 0.056 mmol). The reaction was stirred at rt for 16 h. The crude product was concentrated and purified using flash chromatography (EtOAc/cyclohexane, 1:2) C16 was obtained as a yellow oil (6.3 mg, 12 µmol, 50%):

TLC [EtOAc/cyclohexane, 1:2]: $R_f$=0.70.

HPLC [0-100% Solvent B, 20 min]: $R_t$=24.4 min, purity (220 nm)=90%.

Mass: (ESI⁻), calculated 516.33 [$C_{30}H_{46}NO_6$+H]⁺, found 516.40 [M+H]⁺.

Example 5-17

(S)-allyl-1-((S)-2-cyclohexyl-2-(3,4,5-trimethoxyphenyl)acetyl)piperidine-2-carboxylate C17

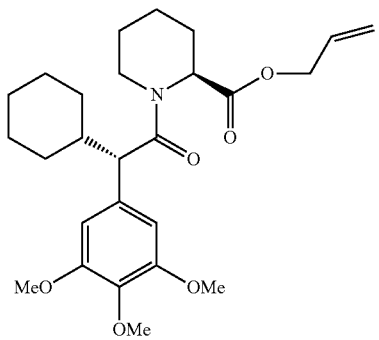

C06 (20 mg, 0.048 mmol) and DBU (8.5 µL, 0.057) were dissolved in 1.0 mL MeCN followed by the addition of bromo-cyclohexane (4.5 µL, 0.052 mmol). The reaction was stirred at rt for 16 h. The crude product was concentrated and purified using flash chromatography (EtOAc/cyclohexane, 1:2). C17 was obtained as a yellow oil (12.0 mg, 26 µmol, 54%).

TLC [EtOAc/cyclohexane, 1:2]: $R_f$=0.49.

HPLC [0-100% Solvent B, 20 min]: $R_t$=22.2 min, purity (220 nm)=98%.

Mass: (ESI⁻), calculated 460.27 [$C_{26}H_{38}NO_6$+H]⁺, found 460.27 [M+H]⁺.

¹H NMR (300 MHz, CDCl₃) δ 6.47 (s, 2H), 5.77-5.59 (m, 1H), 5.41-5.33 (m, 1H), 5.19-5.03 (m, 2H), 4.47 (tt, J=5.5, 1.6 Hz, 1H), 3.98-3.88 (m, 1H), 3.84-3.81 (m, 9H), 3.37 (d, J=9.8 Hz, 1H), 3.01-2.84 (m, 1H), 2.26 (d, J=13.9 Hz, 1H), 2.16-2.00 (m, 2H), 1.88 (d, J=12.5 Hz, 2H), 1.73-1.55 (m, 4H), 1.40-1.04 (m, 6H), 0.97-0.68 (m, 3H).

¹³C NMR (75 MHz, cdcl3) δ 172.51, 170.86, 152.91, 136.76, 134.31, 133.38, 131.69, 117.86, 105.83, 65.29, 60.78, 56.28, 56.14, 55.13, 52.26, 43.63, 41.15, 32.81, 30.70, 29.66, 26.76, 26.57, 26.22, 26.18, 26.09, 25.49, 20.99.

Example 5-18

(S)-2-methoxyethyl-1-((S)-2-cyclohexyl-2-(3,4,5-trimethoxyphenyl)acetyl) piperidine-2-carboxylate C18

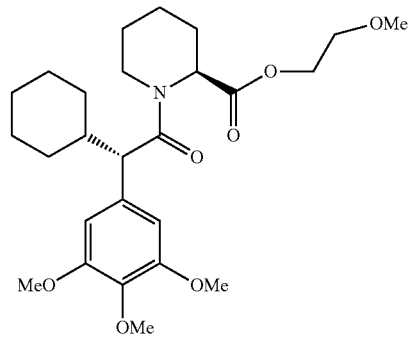

C06 (30 mg, 0.072 mmol) and DBU (13 µL, 0.086) were dissolved in 1.0 mL MeCN followed by the addition of bromo-2-methoxyethane (7.4 µL, 0.079 mmol). The reaction was stirred at rt for 16 h. The crude product was concentrated and purified using flash chromatography (gradient 0-50% EtOAc in cyclohexane). C18 was obtained as a yellow oil (15.5 mg, 32 µmol, 45%).

TLC [EtOAc/cyclohexane, 1:2]: $R_f$=0.19.

HPLC [0-100% Solvent B, 20 min]: $R_t$=21.01 min, purity (220 nm)=97%.

Mass: (ESI⁻), calculated 478.28 [$C_{26}H_{39}NO_7$+H]⁺, found 478.19 [M+H]⁺.

¹H NMR (400 MHz, d6-DMSO) δ 6.60 (s, 2H), 5.18-5.10 (m, 1H), 4.27-4.23 (m, 1H), 3.72-3.72 (m, 7H), 3.63 (s, 3H), 3.57-3.53 (m, 1H), 3.11 (s, 3H), 2.86-2.75 (m, 1H), 2.10-2.03 (m, OH), 2.01-1.87 (m, 1H), 1.75 (t, J=13.9 Hz, 1H), 1.68-1.46 (m, 6H), 1.41-1.26 (m, 3H), 1.25-1.04 (m, 5H), 1.00-0.72 (m, 4H).

¹³C NMR (101 MHz, d6-DMSO) δ 171.99, 170.71, 136.02, 134.75, 105.85, 69.40, 63.29, 59.87, 57.84, 55.75, 52.92, 51.74, 42.83, 40.82, 39.52, 31.85, 29.80, 26.52, 26.10, 25.08, 20.53.

Example 5-19

(S)-2-(benzyloxy)ethyl-1-((S)-2-cyclohexyl-2-(3,4,5-trimethoxyphenyl)acetyl) piperidine-2-carboxylate C19

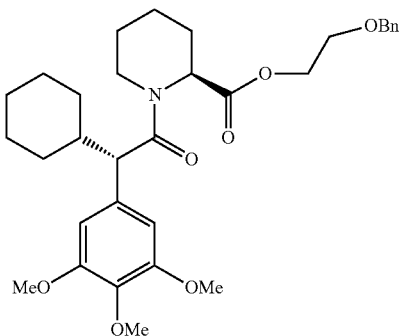

C06 (50.0 mg, 0.119 mmol), potassium iodide (2.0 mg, 0,012 mmol) and Benzyl 2-bromoethyl ether (19.0 µl, 0.119 mmol) were dissolved in 1 ml dry DCM followed by the addition of DBU (20.0 µl, 0.133 mmol). The reaction mixture was stirred at rt for 16 h. The crude product was concentrated and purified using flash chromatography (gradient 0-30% EtOAc in cyclohexane) C19 was obtained as a yellow oil (15.5 mg, 32 µmol, 45%).

TLC [EtOAc/cyclohexane, 2:8]: $R_f$=0.22.

HPLC [0-100% Solvent B, 20 min]: $R_t$=22.7 min, purity (220 nm)=91%.

Mass: (ESI⁻), calculated 554.31 $[C_{32}H_{44}NO_7+H]^+$, found 554.27 $[M+H]^+$.

Example 5-20

(S)-2-hydroxyethyl-1-((S)-2-cyclohexyl-2-(3,4,5-trimethoxyphenyl)acetyl)piperidine-2-carboxylate C20

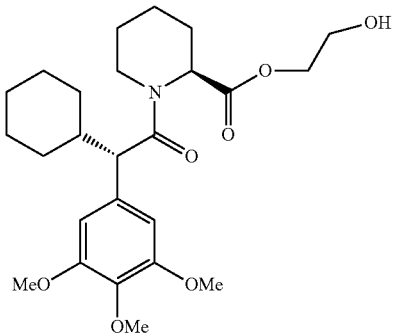

C19 (37.0 mg, 0.067 mmol) was dissolved in 1 mL MeOH (degassed with Argon). Pd/C 10% (21.3 mg, 0.020 mmol) was added and the reaction was put under hydrogen atmosphere. The reaction was stirred for 16 h at rt. The crude product was concentrated and purified using flash chromatography (gradient 0-100% EtOAc in cyclohexane). 19 was obtained as colourless oil (10.0 mg, 0.022 mmol, 33%).

TLC [EtOAc/cyclohexane, 2:8]: $R_f$=0.26.

HPLC [0-100% Solvent B, 20 min]: $R_t$=23.7 min, purity (220 nm)=98%.

Mass: (ESI⁻), calculated 464.26 $[C_{25}H_{38}NO_7+H]^+$, found 464.30 $[M+H]^+$.

¹H NMR (400 MHz, d6-DMSO) major rotamer δ 6.58 (s, 2H), 5.15-5.08 (m, 1H), 4.41 (d, J=13.0 Hz, 1H), 3.72 (s, 6H), 3.63 (s, 3H), 2.88-2.78 (m, 1H), 2.13-2.05 (m, 1H), 2.03-1.89 (m, 2H), 1.81-1.69 (m, 1H), 1.69-1.53 (m, 6H), 1.52-1.44 (m, 1H), 1.29-1.13 (m, 4H), 1.14-1.03 (m, 4H), 0.98-0.88 (m, 2H), 0.87-0.74 (m, 2H).

¹³C NMR (101 MHz, d6-DMSO) major rotamer δ 172.55, 171.22, 152.84, 136.45, 134.10, 106.32, 66.88, 66.34, 60.34, 59.16, 56.37, 56.20, 53.42, 52.28, 43.28, 41.25, 32.31, 30.26, 27.03, 26.55, 26.10, 26.07, 26.00, 25.53, 21.19, 21.04.

Example 5-21

(S)-3-(benzyloxy)propyl-1-((S)-2-cyclohexyl-2-(3,4,5-trimethoxyphenyl)acetyl) piperidine-2-carboxylate C21

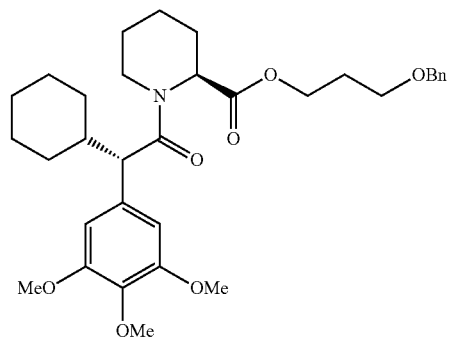

C06 (50.0 mg, 0.119 mmol), sodium iodide (10.0 mg, 0.067 mmol) and ((3-bromopropoxy)methyl)benzene (137 mg, 0.596 mmol) were dissolved in 1 ml dry DMF followed by the addition of DBU (90.0 µL, 0.596 mmol). The reaction mixture was stirred at rt overnight. The reaction mixture was stirred at rt for 16 h. The crude product was concentrated and purified using flash chromatography (gradient 0-30% EtOAc in cyclohexane) C21 was obtained as an colourless oil (35.0 mg, 0.061 mmol, 50%).

TLC [EtOAc/cyclohexane, 4:6]: $R_f$=0.52.

HPLC [0-100% Solvent B, 20 min]: $R_t$=23.2 min, purity (220 nm)=92%.

Mass: (ESI⁻), calculated 568.33 $[C_{33}H_{46}NO_7+H]^+$, found 568.23 $[M+H]^+$.

¹H NMR (300 MHz, CDCl₃) major rotamer δ 6.47 (s, 2H), 5.33 (d, J=5.0 Hz, 1H), 4.40 (d, J=7.1 Hz, 2H), 4.18-4.02 (m, 2H), 3.90 (d, J=13.7 Hz, 1H), 3.84-3.79 (m, 9H), 3.55 (t, J=5.9 Hz, 2H), 3.47 (s, 1H), 3.40-3.23 (m, 2H), 3.11 (d, J=9.7 Hz, 1H), 2.93-2.81 (m, 1H), 2.21 (d, J=14.0 Hz, 1H), 2.14-2.04 (m, 1H), 2.02-1.80 (m, 2H), 1.77-1.49 (m, 6H), 1.46-1.37 (m, 1H), 1.36-1.17 (m, 4H), 1.16-1.00 (m, 2H), 0.97-0.82 (m, 2H), 0.82-0.66 (m, 2H).

¹³C NMR (75 MHz, CDCl₃) major rotamer δ 172.44, 171.12, 152.91, 138.29, 136.76, 133.52, 128.31, 127.51, 105.81, 72.88, 66.28, 62.02, 60.77, 56.14, 52.19, 43.57, 41.25, 32.78, 30.70, 28.83, 26.80, 26.56, 26.21, 26.18, 25.52, 20.99.

Example 5-22

(S)-2-hydroxyethyl-1-((S)-2-cyclohexyl-2-(3,4,5-trimethoxyphenyl)acetyl)piperidine-2-carboxylate C22

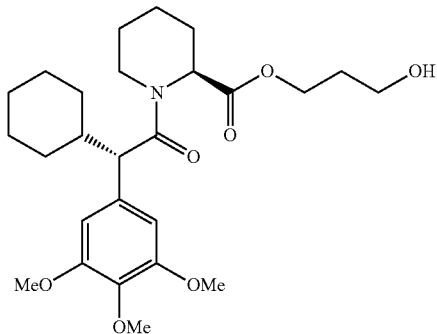

C21 (30.0 mg, 0.053 mmol) was dissolved in 1 mL EtOH (degassed with Argon). Pd/C 10% (16.9 mg, 0.016 mmol) was added and the reaction was put under hydrogen atmosphere. Argon was exchanged by $H_2$ gas and the reaction was stirred for 16 h. The crude product was concentrated and purified using flash chromatography (gradient 0-100% EtOAc in cyclohexane). C22 was obtained as pale yellow oil (15.0 mg, 0.016 mmol, 58%).

TLC [EtOAc/cyclohexane, 1:1]: $R_f$=0.20.
HPLC [0-100% Solvent B, 20 min]: $R_t$=19.1 min, purity (220 nm)=90%.
Mass: (ESI⁻), calculated 478.28 $[C_{26}H_{40}NO_7+H]^+$, found 478.14 $[M+H]^+$.
$^1$H NMR (400 MHz, d6-DMSO) δ 6.61 (s, 2H), 4.99-4.94 (m, 1H), 4.13 (d, J=13.5 Hz, 1H), 3.71 (s, 6H), 3.65-3.61 (m, 3H), 3.60 (s, 3H), 3.54-3.49 (m, 2H), 2.82 (td, J=13.2, 2.7 Hz, 1H), 2.06-1.87 (m, 2H), 1.79-1.47 (m, 4H), 1.45-1.28 (m, 2H), 1.29-1.02 (m, 9H), 0.99-0.71 (m, 2H).
$^{13}$C NMR (100 MHz, d6-DMSO) δ 172.41, 171.27, 152.86, 136.46, 135.24, 134.10, 106.34, 62.07, 60.20, 57.67, 57.30, 56.36, 56.21, 52.19, 43.34, 41.25, 32.27, 31.98, 31.74, 30.24, 26.95, 26.56, 26.07, 25.55, 21.07.

Example 5-23

(S)-4-methoxybutyl-1-((S)-2-cyclohexyl-2-(3,4,5-trimethoxyphenyl)acetyl) piperidine-2-carboxylate C23

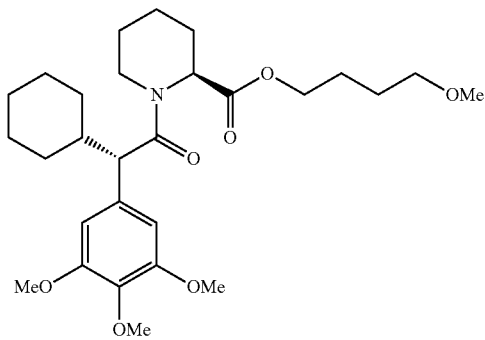

C06 (50.0 mg, 0.119 mmol), sodium iodide (10.0 mg, 0.067 mmol) and 1-bromo-4-methoxybutane (77.0 μL, 0.596 mmol) were dissolved in 1 ml dry DMF followed by the addition of DBU (90.0 μl, 0.596 mmol). The reaction mixture was stirred at it for 16 h. The crude product was concentrated and purified using flash chromatography (gradient 0-30% EtOAc in cyclohexane). C23 was obtained as an yellow oil (37.0 mg, 0.073 mmol, 61%).

TLC [EtOAc/cyclohexane, 1:2]: $R_f$=0.12.
HPLC [0-100% Solvent B, 20 min]: $R_t$=21.6 min, purity (220 nm)=90%.
Mass: (ESI⁻), calculated 506.31 $[C_{28}H_{44}NO_7+H]^+$, found 506.20 $[M+H]^+$.
$^1$H NMR (400 MHz, d6-DMSO) δ 6.56 (s, 2H), 5.13-5.01 (m, 1H), 4.16-4.00 (m, 2H), 3.97-3.88 (m, 1H), 3.89-3.80 (m, 1H), 3.69 (d, J=2.5 Hz, 6H), 3.60 (s, 3H), 3.14 (s, 3H), 2.79-2.70 (m, 1H), 2.07-1.84 (m, 3H), 1.78-1.65 (m, 2H), 1.66-1.39 (m, 6H), 1.38-1.24 (m, 4H), 1.22-1.00 (m, 4H), 0.97-0.68 (m, 4H).
$^{13}$C NMR (100 MHz, d6-DMSO) δ 172.00, 170.73, 152.41, 136.12, 133.56, 105.82, 71.07, 64.09, 59.88, 57.64, 55.68, 52.87, 51.75, 42.91, 40.84, 39.52, 31.82, 29.79, 26.48, 26.10, 25.57, 25.26, 24.85, 20.61.

Example 5-24

(S)-(R)-1-(benzyloxy)propan-2-yl-1-((S)-2-cyclohexyl-2-(3,4,5-trimethoxyphenyl) acetyl)piperidine-2-carboxylate C24

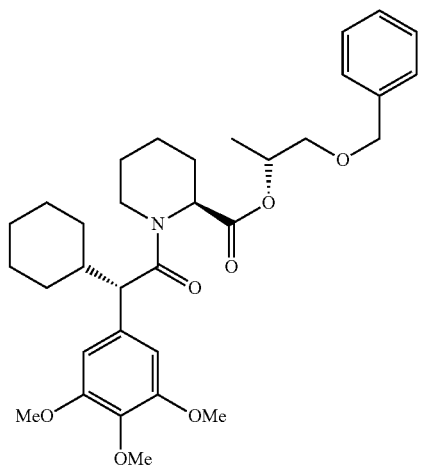

19 (33.4 mg, 0.108 mmol), HATU (41.1 mg, 0.108 mmol) and N-ethyl-N-isopropylpropan-2-amine (74.6 μL, 0.433 mmol) were dissolved in 0.5 mL DMF and stirred for 5 min followed by the addition of (S)-(R)-1-(benzyloxy)propan-2-yl piperidine-2-carboxylate (30.0 mg, 0.108 mmol) dissolved in 0.5 mL DCM. The reaction mixture was stirred for 3 h. The crude product was concentrated and purified using flash chromatography (gradient 0-50% EtOAc in cyclohexane). C24 was obtained as a colorless oil (43 mg, 0.076 mmol, 70%).

TLC [EtOAc/cyclohexane, 3:7]: $R_f$=0.34.
HPLC [0-100% Solvent B, 20 min]: $R_t$=23.7 min, purity (220 nm)=90%.
Mass: (ESI⁻), calculated 568.33 $[C_{33}H_{46}NO_7+H]^+$, found 568.22 $[M+H]^+$.

Example 5-25

(R)-(R)-1-(benzyloxy)propan-2-yl-1-((S)-2-cyclohexyl-2-(3,4,5-trimethoxyphenyl) acetyl)piperidine-2-carboxylate C25

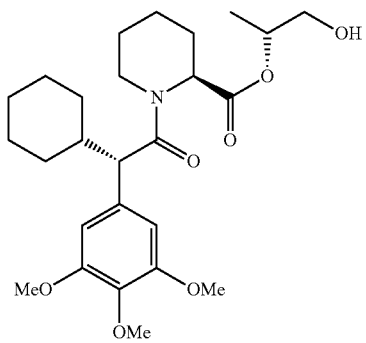

C24 (38.0 mg, 0.067 mmol) was dissolved in EtOH and degassed with Argon. Pd/C 10% (14.25 mg, 9.51 μmol) was added and the reaction was put under hydrogen atmosphere. The reaction mixture was stirred for 16 h. The Pd was filtered and the crude product was concentrated followed by purification using flash chromatography (gradient 0-50% EtOAc in cyclohexane).flash chromatography. C25 (12.0 mg, 25.0 μmol, 37%) was obtained as colorless oil.

TLC [EtOAc/cyclohexane, 3:7]: $R_f$=0.22.
LCMS [30-100% Solvent B, 15 min]: $R_t$=10.1 min, purity (220 nm)=99%.
Mass: (ESI$^-$), calculated 478.28 $[C_{26}H_{39}NO_7+H]^+$, found 478.25 $[M+H]^+$.

Example 6-A

Expression and Purification of FKBPs (FKBP51, FKBP51 (K58T/K60W/F129V), FKBP52, FKBP52 (T58K/W60K/V129F)

The protein expressions were performed according to Kozany, C.; Marz, A.; Kress, C.; Hausch, F., Fluorescent probes to characterise FK506-binding proteins. *Chembiochem* 2009, 10, (8), 1402-10.

Plasmids harbouring the cDNA of FKBP12 and expression plasmids for full-length FKBP51 and FKBP52 with additional carboxy terminal FLAG-tag were kindly provided by Dr. Theo Rein (Max Planck Institute for Psychiatry, Munich, Germany). Plasmids containing the cDNA sequences of FKBP12.6, −13 and −25 were kindly provided by Dr. Gunter Fischer (Max Planck Institute for Enzymology, Halle, Germany). FKBP12 was amplified with the sense primer: 5'-AAA GAA TTC ATG GGA GTG CAG GTG GAA ACC-3', and the antisense primer: 5'-CCC GTC GAC TCA TTC CAG TTT TAG AAG CTC C-3'. Cloning into plasmid pProExHta (Invitrogen, Carlsbad, USA) was performed with the restriction enzymes EcoRI (NEB, Ipswich, USA) and SalI (NEB). For the amplification of the coding sequence of FKBP51FK1 the sense primer: 5'-CAT GCC ATG GCA ATG ACT GAT G-3', and the antisense primer: 5'-GCA GTC GAC TCA CTC TCC TTT GAA ATC AAG GAG C-3', were used. For FKBP52FK1 the sense primer: 5'-GCG CCA TGG GGA TGA CAG CCG AGG AG-3', and the antisense primer: 5'-GTC GAC TCA TTC TCC CTT AAA CTC AAA CAA CTC-3' were utilized. FKBP51FK1 was cloned into pProExHta by using the restriction enzymes NcoI (NEB) and XbaI (NEB), FKBP52FK1 was cloned with NcoI and SalI. FKBP12.6 was amplified by using the sense primer: 5'-CCG GAA TTC ATG GGC GTG GAG ATC GAG-3', and the antisense primer: 5'-CTC GAG TCA CTC TAA GTT GAG CAG CTC-3'. For FKBP13, the sense primer: 5'-CCG GAA TTC AAA AGG AAG CTG CAG ATC GG-3', and the antisense primer: 5'-CTC GAG TTA CAG CTC AGT TCG CTC-3', were used to amplify a truncated fragment of FKBP13 (amino acids 27-142) without a leader peptide. Full-length FKBP25 was amplified by using the sense primer: 5'-CCG GAA TTC ATG GCG GCC GTT CC-3', and the antisense primer: 5'-CTC GAG TCA ATC AAT ATC CAC TAA TTC-3'. The PCR products of FKBP12.6, −13 and −25 were cloned into pProExHta by using the restriction enzymes EcoRI and XhoI (NEB).

Induction of protein expression in *E. coli* BL21(DE3) pLysS was performed by addition of IPTG (0.6 mM; Eppendorf, Hamburg, Germany). FKBP12, FKBP12.6, FKBP13, FKBP25, FKBP52, FKBP51FK1 and FKBP52FK1 were purified by a single Ni-NTA (Qiagen, Hilden, Germany) affinity column. The standard protocol was modified by using HEPES (50 mM, pH 8), NaCl (20 mM), glycerol (10%) and imidazol (30 mM) as washing buffer. The elution buffer was HEPES (50 mM, pH 8), NaCl (20 mM), glycerol (10%) and imidazol (300 mM). For full-length FKBP51 a tandem purification strategy was employed by using Ni-NTA chromatography as the first step and an additional FLAG affinity chromatography as the second step. The eluate from the Ni-NTA column was passed over FLAG M2 affinity gel (Sigma-Aldrich, St. Louis, USA) and eluted with FLAG-peptide (100 μg mL-1; Sigma-Aldrich). Proteins were analysed by SDS-PAGE and stained with Coomassie brilliant blue (Carl Roth GmbH, Karlsruhe, Germany). The protein yield was quantified by UV quantification or Bradford assay (BioRad, Hercules, USA).

Example 6-B

Fluorescence Polarization (FP) Assays

In-vitro fluorescence polarization assays were performed to determine the binding affinities for FKBP51 and 52 according to a literature procedure (Kozany, C.; Marz, A.; Kress, C.; Hausch, F., Fluorescent probes to characterise FK506-binding proteins. *Chembiochem* 2009, 10, (8), 1402-10).

For fluorescence polarization assays the fluorescent ligand F2 or F4 was dissolved in HEPES (20 mm, pH 8), Triton-X100 (0.01%), at double the concentration required for the final sample. The target protein was also diluted in this assay buffer at double the highest concentration required for the final sample. This protein stock was used for a 1:1 serial dilution.

The fluorescent ligand F2 or F4 was diluted in assay buffer to a concentration double the final concentration (20 nM F2, 3 nM F4). The inventive compound was dissolved in DMSO to reach a 100-times concentrated stock solution. This was used for a 1:1 serial dilution in DMSO. Every sample of this serial dilution was diluted by a factor of 50 in assay buffer supplemented with ligand F2 or F4 to achieve a 2× concentrated mixture of ligand F2/F4 and the inventive compound. To each of these competitive ligand double the protein concentration for F2 assay: FKBP51$^{WT}$ 560 nM (2×280 nM), FKBP52$^{WT}$ 800 nM (2×400 nM), FKBP12$^{WT}$ 20 nM (2×10 nM), for F4 assay: FKBP51$^{WT}$ 10 nM diluted in assay buffer was added.

The samples were transferred to black 384-well assay plates (No.: 3575; Corning Life Sciences). After incubation at room temperature for 30 min the fluorescence anisotropy was measured (GENios Pro, Tecan, M_nnedorf, Switzerland) by using an excitation filters of 485/20 nm and emission filters of 535/25 nm. For FKBP12, −51, and −52 the binding assays were performed in duplicates in the plate format.

The competition curves were analyzed by using Sigma-Plot9. Data were fitted to a four parameter logistic curve to deduce the IC$_{50}$ values. For the analysis of K$_i$ values, data were fitted to the following equation (Z. X. Wang, FEBS Lett. 1995, 360, 111-114).

$$A=(A_{max}-A_{min})/[L]_t\times(([L]_t\times((2\times((K_{lig}+K_{comp}+[L]_t+[I]_t-[R]_t)^2-3\times(K_{comp}\times([L]_t-[R]_t)+K_{lig}\times([I]_t-[R]_t)+K_{lig}\times K_{comp})))^{\wedge}0.5\times COS(ARCCOS((-2\times(K_{lig}+K_{comp}+[L]_t+[I]_t-[R]_t)^{\wedge}3+9\times(K_{lig}+K_{comp}+[L]_t+[I]_t-[R]_t)\times(K_{comp}\times([L]_t-[R]_t)+K_{lig}\times([I]_t-[R]_t)+K_{lig}\times K_{comp})-27\times(-1\times K_{lig}\times K_{comp}\times[R]_t))/(2\times((((K_{lig}+K_{comp}+[L]_t+[I]_t-[R]_t)^2-3\times(K_{comp}\times([L]_t-[R]_t)+K_{lig}\times([I]_t-[R]_t)+K_{lig}\times K_{comp}))^{\wedge}3)^{\wedge}0.5)))/3))-(K_{lig}+K_{comp}+[L]_t+[I]_t-[R]_t))/((3\times K_{lig})+((2\times((K_{lig}+K_{comp}+[L]_t+[I]_t-[R]_t)^2-3\times(K_{comp}\times([L]_t-[R]_t)+K_{lig}\times([I]_t-[R]_t)+K_{lig}\times K_{comp}))^{\wedge}0.5\times COS(ARCCOS((-2\times(K_{lig}+K_{comp}+[L]_t+[I]_t-[R]_t)^{\wedge}3+9\times(K_{lig}+K_{comp}+[L]_t+[I]_t-[R]_t)\times(K_{comp}\times([L]_t-[R]_t)+K_{lig}\times([I]_t-[R]_t)+K_{lig}\times K_{comp})-27\times(-1\times K_{lig}\times K_{comp}\times[R]_t))/(2\times((((K_{lig}+K_{comp}+[L]_t+[I]_t-[R]_t)^2-3\times(K_{comp}\times([L]_t-[R]_t)+K_{lig}\times([I]_t-[R]_t)+K_{lig}\times K_{comp}))^{\wedge}3)^{\wedge}0.5)))/3))-(K_{lig}+K_{comp}+[L]_t+[I]_t-[R]_t))))+A_{min}$$

In this equation K$_{lig}$ and K$_{comp}$ stand for the K$_d$ values of the used tracer or competing inhibitor, [I]$_t$ is referring to the total concentration of the titrated inhibitor.

fied FK1-domains of FKBP51WT (4.5 nM) with F4 (3 nM), FKBP52WT (400 nM) with F2 (20 nM).

The compounds A02-A06, A08-A32, A36-A38 are selective FKBP51 inhibitors of which Ki values are:
K$_i$≤0.1 µM ++++
0.1 µM<K$_i$≤1 µM +++
1 µM<K$_i$≤10 µM ++
10 µM<K$_i$≤50 µM +
Selectivity over FKBP52 with a factor of: <5 not selective
>5 +
>50 ++
>500 +++
>5000 ++++

TABLE 5

Summary of Binding Assay (Ki values) of the compounds B01-B35 and C01-C25

| Compound | Ki(FKBP51)/Ki(FKBP52) | Affinity(Ki) for FKBP51 |
|---|---|---|
| Reference A01 | not selective | + |
| A02 | + | + |
| A03 | + | + |
| A04 | + | + |
| A05 | + | ++ |
| A06 | + | + |
| Reference A07 | not selective | + |
| A08 | + | ++ |
| A09 | + | + |
| A10 | + | + |
| A11 | +++ | ++++ |
| A12 | +++ | ++++ |
| A13 | +++ | ++++ |
| A14 | ++ | +++ |
| A15 | +++ | ++++ |
| A16 | ++ | +++ |
| A17 | ++++ | ++++ |

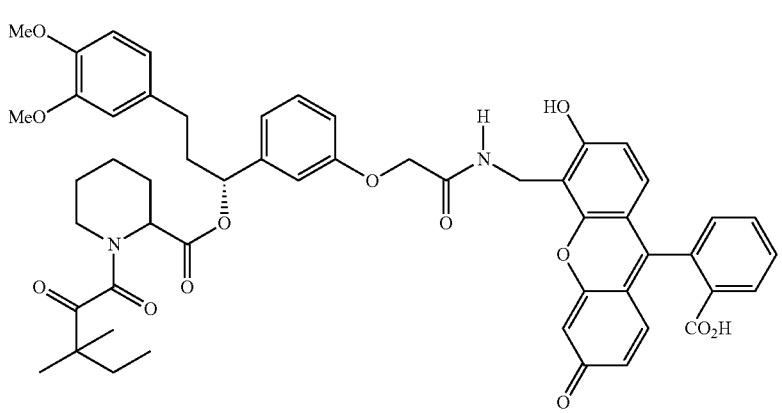

F2

These assays revealed that Cα-substitutents (R*) consistently induced a selectivity for FKBP51 vs. FKBP52. Furthermore, selected R*-substituents substantially increased the affinity for FKBP51 compared to all known FKBP51 ligands so far. Tables 4 and 5 summarize the binding data of exemplary compounds.

Table 4: Summary of Selectivity Factors FKBP51 vs. FKBP52

The Selectivity of the Compounds was Classified by Ki(FKBP51)/Ki(FKBP52)

Inhibition constants were measured in a fluorescence polarization binding assay by titrating the compounds. Puri- TABLE 5-continued Summary of Binding Assay (Ki values) of the compounds B01-B35 and C01-C25

| Compound | Ki(FKBP51)/Ki(FKBP52) | Affinity(Ki) for FKBP51 |
|---|---|---|
| A18 | ++++ | ++++ |
| A19 | +++ | ++++ |
| A20 | ++ | +++ |
| A21 | ++ | ++++ |
| A22 | ++ | +++ |
| A23 | + | + |
| A24 | + | + |

TABLE 5-continued

Summary of Binding Assay (Ki values) of the compounds B01-B35 and C01-C25

| Compound | Ki(FKBP51)/Ki(FKBP52) | Affinity(Ki) for FKBP51 |
|---|---|---|
| A25 | + | + |
| A26 | + | + |
| A27 | + | + |
| A28 | + | + |
| A29 | +++ | + |
| A30 | ++ | + |
| A31 | + | + |
| A32 | + | + |
| Reference A33 | not selective | |
| Reference A34 | not selective | |
| A36 | +++ | ++ |
| A37 | ++ | + |
| A38 | ++ | ++ |

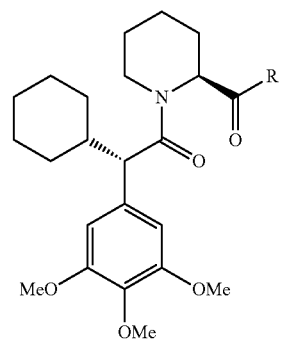

(VI)

The compounds B01-C25 are selective FKBP51 inhibitors of which Ki values are:
$K_i \leq 0.1$ μM ++++
$0.1$ μM $< K_i \leq 1$ μM +++
$1$ μM $< K_i \leq 10$ μM ++
$10$ μM $< K_i \leq 50$ μM +
Selectivity over FKBP52 with a factor of: >5 +
>50 ++
>500 +++
>5000 ++++

| Compound | R | Ki(FKBP51)/Ki(FKBP52) | Affinity(Ki) for FKBP51 |
|---|---|---|---|
| B01 |  | ++ | ++ |
| B02 |  | ++ | ++ |
| B03 |  | + | + |
| B04 |  | + | ++ |
| B05 |  | ++ | ++ |

-continued

| Compound | R | Ki(FKBP51)/Ki(FKBP52) | Affinity(Ki) for FKBP51 |
|---|---|---|---|
| B06 | | ++ | ++ |
| B07 | | + | + |
| B08 | | ++ | ++ |
| B09 | | ++ | + |
| B10 | | + | + |
| B11 | | +++ | ++ |
| B12 | | ++ | ++ |
| B13 | | ++ | ++ |

-continued

| Compound | R | Ki(FKBP51)/Ki(FKBP52) | Affinity(Ki) for FKBP51 |
|---|---|---|---|
| B14 | (S)-isoleucine amide | ++ | ++ |
| B15 | (R)-isoleucine amide | ++ | ++ |
| B16 | (S)-phenylglycine amide | ++ | ++ |
| B17 | (R)-phenylglycine amide | +++ | ++ |
| B18 | cyclohexylglycine amide | ++ | ++ |
| B19 | (S)-homoserine amide | ++ | + |
| B20 | (R)-homoserine amide | ++ | ++ |

-continued

| Compound | R | Ki(FKBP51)/Ki(FKBP52) | Affinity(Ki) for FKBP51 |
|---|---|---|---|
| B21 | (serinamide, S) | ++ | ++ |
| B22 | (serinamide, R) | ++ | ++ |
| B23 | (glutaminamide) | + | + |
| B24 | (glutaminamide) | ++ | ++ |
| B25 | (β-methyl-β-amino butanamide) | +++ | ++ |
| B26 | (1-aminocyclopropanecarboxamide) | ++ | + |
| B27 | (1-aminocyclobutanecarboxamide) | ++ | ++ |
| B28 | (1-aminocyclopentanecarboxamide) | ++++ | +++ |
| B29 | (β-alaninamide) | ++ | ++ |

| Compound | R | Ki(FKBP51)/Ki(FKBP52) | Affinity(Ki) for FKBP51 |
|---|---|---|---|
| B30 | 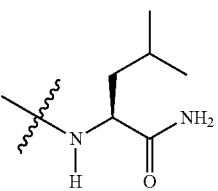 [SMILES: *N[C@@H](CC(C)C)C(N)=O] | ++ | ++ |
| B31 | 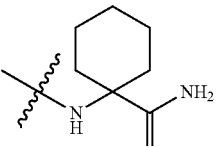 | ++ | ++ |
| B32 | 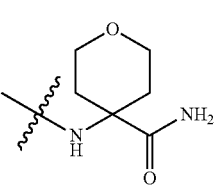 [SMILES: *NC1(C(N)=O)CCOCC1] | ++ | + |
| B33 | 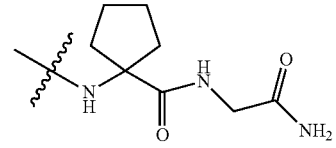 [SMILES: *NC1(C(=O)NCC(N)=O)CCCC1] | +++ | ++ |
| B34 | 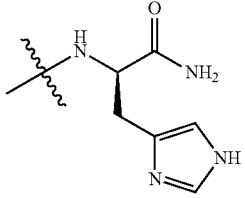 [SMILES: *N[C@H](Cc1c[nH]cn1)C(N)=O] | ++ | + |
| B35 | 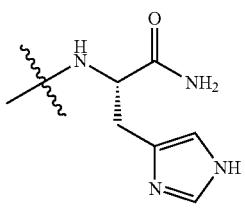 [SMILES: *N[C@@H](Cc1c[nH]cn1)C(N)=O] | + | + |
| C01 | 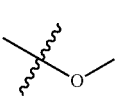 | ++ | ++ |
| C02 | 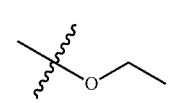 [SMILES: *OCC] | ++ | ++ |
| C03 | 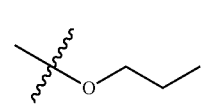 [SMILES: *OCCC] | +++ | ++ |
| C04 | 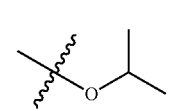 [SMILES: *OC(C)C] | +++ | +++ |

-continued
| Compound | R | Ki(FKBP51)/Ki(FKBP52) | Affinity(Ki) for FKBP51 |
|---|---|---|---|
| C05 | 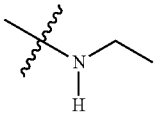 [SMILES: *NCC] | ++ | + |
| C06 | 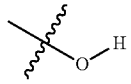 | + | + |
| C07 | 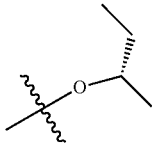 [SMILES: *O[C@@H](C)CC] | ++ | + |
| C08 | 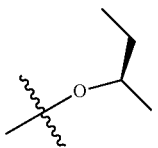 [SMILES: *O[C@H](C)CC] | ++ | ++ |
| C09 | 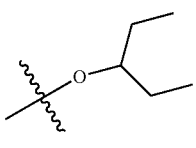 [SMILES: *OC(CC)CC] | ++ | + |
| C10 |  | +++ | ++ |
| C11 | 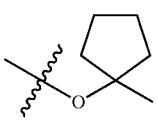 [SMILES: *OC1(C)CCCC1] | +++ | ++ |
| C12 | 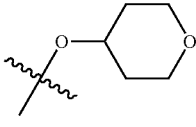 [SMILES: *OC1CCOCC1] | +++ | ++ |
| C13 | 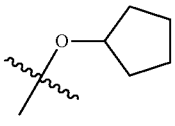 [SMILES: *OC1CCCC1] | +++ | ++ |
| C14 | 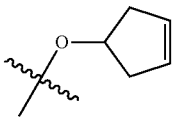 [SMILES: *OC1CC=CC1] | +++ | ++ |
| C15 | 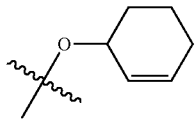 [SMILES: *OC1C=CCCC1] | ++ | ++ |

-continued
| Compound | R | Ki(FKBP51)/Ki(FKBP52) | Affinity(Ki) for FKBP51 |
|---|---|---|---|
| C16 | 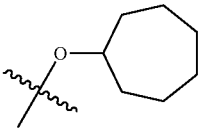 [SMILES: *OC1CCCCCC1] | ++ | + |
| C17 | 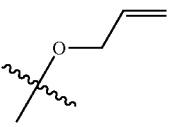 [SMILES: *OCC=C] | ++ | + |
| C18 | 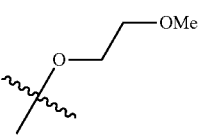 | ++ | ++ |
| C19 | 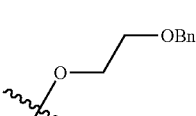 | ++ | ++ |
| C20 | 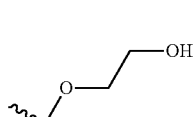 | +++ | ++ |
| C21 | 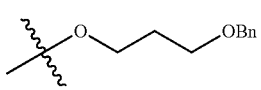 | ++ | ++ |
| C22 | 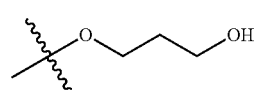 | +++ | ++ |
| C23 | 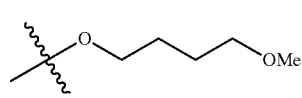 [SMILES: *OCCCCOC] | +++ | ++ |
| C24 | 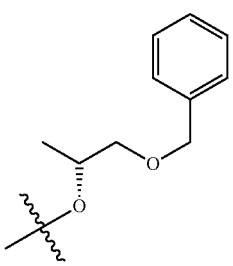 | +++ | ++ |
| C25 | 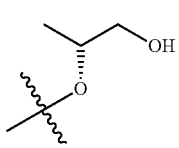 | ++ | ++ |

Example 6-C

Fluorescence Polarization (FP) Assays with FKBP Mutants

In-vitro fluorescence polarization assays were performed to determine the binding affinities for FKBP51, FKBP51 (K58T/K60W/F129V), FKBP52, FKBP52 (T58K/W60K/V129F).

For this fluorescence polarization assay the fluorescent tracer F2 and F4 were used.

Example 8

Crystallization Method of FKBP 51 and Measurement of FKBP 51 Crystal

The protein-ligand complex was prepared by mixing a 1.75 mM solution of a construct of FKBP51 comprising residues 16-140 and carrying mutation A19T in 20 mM Tris-HCl pH 8.0 and 50 mM NaCl with ligand dissolved in DMSO, so that the final ligand concentration was 2 mM and the DMSO concentration smaller than 10%. For crystalli-

F4

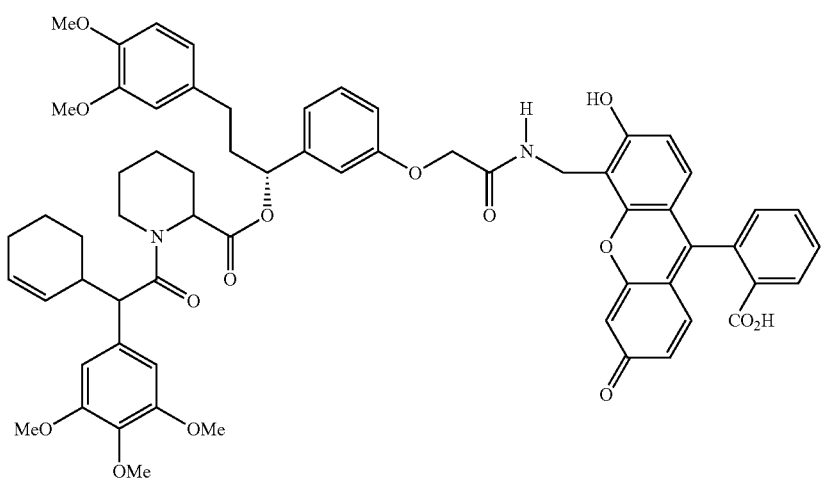

Example 7

N2a Cellular Assay

At day one N2a cells were plated into 24-well plates with cover slips (pretreated with polylysine) at a density of 35,000 cells/well and cultured with DMEM (incl. FCS 10% and Pen/Strep 1%) for 24 h. Next, cells were transfected with 80 ng expression plasmids encoding Venus as well as 720 ng pRK5 (mock transfection) in a total volume of 500 µl starvation media containing different concentrations of compounds or DMSO for 36 h (media without FCS; induction of neurite outgrowth). Therefore media was removed and replaced by 400 µl DMEM (empty). Next an equivalent volume of plasmids were given to 50 µl OPTIMEM and incubated for 5 min at RT. Additionally 1.5 µl Lipofectamine 2000 was separately dissolved in 50 µl OPTIMEM. After 5 min both solutions (plasmids and Lipofactamine 2000 containing media) were combined and incubated again for another 20 min. After that 100 µl of this mixture was given to 400 µl media per well. (See also protocol of the provider—Life Technologies).

Figure 1:
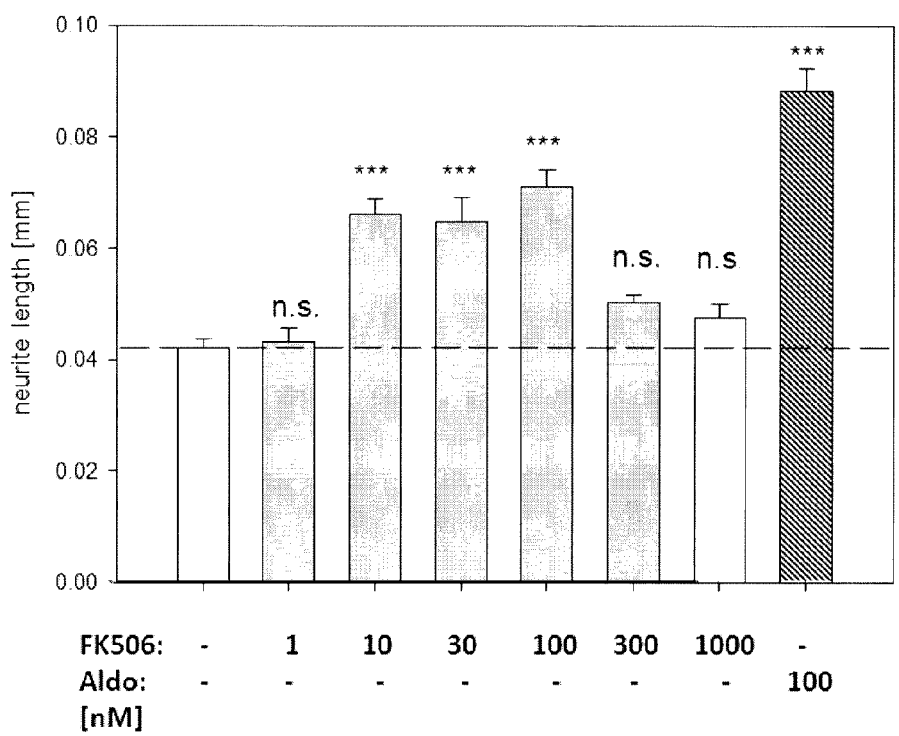
FIG. 1: Effects of FKBP51-selective ligands A17 (A) and A18 (D) on neurite outgrowth of N2a-cells. Both FKBP51-selective ligands promote neurite outgrowth in N2a cells more potently compared to FK506 (B). High concentrations do not lead to reduction of the neuronal differentiation (in contrast to unselective ligands like FK506. (C) FK506 decreases neurite outgrowth of N2a cells in a dose-dependent manner in the presence of 100 nM A17.
Figure 1:
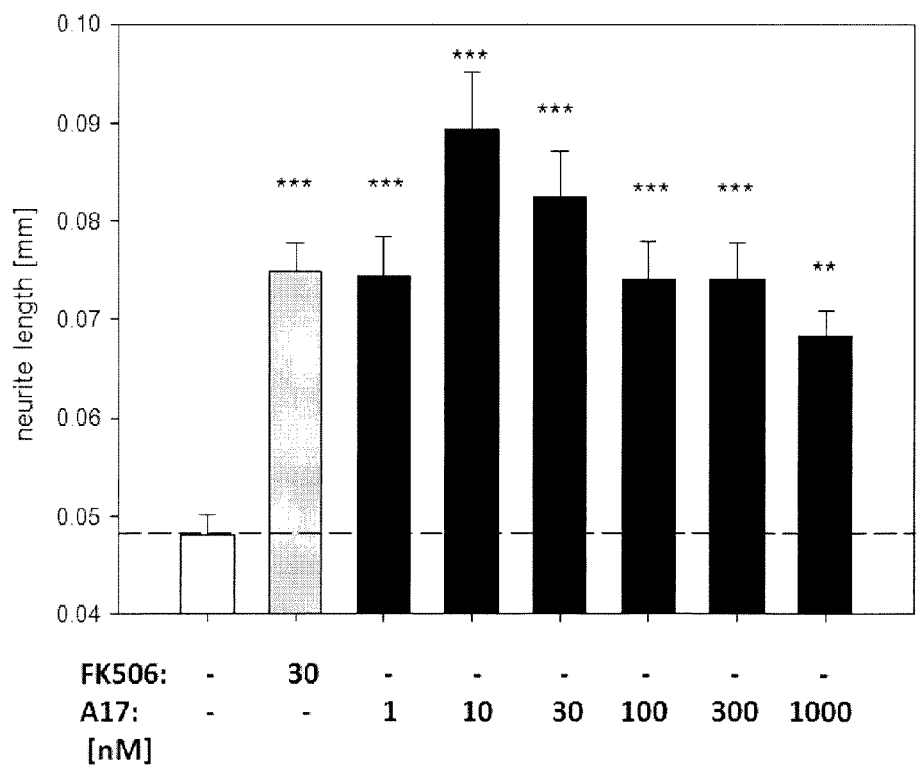
Figure 1:
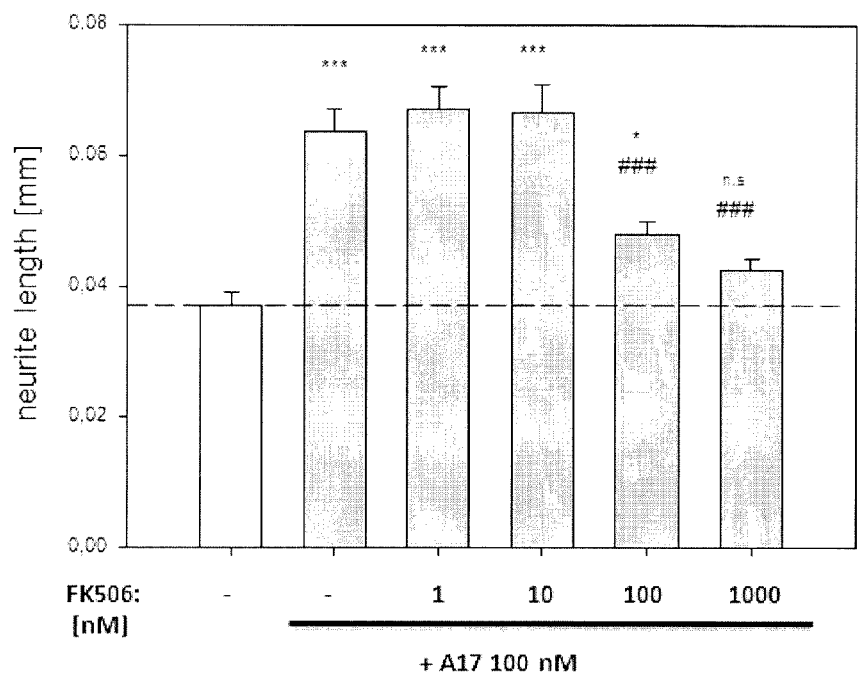
Figure 1:
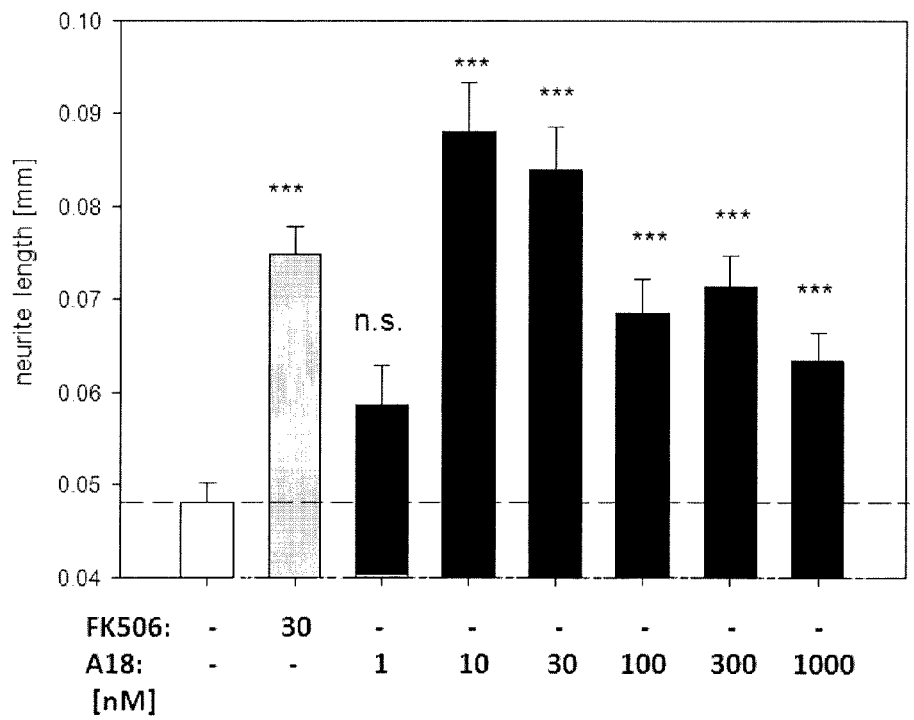
Figure 2:
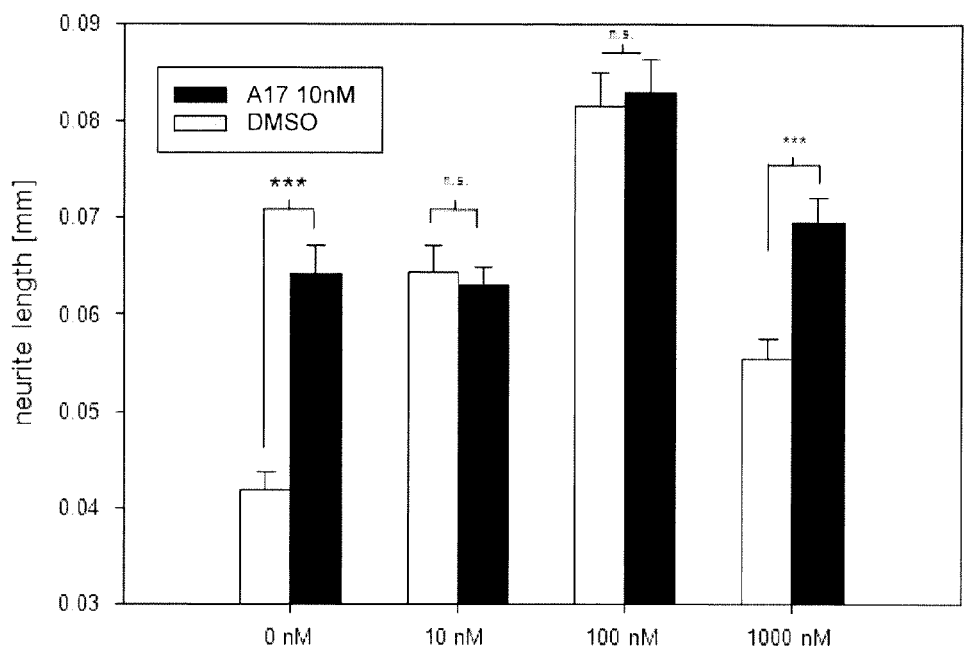
FIG. 2: (A) A17 rescues reduced neurite length triggered by 1 µM Ru26988 of N2a-cells. The GR-agonist Ru26988 enhances neurite outgrowth of N2a-cells until an optimal concentration of 100 nM. Higher concentrations leads to a reduction of neurite outgrowth (U-shaped dose-dependency). Reduction of neuronal differentiation can be blocked by addition of 10 nM A17.
Figure 2:
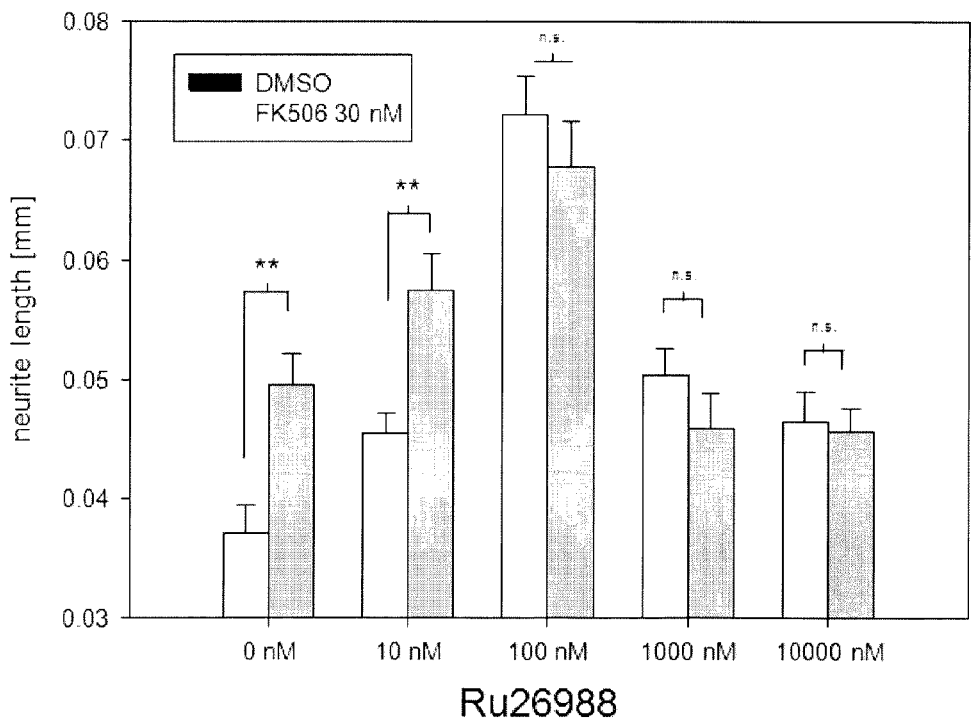
Figure 2:
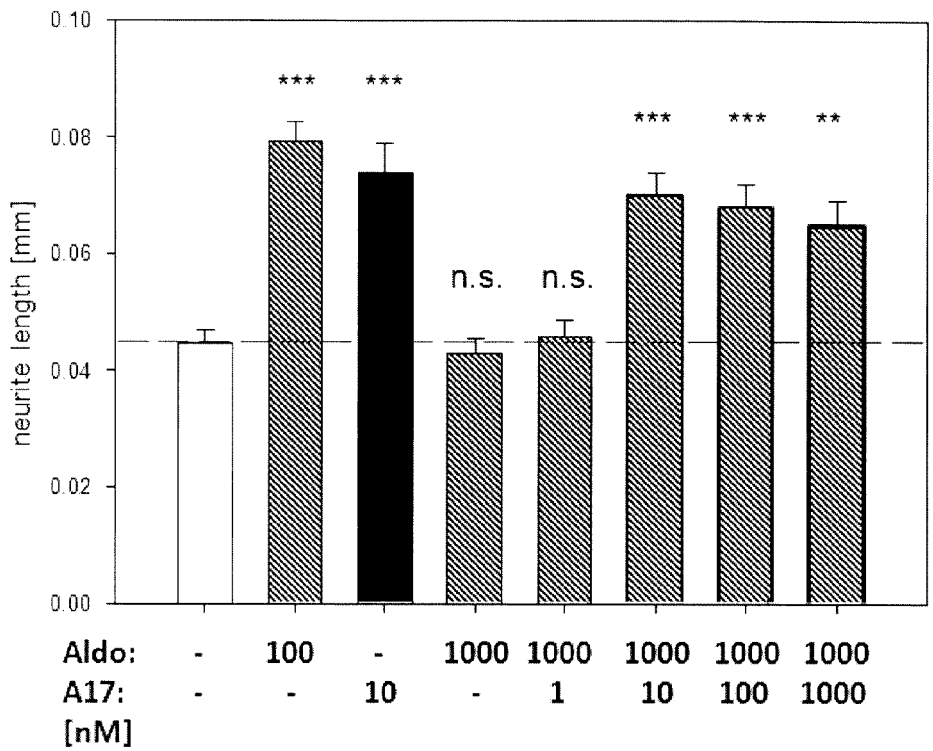
Figure 2:
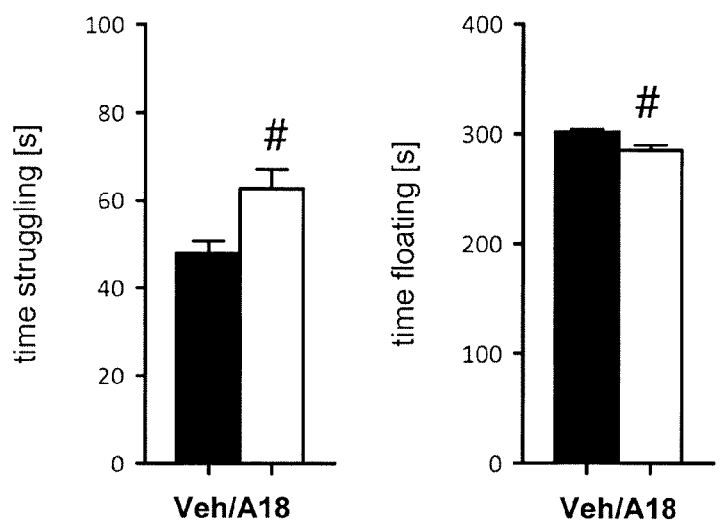
Figure 2:
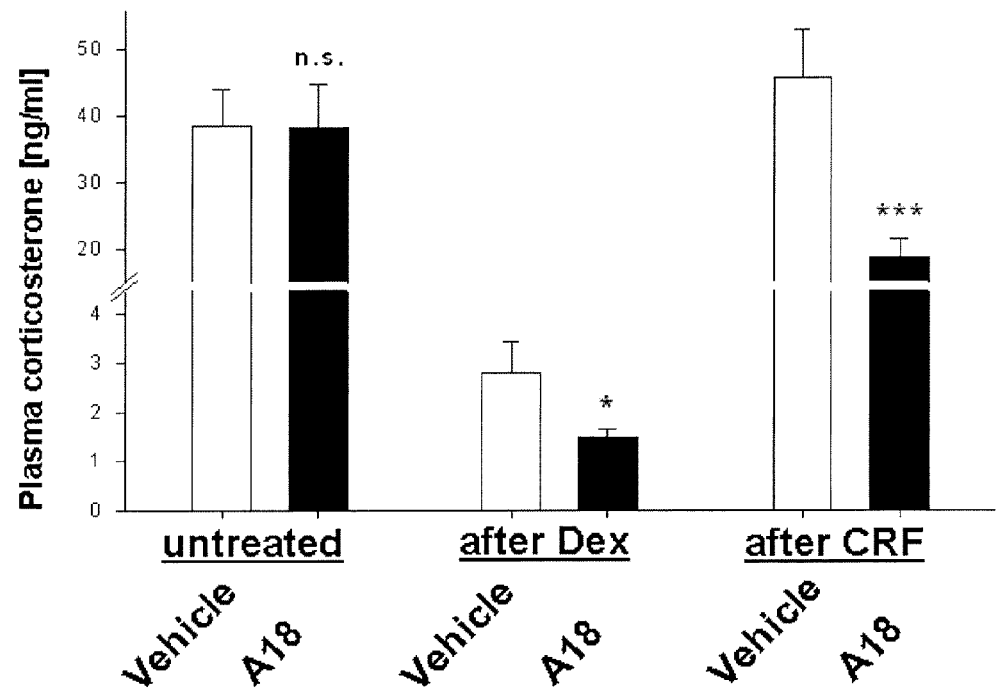

On the next day cells were washed with PBS and incubated for 30 min with 300 µl PFA (4%) and sucrose (5%) to fix cells. After fixation cells were washed three times, mounted onto microscope slides using 4 µl Vectashield (mounting media) and analyzed by fluorescence microscopy. Each bar represents the mean of the neurite length of 30-50 cells after the indicated treatment (FIGS. 1-2).

zation by the hanging-drop isothermal vapor diffusion method, 1 µl of the protein-ligand complex solution was mixed with 1 µl of a precipitant solution containing 25-35% PEG-3350, 0.2 M ammonium acetate and 0.1 M HEPES-NaOH pH 7.5, and equilibrated at 20° C. against 500 µl of the precipitant solution. Crystal formation took several days to weeks.

Single crystals were harvested and cryo-mounted for X-ray diffraction data collection at synchrotron light sources at 100 K. The oscillation data images were integrated and processed using the programs XDS, Pointless, Scala and Truncate. The structures were solved by molecular replacement using the program Molrep and the apo structure as a search template. The programs Coot and Refmac were used for model building and refinement.

Instructions for Superpositions

For superposition of FKBP51 structures, the program Isqkab, as implemented in the program suite CCP4 6.1 (10/04/08), was used. The following program commands were executed:

```
Isqkab xyzinm $name_r xyzinr $name_m\
RMSTAB $filename.tab <<EOF
FIT RESIDUE ALL 20 TO 137 CHAIN $ch_m
MATCH RESIDUE ALL 20 TO 137 CHAIN $ch_r
OUTPUT RMS
END
EOF
```

$name_m and $name_r are the filenames of the pdb-type coordinate files of new structure and reference structure, respectively. $ch_m and $ch_r specify the respective chain identifier of the respective FKBP51 protein chains in the coordinate files. $filename.tab is the name of the output file containing the list of residue rmsds.

Example 12

Behavioral Analysis

For the forced swim test (FST), male C57Bl/6N mice at the age of 12 weeks were single housed and acclimated to the room for 2 weeks before the experiment. Initially, mice were split into two groups (n=11 vehicle, n=11 A18) and received a single injection of either of 20.0 mg/kg bodyweight of compound A18 (solubilized in 4% EtOH, 5% Tween80, 5% PEG400 in 0.9% saline) or vehicle solution in the afternoon, 16 hours prior to testing. The next morning, mice were subjected to a FST to assess stress-coping behavior. Each mouse was put into a 2 l glass beaker for 6 min and analyzed using an automated video-tracking system (Anymaze 4.20, Stoelting, Ill., USA). Time spent immobile (floating) and time spent struggling was scored by an experienced observer, blind to treatment or condition of the animals.

TABLE 6

Coordinates of the atoms of the FKBP51 BINDING SURFACE in the Complex of A12 (Crystal From I)

| A12I | Res | number | x | y | z |
|---|---|---|---|---|---|
| CE1 | TYR(Y57) | 57 | −17.534 | −17.442 | −8.462 |
| CE2 | TYR(Y57) | 57 | −16.800 | −19.672 | −9.000 |
| CZ | TYR(Y57) | 57 | −17.248 | −18.414 | −9.398 |
| OH | TYR(Y57) | 57 | −17.398 | −18.103 | −10.742 |
| CB | ASP(D68) | 68 | −20.240 | −14.289 | −10.552 |
| CG | ASP(D68) | 68 | −19.636 | −15.496 | −11.261 |
| OD2 | ASP(D68) | 68 | −18.475 | −15.829 | −10.963 |
| CE2 | PHE(F77) | 77 | −12.257 | −21.051 | −10.429 |
| CZ | PHE(F77) | 77 | −12.637 | −20.473 | −11.654 |
| CA | VAL(V86) | 86 | −7.362 | −16.910 | −11.307 |
| C | VAL(V86) | 86 | −6.692 | −15.646 | −10.757 |
| CB | VAL(V86) | 86 | −8.099 | −17.687 | −10.170 |
| CG1 | VAL(V86) | 86 | −8.954 | −18.816 | −10.755 |
| N | ILE(I87) | 87 | −7.491 | −14.666 | −10.347 |
| CA | ILE(I87) | 87 | −6.929 | −13.428 | −9.779 |
| CB | ILE(I87) | 87 | −8.025 | −12.396 | −9.410 |
| CG1 | ILE(I87) | 87 | −9.007 | −12.992 | −8.385 |
| CG2 | ILE(I87) | 87 | −8.734 | −11.881 | −10.695 |
| CG | TRP(W90) | 90 | −10.052 | −16.555 | −6.068 |
| CD1 | TRP(W90) | 90 | −10.757 | −15.445 | −5.626 |
| CD2 | TRP(W90) | 90 | −11.016 | −17.584 | −6.279 |
| CE2 | TRP(W90) | 90 | −12.289 | −17.045 | −5.954 |
| CE3 | TRP(W90) | 90 | −10.931 | −18.921 | −6.715 |
| NE1 | TRP(W90) | 90 | −12.101 | −15.739 | −5.554 |
| CZ2 | TRP(W90) | 90 | −13.473 | −17.796 | −6.063 |
| CZ3 | TRP(W90) | 90 | −12.117 | −19.674 | −6.822 |
| CH2 | TRP(W90) | 90 | −13.367 | −19.107 | −6.485 |
| CE2 | TYR(Y13) | 113 | −11.637 | −9.899 | −11.543 |
| CZ | TYR(Y13) | 113 | −11.354 | −10.731 | −12.606 |
| OH | TYR(Y13) | 113 | −11.822 | −12.041 | −12.595 |
| CD1 | ILE(122) | 122 | −15.618 | −8.456 | −12.157 |
| CE1 | PHE(F130) | 130 | −15.015 | −14.048 | −6.814 |
| CZ | PHE(F130) | 130 | −14.033 | −13.070 | −6.945 |
| CAH | DRG(A12) | 1 | −17.624 | −11.138 | −9.034 |
| CAI | DRG(A12) | 1 | −16.507 | −11.773 | −9.572 |
| CAS | DRG(A12) | 1 | −18.758 | −10.764 | −9.764 |
| CAT | DRG(A12) | 1 | −18.554 | −10.734 | −11.278 |

TABLE 7

Coordinates of the atoms of the FKBP51 BINDING SURFACE in the Complex of A12 (Crystal From II)

| | | | | | |
|---|---|---|---|---|---|
| CE1 | TYR(Y57) | 57 | −17.494 | −17.472 | −8.444 |
| CE2 | TYR(Y57) | 57 | −16.813 | −19.687 | −9.026 |
| CZ | TYR(Y57) | 57 | −17.255 | −18.425 | −9.391 |
| OH | TYR(Y57) | 57 | −17.419 | −18.144 | −10.730 |
| CB | ASP(D68) | 68 | −20.142 | −14.330 | −10.466 |
| CG | ASP(D68) | 68 | −19.563 | −15.473 | −11.255 |
| OD2 | ASP(D68) | 68 | −18.396 | −15.823 | −10.984 |
| CE2 | PHE(F77) | 77 | −12.413 | −21.045 | −10.410 |
| CZ | PHE(F77) | 77 | −12.751 | −20.518 | −11.656 |
| CA | VAL(V86) | 86 | −7.464 | −16.858 | −11.315 |
| C | VAL(V86) | 86 | −6.765 | −15.608 | −10.773 |
| CB | VAL(V86) | 86 | −8.163 | −17.615 | −10.141 |
| CG1 | VAL(V86) | 86 | −9.006 | −18.727 | −10.691 |
| N | ILE(I87) | 87 | −7.551 | −14.653 | −10.277 |
| CA | ILE(I87) | 87 | −6.982 | −13.428 | −9.732 |
| CB | ILE(I87) | 87 | −8.080 | −12.418 | −9.367 |
| CG1 | ILE(I87) | 87 | −9.086 | −13.028 | −8.358 |
| CG2 | ILE(I87) | 87 | −8.766 | −11.905 | −10.658 |
| CG | TRP(W90) | 90 | −10.031 | −16.560 | −6.074 |
| CD1 | TRP(W90) | 90 | −10.749 | −15.438 | −5.682 |
| CD2 | TRP(W90) | 90 | −10.995 | −17.596 | −6.282 |
| CE2 | TRP(W90) | 90 | −12.274 | −17.047 | −6.015 |
| CE3 | TRP(W90) | 90 | −10.898 | −18.943 | −6.662 |
| NE1 | TRP(W90) | 90 | −12.095 | −15.736 | −5.635 |
| CZ2 | TRP(W90) | 90 | −13.445 | −17.792 | −6.137 |
| CZ3 | TRP(W90) | 90 | −12.055 | −19.667 | −6.796 |
| CH2 | TRP(W90) | 90 | −13.317 | −19.097 | −6.518 |
| CE2 | TYR(Y13) | 113 | −11.693 | −9.863 | −11.520 |
| CZ | TYR(Y13) | 113 | −11.380 | −10.712 | −12.557 |
| OH | TYR(Y13) | 113 | −11.844 | −12.016 | −12.563 |
| CD1 | ILE(122) | 122 | −15.550 | −8.503 | −12.219 |
| CE1 | PHE(F130) | 130 | −14.919 | −14.038 | −6.827 |
| CZ | PHE(F130) | 130 | −13.983 | −13.032 | −6.979 |
| CAH | DRG(A12) | 1 | −17.583 | −11.165 | −9.069 |
| CAI | DRG(A12) | 1 | −16.495 | −11.873 | −9.610 |
| CAS | DRG(A12) | 1 | −18.698 | −10.717 | −9.797 |
| CAT | DRG(A12) | 1 | −18.511 | −10.730 | −11.322 |

TABLE 8

Coordinates of the atoms of the FKBP51 BINDING SURFACE in the Complex of A22

| A22 | Res | number | x | y | z |
|---|---|---|---|---|---|
| CE1 | TYR(Y57) | 57 | −17.435 | −17.393 | −8.425 |
| CE2 | TYR(Y57) | 57 | −16.849 | −19.655 | −9.078 |
| CZ | TYR(Y57) | 57 | −17.186 | −18.355 | −9.429 |
| OH | TYR(Y57) | 57 | −17.266 | −17.986 | −10.735 |
| CB | ASP(D68) | 68 | −20.255 | −14.402 | −10.452 |
| OD2 | ASP(D68) | 68 | −18.432 | −15.671 | −10.907 |
| CZ | PHE(F77) | 77 | −13.024 | −20.103 | −11.356 |
| CA | VAL(V86) | 86 | −7.370 | −16.959 | −11.336 |
| C | VAL(V86) | 86 | −6.642 | −15.696 | −10.798 |
| CB | VAL(V86) | 86 | −8.045 | −17.714 | −10.131 |
| CG1 | VAL(V86) | 86 | −8.909 | −18.912 | −10.684 |
| N | ILE(I87) | 87 | −7.466 | −14.747 | −10.383 |
| CA | ILE(I87) | 87 | −6.890 | −13.536 | −9.825 |
| CB | ILE(I87) | 87 | −8.019 | −12.493 | −9.454 |
| CG1 | ILE(I87) | 87 | −9.036 | −13.096 | −8.463 |
| CG2 | ILE(I87) | 87 | −8.639 | −11.914 | −10.764 |
| CG | TRP(W90) | 90 | −10.012 | −16.672 | −6.020 |
| CD1 | TRP(W90) | 90 | −10.640 | −15.510 | −5.587 |
| CD2 | TRP(W90) | 90 | −11.017 | −17.620 | −6.226 |
| CE2 | TRP(W90) | 90 | −12.274 | −17.007 | −5.955 |
| CE3 | TRP(W90) | 90 | −10.956 | −18.968 | −6.675 |
| NE1 | TRP(W90) | 90 | −11.994 | −15.700 | −5.559 |
| CZ2 | TRP(W90) | 90 | −13.454 | −17.720 | −6.077 |
| CZ3 | TRP(W90) | 90 | −12.110 | −19.632 | −6.796 |
| CH2 | TRP(W90) | 90 | −13.378 | −19.030 | −6.512 |
| CE2 | TYR(Y13) | 113 | −11.705 | −9.616 | −11.441 |
| CZ | TYR(Y13) | 113 | −11.436 | −10.403 | −12.580 |
| OH | TYR(Y13) | 113 | −11.907 | −11.692 | −12.607 |
| CE1 | PHE(F130) | 130 | −14.935 | −13.999 | −6.763 |
| CZ | PHE(F130) | 130 | −13.966 | −12.990 | −6.872 |
| CAU | DRG(A22) | 1 | −17.304 | −10.566 | −9.106 |
| CAZ | DRG(A22) | 1 | −16.608 | −11.888 | −9.535 |
| CAS | DRG(A22) | 1 | −18.670 | −10.506 | −9.816 |

TABLE 9

Coordinates of the atoms of the FKBP51 BINDING SURFACE in the Complex of A09

| A09 | Res | number | x | y | z |
|---|---|---|---|---|---|
| CE1 | TYR(Y57) | 57 | −17.562 | −17.376 | −8.501 |
| | TYR(Y57) | | | | |
| CZ | TYR(Y57) | 57 | −17.361 | −18.391 | −9.440 |
| OH | TYR(Y57) | 57 | −17.596 | −18.144 | −10.775 |
| CB | ASP(D68) | 68 | −20.411 | −14.383 | −10.579 |
| CG | ASP(D68) | 68 | −19.798 | −15.577 | −11.272 |
| OD2 | ASP(D68) | 68 | −18.629 | −15.887 | −10.940 |
| | PHE(F77) | | | | |
| CZ | PHE(F77) | 77 | −12.697 | −20.488 | −11.661 |
| CA | VAL(V86) | 86 | −7.389 | −16.925 | −11.247 |
| C | VAL(V86) | 86 | −6.719 | −15.637 | −10.731 |
| CB | VAL(V86) | 86 | −8.081 | −17.656 | −10.081 |
| CG1 | VAL(V86) | 86 | −8.917 | −18.800 | −10.595 |
| N | ILE(I87) | 87 | −7.492 | −14.663 | −10.252 |
| CA | ILE(I87) | 87 | −6.920 | −13.441 | −9.685 |
| CB | ILE(I87) | 87 | −7.999 | −12.411 | −9.298 |
| CG1 | ILE(I87) | 87 | −8.975 | −13.000 | −8.271 |
| CG2 | ILE(I87) | 87 | −8.719 | −11.909 | −10.548 |
| | TRP(W90) | | | | |
| | TRP(W90) | | | | |
| CD2 | TRP(W90) | 90 | −10.931 | −17.586 | −6.347 |
| CE2 | TRP(W90) | 90 | −12.197 | −17.009 | −6.071 |
| CE3 | TRP(W90) | 90 | −10.869 | −18.916 | −6.753 |
| NE1 | TRP(W90) | 90 | −11.987 | −15.711 | −5.674 |
| CZ2 | TRP(W90) | 90 | −13.397 | −17.719 | −6.211 |
| CZ3 | TRP(W90) | 90 | −12.069 | −19.625 | −6.910 |
| CH2 | TRP(W90) | 90 | −13.308 | −19.028 | −6.636 |
| CE2 | TYR(Y13) | 113 | −11.687 | −9.984 | −11.502 |
| CZ | TYR(Y13) | 113 | −11.427 | −10.807 | −12.590 |
| OH | TYR(Y13) | 113 | −11.906 | −12.110 | −12.614 |
| CD1 | ILE(122) | 122 | −15.663 | −8.581 | −11.760 |
| CE1 | PHE(F130) | 130 | −14.917 | −13.982 | −6.817 |
| CZ | PHE(F130) | 130 | −14.001 | −12.952 | −6.974 |
| CAY | DRG(A09) | 1 | −16.925 | −11.302 | −8.697 |
| CBX | DRG(A09) | 1 | −17.264 | −12.300 | −9.797 |
| CAX | DRG(A09) | 1 | −18.070 | −11.014 | −9.643 |

TABLE 10

Coordinates of the atoms of the FKBP51 BINDING SURFACE in the Complex of A01

| A01 | Res | number | x | y | z |
|---|---|---|---|---|---|
| CE1 | TYR(Y57) | 57 | −17.399 | −17.498 | −8.429 |
| CE2 | TYR(Y57) | 57 | −16.783 | −19.726 | −9.105 |
| CZ | TYR(Y57) | 57 | −17.104 | −18.425 | −9.435 |
| OH | TYR(Y57) | 57 | −17.188 | −18.051 | −10.772 |
| OD2 | ASP(D68) | 68 | −18.327 | −15.866 | −10.901 |
| CE2 | PHE(F77) | 77 | −12.182 | −20.911 | −10.291 |
| CZ | PHE(F77) | 77 | −12.696 | −20.137 | −11.290 |
| CA | VAL(V86) | 86 | −7.311 | −16.898 | −11.357 |
| C | VAL(V86) | 86 | −6.641 | −15.637 | −10.834 |
| CB | VAL(V86) | 86 | −7.960 | −17.651 | −10.150 |
| CG1 | VAL(V86) | 86 | −8.819 | −18.862 | −10.631 |
| N | ILE(I87) | 87 | −7.455 | −14.696 | −10.370 |
| CA | ILE(I87) | 87 | −6.906 | −13.454 | −9.817 |
| CB | ILE(I87) | 87 | −8.003 | −12.473 | −9.420 |
| CG1 | ILE(I87) | 87 | −9.048 | −13.091 | −8.467 |
| CG2 | ILE(I87) | 87 | −8.656 | −11.899 | −10.679 |
| CG | TRP(W90) | 90 | −10.034 | −16.690 | −6.082 |
| CD1 | TRP(W90) | 90 | −10.680 | −15.542 | −5.683 |
| CD2 | TRP(W90) | 90 | −11.041 | −17.675 | −6.297 |
| CE2 | TRP(W90) | 90 | −12.295 | −17.072 | −5.997 |
| CE3 | TRP(W90) | 90 | −11.013 | −19.023 | −6.707 |
| NE1 | TRP(W90) | 90 | −12.047 | −15.763 | −5.629 |
| CZ2 | TRP(W90) | 90 | −13.513 | −17.785 | −6.116 |
| CZ3 | TRP(W90) | 90 | −12.215 | −19.716 | −6.817 |
| CH2 | TRP(W90) | 90 | −13.447 | −19.106 | −6.506 |
| CE2 | TYR(Y13) | 113 | −11.791 | −9.790 | −11.568 |
| CZ | TYR(Y13) | 113 | −11.416 | −10.642 | −12.595 |
| OH | TYR(Y13) | 113 | −11.878 | −11.936 | −12.632 |
| CE1 | PHE(F130) | 130 | −15.132 | −14.049 | −6.934 |
| CZ | PHE(F130) | 130 | −14.120 | −13.066 | −6.947 |
| CAA | DRG(A01) | 1 | −16.487 | −11.284 | −8.958 |
| CAK | DRG(A01) | 1 | −16.973 | −12.118 | −9.926 |

TABLE 11

Data collection and Refinement Statistics

| Dataset | AB3007 | AA9426 | AA9429 | puck4-1 |
|---|---|---|---|---|
| Ligand | A09 | A12 (Form I) | A12 (Form II) | A22 |
| beamline | SLS, PX-II | ESRF, ID23-1 | ESRF, ID23-1 | SLS, PX-II |
| wavelength (Å) | 1.000 | 0.97780 | 0.97931 | 1.03679 |
| space group | $P2_12_12$ | $C222_1$ | $P2_12_12$ | $P2_12_12_1$ |
| cell dimensions, | | | | |
| a, b, c (Å); | 48.439, | 48.745, | 49.262, | 45.029, |
| | 60.233, | 84.709, | 60.934, | 48.414, |
| | 38.071; | 61.390; | 38.059; | 56.852; |
| α, β, γ (°) | 90, 90, 90 | 90, 90, 90 | 90, 90, 90 | 90, 90, 90 |
| resolution limits (Å)* | 37.75-1.4 | 42.35-1.75 | 38.32-1.25 | 48.41-1.3 |
| | (1.48-1.4) | (1.85-1.75) | (1.32-1.25) | (1.37-1.3) |
| Rmerge**,* | 0.057 (0.421) | 0.087 (0.463) | 0.046 (0.406) | 0.053 (1.043) |
| I/sigma**,* | 11.9 (2.3) | 16.5 (3.7) | 15.8 (2.3) | 15.7 (1.7) |
| multiplicity* | 3.0 (2.3) | 7.0 (7.0) | 3.5 (2.5) | 8.3 (7.4) |
| completeness (%)* | 95.0 (89.2) | 99.4 (96.0) | 92.4 (63.7) | 99.5 (97.0) |
| Wilson B-factor (Å$^2$) | 16.05 | 15.82 | 8.39 | |
| Refinement | | | | |
| resolution range | 20-1.4 | 20-1.75 | 20-1.25 | 20-1.3 |
| reflections (test set) | 19956 (1106) | 12428 (640) | 28325 (1523) | 29475 (1550) |
| Rcryst | 0.20587 | 0.19399 | 0.16999 | 0.19288 |
| Rfree | 0.24668 | 0.23176 | 0.20428 | 0.21853 |
| number of atoms | 1166 | 1143 | 1245 | 1169 |
| r.m.s.d. bonds (Å) | 0.012 | 0.012 | 0.012 | 0.028 |
| r.m.s.d. angles (°) | 1.560 | 1.451 | 1.640 | 2.503 |

TABLE 11-continued

| Data collection and Refinement Statistics | | | | |
|---|---|---|---|---|
| Dataset | AB3007 | AA9426 | AA9429 | puck4-1 |
| Ramachandran plot | | | | |
| % most favored region*** | ? | ? | ? | ? |
| % additionally allowed*** | ? | ? | ? | ? |

*Values in parenthesis for outer shell.
**As defined in Scala.
***As defined in Coot.

Human FKBP51(13-139)$^{A19T}$
SEQ ID NO: 15

GLY ALA PRO ALA THR VAL THR GLU$^{20}$ GLN GLY GLU ASP

ILE THR SER LYS LYS ASP$^{30}$ ARG GLY VAL LEU LYS ILE

VAL LYS ARG VAL$^{40}$ GLY ASN GLY GLU GLU THR PRO MET

ILE GLY$^{50}$ ASP LYS VAL TYR VAL HIS TYR LYS GLY LYS$^{60}$

LEU SER ASN GLY LYS LYS PHE ASP SER SER$^{70}$ HIS ASP

ARG ASN GLU PRO PHE VAL PHE SER$^{80}$ LEU GLY LYS GLY

GLN VAL ILE LYS ALA TRP$^{90}$ ASP ILE GLY VAL ALA THR

MET LYS LYS GLY$^{100}$ GLU ILE CYS HIS LEU LEU CYS LYS

PRO GLU$^{110}$ TYR ALA TYR GLY SER ALA GLY SER LEU

PRO$^{120}$ LYS ILE PRO SER ASN ALA THR LEU PHE PHE$^{130}$

GLU ILE GLU LEU LEU ASP PHE LYS GLY

Residues of the FKBP51 BINDING SITE are highlighted in bold.

Example 13

Neuroendocrine Analysis

The combined Dex/CRH test was performed as described previously (Touma et al., Biol. Psych. 2011, 70, 928-36). Briefly, a reference blood sample was collected by an incision in the ventral tail vessel at 1500, three days prior to the actual test ('untreated' value). On the experimental day, at 0900, the mice (10 week old male C57BL/6 mice, n=10 per group) were injected intraperitoneally (i.p.) with either vehicle or compound A18 (20 mg/kg) immediately followed by an i.p. injection of dexamethasone (Dex, 0.05 mg/kg, ratiopharm GmbH, Ulm, Germany). The injected volume was 0.3 ml for each injection. At 1500, a second blood sample was drawn from the tail vessel ('after Dex' value), immediately followed by an i.p. injection of CRH (0.15 mg/kg). Thirty minutes later, the mice were sacrificed and trunk blood was collected ('after CRH' value). All blood samples were stored frozen at −20° C. until plasma CORT concentrations were analysed as described previously (Touma et al., Psychoneuroendocrinol. 2008, 33, 839-62).

The invention claimed is:

1. Compound of the general formula (I):

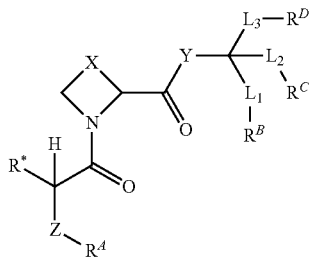

wherein

X represents —CH₂CH₂CH₂—, —CH═CHCH₂—, —CH₂SCH₂—, —CH₂OCH₂—, or —SCH₂CH₂—;

Y represents —NH—, or —O—;

Z represents a covalent bond, —NHCO—, —CHR$^{39}$—NHCO—, or —CH(NHCOR$^{39}$)—;

R* represents —R$^{18}$, —CH₂—R$^{18}$, —R, —CH₂—R, —CH(OR')R", —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —CH₂-cyclo-C₃H₅, —CH₂-cyclo-C₆H₁₁, —CH₂—CH═CH₂, —CH₂-cyclo-C₆H₉, -Ph, —CH₂-Ph, -cyclo-C₆H₁₁, -cyclo-C₅H₉, —CH₂—C(CH₃)═CH₂, —CH(CH₃)-cyclo-C₃H₅, or —CH(CH₃)—CH═CH₂;

R** represents

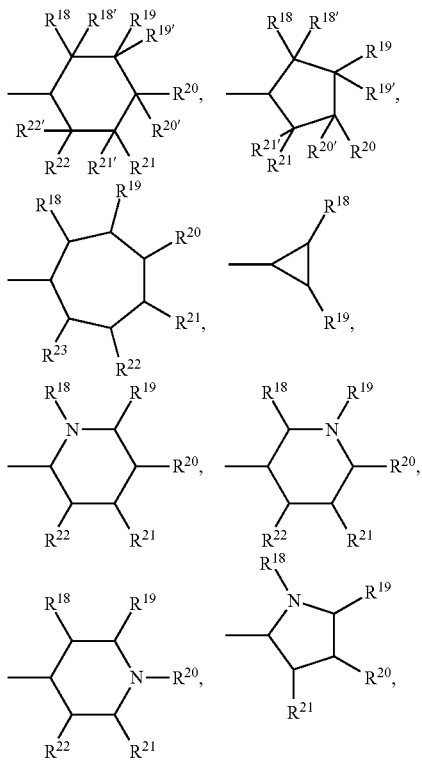
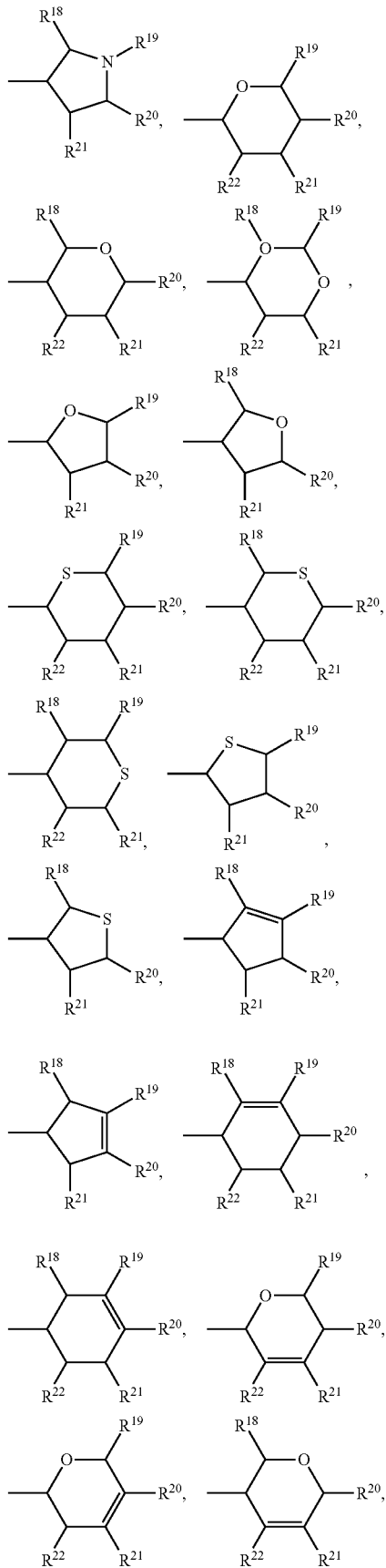

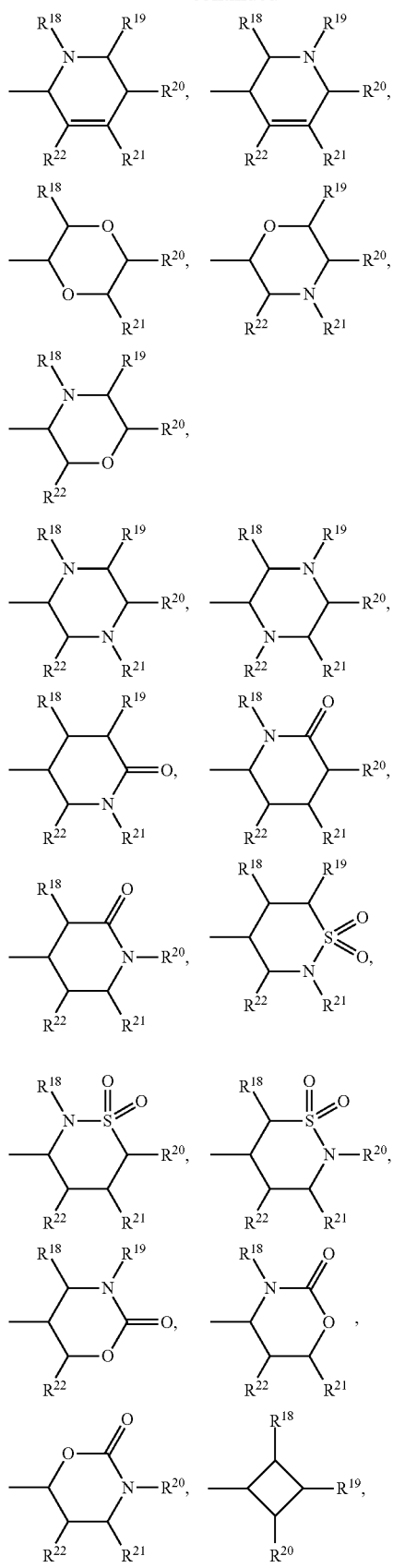
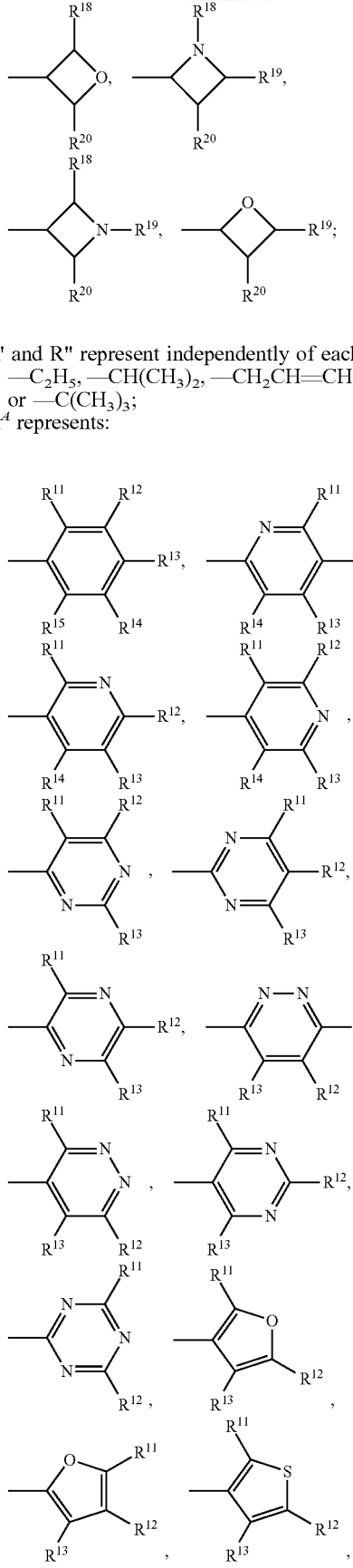
R' and R" represent independently of each other —$CH_3$, —$C_2H_5$, —$CH(CH_3)_2$, —$CH_2CH=CH_2$, -cyclo-$C_3H_5$, or —$C(CH_3)_3$;
$R^A$ represents:

-continued
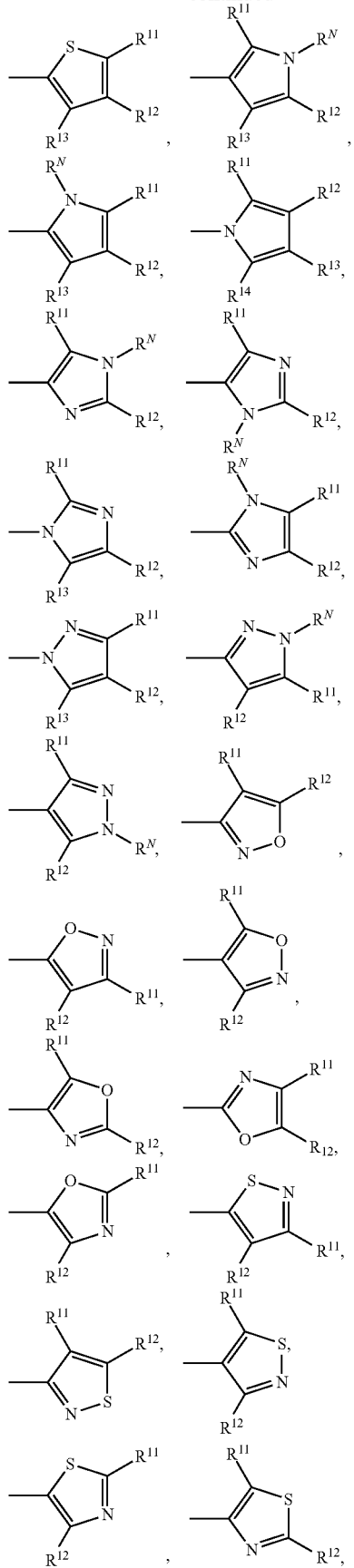
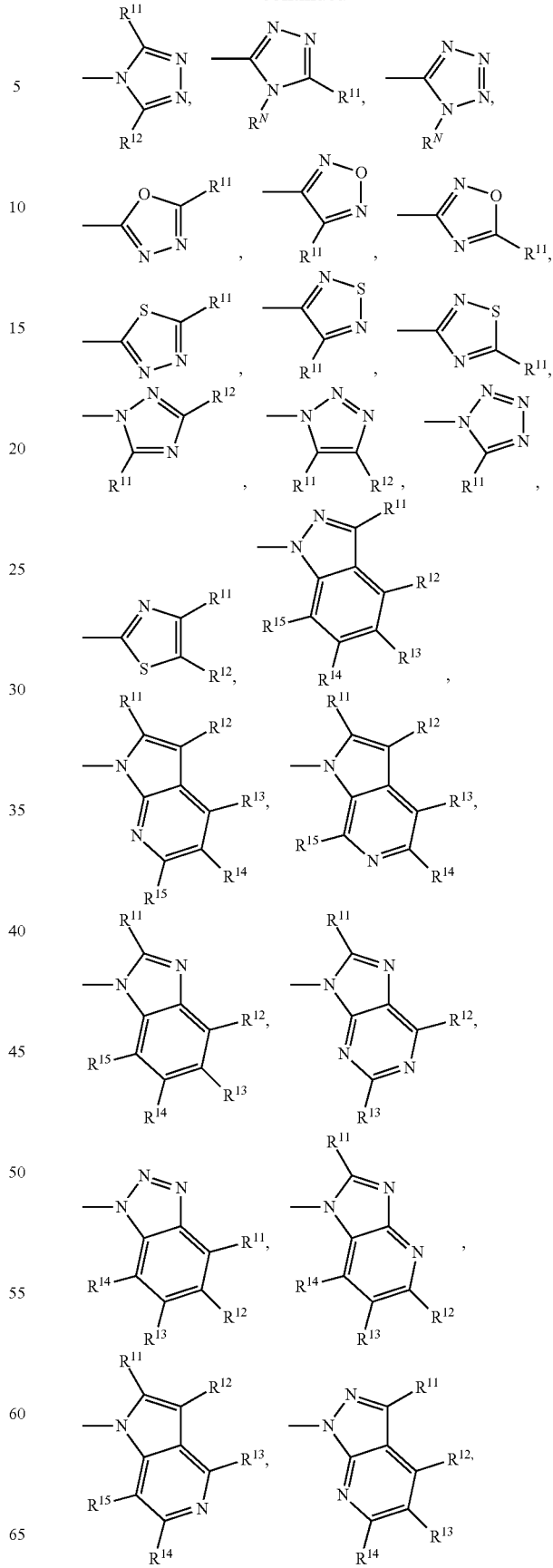

-continued
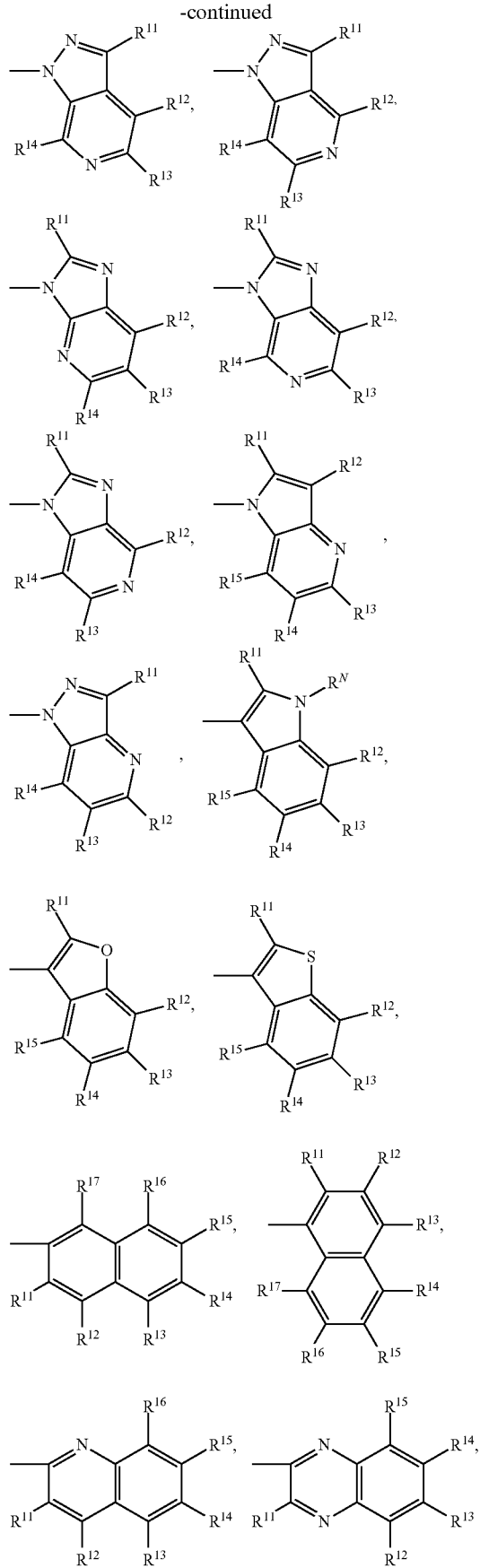
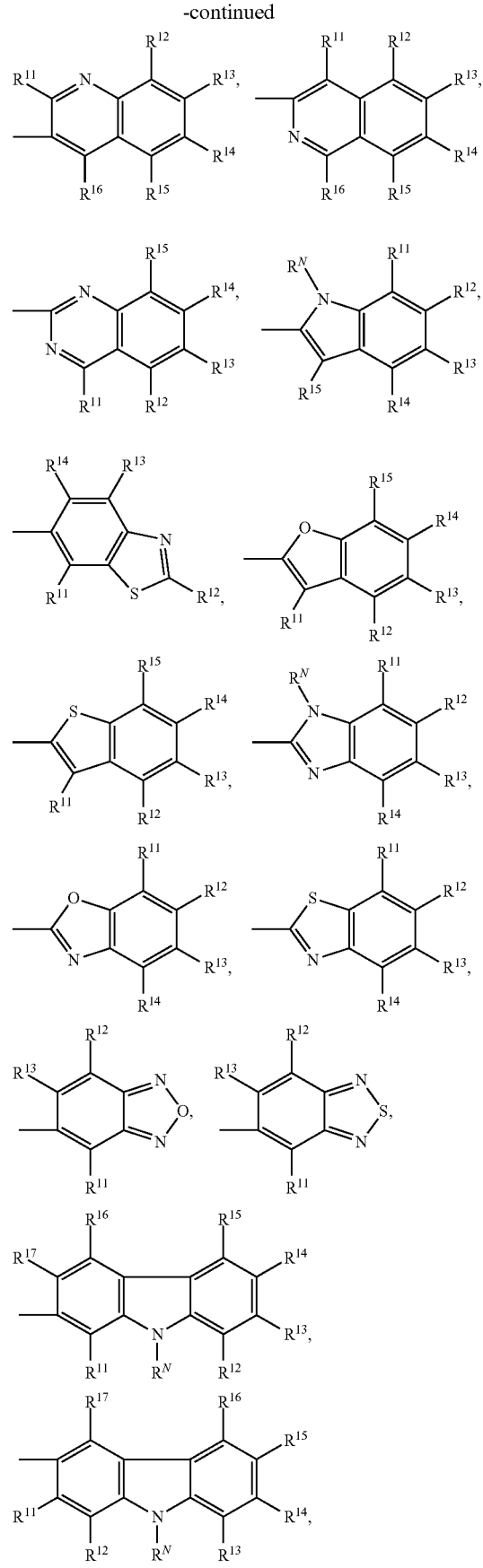

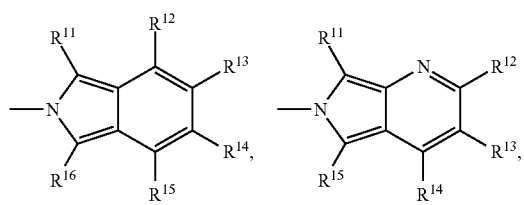
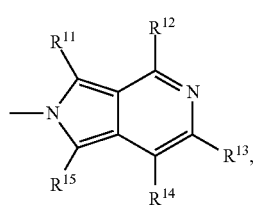
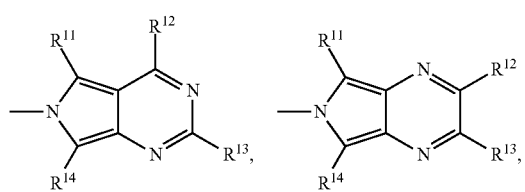
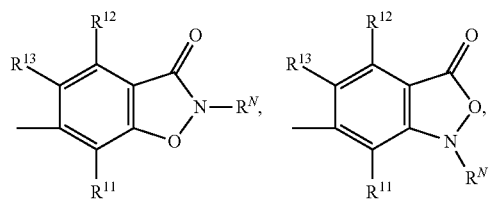
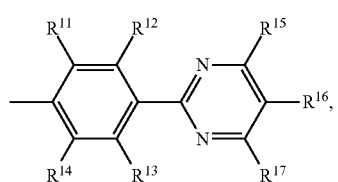
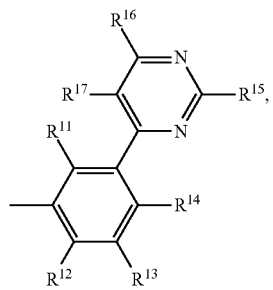
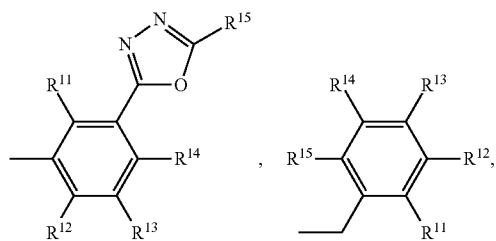
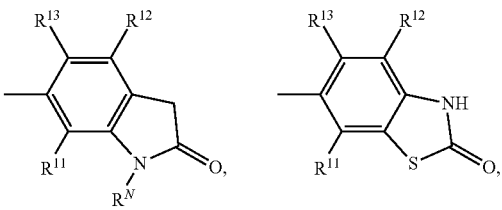
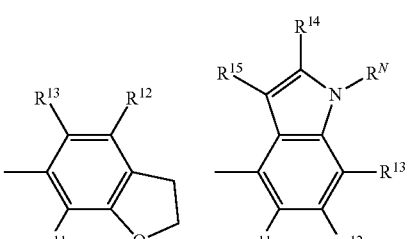
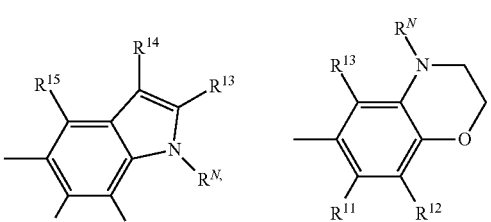
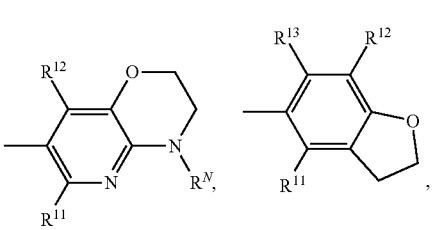
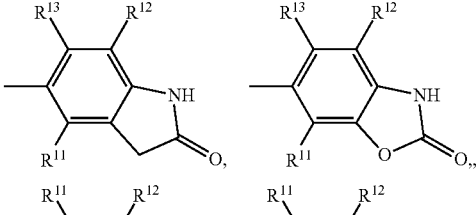
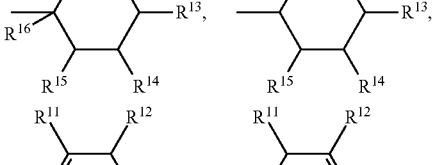
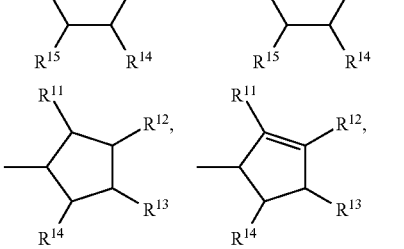

-continued
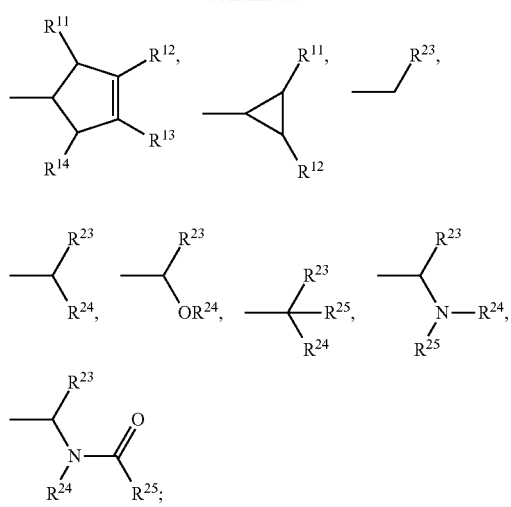
$R^B$ represents: —$R^{26}$ or
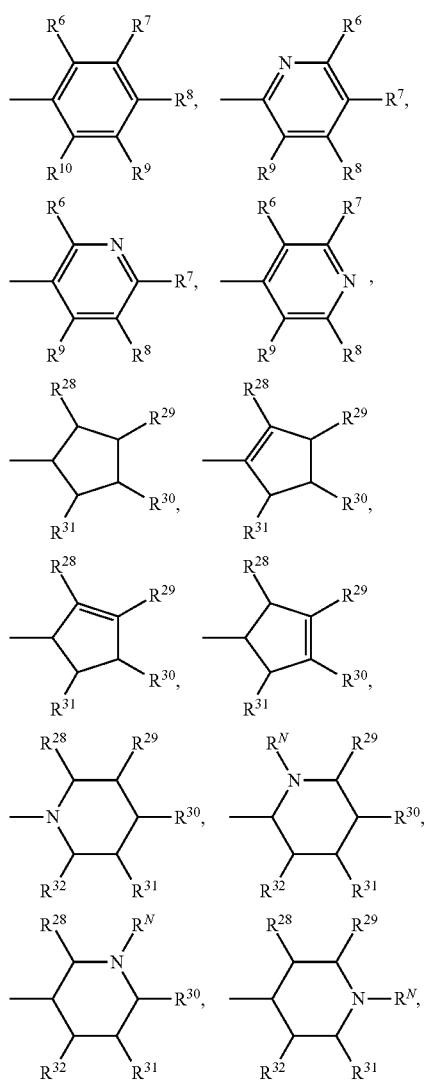
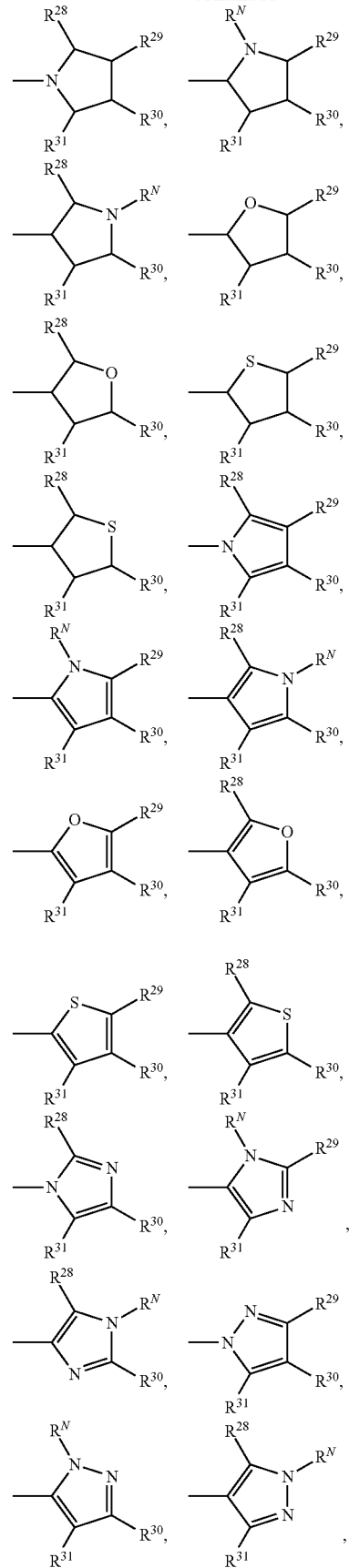

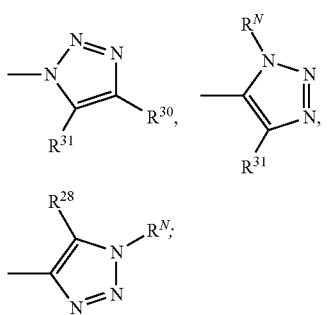
$R^C$ represents: —$R^{27}$ or
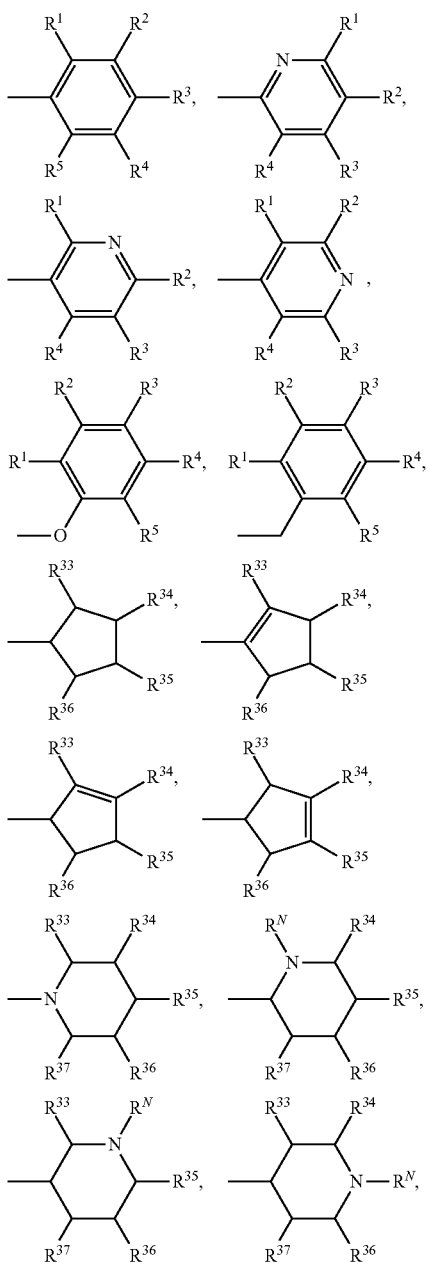
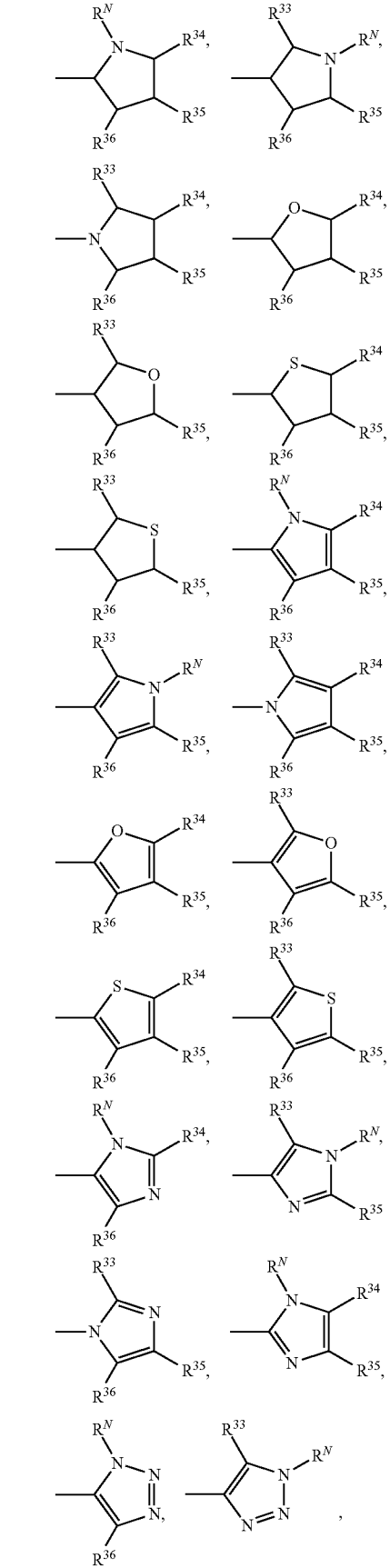

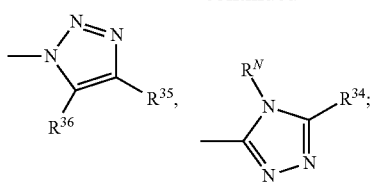
R<sup>D</sup> represents: —R<sup>28</sup> or
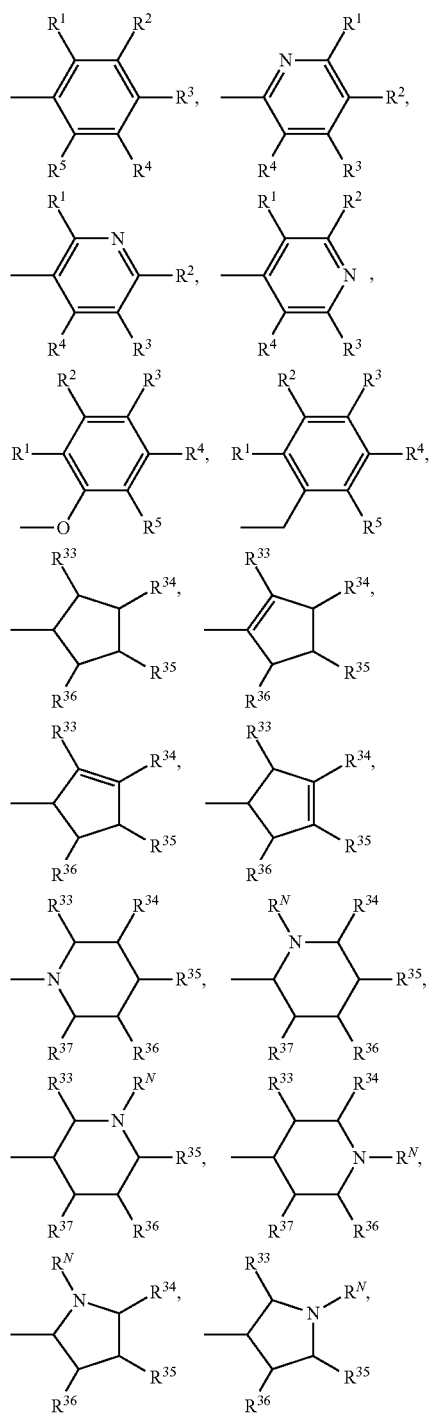
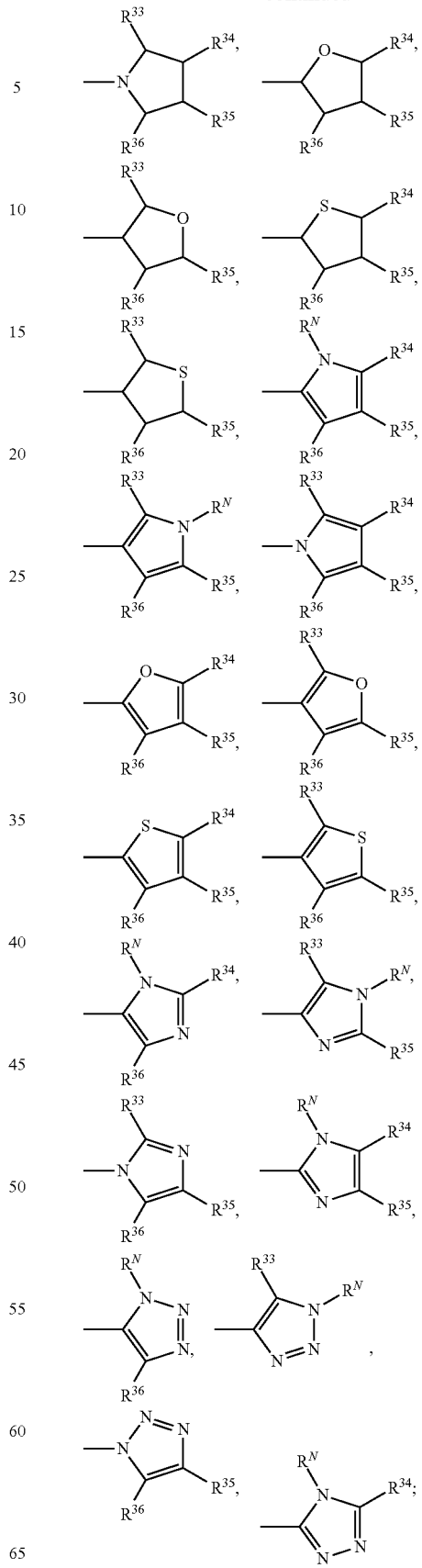

R$^1$-R$^{22}$, R$^{18'}$-R$^{22'}$, R$^{26}$-R$^{39}$ represent independently of each other —H, —OH, —OCH$_3$, —OC$_2$H$_5$, —OC$_3$H$_7$, —O-cyclo-C$_3$H$_5$, —OCH(CH$_3$)$_2$, —OC(CH$_3$)$_3$, —OC$_4$H$_9$, —OCH$_2$—COOH, —OPh, —OCH$_2$-Ph, —OCPh$_3$, —CH$_2$—OH, —C$_2$H$_4$—OH, —C$_3$H$_6$—OH, —CH(OH)—CH$_2$—OH, —CH$_2$—OCH$_3$, —C$_2$H$_4$—OCH$_3$, —C$_4$H$_8$—OCH$_3$, —C$_3$H$_6$—OCH$_3$, —CH$_2$—OC$_2$H$_5$, —C$_2$H$_4$—OC$_2$H$_5$, —C$_3$H$_6$—OC$_2$H$_5$, —C$_4$H$_8$—OC$_2$H$_5$, —CH$_2$—OC$_3$H$_7$, —C$_2$H$_4$—OC$_3$H$_7$, —C$_3$H$_6$—OC$_3$H$_7$, —CH$_2$—O-cyclo-C$_3$H$_5$, —C$_2$H$_4$—O-cyclo-C$_3$H$_5$, —C$_3$H$_6$—O-cyclo-C$_3$H$_5$, —C$_4$H$_8$—O-cyclo-C$_3$H$_5$, —CH$_2$—OCH(CH$_3$)$_2$, —C$_2$H$_4$—OCH(CH$_3$)$_2$, —C$_3$H$_6$—OCH(CH$_3$)$_2$, —C$_4$H$_8$—OCH(CH$_3$)$_2$, —CH$_2$—OC(CH$_3$)$_3$, —C$_2$H$_4$—OC(CH$_3$)$_3$, —C$_3$H$_6$—OC(CH$_3$)$_3$, —C$_4$H$_8$—OC(CH$_3$)$_3$, —CH$_2$—OC$_4$H$_9$, —C$_2$H$_4$—OC$_4$H$_9$, —C$_3$H$_6$—OC$_4$H$_9$, —C$_4$H$_8$—OC$_4$H$_9$, —CH$_2$—OPh, —C$_2$H$_4$—OPh, —C$_3$H$_6$—OPh, —C$_4$H$_8$—OPh, —CH$_2$—OCH$_2$-Ph, —C$_2$H$_4$—OCH$_2$-Ph, —C$_3$H$_6$—OCH$_2$-Ph, —C$_4$H$_8$—OCH$_2$-Ph, —SH, —SCH$_3$, —SC$_2$H$_5$, —SC$_3$H$_7$, —S-cyclo-C$_3$H$_5$, —SCH(CH$_3$)$_2$, —SC(CH$_3$)$_3$, —NO$_2$, —F, —Cl, —Br, —I, —P(O)(OH)$_2$, —P(O)(OCH$_3$)$_2$, —P(O)(OC$_2$H$_5$)$_2$, —P(O)(OCH(CH$_3$)$_2$)$_2$, —C(OH)[P(O)(OH)$_2$]$_2$, —Si(CH$_3$)$_2$(C(CH$_3$)$_3$), —Si(C$_2$H$_5$)$_3$, —Si(CH$_3$)$_3$, —N$_3$, —CN, —OCN, —NCO, —SCN, —NCS, —CHO, —COCH$_3$, —COC$_2$H$_5$, —COC$_3$H$_7$, —CO-cyclo-C$_3$H$_5$, —COCH(CH$_3$)$_2$, —COC(CH$_3$)$_3$, —COOH, —COCN, —COOCH$_3$, —COOC$_2$H$_5$, —COOC$_3$H$_7$, —COO-cyclo-C$_3$H$_5$, —COOCH(CH$_3$)$_2$, —COOC(CH$_3$)$_3$, —OOC—CH$_3$, —OOC—C$_2$H$_5$, —OOC—C$_3$H$_7$, —OOC-cyclo-C$_3$H$_5$, —OOC—CH(CH$_3$)$_2$, —OOC—C(CH$_3$)$_3$, —CONH$_2$, —CH$_2$—CONH$_2$, —CONHCH$_3$, —CONHC$_2$H$_5$, —CONHC$_3$H$_7$, —CONH-cyclo-C$_3$H$_5$, —CONH[CH(CH$_3$)$_2$], —CONH[C(CH$_3$)$_3$], —CON(CH$_3$)$_2$, —CON(C$_2$H$_5$)$_2$, —CON(C$_3$H$_7$)$_2$, —CON(cyclo-C$_3$H$_5$)$_2$, —CON[CH(CH$_3$)$_2$]$_2$, —CON[C(CH$_3$)$_3$]$_2$, —NHCOCH$_3$, —NHCOC$_2$H$_5$, —NHCOC$_3$H$_7$, —NHCO-cyclo-C$_3$H$_5$, —NHCO—CH(CH$_3$)$_2$, —NHCO—C(CH$_3$)$_3$, —NHCO—OCH$_3$, —NHCO—OC$_2$H$_5$, —NHCO—OC$_3$H$_7$, —NHCO—O-cyclo-C$_3$H$_5$, —NHCO—OCH(CH$_3$)$_2$, —NHCO—OC(CH$_3$)$_3$, —NH$_2$, —NHCH$_3$, —NHC$_2$H$_5$, —NHC$_3$H$_7$, —NH-cyclo-C$_3$H$_5$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N(cyclo-C$_3$H$_5$)$_2$, —N[CH(CH$_3$)$_2$]$_2$, —N[C(CH$_3$)$_3$]$_2$, —SOCH$_3$, —SOC$_2$H$_5$, —SOC$_3$H$_7$, —SO-cyclo-C$_3$H$_5$, —SOCH(CH$_3$)$_2$, —SOC(CH$_3$)$_3$, —SO$_2$CH$_3$, —SO$_2$C$_2$H$_5$, —SO$_2$C$_3$H$_7$, —SO$_2$-cyclo-C$_3$H$_5$, —SO$_2$CH(CH$_3$)$_2$, —SO$_2$C(CH$_3$)$_3$, —SO$_3$H, —SO$_3$CH$_3$, —SO$_3$C$_2$H$_5$, —SO$_3$C$_3$H$_7$, —SO$_3$-cyclo-C$_3$H$_5$, —SO$_3$CH(CH$_3$)$_2$, —SO$_3$C(CH$_3$)$_3$, —SO$_2$NH$_2$, —SO$_2$NHCH$_3$, —SO$_2$NHC$_2$H$_5$, —SO$_2$NHC$_3$H$_7$, —SO$_2$NH-cyclo-C$_3$H$_5$, —SO$_2$NHCH(CH$_3$)$_2$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N(cyclo-C$_3$H$_5$)$_2$, —SO$_2$N[CH(CH$_3$)$_2$]$_2$, —SO$_2$N[C(CH$_3$)$_3$]$_2$, —O—S(=O)CH$_3$, —O—S(=O)C$_2$H$_5$, —O—S(=O)C$_3$H$_7$, —O—S(=O)-cyclo-C$_3$H$_5$, —O—S(=O)CH(CH$_3$)$_2$, —O—S(=O)C(CH$_3$)$_3$, —S(=O)(=NH)CH$_3$, —S(=O)(=NH)C$_2$H$_5$, —S(=O)(=NH)C$_3$H$_7$, —S(=O)(=NH)-cyclo-C$_3$H$_5$, —S(=O)(=NH)CH(CH$_3$)$_2$, —S(=O)(=NH)C(CH$_3$)$_3$, —NH—SO$_2$—CH$_3$, —NH—SO$_2$—C$_2$H$_5$, —NH—SO$_2$—C$_3$H$_7$, —NH—SO$_2$-cyclo-C$_3$H$_5$, —NH—SO$_2$—CH(CH$_3$)$_2$, —NH—SO$_2$—C(CH$_3$)$_3$, —O—SO$_2$—CH$_3$, —O—SO$_2$—C$_2$H$_5$, —O—SO$_2$—C$_3$H$_7$, —O—SO$_2$-cyclo-C$_3$H$_5$, —O—SO$_2$—CH(CH$_3$)$_2$, —O—SO$_2$—C(CH$_3$)$_3$, —OCF$_3$, —CH$_2$—OCF$_3$, —C$_2$H$_4$—OCF$_3$, —C$_3$H$_6$—OCF$_3$, —OC$_2$F$_5$, —CH$_2$—OC$_2$F$_5$, —C$_2$H$_4$—OC$_2$F$_5$, —C$_3$H$_6$—OC$_2$F$_5$, —O—COOCH$_3$, —O—COOC$_2$H$_5$, —O—COOC$_3$H$_7$, —O—COO-cyclo-C$_3$H$_5$, —O—COOCH(CH$_3$)$_2$, —O—COOC(CH$_3$)$_3$, —NH—CO—NH$_2$, —NH—CO—NHCH$_3$, —NH—CO—NHC$_2$H$_5$, —NH—CS—N(C$_3$H$_7$)$_2$, —NH—CO—NHC$_3$H$_7$, —NH—CO—N(C$_3$H$_7$)$_2$, —NH—CO—NH[CH(CH$_3$)$_2$], —NH—CO—NH[C(CH$_3$)$_3$], —NH—CO—N(CH$_3$)$_2$, —NH—CO—N(C$_2$H$_5$)$_2$, —NH—CO—NH-cyclo-C$_3$H$_5$, —NH—CO—N(cyclo-C$_3$H$_5$)$_2$, —NH-CO—N[CH(CH$_3$)$_2$]$_2$, —NH—CS—N(C$_2$H$_5$)$_2$, —NH—CO—N[C(CH$_3$)$_3$]$_2$, —NH—CS—NH$_2$, —NH—CS—NHCH$_3$, —NH—CS—N(CH$_3$)$_2$, —NH—CS—NHC$_2$H$_5$, —NH—CS—NHC$_3$H$_7$, —NH—CS—NH-cyclo-C$_3$H$_5$, —NH—CS—NH[CH(CH$_3$)$_2$], —NH—CS—NH[C(CH$_3$)$_3$], —NH—CS—N(cyclo-C$_3$H$_5$)$_2$, —NH—CS—N[CH(CH$_3$)$_2$]$_2$, —NH—CS—N[C(CH$_3$)$_3$]$_2$, —NH—C(=NH)—NH$_2$, —NH—C(=NH)—NHCH$_3$, —NH—C(=NH)—NHC$_2$H$_5$, —NH—C(=NH)—NHC$_3$H$_7$, —O—CO—NH-cyclo-C$_3$H$_5$, —NH—C(=NH)—NH-cyclo-C$_3$H$_5$, —NH—C(=NH)—NH[CH(CH$_3$)$_2$] —O—CO—NH[CH(CH$_3$)$_2$], —NH—C(=NH)—NH[C(CH$_3$)$_3$], —NH—C(=NH)—N(CH$_3$)$_2$, —NH—C(=NH)—N(C$_2$H$_5$)$_2$, —NH—C(=NH)—N(C$_3$H$_7$)$_2$, —NH—C(=NH)—N(cyclo-C$_3$H$_5$)$_2$, —O—CO—NHC$_3$H$_7$, —NH—C(=NH)—N[CH(CH$_3$)$_2$]$_2$, —NH—C(=NH)—N[C(CH$_3$)$_3$]$_2$, —O—CO—NH$_2$, —O—CO—NHCH$_3$, —O—CO—NHC$_2$H$_5$, —O—CO—NH[C(CH$_3$)$_3$], —O—CO—N(CH$_3$)$_2$, —O—CO—N(C$_2$H$_5$)$_2$, —O—CO—N(C$_3$H$_7$)$_2$, —O—CO—N(cyclo-C$_3$H$_5$)$_2$, —O—CO—N[CH(CH$_3$)$_2$]$_2$, —O—CO—N[C(CH$_3$)$_3$]$_2$, —O—CO—OCH$_3$, —O—CO—OC$_2$H$_5$, —O—CO—OC$_3$H$_7$, —O—CO—O-cyclo-C$_3$H$_5$, —O—CO—OCH(CH$_3$)$_2$, —O—CO—OC(CH$_3$)$_3$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, -cyclo-C$_5$H$_9$, -cyclo-C$_6$H$_{11}$, —CH$_2$-cyclo-C$_6$H$_{11}$, —CH$_2$—CH$_2$-cyclo-C$_6$H$_{11}$, -cyclo-C$_7$H$_{13}$, -cyclo-C$_8$H$_{15}$, -Ph, —CH$_2$-Ph, —CH$_2$—CH$_2$-Ph, —CH=CH-Ph, —CPh$_3$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, —C$_5$H$_{11}$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —CH(C$_2$H$_5$)$_2$, —C$_2$H$_4$—CH(CH$_3$)$_2$, —C$_6$H$_{13}$, —C$_7$H$_{15}$, —C$_8$H$_{17}$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH$_2$—CH=CH—CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)

=CH₂, —CH₂—CH(CH₃)—CH=CH₂, —CH(CH₃)—CH₂—CH=CH₂, —CH₂—CH=C(CH₃)₂, —CH₂—C(CH₃)=CH—CH₃, —CH(CH₃)—CH=CH—CH₃, —CH₂—CH—CH(CH₃)₂, —CH=C(CH₃)—C₂H₅, —C(CH₃)=CH—C₂H₅, —C(CH₃)=C(CH₃)₂, —C(CH₃)₂—CH=CH₂, —CH(CH₃)—C(CH₃)=CH₂, —C(CH₃)=CH—CH—CH₂, —CH=C(CH₃)—CH=CH₂, —CH=CH—C(CH₃)=CH₂, —C₄H₈—CH=CH₂, —C₃H₆—CH=CH—CH₃, —C₂H₄—CH=CH—C₂H₅, —CH₂—CH=CH—C₃H₇, —CH=CH—C₄H₉, —C₃H₆—C(CH₃)=CH₂, —C₂H₄—CH(CH₃)—CH=CH₂, —CH₂—CH(CH₃)—CH₂—CH=CH₂, —C₂H₄—CH=C(CH₃)₂, —CH(CH₃)—C₂H₄—CH=CH₂, —C₂H₄—C(CH₃)=CH—CH₃, —CH₂—CH(CH₃)—CH=CH—CH₃, —CH(CH₃)—CH₂—CH=CH—CH₃, —CH₂—CH=CH—CH(CH₃)₂, —CH₂—CH=C(CH₃)—C₂H₅, —CH₂—C(CH₃)=CH—C₂H₅, —CH(CH₃)—CH=CH—C₂H₅, —CH=CH—CH₂—CH(CH₃)₂, —CH=CH—CH(CH₃)—C₂H₅, —CH=C(CH₃)—C₃H₇, —C(CH₃)=CH—C₃H₇, —CH₂—CH(CH₃)—C(CH₃)=CH₂, —C[C(CH₃)₃]=CH₂, —CH(CH₃)—CH₂—C(CH₃)=CH₂, —CH(CH₃)—CH(CH₃)—CH=CH—CH₂—CH₂, —CH=CH—CH₂—CH=CH₂, —C(CH₃)₂—CH=CH₂, —C(CH₃)₂—CH₂—CH=CH₂, —CH₂—C(CH₃)=C(CH₃)₂, —CH(CH₃)—CH=C(CH₃)₂, —C(CH₃)₂—CH=CH—CH₃, —CH=CH—CH₂—CH=CH—CH₃, —CH(CH₃)—C(CH₃)=CH—CH₃, —CH=C(CH₃)—CH(CH₃)₂, —C(CH₃)=CH—CH(CH₃)₂, —C(CH₃)=C(CH₃)—C₂H₅, —CH=CH—C(CH₃)₃, —C(CH₃)₂—C(CH₃)=CH₂, —CH(C₂H₅)—C(CH₃)=CH₂, —C(CH₃)(C₂H₅)—CH=CH₂, —CH(CH₃)—C(C₂H₅)=CH₂, —CH₂—C(C₃H₇)=CH₂, —CH₂—C(C₂H₅)=CH—CH₃, —CH(C₂H₅)—CH=CH—CH₃, —C(C₄H₉)=CH₂, —C(C₃H₇)=CH—CH₃, —C(C₂H₅)=CH—C₂H₅, —C(C₂H₅)=C(CH₃)₂, —C[CH(CH₃)(C₂H₅)]=CH₂, —C[CH₂—CH(CH₃)₂]=CH₂, —C₂H₄—CH=CH—CH=CH₂, —CH₂—CH=CH—CH₂—CH=CH₂, —C₃H₆—C≡C—CH₃, —CH₂—CH=CH—CH=CH—CH₃, —CH=CH—CH=CH—C₂H₅, —CH₂—CH=CH—C(CH₃)=CH₂, —CH₂—CH=C(CH₃)—CH=CH₂, —CH₂—C(CH₃)=CH—CH=CH₂, —CH(CH₃)—CH₂—C≡CH, —CH(CH₃)—CH=CH—CH₂, —CH=CH—CH₂—C(CH₃)=CH₂, —CH(CH₃)—C≡C—CH₃, —CH=CH—CH(CH₃)—CH=CH₂, —CH=C(CH₃)—CH₂—CH=CH₂, —C(CH₃)=CH—CH₂—CH=CH₂, —C(CH₃)—CH—CH₂—CH=CH₂, —C₂H₄—CH(CH₃)—C≡CH, —C(CH₃)=CH—CH₂—CH=CH₂, —CH=CH—CH=C(CH₃)₂, —CH₂—CH(CH₃)—CH₂—C≡CH, —CH=CH—C(CH₃)=CH—CH₃, —CH=C(CH₃)—CH=CH—CH₃, —CH₂—CH(CH₃)—C≡CH, —C(CH₃)=CH—CH=CH—CH₃, —CH=C(CH₃)—C(CH₃)=CH₂, —C(CH₃)=CH—C(CH₃)=CH₂, —C(CH₃)=C(CH₃)—CH=CH₂, —CH=CH—CH=CH—CH=CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH₂—C≡C—CH(CH₃)₂, —C≡C—CH(CH₃)—C₂H₅, —C≡C—CH₂—CH(CH₃)₂, —CH(C₂H₅)—C≡C—CH₃,

—C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃,

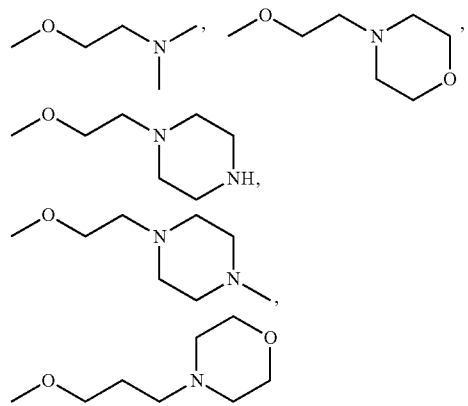

or
R¹⁸ and R¹⁸' or R¹⁹ and R¹⁹' or R²⁰ and R²⁰' or R²¹ and R²¹' or R²² and R²²' form together =O,

or =CR²³'R²⁴', wherein R²³' and R²⁴' represent independently of each other —H, —CH₃, —C₂H₅, —CF₃, —CH₂CF₃, —C₂F₅;
R²³-R²⁵ represent independently of each other —H, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₈H₁₅, -Ph, —CH₂-Ph, —CH₂—CH₂-Ph, —CH=CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH —(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —CH═CH₂, —CH₂—CH═CH₂, —C(CH₃)═CH₂, —CH═CH—CH₃, —C₂H₄—CH═CH₂, —CH₂—CH═CH—CH₃, —CH═CH—C₂H₅, —CH₂—C(CH₃)═CH₂, —CH(CH₃)—CH═CH, —CH═C(CH₃)₂, —C(CH₃)═CH—CH₃, —CH═CH—CH═CH₂, —C₃H₆—CH═CH₂, —C₂H₄—CH═CH—CH₃, —CH₂—CH═CH—C₂H₅, —CH═CH—C₃H₇, —CH₂—CH═CH—CH═CH₂, —CH═CH—CH═CH—CH₃, —CH═CH—CH₂—CH═CH₂, —C(CH₃)═CH—CH═CH₂, —CH═C(CH₃)—CH═CH₂, —CH═CH—C(CH₃)═CH₂, —C₂H₄—C(CH₃)═CH₂, —CH₂—CH(CH₃)—CH═CH₂, —CH(CH₃)—CH₂—CH═CH₂, —CH₂—CH═C(CH₃)₂, —CH₂—C(CH₃)═CH—CH₃, —CH(CH₃)—CH═CH—CH₃, —CH═CH—CH(CH₃)₂, —CH═C(CH₃)—C₂H₅, —C(CH₃)═CH—C₂H₅, —C(CH₃)═C(CH₃)₂, —C(CH₃)₂—CH═CH₂, —CH(CH₃)—C(CH₃)═CH₂, —C(CH₃)₂—CH═CH₂, —CH═C(CH₃)—CH═CH₂, —CH═CH—C(CH₃)═CH₂, —C₄H₈—CH═CH₂, —C₃H₆—CH═CH—CH₃, —C₂H₄—CH═CH—C₂H₅, —CH₂—CH═CH—C₃H₇, —CH═CH—C₄H₉, —C₃H₆—C(CH₃)═CH₂, —C₂H₄—CH(CH₃)—CH═CH₂, —CH₂—CH(CH₃)—CH₂—CH═CH₂, —C₂H₄—CH═C(CH₃)₂, —CH(CH₃)—C₂H₄—CH═CH₂, —C₂H₄—C(CH₃)═CH—CH₃, —CH₂—CH(CH₃)—CH═CH—CH₃, —CH(CH₃)—CH₂—CH═CH—CH₃, —CH₂—CH═CH—CH(CH₃)₂, —CH₂—CH═C(CH₃)—C₂H₅, —CH₂—C(CH₃)═CH—C₂H₅, —CH(CH₃)—CH═CH—C₂H₅, —CH═CH—CH₂—CH(CH₃)₂, —CH═CH—CH(CH₃)—C₂H₅, —CH═C(CH₃)—C₃H₇, —C(CH₃)═CH—C₃H₇, —CH₂—CH(CH₃)—C(CH₃)═CH₂, —C[C(CH₃)₃]═CH₂, —CH(CH₃)—CH₂—C(CH₃)═CH₂, —CH(CH₃)—CH(CH₃)—CH═CH₂, —CH═CH—C₂H₄—CH═CH₂, —CH₂—C(CH₃)₂—CH═CH₂, —C(CH₃)₂—CH₂—CH═CH₂, —CH₂—C(CH₃)═C(CH₃)₂, —CH(CH₃)—CH═C(CH₃)₂, —C(CH₃)₂—CH═CH—CH₃, —CH═CH—CH₂—CH═CH—CH₃, —C(CH₃)═CH—CH(CH₃)₂, —C(CH₃)═C(CH₃)—C₂H₅, —CH═CH—C(CH₃)₃, —C(CH₃)₂—C(CH₃)═CH₂, —CH(C₂H₅)—C(CH₃)═CH₂, —C(CH₃)(C₂H₅)—CH═CH₂, —CH(CH₃)—C(C₂H₅)═CH₂, —CH₂—C(C₃H₇)═CH₂, —CH₂—C(C₂H₅)═CH—CH₃, —CH(C₂H₅)—CH═CH—CH₃, —C(C₄H₉)═CH₂, —C(C₃H₇)═CH—CH₃, —C(C₂H₅)═CH—C₂H₅, —C(C₂H₅)═C(CH₃)₂, —C[CH(CH₃)(C₂H₅)]═CH₂, —C[CH₂—CH(CH₃)₂]═CH₂, —C₂H₄—CH═CH—CH═CH₂, —CH₂—CH═CH—CH₂—CH═CH₂, —C₃H₆—C≡C—CH₃, —CH₂—CH═CH—CH═CH—CH₃, —CH═CH—CH═CH—C₂H₅, —CH₂—CH═CH—C(CH₃)═CH₂, —CH₂—CH═C(CH₃)—CH═CH₂, —CH₂—C(CH₃)═CH—CH═CH₂, —C(CH₃)═CH—CH═CH—CH₃, —CH(CH₃)—CH═CH—CH═CH₂, —CH═CH—CH═C(CH₃)₂, —CH═CH—CH(CH₃)— CH₂—C≡CH, —CH═CH—C(CH₃)═CH—CH₃, —CH═C(CH₃)—CH═CH—CH₃, —CH₂—CH (CH₃)—C≡CH, —C(CH₃)═CH—CH═CH—CH₃, —CH═C(CH₃)—C(CH₃)═CH₂, —C(CH₃)═CH—C(CH₃)═CH₂, —C(CH₃)═C(CH₃)—CH═CH₂, —CH═CH—CH═CH—CH═CH₂, —C≡CH, —C≡C—CH₃, —CH₂—C≡CH, —C₂H₄—C≡CH, —CH₂—C≡C—CH₃, —C≡C—C₂H₅, —C₃H₆—C≡CH, —C₂H₄—C≡C—CH₃, —CH₂—C≡C—C₂H₅, —C≡C—C₃H₇, —CH(CH₃)—C≡CH, —C₄H₈—C≡CH, —C₂H₄—C≡C—C₂H₅, —CH₂—C≡C—C₃H₇, —C≡C—C₄H₉, —C≡C—C(CH₃)₃, —CH(CH₃)—C₂H₄—C≡CH, —CH₂—CH(CH₃)—C≡C—CH₃, —CH(CH₃)—CH₂—C≡C—CH₃, —CH(CH₃)—C≡C—C₂H₅, —CH₂—C≡C—CH(CH₃)₂, —C≡C—CH(CH₃)—C₂H₅, —C≡C—CH₂—CH(CH₃)₂, —CH(C₂H₅)—C≡C—CH₃, —C(CH₃)₂—C≡C—CH₃, —CH(C₂H₅)—CH₂—C≡CH, —CH₂—CH(C₂H₅)—C≡CH, —C(CH₃)₂—CH₂—C≡CH, —CH₂—C(CH₃)₂—C≡CH, —CH(CH₃)—CH(CH₃)—C≡CH, —CH(C₃H₇)—C≡CH, —C(CH₃)(C₂H₅)—C≡CH, —CH₂—CH(C≡CH)₂, —C≡C—C≡CH, —CH₂—C≡C—C≡CH, —C≡C—C≡C—CH₃, —CH(C≡CH)₂, —C₂H₄—C≡C—C≡CH, —CH₂—C≡C—CH₂—C≡CH, —C≡C—C₂H₄—C≡CH, —CH₂—C≡C—C≡C—CH₃, —C≡C—CH₂—C≡C—CH₃, —C≡C—C≡C—C₂H₅, —C(C≡CH)₂—CH₃, —C≡C—CH(CH₃)—C≡CH, —CH(CH₃)—C≡C—C≡CH, —CH(C≡CH)—CH₂—C≡CH, —CH(C≡CH)—C≡C—CH₃;

R^N represents —H, —CH₂—OCH₃, —C₂H₄—OCH₃, —C₃H₆—OCH₃, —CH₂—OC₂H₅, —C₂H₄—OC₂H₅, —C₃H₆—OC₂H₅, —CH₂—OC₃H₇, —C₂H₄—OC₃H₇, —C₃H₆—OC₃H₇, —CH₂—O-cyclo-C₃H₅, —C₂H₄—O-cyclo-C₃H₅, —C₃H₆—O-cyclo-C₃H₅, —CH₂—OCH(CH₃)₂, —C₂H₄—OCH(CH₃)₂, —C₃H₆—OCH(CH₃)₂, —CH₂—OC(CH₃)₃, —C₂H₄—OC(CH₃)₃, —C₃H₆—OC(CH₃)₃, —CH₂—OC₄H₉, —C₂H₄—OC₄H₉, —C₃H₆—OC₄H₉, —CH₂—OPh, —C₂H₄—OPh, —C₃H₆—OPh, —CH₂—OCH₂-Ph, —C₂H₄—OCH₂-Ph, —C₃H₆—OCH₂-Ph, —CHO, —COCH₃, —COC₂H₅, —COC₃H₇, —CO-cyclo-C₃H₅, —COCH(CH₃)₂, —COC(CH₃)₃, —COCN, —COOCH₃, —COOC₂H₅, —COOC₃H₇, —COO-cyclo-C₃H₅, —COOCH(CH₃)₂, —COOC(CH₃)₃, —CONH₂, —CONHCH₃, —CONHC₂H₅, —CONHC₃H₇, —CONH-cyclo-C₃H₅, —CONH[CH(CH₃)₂], —CONH[C(CH₃)₃], —CON(CH₃)₂, —CON(C₂H₅)₂, —CON(C₃H₇)₂, —CON(cyclo-C₃H₅)₂, —CON[CH(CH₃)₂]₂, —CON[C(CH₃)₃]₂, —SO₂CH₃, —SO₂C₂H₅, —SO₂C₃H₇, —SO₂-cyclo-C₃H₅, —SO₂CH(CH₃)₂, —SO₂C(CH₃)₃, —CH₂—OCF₃, —C₂H₄—OCF₃, —C₃H₆—OCF₃, —OC₂F₅, —CH₂—OC₂F₅, —C₂H₄—OC₂F₅, —C₃H₆—OC₂F₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, -cyclo-C₈H₁₅, -Ph, —CH₂-Ph, —CH₂—CH₂-Ph, —CH═CH-Ph, —CPh₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, —C₅H₁₁, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —CH(C₂H₅)₂, —C₂H₄—CH(CH₃)₂, —C₆H₁₃, —C₇H₁₅, —C₈H₁₇, —C₃H₆—CH(CH₃)₂, —C₂H₄—CH(CH₃)—C₂H₅, —CH(CH₃)—C₄H₉, —CH₂—CH(CH₃)—

$C_3H_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —CH=CH$_2$, —CH$_2$—CH=CH$_2$, —C(CH$_3$)=CH$_2$, —CH=CH—CH$_3$, —C$_2$H$_4$—CH=CH$_2$, —CH$_2$—CH=CH—CH$_3$, —CH=CH—C$_2$H$_5$, —CH$_2$—C(CH$_3$)=CH$_2$, —CH(CH$_3$)—CH=CH, —CH=C(CH$_3$)$_2$, —C(CH$_3$)=CH—CH$_3$, —CH=CH—CH=CH$_2$, —C$_3$H$_6$—CH=CH$_2$, —C$_2$H$_4$—CH=CH—CH$_3$, —CH$_2$—CH=CH—C$_2$H$_5$, —CH=CH—C$_3$H$_7$, —CH$_2$—CH=CH—CH=CH$_2$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —C$_2$H$_4$—C(CH$_3$)=CH$_2$, —CH$_2$—CH(CH$_3$)—CH=CH$_2$, —CH(CH$_3$)—CH$_2$—CH=CH$_2$, —CH$_2$—CH=C(CH$_3$)$_2$, —CH$_2$—C(CH$_3$)=CH—CH$_3$, —CH(CH$_3$)—CH=CH—CH$_3$, —CH=CH—CH(CH$_3$)$_2$, —CH=C(CH$_3$)—C$_2$H$_5$, —C(CH$_3$)=CH—C$_2$H$_5$, —C(CH$_3$)$_2$—CH=CH$_2$, —C(CH$_3$)$_2$—CH=CH$_2$, —CH(CH$_3$)—C(CH$_3$)=CH$_2$, —C(CH$_3$)=CH—CH=CH$_2$, —CH=C(CH$_3$)—CH=CH$_2$, —CH=CH—C(CH$_3$)=CH$_2$, —C$_4$H$_8$—CH=CH$_2$, —C$_3$H$_6$—CH=CH—CH$_3$, —C$_2$H$_4$—CH=CH—C$_2$H$_5$, —CH$_2$—CH=CH—C$_3$H$_7$, —CH=CH—C$_4$H$_9$, —C$_3$H$_6$—C(CH$_3$)=CH$_2$, —C$_2$H$_4$—CH(CH$_3$)—CH=CH$_2$, —CH$_2$—CH(CH$_3$)—CH$_2$—CH=CH$_2$, —C$_2$H$_4$—CH=C(CH$_3$)$_2$, —CH(CH$_3$)—C$_2$H$_4$—CH=CH$_2$, —C$_2$H$_4$—C(CH$_3$)=CH—CH$_3$, —CH$_2$—CH(CH$_3$)—CH=CH—CH$_3$, —CH(CH$_3$)—CH$_2$—CH=CH—CH$_3$, —CH$_2$—CH=CH—CH(CH$_3$)$_2$, —CH$_2$—CH=C(CH$_3$)—C$_2$H$_5$, —CH$_2$—C(CH$_3$)=CH—C$_2$H$_5$, —CH(CH$_3$)—CH=CH—C$_2$H$_5$, —CH=CH—CH$_2$—CH(CH$_3$)$_2$, —CH=CH—CH(CH$_3$)—C$_2$H$_5$, —CH=C(CH$_3$)—C$_3$H$_7$, —C(CH$_3$)=CH—C$_3$H$_7$, —CH$_2$—CH(CH$_3$)—C(CH$_3$)=CH$_2$, —C[C(CH$_3$)$_3$]=CH$_2$, —CH(CH$_3$)—CH$_2$—C(CH$_3$)=CH$_2$, —CH(CH$_3$)—CH(CH$_3$)—CH=CH$_2$, —CH=CH—C$_2$H$_4$—CH=CH$_2$, —CH$_2$—C(CH$_3$)$_2$—CH=CH$_2$, —C(CH$_3$)$_2$—CH$_2$—CH=CH$_2$, —CH$_2$—C(CH$_3$)=C(CH$_3$)$_2$, —CH(CH$_3$)—CH=C(CH$_3$)$_2$, —C(CH$_3$)$_2$—CH=CH—CH$_3$, —CH=CH—CH$_2$—CH=CH—CH$_3$, —CH(CH$_3$)—C(CH$_3$)=CH—CH$_3$, —CH=C(CH$_3$)—CH(CH$_3$)$_2$, —C(CH$_3$)=CH—CH(CH$_3$)$_2$, —C(CH$_3$)=C(CH$_3$)—C$_2$H$_5$, —CH=CH—C(CH$_3$)$_3$, —C(CH$_3$)$_2$—C(CH$_3$)=CH$_2$, —CH(C$_2$H$_5$)—C(CH$_3$)=CH$_2$, —C(CH$_3$)(C$_2$H$_5$)—CH=CH$_2$, —CH(CH$_3$)—C(C$_2$H$_5$)=CH$_2$, —CH$_2$—C(C$_3$H$_7$)=CH$_2$, —CH$_2$—C(C$_2$H$_5$)=CH—CH$_3$, —CH(C$_2$H$_5$)—CH=CH—CH$_3$, —C(C$_4$H$_9$)=CH$_2$, —C(C$_3$H$_7$)=CH—CH$_3$, —C(C$_2$H$_5$)=CH—C$_2$H$_5$, —C(C$_2$H$_5$)=C(CH$_3$)$_2$, —C[CH(CH$_3$)(C$_2$H$_5$)]=CH$_2$, —C[CH$_2$—CH(CH$_3$)$_2$]=CH$_2$, —C$_2$H$_4$—CH=CH—CH=CH$_2$, —CH$_2$—CH=CH—CH$_2$—CH=CH$_2$, —C$_3$H$_6$—C≡C—CH$_3$, —CH$_2$—CH=CH—CH=CH—CH$_3$, —CH=CH—CH=CH—CH$_2$—C$_2$H$_5$, —CH$_2$—CH=CH—C(CH$_3$)=CH$_2$, —CH$_2$—CH=C(CH$_3$)—CH=CH$_2$, —CH$_2$—C(CH$_3$)=CH—CH=CH$_2$, —CH(CH$_3$)—CH$_2$—C≡CH, —CH(CH$_3$)—CH=CH—CH=CH$_2$, —CH=CH—CH$_2$—C(CH$_3$)=CH$_2$, —CH(CH$_3$)—C≡C—CH$_3$, —CH=CH—CH(CH$_3$)—CH=CH$_2$, —CH=C(CH$_3$)—CH$_2$—CH=CH$_2$, —C$_2$H$_4$—CH(CH$_3$)—C≡CH, —CH=CH—CH$_2$—CH=CH$_2$, —CH=CH—C(CH$_3$)$_2$, —CH$_2$—C(CH$_3$)=CH—CH=CH$_2$, —CH$_2$—C≡CH, —CH=CH—C(CH$_3$)=CH—CH$_3$,

—CH=C(CH$_3$)—CH=CH—CH$_3$, —CH$_2$—CH(CH$_3$)—C≡CH, —C(CH$_3$)=CH—CH=CH—CH$_3$, —CH=C(CH$_3$)—C(CH$_3$)=CH$_2$, —C(CH$_3$)=CH—C(CH$_3$)=CH$_2$, —C(CH$_3$)=C(CH$_3$)—CH=CH$_2$, —CH=CH—CH=CH—CH=CH$_2$, —C≡CH, —C≡C—CH$_3$, —CH$_2$—C≡CH, —C$_2$H$_4$—C≡CH, —CH$_2$—C≡C—CH$_3$, —C≡C—C$_2$H$_5$, —C$_3$H$_6$—C≡CH, —C$_2$H$_4$—C≡C—CH$_3$, —CH$_2$—C≡C—C$_2$H$_5$, —C≡C—C$_3$H$_7$, —CH(CH$_3$)—C≡CH, —C$_4$H$_8$—C≡CH, —C$_2$H$_4$—C≡C—C$_2$H$_5$, —CH$_2$—C≡C—C$_3$H$_7$, —C≡C—C$_4$H$_9$, —C≡C—C(CH$_3$)$_3$, —CH(CH$_3$)—C$_2$H$_4$—C≡CH, —CH$_2$—CH(CH$_3$)—C≡C—CH$_3$, —CH(CH$_3$)—CH$_2$—C≡C—CH$_3$, —CH(CH$_3$)—C≡C—C$_2$H$_5$, —CH$_2$—C≡C—CH(CH$_3$)$_2$, —C≡C—CH(CH$_3$)—C$_2$H$_5$, —C≡C—CH$_2$—CH(CH$_3$)$_2$, —CH(C$_2$H$_5$)—C≡C—CH$_3$, —C(CH$_3$)$_2$—C≡C—CH$_3$, —CH(C$_2$H$_5$)—CH$_2$—C≡CH, —CH$_2$—CH(C$_2$H$_5$)—C≡CH, —C(CH$_3$)$_2$—CH$_2$—C≡CH, —CH$_2$—C(CH$_3$)$_2$—C≡CH, —CH(CH$_3$)—CH(CH$_3$)—C≡CH, —CH(C$_3$H$_7$)—C≡CH, —C(CH$_3$)(C$_2$H$_5$)—C≡CH, —CH$_2$—CH(C≡CH)$_2$, —C≡C—C≡CH, —CH$_2$—C≡C—C≡CH, —C≡C—C≡C—CH$_3$, —CH(C≡CH)$_2$, —C$_2$H$_4$—C≡C—C≡CH, —CH$_2$—C≡C—CH$_2$—C≡CH, —C≡C—C$_2$H$_4$—C≡CH, —CH$_2$—C≡C—C≡C—CH$_3$, —C≡C—CH$_2$—C≡C—CH$_3$, —C≡C—C≡C—C$_2$H$_5$, —C(C≡CH)$_2$—CH$_3$, —C≡C—CH(CH$_3$)—C≡CH, —CH(CH$_3$)—C≡C—C≡CH, —CH(C≡CH)—CH$_2$—C≡CH, or —CH(C≡CH)—C≡C—CH$_3$;

$L_1$, $L_2$ and $L_3$ represent independently of each other: a bond, —CH$_2$—, —C$_2$H$_4$—, —C$_3$H$_6$—, —C$_4$H$_8$—, —C$_5$H$_{10}$—, —C$_6$H$_{12}$—, —C$_7$H$_{14}$—, —C$_8$H$_{16}$—, —C$_9$H$_{18}$—, —C$_{10}$H$_{20}$—, —CH$_2$CH$_2$O—, —CH(CH$_3$)—, —C[(CH$_3$)$_2$]—, —CH(C$_3$H$_7$)—, —CH$_2$—CH(CH$_3$)—, —CH(CH$_3$)—CH$_2$—, —CH(CH$_3$)—C$_2$H$_4$—, —CH$_2$—CH(CH$_3$)—CH$_2$—, —C$_2$H$_4$—CH(CH$_3$)—, —CH$_2$—C[(CH$_3$)$_2$]—, —C[(CH$_3$)$_2$]—CH$_2$—, —CH(CH$_3$)—CH(CH$_3$)—, —C[(C$_2$H$_5$)(CH$_3$)]—, —(CH$_2$—CH$_2$—O)$_n$—CH$_2$—CH$_2$—, —C(CH$_3$)=CH—C(CH$_3$)=CH—, —C$_2$H$_4$—CH=CH—CH=CH—, —CH$_2$—CH=CH—CH$_2$—CH=CH—, —C$_3$H$_6$—C≡C—CH$_2$—, —CH$_2$—CH=CH—CH=CH—CH$_2$—, —CH(CH$_3$)—C≡C—CH$_2$—, —CH=CH—CH=CH—C$_2$H$_4$—, —CH$_2$—CH=CH—C(CH$_3$)=CH—, —CH$_2$—CH=C(CH$_3$)—CH=CH—, —CH$_2$—C(CH$_3$)=CH—CH=CH—, —CH(CH$_3$)—CH=CH—CH=CH—, —CH=CH—CH$_2$—C(CH$_3$)=CH—, —CONH—, —NHCO—, —CH$_2$—CONH—, —CONH—CH$_2$—, —NHCO—CH$_2$—, —CH$_2$—NHCO—;

wherein n is an integer from 1 to 10; or $L_1$-$R^B$ and $L_2$-$R^C$ or $L_1$-$R^B$ and $L_3$-$R^D$ or $L_2$-$R^C$ and $L_3$-$R^D$ form together a cyclic ring selected from the group consisting of:

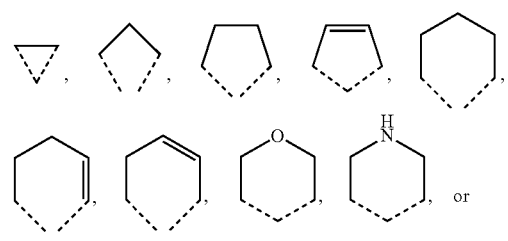

-continued

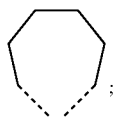;

or enantiomers, stereoisomeric forms, mixtures of enantiomers, anomers, deoxy-forms, diastereomers, mixtures of diastereomers, prodrugs, tautomers, hydrates, solvates and racemates of the above mentioned compounds and pharmaceutically acceptable salts thereof,
with the proviso that the following compounds are excluded:
the compounds having X=—CH$_2$CH$_2$CH$_2$—, and Y=—O—, and Z=a bond, and R*=—CH$_3$, —CH$_2$CH$_3$, —CH(CH$_3$)$_2$, —CH(CH$_3$)CH$_2$CH$_3$, -cyclo-C$_5$H$_9$, -cyclo-C$_6$H$_{11}$, -Ph, or —CH$_2$Ph, and R$^A$=-Ph, L$_1$-R$^B$=—H,

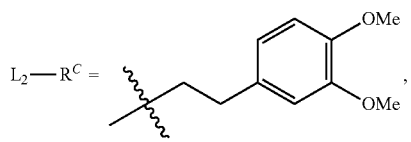

L$_3$-R$^D$=—CH$_3$, or

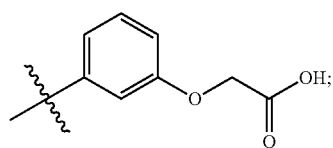 [SMILES: *c1cccc(OCC(=O)O)c1]

the compounds having X=—CH$_2$CH$_2$CH$_2$—, and Y=—O—, and Z=a bond, and R*=—CH$_2$CH$_3$, and

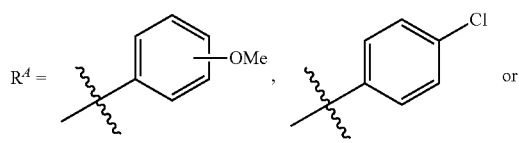

L$_1$-R$^B$=—H,

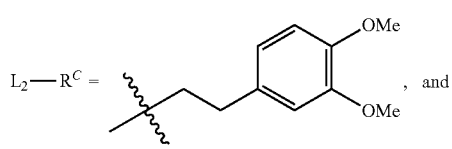, and

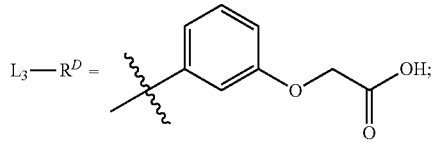

the compounds having X=—CH$_2$CH$_2$CH$_2$—, and Y=—O—, and Z=a bond, and R*=—CH$_2$CH$_3$, —CH$_2$CH$_2$CH$_3$, —CH$_2$CH=CH$_2$, —CH(CH$_3$)$_2$, -cyclo-C$_3$H$_5$, and

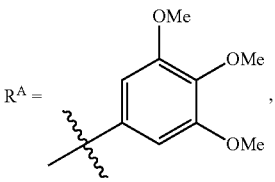 [SMILES: *c1cc(OC)c(OC)c(OC)c1]

L$_1$-R$^B$=—H,

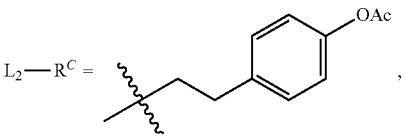,

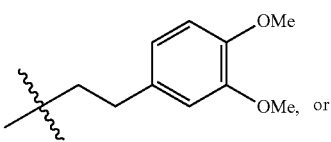, or

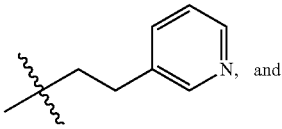 and

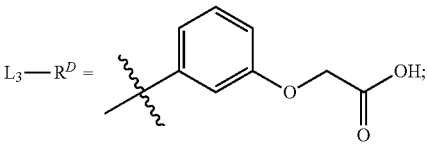

the compounds having X=—CH$_2$CH$_2$CH$_2$—, and Y=—O—, and Z=a bond, and R*=—CH$_3$, —CH$_2$CH$_3$, or —CH$_2$CH$_2$CH$_3$, and R$^A$=—CH$_3$, —CH$_2$CH$_3$, or —CH$_2$CH$_2$CH$_3$, and L$_1$-R$^B$=—H, and

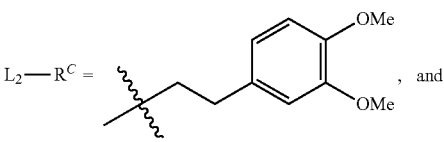, and

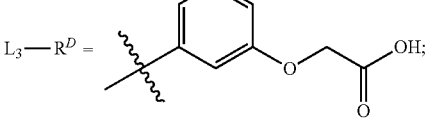

and
the compound having X=—CH$_2$CH$_2$CH$_2$—, and Y=—O—, and Z=a bond, and R*=—OPh, and R$^A$=-cyclo-C$_5$H$_9$, and L$_1$-R$^B$=—H, and L$_2$-R$^C$=—CH$_2$CH$_2$Ph, and

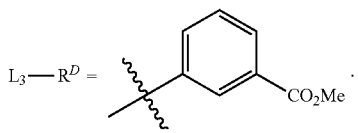

2. Compound according to claim 1 of the general formula (Ia):

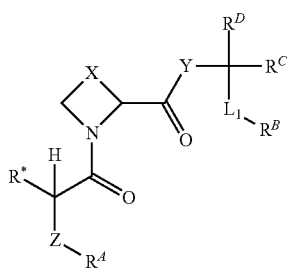

wherein
X, Y, Z, R*, $R^A$ and $R^B$ are defined according to claim 1;
$R^C$ represents —$R^{38}$;
$R^D$ represents —H, —$CH_3$, —$CH_2F$, —$CHF_2$, —$CF_3$, —$C_2H_5$, —$CH_2OH$, —$CH_2OMe$, —$CH_2NH_2$, —$CH_2NHCH_3$, —$CH_2N(CH_3)_2$, —$CH_2NHCOH$, or —$CH_2NHCOCH_3$; or
$R^C$ and $R^D$ can form together a carbocyclic ring selected from the group consisting of:

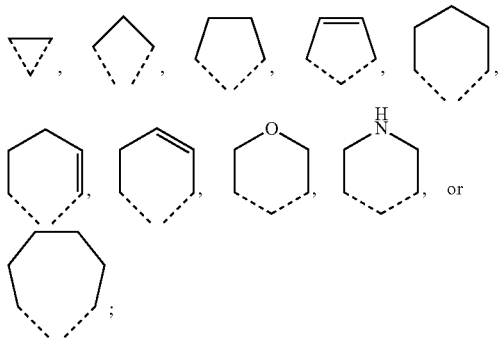

$R^{38}$ and $R^{39}$ are defined according to claim 1;

$L_1$ represents a bond, —$CH_2$—, —$C_2H_4$—, —$C_3H_6$—, —$C_4H_8$—, —$C_5H_{10}$—, —$C_6H_{12}$—, —$C_7H_{14}$—, —$C_8H_{16}$—, —$C_9H_{18}$—, —$C_{10}H_{20}$—, —$CH(CH_3)$—, —$C[(CH_3)_2]$—, —$CH_2$—$CH(CH_3)$—, —$CH(CH_3)$—$CH_2$—, —$CH(CH_3)$—$C_2H_4$—, —$CH_2$—$CH(CH_3)$—$CH_2$—, —$C_2H_4$—$CH(CH_3)$—, —$CH_2$—$C[(CH_3)_2]$—, —$C[(CH_3)_2]$—$CH_2$—, —$CH(CH_3)$—$CH(CH_3)$—, —$C[(C_2H_5)(CH_3)]$—, —$CH(C_3H_7)$—, —$CH_2CH_2O$—, —($CH_2$—$CH_2$—O$)_n$—$CH_2$—$CH_2$—, —$C(CH_3)$=$CH$—$C(CH_3)$=$CH$—, —$CH(CH_3)$—$C$≡$C$—$CH_2$—, —$C_2H_4$—$CH$=$CH$—$CH$=$CH$—, —$CH_2$—$CH$=$CH$—$CH_2$—$CH$=$CH$—, —$C_3H_6$—$C$≡$C$—$CH_2$—, —$CH_2$—$CH$=$CH$—$CH$=$CH$—$CH_2$—, —$CH$=$CH$—$CH$=$CH$—$C_2H_4$—, —$CH_2$—$CH$=$CH$—$C(CH_3)$=$CH$—, —$CH_2$—$CH$=$C(CH_3)$—$CH$=$CH$—, —$CH_2$—$C(CH_3)$=$CH$—$CH$=$CH$—, —$CH(CH_3)$—$CH$=$CH$—$CH$=$CH$—, —$CH$=$CH$—$CH_2$—$C(CH_3)$=$CH$—, —(C=O)NH—, —NH(C=O)—, —$CH_2$(C=O)NH—, —(C=O)NH$CH_2$—, —NH(C=O)$CH_2$—, —$CH_2$NH(C=O)—,
wherein n is an integer from 1 to 10.

3. Compound according to claim 1 of the general formula (VI):

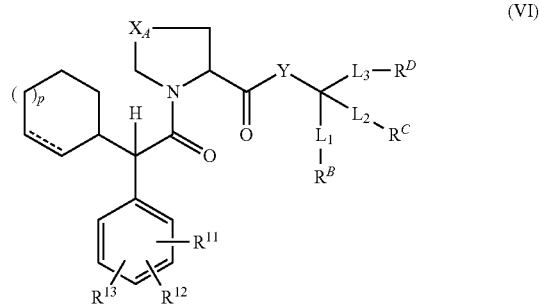

wherein
$X_A$ represents —$CH_2CH_2$—, —$CH$=$CH$—, —$CH_2$—S—, —S—$CH_2$—;
p is an integer of 0 or 1;
$R^{11}$, $R^{12}$, $R^{13}$, $R^B$, $R^C$, $R^D$, $L_1$, $L_2$ and $L_3$ are defined according to claim 1,
wherein at least one of $R^{11}$, $R^{12}$, $R^{13}$ is not —H;

" ⟍ " represents a C=C bond or a C—C bond.

4. Compound according to claim 1 selected from the group consisting of:

| | |
|---|---|
| A02 | 2-(3-((R)-3-(3,4-Dimethoxyphenyl)-1-(((S)-1-((S)-2-(3,4,5-trimethoxyphenyl) pent-4-enoyl)piperidine-2-carbonyl)oxy)propyl) phenoxy)acetic acid, |
| A04 | (S)-1,7-di(pyridin-3-yl)heptan-4-yl 1-((S)-2-(3,4,5-trimethoxyphenyl)pent-4-enoyl)piperidine-2-carboxylate, |
| A05 | (S)-N-((R)-3-(3,4-dimethoxyphenyl)-1-(3-(2-morpholinoethoxy)phenyl)propyl)-1-((S)-2-(3,4,5-trimethoxyphenyl)pent-4-enoyl)piperidine-2-carboxamide, |
| A06 | 2-(3-((R)-3-(3,4-Dimethoxyphenyl)-1-(((S)-1-((S)-2-(3,4,5-trimethoxyphenyl)pent-4-enoyl)-1,2,3,6-tetrahydropyridine-2-carbonyl)oxy)propyl)phenoxy) acetic acid, |
| A08 | (S)-(R)-3-(3,4-dimethoxyphenyl)-1-(3-(2-morpholinoethoxy)phenyl)propyl-1-((S)-3-cyclopropyl-2-(3,4,5-trimethoxyphenyl)propanoyl)piperidine-2-carboxylate, |
| A10 | 2-(3-((R)-3-(3,4-dimethoxyphenyl)-1-(((S)-1-((S)-3-phenyl-2-(3,4,5-trimethoxyphenyl)propanoyl)piperidine-2-carbonyl)oxy)propyl) phenoxy)acetic acid, |

-continued

| | |
|---|---|
| A11 | 2-(3-((R)-1-(((S)-1-((S)-2-((S)-Cyclohex-2-en-1-yl)-2-(3,4,5-trimethoxyphenyl)acetyl)piperidine-2-carbonyl)oxy)-3-(3,4-dimethoxyphenyl)propyl)phenoxy) acetic acid, |
| A12 | (S)-(R)-3-(3,4-Dimethoxyphenyl)-1-(3-(2-morpholinoethoxy)phenyl)propyl-1-((S)-2-((S)-cyclohex-2-en-1-yl)-2-(3,4,5-trimethoxyphenyl)acetyl)piperidine-2-carboxylate, |
| A13 | (S)-1,7-Di(pyridin-3-yl)heptan-4-yl-1-((S)-2-((S)-cyclohex-2-en-1-yl)-2-(3,4,5-trimethoxy phenyl) acetyl)piperidine-2-carboxylate, |
| A14 | (S)-2-(3,4-Dimethoxyphenoxy)ethyl-1-((S)-2-((R)-cyclohex-2-en-1-yl)-2-(3,4,5-trimethoxy phenyl)acetyl)piperidine-2-carboxylate, |
| A16 | 2-(3-((R)-1-((S)-1-((S)-2-((R)-Cyclohex-2-en-1-yl)-2-(3,4,5-trimethoxyphenyl)acetyl)piper-idine-2-carboxamido)-3-(3,4-dimethoxyphenyl)propyl)phenoxy) acetic acid, |
| A17 | 2-(3-((R)-1-(((S)-1-((S)-2-Cyclohexyl-2-(3,4,5-trimethoxyphenyl)acetyl)piperidine-2-carbonyl)oxy)-3-(3,4-dimethoxyphenyl)propyl)phenoxy)acetic acid, |
| A18 | (S)-(R)-3-(3,4-dimethoxyphenyl)-1-(3-(2-morpholinoethoxy)phenyl)propyl-1-((S)-2-cyclohexyl-2-(3,4,5-trimethoxyphenyl)acetyl)piperidine-2-carboxylate, |
| A19 | (2S)-1,7-di(pyridin-3-yl)heptan-4-yl 1-(2-cyclohexyl-2-(3,4,5-trimethoxy phenyl)acetyl)piperidine-2-carboxylate, |
| A20 | (S)-2-(3,4-dimethoxyphenoxy)ethyl-1-((S)-2-cyclohexyl-2-(3,4,5-trimethoxy phenyl)acetyl)piperidine-2-carboxylate, |
| A22 | 2-(3-((R)-1-((S)-1-((S)-2-cyclohexyl-2-(3,4,5-trimethoxyphenyl)acetyl)piperidine-2-carboxamido)-3-(3,4-dimethoxyphenyl)propyl)phenoxy)acetic acid, |
| A23 | 2-(3-(1-(((2S)-1-(2-benzamido-2-cyclohexylacetyl) piperidine-2-carbonyl)oxy)-3-(3,4-dimethoxyphenyl)propyl)phenoxy)acetic acid, |
| A24 | 2-(3-(1-(((2S)-1-(2-cyclohexyl-2-(2-hydroxy benzamido)acetyl)piperidine-2-carbonyl)oxy)-3-(3,4-dimethoxyphenyl) propyl)phenoxy)acetic acid, |
| A25 | 2-(3-(1-(((2S)-1-(2-cyclohexyl-2-(picolinamido) acetyl)piperidine-2-carbonyl)oxy)-3-(3,4-dimethoxyphenyl)propyl)phenoxy) acetic acid, |
| A26 | 2-(3-(1-(((2S)-1-(2-(cyclohexanecarboxamido)-2-cyclohexylacetyl)piperidine-2-carbonyl)oxy)-3-(3,4-dimethoxyphenyl)propyl)phenoxy)acetic acid, |
| A27 | 2-(3-(1-(((2S)-1-(2-cyclohexyl-2-(3H-1,2,4-triazole-3-carboxamido)acetyl)piperidine-2-carbonyl)oxy)-3-(3,4-dimethoxyphenyl) propyl)phenoxy)acetic acid, |
| A28 | 2-(3-(1-(((2S)-1-(2-cyclohexyl-2-(3,5-dichloro benzamido)acetyl)piperidine-2-carbonyl)oxy)-3-(3,4-dimethoxyphenyl) propyl)phenoxy)acetic acid, |
| A29 | (S)-(R)-3-(3,4-dimethoxyphenyl)-1-(3-(2-morpholinoethoxy)phenyl)propyl 1-((2S,3R)-2-cyclohexyl-3-hydroxybutanoyl)piperidine-2-carboxylate, |
| A30 | (S)-(R)-3-(3,4-dimethoxyphenyl)-1-(3-(2-morpholinoethoxy)phenyl)propyl 1-((2S,3R,E)-2-cyclohexyl-3-hydroxyhex-4-enoyl)piperidine-2-carboxylate, |
| A31 | (S)-(R)-3-(3,4-dimethoxyphenyl)-1-(3-(2-morpholinoethoxy)phenyl)propyl 1-((2S,3R)-2-cyclohexyl-3-(methoxymethoxy)-5-methylhexanoyl)piperidine-2-carboxylate, |
| A32 | (S)-(R)-3-(3,4-dimethoxyphenyl)-1-(3-(2-morpholinoethoxy)phenyl)propyl 1-((2S,3R)-2-cyclohexyl-3-hydroxy-5-methylhexanoyl)piperidine-2-carboxylate, |
| A36 | 2-(3-((R)-1-(((S)-1-((S)-2-cyclohexyl-2-(3-fluorophenyl)acetyl)piperidine-2-carbonyl)oxy)-3-(3,4-dimethoxyphenyl)propyl) phenoxy)acetic acid |
| A37 | 2-(3-((R)-1-(((S)-1-((R)-2-cyclohexylpropanoyl)piperidine-2-carbonyl)oxy)-3-(3,4-dimethoxyphenyl)propyl)phenoxy)acetic acid |
| A38 | 2-(3-((R)-1-(((S)-1-((R)-2-cyclohexylpent-4-enoyl)piperidine-2-carbonyl)oxy)-3-(3,4-dimethoxyphenyl)propyl)phenoxy) acetic acid |
| B03 | (S)-N-((S)-1-amino-3-methyl-1-oxobutan-2-yl)-1-((S)-2-cyclohexyl-2-(3,4,5-trimethoxyphenyl)acetyl)piperidine-2-carboxamide, |
| B04 | (S)-N-((R)-1-amino-3-methyl-1-oxobutan-2-yl)-1-((S)-2-cyclohexyl-2-(3,4,5-trimethoxyphenyl)acetyl)piperidine-2-carboxamide, |
| B05 | (S)-N-((S)-1-amino-1-oxo-3-phenylpropan-2-yl)-1-((S)-2-cyclohexyl-2-(3,4,5-trimethoxyphenyl)acetyl)piperidine-2-carboxamide, |
| B06 | (S)-N-((R)-1-amino-1-oxo-3-phenylpropan-2-yl)-1-((S)-2-cyclohexyl-2-(3,4,5-trimethoxyphenyl)acetyl)piperidine-2-carboxamide, |
| B07 | (S)-N-((S)-1-amino-3-cyclohexyl-1-oxopropan-2-yl)-1-((S)-2-cyclohexyl-2-(3,4,5-trimethoxyphenyl)acetyl)piperidine-2-carboxamide, |
| B08 | (S)-N-((S)-1-amino-1-oxo-4-phenylbutan-2-yl)-1-((S)-2-cyclohexyl-2-(3,4,5-trimethoxyphenyl)acetyl)piperidine-2-carboxamide, |
| B09 | (S)-N-((S)-1-amino-4-cyclohexyl-1-oxobutan-2-yl)-1-((S)-2-cyclohexyl-2-(3,4,5-trimethoxyphenyl)acetyl)piperidine-2-carboxamide, |
| B10 | (S)-N-(2-amino-2-oxoethyl)-1-((S)-2-cyclohexyl-2-(3,4,5-trimethoxyphenyl)acetyl)piperidine-2-carboxamide, |
| B11 | (S)-N-(1-amino-2-methyl-1-oxopropan-2-yl)-1-((S)-2-cyclohexyl-2-(3,4,5-trimethoxyphenyl)acetyl)piperidine-2-carboxamide, |
| B12 | (S)-N-((S)-1-amino-1-oxobutan-2-yl)-1-((S)-2-cyclohexyl-2-(3,4,5-trimethoxyphenyl)acetyl)piperidine-2-carboxamide, |
| B13 | (S)-N-((R)-1-amino-1-oxobutan-2-yl)-1-((S)-2-cyclohexyl-2-(3,4,5-trimethoxyphenyl)acetyl)piperidine-2-carboxamide, |

-continued

| | |
|---|---|
| B14 | (S)-N-((2S,3S)-1-amino-3-methyl-1-oxopentan-2-yl)-1-((S)-2-cyclohexyl-2-(3,4,5-trimethoxyphenyl)acetyl)piperidine-2-carboxamide, |
| B15 | (S)-N-((2R,3R)-1-amino-3-methyl-1-oxopentan-2-yl)-1-((S)-2-cyclohexyl-2-(3,4,5-trimethoxyphenyl)acetyl)piperidine-2-carboxamide, |
| B16 | (S)-N-((S)-2-amino-2-oxo-1-phenylethyl)-1-((S)-2-cyclohexyl-2-(3,4,5-trimethoxyphenyl)acetyl)piperidine-2-carboxamide, |
| B17 | (S)-N-((R)-2-amino-2-oxo-1-phenylethyl)-1-((S)-2-cyclohexyl-2-(3,4,5-trimethoxyphenyl)acetyl)piperidine-2-carboxamide, |
| B18 | (S)-N-((S)-2-amino-1-cyclohexyl-2-oxoethyl)-1-((S)-2-cyclohexyl-2-(3,4,5-trimethoxyphenyl)acetyl)piperidine-2-carboxamide, |
| B19 | (S)-N-((S)-1-amino-4-hydroxy-1-oxobutan-2-yl)-1-((S)-2-cyclohexyl-2-(3,4,5-trimethoxyphenyl)acetyl)piperidine-2-carboxamide, |
| B20 | (S)-N-((R)-1-amino-4-hydroxy-1-oxobutan-2-yl)-1-((S)-2-cyclohexyl-2-(3,4,5-trimethoxyphenyl)acetyl)piperidine-2-carboxamide, |
| B21 | (S)-N-((R)-1-amino-3-hydroxy-1-oxopropan-2-yl)-1-((S)-2-cyclohexyl-2-(3,4,5-trimethoxyphenyl)acetyl)piperidine-2-carboxamide, |
| B22 | (S)-N-((S)-1-amino-3-hydroxy-1-oxopropan-2-yl)-1-((S)-2-cyclohexyl-2-(3,4,5-trimethoxyphenyl)acetyl)piperidine-2-carboxamide, |
| B23 | (S)-2-((S)-1-((S)-2-cyclohexyl-2-(3,4,5-trimethoxyphenyl)acetyl)piperidine-2-carboxamido)pentanediamide, |
| B24 | (R)-2-((S)-1-((S)-2-cyclohexyl-2-(3,4,5-trimethoxyphenyl)acetyl)piperidine-2-carboxamido)pentanediamide, |
| B25 | (S)-N-(4-amino-2-methyl-4-oxobutan-2-yl)-1-((S)-2-cyclohexyl-2-(3,4,5-trimethoxyphenyl)acetyl)piperidine-2-carboxamide, |
| B26 | (S)-N-(1-carbamoylcyclopropyl)-1-((S)-2-cyclohexyl-2-(3,4,5-trimethoxyphenyl)acetyl)piperidine-2-carboxamide, |
| B27 | (S)-N-(1-carbamoylcyclobutyl)-1-((S)-2-cyclohexyl-2-(3,4,5-trimethoxyphenyl)acetyl)piperidine-2-carboxamide, |
| B28 | (S)-N-(1-carbamoylcyclopentyl)-1-((S)-2-cyclohexyl-2-(3,4,5-trimethoxyphenyl)acetyl)piperidine-2-carboxamide, |
| B29 | (S)-N-(3-amino-3-oxopropyl)-1-((S)-2-cyclohexyl-2-(3,4,5-trimethoxyphenyl)acetyl)piperidine-2-carboxamide, |
| B30 | (S)-N-((S)-1-amino-4-methyl-1-oxopentan-2-yl)-1-((S)-2-cyclohexyl-2-(3,4,5-trimethoxyphenyl)acetyl)piperidine-2-carboxamide, |
| B31 | (S)-N-(1-carbamoylcyclohexyl)-1-((S)-2-cyclohexyl-2-(3,4,5-trimethoxyphenyl) acetyl)piperidine-2-carboxamide |
| B32 | (S)-N-(1-carbamoylcyclohexyl)-1-((S)-2-cyclohexyl-2-(3,4,5-trimethoxyphenyl) acetyl)piperidine-2-carboxamide |
| B33 | (S)-N-(1-((2-amino-2-oxoethyl)carbamoyl)cyclopentyl)-1-((S)-2-cyclohexyl-2-(3,4,5-trimethoxyphenyl)acetyl)piperidine-2-carboxamide |
| B34 | (S)-N-((R)-1-amino-3-(1H-imidazol-4-yl)-1-oxopropan-2-yl)-1-((S)-2-cyclohexyl-2-(3,4,5-trimethoxyphenyl)acetyl)piperidine-2-carboxamide |
| B35 | (S)-N-((S)-1-amino-3-(1H-imidazol-4-yl)-1-oxopropan-2-yl)-1-((S)-2-cyclohexyl-2-(3,4,5-trimethoxyphenyl)acetyl)piperidine-2-carboxamide |
| C01 | (S)-methyl 1-((S)-2-cyclohexyl-2-(3,4,5-trimethoxyphenyl)acetyl)piperidine-2-carboxylate, |
| C02 | (S)-ethyl 1-((S)-2-cyclohexyl-2-(3,4,5-trimethoxyphenyl)acetyl)piperidine-2-carboxylate, |
| C03 | (S)-propyl 1-((S)-2-cyclohexyl-2-(3,4,5-trimethoxyphenyl)acetyl)piperidine-2-carboxylate, |
| C04 | (S)-isopropyl 1-((S)-2-cyclohexyl-2-(3,4,5-trimethoxyphenyl)acetyl)piperidine-2-carboxylate, |
| C05 | (S)-1-((S)-2-cyclohexyl-2-(3,4,5-trimethoxyphenyl)acetyl)-N-ethylpiperidine-2-carboxamide, |
| C07 | (S)-(S)-sec-butyl-1-((S)-2-cyclohexyl-2-(3,4,5-trimethoxyphenyl)acetyl) piperidine-2-carboxylate |
| C08 | (S)-(R)-sec-butyl-1-((S)-2-cyclohexyl-2-(3,4,5-trimethoxyphenyl)acetyl) piperidine-2-carboxylate |
| C09 | (S)-pentan-3-yl-1-((S)-2-cyclohexyl-2-(3,4,5-trimethoxyphenyl)acetyl) piperidine-2-carboxylate |
| C10 | (S)-tert-butyl-1-((S)-2-cyclohexyl-2-(3,4,5-trimethoxyphenyl)acetyl) piperidine-2-carboxylate |
| C11 | (S)-1-methylcyclopentyl-1-((S)-2-cyclohexyl-2-(3,4,5-trimethoxyphenyl) acetyl)piperidine-2-carboxylate |
| C12 | (S)-tetrahydro-2H-pyran-4-yl-1-((S)-2-cyclohexyl-2-(3,4,5-trimethoxyphenyl)acetyl)piperidine-2-carboxylate |
| C13 | (S)-cyclopentyl-1-((S)-2-cyclohexyl-2-(3,4,5-trimethoxyphenyl)acetyl) piperidine-2-carboxylate |
| C14 | (S)-cyclopent-3-en-1-yl-1-((S)-2-cyclohexyl-2-(3,4,5-trimethoxyphenyl) acetyl)piperidine-2-carboxylate |
| C15 | (2S)-cyclohex-2-en-1-yl-1-((S)-2-cyclohexyl-2-(3,4,5-trimethoxyphenyl) acetyl)piperidine-2-carboxylate |
| C16 | (S)-cycloheptyl-1-((S)-2-cyclohexyl-2-(3,4,5-trimethoxyphenyl)acetyl) piperidine-2-carboxylate |
| C17 | (S)-allyl-1-((S)-2-cyclohexyl-2-(3,4,5-trimethoxyphenyl)acetyl)piperidine-2-carboxylate |
| C18 | (S)-2-methoxyethyl-1-((S)-2-cyclohexyl-2-(3,4,5-trimethoxyphenyl)acetyl) piperidine-2-carboxylate |

-continued

| | |
|---|---|
| C19 | (S)-2-(benzyloxy)ethyl-1-((S)-2-cyclohexyl-2-(3,4,5-trimethoxyphenyl)acetyl)piperidine-2-carboxylate |
| C20 | (S)-2-hydroxyethyl-1-((S)-2-cyclohexyl-2-(3,4,5-trimethoxyphenyl)acetyl)piperidine-2-carboxylate |
| C21 | (S)-3-(benzyloxy)propyl-1-((S)-2-cyclohexyl-2-(3,4,5-trimethoxyphenyl)acetyl)piperidine-2-carboxylate |
| C22 | (S)-2-hydroxyethyl-1-((S)-2-cyclohexyl-2-(3,4,5-trimethoxyphenyl)acetyl)piperidine-2-carboxylate |
| C23 | (S)-4-methoxybutyl-1-((S)-2-cyclohexyl-2-(3,4,5-trimethoxyphenyl)acetyl)piperidine-2-carboxylate |
| C24 | (S)-(R)-1-(benzyloxy)propan-2-yl-1-((S)-2-cyclohexyl-2-(3,4,5-trimethoxyphenyl)acetyl)piperidine-2-carboxylate |
| C25 | (R)-(R)-1-(benzyloxy)propan-2-yl-1-((S)-2-cyclohexyl-2-(3,4,5-trimethoxyphenyl)acetyl)piperidine-2-carboxylate. |

5. A method or inhibiting a FK506-binding protein comprising contacting a cell with an effective amount of a compound according to claim 1.

6. Pharmaceutical composition comprising at least one compound according to claim 1 together with at least one pharmaceutically acceptable carrier, solvent or excipient.

* * * * *

SEQUENCE LISTING

```
<160> NUMBER OF SEQ ID NOS: 13

<210> SEQ ID NO 1
<211> LENGTH: 127
<212> TYPE: PRT
<213> ORGANISM: Homo sapiens
<220> FEATURE:
<221> NAME/KEY: MUTAGEN
<222> LOCATION: (7)..(7)
<223> OTHER INFORMATION: Human FKBP51(13-139)A19T

<400> SEQUENCE: 1

Gly Ala Pro Ala Thr Val Thr Glu Gln Gly Glu Asp Ile Thr Ser Lys
1               5                   10                  15

Lys Asp Arg Gly Val Leu Lys Ile Val Lys Arg Val Gly Asn Gly Glu
            20                  25                  30

Glu Thr Pro Met Ile Gly Asp Lys Val Tyr Val His Tyr Lys Gly Lys
        35                  40                  45

Leu Ser Asn Gly Lys Lys Phe Asp Ser Ser His Asp Arg Asn Glu Pro
    50                  55                  60

Phe Val Phe Ser Leu Gly Lys Gly Gln Val Ile Lys Ala Trp Asp Ile
65                  70                  75                  80

Gly Val Ala Thr Met Lys Lys Gly Glu Ile Cys His Leu Leu Cys Lys
                85                  90                  95
```

Pro Glu Tyr Ala Tyr Gly Ser Ala Gly Ser Leu Pro Lys Ile Pro Ser
            100                 105                 110

Asn Ala Thr Leu Phe Phe Glu Ile Glu Leu Leu Asp Phe Lys Gly
        115                 120                 125

<210> SEQ ID NO 2
<211> LENGTH: 30
<212> TYPE: DNA
<213> ORGANISM: Artificial Sequence
<220> FEATURE:
<223> OTHER INFORMATION: sense primer FKBP12

<400> SEQUENCE: 2
aaagaattca tgggagtgca ggtggaaacc                                    30

<210> SEQ ID NO 3
<211> LENGTH: 31
<212> TYPE: DNA
<213> ORGANISM: Artificial Sequence
<220> FEATURE:
<223> OTHER INFORMATION: antisense primer FKBP12

<400> SEQUENCE: 3
cccgtcgact cattccagtt ttagaagctc c                                  31

<210> SEQ ID NO 4
<211> LENGTH: 25
<212> TYPE: DNA
<213> ORGANISM: Artificial Sequence
<220> FEATURE:
<223> OTHER INFORMATION: sense primer FKBP51FK1

<400> SEQUENCE: 4
catgccatgg caatgactac tgatg                                         25

<210> SEQ ID NO 5
<211> LENGTH: 34
<212> TYPE: DNA
<213> ORGANISM: Artificial Sequence
<220> FEATURE:
<223> OTHER INFORMATION: antisense primer FKBP51FK1

<400> SEQUENCE: 5
gcagtcgact cactctcctt tgaaatcaag gagc                               34

<210> SEQ ID NO 6
<211> LENGTH: 26
<212> TYPE: DNA
<213> ORGANISM: Artificial Sequence
<220> FEATURE:
<223> OTHER INFORMATION: sense primer FKBP52FK1

<400> SEQUENCE: 6
gcgccatggg gatgacagcc gaggag                                        26

<210> SEQ ID NO 7
<211> LENGTH: 33
<212> TYPE: DNA
<213> ORGANISM: Artificial Sequence
<220> FEATURE:
<223> OTHER INFORMATION: antisense primer FKBP52FK1

```
<400> SEQUENCE: 7
gtcgactcat tctcccttaa actcaaacaa ctc                         33

<210> SEQ ID NO 8
<211> LENGTH: 27
<212> TYPE: DNA
<213> ORGANISM: Artificial Sequence
<220> FEATURE:
<223> OTHER INFORMATION: sense primer FKBP12.6

<400> SEQUENCE: 8
ccggaattca tgggcgtgga gatcgag                                27

<210> SEQ ID NO 9
<211> LENGTH: 27
<212> TYPE: DNA
<213> ORGANISM: Artificial Sequence
<220> FEATURE:
<223> OTHER INFORMATION: antisense primer FKBP12.6

<400> SEQUENCE: 9
ctcgagtcac tctaagttga gcagctc                                27

<210> SEQ ID NO 10
<211> LENGTH: 29
<212> TYPE: DNA
<213> ORGANISM: Artificial Sequence
<220> FEATURE:
<223> OTHER INFORMATION: sense primer FKBP13

<400> SEQUENCE: 10
ccggaattca aaaggaagct gcagatcgg                              29

<210> SEQ ID NO 11
<211> LENGTH: 27
<212> TYPE: DNA
<213> ORGANISM: Artificial Sequence
<220> FEATURE:
<223> OTHER INFORMATION: antisense primer FKBP13

<400> SEQUENCE: 11
ctcgagttac agctcagttc gtcgctc                                27

<210> SEQ ID NO 12
<211> LENGTH: 26
<212> TYPE: DNA
<213> ORGANISM: Artificial Sequence
<220> FEATURE:
<223> OTHER INFORMATION: sense primer FKBP25

<400> SEQUENCE: 12
ccggaattca tggcggcggc cgttcc                                 26

<210> SEQ ID NO 13
<211> LENGTH: 27
<212> TYPE: DNA
<213> ORGANISM: Artificial Sequence
<220> FEATURE:
<223> OTHER INFORMATION: antisense primer FKBP25

<400> SEQUENCE: 13
ctcgagtcaa tcaatatcca ctaattc                                27
```